(12) United States Patent
Wang et al.

(10) Patent No.: US 10,882,856 B2
(45) Date of Patent: Jan. 5, 2021

(54) 5 OR 8-SUBSTITUTED IMIDAZO [1,5-A] PYRIDINES AS SELECTIVE INHIBITORS OF INDOLEAMINE AND/OR TRYPTOPHANE 2,3-DIOXYGENASES

(71) Applicant: BeiGene, Ltd., Grand Cayman (KY)

(72) Inventors: Hexiang Wang, Beijing (CN); Yunhang Guo, Beijing (CN); Bo Ren, Beijing (CN); Zhiwei Wang, Beijing (CN); Guoliang Zhang, Beijing (CN); Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 58 days.

(21) Appl. No.: 16/335,811

(22) PCT Filed: Sep. 23, 2017

(86) PCT No.: PCT/CN2017/103051
§ 371 (c)(1),
(2) Date: Mar. 22, 2019

(87) PCT Pub. No.: WO2018/054365
PCT Pub. Date: Mar. 29, 2018

(65) Prior Publication Data
US 2020/0024273 A1    Jan. 23, 2020

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS

| | | | |
|---|---|---|---|
| 7,220,856 B2 | 5/2007 | Dunning et al. | |
| 7,442,701 B2 | 10/2008 | Blurton et al. | |
| 7,915,284 B2 | 3/2011 | Almario Garcia et al. | |
| 9,260,434 B2 | 2/2016 | Mautino et al. | |
| 10,233,190 B2 | 3/2019 | Mautino et al. | |
| 10,280,163 B2 | 5/2019 | Wang et al. | |
| 10,647,714 B2 | 5/2020 | Wang et al. | |
| 2005/0282853 A1 | 12/2005 | Boykin et al. | |
| 2016/0002249 A1 | 1/2016 | Mautino et al. | |
| 2018/0072716 A1 | 3/2018 | Wang et al. | |
| 2018/0354908 A1* | 12/2018 | Cowley ............... | C07D 261/20 |
| 2019/0284184 A1 | 9/2019 | Wang et al. | |

FOREIGN PATENT DOCUMENTS

| | | |
|---|---|---|
| CN | 1678586 A | 10/2005 |
| CN | 1930159 A | 3/2007 |
| CN | 101516881 A | 8/2009 |
| CN | 102532144 A | 7/2012 |
| CN | 103547579 A | 1/2014 |
| CN | 105189466 A | 12/2015 |
| JP | H09-071586 | 3/1997 |
| JP | 2014-511876 A | 5/2014 |
| WO | WO 2004/002960 | 1/2004 |
| WO | WO 2004/035549 | 4/2004 |
| WO | WO 2008/034974 | 3/2008 |
| WO | WO 2008/110523 | 9/2008 |
| WO | WO 2012/142237 | 10/2012 |
| WO | WO 2014/159248 | 10/2014 |
| WO | WO 2016/071293 | 5/2016 |
| WO | WO 2016/161960 | 10/2016 |
| WO | WO 2018/039512 | 3/2018 |
| WO | WO 2018/054365 | 3/2018 |
| WO | WO 2019/101188 | 5/2019 |

OTHER PUBLICATIONS

Extended European Search Report for European Application No. 17852432.8, dated Mar. 18, 2020, 8 pages.
Potula, R. et al., "Inhibition of indoleamine 2,3-dioxygenase (IDO) enhances elimination of virus-infected macrophages in an animal model of HIV-1 encephalitis," Blood, vol. 106, Issue 7, Oct. 2005, pp. 2382-2390.
Boasso, A. et al., "Combined Effect of Antiretroviral Therapy and Blockade of IDO in SIV-Infected Rhesus Macaques," The Journal of Immunology, 2009, vol. 182, pp. 4313-4320.
Pilotte, L. et al., "Reversal of tumoral immune resistance by inhibition of tryptophan 2,3-dioxygenase," PNAS, Feb. 14, 2012, vol. 109, No. 7, pp. 2497-2502.
Fallarino, F. et al., "T cell apoptosis by tryptophan catabolism," Cell Death and Differentiation, 2002, vol. 9, pp. 1069-1077.
Smith, C. et al., "IDO Is a Nodal Pathogenic Driver of Lung Cancer and Metastasis Development," Cancer Discovery, vol. 2, No. 8, pp. 722-735 (Aug. 2012).
International Search Report and Written Opinion for International Application No. PCT/CN2016/078787, dated Jun. 30, 2016, 12 pages.
Extended European Search Report for European Application No. 16776135.2, dated Feb. 13, 2019, 4 pages.
International Search Report and Written Opinion for International Application No. PCT/CN2017/103051, dated Dec. 27, 2017, 12 pages.
International Search Report and Written Opinion for International Application No. PCT/CN2018/117347, dated Feb. 25, 2019, 11 pages.
Blatcher, P. et al., "A direct method for the substitution of imidazo[1,5-a]pyridines at position 5," Tetrahedron Letters, vol. 21, Issue 22, pp. 2195-2196 (Dec. 1980).
Davey, D. et al., "Cardiotonic Agents, 1. Novel 8-Aryl-Substituted Imidazo[1, 2-a]-and-[1, 5-a]pyridines and Imidazo[1, 5-a]pyridinones as potential positive inotropic agents," J. Med. Chem., vol. 30, No. 8, Dec. 1987, pp. 1337-1342.

(Continued)

*Primary Examiner* — Timothy R Rozof
(74) *Attorney, Agent, or Firm* — Cooley LLP

(57) ABSTRACT

Disclosed herein are 5 or 8-substituted imidazo [1, 5-a] pyridines and pharmaceutical compositions comprising at least one such 5 or 8-substituted imidazo [1, 5-a] pyridines, processes for the preparation thereof and the use thereof in therapy. Disclosed herein are certain 5 or 8-substituted imidazo [1, 5-a] pyridines that can be useful for inhibiting indoleamine 2, 3-dioxygenase and/or tryptophane 2, 3-dioxygenase and for treating diseases or disorders mediated thereby.

33 Claims, 1 Drawing Sheet

(56) References Cited

OTHER PUBLICATIONS

Jeankumar, V. U. et al., "Engineering another class of antitubercular lead: Hit to lead optimization of an intriguing class of gyrase ATPase inhibitors," European Journal of Medicinal Chemistry, vol. 122, Oct. 2016, pp. 216-231.

Kumar, S. et al., "Structure Based Development of Phenylimidazole-Derived Inhibitors of Indoleamine 2,3-Dioxygenase," J. Med. Chem., vol. 51, No. 16, Jul. 2008, pp. 4968-4977.

Tojo, S. et al., "Crystal structures and structure activity relationships of imidazothiazole derivatives as IDO1 inhibitors," ACS Medicinal Chemistry Letters, vol. 5, Issue 10, pp. 1119-1123 (Aug. 2014).

\* cited by examiner

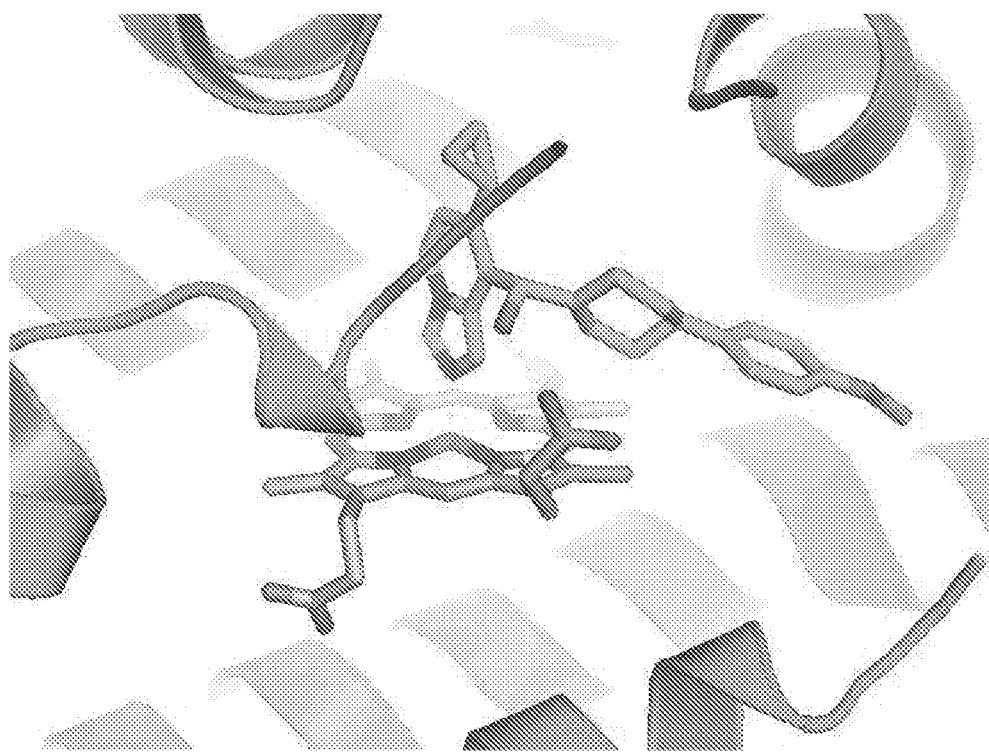

5 OR 8-SUBSTITUTED IMIDAZO [1,5-A] PYRIDINES AS SELECTIVE INHIBITORS OF INDOLEAMINE AND/OR TRYPTOPHANE 2,3-DIOXYGENASES

CROSS-REFERENCE TO RELATED APPLICATION

This application is a U.S. National Stage Application under 35 U.S.C. § 371 of International Application No. PCT/CN2017/103051, filed Sep. 23, 2017, which claims the benefit of priority to International Patent Application No. PCT/CN2016/100001 filed Sep. 24, 2016, the disclosures of which are hereby incorporated by reference in its entirety their entireties for all purposes.

FIELD OF THE INVENTION

Disclosed herein are 5 or 8-substituted imidazo[1,5-a] pyridines and pharmaceutical compositions comprising at least one such 5 or 8-substituted imidazo[1,5-a]pyridines, processes for the preparation thereof, and the use thereof in therapy. In particular, disclosed herein are certain 5 or 8-substituted imidazo[1,5-a]pyridines that can be useful for inhibiting indoleamine 2,3-dioxygenase and/or tryptophane 2,3-dioxygenase and for treating diseases or disorders mediated thereby.

BACKGROUND OF THE INVENTION

Indoleamine 2,3-dioxygenase 1 (IDO1, EC 1.13.11.42, also known as indoleamine 2,3-dioxygenase) is the first and rate-limiting enzyme in the tryptophan-kynurenine pathway that degrades the essential amino acid L-tryptophan (L-Trp) to N-formal-kynurenine, which can be subsequently metabolized through a series of steps to form NAD. IDO1 enzyme is expressed in the placenta, the mucosal and lymphoid tissues, and in inflammatory lesions (Yamazaki F, et. al., Biochem J. 1985; 230:635-8; Blaschitz A, et. al., *PLoS ONE*. 2011; 6:e21774). In the latter two, it is expressed primarily by antigen-presenting cells (APC), mainly dendritic cells (DC) and macrophages, and in cells exposed to interferon-gamma (IFNγ) and other pro-inflammatory stimuli. In human cells, the depletion of L-Trp resulting from IDO1 activity as well as the production of a series of immunoregulatory metabolites, collectively known as "kynurenines", can suppress the proliferation and differentiation of effector T cells [Frumento G, et. al., (2002), *Journal of Experimental Medicine* 196: 459-468], and markedly enhance the suppressor activity of regulatory T cells [Sharma M D, et al. (2009), *Blood* 113: 6102-6111]. As a result, IDO1 controls and fine-tunes both innate and adaptive immune responses [Grohmann U, et al. (2002), *Nature Immunology* 3: 1097-1101] under a variety of conditions, including pregnancy [Munn D H, et al. (1998), *Science* 281: 1191-1193], transplantation [Palafox D, et al. (2010), *Transplantation Reviews* 24: 160-165], infection [Boasso A, et al. (2009), *Amino Acids* 37: 89-89], chronic inflammation [Romani L, et al. (2008), *Nature* 451: 211-U212], autoimmunity [Platten M, et al. (2005), Science 310: 850-855], neoplasia, and depression [Maes M, et. al., Life Sci. 2002 6:71(16): 1837-48; Myint A M, et. al., (2012), Journal of Neural Transmission 119: 245-251].

Several lines of evidence suggest that IDO is involved in induction of immune tolerance. The immunosuppressive effect of IDO1 was demonstrated first in a mouse model of fetal protection against maternal immune rejection. Treatment of pregnant mice with a tryptophan analog that inhibits IDO1, which is constitutively expressed in the placenta, resulted in T cell-mediated rejection of allogeneic embryos [Munn D H, et al. (1998), *Science* 281: 1191-1193]. Subsequent studies developed this concept as a mechanism to defeat immune surveillance in cancer (reviewed in [Prendergast G C (2008), Oncogene 27(28):3889-3900; Munn D H, et. al., (2007), J Clin Invest 117(5):1147-1154]). Indoleamine 2,3-dioxygenase is widely overexpressed in tumor cells where it is has been associated predominantly with poor prognosis [Uyttenhove C, et. al., (2003), Nat Med 9(10):1269-1274; Liu X, et. al., (2009), Curr Cancer Drug Targets 9(8):938-95]. Expression of IDO by immunogenic mouse tumor cells prevents their rejection by preimmunized mice [Uyttenhove C. et. al., Nat Med. 2003 October; 9(10): 1269-74. Epub 2003 Sep. 21]. IDO activity is shown to suppress T cells [Fallarino F, et. al., (2002), Cell Death Differ 9:1069-1077; Frumento G, et. al., (2002), J Exp Med 196(4):459-468; Terness P, et. al., (2002), J Exp Med 196(4):447-457] and NK cells [Della Chiesa M, et. al., (2006), Blood 108(13):4118-4125], and also that IDO was critical to support the formation and activity of Tregs [Fallarino F, et. al., (2003), Nat Immunol 4(12):1206-1212] and myeloid-derived suppressor cells (MDSCs) [Smith C, et. al., (2012), Cancer Discovery 2(8):722-735.]. It has been suggested that the efficacy of therapeutic vaccination of cancer patients might be improved by concomitant administration of an IDO inhibitor [Uyttenhove C. et. al., Nat Med. 2003 October; 9(10):1269-74. Epub 2003 Sep. 21]. It has been shown that the IDO inhibitor, 1-MT, can synergize with chemotherapeutic agents to reduce tumor growth in mice, suggesting that IDO inhibition may also enhance the antitumor activity of conventional cytotoxic therapies [Muller A J, et. al., Nat Med. 2005 March, 11(3):312-9]. It has been shown that IDO inhibitors can synergize with anti-CTLA-4 antibody or anti-PDL-1 antibody in inhibiting tumor growth in mouse models [Holmgaard R B, et. al., J Exp Med. 2013 Jul. 1:210(7):1389-402; Spranger S, et. al., J Immunother Cancer. 2014, 2:3].

It has been proposed that IDO is induced chronically by HIV infection, and is further increased by opportunistic infections, and that the chronic loss of Trp initiates mechanisms responsible for cachexia, dementia and diarrhea and possibly immunosuppression of AIDS patients [Brown, et al., 1991, Adv. Exp. Med. Biol., 294: 425-35]. To this end, it has recently been shown that IDO inhibition can enhance the levels of virus-specific T cells and, concomitantly, reduce the number of virally infected macrophages in a mouse model of HIV [Portula et al., 2005, Blood, 106:2382-90]. Simian Immunodeficiency Virus (SIV) is very similar to Human Immunodeficiency Virus (HIV) and it is used to study the condition in animal models. In both HIV and SIV, the level of virus in the blood, or 'viral load', is important because when the viral load is high, the disease progresses and it depletes the patient's immune system. This eventually leads to the onset of Acquired Immune Deficiency Syndrome (AIDS), where the patient cannot fight infections which would be innocuous in healthy individuals. It has also been reported that monkeys with the simian form of HIV treated with an IDO inhibitor, called D-1mT alongside Anti-Retroviral Therapy (ART), reduced their virus levels in the blood to undetectable levels, therefore when combined with ARTs, IDO inhibitors may help HIV patients not responding to treatment in the future [Adriano Boasso, et. al., J. Immunol., April 2009; 182: 4313-4320].

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis) and depression, therapeutic agents aimed at suppression of tryptophan degradation by inhibiting IDO activity are of interests. Inhibitors of IDO can be used as effective cancer therapy as they could reverse the immunosuppressive effects of tumor microenvironment and activate anti-tumor activity of T cells. IDO inhibitors could also be useful in activation of immune responses in HIV infection. Inhibition of IDO may also be an important treatment strategy for patients with neurological or neuropsychiatric diseases or disorders such as depression. The compounds, compositions and methods herein help meet the current need for IDO modulators.

Tryptophan 2,3-dioxygenase (TDO, EC 1.13.11.11) catalyzes the same Trp degradation reaction as IDO1. TDO is primarily expressed in the liver in humans, where acts as the main regulator of systemic tryptophan levels. More recently, TDO was also found to be expressed in the brain, where it may regulate the production of neuroactive tryptophan metabolites such as kynurenic acid and quinolinic acid [Kanai M, et. al., Mol Brain 2009; 2:8]. Two recent studies [Opitz C A, et. al., Nature 2011; 478:197-203; Pilotte L, et. al., Proc Natl Acad Sci USA. 2012, 109(7):2497-502] point to the significance of TDO activity in certain cancers where it is expressed constitutively (particularly malignant glioma, hepatocellular carcinoma, melanoma, and bladder cancer). Functional studies in human tumors indicate that constitutive TDO enzymatic activity is sufficient to sustain biologically relevant tryptophan catabolism that is capable of suppressing antitumor immune responses [Opitz C A, et. al., Nature 2011; 478:197-203; Pilotte L, et. al., Proc Natl Acad Sci USA. 2012, 109(7):2497-502]. TDO expression by tumors is reported to prevent rejection by immunized mice. A specific TDO inhibitor is shown to restore the ability of mice to reject TDO-expressing tumors without causing significant toxicity [Pilotte L, et. al., Proc Natl Acad Sci USA. 2012, 109(7):2497-502]. Therefore, inhibitors of TDO can potentially be used as a single agent or in combination with other anti-cancer therapies to treat a variety of human cancers.

Small molecule inhibitors of IDO are being developed to treat or prevent IDO-related diseases such as those described above. Fox example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; WO 2006/122150; WO 2009/073620; WO 2009/132238; WO 2011/056652, WO 2012/142237; WO 2013/107164; WO 2014/066834; WO 2014/081689; WO 2014/141110; WO 2014/150646; WO 2014/150677; WO 2015006520; WO 2015/067782; WO 2015/070007; WO 2015/082499; WO 2015/119944; WO 2015/121812; WO 2015/140717; WO 2015/150697; WO 2015/173764; WO2015/188085; WO 2016/026772; WO 2016/024233; WO2016/026772; WO 2016/037026; WO 2016/040458; WO 2016/051181; WO 2016/059412; WO 2016/071283; WO 2016/071293; WO 2016/073738; WO 2016/073770; WO 2016/073774; US 2015328228 and US 2015266857. In particular, the compounds of WO 2012/142237 and WO 2014/159248 encompass a series of tricyclic imidazoisoindoles with potent IDO inhibitory activity.

Some substituted imidazo[1,5-a] pyridines are known in the literatures. For example, WO 2008110523 A1 (published on Sep. 18, 2008) has disclosed imidazo[1,5-a] pyridines as glutaminyl cyclase inhibitors; GB2174094A (published on Oct. 29, 1986) discloses imidazo[1,5-a] pyridine derivatives as thromboxane synthetase inhibitors; and JP1997071586A (published on Mar. 18, 1997) discloses imidazo[1,5-a] pyridines as inhibitors of the aldosterone biosynthetic enzyme cytochrome P450C18 for the treatment of primary or secondary aldosteronism, renal hypertension and so on.

However, no imidazo[1,5-a] pyridine has been reported as an IDO/TDO inhibitor. Disclosed herein are novel 5 or 8-substituted imidazo[1,5-a]pyridines exhibiting IDO, in particular IDO1, TDO, or IDO/TDO dual inhibitory activity. Specifically, disclosed herein are novel 5 or 8-substituted imidazo[1,5-a]pyridines exhibiting selective inhibitory activity for IDO over TDO. The inventors of the present application have unexpectedly found that substitution of hydroxyl group on the chiral α-carbon atom attached to position 5 or 8 of the imidazo[1,5-a]pyridine structure and/or ortho or meta substitution in relation to the hydroxyl-substituted chiral α-carbon atom on the pyridine moiety of the imidazo[1,5-a]pyridine structure impart unexpected enzymatic and cellular activity to the novel 5 or 8-substituted imidazo[1,5-a]pyridines disclosed herein. The inventors of the present application have also found the selective inhibitory activity of the compound disclosed herein for IDO1 over TDO may be attributed to chirality of α-carbon atom attached to position 5 or 8 of the imidazo[1,5-a] pyridine structure, ortho or meta substitution (in particular, ortho substitution) in relation to the hydroxyl-substituted chiral α-carbon atom on the pyridine moiety of the imidazo [1,5-a]pyridine structure, and the conformational isomerism of the hexyl ring in the molecule.

SUMMARY OF THE INVENTION

Provided is a compound selected from 5 or 8-substituted imidazo[1,5-a]pyridines of Formulas (IA) and/or (IB):

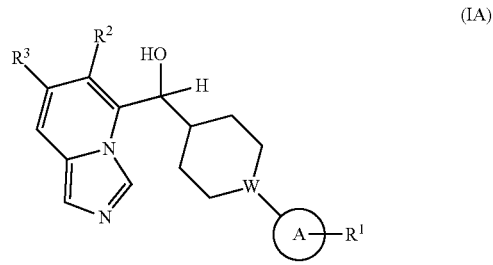

(IA)

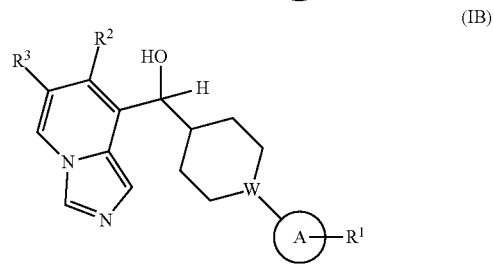

(IB)

or a stereoisomer thereof, or a pharmaceutically acceptable salt thereof, wherein:

W is CH or N;

Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$ as long as valence and stability permit;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^6$;

$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^4$, and —$SR^4$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^6$, provided that at least one of $R^2$ and $R^3$ is not hydrogen;

$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;

$R^5$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;

$R^6$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-$NR^aR^b$, —CN, —$OR^a$, —$NR^aR^b$, —$COR^a$, —$CO_2R$, —$CONR^aR^b$, —$C(=NR^a)NR^bR^c$, nitro, —$NR^aCOR^b$, —$NR^aCONR^aR^b$, —$NR^aCO_2R^b$, —$SO_2R^a$, —$SO_2$aryl, —$NR^aSO_2NR^bR^c$, $NR^aSO_2R^b$, and —$NR^aSO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein $R^a$, $R^b$, and $R^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl, or ($R^a$ and $R^b$), and/or ($R^b$ and $R^c$) together with the atoms to which they are attached, form a ring selected from heterocyclyl optionally substituted by halogen, $C_{1-4}$ haloalkyl and $C_{1-4}$ alkyl and heteroaryl rings optionally substituted by halogen, $C_{1-4}$ haloalkyl and $C_{1-4}$ alkyl, with the proviso that the compound is not (7-cyclopropylimidazo[1,5-a]pyridin-8-yl)(4-phenylcyclohexyl)methanol.

Also provided is a pharmaceutical composition comprising at least one pharmaceutically acceptable excipient and a compound selected from compounds of Formulas (IA) and/or (IB), or a stereoisomer thereof, or a pharmaceutically acceptable salt thereof disclosed herein.

Also provided is a method of treating cancer responsive to inhibition of IDO and/or TDO comprising administering to a subject in need of treating for such cancer an amount of a compound selected from compounds of Formulas (IA) and/or (IB), or a stereoisomer thereof, or a pharmaceutically acceptable salt thereof disclosed herein effective to treat the cancer.

Also provided is a use of a compound selected from compounds of Formulas (IA) and/or (IB), or a stereoisomer thereof, or a pharmaceutically acceptable salt thereof disclosed herein in manufacture of a medicament for treatment of the disorders or diseases above.

Also provided is a use of a compound selected from compounds of Formulas (IA) and/or (IB), or a stereoisomer thereof, or a pharmaceutically acceptable salt thereof disclosed herein in manufacture of a medicament for inhibition of IDO and/or TDO.

Also provided is a use of a compound selected from compounds of Formulas (IA) and/or (IB), or a stereoisomer thereof, or a pharmaceutically acceptable salt thereof disclosed herein in the manufacture of a medicament for treating cancer.

BRIEF DESCRIPTION OF THE DRAWINGS

FIG. 1 shows C101a/IDO1 cocrystal (Resolution=50.00-2.67 Å).

DETAILED DESCRIPTION OF THE INVENTION

As used herein, the following words, phrases and symbols are generally intended to have the meanings as set forth below, except to the extent that the context in which they are used indicates otherwise.

The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "alkyloxy" herein refers to an alkyl group as defined above bonded to oxygen, represented by —Oalkyl. Examples of an alkyloxy, e.g., $C_{1-6}$ alkyloxy or $C_{1-4}$ alkyloxy includes, but not limited to, methoxy, ethoxyl, isopropoxy, propoxy, n-butoxy, tert-butoxy, pentoxy and hexoxy and the like.

The term "haloalkyl" herein refers to an alkyl group in which one or more hydrogen is/are replaced by one or more halogen atoms such as fluoro, chloro, bromo, and iodo. Examples of the haloalkyl include $C_{1-6}$haloalkyl or $C_{1-4}$haloalkyl, but not limited to $F_3C$—, $ClCH_2$—, $CF_3CH_2$—, $CF_3CCl_2$—, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-4}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, I-propynyl, 2-propynyl (propargyl), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$ cycloalkyl, include, but not limited to cyclopropyl, cyclobutyl, cyclopentyl, cyclohexyl, cycloheptyl, and cyclooctyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems, such as

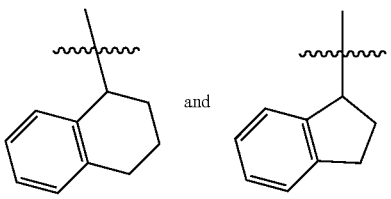 [SMILES: *C1CCCc2ccccc21 ; *C1CCc2ccccc21]

and herein the wavy lines indicate the points of attachment. The ring may be saturated or have at least one double bond (i.e. partially unsaturated), but is not fully conjugated, and is not aromatic, as aromatic is defined herein.

The term "aryl" used alone or in combination with other terms refers to a group selected from:
5- and 6-membered carbocyclic aromatic rings, for example, phenyl;
bicyclic ring systems such as 7 to 12 membered bicyclic ring systems wherein at least one ring is carbocyclic and aromatic, selected, for example, from naphthalene, and indane; and
tricyclic ring systems such as 10 to 15 membered tricyclic ring systems wherein at least one ring is carbocyclic and aromatic, for example, fluorene.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, for example, but not limited to, phenyl, naphth-1-yl, naphth-2-yl, anthracenyl, phenanthrenyl rings, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "halogen" or "halo" herein refers to F, Cl, Br or I.

The term "heteroaryl" herein refers to a group selected from:
5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;
8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The terms "aromatic heterocyclic ring" and "heteroaryl" are used interchangeable throughout the disclosure herein. In some embodiments, a monocyclic or bicyclic aromatic heterocyclic ring has 5- to 10-ring forming members with 1, 2, 3, or 4 heteroatom ring members independently selected from nitrogen, sulfur and oxygen and the remaining ring members being carbon. In some embodiments, the monocyclic or bicyclic aromatic heterocyclic ring is a monocyclic or bicyclic ring comprising 1 or 2 heteroatom ring members independently selected from nitrogen, sulfur and oxygen. In some embodiments, the monocyclic or bicyclic aromatic heterocyclic ring is a 5- to 6-membered heteroaryl ring, which is monocyclic and which has 1 or 2 heteroatom ring members independently selected from nitrogen, sulfur and oxygen. In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. In some embodiments, a heterocyclyl group is 4- to 7-membered monocyclic ring with one heteroatom selected from N, O and S. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

Some of the compounds disclosed herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher$^a$s acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formulas (IA) and/or (IB), and salts of the stereoisomers of at least one compound of Formulas (IA) and/or (IB), such as salts of enantiomers, and/or salts of diastereomers.

"Treating", "treat" or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat" as defined above, a disease or disorder in a subject.

The term "at least one substituent" disclosed herein includes, for example, from 1 to 4, such as from 1 to 3, further as 1 or 2, substituents, provided that the valence allows. For example, "at least one substituent $R^6$" disclosed herein includes from 1 to 4, such as from 1 to 3, further as 1 or 2, substituents selected from the list of $R^6$ as disclosed herein; and "at least one substituent $R^1$" disclosed herein includes from 1 to 4, such as from 1 to 3, further as 1 or 2, substituents selected from the list of $R^1$ as disclosed herein.

In the first aspect, provided is a compound selected from 5 or 8-substituted imidazo[1,5-a]pyridines of Formulas (IA) and/or (IB):

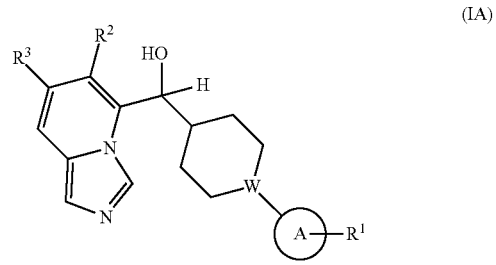

(IA)

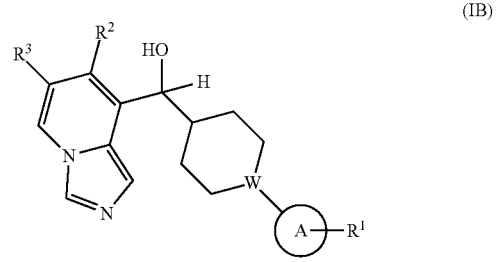

(IB)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members: Ring A is substituted with at least one substituent $R^1$;
$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^6$;
$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^4$, and —$SR^4$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^6$, provided that $R^2$ and $R^3$ are not both hydrogen;

$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;

$R^5$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;

$R^6$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-$NR^aR^b$, —CN, —$OR^a$, —$NR^aR^b$, —$COR^a$, —$CO_2R^a$, —$CONR^aR^b$, —$C(=NR^a)NR^bR^c$, nitro, —$NR^aCOR^b$, —$NR^aCONR^aR^b$, —$NR^aCO_2R^b$, —$SO_2R^a$, —$SO_2$aryl, —$NR^aSO_2NR^bR^c$, $NR^aSO_2R^b$, and —$NR^aSO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein $R^a$, $R^b$, and $R^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl;

with the proviso that the compound is not (7-cyclopropylimidazo[1,5-a]pyridin-8-yl)(4-phenylcyclohexyl)methanol.

In some embodiments of the first aspect, the compound disclosed herein is a compound selected from 5 or 8-substituted imidazo[1,5-a]pyridines of Formulas (IA) and/or (IB):

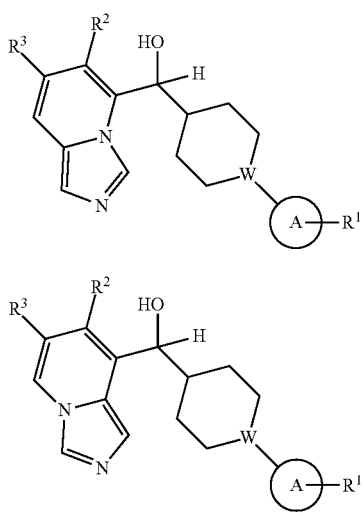

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, or aryl, wherein said $C_{1-8}$ alkyl is optionally substituted with at least one substituent $R^6$;

$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, or $C_{1-8}$ haloalkyl, provided that $R^2$ and $R^3$ are not both hydrogen;

$R^4$ is independently selected from hydrogen, $C_{1-8}$ alkyl, $C_{2-8}$ alkenyl, $C_{2-8}$ alkynyl, $C_{2-8}$ haloalkyl, $C_{3-8}$ cycloalkyl, heterocyclyl, or aryl, wherein said $C_{1-8}$ alkyl is optionally substituted with 1 or 2 substituent $R^6$;

$R^5$ is independently selected from hydrogen, $C_{1-8}$ alkyl, $C_{2-8}$ alkenyl, $C_{2-8}$ alkynyl, or $C_{1-8}$ haloalkyl, wherein said $C_{1-8}$ alkyl is optionally substituted with 1 or 2 substituent $R^6$;

$R^6$ is selected from hydrogen, halogen, aryl, —$OR^3$, or —$COR^a$, wherein $R^a$ is selected from H, $C_{1-4}$ haloalkyl, $C_{1-4}$ alkyl, $C_{2-4}$ alkenyl, $C_{2-4}$ alkynyl, or aryl;

with the proviso that the compound is not (7-cyclopropylimidazo[1,5-a]pyridin-8-yl)(4-phenylcyclohexyl)methanol.

In some embodiments of the first aspect, the compound disclosed herein is a compound selected from 5 or 8-substituted imidazo[1,5-a]pyridines of Formulas (IA) and/or (IB):

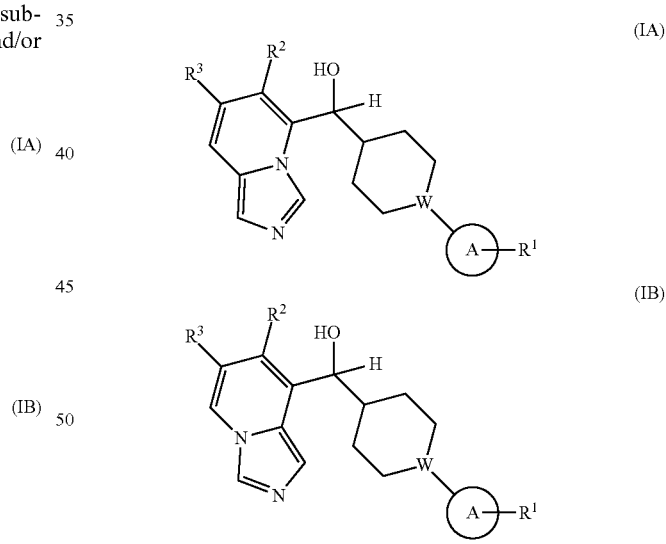

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{1-8}$ haloalkyl, $C_{2-8}$ alkenyl, $C_{2-8}$ alkynyl, or aryl; $R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, or $C_{1-8}$ haloalkyl, provided that $R^2$ and $R^3$ are not both hydrogen;

$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, or aryl, wherein said $C_{1-8}$ alkyl is optionally substituted with halogen, OH, —$OC_{1-4}$alkyl, —$C(O)C_{1-4}$alkyl or —$C(O)$phenyl, and said aryl optionally substituted by halogen;

$R^5$ is independently selected from hydrogen, $C_{1-8}$ alkyl, $C_{2-8}$ alkenyl, $C_{2-8}$ alkynyl, or $C_{1-8}$ haloalkyl, wherein said $C_{1-8}$ alkyl is optionally substituted with phenyl;

with the proviso that the compound is not (7-cyclopropylimidazo[1,5-a]pyridin-8-yl)(4-phenylcyclohexyl)methanol.

In some embodiments of the first aspect, the compound disclosed herein is a compound selected from 5 or 8-substituted imidazo[1,5-a]pyridines of Formulas (IA) and/or (IB):

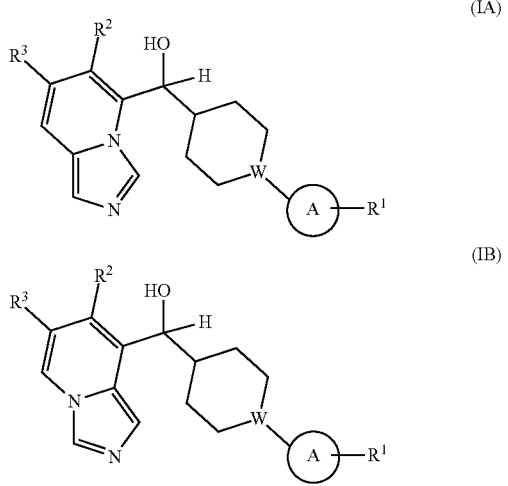

or a stereoisomer thereof, or a pharmaceutically acceptable salt thereof,
wherein:
W is CH or N;

Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{1-8}$ haloalkyl, or aryl;

$R^2$ and $R^3$ are each independently selected from hydrogen, halogen, $C_{1-8}$ alkyl, or $C_{3-8}$ cycloalkyl, provided that $R^2$ and $R^3$ are not both hydrogen;

$R^4$ is independently selected from hydrogen, $C_{1-8}$ alkyl, $C_{1-8}$ haloalkyl, $C_{3-8}$ cycloalkyl, heterocyclyl, or aryl, wherein said $C_{1-8}$ alkyl is optionally substituted with halogen, OH, —$OC_{1-4}$ alkyl, —$C(O)C_{1-4}$alkyl or —$C(O)$phenyl, and said aryl optionally substituted by halogen; $R^5$ is independently selected from hydrogen, or $C_{1-8}$ alkyl, wherein said $C_{1-8}$ alkyl is optionally substituted with phenyl;

with the proviso that the compound is not (7-cyclopropylimidazo[1,5-a]pyridin-8-yl)(4-phenylcyclohexyl)methanol.

In some embodiments of the first aspect, ring A is a $C_{3-8}$ cycloalkyl ring and W is N.

In some embodiments of the first aspect, ring A is phenyl or naphthalenyl ring.

In some embodiments of the first aspect, ring A is a monocyclic or bicyclic aromatic heterocyclic ring having 5- to 10-ring members comprising 1, 2, 3, or 4 heteroatoms selected from O, S, and N.

In some embodiments of the first aspect, ring A is a monocyclic aromatic heterocyclic ring having 5- to 6-ring members comprising 1 or 2 heteroatoms selected from O, S, and N. In other embodiments, ring A is pyridinyl, furanyl, pyrazinyl, pyrimidinyl, pyridazinyl, pyrrolyl, thienyl, triazinyl, or pyrazolyl. In some preferred embodiments, ring A is pyridinyl or furanyl.

In some embodiments of the first aspect, ring A is a bicyclic aromatic heterocyclic ring having 8- to 10-ring members comprising 1 or 2 or 3 heteroatoms selected from O, S, and N. In other embodiments, ring A is cinnolinyl, benzothienyl, benzofuryl, benzoimidazolyl, indolyl, isoindolyl, indolinyl, phthalazinyl, quinolinyl, isoquinolinyl, pyrrolopyridinyl, pyrazolopyridinyl, benzodioxolyl, benzoxazolyl, pteridinyl, purinyl, benzofurazanyl, benzothiophenyl, benzothiazolyl, benzoxazolyl, quinazolinyl, quinoxalinyl, naphthyridinyl, furopyridinyl, benzothiazolyl, or indazolyl. In some preferred embodiments, ring A is benzothiophenyl (such as benzo[b]thiophen-2-yl, benzo[b]thiophen-3-yl, benzo[b]thiophen-5-yl, or benzo[b]thiophen-6-yl) or quinolinyl (such as quinolin-4-yl, quinolin-5-yl, quinolin-6-yl, or quinolin-8-yl) or benzodioxolyl (such as benzo[d][1,3]dioxol-5-yl).

In some embodiments of the first aspect, $R_2$ is halogen, $C_{1-4}$alkyl, $C_{1-4}$haloalkyl, or $C_{3-6}$ cycloalkyl, and $R^3$ is hydrogen. In some preferred embodiments, $R_2$ is halogen, $C_{1-3}$alkyl, or $C_{3-4}$ cycloalkyl, and $R^3$ is hydrogen. In some further preferred embodiments, $R_2$ is isopropyl or cyclopropyl, and $R^3$ is hydrogen.

In some embodiments of the first aspect, $R_2$ is hydrogen, and $R^3$ is halogen, $C_{1-4}$alkyl, $C_{1-4}$haloalkyl, or $C_{3-6}$cycloalkyl.

In some embodiments of the first aspect, ring A is a phenyl group, which is optionally substituted by one or two or three substituents $R^1$, which is halogen such as F, Cl or Br, $C_{1-6}$alkyl, $C_{1-6}$haloalkyl, —$OR^4$ (wherein $R^4$ is hydrogen; $C_{1-6}$alkyl optionally substituted by halogen, $C_{1-6}$alkyl-O—, —$C(O)C_{1-6}$alkyl or —$C(O)$phenyl; heterocyclyl; aryl or $C_{3-6}$cycloalkyl). In other embodiments, ring A is a phenyl group, which is optionally substituted by one or two or three substituents $R^1$, which is halogen such as F, Cl or Br, —Ohio, $C_{1-4}$alkyl, $C_{1-4}$haloalkyl, $C_{1-4}$alkyl-O—, $C_{1-4}$alkyl-O—$C_{1-4}$alkyl-O—, —$OC_{1-4}$haloalkyl, phenoxy, —$OC_{3-6}$cycloalkyl or —O-(4- to 6-membered heterocyclyl comprising one oxygen heteroatom). In some preferred embodiments, ring A is a phenyl group, which is optionally substituted by one or two or three substituents $R^1$, which is halogen such as F, Cl or Br, —Ohio, methyl, $CF_3$, —$OCF_3$, methoxy or methoxyethoxy. In some yet preferred embodiments, ring A is a phenyl group which is substituted by one substituent $R^1$, which is OH, F, Cl, Br or methoxy.

In some embodiments of the first aspect, $R_2$ is isopropyl or cyclopropyl, $R^3$ is hydrogen, ring A is a phenyl group which is substituted by one or two substituents $R^1$, which is F, Cl, Br OH, or methoxy. In other embodiments of the first aspect, $R_2$ is cyclopropyl, $R^3$ is hydrogen, ring A is a phenyl group which is substituted by one substituent $R^1$, which is F, Cl, Br, Ohio or methoxy. In other embodiments of the first aspect, $R_2$ is cyclopropyl, $R^3$ is hydrogen, ring A is a phenyl group which is substituted by one substituent $R^1$, which is F, Cl, or Br.

In some embodiments of the first aspect, heterocyclyl in the definition of $R^4$ is 4- to 6-membered heterocyclyl comprising one oxygen heteroatom. In other embodiments of the first aspect, heterocyclyl in the definition of $R^4$ is oxetanyl (e.g., oxetan-3-yl) or tetrahydropyranyl (e.g., tetrahydro-2H-pyran-4-yl).

In some embodiments of the first aspect, $C_{3-8}$ cycloalkyl in the definition of $R^4$ is $C_{3-6}$ cycloalkyl. In other embodiments of the first aspect, $C_{3-8}$ cycloalkyl in the definition of $R^4$ is cyclopentyl.

In some embodiments of the first aspect, ring A is an unsubstituted quinolinyl group. In other embodiments, ring A is a quinolinyl group substituted by $R^1$, which is fluoro or chloro. In still other embodiments, ring A is quinolin-4-yl or quinolin-5-yl.

In some embodiments of the first aspect, the chiral α-carbon atom attached to the imidazo[1,5-a]pyridine structure is in an S-configuration.

In some embodiments of the first aspect, ring A is attached to the 4-cyclohexyl structure in a trans-configuration.

In some embodiments of the first aspect, the compounds of Formulas (IA) and (IB) have the following configurations, respectively

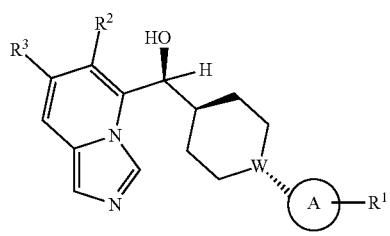

(IA)

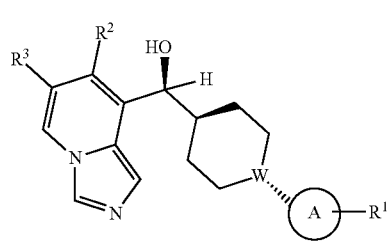

(IB)

In the second aspect, provided is 5-substituted imidazo [1,5-a]pyridines of Formula (IA):

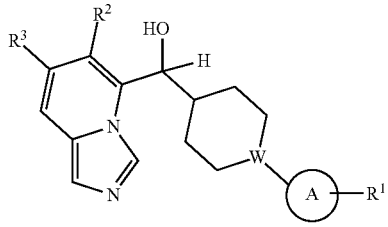

(IA)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;
$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^6$;
$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^4$, and —$SR^4$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^6$, provided that $R^2$ and $R^3$ are not both hydrogen;
$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ haloalkyl, $C_{3-8}$ cycloalkyl, heterocyclyl, aryl, and heteroaryl are each independently optionally substituted with 1 or 2 substituent $R^6$.
$R^5$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;
$R^6$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-$NR^aR^b$, —CN, —$OR^a$, —$NR^aR^b$, —$COR^a$, —$CO_2R^a$, —$CONR^aR^b$, —$C(=NR^a)NR^bR^c$, nitro, —$NR^aCOR^b$, —$NR^aCONR^aR^b$, —$NR^aCO_2R^b$, —$SO_2R^a$, —$SO_2$aryl, —$NR^aSO_2NR^bR^c$, $NR^aSO_2R^b$, and —$NR^aSO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein $R^a$, $R^b$, and $R^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl.

In some embodiments of the second aspect, the compound disclosed herein is 5-substituted imidazo[1,5-a]pyridines of Formula (IA):

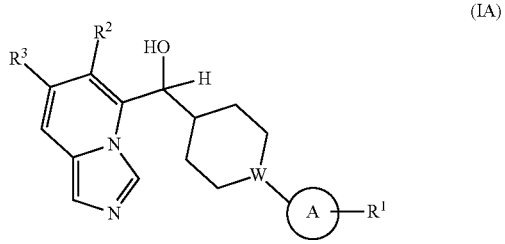

(IA)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, or aryl, wherein said $C_{1-4}$ alkyl is optionally substituted with at least one substituent $R^6$;

$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, or $C_{1-8}$ haloalkyl, provided that $R^2$ and $R^3$ are not both hydrogen;

$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, or aryl, wherein said $C_{1-8}$ alkyl is optionally substituted with 1 or 2 substituent $R^6$;

$R^5$ is independently selected from hydrogen, $C_{1-8}$ alkyl, $C_{2-8}$ alkenyl, $C_{2-8}$ alkynyl or $C_{1-8}$ haloalkyl, wherein said $C_{1-8}$ alkyl is optionally substituted with 1 or 2 substituent $R^6$;

$R^6$ is selected from hydrogen, halogen, aryl, $-OR^a$, or $-COR^a$, wherein $R^a$ is selected from H, $C_{1-4}$ haloalkyl, $C_{1-4}$ alkyl, $C_{2-4}$ alkenyl, $C_{2-4}$ alkynyl, or aryl.

In some embodiments of the second aspect, the compound disclosed herein is 5-substituted imidazo[1,5-a]pyridines of Formula (IA):

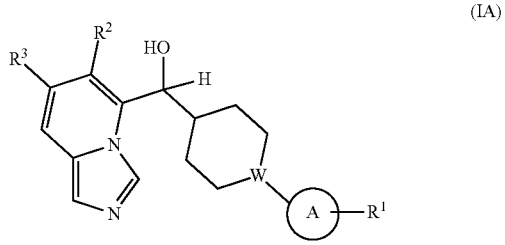

(IA)

or a stereoisomer thereof, or a pharmaceutically acceptable salt thereof, wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{1-8}$ haloalkyl, $C_{2-8}$ alkenyl, $C_{2-8}$ alkynyl, or aryl;

$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, or $C_{1-8}$ haloalkyl, provided that $R^2$ and $R^3$ are not both hydrogen;

$R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, or aryl, wherein said $C_{1-8}$ alkyl is optionally substituted with halogen, OH, $-C(O)C_{1-4}$alkyl or $-C(O)$phenyl, and said aryl optionally substituted by halogen;

$R^5$ is independently selected from hydrogen, $C_{1-8}$ alkyl, $C_{2-8}$ alkenyl, $C_{2-8}$ alkynyl, or $C_{1-8}$ haloalkyl, wherein said $C_{1-8}$ alkyl is optionally substituted with phenyl.

In some embodiments of the second aspect, the compound disclosed herein is 5-substituted imidazo[1,5-a]pyridines of Formula (IA):

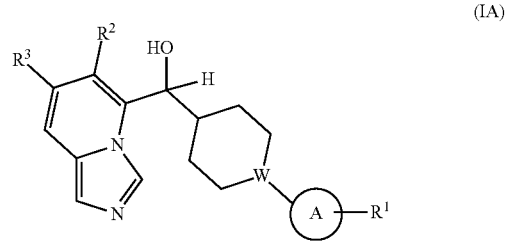

(IA)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{1-8}$ haloalkyl, or aryl;

$R^2$ and $R^3$ are each independently selected from hydrogen, halogen, $C_{1-8}$ alkyl, or $C_{3-8}$ cycloalkyl, provided that $R^2$ and $R^3$ are not both hydrogen;

$R^4$ is independently selected from hydrogen, $C_{1-8}$ alkyl, $C_{1-8}$ haloalkyl, $C_{3-8}$ cycloalkyl, heterocyclyl, or aryl, wherein said $C_{1-8}$ alkyl is optionally substituted with halogen, OH, $-C(O)C_{1-4}$alkyl or $-C(O)$phenyl, and said aryl optionally substituted by halogen; $R^5$ is independently selected from hydrogen, or C$_{1-8}$ alkyl, wherein said C$_{1-8}$ alkyl is optionally substituted with phenyl.

In some embodiments of the second aspect, ring A is a C$_{3-8}$ cycloalkyl ring and W is N.

In some embodiments of the second aspect, ring A is phenyl or naphthalenyl ring.

In some embodiments of the second aspect, ring A is a monocyclic or bicyclic aromatic heterocyclic ring having 5- to 10-ring members comprising 1, 2, 3, or 4 heteroatoms selected from O, S, and N.

In some embodiments of the second aspect, ring A is a monocyclic aromatic heterocyclic ring having 5- to 6-ring members comprising 1 or 2 heteroatoms selected from O, S, and N. In other embodiments, ring A is pyridinyl, furanyl, pyrazinyl, pyrimidinyl, pyridazinyl, pyrrolyl, thienyl, triazinyl, or pyrazolyl. In some preferred embodiments, ring A is pyridinyl or furanyl.

In some embodiments of the second aspect, ring A is a bicyclic aromatic heterocyclic ring having 8- to 10-ring members comprising 1 or 2 or 3 heteroatoms selected from O, S, and N. In other embodiments, ring A is cinnolinyl, benzothienyl, benzofuryl, benzoimidazolyl, indolyl, isoindolyl, indolinyl, phthalazinyl, quinolinyl, isoquinolinyl, pyrrolopyridinyl, pyrazolopyridinyl, benzodioxolyl, benzoxazolyl, pteridinyl, purinyl, benzofurazanyl, benzothiophenyl, benzothiazolyl, benzoxazolyl, quinazolinyl, quinoxalinyl, naphthyridinyl, furopyridinyl, benzothiazolyl, or indazolyl. In some preferred embodiments, ring A is benzothiophenyl (such as benzo[b]thiophen-2-yl, benzo[b]thiophen-3-yl, benzo[b]thiophen-5-yl, or benzo[b]thiophen-6-yl) or quinolinyl (such as quinolin-4-yl, quinolin-5-yl, quinolin-6-yl, or quinolin-8-yl).

In some embodiments of the second aspect, R$_2$ is halogen, C$_{1-4}$alkyl, C$_{1-4}$haloalkyl, or C$_{3-6}$ cycloalkyl, and R$^3$ is hydrogen. In some preferred embodiments, R$_2$ is halogen, C$_{1-3}$alkyl, or C$_{3-4}$ cycloalkyl, and R$^3$ is hydrogen. In some further preferred embodiments, R$_2$ is isopropyl or cyclopropyl, and R$^3$ is hydrogen.

In some embodiments of the second aspect, R$_2$ is hydrogen, and R$^3$ is halogen, C$_{1-4}$alkyl, C$_{1-4}$haloalkyl, or C$_{3-6}$cycloalkyl.

In some embodiments of the second aspect, ring A is a phenyl group, which is optionally substituted by one or two or three substituents R$^1$, which is halogen such as F, Cl or Br, C$_{1-6}$alkyl, C$_{1-6}$haloalkyl, or —OR$^4$ (wherein R$^4$ is hydrogen; aryl, heterocyclyl; or C$_{1-6}$alkyl optionally substituted by halogen, OH, —C(O)C$_{1-6}$alkyl or —C(O)phenyl). In other embodiments, ring A is a phenyl group, which is optionally substituted by one or two or three substituents R$^1$, which is halogen such as F, Cl or Br, —Ohio, C$_{1-4}$alkyl, C$_{1-4}$haloalkyl, —OC$_{1-4}$alkyl, —OC$_{1-4}$haloalkyl, phenoxy, or —O-(4- to 6-membered heterocyclyl comprising one oxygen heteroatom). In some preferred embodiments, ring A is a phenyl group, which is optionally substituted by one or two or three substituents R$^1$, which is halogen such as F, Cl, Br, —Ohio, methyl, CF$_3$, —OCF$_3$, or methoxy. In some yet preferred embodiments, ring A is a phenyl group which is substituted by one substituent R$^1$, which is F, Cl, Br, Ohio or methoxy.

In some embodiments of the second aspect, R$_2$ is isopropyl or cyclopropyl, R$^3$ is hydrogen, ring A is a phenyl group which is substituted by one or two substituents R$^1$, which is F, Cl, Br, Ohio or methoxy. In other embodiments of the second aspect, R$_2$ is cyclopropyl, R$^3$ is hydrogen, ring A is a phenyl group which is substituted by one substituent R$^1$, which is F, Cl, or Br.

In some embodiments of the second aspect, ring A is an unsubstituted quinolinyl group. In other embodiments, ring A is a quinolinyl group substituted by fluoro or chloro. In still other embodiments, ring A is quinolin-4-yl or quinolin-5-yl.

In some embodiments of the second aspect, the chiral α-carbon atom attached to the imidazo[1,5-a]pyridine structure is in an S-configuration.

In some embodiments of the second aspect, ring A is attached to the 4-cyclohexyl structure in a trans-configuration.

In some embodiments of the second aspect, the compound of Formulas (IA) has the following configuration

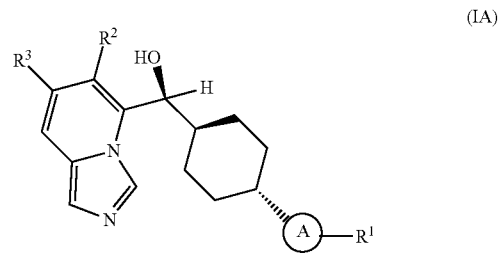

(IA)

In the third aspect, provided is 8-substituted imidazo[1,5-a]pyridines of Formula (IB):

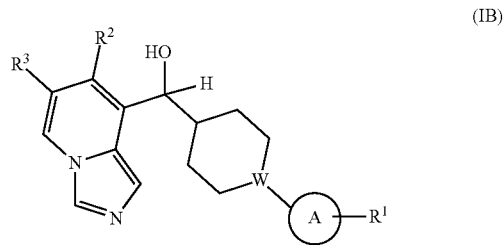

(IB)

wherein:
W is CH or N;
Ring A is a C$_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent R$^1$;
R$^1$, at each occurrence, is independently hydrogen, halogen, cyano, OR$^4$, NR$^4$R$^5$, COR$^4$, SO$_2$R$^4$, C(=O)OR$^4$, C(=O)NR$^4$R$^5$, C$_{1-8}$ alkyl, C$_{2-8}$ alkenyl, C$_{2-8}$ alkynyl, C$_{3-8}$ cycloalkyl, heterocyclyl, aryl, and heteroaryl, wherein said C$_{1-8}$ alkyl, C$_{2-8}$ alkenyl, C$_{2-8}$ alkynyl, C$_{3-8}$ cycloalkyl, heterocyclyl, aryl, and heteroaryl are each independently optionally substituted with at least one substituent R$^6$;
R$^2$ and R$^3$ are each independently selected from hydrogen, halogen, C$_{1-8}$ alkyl, C$_{2-8}$ alkenyl, C$_{2-8}$ alkynyl, C$_{3-8}$ cycloalkyl, C$_{1-8}$ haloalkyl, aryl, heterocyclyl, heteroaryl, —CN, —OR$^4$, and —SR$^4$, wherein said C$_{1-8}$ alkyl, C$_{2-8}$ alkenyl, C$_{2-8}$ alkynyl, C$_{3-8}$ cycloalkyl, C$_{1-8}$ haloalkyl, aryl, heterocyclyl, and heteroaryl are each independently optionally substituted with at least one substituted R$^6$, provided that R$^2$ and R$^3$ are not both hydrogen;
R$^4$ is independently selected from hydrogen, C$_{1-8}$ alkyl, C$_{2-8}$ alkenyl, C$_{2-8}$ alkynyl, C$_{1-8}$ haloalkyl, C$_{3-8}$ cycloalkyl, heterocyclyl, aryl, or heteroaryl, wherein said C$_{1-8}$ alkyl, C$_{2-8}$ alkenyl, C$_{2-8}$ alkynyl, C$_{1-8}$ haloalkyl, C$_{3-8}$ cycloalkyl, heterocyclyl, aryl, and heteroaryl are each independently optionally substituted with 1 or 2 substituent $R^6$;

$R^5$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;

$R^6$ is selected from hydrogen, halogen, $C_{1-4}$ haloalkyl, $C_{1-8}$ alkyl, $C_{2-8}$ alkenyl, $C_{3-6}$ cycloalkyl, aryl, heteroaryl, heterocyclyl, alkynyl, oxo, —$C_{1-4}$ alkyl-$NR^aR^b$, —CN, —$OR^a$, —$NR^aR^b$, —$COR^a$, —$CO_2R^a$, —$CONR^aR^b$, —$C(=NR^a)NR^bR^c$, nitro, —$NR^aCOR^b$, —$NR^aCONR^aR^b$, —$NR^aCO_2R^b$, —$SO_2R^1$, —$SO_2$aryl, —$NR^aSO_2NR^bR^c$, $NR^aSO_2R^b$, and —$NR^aSO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein $R^a$, $R^b$, and R are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl;

with the proviso that the compound is not (7-cyclopropylimidazo[1,5-a]pyridin-8-yl)(4-phenylcyclohexyl)methanol.

In some embodiments of the third aspect, the compound disclosed herein is 8-substituted imidazo[1,5-a]pyridines of Formula (IB):

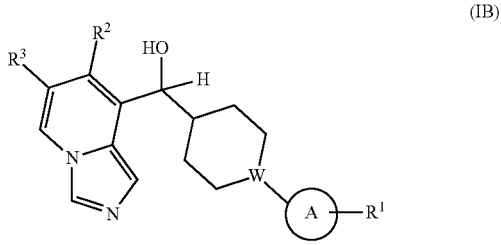

(IB)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $COR^4$, $C(=O)NR^4R^5$, $C_{1-8}$ alkyl, $C_{2-8}$ alkenyl, or $C_{2-8}$ s alkynyl, wherein said $C_{1-8}$ alkyl is optionally substituted with at least one substituent $R^6$;

$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, or $C_{1-8}$ haloalkyl, provided that $R^2$ and $R^3$ are not both hydrogen; $R^4$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, or heterocyclyl, wherein said $C_{1-8}$ alkyl is optionally substituted with 1 or 2 substituent $R^6$;

$R^5$ is independently selected from hydrogen;

$R^6$ is selected from hydrogen, halogen, or —$OR^a$, wherein $R^4$ is independently selected from H, $C_{1-4}$ haloalkyl, $C_{1-4}$ alkyl, $C_{2-4}$ alkenyl, or $C_{2-4}$ alkynyl;

with the proviso that the compound is not (7-cyclopropylimidazo[1,5-a]pyridin-8-yl)(4-phenylcyclohexyl)methanol.

In some embodiments of the third aspect, the compound disclosed herein is 8-substituted imidazo[1,5-a]pyridines of Formula (IB):

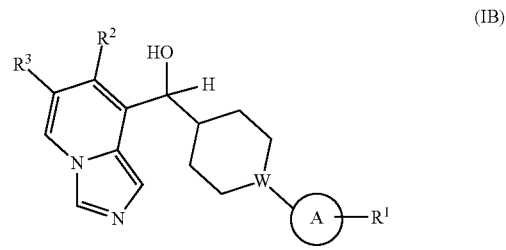

(IB)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;

$R^1$, at each occurrence, is independently hydrogen, halogen, cyano, $OR^4$, $COR^4$, $C(=O)NR^4R^5$, or $C_{1-8}$ alkyl, wherein said $C_{1-4}$ alkyl is optionally substituted with at least one substituent $R^6$;

$R^2$ and $R^3$ are each independently selected from hydrogen, halogen, $C_{1-8}$ alkyl, or $C_{3-8}$ cycloalkyl, provided that $R^2$ and $R^3$ are not both hydrogen;

$R^4$ is independently selected from hydrogen, $C_{1-8}$ alkyl, $C_{1-8}$ haloalkyl, $C_{3-8}$ cycloalkyl, or heterocyclyl, wherein said $C_{1-8}$ alkyl is optionally substituted with 1 or 2 substituent $R^6$;

$R^5$ is independently selected from hydrogen;

$R^6$ is selected from hydrogen, halogen, or —$OR^a$, wherein $R^a$ is independently selected from H, $C_{1-4}$ haloalkyl, or $C_{1-4}$ alkyl;

with the proviso that the compound is not (7-cyclopropylimidazo[1,5-a]pyridin-8-yl)(4-phenylcyclohexyl)methanol.

In some embodiments of the third aspect, the compound disclosed herein is 8-substituted imidazo[1,5-a]pyridines of Formula (IB):

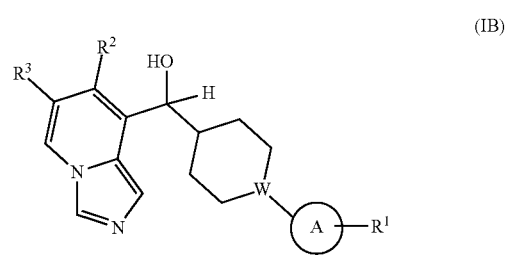

(IB)

or a stereoisomer thereof, or a pharmaceutically acceptable salt thereof, wherein:

W is CH or N;

Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members: Ring A is substituted with at least one substituent $R^1$;

$R^1$, at each occurrence, is independently hydrogen, halogen, cyano, $OR^4$, $COR^4$, $C(=O)NR^4R^5$, $C_{1-8}$ alkyl, or $C_{1-8}$ haloalkyl;

$R^2$ and $R^3$ are each independently selected from hydrogen, halogen, $C_{1-8}$ alkyl, or $C_{3-8}$ cycloalkyl, provided that $R^2$ and $R^3$ are not both hydrogen;

$R^4$ is independently selected from hydrogen, $C_{1-8}$ alkyl, $C_{1-8}$ haloalkyl, $C_{3-8}$ cycloalkyl, or heterocyclyl, wherein said $C_{1-8}$ alkyl is optionally substituted with —$OC_{1-4}$alkyl;

$R^5$ is independently selected from hydrogen;

with the proviso that the compound is not (7-cyclopropylimidazo[1,5-a]pyridin-8-yl)(4-phenylcyclohexyl)methanol.

In some embodiments of the third aspect, ring A is a $C_{3-8}$ cycloalkyl ring and W is N.

In some embodiments of the third aspect, ring A is phenyl or naphthalenyl ring.

In some embodiments of the third aspect, ring A is a monocyclic or bicyclic aromatic heterocyclic ring having 5- to 10-ring members comprising 1, 2, 3, or 4 heteroatoms selected from O, S, and N.

In some embodiments of the third aspect, ring A is a monocyclic aromatic heterocyclic ring having 5- to 6-ring members comprising 1 or 2 heteroatoms selected from O, S, and N. In other embodiments, ring A is pyridinyl, furanyl, pyrazinyl, pyrimidinyl, pyridazinyl, pyrrolyl, thienyl, triazinyl, or pyrazolyl. In some preferred embodiments, ring A is pyridinyl.

In some embodiments of the third aspect, ring A is a bicyclic aromatic heterocyclic ring having 8- to 10-ring members comprising 1 or 2 or 3 heteroatoms selected from O, S, and N. In other embodiments, ring A is cinnolinyl, benzothienyl, benzofuryl, benzoimidazolyl, indolyl, isoindolyl, indolinyl, phthalazinyl, quinolinyl, isoquinolinyl, pyrrolopyridinyl, pyrazolopyridinyl, benzodioxolyl, benzoxazolyl, pteridinyl, purinyl, benzofurazanyl, benzothiophenyl, benzothiazolyl, benzoxazolyl, quinazolinyl, quinoxalinyl, naphthyridinyl, furopyridinyl, benzothiazolyl, or indazolyl. In some preferred embodiments, ring A is quinolinyl (such as quinolin-4-yl, quinolin-5-yl, quinolin-6-yl, or quinolin-8-yl) or benzodioxolyl (such as benzo[d][1,3]dioxol-5-yl).

In some embodiments of the third aspect, $R_2$ is halogen, $C_{1-4}$alkyl, $C_{1-4}$haloalkyl, or $C_{3-6}$ cycloalkyl, and $R^3$ is hydrogen. In some preferred embodiments, $R_2$ is halogen, $C_{1-3}$alkyl, or $C_{3-4}$cycloalkyl, and $R^3$ is hydrogen. In some further preferred embodiments, $R_2$ is isopropyl or cyclopropyl, and $R^3$ is hydrogen.

In some embodiments of the third aspect, $R_2$ is hydrogen, and $R^3$ is halogen, $C_1$-4alkyl, $C_{1-4}$haloalkyl, or $C_{3-6}$cycloalkyl.

In some embodiments of the third aspect, ring A is a phenyl group, which is optionally substituted by one or two or three substituents $R^1$, which is halogen such as F, Cl or Br, —Ohio, $C_{1-6}$ alkyl, $C_{1-6}$haloalkyl, $C_{1-6}$alkyl-O—, $C_{1-6}$alkyl-O—$C_{1-6}$-alkyl-O—, or —$OC_{1-6}$haloalkyl. In other embodiments, ring A is a phenyl group, which is optionally substituted by one or two or three substituents $R^1$, which is halogen such as F, $C_1$ or Br, —Ohio, $C_{1-4}$alkyl, $C_{1-4}$haloalkyl, $C_{1-4}$alkyl-O—, $C_{1-4}$alkyl-O—$C_{1-4}$alkyl-O—, —$OC_{1-4}$haloalkyl or —O-(4- to 6-membered heterocyclyl comprising one oxygen heteroatom). In some preferred embodiments, ring A is a phenyl group, which is optionally substituted by one or two or three substituents $R^1$, which is halogen such as F, Cl or Br, —Ohio, methyl, $CF_3$, —$OCF_3$, methoxy, methoxyethoxy, oxetan-3-yloxy or (tetrahydro-2H-pyran-4-yl)oxy. In some yet preferred embodiments, ring A is a phenyl group which is substituted by one substituent $R^1$, which is F, Cl, Br, Ohio or methoxy.

In some embodiments of the second aspect, $R_2$ is isopropyl or cyclopropyl, $R^3$ is hydrogen, ring A is a phenyl group which is substituted by one or two substituents $R^1$, which is F, Cl, Br, Ohio or methoxy. In other embodiments of the second aspect, $R_2$ is cyclopropyl, $R^3$ is hydrogen, ring A is a phenyl group which is substituted by one substituent $R^1$, which is F, Cl, or Br.

In some embodiments of the third aspect, ring A is an unsubstituted quinolinyl group. In other embodiments, ring A is a quinolinyl group substituted by fluoro or chloro. In still other embodiments, ring A is quinolin-4-yl or quinolin-5-yl.

In some embodiments of the third aspect, the chiral α-carbon atom attached to the imidazo[1,5-a]pyridine structure is in an S-configuration.

In some embodiments of the third aspect, ring A is attached to the 4-cyclohexyl structure in a trans-configuration.

In some embodiments of the third aspect, the compounds of Formula (IB) has the following configuration

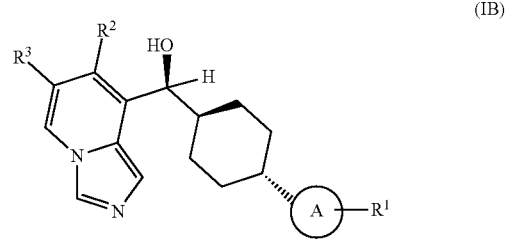

(IB)

Also provided herein is a compound selected from the following compounds of Table A, or a stereoisomer thereof, or a pharmaceutically acceptable salt thereof:

TABLE A

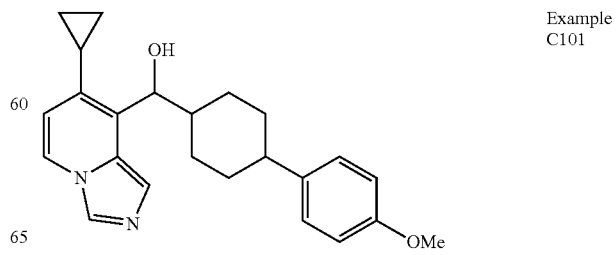

Example C101

TABLE A-continued
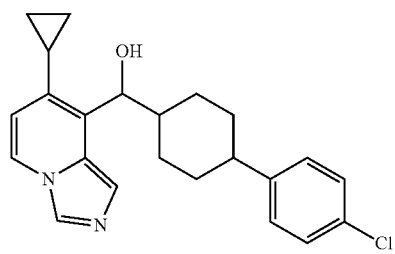 [SMILES: OC(c1c(C2CC2)ccn2cncc12)C1CCC(c2ccc(Cl)cc2)CC1] Example C102
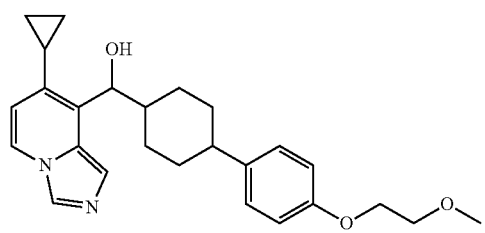 [SMILES: COCCOc1ccc(C2CCC(C(O)c3c(C4CC4)ccn4cncc34)CC2)cc1] Example C103
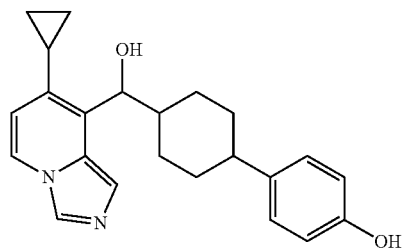 Example C104
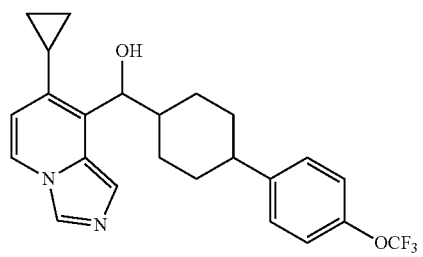 [SMILES: OC(c1c(C2CC2)ccn2cncc12)C1CCC(c2ccc(OC(F)(F)F)cc2)CC1] Example C105
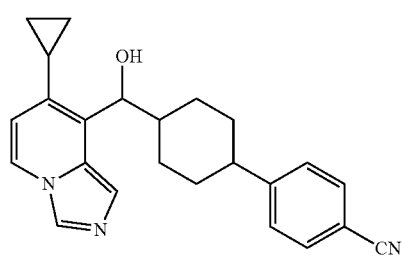 Example C106
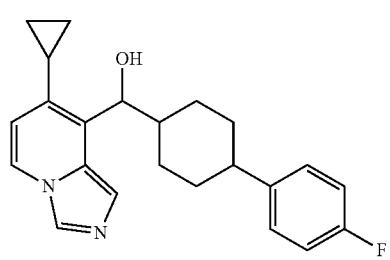 [SMILES: OC(c1c(C2CC2)ccn2cncc12)C1CCC(c2ccc(F)cc2)CC1] Example C107
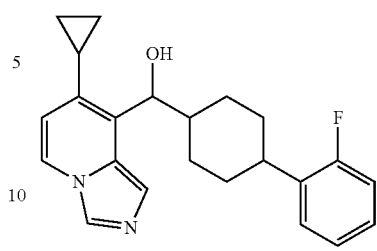 Example C108
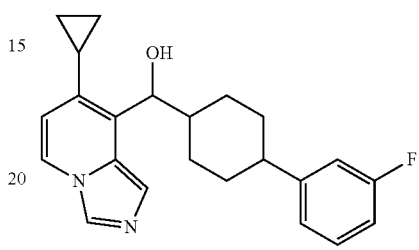 Example C109
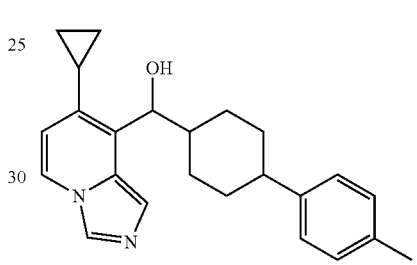 Example C110
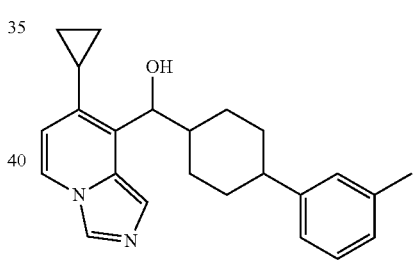 Example C111
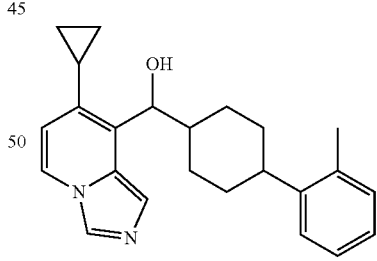 Example C112
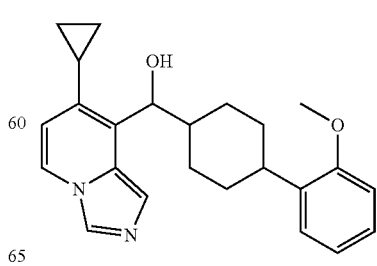 Example C113

TABLE A-continued
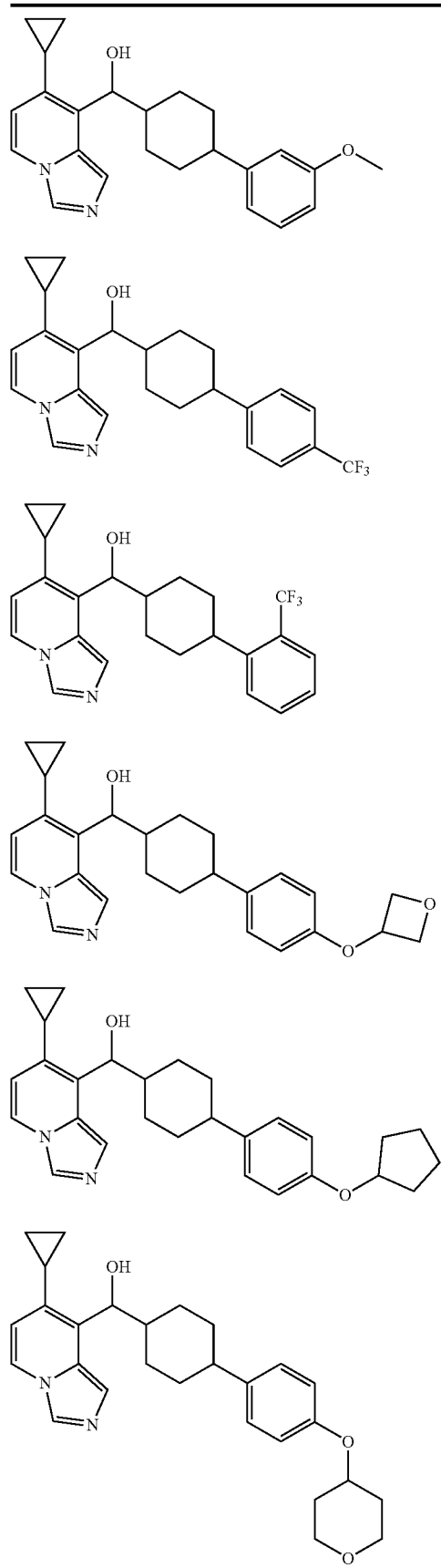
| | |
|---|---|
| | Example C114 |
| | Example C115 |
| | Example C116 |
| | Example C117 |
| | Example C118 |
| | Example C119 |
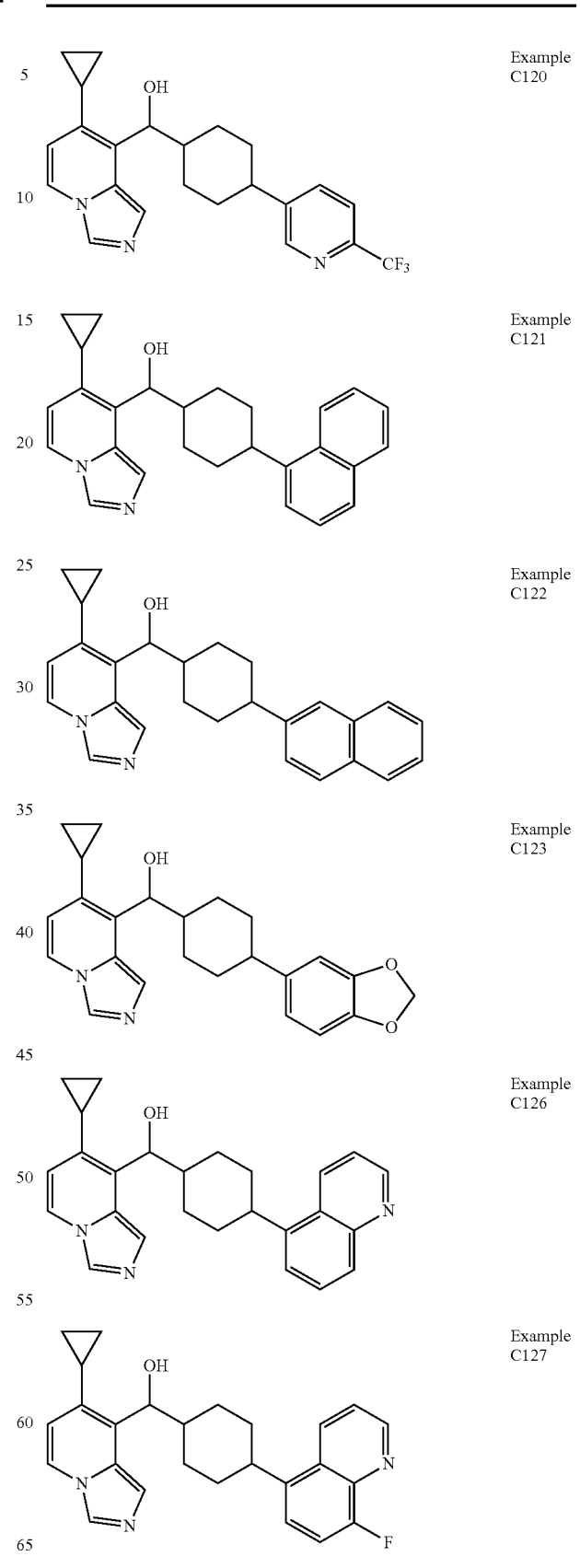
| | |
|---|---|
| | Example C120 |
| | Example C121 |
| | Example C122 |
| | Example C123 |
| | Example C126 |
| | Example C127 |

TABLE A-continued
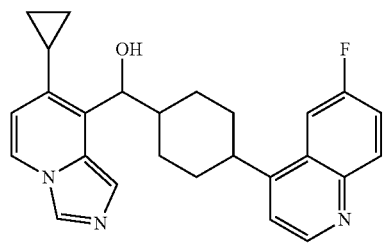 [SMILES: OC(c1c(C2CC2)ccn2cncc12)C1CCC(c2ccnc3ccc(F)cc23)CC1]
Example C128
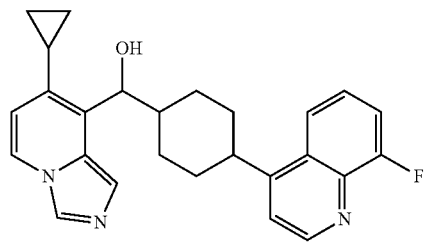 [SMILES: OC(c1c(C2CC2)ccn2cncc12)C1CCC(c2ccnc3c(F)cccc23)CC1]
Example C129
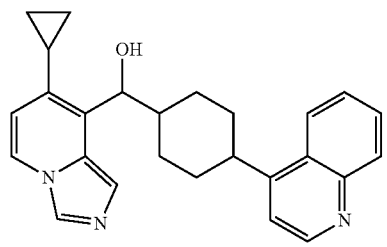 [SMILES: OC(c1c(C2CC2)ccn2cncc12)C1CCC(c2ccnc3ccccc23)CC1]
Example C130
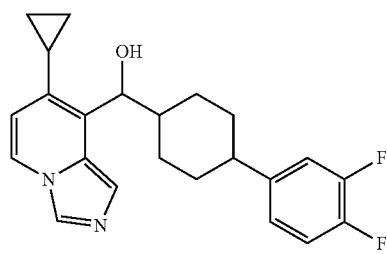
Example C131
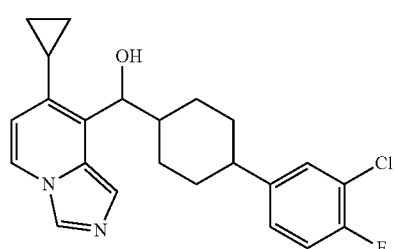
Example C132
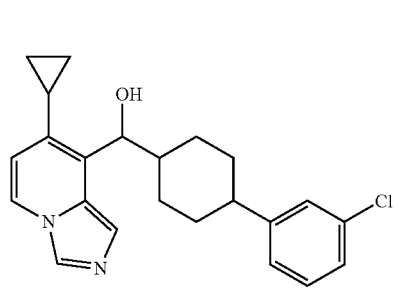 [SMILES: OC(c1c(C2CC2)ccn2cncc12)C1CCC(c2cccc(Cl)c2)CC1]
Example C133
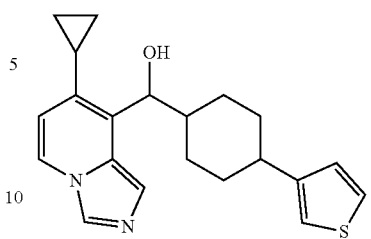
Example C134
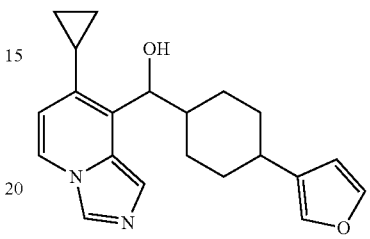
Example C135
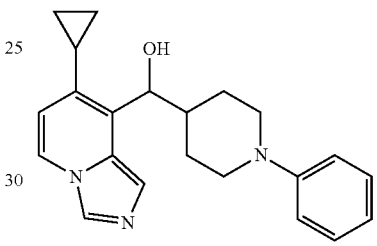
Example C136
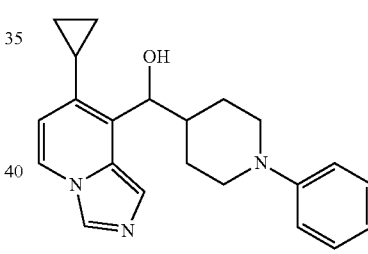
Example C137
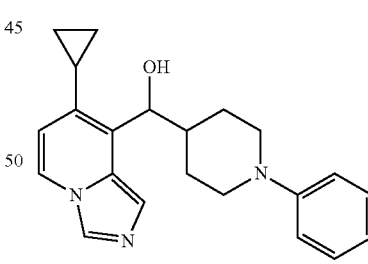
Example C138
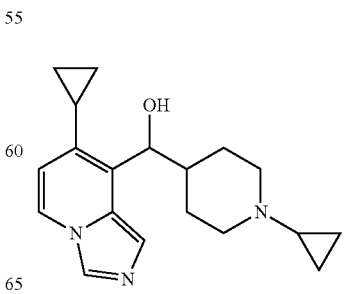
Example C139

TABLE A-continued
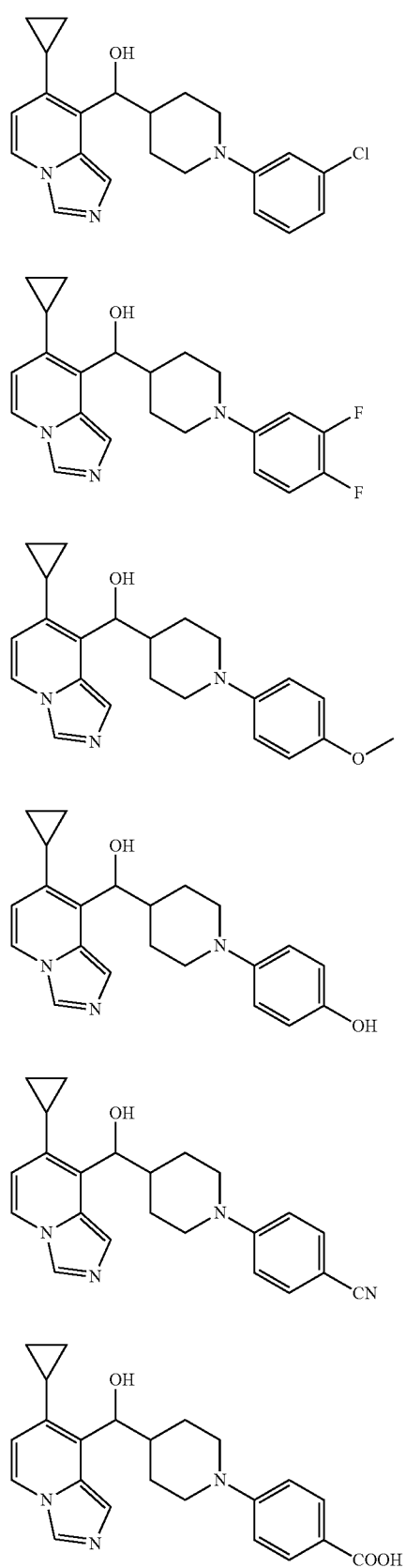
Example C140
Example C141
Example C142
Example C143
Example C144
Example C145
TABLE A-continued
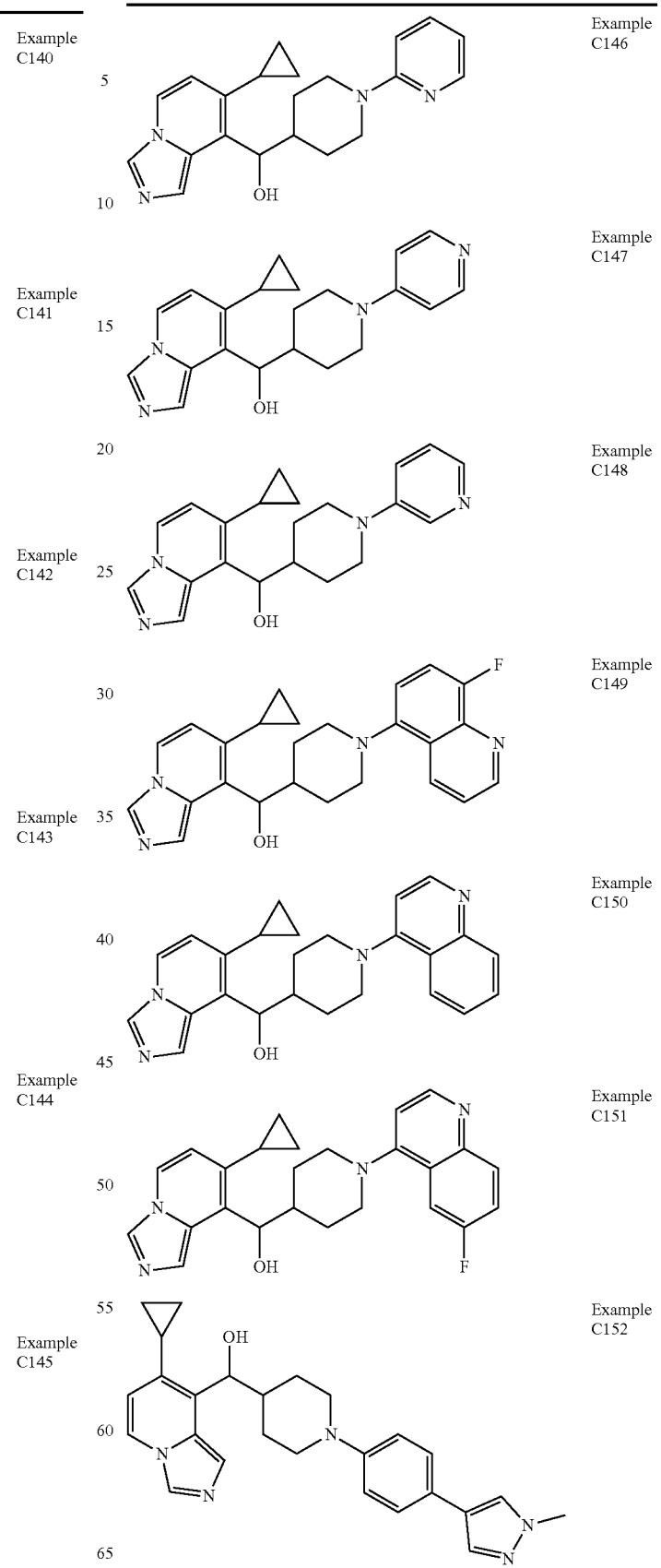
Example C146
Example C147
Example C148
Example C149
Example C150
Example C151
Example C152

TABLE A-continued
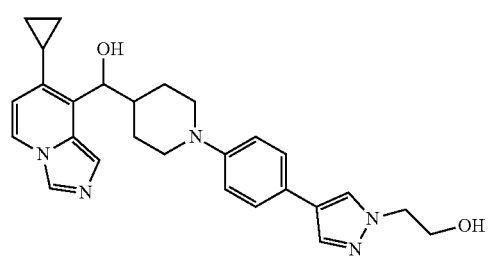 [SMILES: OCCn1cc(-c2ccc(N3CCC(C(O)c4c(C5CC5)ccn5cncc45)CC3)cc2)cn1] Example C153
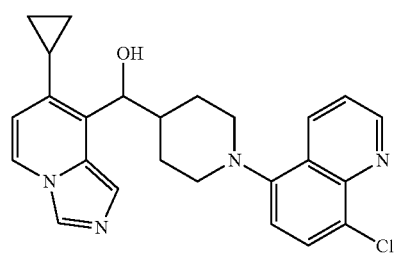 [SMILES: OC(c1c(C2CC2)ccn2cncc12)C1CCN(c2ccc(Cl)c3ncccc23)CC1] Example C154
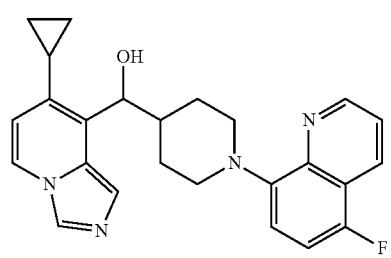 [SMILES: OC(c1c(C2CC2)ccn2cncc12)C1CCN(c2ccc(F)c3cccnc23)CC1] Example C155
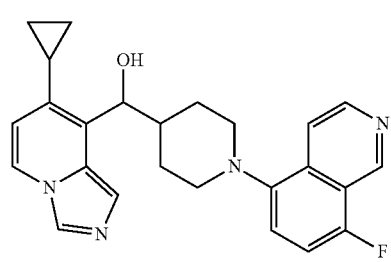 [SMILES: OC(c1c(C2CC2)ccn2cncc12)C1CCN(c2ccc(F)c3cnccc23)CC1] Example C156
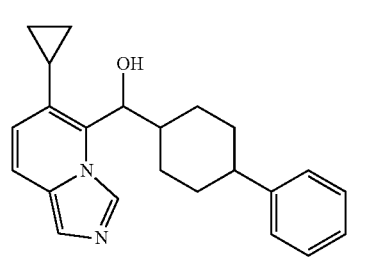 [SMILES: OC(c1c(C2CC2)ccc2cncn12)C1CCC(c2ccccc2)CC1] Example D101
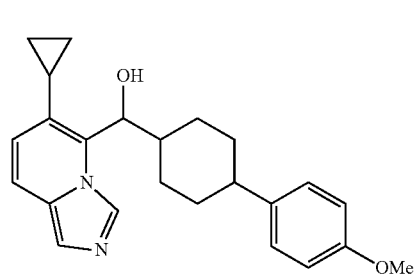 [SMILES: COc1ccc(C2CCC(C(O)c3c(C4CC4)ccc4cncn34)CC2)cc1] Example D102
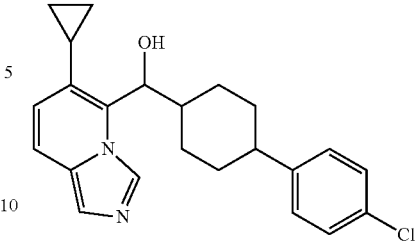 Example D103
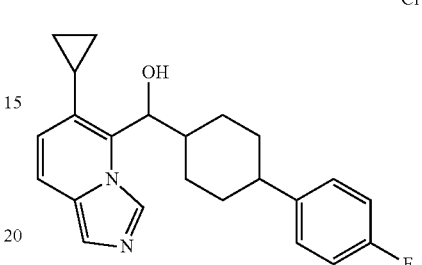 Example D104
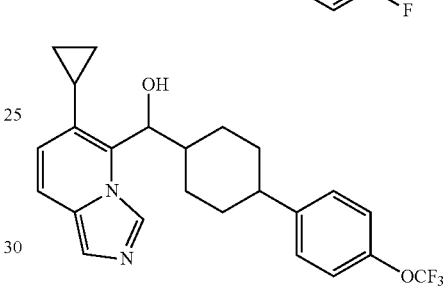 Example D105
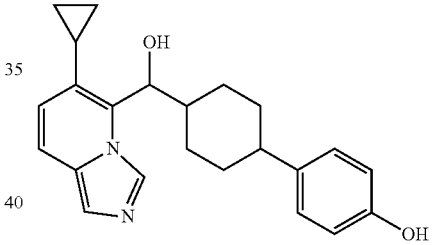 Example D106
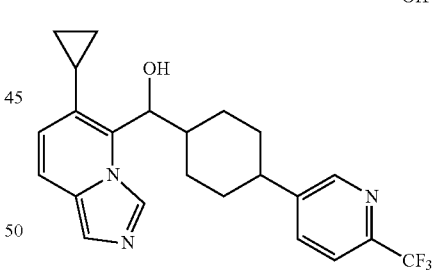 Example D107
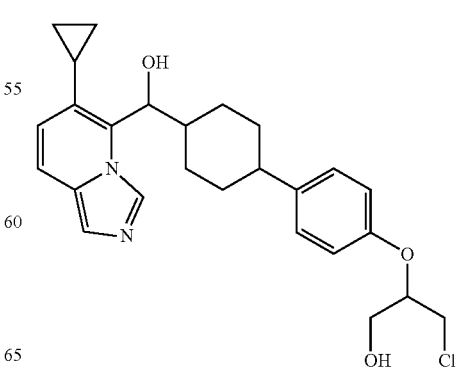 Example D108

TABLE A-continued
| | |
|---|---|
| 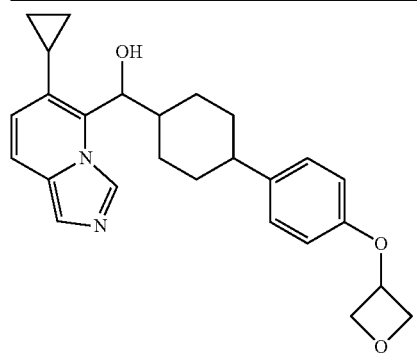 | Example D109 |
| 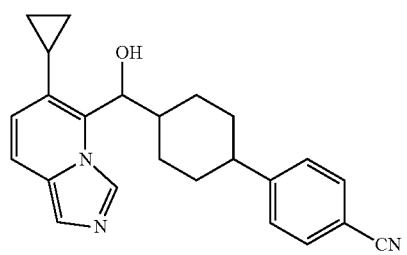 [SMILES: N#Cc1ccc(C2CCC(C(O)c3c(C4CC4)ccc4cncn34)CC2)cc1] | Example D110 |
| 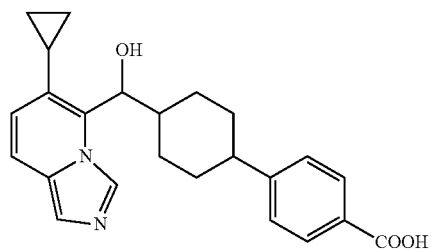 [SMILES: O=C(O)c1ccc(C2CCC(C(O)c3c(C4CC4)ccc4cncn34)CC2)cc1] | Example D111 |
| 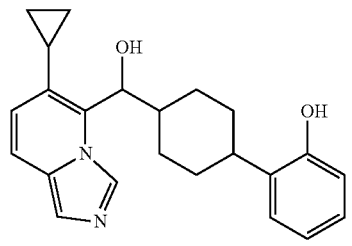 [SMILES: Oc1ccccc1C1CCC(C(O)c2c(C3CC3)ccc3cncn23)CC1] | Example D112 |
| 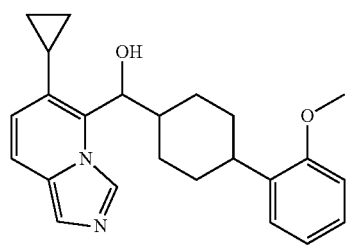 [SMILES: COc1ccccc1C1CCC(C(O)c2c(C3CC3)ccc3cncn23)CC1] | Example D113 |
TABLE A-continued
| | |
|---|---|
| 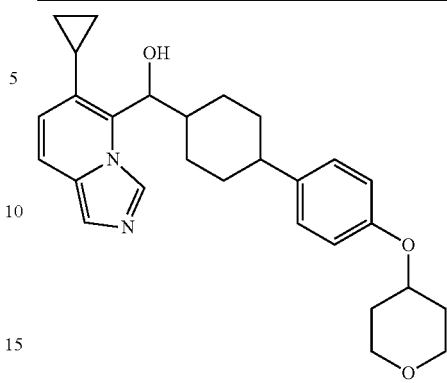 | Example D114 |
| 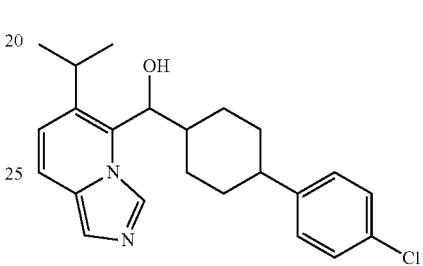 | Example D115 |
| 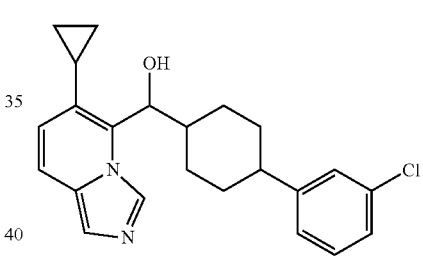 | Example D116 |
| 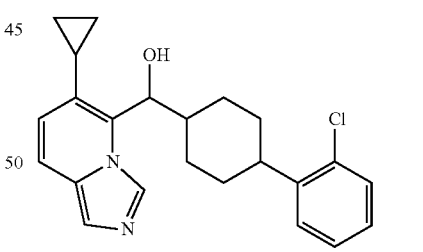 | Example D117 |
| 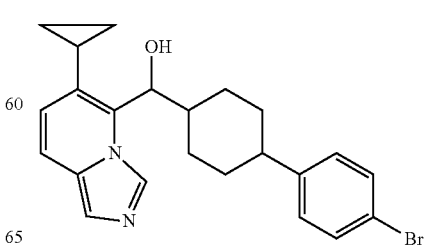 | Example D118 |

TABLE A-continued
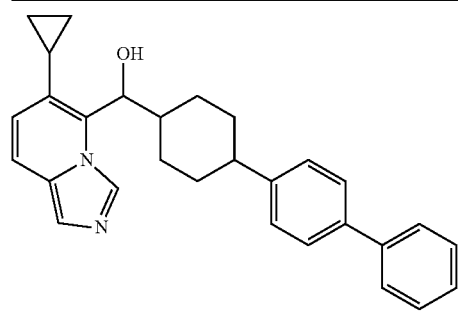 Example D119
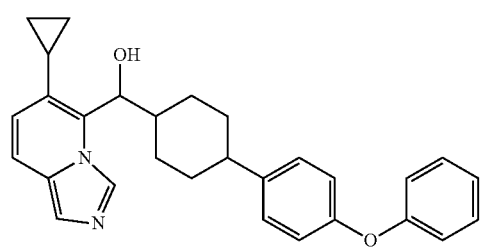 [SMILES: OC(c1c(C2CC2)ccc2cncn12)C1CCC(c2ccc(Oc3ccccc3)cc2)CC1] Example D120
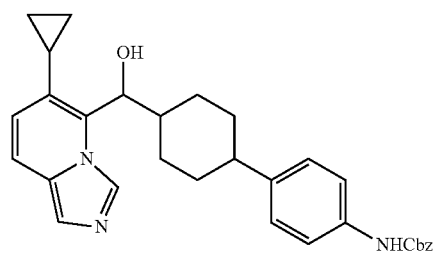 [SMILES: O=C(Nc1ccc(C2CCC(C(O)c3c(C4CC4)ccc4cncn34)CC2)cc1)OCc1ccccc1] Example D121
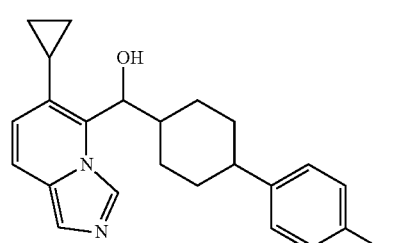 Example D122
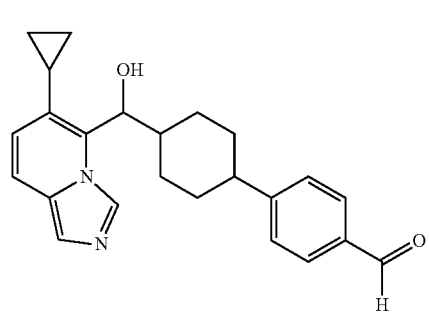 [SMILES: O=Cc1ccc(C2CCC(C(O)c3c(C4CC4)ccc4cncn34)CC2)cc1] Example D123
TABLE A-continued
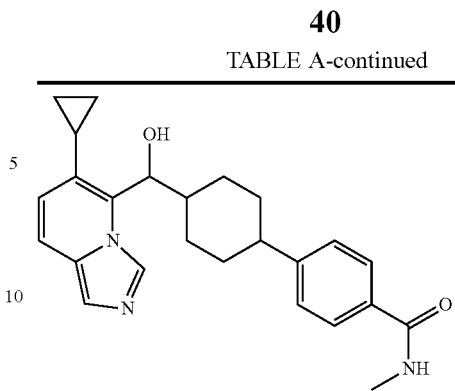 Example D124
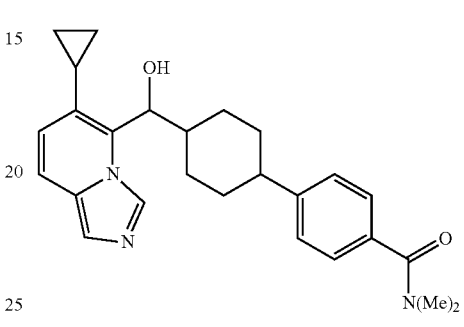 Example D125
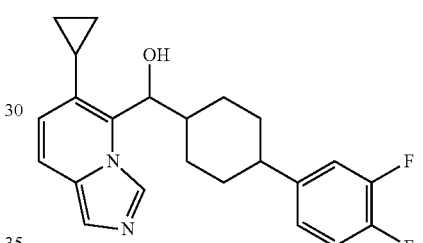 Example D126
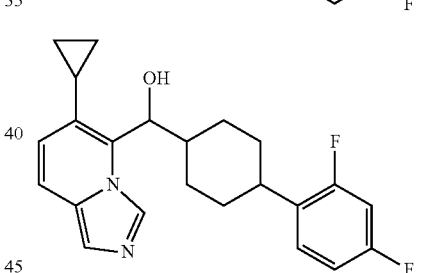 Example D127
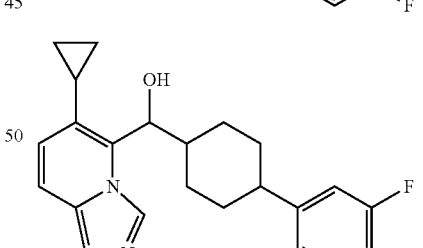 Example D128
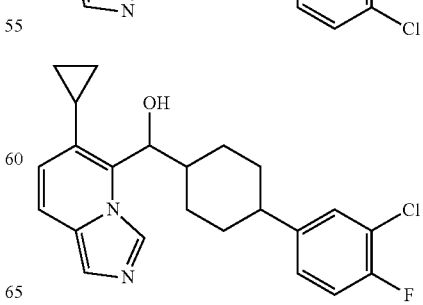 Example D129

TABLE A-continued
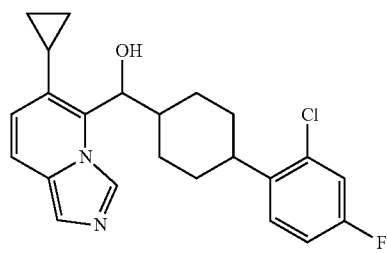 [SMILES: OC(c1c(C2CC2)ccc2cncn12)C1CCC(c2ccc(F)cc2Cl)CC1] Example D130
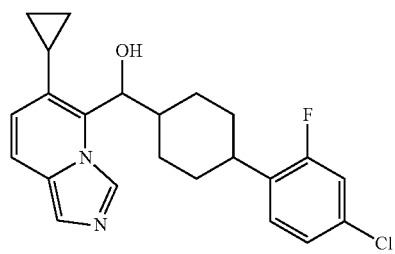 [SMILES: OC(c1c(C2CC2)ccc2cncn12)C1CCC(c2ccc(Cl)cc2F)CC1] Example D131
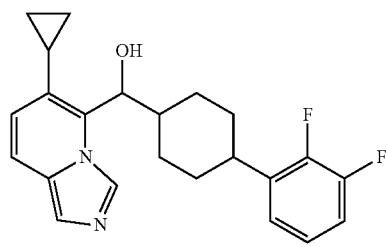 Example D132
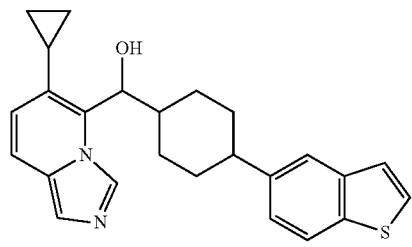 [SMILES: OC(c1c(C2CC2)ccc2cncn12)C1CCC(c2ccc3sccc3c2)CC1] Example D133
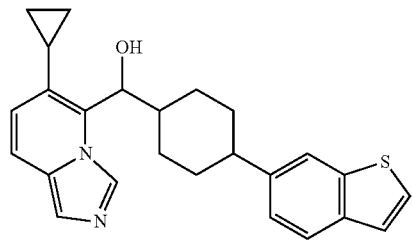 [SMILES: OC(c1c(C2CC2)ccc2cncn12)C1CCC(c2ccc3ccsc3c2)CC1] Example D134
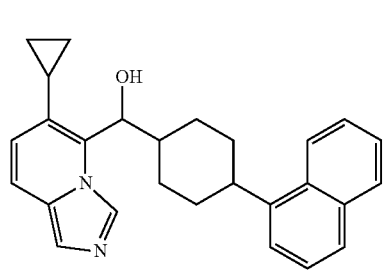 [SMILES: OC(c1c(C2CC2)ccc2cncn12)C1CCC(c2cccc3ccccc23)CC1] Example D135
TABLE A-continued
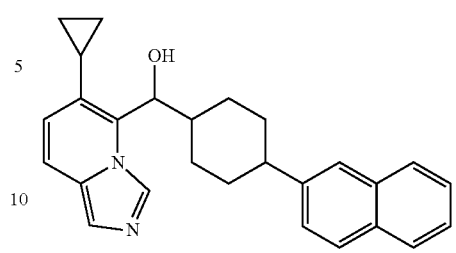 Example D136
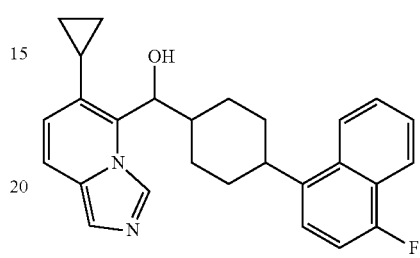 Example D137
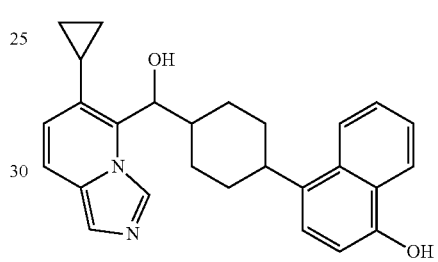 Example D138
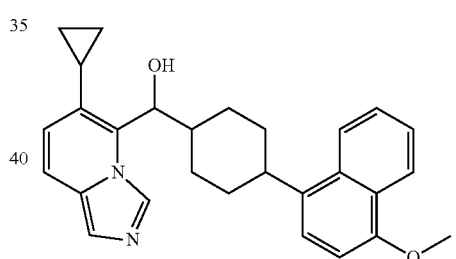 Example D139
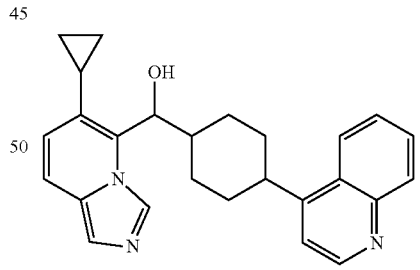 Example D140
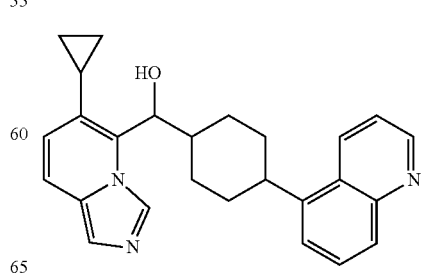 Example D141

TABLE A-continued
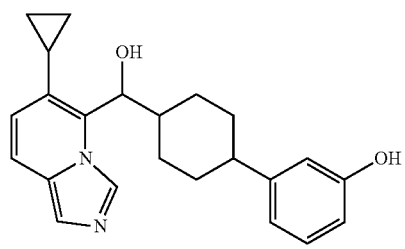 [SMILES: Oc1cccc(C2CCC(C(O)c3c(C4CC4)ccc4cncn34)CC2)c1] Example D142
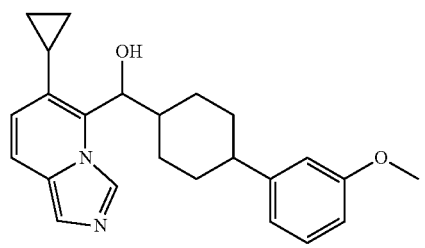 [SMILES: COc1cccc(C2CCC(C(O)c3c(C4CC4)ccc4cncn34)CC2)c1] Example D143
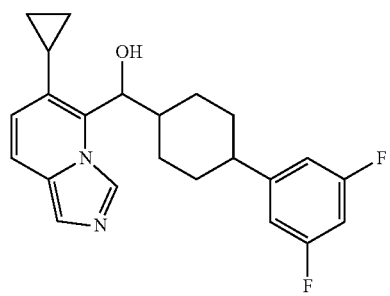 [SMILES: OC(c1c(C2CC2)ccc2cncn12)C1CCC(c2cc(F)cc(F)c2)CC1] Example D144
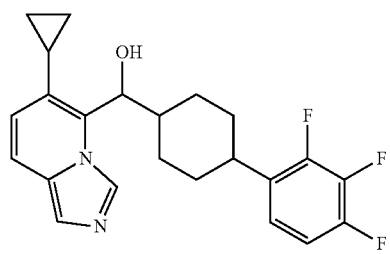 [SMILES: OC(c1c(C2CC2)ccc2cncn12)C1CCC(c2ccc(F)c(F)c2F)CC1] Example D145
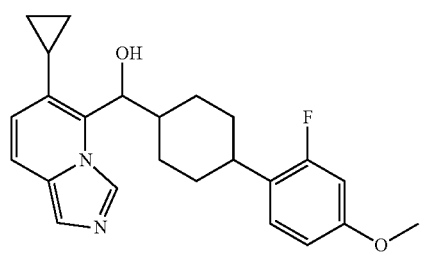 [SMILES: COc1ccc(C2CCC(C(O)c3c(C4CC4)ccc4cncn34)CC2)c(F)c1] Example D146
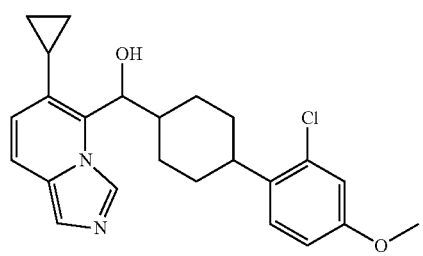 [SMILES: COc1ccc(C2CCC(C(O)c3c(C4CC4)ccc4cncn34)CC2)c(Cl)c1] Example D147
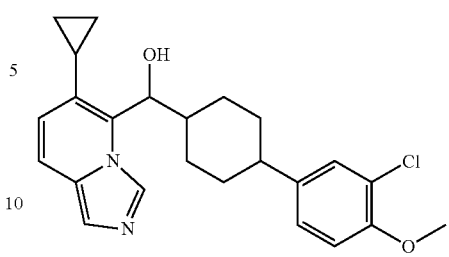 Example D148
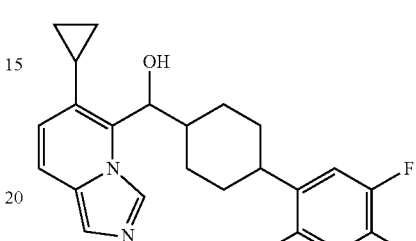 Example D149
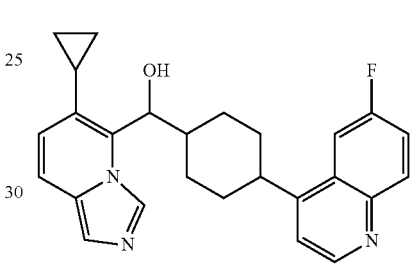 Example D150
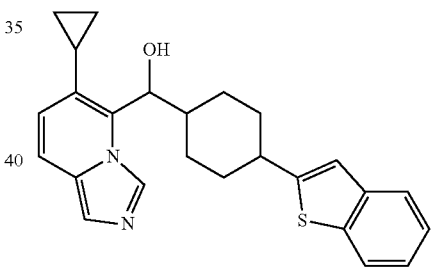 Example D154
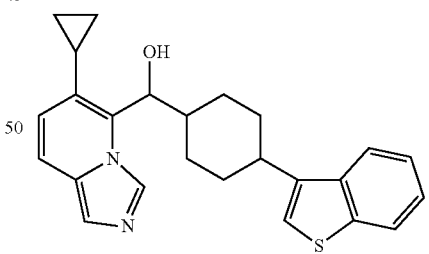 Example D155
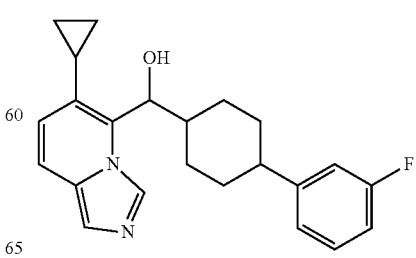 Example D156

TABLE A-continued
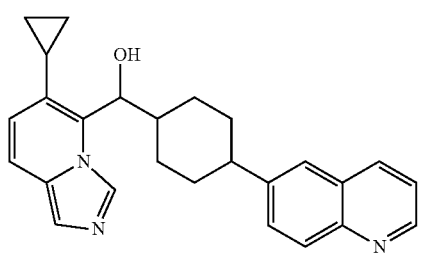 [SMILES: OC(c1c(C2CC2)ccc2cncn12)C1CCC(c2ccc3ncccc3c2)CC1] Example D157
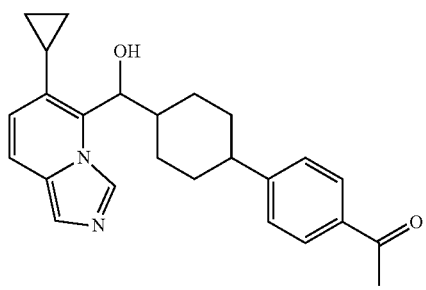 [SMILES: CC(=O)c1ccc(C2CCC(C(O)c3c(C4CC4)ccc4cncn34)CC2)cc1] Example D158
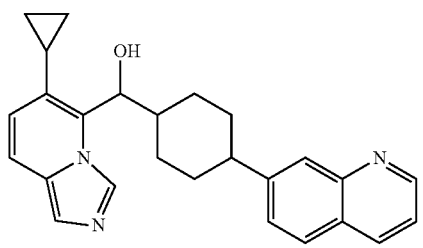 [SMILES: OC(c1c(C2CC2)ccc2cncn12)C1CCC(c2ccc3cccnc3c2)CC1] Example D161
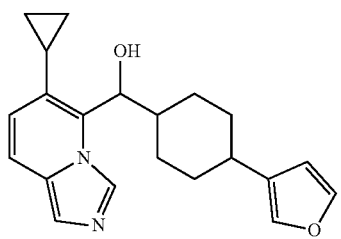 [SMILES: OC(c1c(C2CC2)ccc2cncn12)C1CCC(c2ccoc2)CC1] Example D162
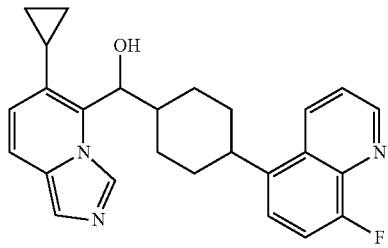 [SMILES: OC(c1c(C2CC2)ccc2cncn12)C1CCC(c2ccc(F)c3ncccc23)CC1] Example D163
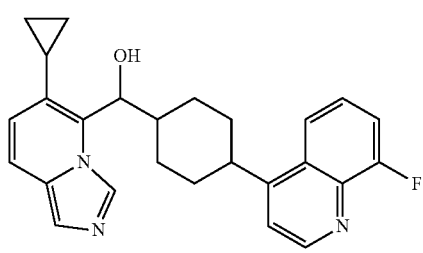 [SMILES: OC(c1c(C2CC2)ccc2cncn12)C1CCC(c2ccnc3c(F)cccc23)CC1] Example D164
TABLE A-continued
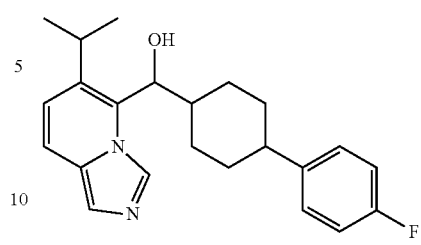 Example D166
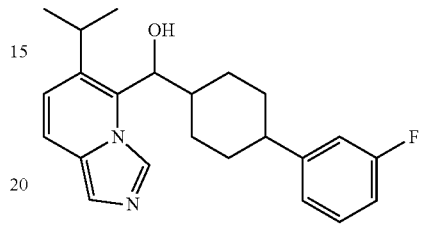 Example D167
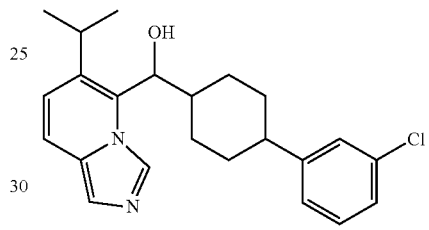 Example D168
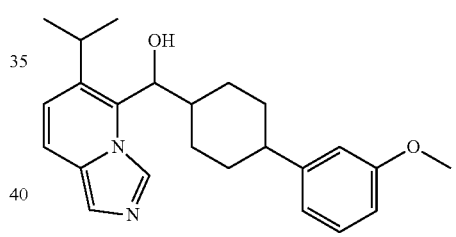 Example D169
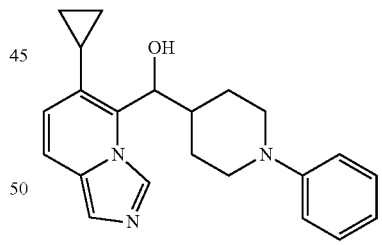 Example D170
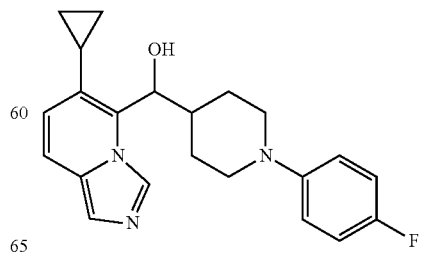 Example D171

TABLE A-continued
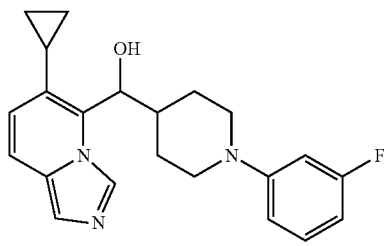 [SMILES: OC(c1c(C2CC2)ccc2cncn12)C1CCN(c2cccc(F)c2)CC1]
Example D172
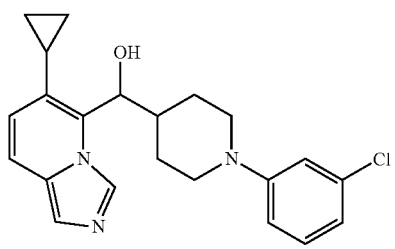 [SMILES: OC(c1c(C2CC2)ccc2cncn12)C1CCN(c2cccc(Cl)c2)CC1]
Example D173
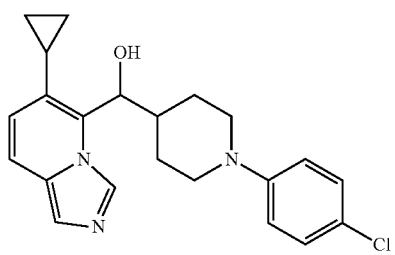 [SMILES: OC(c1c(C2CC2)ccc2cncn12)C1CCN(c2ccc(Cl)cc2)CC1]
Example D174
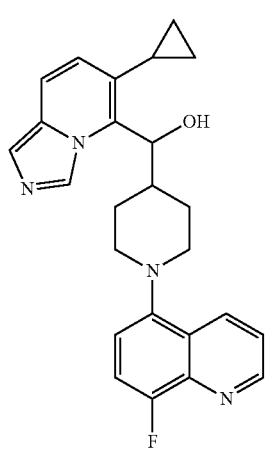 [SMILES: OC(c1c(C2CC2)ccc2cncn12)C1CCN(c2ccc(F)c3ncccc23)CC1]
Example D175
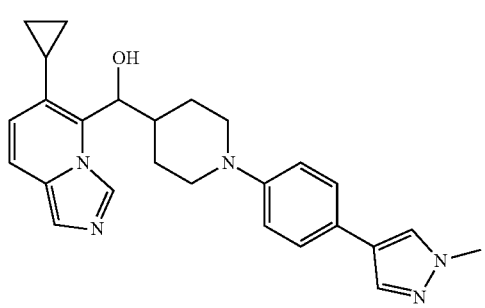 [SMILES: Cn1cc(-c2ccc(N3CCC(C(O)c4c(C5CC5)ccc5cncn45)CC3)cc2)cn1]
Example D176
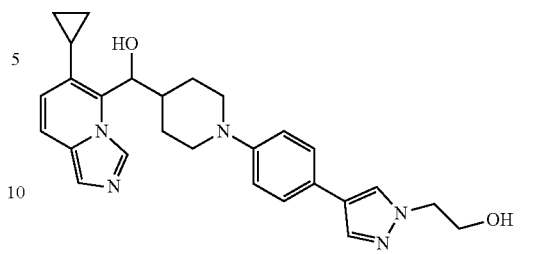
Example D177
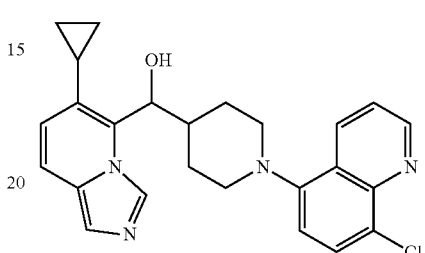
Example D178
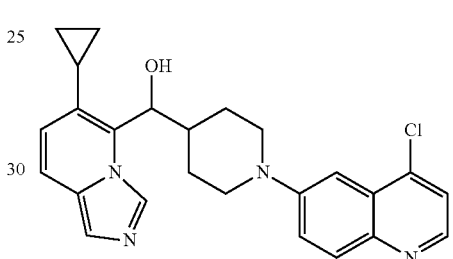
Example D179
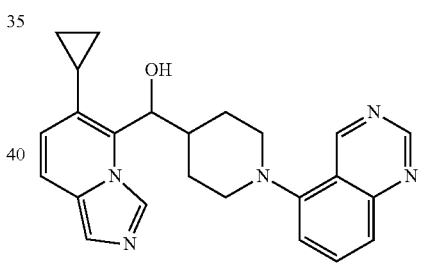
Example D180
Example D181
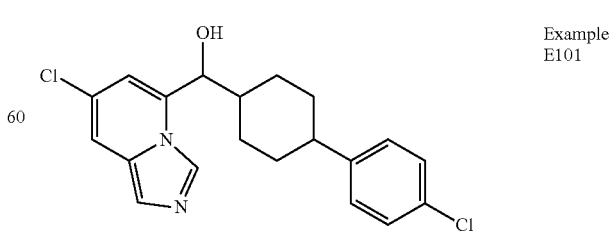
Example E101

TABLE A-continued
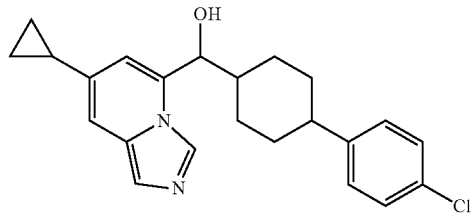 [SMILES: OC(c1cc(C2CC2)cc2cncn12)C1CCC(c2ccc(Cl)cc2)CC1]
Example E102
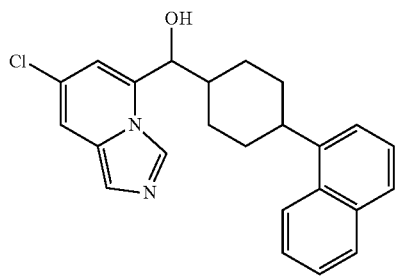 [SMILES: OC(c1cc(Cl)cc2cncn12)C1CCC(c2cccc3ccccc23)CC1]
Example E103
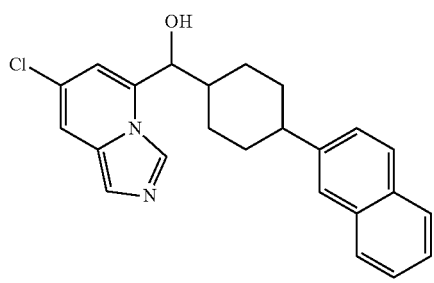 [SMILES: OC(c1cc(Cl)cc2cncn12)C1CCC(c2ccc3ccccc3c2)CC1]
Example E104
Also provided herein is a compound selected from the following compounds of Table B showing the following stereochemistry:
TABLE B
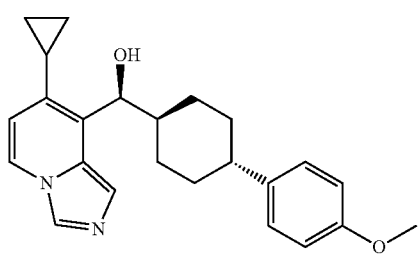 [SMILES: COc1ccc([C@H]2CC[C@H]([C@H](O)c3c(C4CC4)ccn4cncc34)CC2)cc1]
Example C101a
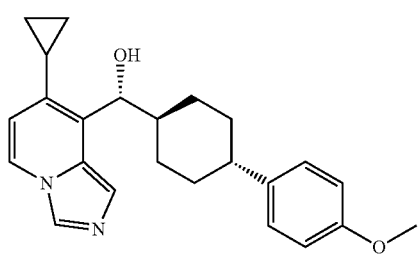 [SMILES: COc1ccc([C@H]2CC[C@H]([C@@H](O)c3c(C4CC4)ccn4cncc34)CC2)cc1]
Example C101b
TABLE B-continued
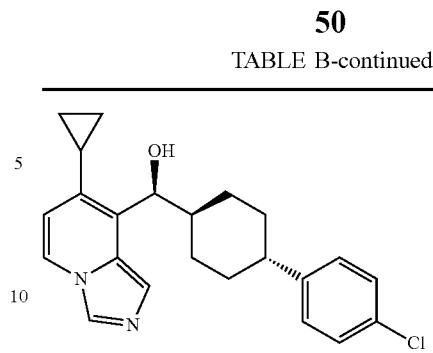
Example C102a
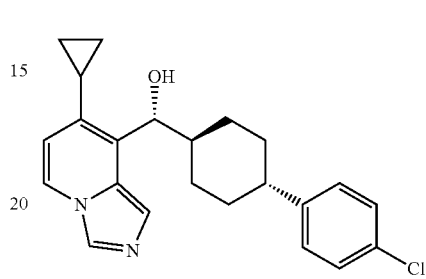
Example C102b
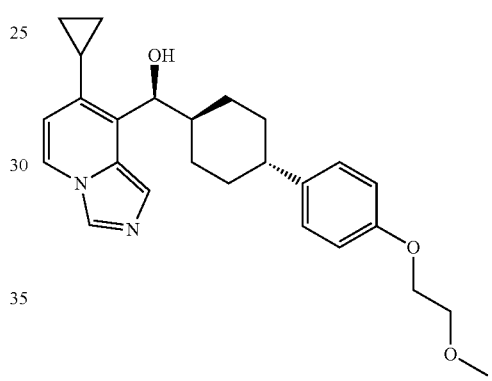
Example C103a
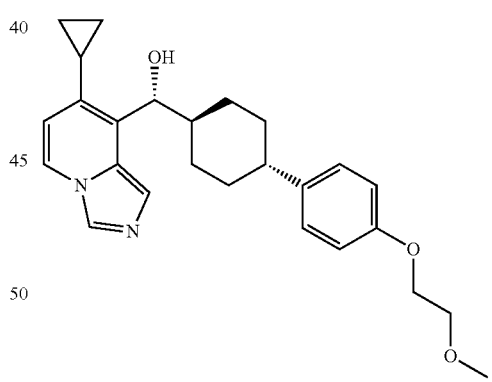
Example C103b
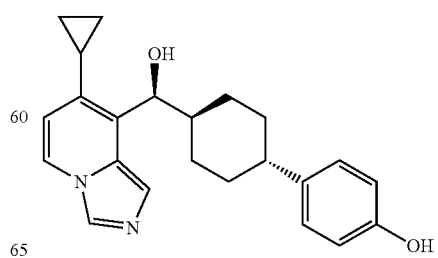
Example C104a TABLE B-continued
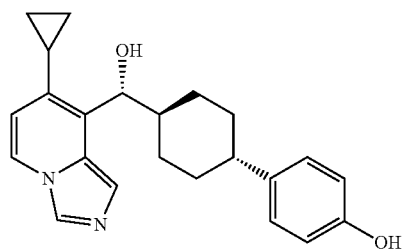 [SMILES: Oc1ccc([C@H]2CC[C@H]([C@@H](O)c3c(C4CC4)ccn4cncc34)CC2)cc1] Example C104b
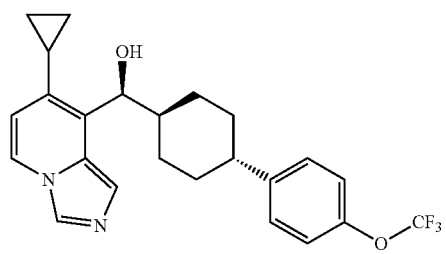 [SMILES: O[C@H](c1c(C2CC2)ccn2cncc12)[C@H]1CC[C@H](c2ccc(OC(F)(F)F)cc2)CC1] Example C105a
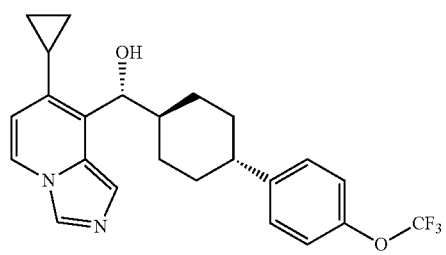 [SMILES: O[C@@H](c1c(C2CC2)ccn2cncc12)[C@H]1CC[C@H](c2ccc(OC(F)(F)F)cc2)CC1] Example C105b
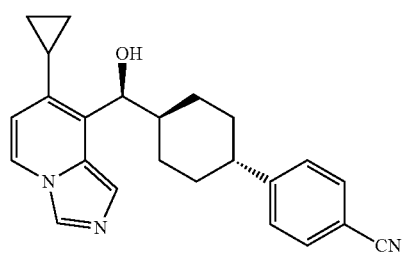 [SMILES: N#Cc1ccc([C@H]2CC[C@H]([C@H](O)c3c(C4CC4)ccn4cncc34)CC2)cc1] Example C106a
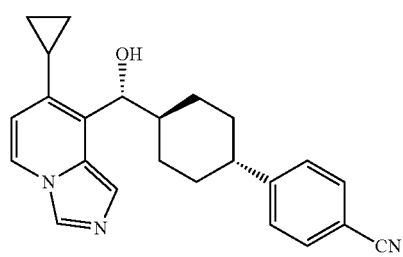 [SMILES: N#Cc1ccc([C@H]2CC[C@H]([C@@H](O)c3c(C4CC4)ccn4cncc34)CC2)cc1] Example C106b
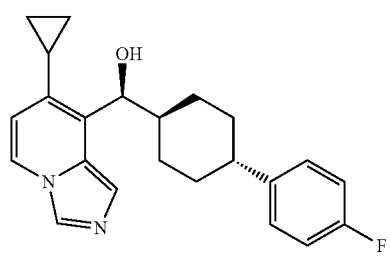 [SMILES: O[C@H](c1c(C2CC2)ccn2cncc12)[C@H]1CC[C@H](c2ccc(F)cc2)CC1] Example C107a
TABLE B-continued
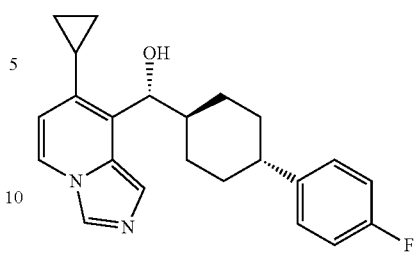 Example C107b
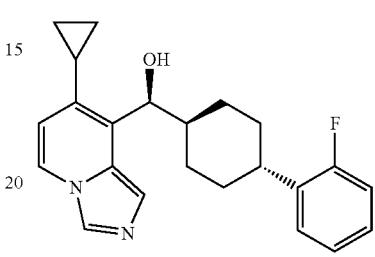 Example C108a
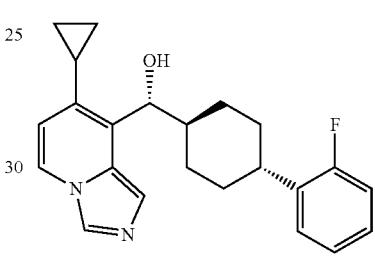 Example C108b
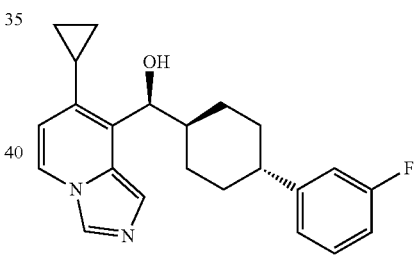 Example C109a
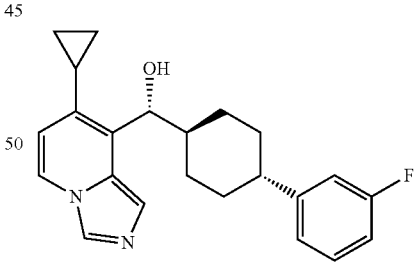 Example C109b
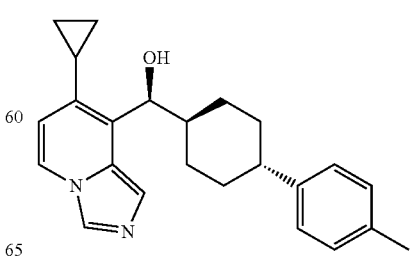 Example C110a

TABLE B-continued
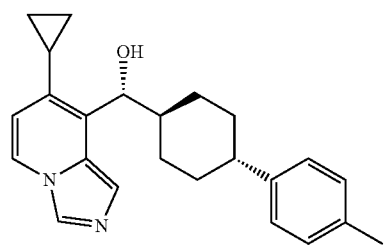 [SMILES: Cc1ccc([C@H]2CC[C@H]([C@@H](O)c3c(C4CC4)ccn4cncc34)CC2)cc1]
Example C110b
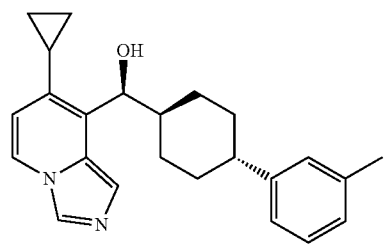 [SMILES: Cc1cccc([C@H]2CC[C@H]([C@H](O)c3c(C4CC4)ccn4cncc34)CC2)c1]
Example C111a
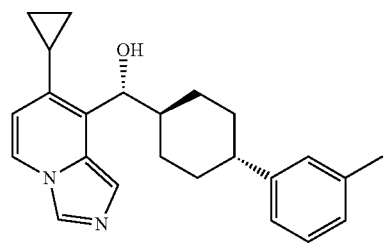 [SMILES: Cc1cccc([C@H]2CC[C@H]([C@@H](O)c3c(C4CC4)ccn4cncc34)CC2)c1]
Example C111b
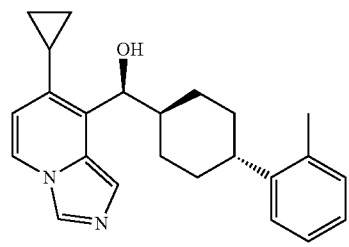
Example C112a
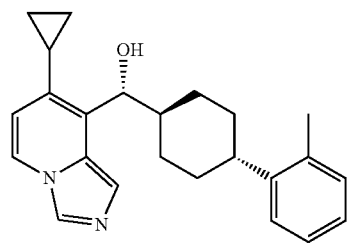 [SMILES: Cc1ccccc1[C@H]1CC[C@H]([C@@H](O)c2c(C3CC3)ccn3cncc23)CC1]
Example C112b
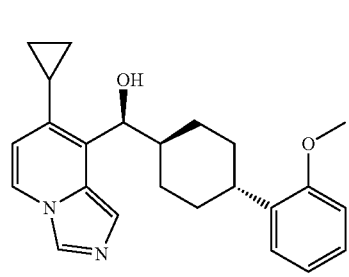 [SMILES: COc1ccccc1[C@H]1CC[C@H]([C@H](O)c2c(C3CC3)ccn3cncc23)CC1]
Example C113a
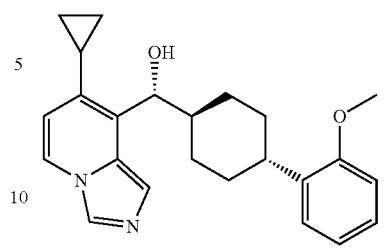
Example C113b
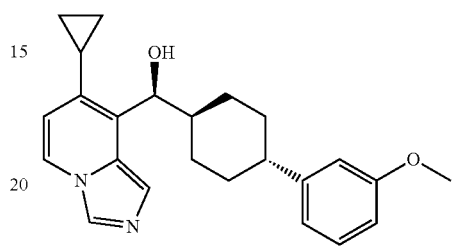
Example C114a
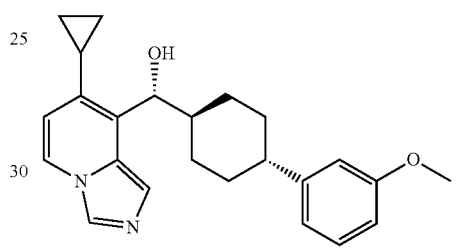
Example C114b
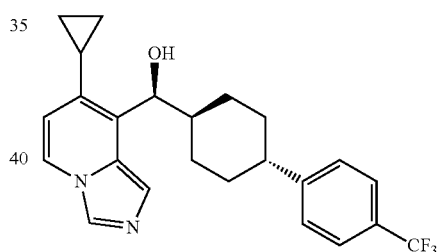
Example C115a
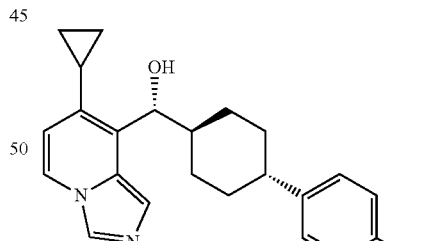
Example C115b
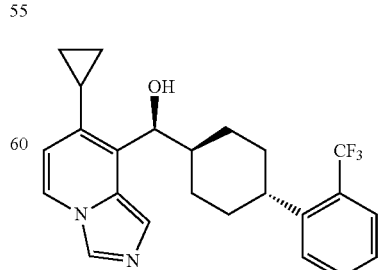
Example C116a

TABLE B-continued
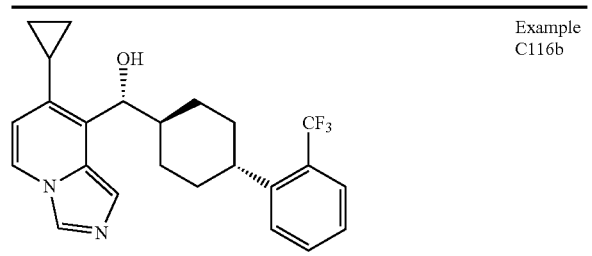
Example C116b
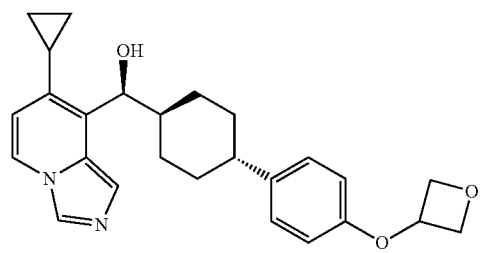 [SMILES: O[C@H](c1c(C2CC2)ccn2cncc12)[C@H]1CC[C@H](c2ccc(OC3COC3)cc2)CC1]
Example C117a
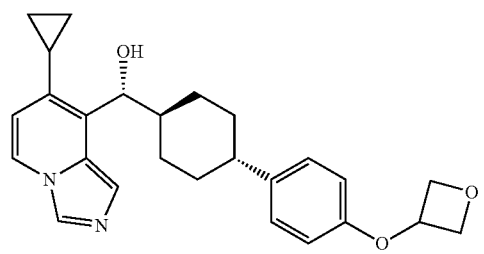 [SMILES: O[C@@H](c1c(C2CC2)ccn2cncc12)[C@H]1CC[C@H](c2ccc(OC3COC3)cc2)CC1]
Example C117b
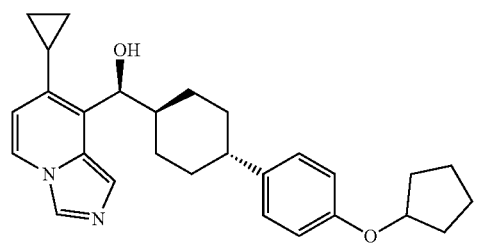 [SMILES: O[C@H](c1c(C2CC2)ccn2cncc12)[C@H]1CC[C@H](c2ccc(OC3CCCC3)cc2)CC1]
Example C118a
Fast isomer in CHIRALPAK IC-3
Eluting reagent: Hex(0.1% DEA):EtOH = 60:40
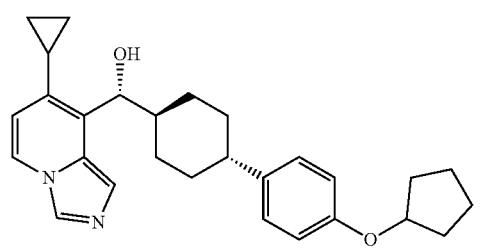 [SMILES: O[C@@H](c1c(C2CC2)ccn2cncc12)[C@H]1CC[C@H](c2ccc(OC3CCCC3)cc2)CC1]
Example C118b
Slow isomer in CHIRALPAK IC-3
Eluting reagent: Hex(0.1% DEA):EtOH = 60:40
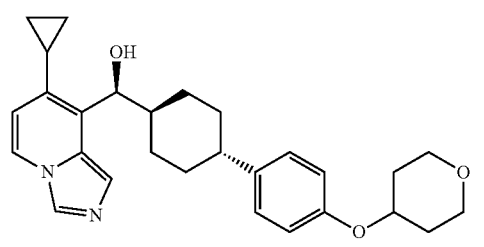 [SMILES: O[C@H](c1c(C2CC2)ccn2cncc12)[C@H]1CC[C@H](c2ccc(OC3CCOCC3)cc2)CC1]
Example C119a
TABLE B-continued
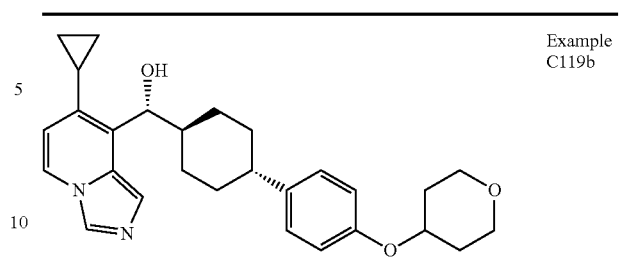
Example C119b
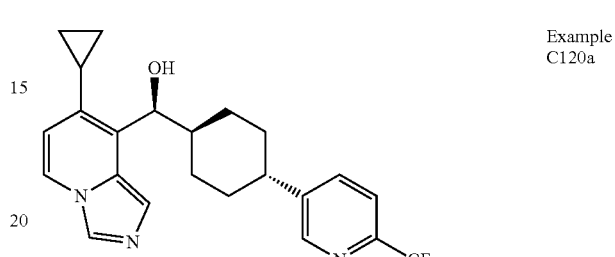
Example C120a
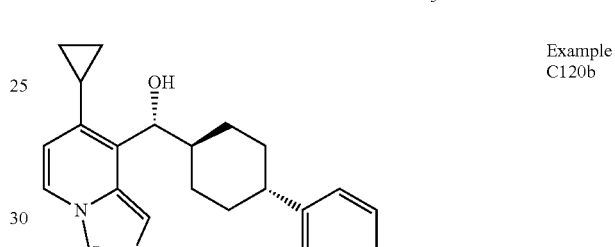
Example C120b
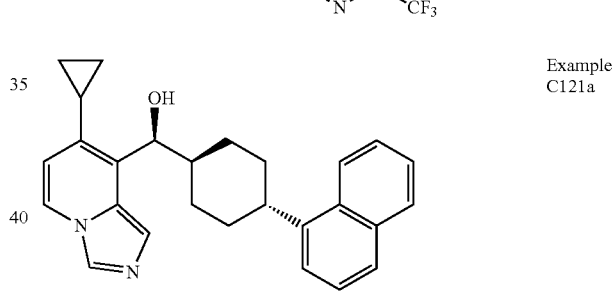
Example C121a
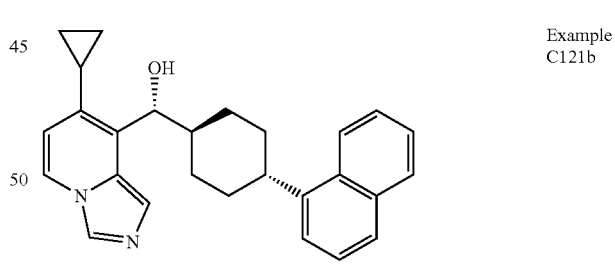
Example C121b
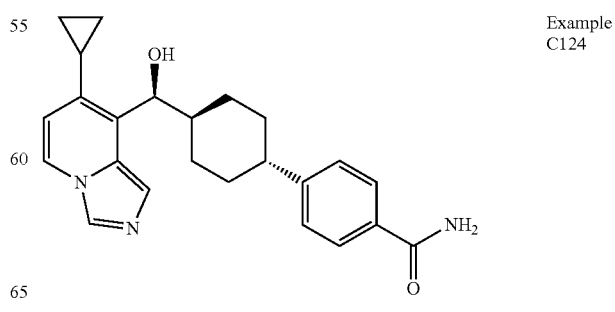
Example C124

TABLE B-continued
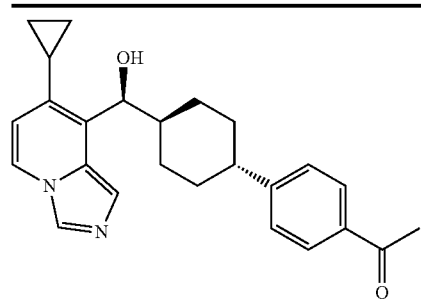 Example C125
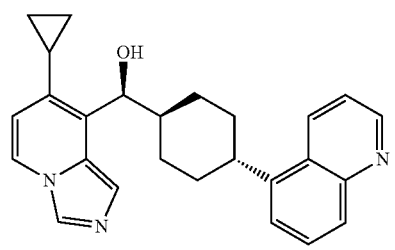 [SMILES: O[C@H](c1c(C2CC2)ccn2cncc12)[C@H]1CC[C@H](c2cccc3ncccc32)CC1] Example C126a
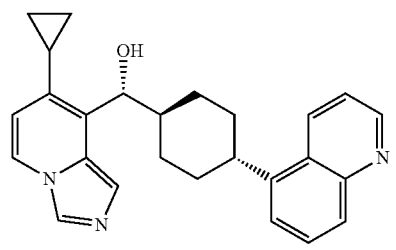 [SMILES: O[C@@H](c1c(C2CC2)ccn2cncc12)[C@H]1CC[C@H](c2cccc3ncccc32)CC1] Example C126b
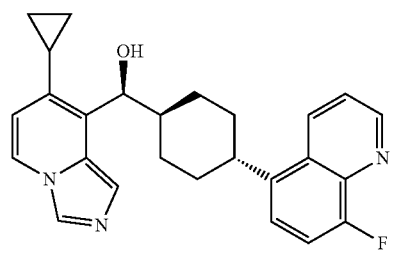 [SMILES: O[C@H](c1c(C2CC2)ccn2cncc12)[C@H]1CC[C@H](c2ccc(F)c3ncccc32)CC1] Example C127a
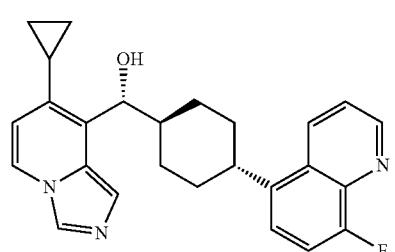 Example C127b
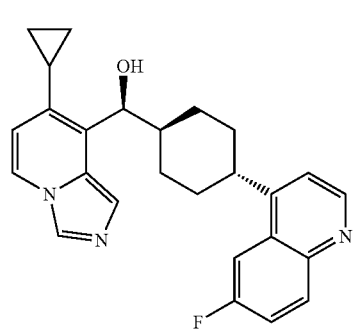 [SMILES: O[C@H](c1c(C2CC2)ccn2cncc12)[C@H]1CC[C@H](c2ccnc3ccc(F)cc32)CC1] Example C128a
TABLE B-continued
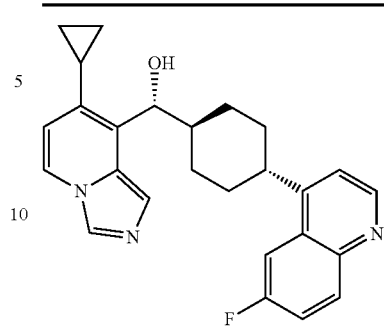 Example C128b
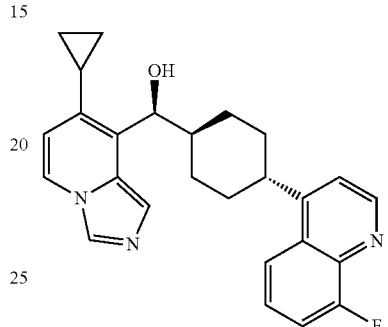 Example C129a
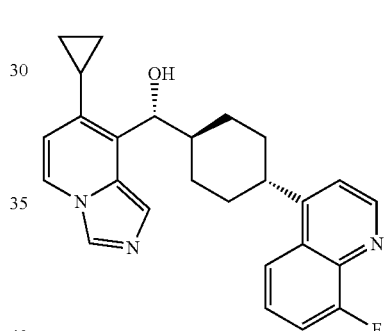 Example C129b
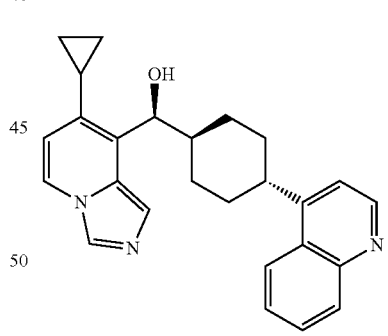 Example C130a
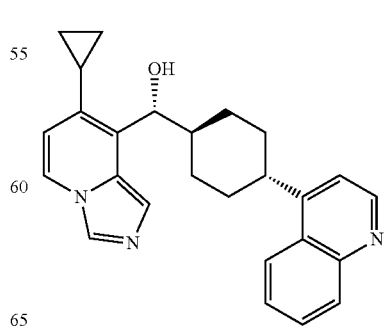 Example C130b TABLE B-continued
| | |
|---|---|
| 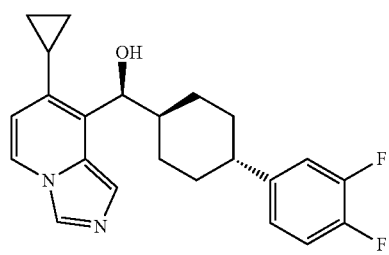 [SMILES: O[C@H](c1c(C2CC2)ccn2cncc12)[C@H]1CC[C@H](c2ccc(F)c(F)c2)CC1] | Example C131a |
| 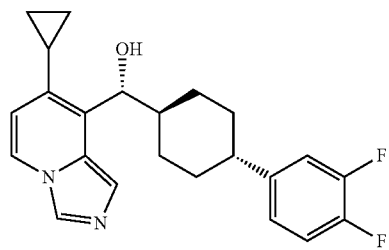 [SMILES: O[C@@H](c1c(C2CC2)ccn2cncc12)[C@H]1CC[C@H](c2ccc(F)c(F)c2)CC1] | Example C131b |
| 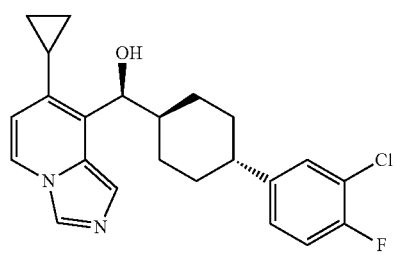 [SMILES: O[C@H](c1c(C2CC2)ccn2cncc12)[C@H]1CC[C@H](c2ccc(F)c(Cl)c2)CC1] | Example C132a |
| 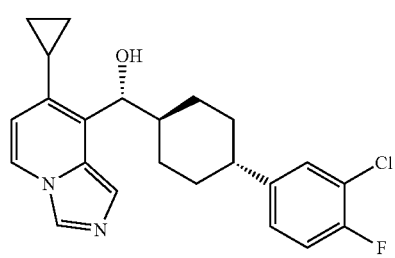 [SMILES: O[C@@H](c1c(C2CC2)ccn2cncc12)[C@H]1CC[C@H](c2ccc(F)c(Cl)c2)CC1] | Example C132b |
| 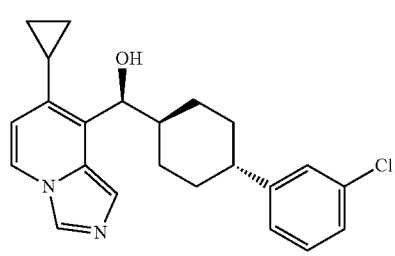 [SMILES: O[C@H](c1c(C2CC2)ccn2cncc12)[C@H]1CC[C@H](c2cccc(Cl)c2)CC1] | Example C133a |
| 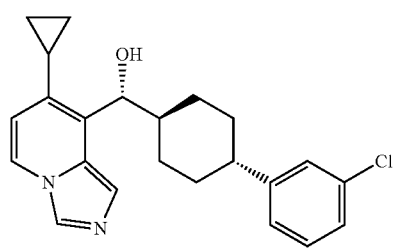 [SMILES: O[C@@H](c1c(C2CC2)ccn2cncc12)[C@H]1CC[C@H](c2cccc(Cl)c2)CC1] | Example C133b |
TABLE B-continued
| | |
|---|---|
| 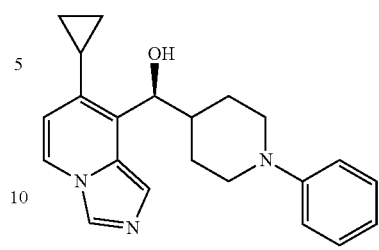 | Example C136a |
| | Example C136b |
| 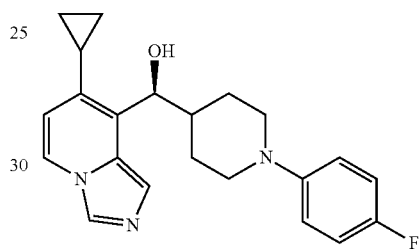 | Example C137a |
| 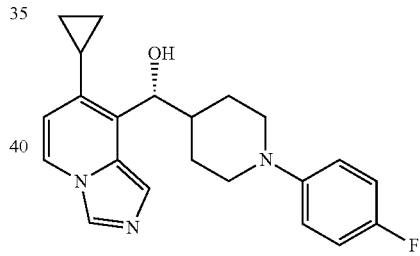 | Example C137b |
| 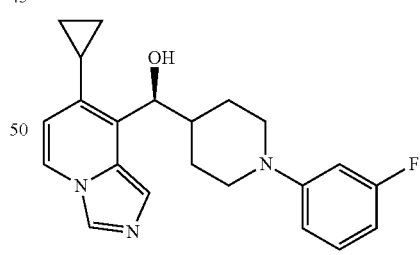 | Example C138a |
| 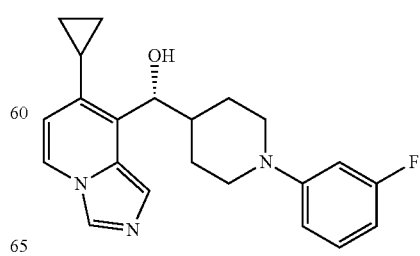 | Example C138b |

TABLE B-continued
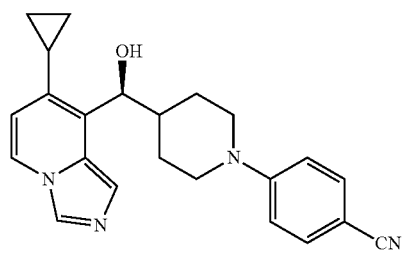 [SMILES: N#Cc1ccc(N2CCC([C@H](O)c3c(C4CC4)ccn4cncc34)CC2)cc1]
Example C144a
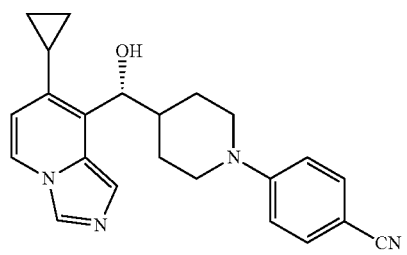 [SMILES: N#Cc1ccc(N2CCC([C@@H](O)c3c(C4CC4)ccn4cncc34)CC2)cc1]
Example C144b
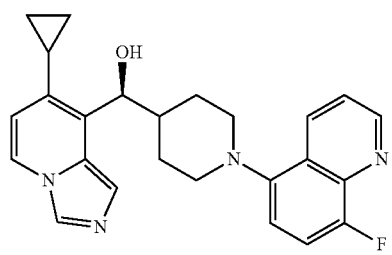 [SMILES: O[C@H](c1c(C2CC2)ccn2cncc12)C1CCN(c2ccc(F)c3ncccc23)CC1]
Example C149a
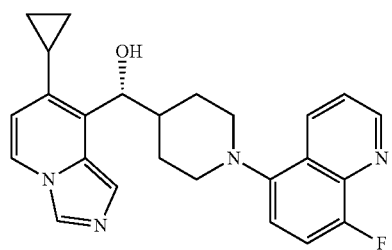
Example C149b
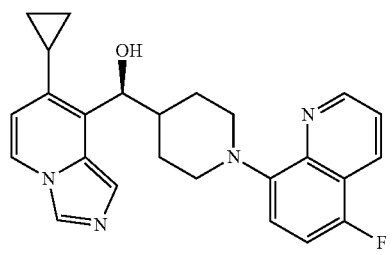 [SMILES: O[C@H](c1c(C2CC2)ccn2cncc12)C1CCN(c2ccc(F)c3cccnc23)CC1]
Example C155a
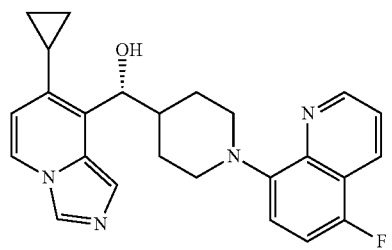
Example C155b
TABLE B-continued
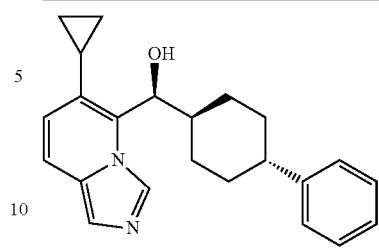
Example D101a
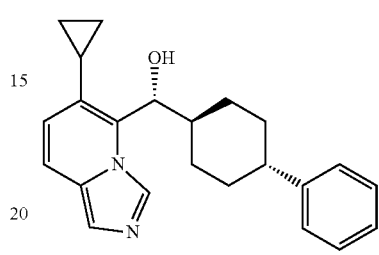
Example D101b
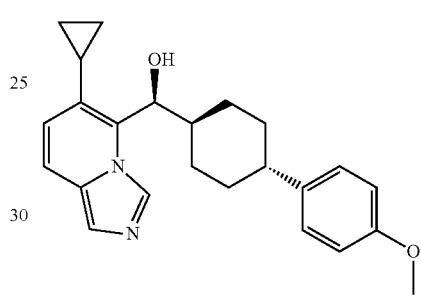
Example D102a
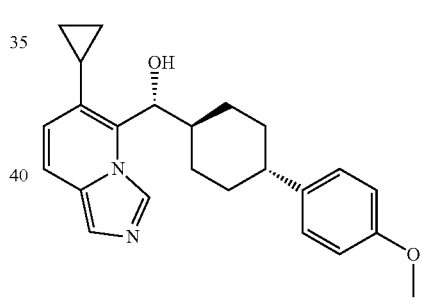
Example D102b
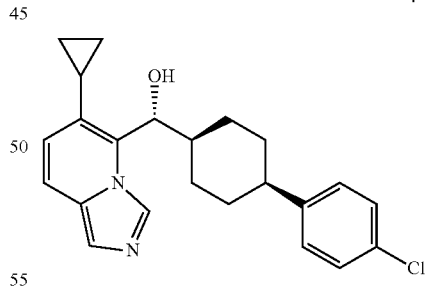
Example D103a
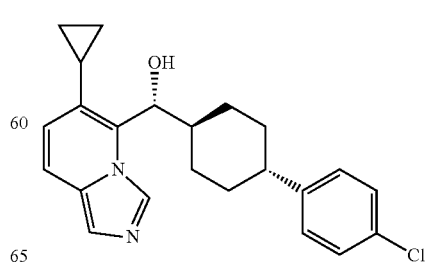
Example D103b TABLE B-continued
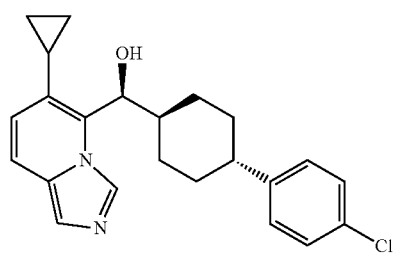 [SMILES: O[C@H](c1c(C2CC2)ccc2cncn12)[C@H]1CC[C@H](c2ccc(Cl)cc2)CC1]
Example D103c
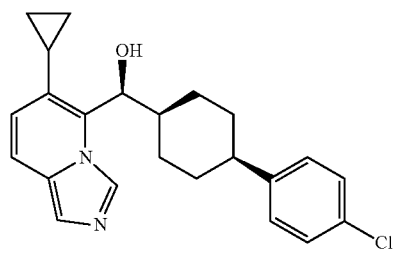 [SMILES: O[C@H](c1c(C2CC2)ccc2cncn12)[C@H]1CC[C@@H](c2ccc(Cl)cc2)CC1]
Example D103d
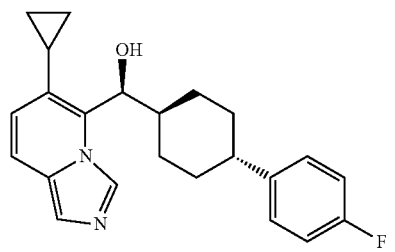 [SMILES: O[C@H](c1c(C2CC2)ccc2cncn12)[C@H]1CC[C@H](c2ccc(F)cc2)CC1]
Example D104a
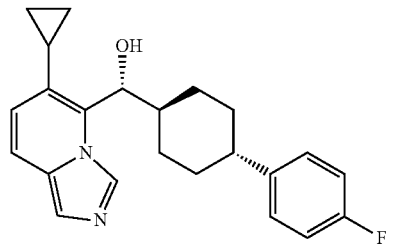 [SMILES: O[C@@H](c1c(C2CC2)ccc2cncn12)[C@H]1CC[C@H](c2ccc(F)cc2)CC1]
Example D104b
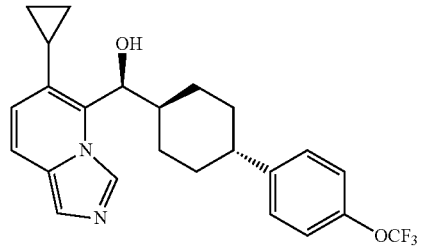 [SMILES: O[C@H](c1c(C2CC2)ccc2cncn12)[C@H]1CC[C@H](c2ccc(OC(F)(F)F)cc2)CC1]
Example D105a
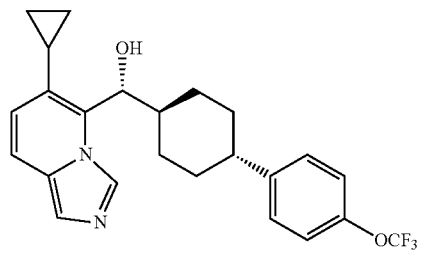 [SMILES: O[C@@H](c1c(C2CC2)ccc2cncn12)[C@H]1CC[C@H](c2ccc(OC(F)(F)F)cc2)CC1]
Example D105b
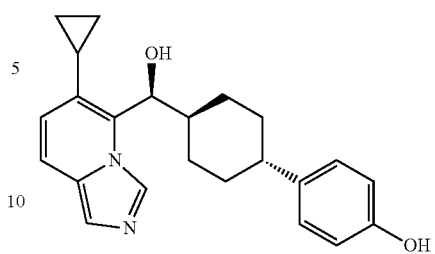
Example D106a
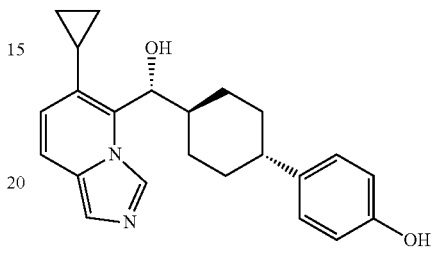
Example D106b
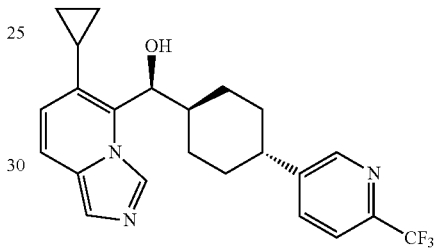
Example D107a
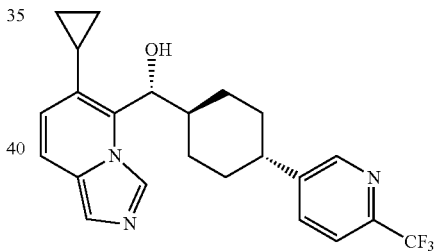
Example D107b
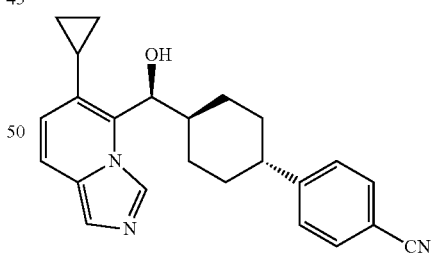
Example D110a
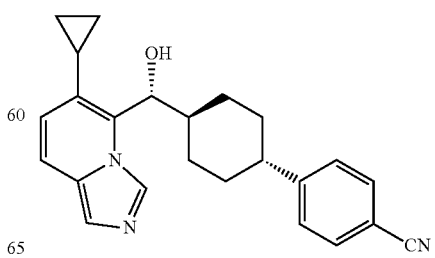
Example D110b TABLE B-continued
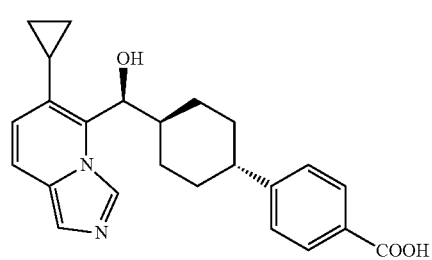 [SMILES: O=C(O)c1ccc([C@H]2CC[C@H]([C@H](O)c3c(C4CC4)ccc4cncn34)CC2)cc1]
Example D111a
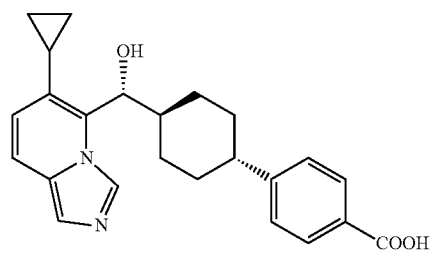 [SMILES: O=C(O)c1ccc([C@H]2CC[C@H]([C@@H](O)c3c(C4CC4)ccc4cncn34)CC2)cc1]
Example D111b
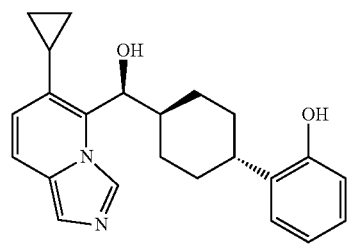 [SMILES: Oc1ccccc1[C@H]1CC[C@H]([C@H](O)c2c(C3CC3)ccc3cncn23)CC1]
Example D112a
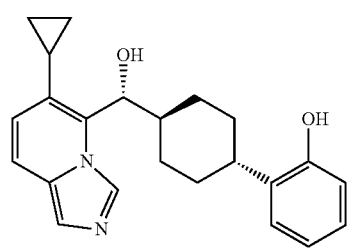 [SMILES: Oc1ccccc1[C@H]1CC[C@H]([C@@H](O)c2c(C3CC3)ccc3cncn23)CC1]
Example D112b
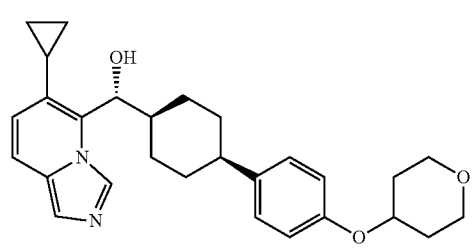 [SMILES: O[C@@H](c1c(C2CC2)ccc2cncn12)[C@H]1CC[C@@H](c2ccc(OC3CCOCC3)cc2)CC1]
Example D114a
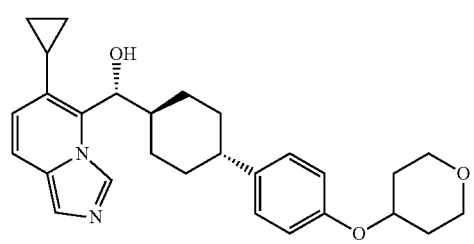 [SMILES: O[C@@H](c1c(C2CC2)ccc2cncn12)[C@H]1CC[C@H](c2ccc(OC3CCOCC3)cc2)CC1]
Example D114b
TABLE B-continued
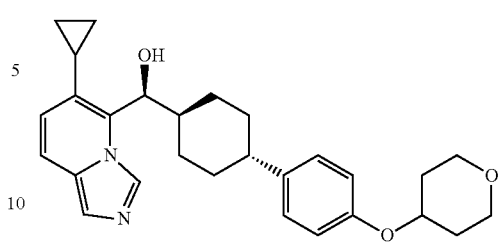
Example D114c
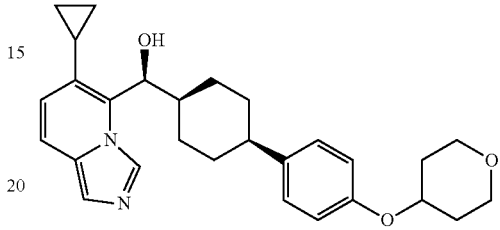
Example D114d
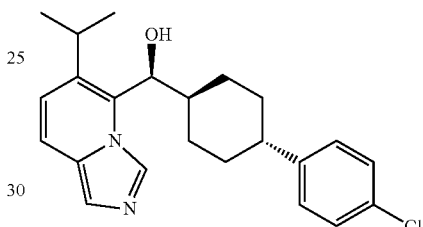
Example D115a
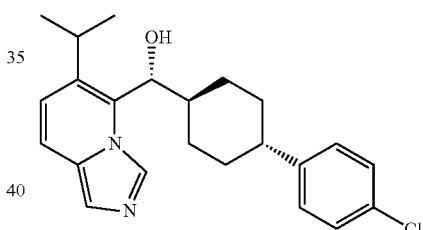
Example D115b
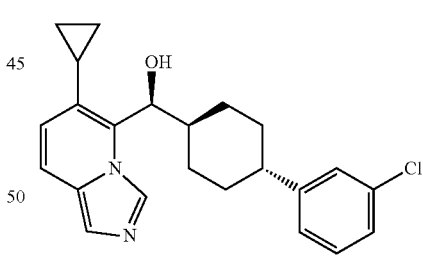
Example D116a
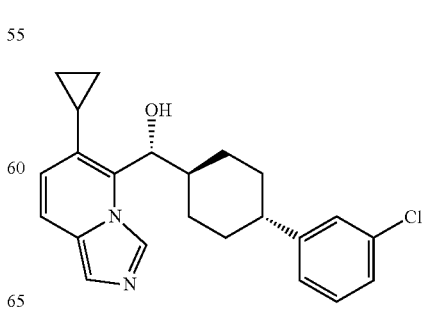
Example D116b TABLE B-continued
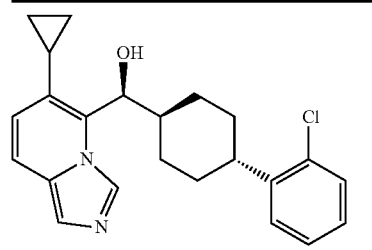 Example D117a
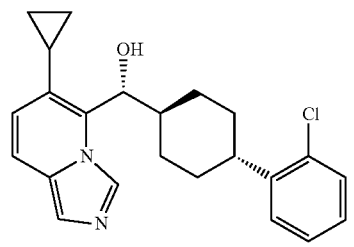 [SMILES: O[C@@H](c1c(C2CC2)ccc2cncn12)[C@H]1CC[C@H](c2ccccc2Cl)CC1] Example D117b
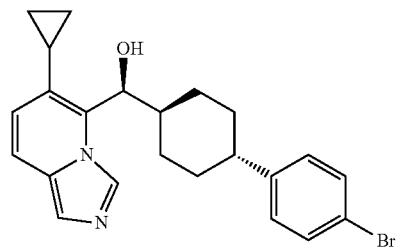 [SMILES: O[C@H](c1c(C2CC2)ccc2cncn12)[C@H]1CC[C@H](c2ccc(Br)cc2)CC1] Example D118a
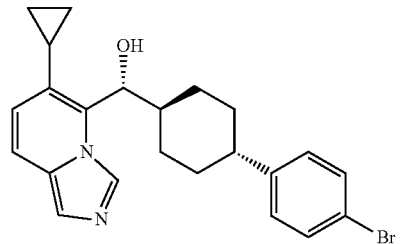 [SMILES: O[C@@H](c1c(C2CC2)ccc2cncn12)[C@H]1CC[C@H](c2ccc(Br)cc2)CC1] Example D118b
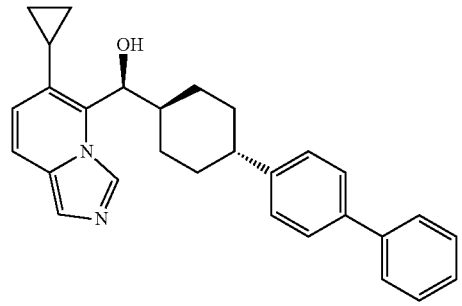 [SMILES: O[C@H](c1c(C2CC2)ccc2cncn12)[C@H]1CC[C@H](c2ccc(-c3ccccc3)cc2)CC1] Example D119a
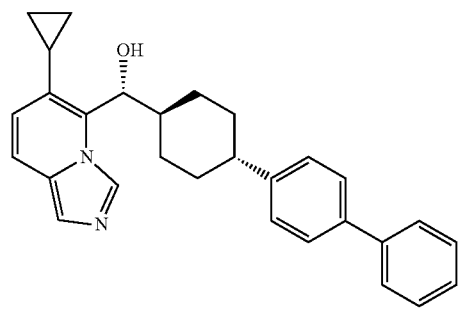 [SMILES: O[C@@H](c1c(C2CC2)ccc2cncn12)[C@H]1CC[C@H](c2ccc(-c3ccccc3)cc2)CC1] Example D119b
TABLE B-continued
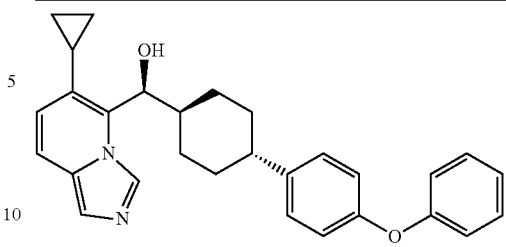 Example D120a
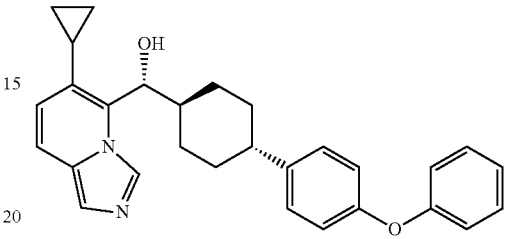 Example D120b
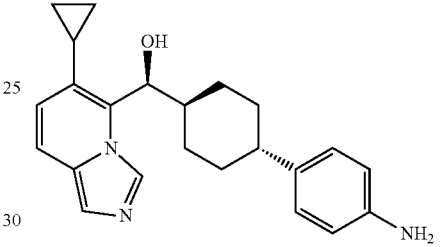 Example D122a
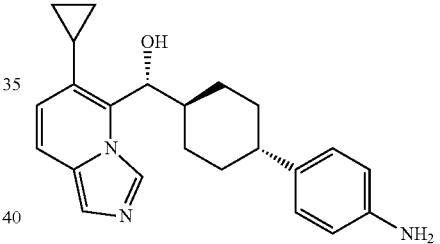 Example D122b
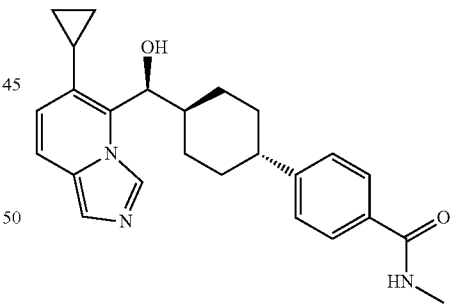 Example D124a
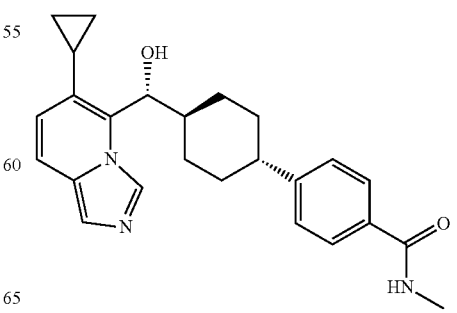 Example D124b TABLE B-continued
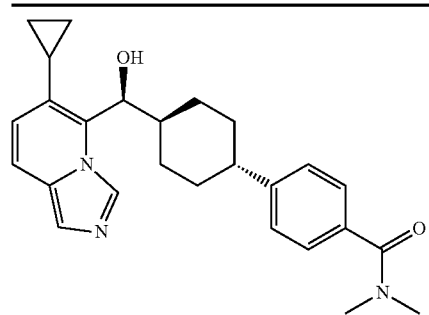
Example D125a
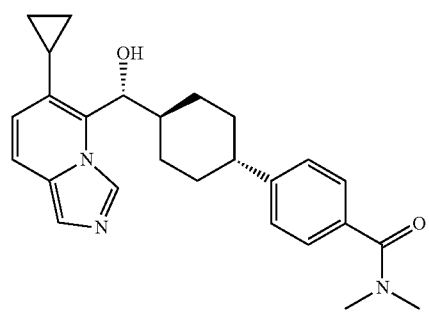 [SMILES: CN(C)C(=O)c1ccc([C@H]2CC[C@H]([C@@H](O)c3c(C4CC4)ccc4cncn34)CC2)cc1]
Example D125b
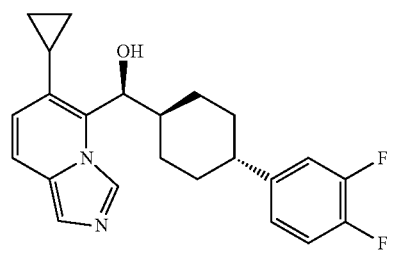 [SMILES: O[C@H](c1c(C2CC2)ccc2cncn12)[C@H]1CC[C@H](c2ccc(F)c(F)c2)CC1]
Example D126a
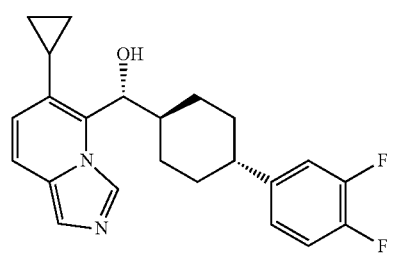 [SMILES: O[C@@H](c1c(C2CC2)ccc2cncn12)[C@H]1CC[C@H](c2ccc(F)c(F)c2)CC1]
Example D126b
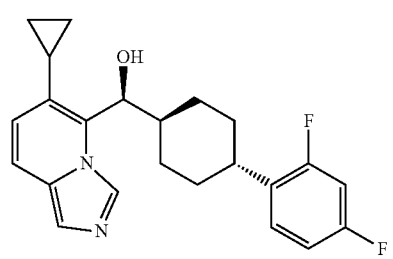 [SMILES: O[C@H](c1c(C2CC2)ccc2cncn12)[C@H]1CC[C@H](c2ccc(F)cc2F)CC1]
Example D127a
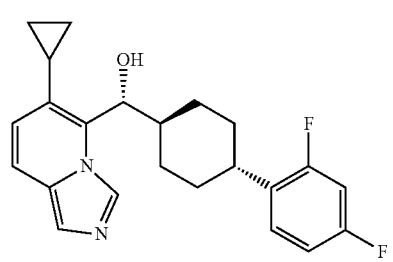 [SMILES: O[C@@H](c1c(C2CC2)ccc2cncn12)[C@H]1CC[C@H](c2ccc(F)cc2F)CC1]
Example D127b
TABLE B-continued
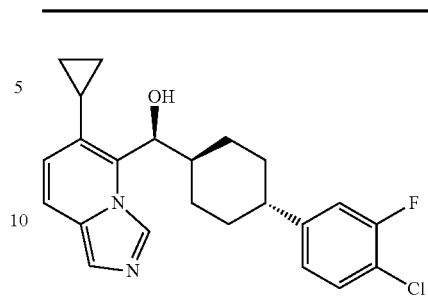
Example D128a
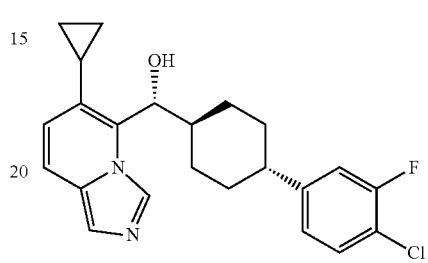
Example D128b
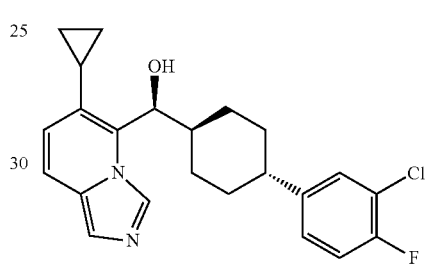
Example D129a
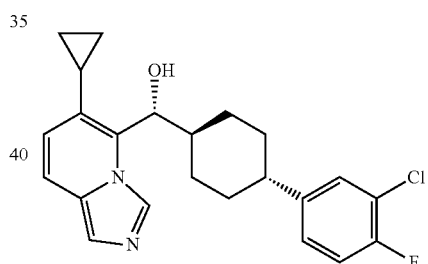
Example D129b
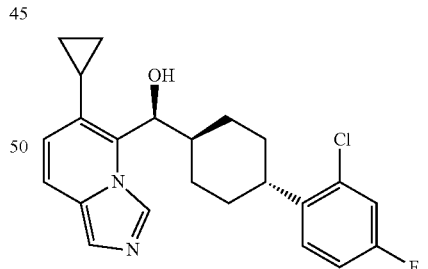
Example D130a
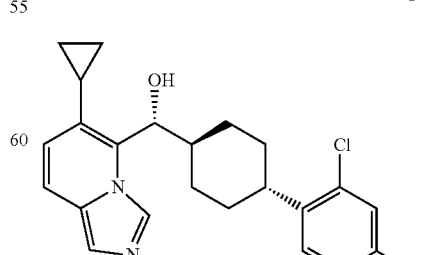
Example D130b

| | |
|---|---|
| 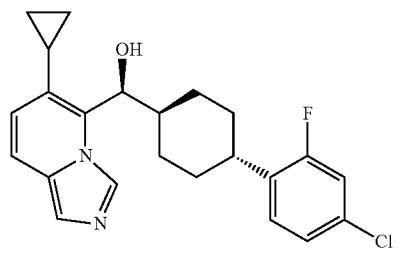 [SMILES: O[C@H](c1c(C2CC2)ccc2cncn12)[C@H]1CC[C@H](c2ccc(Cl)cc2F)CC1] | Example D131a |
| 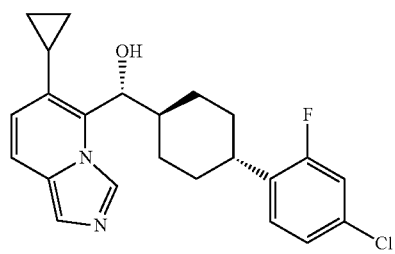 [SMILES: O[C@@H](c1c(C2CC2)ccc2cncn12)[C@H]1CC[C@H](c2ccc(Cl)cc2F)CC1] | Example D131b |
| 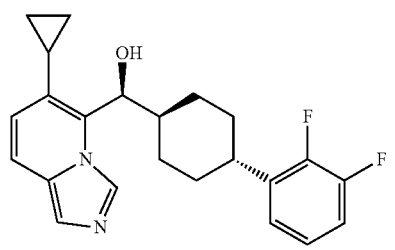 [SMILES: O[C@H](c1c(C2CC2)ccc2cncn12)[C@H]1CC[C@H](c2cccc(F)c2F)CC1] | Example D132a |
| 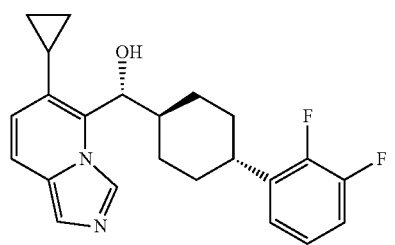 [SMILES: O[C@@H](c1c(C2CC2)ccc2cncn12)[C@H]1CC[C@H](c2cccc(F)c2F)CC1] | Example D132b |
| 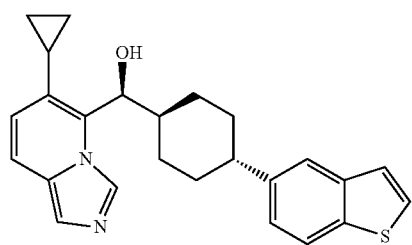 [SMILES: O[C@H](c1c(C2CC2)ccc2cncn12)[C@H]1CC[C@H](c2ccc3sccc3c2)CC1] | Example D133a |
| 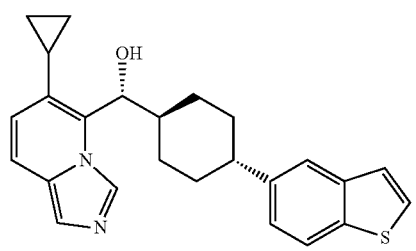 [SMILES: O[C@@H](c1c(C2CC2)ccc2cncn12)[C@H]1CC[C@H](c2ccc3sccc3c2)CC1] | Example D133b |
| 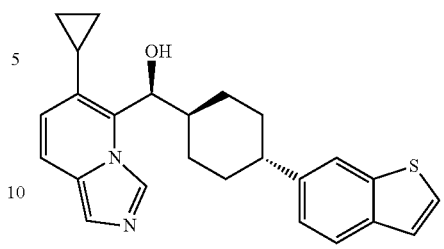 | Example D134a |
| 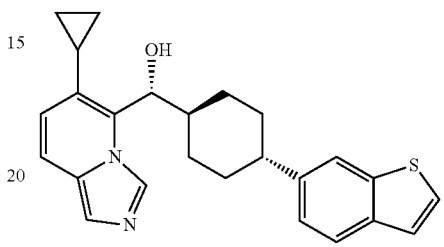 | Example D134b |
| 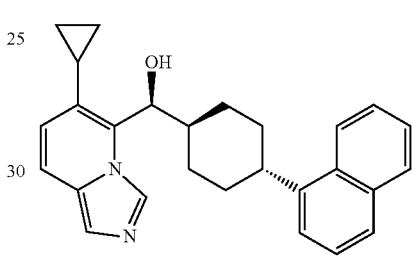 | Example D135a |
| 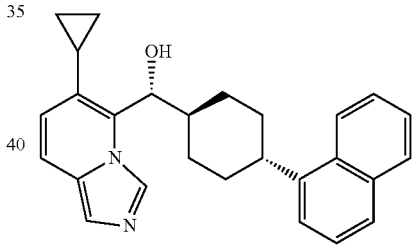 | Example D135b |
| 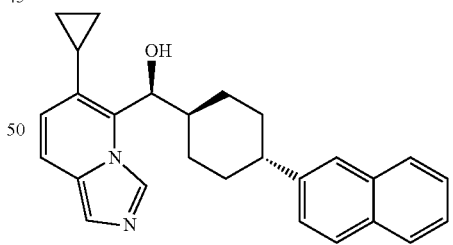 | Example D136a |
| 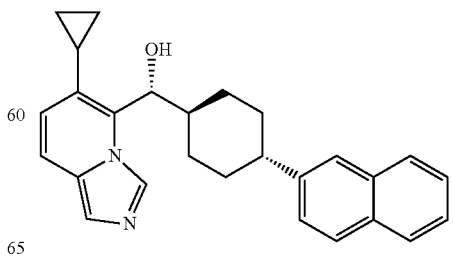 | Example D136b |

TABLE B-continued
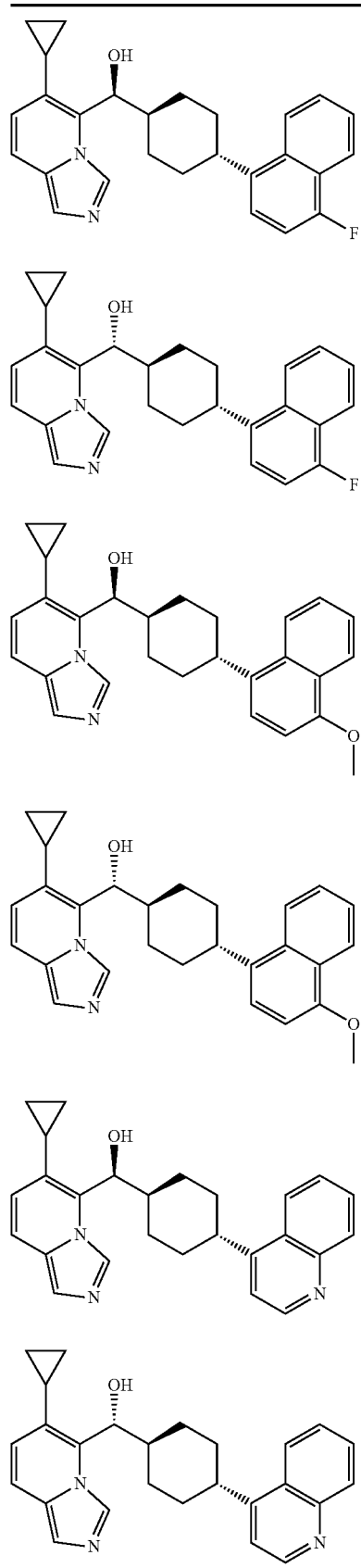
| | |
|---|---|
| | Example D137a |
| | Example D137b |
| | Example D139a |
| | Example D139b |
| | Example D140a |
| | Example D140b |
TABLE B-continued
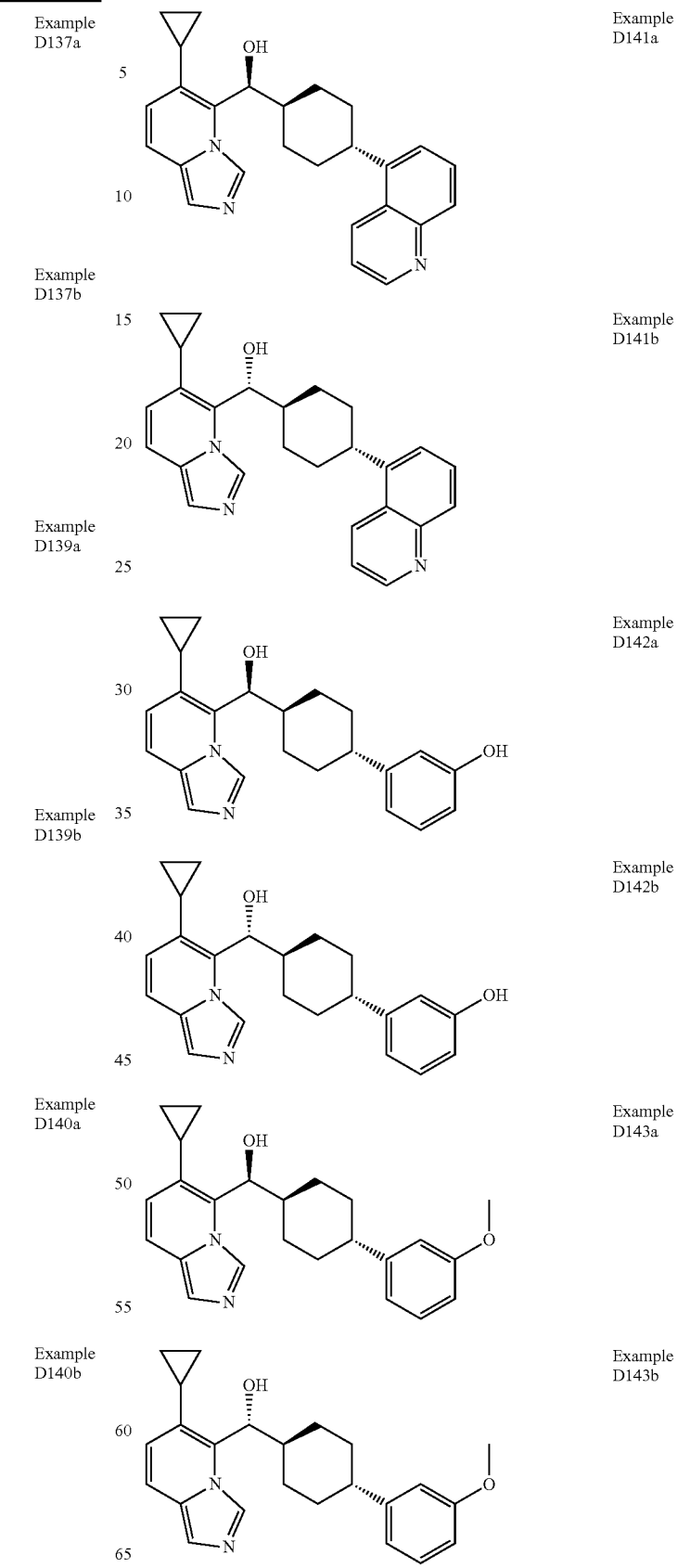
| | |
|---|---|
| | Example D141a |
| | Example D141b |
| | Example D142a |
| | Example D142b |
| | Example D143a |
| | Example D143b |

TABLE B-continued
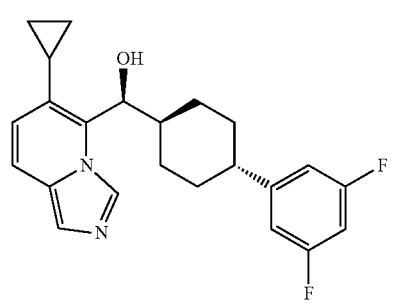 [SMILES: O[C@H](c1c(C2CC2)ccc2cncn12)[C@H]1CC[C@H](c2cc(F)cc(F)c2)CC1]
Example D144a
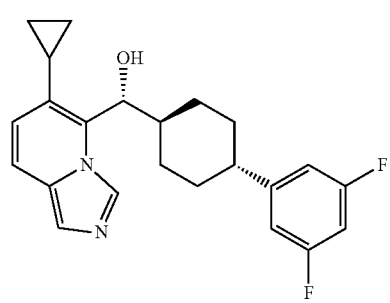 [SMILES: O[C@@H](c1c(C2CC2)ccc2cncn12)[C@H]1CC[C@H](c2cc(F)cc(F)c2)CC1]
Example D144b
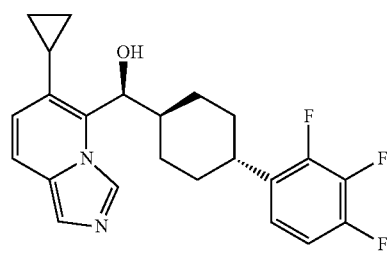 [SMILES: O[C@H](c1c(C2CC2)ccc2cncn12)[C@H]1CC[C@H](c2ccc(F)c(F)c2F)CC1]
Example D145a
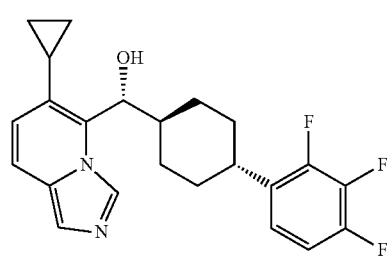 [SMILES: O[C@@H](c1c(C2CC2)ccc2cncn12)[C@H]1CC[C@H](c2ccc(F)c(F)c2F)CC1]
Example D145b
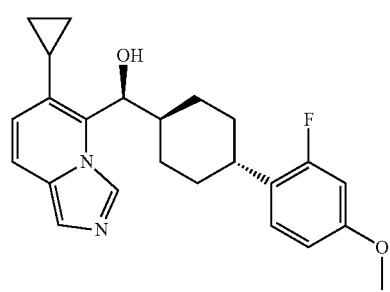 [SMILES: COc1ccc([C@H]2CC[C@H]([C@H](O)c3c(C4CC4)ccc4cncn34)CC2)c(F)c1]
Example D146a
TABLE B-continued
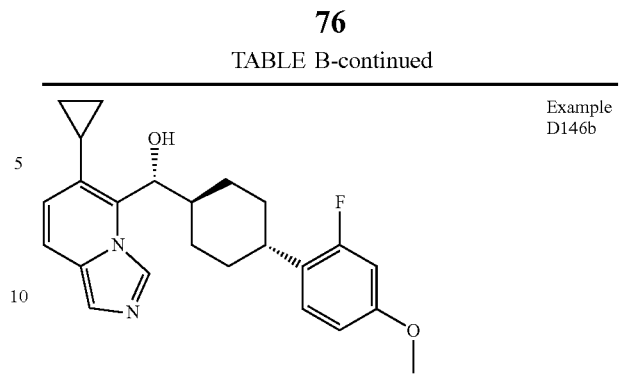
Example D146b
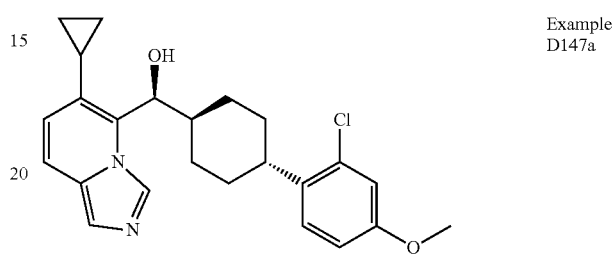
Example D147a

Example D147b
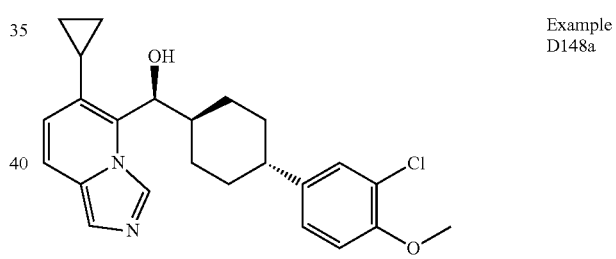
Example D148a
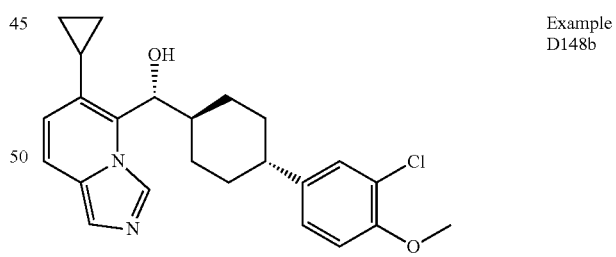
Example D148b
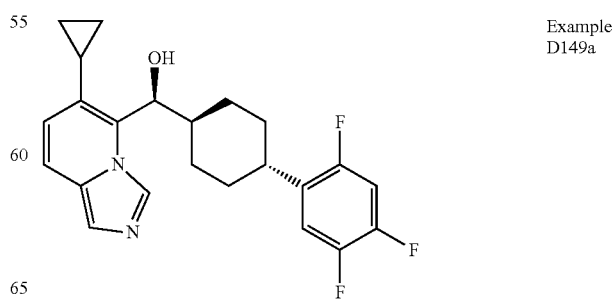
Example D149a

TABLE B-continued
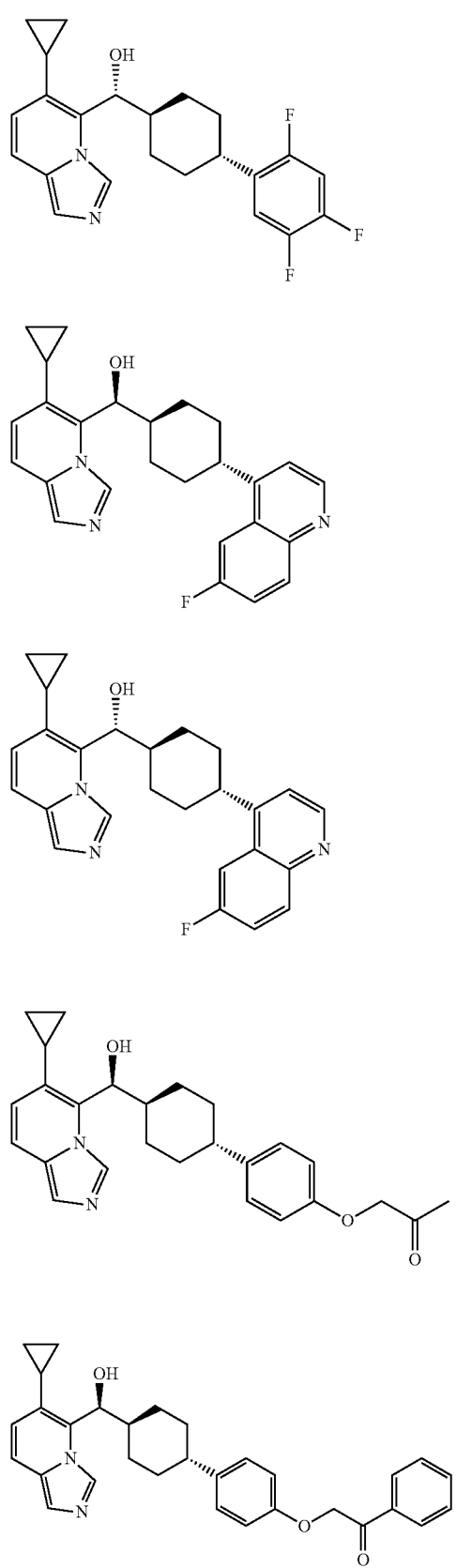
Example D149b
Example D150a
Example D150b
Example D151
Example D152
TABLE B-continued
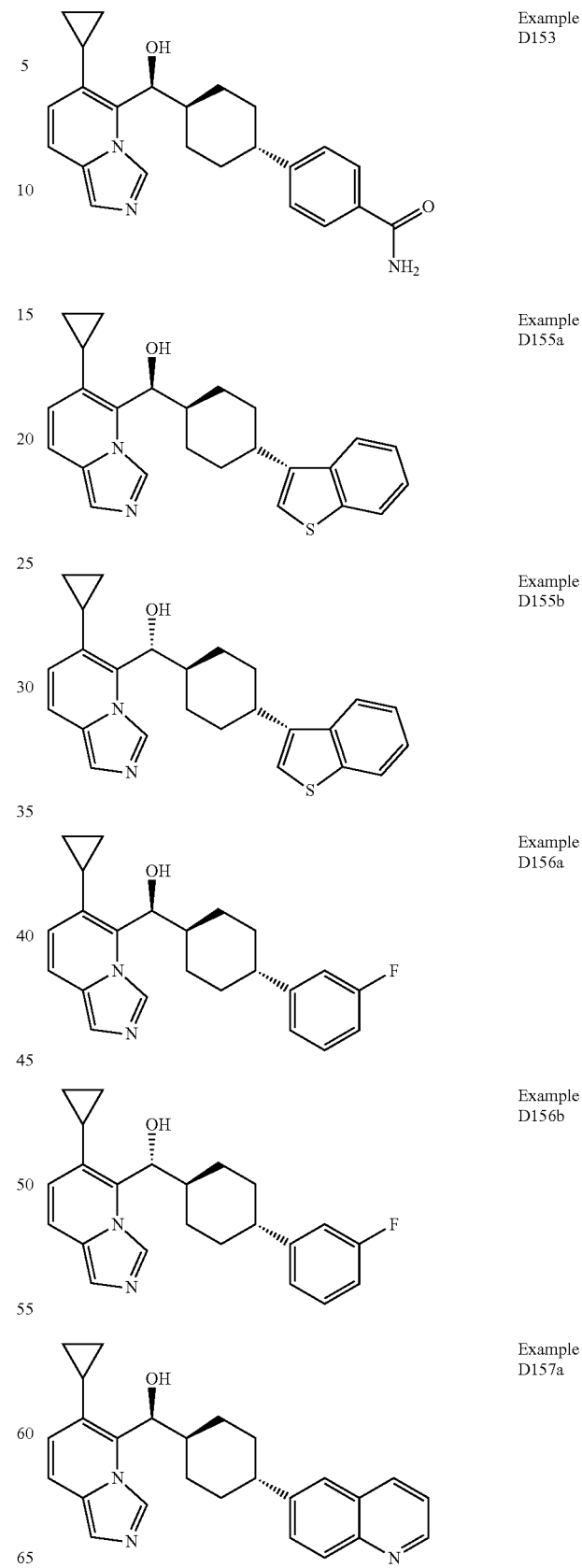
Example D153
Example D155a
Example D155b
Example D156a
Example D156b
Example D157a TABLE B-continued
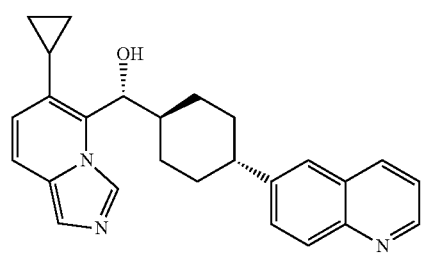 [SMILES: O[C@@H](c1c(C2CC2)ccc2cncn12)[C@H]1CC[C@H](c2ccc3ncccc3c2)CC1] Example D157b
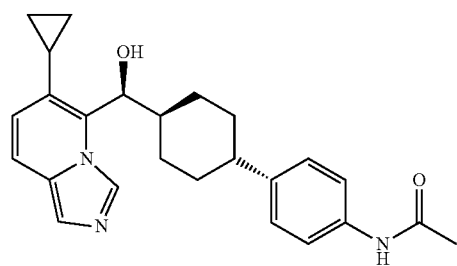 Example D159
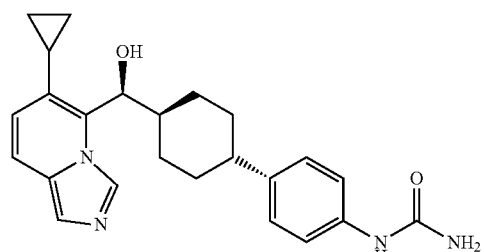 Example D160
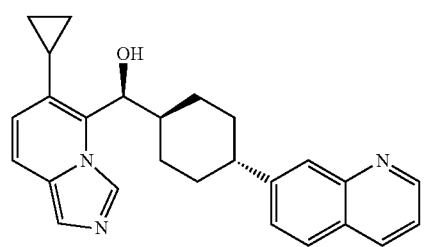 [SMILES: O[C@H](c1c(C2CC2)ccc2cncn12)[C@H]1CC[C@H](c2ccc3cccnc3c2)CC1] Example D161a
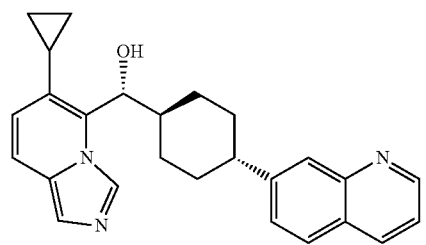 [SMILES: O[C@@H](c1c(C2CC2)ccc2cncn12)[C@H]1CC[C@H](c2ccc3cccnc3c2)CC1] Example D161b
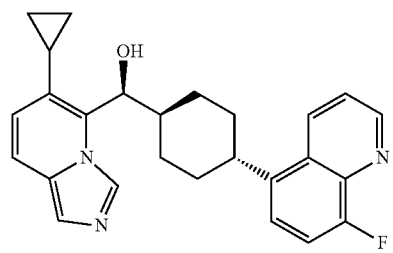 [SMILES: O[C@H](c1c(C2CC2)ccc2cncn12)[C@H]1CC[C@H](c2ccc(F)c3ncccc32)CC1] Example D163a
TABLE B-continued
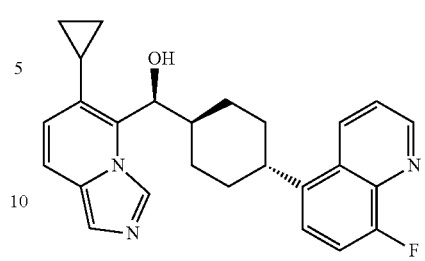 Example D163b
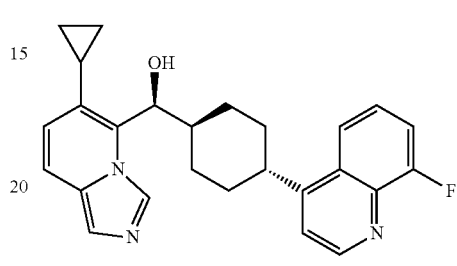 Example D164a
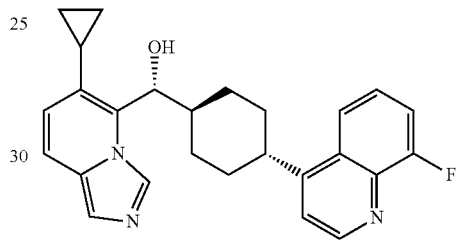 Example D164b
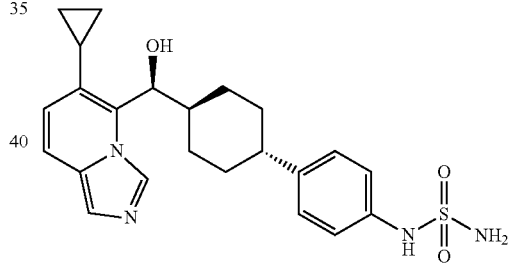 Example D165
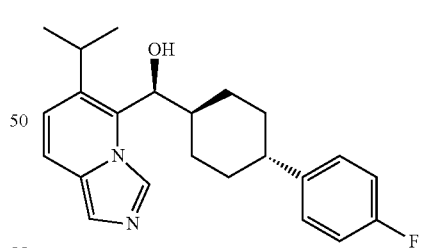 Example D166a
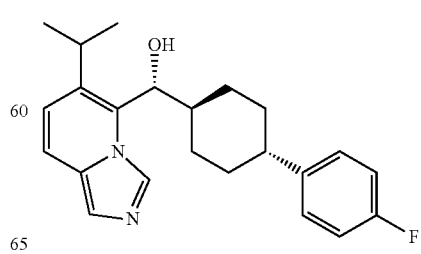 Example D166b TABLE B-continued
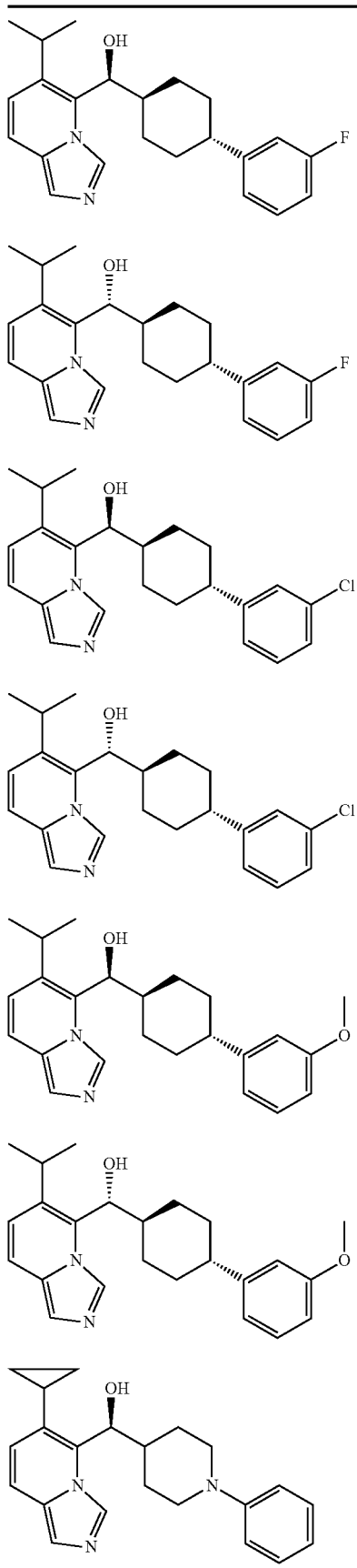
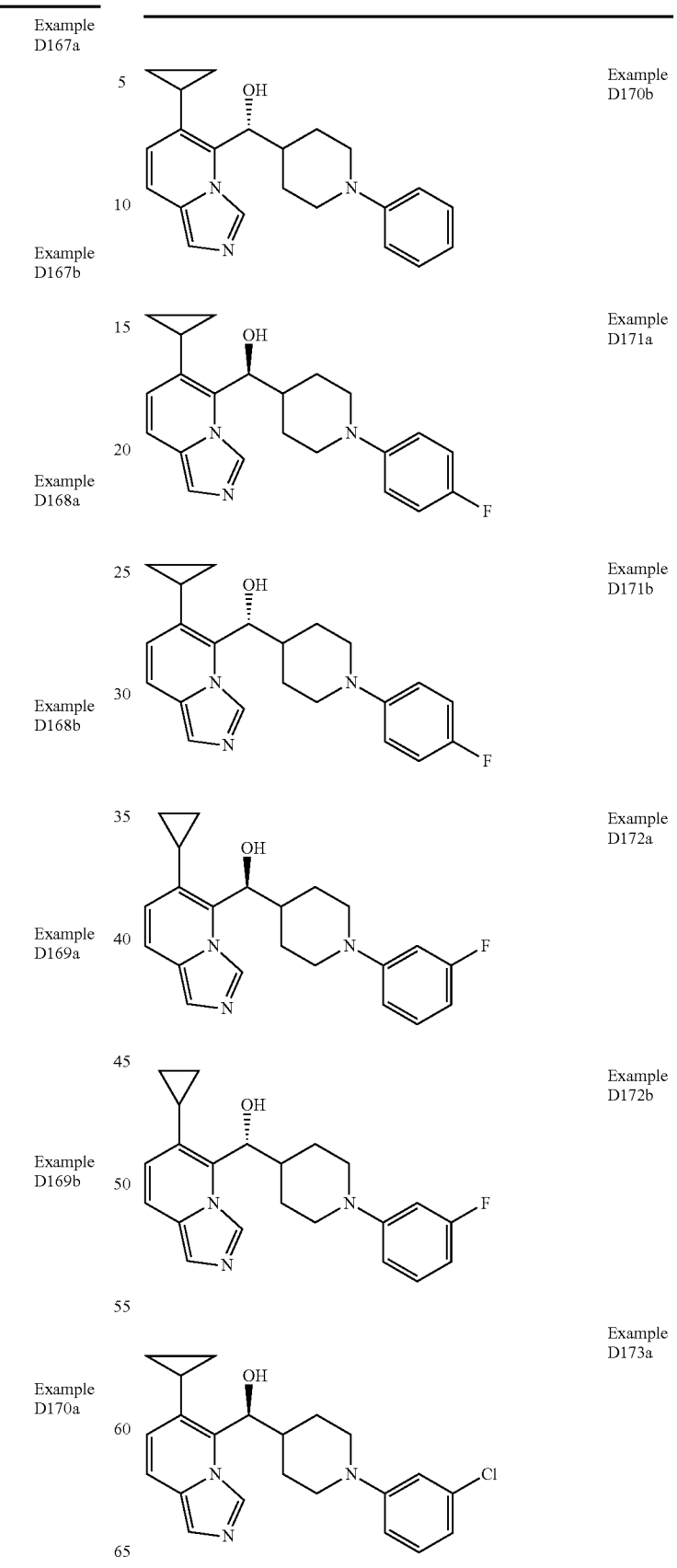

| | |
|---|---|
| 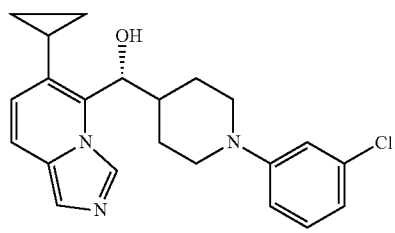 [SMILES: O[C@@H](c1c(C2CC2)ccc2cncn12)C1CCN(c2cccc(Cl)c2)CC1] | Example D173b |
| 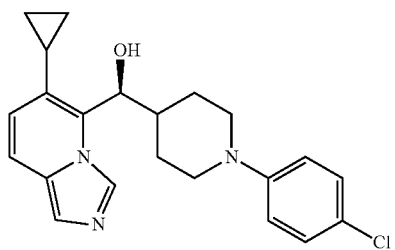 [SMILES: O[C@H](c1c(C2CC2)ccc2cncn12)C1CCN(c2ccc(Cl)cc2)CC1] | Example D174a |
| 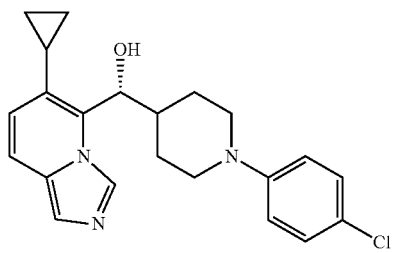 [SMILES: O[C@@H](c1c(C2CC2)ccc2cncn12)C1CCN(c2ccc(Cl)cc2)CC1] | Example D174b |
| 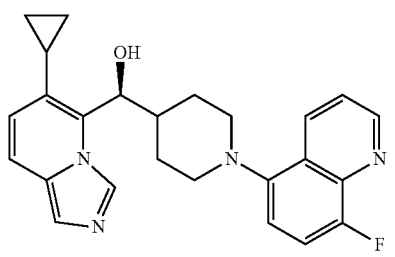 | Example D175a |
| 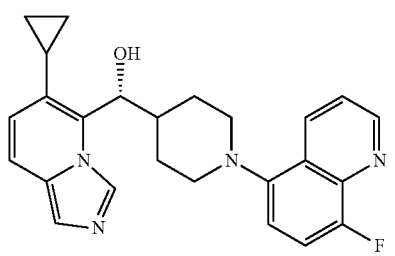 [SMILES: O[C@@H](c1c(C2CC2)ccc2cncn12)C1CCN(c2ccc(F)c3ncccc23)CC1] | Example D175b |
| 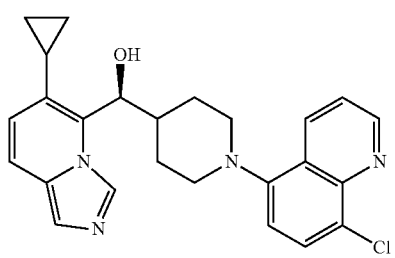 [SMILES: O[C@H](c1c(C2CC2)ccc2cncn12)C1CCN(c2ccc(Cl)c3ncccc23)CC1] | Example D178a |
| 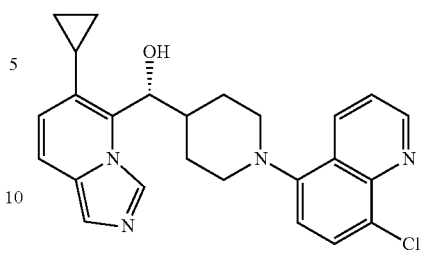 | Example D178b |
| 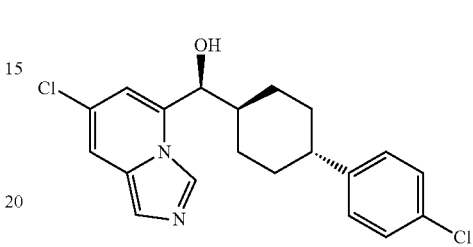 | Example E101a |
| 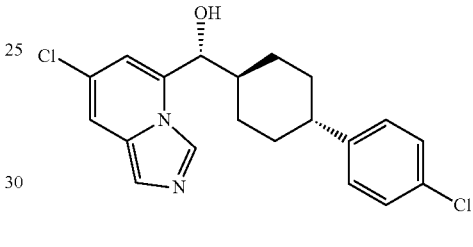 | Example E101b |
| 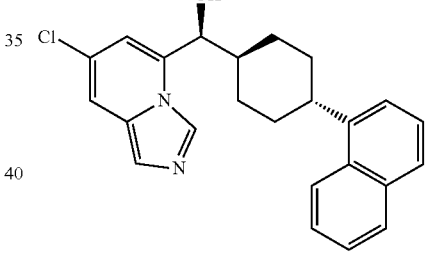 | Example E103a |
| 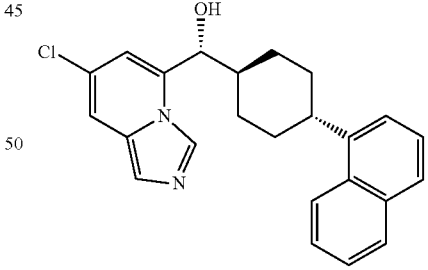 | Example E103b |
| 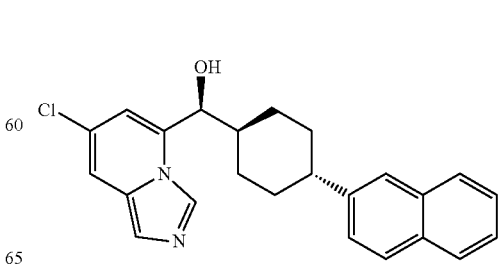 | Example E104a |

TABLE B-continued

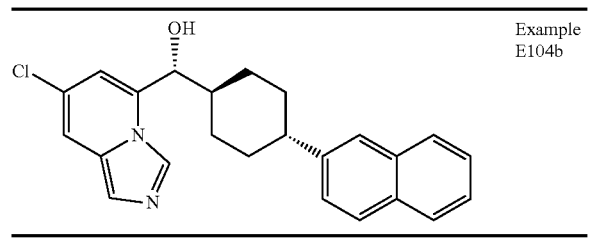

Example E104b or a pharmaceutically acceptable salt thereof.

The results of the "biological assays" part of the description have demonstrated that substitution of hydroxyl group on the chiral α-carbon atom attached to position 5 or 8 of the imidazo[1,5-a]pyridine structure and/or ortho or meta substitution in relation to the hydroxyl-substituted chiral α-carbon atom on the pyridine moiety of the imidazo[1,5-a]pyridine structure impart both unexpected enzymatic and cellular activity to the novel 5 or 8-substituted imidazo[1,5-a]pyridines disclosed herein. For example, each of Examples C101 to C156, Examples D101 to D181 and Examples E101 to E104 exhibited activity of inhibiting both IDO1 and TDO with $IC_{50}$ values ranging from 0.1 nM to 10 μM as well as activity of inhibiting Hela Cell-Based IDO1 with $EC_{50}$ values ranging less than 10000 nM.

The results also demonstrated that 5-substituted imidazo[1,5-a]pyridines having hydroxyl-substituted chiral α-carbon atom at position 5 and further ortho substitution on the pyridine moiety of the imidazo[1,5-a]pyridine structure and 8-substituted imidazo[1,5-a]pyridines having hydroxyl-substituted chiral α-carbon atom at position 8 and further ortho substitution on the pyridine moiety of the imidazo[1,5-a]pyridine structure, together with the trans-configuration of the cyclohexyl structure, exhibit selective inhibition of IDO1 over TDO. For example, (S)-isomer Example D103c exhibited an enzymatic IC50 value to IDO1 of 22 nM and another (S)-isomer Example D103d exhibited an enzymatic $IC_{50}$ value to IDO1 of 67 nM. However, trans-cyclohexyl isomer D103c exhibited a cell-based EC50 value of 130 nM but cis-cyclohexyl isomer D103d was not active (EC50>10,000 nM) in the same cellular assay (IDO1 expressed Hela cells). In addition, none of the four isomers (D103a, D103b, D103c and D103d) are active in 293-TDO2 cell based assay ($EC_{50}$>10,000 nM).

In the fourth aspect, provided herein is the process for preparing the compounds of formula (IA) or (IB) disclosed herein.

The compounds disclosed herein, and/or the pharmaceutically acceptable salts thereof, can be synthesized from commercially available starting materials taken together with the disclosure herein.

Compounds of Formula (IA and IB) may be prepared by the exemplary processes described in the working Examples, as well as relevant published literature procedures that are used by one skilled in the art. Exemplary reagents and procedures for these reactions appear hereinafter and in the working Examples. Protection and deprotection in the processes below may be carried out by procedures generally known in the art (see, for example, Greene, T. W. et al., eds., *Protecting Groups in Organic Synthesis*, 3<sup>rd</sup> Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Reactions, Mechanisms, and Structure*. 4<sup>th</sup> Edition, Wiley & Sons, New York, N.Y. (1992); Katritzky, A. R. et al., eds., *Comprehensive Organic Functional Groups Transformations*, 1' Edition, Elsevier Science Inc., Tarrytown, N.Y. (1995); Larock, R. C., *Comprehensive Organic Transformations*, VCH Publishers, Inc., New York, N.Y. (1989), and references therein.

Compounds of the invention (IA) may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, *Wiley-Interscience*, New York, 2001, or other standard texts on the topic of synthetic organic chemistry.

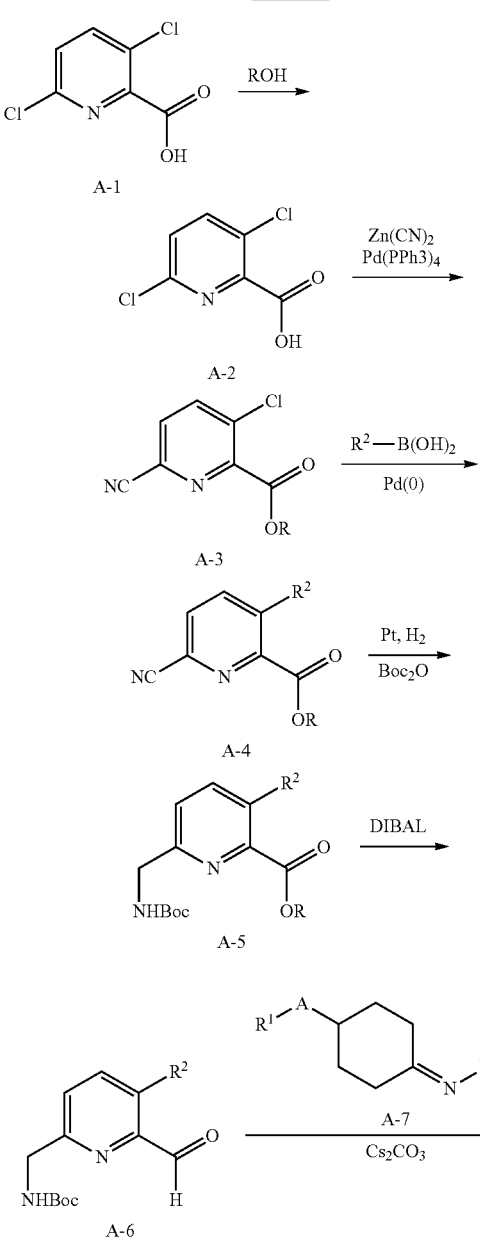

Scheme A

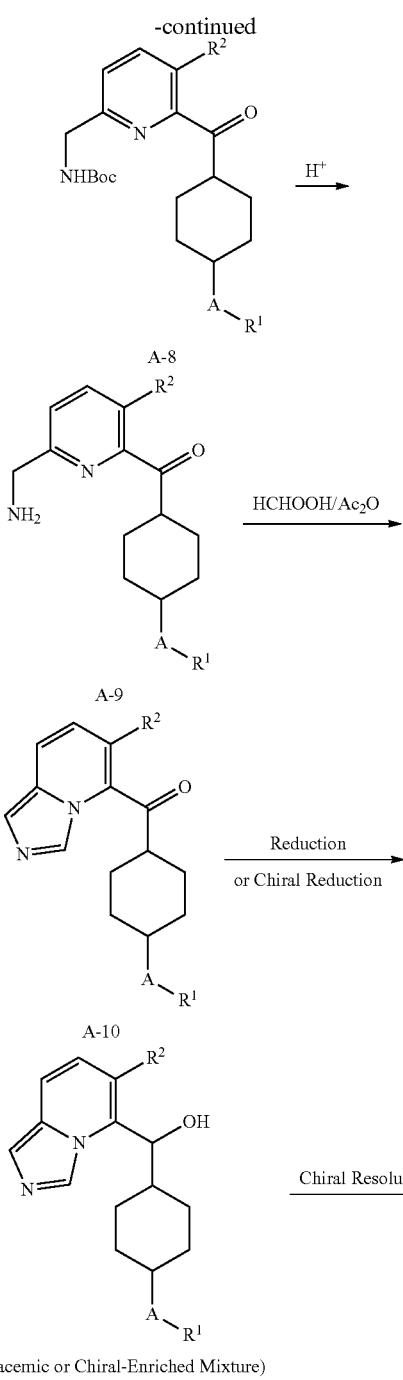

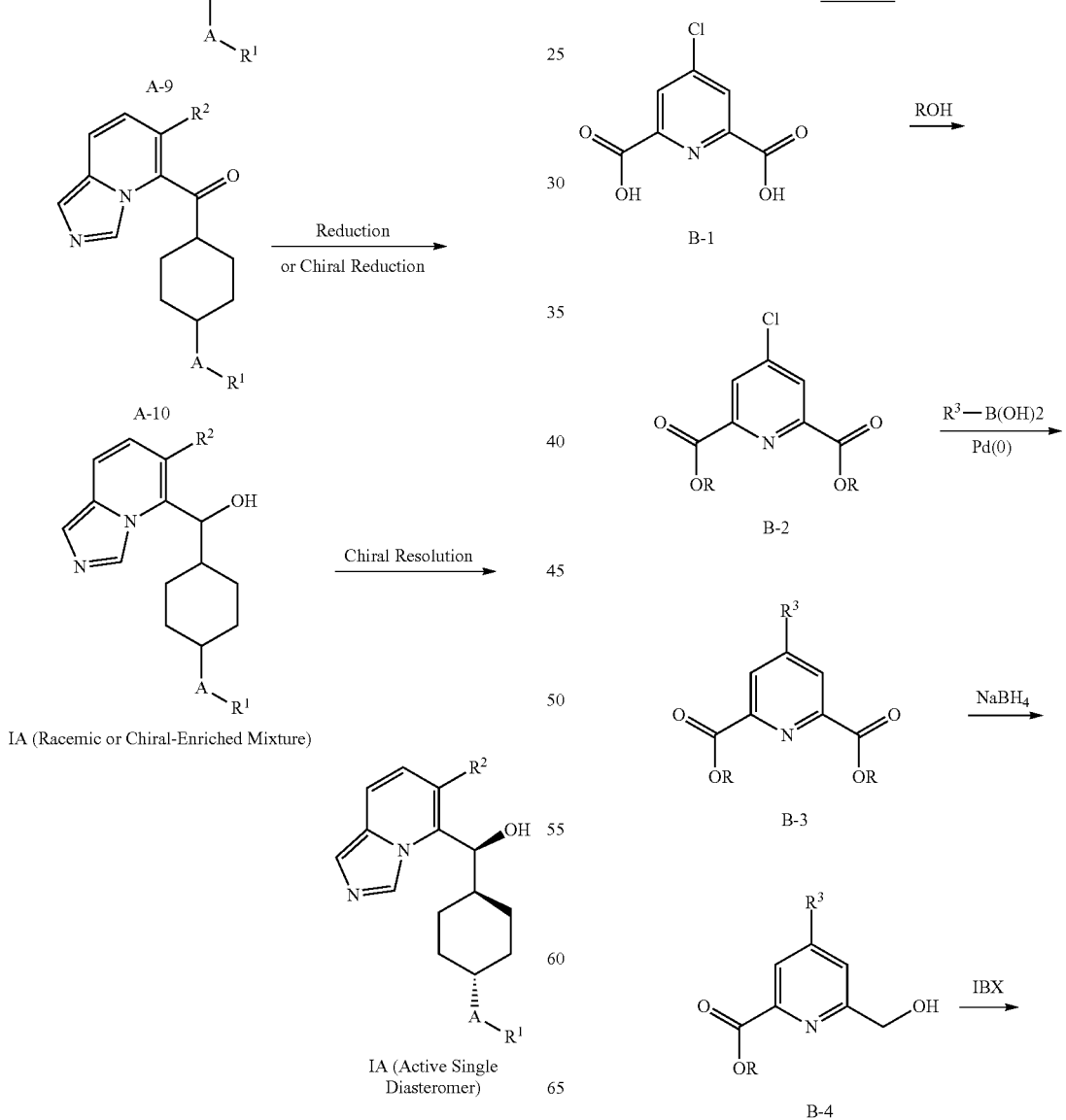

Compounds Iowa (A, $R^1$ and $R^2$ are defined as above) can be prepared by a procedure depicted in Scheme A. The commercially available Compound A-1 is converted into the 3,6-dichloro-2-carboxylate ester A-2 first. After selective replacement of 6-chloro atom by cyano group, the resulting 6-cyano-3-chloro-2-carboxylate ester pyridine A-3 undergoes Suzuki coupling to give the ester A-4 which is hydrogenated to give 6-Boc-aminomethyl-2-carboxylate ester pyridine A-5 in the simultaneous presence of $Boc_2O$ and platinum catalyst. Treatment of the ester A-5 with DIBAL produces the aldehyde A-6. Heating A-6 with hydrazone A-7 in the presence of cesium carbonate gives the key intermediate A-8. The following de-protection of Boc produces the free amine A-9 which is further cyclization into imidazo[1,5-a]pyridine ester A-10 is effected by treatment of HCOOH/$Ac_2O$. Reduction of Compound A-10 gives the racemic alcohol IA with sodium tetrahydroboride or chiral enriched alcohol IA with chiral borane. Further chiral separation yields single enantiomers.

-continued

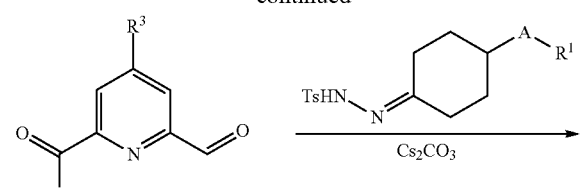
B-5

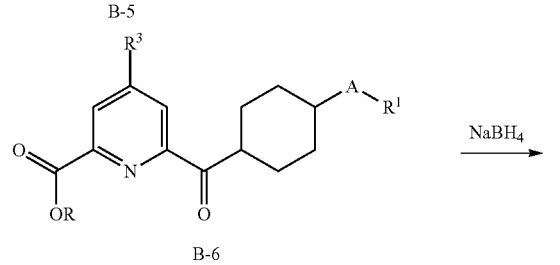
B-6

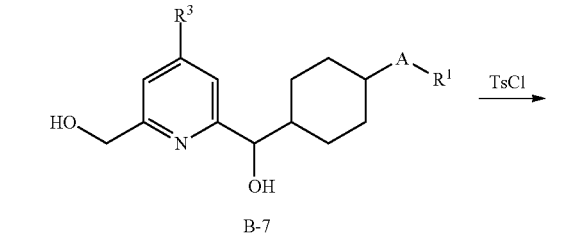
B-7

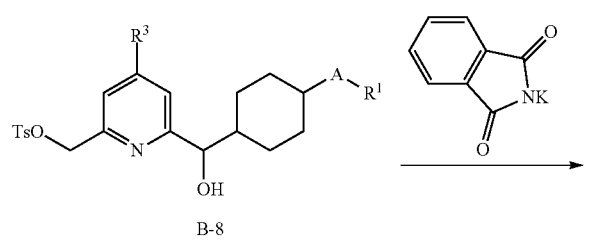
B-8

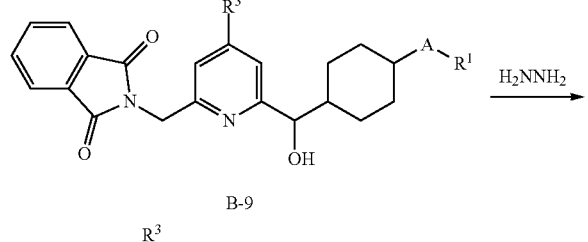
B-9

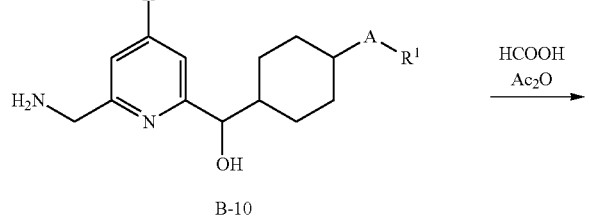
B-10

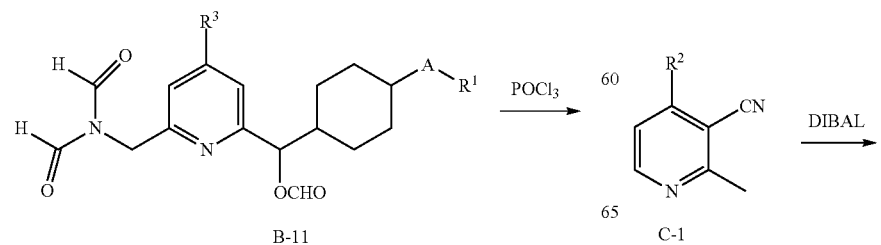
B-11

-continued

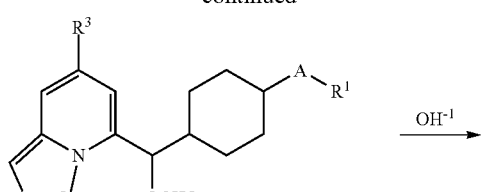
B-12

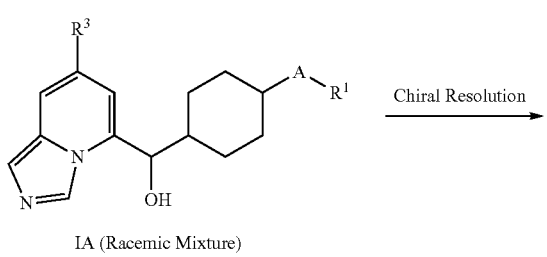
IA (Racemic Mixture)

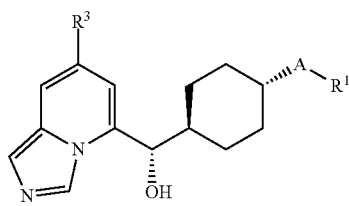
IA (Active Single Diasteromer)

Compounds Iowa (A, $R^1$ and $R^3$ are defined as above) can also be prepared by a similar procedure depicted in Scheme B. The commercially available Compound B-1 is converted into the 4-chloro-2,6-dicarboxylate ester pyridine B-2 first. B-2 undergoes Suzuki coupling to give dicarboxylate ester B-3 which is selectively reduced to 6-hydroxylmethyl-2-carboxylate ester pyridine B-4 with sodium tetrahydroboride. IBX oxidation of the alcohol B-4 gives 2-formyl-6-carboxylate ester pyridine B-5. Heating B-5 with hydrazone A-7 in the presence of cesium carbonate gives the key intermediate B-6 which is reduced into diol B-7 with excess sodium tetraborohydride. Selective tosylation of the diol B-7 offers the tosyl ester B-8. Replacement of tosyl ester with potassium 1,3-dioxoisoindolin-2-ide gives the ester B-9 which is converted into the amine B-10 with hydrazine hydrate. Treatment of B-10 in HCOOH/acetic anhydride gives the B-11 which is cyclizated with $POCl_3$ gives imidazo[1,5-a]pyridine B-12. Treatment of the ester B-12 with sodium hydroxide produces the racemic IA. Further chiral separation yields single enantiomers.

Scheme C

C-1

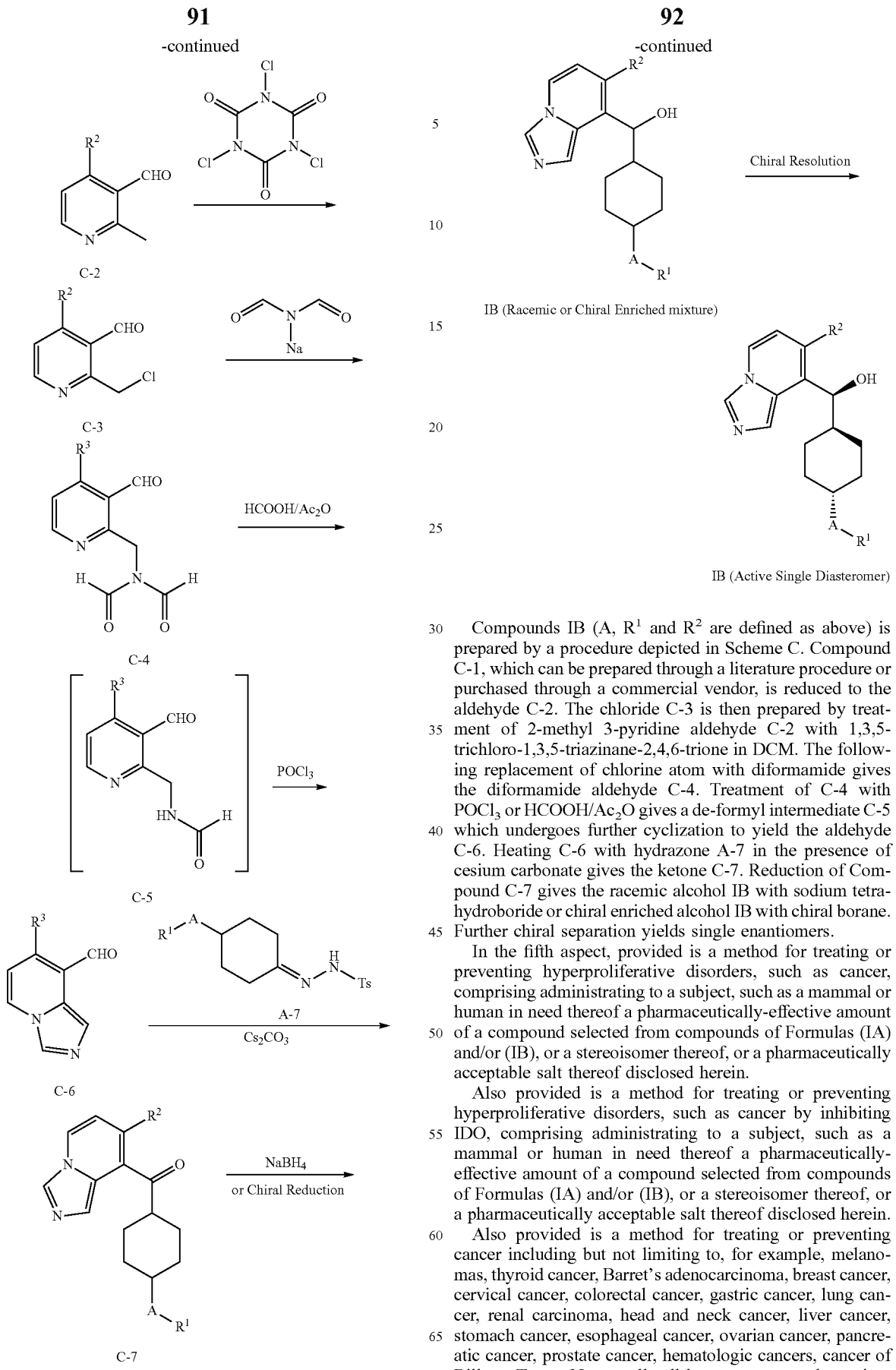

Compounds IB (A, $R^1$ and $R^2$ are defined as above) is prepared by a procedure depicted in Scheme C. Compound C-1, which can be prepared through a literature procedure or purchased through a commercial vendor, is reduced to the aldehyde C-2. The chloride C-3 is then prepared by treatment of 2-methyl 3-pyridine aldehyde C-2 with 1,3,5-trichloro-1,3,5-triazinane-2,4,6-trione in DCM. The following replacement of chlorine atom with diformamide gives the diformamide aldehyde C-4. Treatment of C-4 with $POCl_3$ or $HCOOH/Ac_2O$ gives a de-formyl intermediate C-5 which undergoes further cyclization to yield the aldehyde C-6. Heating C-6 with hydrazone A-7 in the presence of cesium carbonate gives the ketone C-7. Reduction of Compound C-7 gives the racemic alcohol IB with sodium tetrahydroboride or chiral enriched alcohol IB with chiral borane. Further chiral separation yields single enantiomers.

In the fifth aspect, provided is a method for treating or preventing hyperproliferative disorders, such as cancer, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof disclosed herein.

Also provided is a method for treating or preventing hyperproliferative disorders, such as cancer by inhibiting IDO, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof disclosed herein.

Also provided is a method for treating or preventing cancer including but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-samll-cell-lung cancer, endometrium cancer, blood cancer, large intestinal colon carcinoma, histiocytic lymphoma, lung adenocarcinoma, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof disclosed herein.

Also provided is a method for treating or preventing HIV/AIDS, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof disclosed herein.

Also provided is a method for enhancing the effectiveness of an anti-retroviral therapy, comprising administrating to a subject, such as a mammal or human in need thereof an anti-retroviral agent and a pharmaceutically-effective amount of a compound selected from compounds of Formulas (IA) and/or (IB), or a stereoisomer thereof, or a pharmaceutically acceptable salt thereof disclosed herein.

Also provided herein is a method of treating cancer responsive to inhibition of IDO and/or TDO comprising administering to a subject, such as a mammal or human, in need of treating for the cancer a pharmaceutically-effective amount of a compound selected from compounds of (IA) or (IB), or a stereoisomer thereof, or a pharmaceutically acceptable salt thereof disclosed herein, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-samll-cell-lung cancer, endometrium cancer, blood cancer, large intestinal colon carcinoma, histiocytic lymphoma, lung adenocarcinoma.

Also provided herein is a use of a compound selected from compounds of (IA) or (IB), or a stereoisomer thereof, or a pharmaceutically acceptable salt thereof disclosed herein in the manufracture of a medicament for the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-samll-cell-lung cancer, endometrium cancer, blood cancer, large intestinal colon carcinoma, histiocytic lymphoma, lung adenocarcinoma.

Also provided herein is a compound selected from compounds of (IA) or (IB), or a stereoisomer thereof, or a pharmaceutically acceptable salt thereof disclosed herein for use in the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-samll-cell-lung cancer, endometrium cancer, blood cancer, large intestinal colon carcinoma, histiocytic lymphoma, lung adenocarcinoma.

The compound selected from compounds of Formulas (IA) and/or (IB), or a stereoisomer thereof, or a pharmaceutically acceptable salt thereof may be employed alone or in combination with at least one other therapeutic agent for treatment. In some embodiments, the compound selected from compounds of Formulas (IA) and/or (IB), or a stereoisomer thereof, or a pharmaceutically acceptable salt thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-a and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); Trametinib (GSK1120212); Selumetinib (AZD6244); Binimetinib (MEK162); Pimasertib; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB 1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine;

antibiotics such as the enediyne antibiotics (e.g., calicheamicin, such as calicheamicin gammaII and calicheamicin omegaII (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantronc; vincristine; NAVELBINE® (vinorelbine); novantrone; teniposide; edatrexate; daunomycin; aminopterin; capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal gl and s, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goserelin; as well as troxacitabine (a 1,3-dioxolane nucleoside cytosine analog); (iv) protein kinase inhibitors such as MEK1/2 inhibitors, for example, trametinib, selumetinib, pimasertib and GDC-0973; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and $HER^2$ expression inhibitors; (viii) anti-retroviral protease inhibitors, such as lopinavir, indinavir, nelfinavir, amprenavir, darunavir and atazanavir; (ix) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (x) anti-angiogenic agents such as bevacizumab (AVASTIN®, Genentech); and (xi) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTI®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the compound selected from compounds of Formulas (IA) and/or (IB), stereoisomers thereof, and pharmaceutically acceptable salt thereofmay, for example, be selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, elotuzumab, epratuzumab, erlizumab, felvizumab, fontolizumab, gemtuzumab ozogamicin, inotuzumab ozogamicin, ipilimumab, labetuzumab, lintuzumab, mpdl13280A, matuzumab, medi4736, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, Pembroluzima, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tremelizumab, tucotuzumab celmoleukin, tucusituzumab, umavizumab, urtoxazumab, and visilizumab.

In the sixth aspect, provided is a pharmaceutical composition comprising a compound selected from compounds of Formulas (IA) and/or (IB), or a stereoisomer thereof, or a pharmaceutically acceptable salt thereof disclosed herein and a pharmaceutically-acceptable excipient, e.g., a carrier, a diluent, or a adjuvant.

Also provided herein is a composition comprising a compound selected from compounds of Formulas (IA) and/ or (IB), or a stereoisomer thereof, or a pharmaceutically acceptable salt thereof, and at least one pharmaceutically acceptable excipient.

The composition comprising a compound selected from compounds of Formulas (IA) and/or (IB), or a stereoisomer thereof, or a pharmaceutically acceptable salt thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound selected from Formulas (IA) and/or (IB), or a stereoisomer thereof, or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound selected from compounds of Formulas (IA) and/or (IB), or a stereoisomer thereof, or a pharmaceutically acceptable salt thereof disclosed herein can also be administered parenterally, in sterile liquid dosage forms, such as dispersions, suspensions or solutions. Other dosages forms that can also be used to administer the compound selected from Formulas (IA) and/or (IB), or a stereoisomer thereof, or a pharmaceutically acceptable salt thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, suitable oil, saline, aqueous dextrose (glucose), and related sugar solutions and glycols such as propylene glycol or polyethylene gycols can be Examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be Examples of suitable stabilizing agents. Citric acid and its salts and sodium EDTA can also be used as Examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The compound selected from compounds of Formulas (IA) and/or (IB), or a stereoisomer thereof, or a pharmaceutically acceptable salt thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound selected from compounds of Formulas (IA) and/or (IB), or a stereoisomer thereof, or a pharmaceutically acceptable salt thereof disclosed herein may be conveniently delivered in the form of an aerosol spray presentation from pressurized packs or nebulisers. The compound selected from compounds of Formulas (IA) and/or (IB), or a stereoisomer thereof, or a pharmaceutically acceptable salt thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound selected from compounds of Formulas (IA) and/or (IB), or a stereoisomer thereof, or a pharmaceutically acceptable salt thereof disclosed herein in at least one suitable propellant, selected, for example, from fluorocarbons and hydrocarbons.

For ocular administration, an ophthalmic preparation may be formulated with an appropriate weight percentage of a solution or suspension of the compound selected from compounds of Formulas (IA) and/or (IB), or a stereoisomer thereof, or a pharmaceutically acceptable salt thereof disclosed herein in an appropriate ophthalmic vehicle, such that the compound selected from compounds of Formulas (IA) and/or (IB), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the compound selected from compounds of Formulas (IA) and/or (IB), or a stereoisomer thereof, or a pharmaceutically acceptable salt thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 1(00) milligrams of the compound selected from compounds of Formulas (IA) and/or (IB), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound selected from compounds of Formulas (IA) and/or (IB), or a stereoisomer thereof, or a pharmaceutically acceptable salt thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound selected from compounds of Formulas (IA) and/or (IB), or a stereoisomer thereof, or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided a compound selected from compounds of Formulas (IA) and/or (IB), or a stereoisomer thereof, or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound selected from compounds of Formulas (IA) and/or (IB), or a stereoisomer thereof, or a pharmaceutically acceptable salt thereof are administered stepwise or in conjunction with at least one other therapeutic agent. When drugs are administered in physical combination, the dosage form and administration route should be selected depending on the compatibility of the combined drugs. Thus the term "coadministration" is understood to include the administration of at least two agents concomitantly or sequentially, or alternatively as a fixed dose combination of the at least two active components.

The compound selected from compounds of Formulas (IA) and/or (IB), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

EXAMPLES

The Examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following Examples, the abbreviations below are used:
AcOH Acetic acid
Aq Aqueous
Brine Saturated aqueous sodium chloride solution
Bn Benzyl
BnBr Benzyl Bromide
Boc Tert-butyloxycarbonyl
Cbz benzyloxycarbonyl
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DIBAL-H Diisobutylaluminium hydride
DMAP 4-N,N-dimethylaminopyridine
DMF N,N-dimethyl formamide
DMSO Dimethyl sulfoxide
EA or EtOAc Ethyl acetate
EtOH Ethanol
$Et_2O$ or ether Diethyl ether
g Grams
h or hr Hour
HATU O-(7-Azabenzotriazol-1-yl)-N,N,N',N'-tetramethyluronium hexafluorophosphate HBTU O-(7-Azabenzotriazol-1-yl)-N,N,N',N'-tetramethyl-
 uronium hexafluorophosphate
HCl Hydrochloric acid
Hex Hexane
HPLC High-performance liquid chromatography
IPA 2-propanol
i-PrOH Isopropyl alcohol
mg Milligrams
mL Milliliters
Mmol Millimole
MeCN Acetonitrile
MeOH Methanol
Min Minutes
ms or MS Mass spectrum
$Na_2SO_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF Tetrahydrofuran
TLC thin layer chromatography
Ts para-toluenesulfonyl
TBS tert-butyldimethylsilyl
μL Microliters

Example C: Synthesis of 8-substituted imidazo[1,5-a]pyridines

Example C101: (7-cyclopropylimidazo[1,5-a]pyridin-8-yl)(4-(4-methoxyphenyl)cyclohexyl)methanol

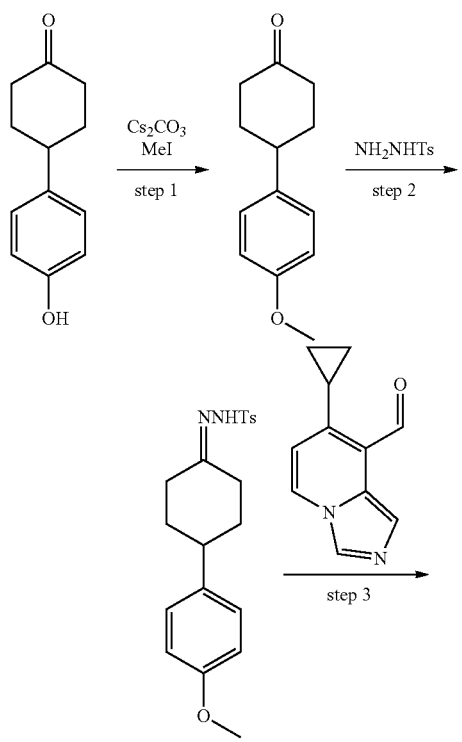

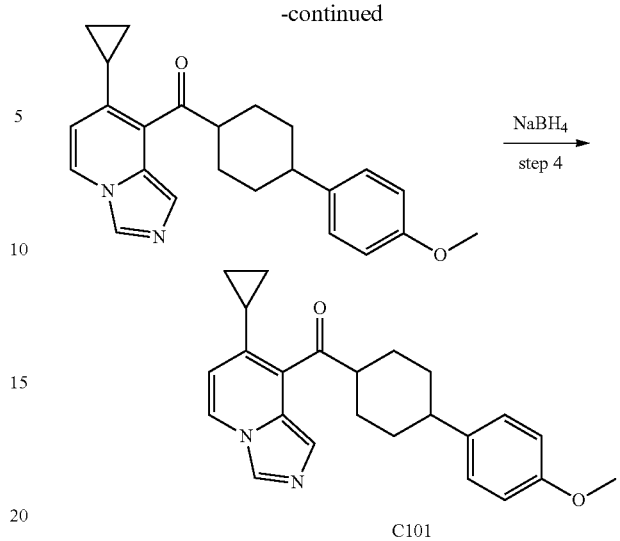

Step 1: 4-(4-methoxyphenyl)cyclohexan-1-one

To a solution of 4-(4-hydroxyphenyl)cyclohexan-1-one (10 g, 52.6 mmol) in DMF (60 mL) was added $Cs_2CO_3$ (34 g, 105.2 mmol) and MeI (4.87 mL). The mixture was stirred overnight at r.t. The solid was filtered and to the filtrate was added $H_2O$ (200 mL), extracted with EA (100 mL×2). The organic layer was washed with brine (100 mL×2), dried over with $Na_2SO_4$, filtered and concentrated to give the crude product (11.3 g) as a white solid, which was used for the next step without further purification. $^1$H NMR (400 MHz, DMSO-$d_6$) $\delta_H$ 7.21 (d, J=8.4 Hz, 2H), 6.86 (d, J=8.4 Hz, 2H). 3.72 (s, 3H), 2.96-3.03 (m, 1H), 2.50-2.61 (m, 2H), 2.23-2.27 (m, 2H), 2.01-2.05 (m, 2H) and 1.80-1.85 (m, 2H).

Step 2: N'-(4-(4-methoxyphenyl)cyclohexylidene)-4-methylbenzenesulfonohydrazide

To a solution of 4-(4-methoxyphenyl)cyclohexan-1-one (10.7 g, 52.5 mmol) in MeOH (70 mL) was added 4-methylbenzenesulfonohydrazide (9.8 g, 52.5 mmol). The mixture was stirred overnight at r.t. under $N_2$. Water (70 mL) was added to the mixture, the solid was filtered and dried to give the product (17.2 g, 87.8%) as a white solid. $^1$H NMR (400 MHz, DMSO-$d_6$) $\delta_H$ 10.16 (s, 1H), 7.74 (d, J=8.2 Hz, 2H), 7.40 (d, J=7.6 Hz, 2H), 7.13 (d, J=8.2 Hz, 2H), 6.84 (d, J=7.6 Hz, 2H), 3.70 (s, 3H), 2.88-2.92 (m, 1H), 2.69-2.76 (m, 1H), 2.39 (s, 3H), 2.23-2.25 (m, 2H), 1.86-1.95 (m, 3H) and 1.40-1.52 (m, 2H).

Step 3: (7-cyclopropylimidazo[1,5-a]pyridin-8-yl)(4-(4-methoxyphenyl)cyclohexyl)methanone To a solution of 7-cyclopropylimidazo[1,5-a]pyridine-8-carbaldehyde (2 g, 10.7 mmol) in 1,4-dioxane (70 mL) was added N'-(4-(4-methoxyphenyl)cyclohexylidene)-4-methylbenzenesulfonohydrazide (6 g, 16.05 mmoL) and $Cs_2CO_3$ (5.2 g, 16.05 mmol). The mixture was stirred overnight at 100° C. under $N_2$. The solid was filtered and the filtrate was further purified by column chromatography, eluting with EA:PE=1:1-1:0 to give the product (1.8 g), which was further purified by prepare HPLC to give product (810 mg, 20%) as a white solid. $^1$H NMR (DMSO-$d_6$) $\delta_H$ 8.35 (s, 1H), 8.32 (d, J=7.6 Hz, 1H), 7.11-7.14 (m, 3H), 6.81-6.85 (m, 2H), 6.23 (d, J=7.6 Hz, 1H), 3.71 (s, 3H), 3.15-3.17 (m, 1H), 2.40-2.47 (m, 1H), 2.01-2.05 (m, 2H), 1.80-1.83 (m, 3H), 1.44-1.58 (m, 4H), 0.95-1.01 (m, 2H) and 0.77-0.81 (m, 2H).

Step 4: (7-cyclopropylimidazo[1,5-a]pyridin-8-yl)(4-(4-methoxyphenyl)cyclohexyl)methanol

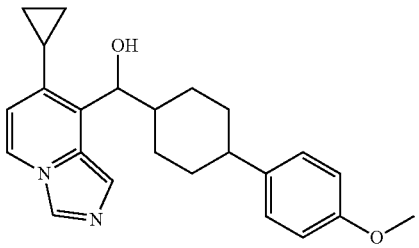

To a solution of (7-cyclopropylimidazo[1,5-a]pyridin-8-yl)(4-(4-methoxyphenyl)cyclohexyl)methanone (810 mg, 2.2 mmol) in MeOH (80 mL) was added NaBH$_4$ (167 mg, 4.4 mmol). The mixture was stirred for 2 h at r.t, the solvent was removed under vacuo. H$_2$O (50 ml) was added to the residue, the solid was filtered and dried to give the product (580 mg, 86%) as a white solid. $^1$H NMR (400 MHz, DMSO-d$_6$) $\delta_H$ 8.21 (s, 1H), 8.11 (d, J=6.8 Hz, 1H), 7.43 (s, 1H), 7.10 (d, J=8.4 Hz, 2H), 6.80 (d, J=8.4 Hz, 2H), 6.16 (d, J=6.8 Hz, 1H), 5.32 (d, J=3.2 Hz, 1H), 4.96 (dd, J=3.2, 8.0 Hz, 1H), 3.69 (s, 3H), 2.30-2.39 (m, 2H), 2.17-2.19 (m, 1H), 1.98-2.01 (m, 1H), 1.81-1.85 (m, 1H), 1.65-1.67 (m, 1H), 1.19-1.41 (m, 5H), 0.88-0.94 (m, 2H), and 0.69-0.71 (m, 2H).

Example C101a and C101b: (S)-(7-cyclopropylimidazo[1,5-a]pyridin-8-yl)(4-(4-methoxyphenyl)cyclohexyl)methanol and (R)-(7-cyclopropylimidazo[1,5-a]pyridin-8-yl)(4-(4-methoxyphenyl)cyclohexyl)methanol

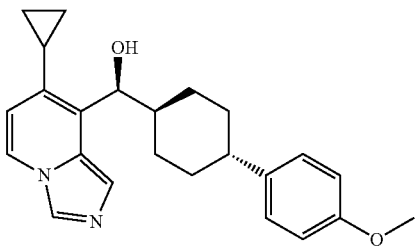

Fast isomer in chiral IC HPLC
Eluting reagent: Hex (0.1% DEA): EtOH = 60:40 (v/v)

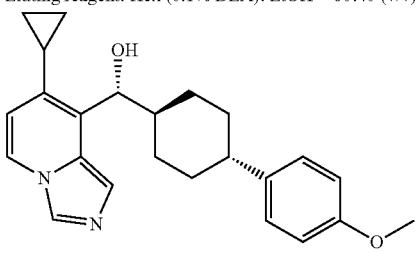

Slow isomer in chiral IC HPLC
Eluting reagent: Hex (0.1% DEA): EtOH = 60:40 (v/v)

Each enantiomer of racemic C101a and C101b was separated using preparative HPLC on a Chiralpak IC with Hex (0.1% DEA):EtOH=60:40 as an eluent. The first one enantiomer eluted at the retention time of 3.100 min, which was dissolved in DCM (5 mL), and HCl in EA(3N, 3 mL) was added and stirred at r.t for 1 h, the solid was filtered to give product as white solid, $^1$H NMR (DMSO-d$_6$) δ 9.40 (s, 1H), 8.36 (d, J=7.6 Hz, 1H), 8.01 (s, 1H), 7.10 (d, J=8.4 Hz, 2H), 6.82 (d, J=8.4 Hz, 2H), 6.60 (d, J=7.6 Hz, 1H), 5.71 (brs, 1H), 5.06 (d, J=8.0 Hz, 1H), 3.69 (s, 3H), 2.20-2.43 (m, 3H), 1.81-1.93 (m, 2H), 1.68-1.71 (m, 1H), 1.21-1.44 (m, 5H), 1.03-1.08 (m, 2H) and 0.79-0.86 (m, 2H), MS (ESI) m/e [M+1]$^+$377; and the other enantiomer eluted at the retention time of 5.765 min, which was dissolved in DCM (5 ml), and HCl in EA(3N, 3 mL) was added and stirred at r.t for 1 h, the solid was filtered to give product as white solid, $^1$H NMR (DMSO-d$_6$) $\delta_H$ 9.25 (s, 1H), 8.33 (d, J=7.2 Hz, 1H), 7.95 (s, 1H), 7.10 (d, J=8.4 Hz, 2H), 6.80 (d, J=8.4 Hz, 2H), 6.55 (d, J=7.2 Hz, 1H), 5.65 (brs, 1H), 5.04 (d, J=7.6 Hz, 1H), 2.69 (s, 3H), 2.32-2.49 (m, 2H), 2.22-2.25 (m, 2H), 1.82-1.93 (m, 2H), 1.67-1.71 (m, 1H), 1.21-1.41 (m, 5H), 1.00-1.06 (m, 2H) and 0.76-0.84 (m, 2H), MS (ESI) m/e [M+1]$^+$=377;

The absolute stereochemistry of the more potent compound C101a in enzymatic and cellular assays is assigned as (S)-configuration on the chiral α-carbon atom, and the relative stereochemistry on cyclohexane is assigned as trans-configuration based on its cocrystal structure with IDO1 enzyme.

Example C102: (4-(4-chlorophenyl)cyclohexyl)(7-cyclopropylimidazo[1,5-a]pyridin-8-yl)methanol

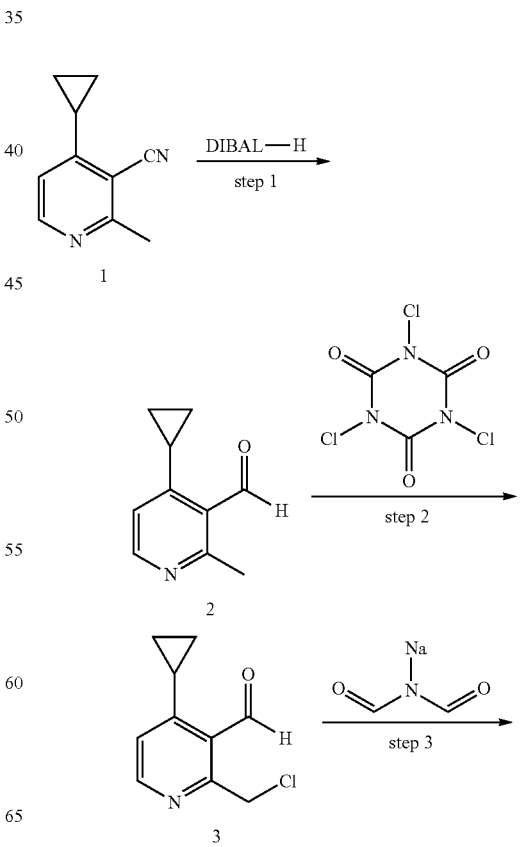

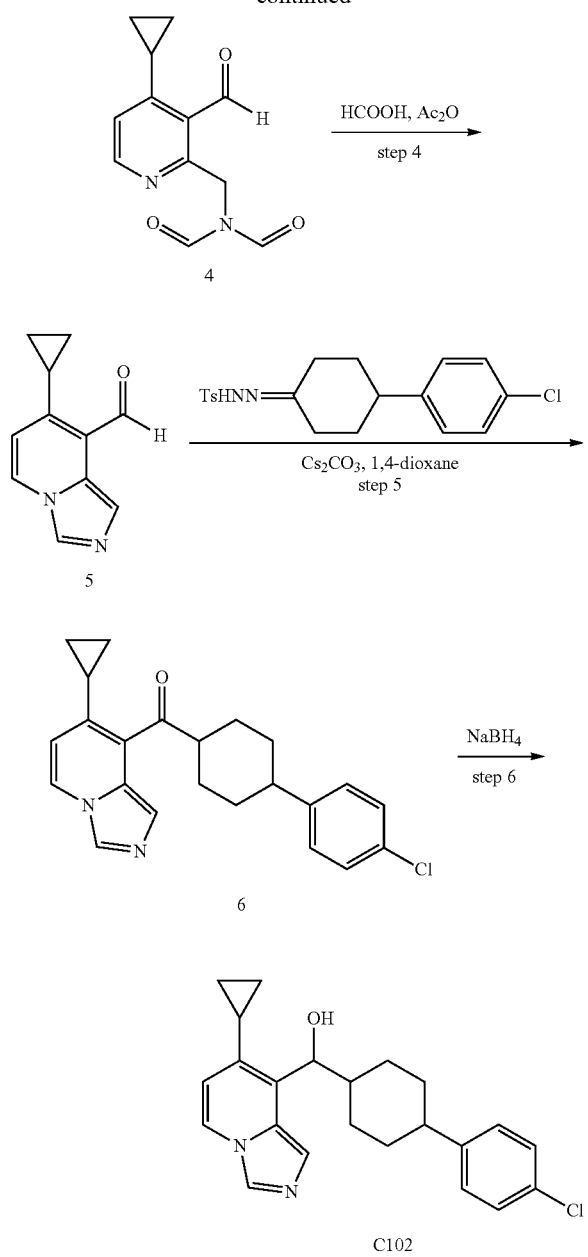

Step 2:
2-(chloromethyl)-4-cyclopropylnicotinaldehyde

To a solution of 4-cyclopropyl-2-methylnicotinaldehyde (60 g, 373 mmol) in DCM (500 mL) was slowly added 1,3,5-trichloro-1,3,5-triazinane-2,4,6-trione (129.8 g, 559.5 mmol) at 0° C. The mixture was stirred overnight at r.t, the precipitate was filtered and the filtrate was washed with aq.NaHCO$_3$ (100 mL×3). The organic layer was dried over with Na$_2$SO$_4$, filtered and concentrated to give the crude product (60 g, crude) as brown oil, which was used to the next step without further purification.

Step 3: N-((4-cyclopropyl-3-formylpyridin-2-yl)methyl)-N-formylformamide

To a solution of 2-(chloromethyl)-4-cyclopropylnicotinaldehyde (60 g, 306 mmol) in DMF (150 mL) was added sodium diformylamide (58 g, 612 mmol). The mixture was stirred overnight at r.t. The solid was filtered and the filtrate was concentrated to give crude product, which was purified by column chromatography, eluting with PE:EA=0~1:1 to give the product (35 g, 49%) as a yellow solid. $^1$H NMR (DMSO-d$_6$) $\delta_H$ 10.85 (s, 1H), 9.20 (s, 2H), 8.44 (d, J=5.2 Hz, 1H), 7.08 (d, J=5.2 Hz, 1H), 5.05 (s, 2H), 2.64-2.73 (m, 1H), 1.11-1.19 (m, 2H) and 0.89-0.94 (m, 2H), MS (ESI) m/e [M+1]$^+$233;

Step 4: 7-Cyclopropylimidazo[1,5-a]pyridine-8-carbaldehyde

A mixture of Ac$_2$O (100 mL) and HCOOH (100 mL) was stirred for 4 h at 50° C., after cooling to room temperature, N-((4-cyclopropyl-3-formylpyridin-2-yl)methyl)-N-formylformamide (35 g, 151 mmol) was added and stirred overnight at r.t. The solvent was removed under vacuo, which was adjusted pH=13 with aq. Na$_2$CO$_3$, extracted with DCM (200 ml×3), concerned and the crude product was further purified by column chromatography, eluting with EA:PE=1:1 to give the product (17 g, 61%) as a yellow solid. $^1$H NMR (DMSO-d$_6$) $\delta_H$ 10.73 (s, 1H), 8.54 (d, J=7.6 Hz, 1H), 8.34 (s, 1H), 7.80 (s, 1H), 6.36 (d, J=7.6 Hz, 1H), 2.84-2.91 (m, 1H), 1.12-1.75 (m, 2H) and 0.96-1.01 (m, 2H), MS (ESI) m/e [M+1]$^+$=187:

Step 5: (4-(4-chlorophenyl)cyclohexyl)(7-cyclopropylimidazo[1,5-a]pyridin-8-yl)methanone To a solution of 7-cyclopropylimidazo[1,5-a]pyridine-8-carbaldehyde (2.0 g, 10.7 mmol) in 1,4-dioxane (0.2 L) was added 7-cyclopropylimidazo[1,5-a]pyridine-8-carbaldehyde (5.77 g, 16 mmol) and Cs$_2$CO$_3$ (7 g, 21.4 mmol) at room temperature, and the mixture was heated at 100° C. for overnight. The solvent was evaporated under reduced pressure and water (100 mL) was added, extracted with ethyl acetate (50 ml×3), combined the organic layer, the solvent was evaporated under reduced pressure and the residue was purified by column chromatography (PE:EA=1:1 to EA) to give crude product as a solid (1.2 g, 31.57% yield), which was used for next step without further purification.

Step 1: 4-cyclopropyl-2-methylnicotinaldehyde

To a solution of 4-cyclopropyl-2-methylnicotinonitrile (100 g, 63.3 mmol) in DCM (1 L) was added DIBAL-H (1.5 mol) by dropwise at −60° C. for about 3 h. After starting material was disappeared completely, the mixture was poured into HCl/ice solution. It was then adjusted pH=13 with NaOH. The mixture was extracted with EA (1 L×2). The organic layer was dried over with Na$_2$SO$_4$, filtered and concerned in vacuo to give crude product, which was purified by silica gel on chromatography column (eluting with EA:PE=1:1) to give the product (60 g, 59%) as a brown oil. $^1$H NMR (DMSO-d$_6$) $\delta_H$ 10.73 (s, 1H), 8.43 (d, J=4.2 Hz, 1H), 6.94 (d, J=4.2 Hz, 1H), 2.67-2.72 (m, 4H), 1.08-1.14 (m, 2H) and 0.83-0.88 (m, 2H).

Step 6: (4-(4-chlorophenyl)cyclohexyl)(7-cycloro-pylimidazo[1,5-a]pyridin-8-yl)methanol

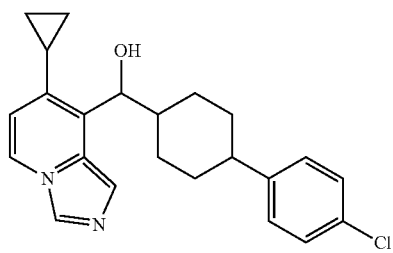

To a solution of crude (4-(4-chlorophenyl)cyclohexyl)(7-cyclopropylimidazo[1,5-a]pyridin-8-yl)methanone (0.5 g, 1.32 mmol) in EtOH (20 mL) was added NaBH$_4$ (100 mg, 2.64 mmol) at room temperature, and the mixture was stirred overnight. Then the solvent was evaporated under reduced pressure and water (50 mL) was added, extracted with ethyl acetate (50 ml×3), combined the organic layer, evaporated the solvent under reduced pressure and the residue was purified by column chromatography (PE:EA=1:1 to EA) to give crude product, which was washed with methol to give product as a white solid (230 mg, 46% yield). $^1$H NMR (400 MHz, DMSO-d$_6$) δ$_H$ 8.21 (s, 1H), 8.11 (d, 1H, J=7.2 Hz), 7.43 (s, 1H), 7.29 (d, J=8.4 Hz, 2H), 7.23 (d, J=8.4 Hz, 2H), 6.16 (d, J=7.2 Hz, 1H), 5.33 (d, J=3.6 Hz, 1H), 4.96 (dd, J=8.4, 3.6 Hz, 1H), 2.46-2.49 (m, 1H), 2.31-2.33 (m, 1H), 2.16-2.18 (m, 1H), 1.99-2.01 (m, 1H), 1.83-1.86 (m, 1H), 1.66-1.68 (min, 1H), 1.40-1.44 (m, 2H), 1.11-1.30 (m, 4H), 0.91-0.94 (m, 2H), 0.69-0.71 (m, 2H). LC-MS (M+H)$^+$=379.

Example C102a and C102b: (S)-(4-(4-chlorophenyl)cyclohexyl)(7-cyclopropylimidazo[1,5-a]pyridin-8-yl)methanol and (R)-(4-(4-chlorophenyl)cyclohexyl)(7-cyclopropylimidazo[1,5-a]pyridin-8-yl)methanol

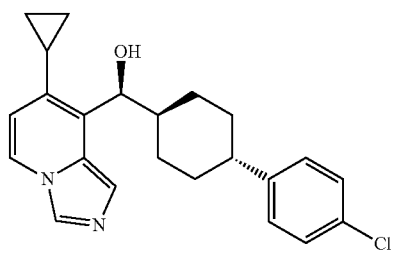

Fast isomer in CHIRALPAK IC-3
Eluting reagent: Hex (0.1% DEA): EtOH = 60:40

-continued

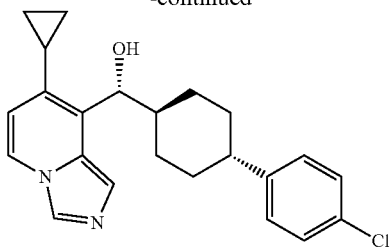

Slow isomer in CHIRALPAK IC-3
Eluting reagent: Hex (0.1% DEA): EtOH = 60:40

Each enantiomer of racemic C102a and C102b was separated using preparative HPLC on a CHIRAL PAK IC-3 with Hex (0.1% DEA): EtOH=60:40 as an eluent. The enantiomeric excesses were determined by using HPLC on a CHIRAL PAK IC-3 with Hex (0.1% DEA):EtOH=60:40 as an eluent at a flow rate of 1.0 mL/min. The first one enantiomer eluted at the retention time of 1.431 min, and then was dissolved in 4 M HCl(gas)/EA and stirred for 0.5 h, concerned in vacuo to give C102a, $^1$H NMR (400 MHz, DMSO-d$_6$) δ$_H$ 9.33 (s, 1H), 8.34 (d, J=7.6 Hz, 1H), 7.98 (s, 1H), 7.30 (d, J=8.4 Hz, 2H), 7.22 (d, J=8.4 Hz, 2H), 6.58 (d, J=7.6 Hz, 1H), 5.69 (s, 1H), 5.05 (d, J=8.4 Hz, 1H), 2.47-2.40 (m, 1H), 2.24-2.25 (m, 2H), 1.83-1.92 (m, 1H), 1.72-1.74 (m, 1H), 1.46-1.22 (m, 6H), 1.04 (m, 2H), 0.81 (m, 2H); and the other enantiomer eluted at the retention time of 2.432 min, and then was dissolved in 4 M HCl(gas)/EA and stirred for 0.5 h, concerned in vocuo to give C102b, $^1$H NMR (400 MHz, DMSO-d$_6$) δ$_H$ 9.29 (s, 1H), 8.34 (d, J=7.6 Hz, 1H), 7.95 (s, 1H), 7.29 (d, J=8.4 Hz, 2H), 7.21 (d, J=8.4 Hz, 2H), 6.57 (d, J=7.6 Hz, 1H), 5.68 (s, 1H), 5.04 (d, J=8.0 Hz, 1H), 2.47-2.40 (m, 1H), 2.24-2.25 (m, 2H), 1.83-1.92 (m, 1H), 1.72-1.74 (m, 1H), 1.46-1.22 (m, 6H), 1.02-1.04 (m, 2H), 0.79-0.81 (m, 2H); The absolute configurations of chiral carbons in C102a and C102b are tentatively assigned as (S) and (R) respectively based on assumption that the binding model of the more potent isomer C102a is the same as that of C101a with IDO1 enzyme, and the relative stereochemistry on cyclohexane is assigned as trans configuration on the cyclohexane.

Example C103 was prepared with the same procedure as example C102.

Example C103: (7-cyclopropylimidazo[1,5-a]pyridin-8-yl)(4-(4-(2-methoxyethoxy)phenyl)cyclohexyl)methanol

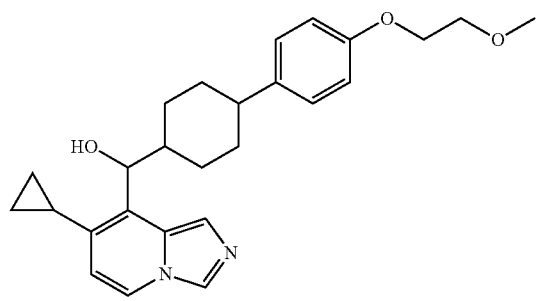 [SMILES: COCCOc1ccc(C2CCC(C(O)c3c(C4CC4)ccn4cncc34)CC2)cc1]

$^1$H NMR (DMSO-d$_6$) δ$_H$ 8.21 (s, 1H), 8.11 (d, J=7.2 Hz, 1H), 7.43 (s, 1H), 7.10 (d, J=8.4 Hz, 2H), 6.80 (d, J=8.4 Hz,

2H), 6.16 (d, J=7.2 Hz, 1H), 5.30 (d, J=3.6 Hz, 1H), 4.96 (dd, J=3.6, 8.0 Hz, 1H), 4.00-4.03 (m, 2H), 3.60-3.63 (m, 3H), 3.29 (s, 3H), 2.30-2.39 (m, 2H), 2.14-2.17 (m, 1H), 1.95-2.00 (m, 1H), 1.81-1.85 (m, 1H), 1.64-1.68 (m, 1H), 1.18-1.41 (m, 5H), 0.88-0.96 (m, 2H) and 0.67-0.73 (m, 2H). MS (ESI) m/e [M+1]$^+$=422.

Examples C103a and C103b: (S)-(7-cyclopropylimidazo[1,5-a]pyridin-8-yl)((1r,4S)-4-(4-(2-methoxyethoxy)phenyl)cyclohexyl)methanol and (R)-(7-cyclopropylimidazo[1,5-a]pyridin-8-yl)((1r,4R)-4-(4-2-methoxyethoxy)phenyl)cyclohexyl)methanol

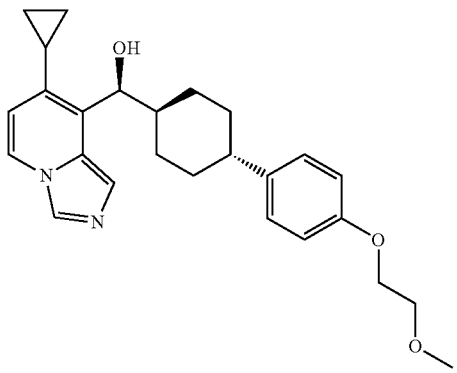

Fast isomer in chiral Cellulose-SB HPLC
Eluting reagent: Hex:EtOH = 80:20(v/v)

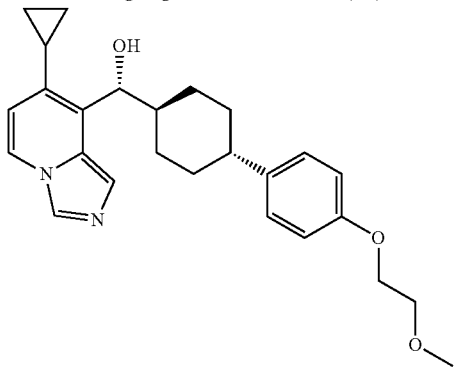

Slow isomer in chiral Cellulose-SB HPLC
Eluting reagent: Hex:EtOH = 80:20(v/v)

Each enantiomer of racemic C103a and C103b was separated using preparative HPLC on a CHIRALART Cellulose-SB with Hex:EtOH=80:20 as an eluent. The enantiomeric excesses were determined by using HPLC on a CHIRAL PAK IC-3 with Hex (0.1% DEA):EtOH=80:20 as an eluent at a flow rate of 1 mL/min. The first one enantiomer eluted at the retention time of 6.12 min (C103a), which was dissolved in THF (10 mL), Ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid. MS (ESI) m/e [M+1]$^+$422; $^1$H NMR (DMSO-d$_6$) δ 9.43 (s, 1H), 8.36 (d, 1H, J=7.6 Hz), 8.03 (s, 1H), 7.08 (d, 2H, J=8.4 Hz), 6.81 (d, 2H, J=8.4 Hz), 6.61 (d, 1H, J=7.6 Hz), 5.71 (brs, 1H), 5.06 (d, 1H, J=7.6 Hz), 4.00-4.03 (m, 2H), 3.60-3.63 (m, 2H), 3.29 (s, 3H), 2.20-2.40 (m, 3H), 1.82-1.92 (m, 2H), 1.68-1.73 (m, 1H), 1.18-1.43 (m, 5H), 1.03-1.06 (m, 2H) and 0.79-0.83 (m, 2H); and the other enantiomer eluted at the retention time of 9.42 min (C103b), which was dissolved in THF (10 mL), Ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid, MS (ESI) m/e [M+1]$^+$422; $^1$H NMR (DMSO-d$_6$) δ 9.41 (s, 1H), 8.36 (d, 1H, J=7.6 Hz), 8.02 (s, 1H), 7.08 (d, 2H, J=8.8 Hz), 6.81 (d, 2H, J=8.8 Hz), 6.61 (d, 1H, J=7.6 Hz), 5.71 (brs, 1H), 5.06 (d, 1H, J=8.0 Hz), 4.00-4.03 (m, 2H), 3.60-3.63 (m, 2H), 3.29 (s, 3H), 2.20-2.40 (m, 3H), 1.82-1.92 (m, 2H), 1.68-1.73 (m, 1H), 1.18-1.43 (m, 5H), 1.03-1.06 (m, 2H) and 0.79-0.83 (m, 2H). The absolute configurations of chiral carbons in C103a and C103b are tentatively assigned as (S) and (R) respectively based on assumption that the binding model of the more potent isomer C103a is the same as that of C101a with IDO1 enzyme, and the relative stereochemistry on cyclohexane is assigned as trans configuration on the cyclohexane Example C104: 4-(4-((7-cyclopropylimidazo[1,5-a]pyridin-8-yl) hydroxy)methyl)cyclohexyl)phenol

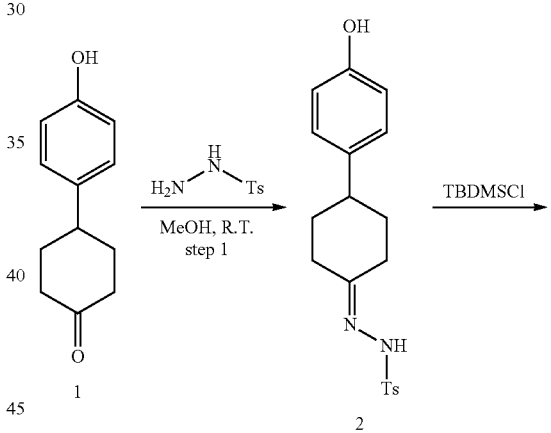

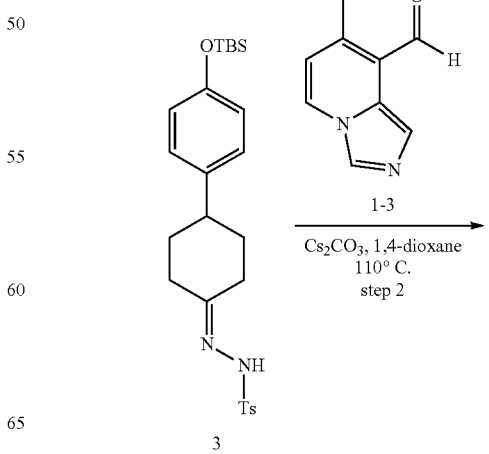

-continued

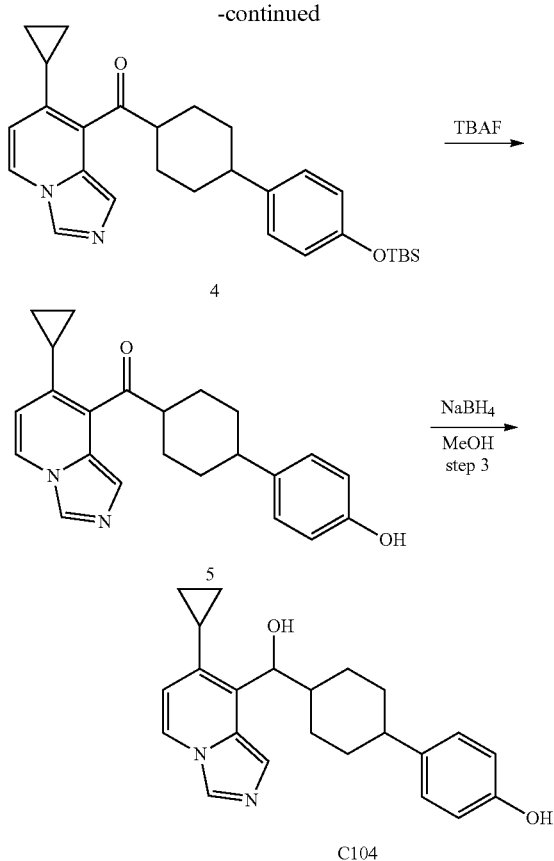

Step 1: N'-(4-(4-hydroxyphenyl)cyclohexylidene)-4-methylbenzenesulfonohydrazide

To a solution of 4-(4-hydroxyphenyl)cyclohexan-1-one (10 g, 52.63 mmol) in methanol (200 mL) was added 4-methylbenzenesulfonohydrazide (9.79 g, 52.63 mmol) at room temperature, and the mixture was stirred for 5 hours, then filtered to give the product as a white solid (15 g in 79% yield). MS (ESI) m/e [M+1]$^+$=359.

Step 2: N'-(4-(4-((tert-butyldimethylsilyl)oxy)phenyl)cyclohexylidene)-4-methylbenzenesulfonohydrazide N'-(4-(4-hydroxyphenyl)cyclohexylidene)-4-methylbenzenesulfonohydrazide (2 g) was dissolved in DMF (20 mL), and TBDMSCl (1.09 g, 7.26 mmol) and imidazole (0.76 g, 11.18 mmol) were added, the mixture was stirred at 70° C. overnight. TLC (PE:EA=3:1, Rf=0.5) showed the reaction was completed. H$_2$O (100 ml) was added to the mixture, extracted with EA (50 ml×3), combined organic layer, dried over Na$_2$SO$_4$, filtered and concentrated to give crude product, which was purified by silica gel chromatography (PE: EA=20:1-6:1) to give compound N'-(4-(4-((tert-butyldimethylsilyl)oxy)phenyl)cyclohexylidene)-4-methylbenzenesulfonohydrazide (2.6 g, 99%) as a white solid.

Step 3: (4-(4-((tert-butyldimethylsilyl)oxy)phenyl)cyclohexyl)(7-cyclopropylimidazo-[1,5-a]pyridin-8-yl)methanone To a solution of 7-cyclopropylimidazo[1,5-a]pyridine-8-carbaldehyde (1 g, 5.37 mmol) in 1,4-dioxane (50 mL) was added N'-(4-(4-((tert-butyldimethylsilyl)oxy)phenyl)cyclohexylidene)-4-methylbenzenesulfonohydrazide (3.8 g, 8 mmol) and Cs$_2$CO$_3$ (2.6 g, 8 mmol) at room temperature and the mixture was heated at 100° C. for overnight. The solvent was evaporated under reduced pressure and water (100 mL) was added, extracted with ethyl acetate (50 ml×3), combined the organic layer, evaporated the solvent and the residue was purified by column chromatography (PE:EA=1:1 to EA) to give crude product as a solid (0.3 g in 12% yield), which was used for the next step without further purification. MS (ESI) m/e [M+1]$^+$=475.

Step 4: (7-cyclopropylimidazo[1,5-a]pyridin-8-yl)(4-(4-hydroxyphenyl)cyclohexyl)methanone To a solution of (4-(4-((tert-butyldimethylsilyl)oxy)phenyl)cyclohexyl)(7-cyclopropylimidazo-[1,5-a]pyridin-8-yl)methanone (1.0 g, 2.1 mmol) in THF (20 mL) was added a 1 M solution of tetrabutylammonium fluoride in THF (5 mL, 5 mmol) at 22-24° C. The solution was stirred for 2 h and diluted with EtOAc (20 mL). The organic layer was separated and washed with H$_2$O (30 ml×3), extract with EtOAc (50 ml×2), and the organic layers were combined and dried over Na$_2$SO$_4$. The solvent was evaporated in vacuo to give (7-cyclopropylimidazo[1,5-a]pyridin-8-yl)(4-(4-hydroxyphenyl)cyclohexyl)methanone (303 mg, 40%) as yellow solid. MS (ESI) m/e [M+1]$^+$=361.

Step 5: 4-(4-((7-cyclopropylimidazo[1,5-a]pyridin-8-yl)(hydroxy)methyl)cyclohexyl)phenol

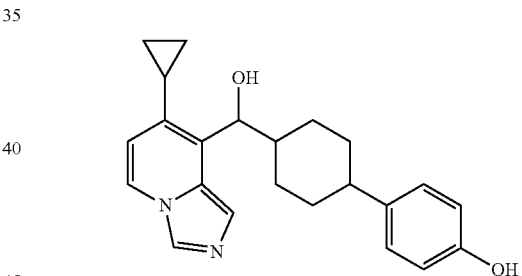

To a solution of (7-cyclopropylimidazo[1,5-a]pyridin-8-yl)(4-(4-hydroxyphenyl)cyclohexyl)methanone (303 mg, 0.84 mmol) in methol (50 mL) was added NaBH$_4$ (64 mg, 1.68 mmol) at room temperature, and the mixture was stirred overnight. Then the solvent was evaporated under reduced pressure and water (50 mL) was added, extracted with ethyl acetate (50 ml×3) and combined the organic layer, evaporated the solvent and the residue was purified by column chromatography (PE:EA=1:1 to EA) to give a crude product, which was purified with Pre-HPLC to give 4-(4-((7-cyclopropylimidazo[1,5-a]pyridin-8-yl)(hydroxy)methyl)cyclohexyl)phenol 2,2,2-trifluoroacetate as a white solid (100 mg in 33% yield). $^1$H NMR (DMSO-d$_6$) $\delta_H$ 9.24 (s, 2H), 9.09 (s, 1H), 8.32 (d, J=7.2 Hz, 1H), 7.95 (s, 1H), 6.96 (d, J=8.4 Hz, 2H), 6.63 (d, J=8.4 Hz, 2H), 6.55 (d, J=7.6 Hz, 1H), 5.64 (s, 1H), 5.04 (d, J=8.4 Hz, 1H), 2.31-2.36 (m, 1H), 2.21-2.26 (m, 2H), 1.80-1.94 (m, 2H), 1.66-1.69 (m, 1H), 1.16-1.27 (m, 5H), 0.97-1.04 (m, 2H), and 0.76-0.85 (m, 2H).

Example C104a and C104b: 4-((1 S,4r)-4-((S)-(7-cyclopropylimidazo[1,5-a]pyridin-8-yl)(hydroxy)methyl)cyclohexyl)phenol and 4-((1R,4r)-4-((R)-(7-cyclopropylimidazo[1,5-a]pyridin-8-yl)(hydroxy)methyl)cyclohexyl)phenol

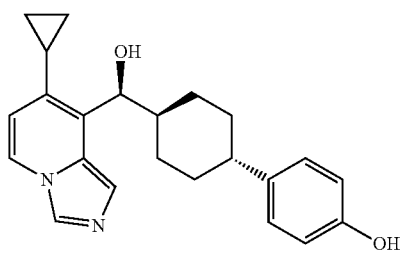

Fast isomer in chiral CHIRALPAK IC-3
Eluting reagent: Hex(0.1% DEA):IPA = 50:50

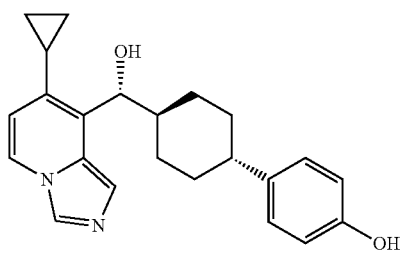

Slow isomer in chiral CHIRALPAK IC-3
Eluting reagent: Hex(0.1% DEA):IPA = 50:50

Each enantiomer of racemic C104a and C104b was separated using preparative HPLC on a CHIRAL PAK IC-3 with Hex (0.1% DEA):IPA=50:50 as an eluent. The enantiomeric excesses were determined by using HPLC on a CHIRAL Cellulose-SB with Hex (0.1% DEA):IPA=50:50 as an eluent at a flow rate of 1.0 mL/min. The first one enantiomer eluted at the retention time of 1.268 min, $^1$H NMR (DMSO-d$_6$) $\delta_H$ 9.09 (s, 1H), 8.21 (s, 1H), 8.11 (d, J=7.2 Hz, 1H), 7.43 (s, 1H), 6.97 (d, J=8.4 Hz, 2H), 6.63 (d, J=8.4 Hz, 2H), 6.16 (d, J=7.2 Hz, 1H), 5.31 (d, J=3.2 Hz, 1H), 4.95 (dd, J=8.2, 3.2 Hz, 1H), 2.31-2.33 (m, 2H), 2.16-2.18 (m, 1H), 1.98-2.00 (m, 1H), 1.81-1.84 (m, 1H), 1.63-1.67 (m, 1H), 1.36-1.38 (m, 1H), 1.22-1.27 (m, 4H), 0.87-0.98 (m, 2H), 0.69-0.72 (m, 2H); and the other enantiomer eluted at the retention time of 1.841 min, $^1$H NMR (DMSO-d$_6$) $\delta_H$ 9.18 (br s, 1H), 8.20 (s, 1H), 8.11 (d, J=7.2 Hz, 1H), 7.42 (s, 1H), 6.96 (d, J=8.4 Hz, 2H), 6.63 (d, J=8.4 Hz, 2H), 6.15 (d, J=7.2 Hz, 1H), 5.31 (d, J=3.2 Hz, 1H), 4.95 (dd, J=8.4, 3.2 Hz, 1H), 2.31-2.33 (m, 2H), 2.16-2.18 (m, 1H), 1.98-2.00 (m, 1H), 1.81-1.84 (m, 1H), 1.63-1.67 (m, 1H), 1.36-1.38 (m, 1H), 1.22-1.27 (m, 4H), 0.87-0.98 (m, 2H), 0.69-0.72 (m, 2H). The absolute configurations of chiral carbons in C104a and C104b are tentatively assigned as (S) and (R) respectively based on assumption that the binding model of the more potent isomer C104a is the same as that of C101a with IDO1 enzyme, and the relative stereochemistry on cyclohexane is assigned as trans configuration on the cyclohexane.

Example C105: (7-cyclopropylimidazo[1,5-a]pyridin-8-yl)(4-(4-trifluoromethoxy)phenyl)cyclohexyl)methanol

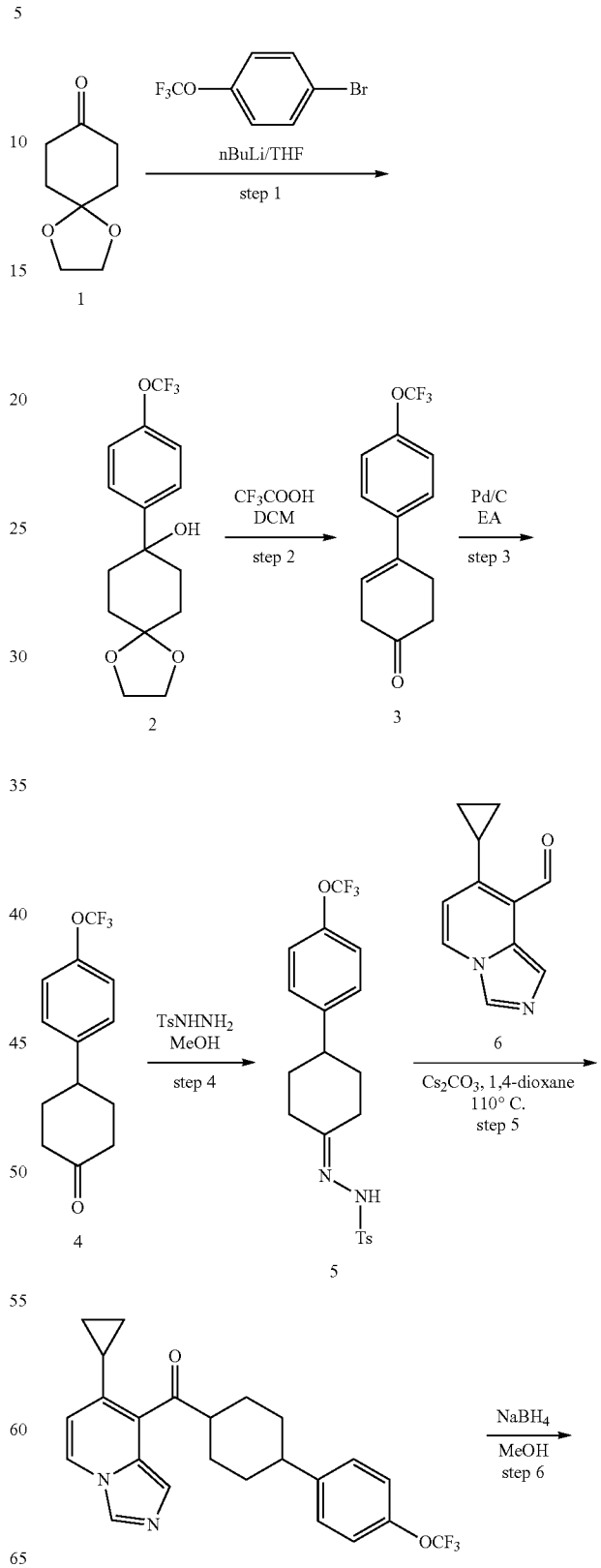

-continued

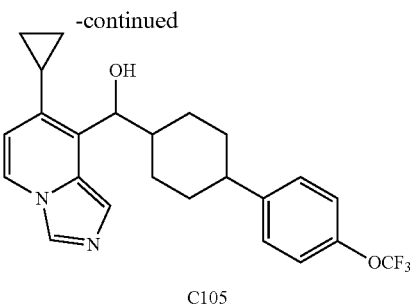

C105

Step 1: 8-(4-(trifluoromethoxy)phenyl)-1,4-dioxaspiro[4.5]decan-8-ol

To a solution of n-Bu-Li (52 mL, 2.4 M) in dry THF (100 mL) was added a solution of 1-bromo-4-(trifluoromethoxy)benzene (30 g, 124 mmol) in dry THF (30 mL) by dropwised at −70° C., the mixture was stirred for 0.5 h before a solution of 1,4-dioxaspiro[4.5]decan-8-one (13 g, 83 mmol) in dry THF (30 mL) was added at −70° C., and the mixture was stirred for 2 hours. Quenched with saturated aqueous of NH$_4$Cl and extracted with ethyl acetate (100 mL×3), combined the organic layer and evaporated under reduced pressure to give crude product, which was used for next step without further purification.

Step 2: 4'-(trifluoromethoxy)-2,5-dihydro-[1,1'-biphenyl]-4(3H)-one

To a solution of 8-(4-(trifluoromethoxy)phenyl)-1,4-dioxaspiro[4.5]decan-8-ol (83 mmol) in dichloromethane (200 mL) was added trifluoroacetic acid (100 mL) at room temperature and the mixture was stirred for overnight. The solvent was evaporated under reduced pressure and water (100 mL) was added, extracted with ethyl acetate (100 mL×3), combined the organic layer and washed with saturated aqueous of NaHCO$_3$ then the organic layer was combined and evaporated under reduced pressure to give crude product, which was used for next step without further purification.

Step 3: 4-(4-(trifluoromethoxy)phenyl)cyclohexan-1-one

To a solution of 4'-(trifluoromethoxy)-2,5-dihydro-[1,1'-biphenyl]-4(3H)-one (83 mmol) in ethyl acetate (200 mL) was added Pd/C (2.0 g, 10%) and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give 30 g oil as crude product.

Step 4: 4-methyl-N'-(4-(4-(trifluoromethoxy)phenyl)cyclohexylidene)benzene-sulfonohydrazide To a solution of 4-(4-(trifluoromethoxy)phenyl)cyclohexan-1-one (30 g, 116 mmol) in methol (150 mL) was added 4-methylbenzenesulfonohydrazide (21 g, 116 mmol) at room temperature, and the mixture was stirred for overnight. Evaporate half the solvent under reduced pressure and then filtered to give product (20 g) as a white solid. $^1$H NMR (DMSO-d$_6$) $\delta_H$ 10.20 (s, 1H), 7.74 (d, J=8.0 Hz, 2H), 7.40 (d, J=8.0 Hz, 2H), 7.35 (d, J=8.0 Hz, 2H), 7.26 (d, J=8.4 Hz, 2H), 2.82-2.94 (m, 2H), 2.39 (s, 3H), 2.25-2.28 (m, 2H), 1.90-1.97 (m, 3H), and 1.45-1.57 (m, 2H).

Step 5: (7-cyclopropylimidazo[1,5-a]pyridin-8-yl)(4-(4-(trifluoromethoxy)phenyl)cyclohexyl)methanone To a solution of 7-cyclopropylimidazo[1,5-a]pyridine-8-carbaldehyde (1.86 g, 10 mmol) in 1,4-dioxane (0.2 L) was added 4-methyl-N'-(4-(4-(trifluoromethoxy)phenyl)cyclohexylidene)-benzenesulfonohydrazide (8.5 g, 20 mmol) and Cs$_2$CO$_3$ (6.5 g, 40 mmol) at room temperature, and the mixture was heated at 100° C. for overnight. The solvent was evaporated under reduced pressure, water (100 mL) was added, extracted with ethyl acetate (50 mL×3) and combined the organic layer, the solvent was evaporated under reduced pressure and the residue was purified by column chromatography (PE:EA=1:1) to give crude product as a solid (1.7 g in 40% yield), which was used for next step without further purification. MS (ESI) m/e [M+1]$^+$=429.

Step 6: (7-cyclopropylimidazo[1,5-a]pyridin-8-yl)(4-(4-trifluoromethoxy)phenyl)cyclohexyl)methanol

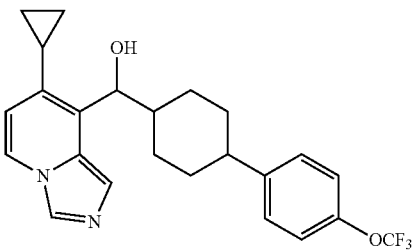

To a solution of crude (7-cyclopropylimidazo[1,5-a]pyridin-8-yl)(4-(4-(trifluoromethoxy)phenyl)cyclohexyl)methanone (1.7 g, 4 mmol) in methol (50 mL) was added NaBH$_4$ (0.8 g, 20 mol) at room temperature and, the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was purified by column chromatography (PE/EA=1:1) to give product as a white solid (800 mg in 47% yield). $^1$H NMR (DMSO-d$_6$) $\delta_H$ 8.20 (s, 1H), 8.11 (d, J=7.6 Hz, 1H), 7.43 (s, 1H), 7.33 (d, J=8.8 Hz, 2H), 7.23 (d, J=8.0 Hz, 1H), 6.16 (d, J=7.6 Hz, 1H), 5.32 (d, J=3.6 Hz, 1H), 4.97 (dd, J=3.6, 8.4 Hz, 1H), 2.32-2.35 (m, 1H), 2.17-2.20 (m, 1H), 2.00-2.03 (m, 1H), 1.85-1.88 (m, 1H), 1.68-1.71 (m, 1H), 1.38-1.46 (m, 1H), 1.19-1.32 (m, 4H), 0.89-0.95 (m, 2H), and 0.68-0.73 (m, 2H).

Example C105a and C105b: (S)-(7-cyclopropylimidazo[1,5-a]pyridin-8-yl)((1r,4S)-4-(4-(trifluoromethoxy)phenyl)cyclohexyl)methanol and (R)-(7-cyclopropylimidazo[1,5-a]pyridin-8-yl)((1 r,4R)-4-(4-(trifluoromethoxy)phenyl)cyclohexyl)methanol

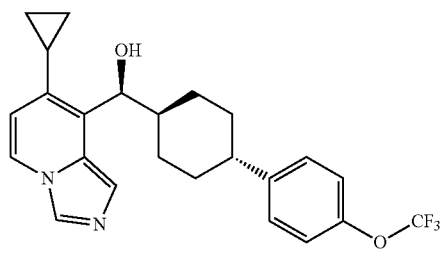

Fast isomer in CHIRALPAK IC-3 HPLC
Eluting reagent: Hex:EtOH = 70:30

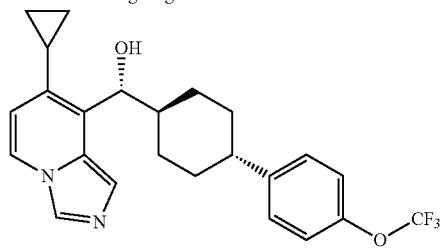

Slow isomer in CHIRALPAK IC-3 HPLC
Eluting reagent: Hex:EtOH = 70:30

Each enantiomer of racemic C105a and C105b was separated using preparative HPLC on a CHIRALPAK IC Hex: EtOH=70:30 as an eluent. The enantiomeric excesses were determined by using HPLC on a CHIRALPAK IC-3 with Hex (0.1% DEA):EtOH=70:30 as an eluent at a flow rate of 1.0 mL/min. The first one enantiomer eluted at the retention time of 2.509 min (C105a), which was then dissolved in THF (10 mL), and Ethyl acetate solution of hydrochloric acid (0.5 mL, 4.0M) was added by dropwise at room temperature, followed by addition of methol until the precipitate was dissolved, then the solvent was evaporated under reduced pressure and the residue was washed by PE to give the desired product as white solid, $^1$H NMR (DMSO-$d_6$) $\delta_H$ 9.40 (s, 1H), 8.36 (d, J=7.6 Hz, 1H), 8.02 (s, 1H), 7.33 (d, J=8.8 Hz, 2H), 7.23 (d, J=8.0 Hz, 1H), 6.60 (d, J=7.6 Hz, 1H), 5.72 (s, 1H), 5.05 (d, J=7.6 Hz, 1H), 2.32-2.35 (m, 1H), 2.17-2.20 (m, 1H), 2.00-2.03 (m, 1H), 1.85-1.88 (m, 1H), 1.68-1.71 (m, 1H), 1.38-1.46 (m, 1H), 1.19-1.32 (m, 4H), 0.89-0.95 (m, 2H), 0.68-0.73 (m, 2H); and the other enantiomer eluted at the retention time of 4.124 min (C105b), which was then dissolved in THF (10 mL), and Ethyl acetate solution of hydrochloric acid (0.5 mL, 4.0M) was added by dropwise at room temperature, followed by addition of methol until the precipitate was dissolved, then the solvent was evaporated under reduced pressure and the residue was washed by PE to give the desired product as white solid, $^1$H NMR (DMSO-$d_6$) $\delta_H$ 9.41 (s, 1H), 8.36 (d, J=7.6 Hz, 1H), 8.02 (s, 1H), 7.32 (d, J=8.8 Hz, 2H), 7.24 (d, J=8.0 Hz, 1H), 6.60 (d, J=7.6 Hz, 1H), 5.72 (s, 1H), 5.06 (d, J=7.6 Hz, 1H), 2.32-2.35 (m, 1H), 2.17-2.20 (m, 1H), 2.00-2.03 (m, 1H), 1.85-1.88 (m, 1H), 1.68-1.71 (m, 1H), 1.38-1.46 (m, 1H), 1.19-1.32 (m, 4H), 0.89-0.95 (m, 2H), 0.68-0.73 (m, 2H). The absolute configurations of chiral carbons in C105a and C105b are tentatively assigned as (S) and (R) respectively based on assumption that the binding model of the more potent isomer C105a is the same as that of C101a with IDO1 enzyme, and the relative stereochemistry on cyclohexane is assigned as trans configuration on the cyclohexane.

Example C106: 4-(4-((7-cyclopropylimidazo[1,5-a]pyridin-8-yl)(hydroxy)methyl)cyclohexyl)benzonitrile

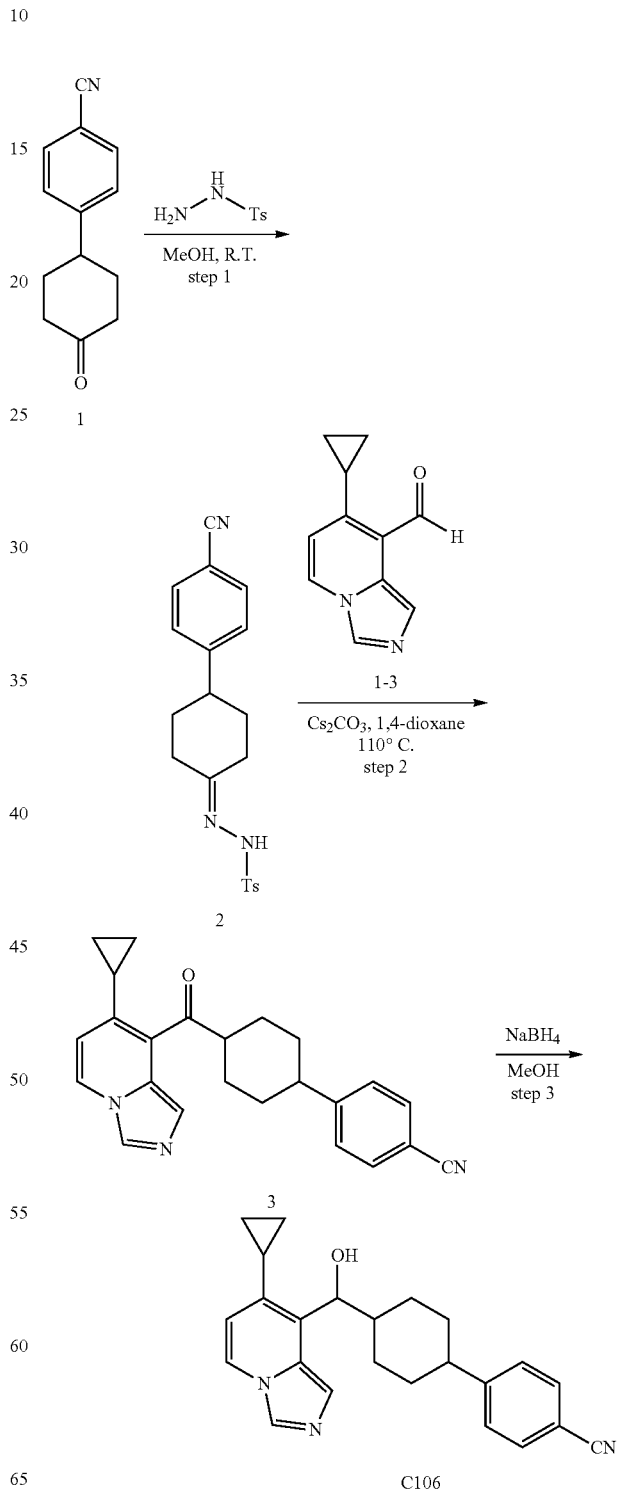

Step 1: N'-(4-(4-cyanophenyl)cyclohexylidene)-4-methylbenzenesulfonohydrazide To a solution of 4-(4-oxocyclohexyl)benzonitrile (5.0 g, 25 mmol) in methanol (100 mL) was added 4-methylbenzenesulfonohydrazide (4.7 g, 25 mmol) at room temperature and the mixture was stirred for 5 hours. White solid was precipitated form the solution, then the solid was filtered to give the product (6.8 g in 74% yield), MS (ESI) m/e [M+1]$^+$=368.

Step 2: 4-(4-(7-cyclopropylimidazo[1,5-a]pyridine-8-carbonyl)cyclohexyl)benzonitrile To a solution of 7-cyclopropylimidazo[1,5-a]pyridine-8-carbaldehyde (2.4 g, 13 mmol) in 1,4-dioxane (200 mL) was added N'-(4-(4-cyanophenyl)cyclohexylidene)-4-methylbenzenesulfonohydrazide (4.8 g, 13 mmol) and Cs$_2$CO$_3$ (8.4 g, 26 mmol) at room temperature, and the mixture was heated at 100° C. for overnight. The solvent was evaporated under reduced pressure and water (100 mL) was added, extracted with ethyl acetate (50 mL×3), combined the organic layer, evaporated the solvent and the residue was purified by column chromatography (PE:EA=1:1 to EA) to give crude product as a solid (1.0 g in 21% yield), which was used for next step without further purification, MS (ESI) m/e [M+1]$^+$=370.

Step 3: 4-(4-((7-cyclopropylimidazo[1,5-a]pyridin-8-yl)(hydroxy)methyl)cyclohexyl)benzonitrile

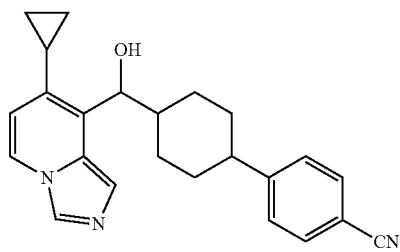

To a solution of 4-(4-(7-cyclopropylimidazo[1,5-a]pyridine-8-carbonyl)cyclohexyl)benzonitrile (1.0 g, 2.7 mmol) in methanol (50 mL) was added NaBH$_4$ (1.0 g, 27 mol) at room temperature, and the mixture was stirred overnight. Then the solvent was evaporated under reduced pressure and water (50 mL) was added, extracted with ethyl acetate (50 mL×3) and combined the organic layer, evaporated the solvent and the residue was purified by column chromatography (PE:EA=1:1 to EA) to give a crude product, and washed with methanol to give crude product, which was then dissolved in THF (10 mL), and Ethyl acetate solution of hydrochloric acid (0.5 mL, 4.0M) was added by dropwise at room temperature, followed by addition of methol until the precipitate was dissolved, then the solvent was evaporated under reduced pressure and the residue was washed by PE to give the desired product as white solid. $^1$H NMR (400 MHz, DMSO-d$_6$) δ$_H$ 9.53 (s, 1H), 8.39 (d, J=7.6 Hz, 1H), 8.05 (s, 1H), 7.72 (d, J=7.6 Hz, 2H), 7.41 (d, J=7.6 Hz, 2H), 6.64 (d, J=7.6 Hz, 1H), 5.07 (d, J=7.2 Hz, 1H), 2.20-2.23 (m, 2H), 1.82-1.99 (m, 2H), 1.72-1.78 (m, 1H), 1.68-1.73 (m, 4H), 0.92-0.95 (m, 2H), and 0.70-0.73 (m, 2H), MS (ESI) m/e [M+1]$^+$=372.

Example C106a and C106b: 4-((1S,4r)-4-((S)-(7-cyclopropylimidazo[1,5-a]pyridin-8-yl)(hydroxy)methyl)cyclohexyl)benzonitrile and 4-((1R,4r)-4-((R)-(7-cyclopropylimidazo[1,5-a]pyridin-8-yl)(hydroxy)methyl)cyclohexyl)benzonitrile

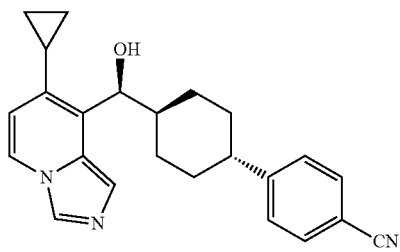

Fast isomer in CHIRAL Cellulose-SB HPLC
Eluting reagent: Hex(0.1% DEA):IPA = 50:50

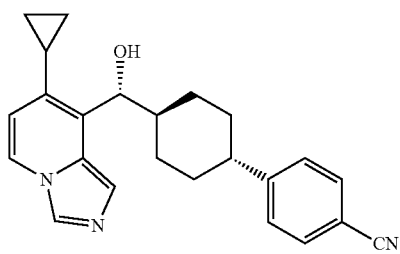

Slow isomer in CHIRAL Cellulose-SB HPLC
Eluting reagent: Hex(0.1% DEA):IPA = 50:50

Each enantiomer of racemic C106a and C106b was separated using preparative HPLC on a CHIRAL Cellulose-SB with Hex (0.1% DEA):IPA=50:50 as an eluent. The enantiomeric excesses were determined by using HPLC on a CHIRAL Cellulose-SB with Hex (0.1% DEA):IPA=50:50 as an eluent at a flow rate of 1.0 mL/min. The first one enantiomer eluted at the retention time of 3.560 min, $^1$H NMR (400 MHz, DMSO-d$_6$) δ$_H$ 8.22 (s, 1H), 8.11 (d, J=7.2 Hz, 1H), 7.72 (d, J=7.2 Hz, 2H), 7.41-7.44 (m, 3H), 6.16 (d, J=7.6 Hz, 1H), 5.34 (d, J=3.2 Hz, 1H), 4.97 (dd, J=3.2, 8.4 Hz, 1H), 2.55-2.57 (m, 1H), 2.32-2.34 (m, 1H), 2.16-2.18 (m, 1H), 2.01-2.03 (m, 1H), 1.84-1.87 (m, 1H), 1.68-1.71 (m, 1H), 1.45-1.48 (m, 1H), 1.20-1.32 (m, 4H), 0.92-0.95 (m, 2H), and 0.70-0.73 (m, 2H), and the other enantiomer eluted at the retention time of 4.988 min, $^1$H NMR (400 MHz, DMSO-d$_6$) δ$_H$ 8.24 (s, 1H), 8.12 (d, J=7.2 Hz, 1H), 7.71 (d, J=8.0 Hz, 2H), 7.41-7.44 (m, 3H), 6.17 (d, J=7.2 Hz, 1H), 5.34 (d, J=3.2 Hz, 1H), 4.97 (dd, J=3.2, 8.4 Hz, 1H), 2.55-2.57 (m, 1H), 2.32-2.34 (m, 1H), 2.16-2.18 (m, 1H), 2.01-2.03 (m, 1H), 1.84-1.87 (m, 1H), 1.68-1.71 (m, 1H), 1.45-1.48 (m, 1H), 1.20-1.32 (m, 4H), 0.92-0.95 (m, 2H), and 0.70-0.73 (m, 2H). The absolute configurations of chiral carbons in C106a and C106b are tentatively assigned as (S) and (R) respectively based on assumption that the binding model of the more potent isomer C106a is the same as that of C101a with IDO1 enzyme, and the relative stereochemistry on cyclohexane is assigned as trans configuration on the cyclohexane.

Example C107: (7-cyclopropylimidazo[1,5-a]pyridin-8-yl)(4-(4-fluorophenyl)cyclohexyl)methanol

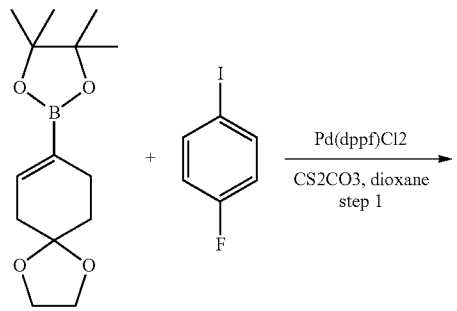

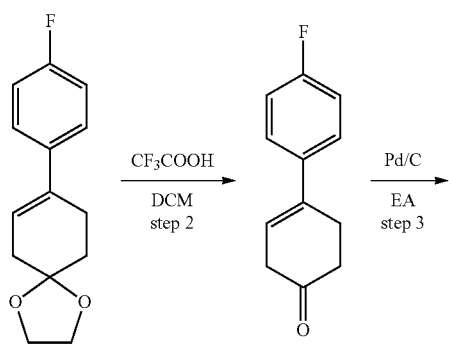

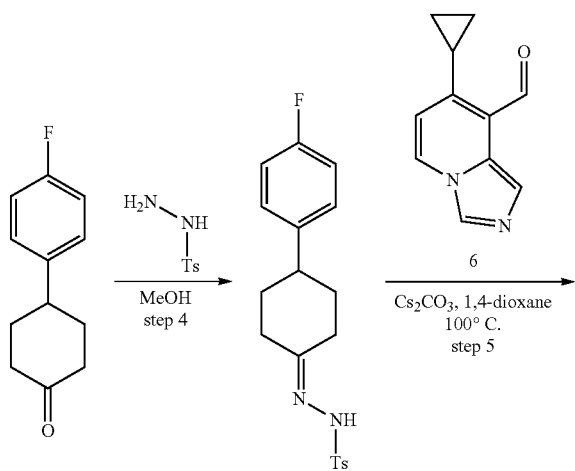

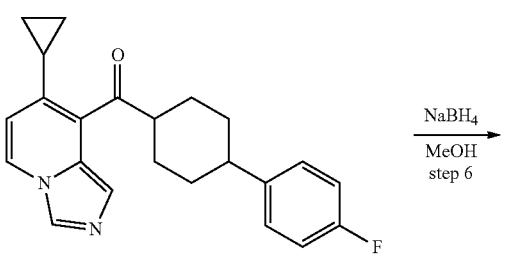

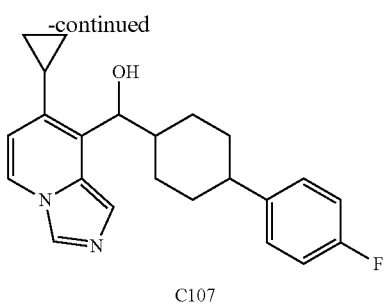

C107

Step 1: 8-(4-fluorophenyl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (20 g, 75 mmol), 1-fluoro-4-iodobenzene (20 g, 90 mmol), Pd(dppf)Cl$_2$ (5.5 g, 7.5 mmol) and Cs$_2$CO$_3$ (36.6 g, 112.5 mmol) in dioxane (200 mL), the mixture was stirred at 90° C. under N$_2$ for 3 h. TLC (PE:EA=5:1, Rf=0.5) showed the reaction was completed. Filtered and concentrated, H$_2$O (100 ml) was was added and extracted with EA (50 mix 3). The combined organic layer was dried over Na$_2$SO$_4$, filtered and concentrated to give crude product, which was purified by silica gel chromatography (PE:EA=20:1-6:1) to give compound 3 (15 g, 85.7%) as a red solid.

Step 2: 4'-fluoro-2,5-dihydro-[1,1'-biphenyl]-4(3H)-one

To a solution of 8-(4-fluorophenyl)-1,4-dioxaspiro[4.5]dec-7-ene (13 g, 52.63 mmol) in dichloromethane (200 mL) was added trifluoroacetic acid (100 mL) at room temperature, and the mixture was stirred for overnight. The solvent was evaporated under reduced pressure and water (100 mL) was added, extracted with ethyl acetate (100 mL×3), combined the organic layer and washed with saturated aqueous of NaHCO$_3$ then the organic layer was evaporated to give crude product, which was used for next step without further purification.

Step 3: 4-(4-fluorophenyl)cyclohexan-1-one

To a solution of 4'-fluoro-2,5-dihydro-[1,1'-biphenyl]-4(3H)-one (5 g, 26.3 mmol) in ethyl acetate:EA=1:1 (100 mL) was added Pd/C (2.5 g, 50%) and the mixture was stirred for 6 hours at room temperature under H$_2$ (0.4 Mpa). Then filtered to remove Pd/C and the filtrate was evaporated under reduced pressure to give a crude product, which was used for next step without further purification.

Step 4: N'-(4-(4-fluorophenyl)cyclohexylidene)-4-methylbenzenesulfonohydrazide To a solution of 4-(4-fluorophenyl)cyclohexan-1-one (4.5 g, 23.3 mmol) in methol (50 mL) was added 4-methylbenzenesulfonohydrazide (4.3 g, 23.3 mmol) at room temperature, and the mixture was stirred for overnight. The solvent was evaporate under reduced pressure and the residue was purified by column chromatography (PE:EA=4:1) to give 7 g as a white solid. MS (ESI) m/e [M+1]$^+$=361.

Step 5: (7-cyclopropylimidazo[1,5-a]pyridin-8-yl)(4-(p-tolyl)cyclohexyl)methanone To a solution of 7-cyclopropylimidazo[1,5-a]pyridine-8-carbaldehyde (2.0 g, 10.7 mmol) in 1,4-dioxane (0.2 L) was added compound 6 (5.77 g, 16 mmol) and Cs$_2$CO$_3$ (7 g, 21.4 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE: EA=1:1 to EA) to give crude product as a solid (1.2 g in 31.57% yield), which was used for next step without further purification. MS (ESI) m/e [M+1]$^+$=363.

Step 6: (7-cyclopropylimidazo[1,5-a]pyridin-8-yl) (4-fluorophenyl)cyclohexyl)methanol

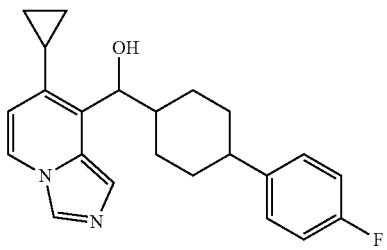 [SMILES: OC(c1c(C2CC2)ccn2cncc12)C1CCC(c2ccc(F)cc2)CC1]

To a solution of crude compound 7 (0.7 g, 2.2 mmol) in methol (100 mL) was added NaBH$_4$ (167 mg, 4.4 mmol) at room temperature and the mixture was stirred overnight. Then the solvent was evaporated under reduced pressure and water (50 mL) was added, extracted with ethyl acetate (50 ml×3) and combined the organic layer, evaporated the solvent under reduced pressure and the residue was purified by column chromatography (PE:EA=1:1 to EA) to give crude product, which was washed with methol to give product as a white solid (250 mg in 25% yield). $^1$H NMR (DMSO-d$_6$) δ$_H$ 8.20 (s, 1H), 8.11 (d, J=7.6 Hz, 1H), 7.43 (s, 1H), 7.21 (dd, J=8.2, 6.0 Hz, 2H), 7.06 (t, J=8.2 Hz, 2H), 6.16 (d, J=7.2 Hz, 1H), 5.32 (d, J=3.6 Hz, 1H), 4.96 (d, J=4.8 Hz, 1H), 2.44-2.48 (m, 2H), 2.32-2.34 (m, 1H), 2.17-2.19 (m, 1H), 1.99-2.01 (m, 1H), 1.85-1.87 (m, 1H), 1.66-1.68 (m, 1H), 1.42-1.44 (m, 1H), 1.33-1.18 (m, 4H), 0.93-1.02 (m, 2H), 0.70-0.72 (m, 2H). MS (ESI) m/e [M+1]$^+$=365.

Example C107a and C107b: (S)-(7-cyclopropylimidazo[1,5-a]pyridin-8-yl)((1r,4S)-4-(4-fluorophenyl) cyclohexyl)methanol and (R)-(7-cyclopropylimidazo[1,5-a]pyridin-8-yl)((r,4R)-4-(4-fluorophenyl) cyclohexyl)methanol

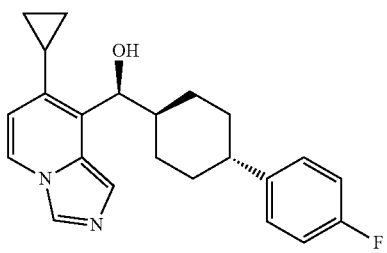

Fast isomer in CHIRALPAK IC-3
Eluting reagent: Hex(0.2% IPAmine):EtOH = 60:40

-continued

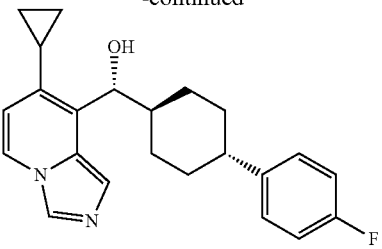

Slow isomer in CHIRALPAK IC-3
Eluting reagent: Hex(0.2% IPAmine):EtOH = 60:40

Each enantiomer of racemic C107a and C107b was separated using preparative HPLC on a CHIRAL PAK IC-3 with Hex (0.2% IPAmine):EtOH=60:40 as an eluent. The enantiomeric excesses were determined by using HPLC on a CHIRAL PAK IC-3 with Hex (0.2% IPAmine):EtOH=60:40 as an eluent at a flow rate of 1.0 mL/min. The first one enantiomer eluted at the retention time of 1.431 min (C107a), which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-d$_6$) δ$_H$ 8.84 (s, 1H), 8.24 (d, J=7.4 Hz, 1H), 7.74 (s, 1H), 7.22 (dd, J=8.4, 6.0 Hz, 2H), 7.06 (t, J=8.8 Hz, 2H), 6.40 (d, J=7.6 Hz, 1H), 5.53 (s, 1H), 5.01 (d, J=8.4 Hz, 1H), 2.49-2.42 (m, 2H), 2.27-2.29 (m, 3H), 1.95-2.00 (m, 1H), 1.85-1.87 (m, 1H), 1.69-1.72 (m, 1H), 1.35-1.49 (m, 2H), 1.35 (m, 5H), 0.92-1.00 (m, 2H), 0.76-0.80 (m, 2H); and the other enantiomer eluted at the retention time of 2.432 min (C107b), $^1$H NMR (DMSO-d$_6$) δ$_H$ 8.42 (s, 1H), 8.16 (d, J=7.2 Hz, 1H), 7.54 (s, 1H), 7.23 (dd, J=8.4, 5.6 Hz, 2H), 7.06 (t, J=8.8 Hz, 2H), 6.24 (d, J=7.2 Hz, 1H), 5.39 (s, 1H), 4.98 (d, J=7.2 Hz, 1H), 2.47-2.29 (m, 1H), 2.31-2.34 (m, 1H), 2.21-2.23 (m, 1H), 1.99-2.00 (m, 1H), 1.85-1.87 (m, 1H), 1.67-1.69 (m, 1H), 1.42-1.44 (m, 1H), 1.19-1.34 (m, 4H), 0.95-1.00 (m, 2H), 0.73-0.80 (m, 2H). The absolute configurations of chiral carbons in C107a and C107b are tentatively assigned as (S) and (R) respectively based on assumption that the binding model of the more potent isomer C107a is the same as that of C101a with IDO1 enzyme, and the relative stereochemistry on cyclohexane is assigned as trans configuration on the cyclohexane.

Example C108: (7-cyclopropylimidazo[1,5-a]pyridin-8-yl)(4-(2-fluorophenyl)cyclohexyl)methanol

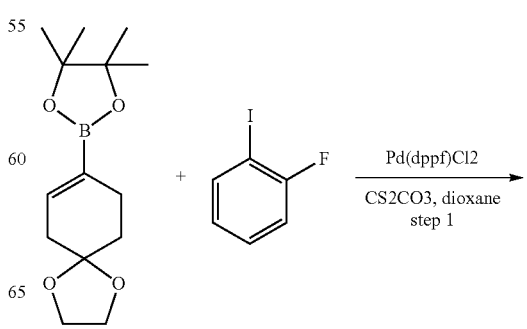

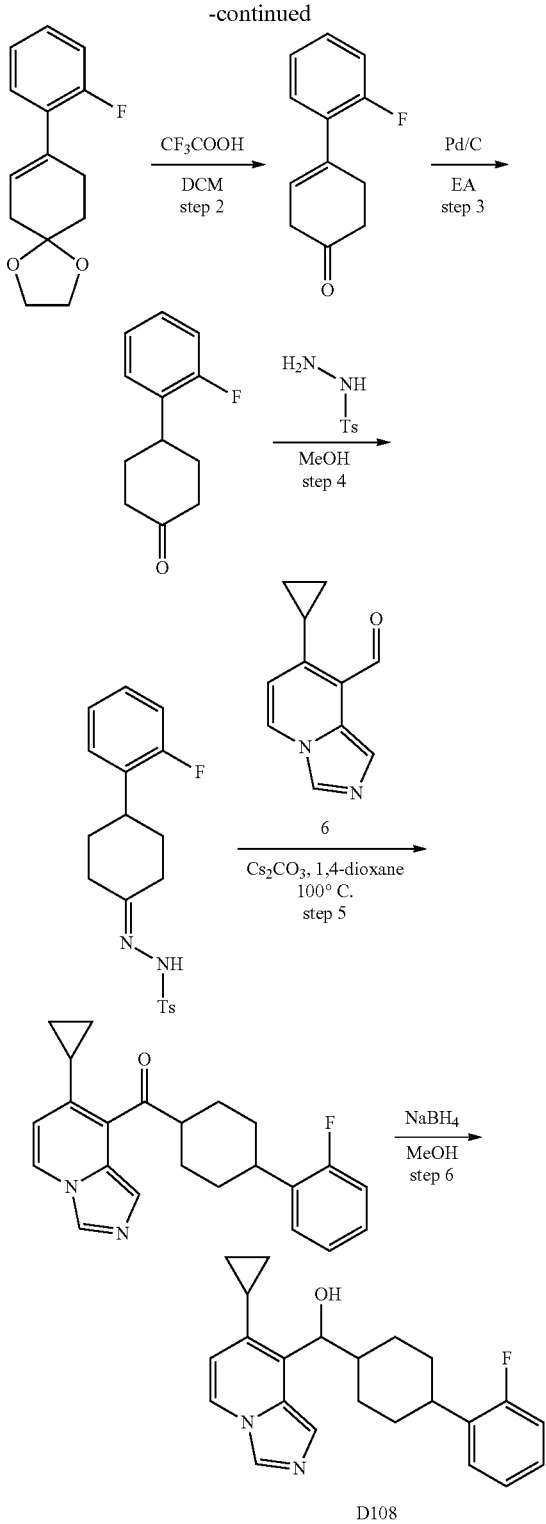

Step 1: 8-(2-fluorophenyl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (20 g, 75 mmol), 1-fluoro-2-iodobenzene (20 g, 90 mmol), Pd(dppf)Cl$_2$(5.5 g, 7.5 mmol) and CS$_2$CO$_3$ (36.6 g, 112.5 mmol) in dioxane (200 mL), the mixture was stirred at 90° C. under N$_2$ for 3 h. TLC (PE:EA=5:1, Rf=0.5) showed the reaction was completed. Filtered and concentrated, H$_2$O (100 ml) was added, extracted with EA (50 ml×3). The combined organic layer was dried over Na$_2$SO$_4$, filtered and concentrated to give crude product, which was purified by silica gel chromatography (PE:EA=20:1-6:1) to give compound 3 (15 g, 85.7%) as a red solid.

Step 2: 2'-fluoro-2,5-dihydro-[1,1'-biphenyl]-4(3H)-one

To a solution of 8-(2-fluorophenyl)-1,4-dioxaspiro[4.5]dec-7-ene (13 g, 52.63 mmol) in dichloromethane (200 mL) was added trifluoroacetic acid (100 mL) at room temperature, and the mixture was stirred for overnight. The solvent was evaporated under reduced pressure and water (100 mL) was added, extracted with ethyl acetate (100 mL×3), combined the organic layer and washed with saturated aqueous of NaHCO$_3$, then the organic layer was evaporated to give crude product, which was used for the next step without further purification.

Step 3: 4-(2-fluorophenyl)cyclohexan-1-one

To a solution of 2'-fluoro-2,5-dihydro-[,1'-biphenyl]-4(3H)-one (5 g, 26.3 mmol) in ethyl acetate:EA=1:1 (100 mL) was added Pd/C (2.5 g, 50%) and the mixture was stirred for 6 hours at room temperature under H$_2$ (0.4 Mpa). Then filtered to remove Pd/C and the filtrate was evaporated under reduced pressure to give a crude product, which was used for the next step without further purification.

Step 4: N'-(4-(2-fluorophenyl)cyclohexylidene)-4-methylbenzenesulfonohydrazide

To a solution of 4-(2-fluorophenyl)cyclohexan-1-one (4.5 g, 23.3 mmol) in methol (50 mL) was added 4-methylbenzenesulfonohydrazide (4.3 g, 23.3 mmol) at room temperature, and the mixture was stirred for overnight. The solvent was evaporate under reduced pressure and the residue was purified by column chromatography (PE:EA=4:1) to give 7 g as a white solid. MS (ESI) m/e [M+1]$^+$=361.

Step 5: (7-cyclopropylimidazo[1,5-a]pyridin-8-yl)(4-(2-fluorophenyl)cyclohexyl)methanone To a solution of 7-cyclopropylimidazo[1,5-a]pyridine-8-carbaldehyde (2.0 g, 10.7 mmol) in 1,4-dioxane (0.2 L) was added compound 6 (5.77 g, 16 mmol) and Cs$_2$CO$_3$ (7 g, 21.4 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE:EA=1:1 to EA) to give crude product as a solid (1.0 g in 29% yield), which was used for the next step without further purification.

Step 6: (7-cyclopropylimidazo[1,5-a]pyridin-8-yl)(4-(2-fluorophenyl)cyclohexyl)methanol

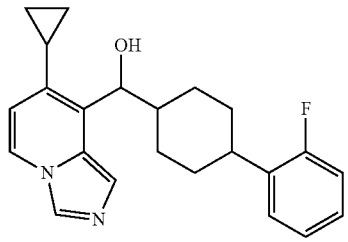 [SMILES: OC(c1c(C2CC2)ccn2cncc12)C1CCC(c2ccccc2F)CC1]

To a solution of crude (7-cyclopropylimidazo[1,5-a]pyridin-8-yl)(4-(2-fluorophenyl)cyclohexyl)methanone (0.7 g, 2.2 mmol) in methanol (100 mL) was added $NaBH_4$ (167 mg, 4.4 mmol) at room temperature, and the mixture was stirred overnight. Then the solvent was evaporated under reduced pressure and water (50 mL) was added, extracted with ethyl acetate (50 ml×3) and combined the organic layer, evaporated the solvent under reduced pressure and the residue was purified by column chromatography (PE:EA=1:1 to EA) to give crude product, which was washed with methol to give product as a white solid (28 mg in 28% yield). $^1H$ NMR (DMSO-$d_6$) $\delta_H$ 8.21 (s, 1H), 8.12 (d, J=7.2 Hz, 1H), 7.44 (s, 1H), 7.30 (t, J=7.6 Hz, 1H), 7.20 (dd, J=13.6, 7.2 Hz, 1H), 7.13-7.05 (m, 2H), 6.16 (d, J=7.2 Hz, 1H), 5.33 (d, J=2.8 Hz, 1H), 4.98 (d, J=5.2 Hz, 1H), 2.77-2.79 (m, 1H), 2.33-2.37 (m, 1H), 2.18-2.20 (m, 1H), 2.01-2.04 (m, 1H), 1.82-1.86 (m, 1H), 1.66-1.68 (min, 1H), 1.48-1.52 (min, 1H), 1.21-1.26 (m, 4H), 0.92-0.95 (m, 2H), 0.70-0.72 (m, 2H).

Example C108a and C108b: (S)-(7-cyclopropylimidazo[1,5-a]pyridin-8-yl)((1 r,4S)-4-(2-fluorophenyl)cyclohexyl)methanol (R)-(7-cyclopropylimidazo[1,5-a]pyridin-8-yl)((1r,4R)-4-(2-fluorophenyl)cyclohexyl)methanol

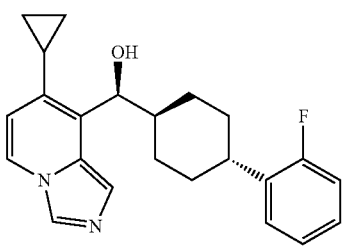

Fast isomer in CHIRALPAK IC-3
Eluting reagent: Hex(0.2% IPAmine):EtOH = 70:30

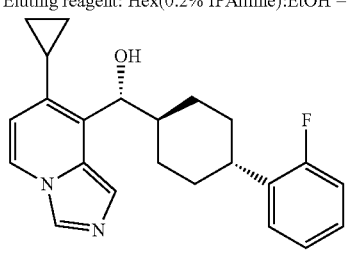

Slow isomer in CHIRALPAK IC-3
Eluting reagent: Hex(0.2% IPAmine):EtOH = 70:30

Each enantiomer of racemic C108a and C108b was separated using preparative HPLC on a CHIRAL PAK IC-3 with Hex:EtOH=70:30 as an eluent. The enantiomeric excesses were determined by using HPLC on a CHIRAL PAK IC-3 with Hex (0.2% IPAmine):EtOH=70:30 as an eluent at a flow rate of 1.0 mL/min. The first one enantiomer eluted at the retention time of 3.083 min (C108a), which was dissolved in THF (10 mL) was added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1H$ NMR (DMSO-$d_6$) $\delta_H$ 9.42 (s, 1H), 8.37 (d, J=7.6 Hz, 1H), 8.02 (s, 1H), 7.31-7.26 (m, 1H), 7.20-7.23 (m, 1H), 7.07-7.14 (m, 2H), 6.60 (d, J=8.4 Hz, 1H), 5.73 (s, 1H), 5.07 (d, J=7.6 Hz, 1H), 2.77-2.79 (m, 1H), 2.25-2.28 (m, 2H), 1.96-2.00 (m, 1H), 1.82-1.85 (m, 1H), 1.69-1.71 (m, 1H), 1.41-1.57 (m, 1H), 1.40-1.45 (m, 4H), 0.98-1.05 (m, 2H), 0.75-0.88 (m, 2H); and the other enantiomer eluted at the retention time of 5.122 min (C108b), which was dissolved in THF (10 mL) was added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1H$ NMR (DMSO-$d_6$) $\delta_H$ 9.42 (s, 1H), 8.37 (d, J=7.6 Hz, 1H), 8.02 (s, 1H), 7.31-7.26 (m, 1H), 7.20-7.23 (m, 1H), 7.07-7.14 (m, 2H), 6.60 (d, J=8.4 Hz, 1H), 5.73 (s, 1H), 5.07 (d, J=7.6 Hz, 1H), 2.77-2.79 (m, 1H), 2.25-2.28 (m, 2H), 1.96-2.00 (m, 1H), 1.82-1.85 (m, 1H), 1.69-1.71 (m, 1H), 1.41-1.57 (m, 1H), 1.40-1.45 (m, 4H), 0.98-1.05 (m, 2H), 0.80-0.85 (m, 2H). The absolute configurations of chiral carbons in C108a and C108b are tentatively assigned as (S) and (R) respectively based on assumption that the binding model of the more potent isomer $C_{108}a$ is the same as that of C101a with IDO1 enzyme, and the relative stereochemistry on cyclohexane is assigned as trans configuration on the cyclohexane Example C109: (7-cyclopropylimidazo[1,5-a]pyridin-8-yl)(4-(3-fluorophenyl)cyclohexyl)methanol

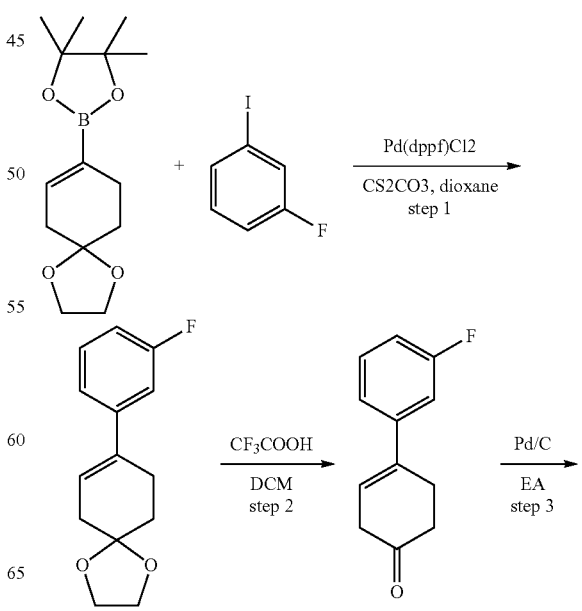

-continued

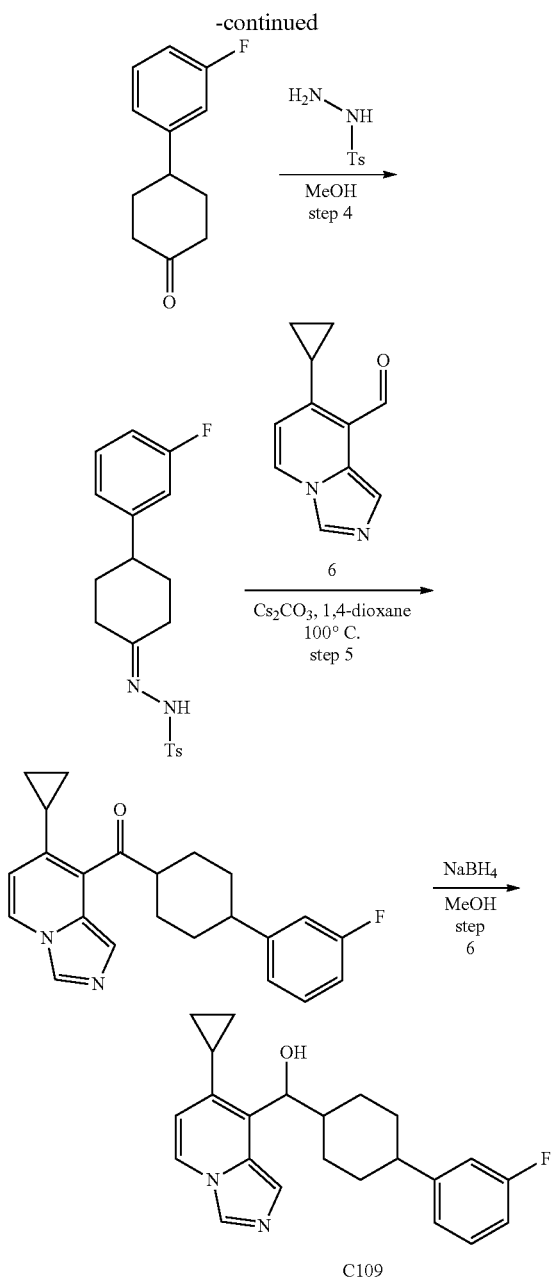

Step 1: 8-(3-fluorophenyl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (20 g, 75 mmol), 1-fluoro-3-iodobenzene (20 g, 90 mmol), Pd(dppf)Cl₂ (5.5 g, 7.5 mmol) and Cs₂CO₃ (36.6 g, 112.5 mmol) in dioxane (200 mL), the mixture was stirred at 90° C. under N₂ for 3 h. TLC (PE:EA=5:1, Rf=0.5) showed the reaction was completed. Filtered and concentrated, H₂O (100 ml) was added, extracted with EA (50 ml×3). The combined organic layer was dried over Na₂SO₄, filtered and concentrated to give crude product, which was purified by silica gel chromatography (PE:EA=20:1-6:1) to give product (15 g, 85.7%) as a red solid.

Step 2: 3'-fluoro-2,5-dihydro-[1,1'-biphenyl]-4(3H)-one

To a solution of 8-(3-fluorophenyl)-1,4-dioxaspiro[4.5]dec-7-ene (13 g, 52.63 mmol) in dichloromethane (200 mL) was added trifluoroacetic acid (100 mL) at room temperature and the mixture was stirred for overnight. The solvent was evaporated under reduced pressure and water (100 mL) was added, extracted with ethyl acetate (100 ml×3), combined the organic layer and washed with saturated aqueous of NaHCO₃, then the organic layer was evaporated to give crude product, which was used for the next step without further purification.

Step 3: 4-(3-fluorophenyl)cyclohexan-1-one

To a solution of 3'-fluoro-2,5-dihydro-[1,1'-biphenyl]-4(3H)-one (5 g, 26.3 mmol) in ethyl acetate:EA=1:1 (100 mL) was added Pd/C (2.5 g, 50%) and the mixture was stirred for 6 hours at room temperature under H₂ (0.4 Mpa). Then filtered to remove Pd/C and the filtrate was evaporated under reduced pressure to give crude product, which was used for next step without further purification.

Step 4: N'-(4-(3-fluorophenyl)cyclohexylidene)-4-methylbenzenesulfonohydrazide

To a solution of 4-(3-fluorophenyl)cyclohexan-1-one (4.5 g, 23.3 mmol) in methol (50 mL) was added 4-methylbenzenesulfonohydrazide (4.3 g, 23.3 mmol) at room temperature and the mixture was stirred for overnight. The solvent was evaporate under reduced pressure and the residue was purified by column chromatography (PE:EA=4:1) to give product (7 g) as a white solid. [M+1]⁺=361.

Step 5: (7-cyclopropylimidazo[1,5-a]pyridin-8-yl)(4-(3-fluorophenyl)cyclohexyl)methanone To a solution of 7-cyclopropylimidazo[1,5-a]pyridine-8-carbaldehyde (2.0 g, 10.7 mmol) in 1,4-dioxane (0.2 L) was added compound 6 (5.77 g, 16 mmol) and Cs₂CO₃ (7 g, 21.4 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE: EA=1:1 to EA) to give crude product as a solid (1.0 g in 29% yield), which was used for the next step without further purification. [M+1]⁺=363.

Step 6: (7-cyclopropylimidazo[1,5-a]pyridin-8-yl)(4-(3-fluorophenyl)cyclohexyl)methanol

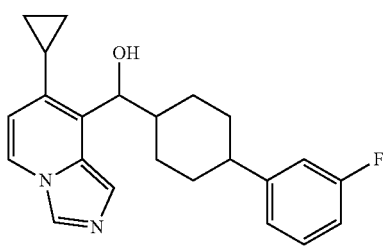 [SMILES: OC(c1c(C2CC2)ccn2cncc12)C1CCC(c2cccc(F)c2)CC1]

To a solution of crude compound 7 (0.7 g, 2.2 mmol) in methol (100 mL) was added NaBH₄ (167 mg, 4.4 mmol) at room temperature and the mixture was stirred overnight. Then the solvent was evaporated under reduced pressure and water (50 mL) was added, extracted with ethyl acetate (50 ml×3) and combined the organic layer, evaporated the solvent under reduced pressure and the residue was purified by column chromatography (PE:EA=1:1 to EA) to give crude product, which was washed with methol to give product as a white solid (28 mg in 28% yield). ¹H NMR (DMSO-d₆) $\delta_H$ 8.21 (s, 1H), 8.11 (d, J=7.2 Hz, 1H), 7.43 (s, 1H), 7.28 (dd, J=14.4, 8.0 Hz, 1H), 7.07-7.01 (m, 2H), 6.96 (t, J=8.4 Hz, 1H), 6.16 (d, J=7.2 Hz, 1H), 5.33 (d, J=3.2 Hz, 1H), 4.97 (dd, J=8.4, 3.2 Hz, 1H), 2.32-2.34 (m, 1H), 2.17-2.20 (m, 1H), 1.98-2.02 (m, 1H), 1.86-1.88 (m, 1H), 1.69-1.70 (m, 1H), 1.41-1.46 (m, 1H), 1.21-1.26 (m, 4H), 0.93-1.02 (m, 2H), 0.70-0.71 (m, 2H).

Example C109a and C109b: (S)-(7-cyclopropylimidazo[1,5-a]pyridin-8-yl)((1r,4S)-4-(3-fluorophenyl)cyclohexyl)methanol and (R)-(7-cyclopropylimidazo[1,5-a]pyridin-8-yl)((1 r,4R)-4-(3-fluorophenyl)cyclohexyl)methanol

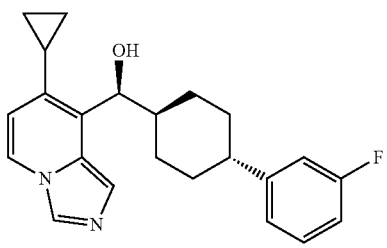

Fast isomer in CHIRALPAK IC-3
Eluting reagent: Hex(0.1% DEA):EtOH = 70:30

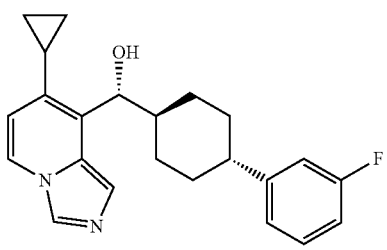

Slow isomer in CHIRALPAK IC-3
Eluting reagent: Hex(0.1% DEA):EtOH = 70:30

Each enantiomer of racemic C109a and C109b were separated using preparative HPLC on a CHIRAL PAK IC-3 with Hex:EtOH=70:30 as an eluent. The enantiomeric excesses were determined by using HPLC on a CHIRAL PAK IC-3 with Hex (0.1% DEA):EtOH=70:30 as an eluent at a flow rate of 1.0 mL/min. The first one enantiomer eluted at the retention time of 3.587 min (C109a), which was dissolved in THF (10 mL), Ethyl acetate solution of hydrochloric acid (0.5 mL, 4.0M) was added and stirred at room temperature, followed by addition of methol until the precipitate was dissolved, then the solvent was evaporated under reduced pressure and the residue was washed by PE to give the desired product as white solid, ¹H NMR (DMSO-d₆) $\delta_H$ 9.41 (s, 1H), 8.37 (d, J=7.2 Hz, 1H), 8.00 (s, 1H), 7.29 (dd, J=14.4, 7.6 Hz, 1H), 7.03 (t, J=8.2 Hz, 2H), 6.97 (t, J=8.4 Hz, 1H), 6.60 (d, J=7.2 Hz, 1H), 5.74 (br s, 1H), 5.06 (d, J=8.0 Hz, 1H), 2.21-2.25 (m, 2H), 1.81-1.99 (m, 2H), 1.73-1.76 (m, 1H), 1.50-1.20 (m, 6H), 0.98-1.05 (m, 2H), 0.78-0.82 (m, 2H); and the other enantiomer eluted at the retention time of 6.427 min (C109b), which was dissolved in THF (10 mL), Ethyl acetate solution of hydrochloric acid (0.5 mL, 4.0M) was added and stirred at room temperature, followed by addition of methol until the precipitate was dissolved, then the solvent was evaporated under reduced pressure and the residue was washed by PE to give the desired product as white solid, ¹H NMR (DMSO-ds) $\delta_H$ 9.45 (s, 1H), 8.37 (d, J=7.2 Hz, 1H), 8.02 (s, 1H), 7.26 (dd, J=14.4, 7.6 Hz, 1H), 7.01 (t, J=8.2 Hz, 2H), 6.95 (t, J=8.4 Hz, 1H), 6.61 (d, J=7.2 Hz, 1H), 5.74 (br s, 1H), 5.06 (d, J=8.0 Hz, 1H), 2.21-2.25 (m, 2H), 1.81-1.99 (m, 2H), 1.73-1.76 (min, 1H), 1.50-1.20 (m, 6H), 0.98-1.05 (m, 2H), 0.78-0.82 (m, 2H). The absolute configurations of chiral carbons in C109a and C109b are tentatively assigned as (S) and (R) respectively based on assumption that the binding model of the more potent isomer C109a is the same as that of C101a with IDO1 enzyme, and the relative stereochemistry on cyclohexane is assigned as trans configuration on the cyclohexane.

Example C110: (7-cyclopropylimidazo[1,5-a]pyridin-8-yl)(4-(p-tolyl)cyclohexyl)methanol

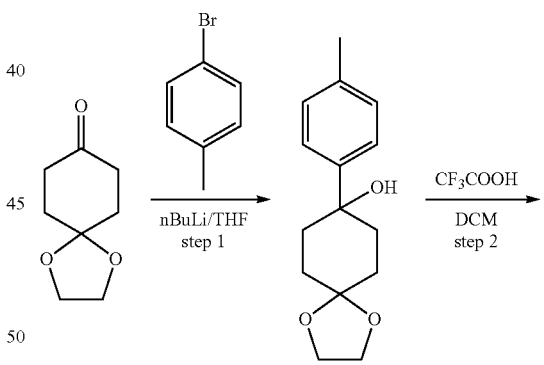

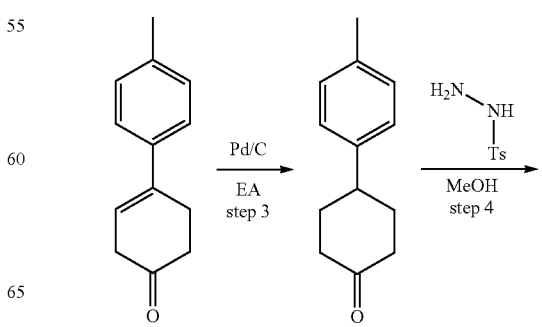

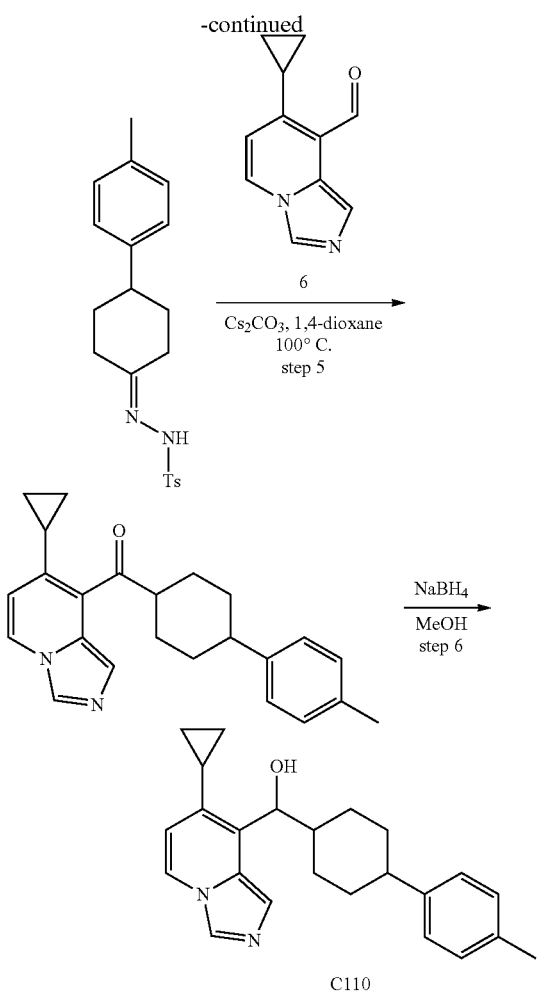

Step 1: 8-(D-tolyl)-1,4-dioxaspiro[4.5]decan-8-ol

To a solution of n-Bu-Li (48 mL, 2.4 M) in dry THF (100 mL) was added 1-bromo-4-methylbenzene (20 g, 117 mmol) in dry THF (30 mL) by dropwised at −70° C., and the mixture was stirred for 0.5 h before a solution of 1,4-dioxaspiro[4.5]decan-8-one (12 g, 78 mmol) in dry THF (30 mL) at −70° C. and the mixture was stirred for 2 hours. Quenched with saturated aqueous of $NH_4Cl$ and extracted with ethyl acetate (100 mL×3), combined the organic layer and evaporated to give crude product, which this was used for next step without further purification.

Step 2: 4'-methyl-2,5-dihydro-[1,1'-biphenyl]-4 (3H)-one

To a solution of 8-(p-tolyl)-1,4-dioxaspiro[4.5]decan-8-ol (78 mmol) in dichloromethane (200 mL) was added trifluoroacetic acid (100 mL) at room temperature and the mixture was stirred for overnight. The solvent was evaporated under reduced pressure and water (100 mL) was added, extracted with ethyl acetate (100 mL×3), combined the organic layer and washed with saturated aqueous of $NaHCO_3$, the organic layer was evaporated to give crude product, which was used for next step without further purification.

Step 3: 4-(p-tolyl)cyclohexan-1-one

To a solution of 4'-methyl-2,5-dihydro-[1,1'-biphenyl]-4 (3H)-one (78 mmol) in ethyl acetate (200 mL) was added Pd/C (2.0 g, 10%), and the mixture was stirred for 6 hours at room temperature under $H_2$ (0.4 Mpa). Then filtered to remove Pd/C and the filtrate was evaporated under reduced pressure to give a crude product, which was used for next step without further purification.

Step 4: 4-methyl-N'-(4-(p-tolyl)cyclohexylidene) benzenesulfonohydrazide

To a solution of 4-(p-tolyl)cyclohexan-1-one (78 mmol) in methol (200 mL) was added 4-methylbenzenesulfonohydrazide (14.5 g, 78 mmol) at room temperature and the mixture was stirred for overnight. The solvent was evaporate under reduced pressure and the residue was purified by column chromatography (PE:EA=4:1) to give 4.5 g as a white solid. MS (ESI) m/e $[M+1]^+=357$.

Step 5: (7-cyclopropylimidazo[1,5-a]pyridin-8-yl) (4-(p-tolyl)cyclohexyl)methanone To a solution of 7-cyclopropylimidazo[1,5-a]pyridine-8-carbaldehyde (2.4 g, 12.7 mmol) in 1,4-dioxane (0.2 L) was added 4-methyl-N'-(4-(p-tolyl)cyclohexylidene) benzenesulfono-hydrazide (4.5 g, 12.7 mmol) and $Cs_2CO_3$ (8.4 g, 26 mmol) at room temperature, and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1 to EA) to give crude product as a solid (1.4 g in 38% yield), and which was used for next step without further purification. MS (ESI) m/e $[M+1]^+=359$ Step 6: (7-cyclopropylimidazo[1,5-a]pyridin-8-yl) (4-(p-tolyl)cyclohex 1)methanol

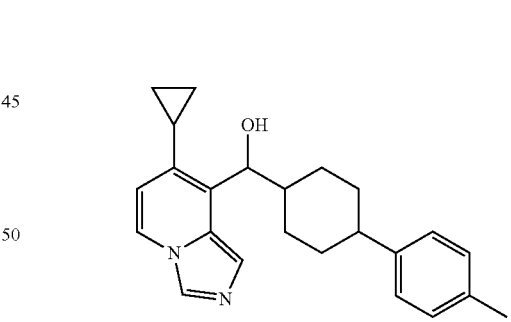

To a solution of crude (7-cyclopropylimidazo[1,5-a]pyridin-8-yl)(4-(p-tolyl)cyclohexyl)methanone (1.4 g, 3.9 mmol) in methol (100 mL) was added $NaBH_4$ (1.6 g, 39 mol) at room temperature, and the mixture was stirred overnight. Then the solvent was evaporated under reduced pressure and water (50 mL) was added, extracted with ethyl acetate (50 mL×3) and combined the organic layer, evaporated the solvent under reduced pressure and the residue was purified by column chromatography (PE:EA=1:1 to EA) to give crude product, which was purified with chiral HPLC to give compounds C110a and C110b.

Example C110a and C110b: (S)-(7-cyclopropylimidazo[1,5-a]pyridin-8-yl)((1r,4S)-4-(p-tolyl)cyclohexyl)methanol and (R)-(7-cyclopropylimidazo[1,5-a]pyridin-8-yl)((1r,4R)-4-(p-tolyl)cyclohexyl)methanol

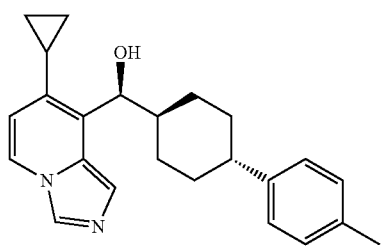

Fast isomer in CHIRAL Cellulose-SB HPLC
Eluting reagent: Hex(0.1% DEA):IPA = 70:30

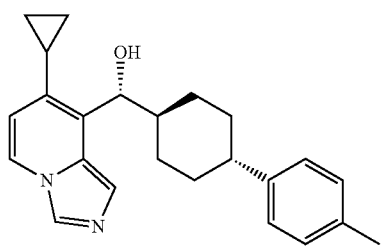

Slow isomer in CHIRAL Cellulose-SB HPLC
Eluting reagent: Hex(0.1% DEA):IPA = 70:30

Each enantiomer of racemic C110a and C110b separated using preparative HPLC on a CHIRAL Cellulose-SB with Hex (0.1% DEA):IPA=70:30 as an eluent. The enantiomeric excess was determined by using HPLC on a CHIRAL Cellulose-SB with Hex (0.1% DEA):IPA=70:30 as an eluent at a flow rate of 1.0 mL/min. The first one enantiomer eluted at the retention time of 5.454 min (C110a), $^1$H NMR (DMSO-d$_6$) $\delta_H$ 8.27 (s, 1H), 8.12 (d, J=7.2 Hz, 1H), 7.46 (s, 1H), 7.03-7.08 (m, 4H), 6.18 (d, J=7.6 Hz, 1H), 5.34 (d, J=3.2 Hz, 1H), 4.95-4.98 (m, 1H), 2.18-2.40 (m, 6H), 1.98-2.00 (m, 1H), 1.82-1.85 (m, 1H), 1.65-1.67 (m, 1H), 1.39-1.43 (m, 1H), 1.20-1.30 (m, 4H), 0.93-0.95 (m, 2H), 0.70-0.72 (m, 2H); and the other enantiomer eluted at the retention time of 9.386 min (C110b), $^1$H NMR (DMSO-d$_6$) $\delta_H$ 8.28 (s, 1H), 8.12 (d, J=7.2 Hz, 1H), 7.46 (s, 1H), 7.03-7.08 (m, 4H), 6.18 (d, J=7.6 Hz, 1H), 5.34 (d, J=3.2 Hz, 1H), 4.95-4.98 (m, 1H), 2.18-2.40 (m, 6H), 1.98-2.00 (m, 1H), 1.82-1.85 (m, 1H), 1.65-1.67 (m, 1H), 1.39-1.43 (m, 1H), 1.20-1.30 (m, 4H), 0.93-0.95 (m, 2H), 0.70-0.72 (m, 2H). The absolute configurations of chiral carbons in C110a and C110b are tentatively assigned as (S) and (R) respectively based on assumption that the binding model of the more potent isomer C110a is the same as that of C101a with IDO1 enzyme, and the relative stereochemistry on cyclohexane is assigned as trans configuration on the cyclohexane.

Example C111: (7-cyclopropylimidazo[1,5-a]pyridin-8-yl)(4-(m-tolyl)cyclohexyl)methanol

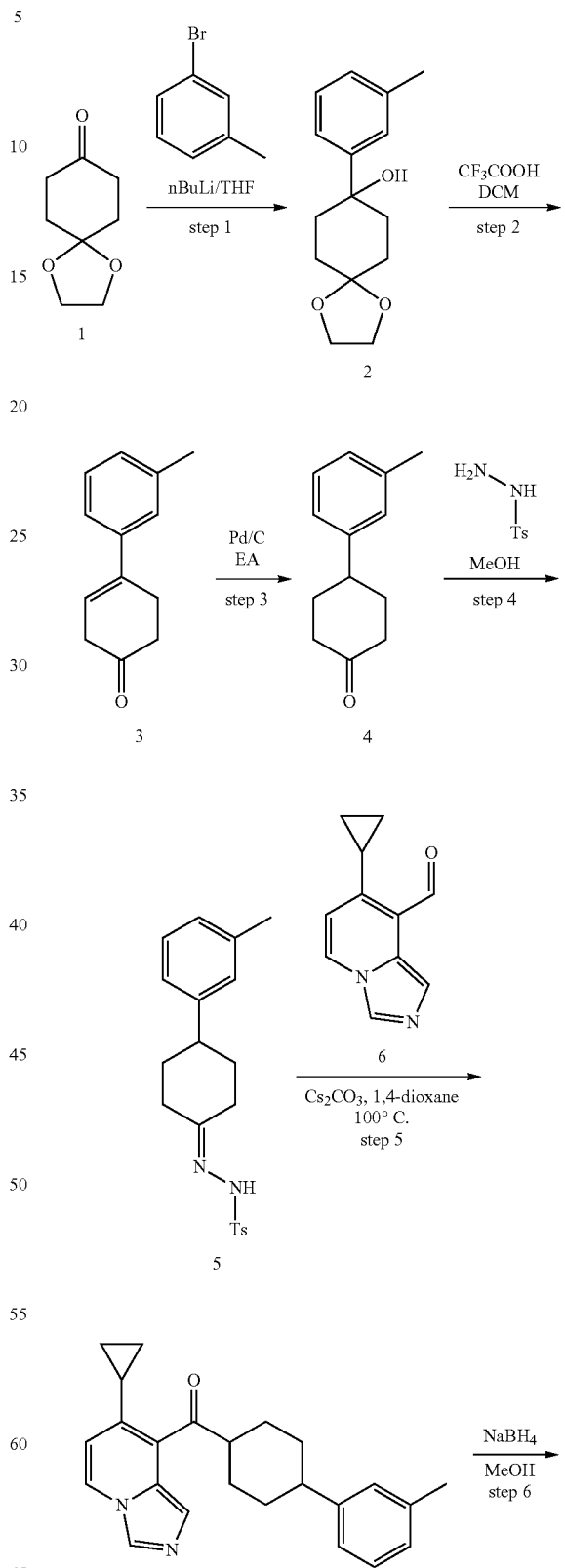

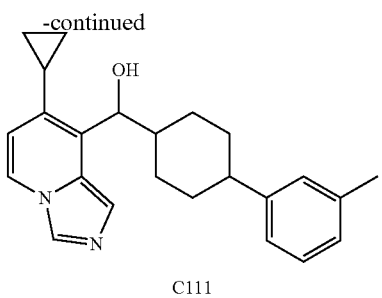

C111

Step 1: 8-(m-tolyl)-1,4-dioxaspiro[4.5]decan-8-ol

To a solution of n-BuLi (48 mL, 2.4 M) in dry THF (100 mL) was added a solution of 1-bromo-3-methylbenzene (20 g, 117 mmol) by dropwised in dry THF (30 mL) at −70° C. and the mixture was stirred for 0.5 h before a solution of 1,4-dioxaspiro[4.5]decan-8-one (12 g, 78 mmol) in dry THF (30 mL) at ~70° C. was added, and the mixture was stirred for 2 hours. Quenched with saturated aqueous of NH$_4$Cl, and extracted with ethyl acetate (100 mL×3), combined the organic layer and evaporated to give crude product, which was used for next step without further purification.

Step 2: 3'-methyl-2,5-dihydro-[1,1'-biphenyl]-4 (3H)-one

To a solution of 8-(m-tolyl)-1,4-dioxaspiro[4.5]decan-8-ol (78 mmol) in dichloromethane (200 mL) was added trifluoroacetic acid (100 mL) at room temperature, and the mixture was stirred for overnight. The solvent was evaporated under reduced pressure and water (100 mL) was added, extracted with ethyl acetate (100 mL×3), combined the organic layer and washed with saturated aqueous of NaHCO$_3$, the organic layer was evaporated under reduced pressure to give crude product, which was used for next step without further purification.

Step 3: 4-(m-tolyl)cyclohexan-1-one

To a solution of 3'-methyl-2,5-dihydro-[1,1'-biphenyl]-4 (3H)-one (78 mmol) in ethyl acetate (200 mL) was added Pd/C (2.0 g, 10%), and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give 13 g oil. MS (ESI) m/e [M+1]$^+$=189.

Step 4: 4-methyl-N'-(4-(m-tolyl)cyclohexylidene) benzenesulfonohydrazide

To a solution of 4-(m-tolyl)cyclohexan-1-one (13 g, 69 mmol) in methol (200 mL) was added 4-methylbenzenesulfonohydrazide (11 g, 69 mmol) at room temperature, and the mixture was stirred for overnight. Evaporate half the solvent under reduced pressure and then filtered to give 4-methyl-N'-(4-(m-tolyl)cyclohexylidene)benzenesulfonohydrazide (13 g) as a white solid. MS (ESI) m/e [M+1]$^+$=357.

Step 5: (7-cyclopropylimidazo[1,5-a]pyridin-8-yl)(4-(m-tolyl)cyclohexyl)methanone To a solution of 7-cyclopropylimidazo[1,5-a]pyridine-8-carbaldehyde (2.0 g, 11 mmol) in 1,4-dioxane (0.2 L) was added 4-methyl-N'-(4-(m-tolyl)cyclohexylidene) benzene-sulfono-hydrazide (7.8 g, 22 mmol) and Cs$_2$CO$_3$ (7.2 g, 22 mmol) at room temperature and the mixture was heated at 100° C. for overnight. The solvent was evaporated under reduced pressure and water (100 mL) was added, extracted with ethyl acetate (50 mL×3) and combined the organic layer, evaporated the solvent under reduced pressure and the residue was purified by column chromatography (PE:EA=1:1) to give crude product as a solid (1.5 g in 38% yield), and which was used for next step without further purification. MS (ESI) m/e [M+1]$^+$=359.

Step 6: (7-cyclopropylimidazo[1,5-a]pyridin-8-yl)(4-(m-tolyl)cyclohexyl)methanol

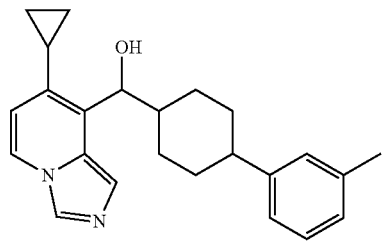 [SMILES: Cc1cccc(C2CCC(C(O)c3c(C4CC4)ccn4cncc34)CC2)c1]

To a solution of crude (7-cyclopropylimidazo[1,5-a]pyridin-8-yl) (4-(m-tolyl)cyclohexyl)methanone (1.5 g, 4.2 mmol) in methol (100 mL) was added NaBH$_4$ (0.8 g, 21 mol) at room temperature, and the mixture was stirred for 0.5 h. Then the solvent was evaporated under reduced pressure and water (50 mL) was added, extracted with ethyl acetate (50 mL×3) and combined the organic layer, evaporated the solvent under reduced pressure and the residue was washed with methol to give product as a white solid (630 mg in 42% yield). $^1$H NMR (DMSO-d$_6$) $\delta_H$ 8.21 (s, 1H), 8.11 (d, J=7.6 Hz, 1H), 7.43 (s, 1H), 7.12 (t, J=7.6 Hz, 1H), 6.94-7.00 (m, 3H), 6.16 (d, J=7.6 Hz, 1H), 5.32 (d, J=3.6 Hz, 1H), 2.37-2.43 (m, 1H), 2.27-2.31 (m, 1H), 2.25 (s, 1H), 2.17 (s, 1H), 1.99-2.02 (m, 1H), 1.83-1.86 (m, 1H), 1.66-1.68 (m, 1H), 1.41-1.45 (m, 1H), 1.17-1.24 (m, 4H), 0.91-0.95 (m, 2H), 0.69-0.73 (m, 2H).

Example C111a and C111b: (S)-(7-cyclopropylimidazo[1,5-a]pyridin-8-yl)((1r,4S)-4-(m-tolyl)cyclohexyl)methanol and (R)-(7-cyclopropylimidazo[1,5-a]pyridin-8-yl)((1r,4R)-4-(m-tolyl)cyclohexyl)methanol

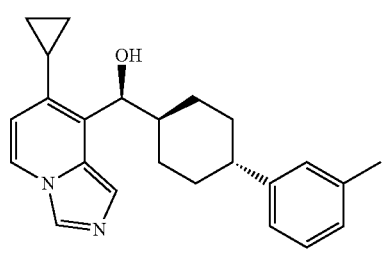

Fast isomer in CHIRALPAK IC HPLC
Eluting reagent: Hex(0.1% DEA):EtOH = 60:40

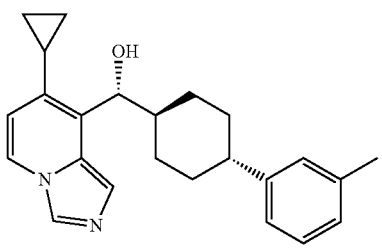

Slow isomer in CHIRALPAK IC HPLC
Eluting reagent: Hex(0.1% DEA):EtOH = 60:40

Each enantiomer of racemic C111a and C111b was separated using preparative HPLC on a CHIRALPAK IC Hex (0.1% DEA):EtOH=60:40 as an eluent. The enantiomeric excesses were determined by using HPLC on a CHIRAL Cellulose-SB with Hex (0.1% DEA):EtOH=60:40 as an eluent at a flow rate of 1.0 mL/min. The first one enantiomer eluted at the retention time of 1.386 min (C111a), $^1$H NMR (DMSO-d$_6$) $\delta_H$ 8.25 (s, 1H), 8.12 (d, J=7.2 Hz, 1H), 7.45 (s, 1H), 7.12 (t, J=7.6 Hz, 1H), 6.94-7.00 (m, 3H), 6.16 (d, J=7.6 Hz, 1H), 5.32 (d, J=3.6 Hz, 1H), 2.37-2.43 (m, 1H), 2.27-2.31 (m, 1H), 2.25 (s, 1H), 2.17 (s, 1H), 1.99-2.02 (m, 1H), 1.83-1.86 (m, 1H), 1.66-1.68 (m, 1H), 1.41-1.45 (m, 1H), 1.17-1.24 (m, 4H), 0.91-0.95 (m, 2H), 0.69-0.73 (m, 2H). and the other enantiomer eluted at the retention time of 2.204 min (C111b), $^1$H NMR (DMSO-d$_6$) $\delta_H$ 8.21 (s, 1H), 8.11 (d, J=7.6 Hz, 1H), 7.43 (s, 1H), 7.12 (t, J=7.6 Hz, 1H), 6.94-7.00 (m, 3H), 6.16 (d, J=7.6 Hz, 1H), 5.32 (d, J=3.6 Hz, 1H), 2.37-2.43 (m, 1H), 2.27-2.31 (m, 1H), 2.25 (s, 1H), 2.17 (s, 1H), 1.99-2.02 (m, 1H), 1.83-1.86 (m, 1H), 1.66-1.68 (m, 1H), 1.41-1.45 (m, 1H), 1.17-1.24 (m, 4H), 0.91-0.95 (m, 2H), 0.69-0.73 (m, 2H). The absolute configurations of chiral carbons in C111a and C111b are tentatively assigned as (S) and (R) respectively based on assumption that the binding model of the more potent isomer C111a is the same as that of C101a with IDO1 enzyme, and the relative stereochemistry on cyclohexane is assigned as trans configuration on the cyclohexane.

Example C112: (7-cyclopropylimidazo[1,5-a]pyridin-8-yl)(4-(o-tolyl)cyclohexyl)methanol

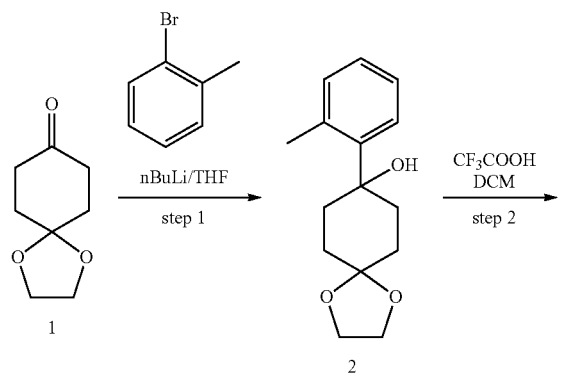

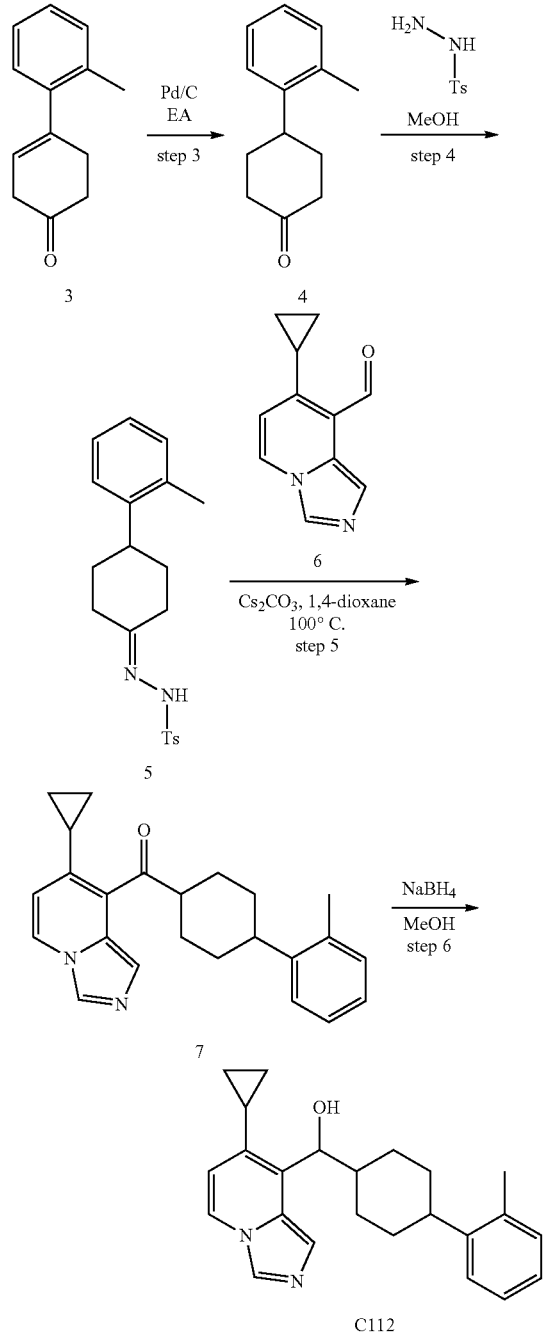

Step 1: 8-(o-tolyl)-1,4-dioxaspiro[4.5]decan-8-ol

To a solution of n-BuLi (48 mL, 2.4 M) in dry THF (100 mL) was added a solution of 1-bromo-2-methylbenzene (20 g, 117 mmol) by dropwised in dry THF (30 mL) at −70° C., and the mixture was stirred for 0.5 h before a solution of 1,4-dioxaspiro[4.5]decan-8-one (12 g, 78 mmol) in dry THF (30 mL) was added at −70° C., and the mixture was stirred for 2 hours. Quenched with saturated aqueous of NH$_4$Cl, and extracted with ethyl acetate (100 mL×3), combined the organic layer and evaporated under reduced pressure to give crude product, and which was used for next step without further purification.

Step 2: 2'-methyl-2,5-dihydro-[1',biphenyl]-4(3H)-one

To a solution of 8-(o-tolyl)-1,4-dioxaspiro[4.5]decan-8-ol (78 mmol) in dichloromethane (200 mL) was added trifluoroacetic acid (100 mL) at room temperature, and the mixture was stirred for overnight. The solvent was evaporated under reduced pressure and water (100 mL) was added, extracted with ethyl acetate (100 mL×3), combined the organic layer and washed with saturated aqueous of $NaHCO_3$ then the organic layer was evaporated under reduced pressure to give crude product, which was used for next step without further purification.

Step 3: 4-(o-tolyl)cyclohexan-1-one

To a solution of 2'-methyl-2,5-dihydro-[1,1'-biphenyl]-4 (3H)-one (78 mmol) in ethyl acetate (200 mL) was added Pd/C (2.0 g, 10%), and the mixture was stirred for 6 hours at room temperature under $H_2$ (0.4 Mpa). Then filtered to remove Pd/C and the filtrate was evaporated under reduced pressure to give a crude product, which was purified by column chromatography (PE as eluent) to give 4-(o-tolyl)cyclohexan-1-one (6.3 g, oil). MS (ESI) m/e $[M+1]^+=189$.

Step 4: 4-methyl-N'-(4-(o-tolyl)cyclohexylidene)benzenesulfonohydrazide

To a solution of 4-(o-tolyl)cyclohexan-1-one (6.3 g, 33 mmol) in methol (150 mL) was added 4-methylbenzenesulfonohydrazide (6.2 g, 33 mmol) at room temperature, and the mixture was stirred for overnight. Evaporate half the solvent under reduced pressure and then filtered to give 4-methyl-N'-(4-(o-tolyl)cyclohexylidene)benzenesulfonohydrazide (4.0 g) as a white solid. MS (ESI) m/e $[M+1]^+=357$.

Step 5: (7-cyclopropylimidazo[1,5-a]pyridin-8-yl)(4-(o-tolyl)cyclohexyl)methanone To a solution of 7-cyclopropylimidazo[1,5-a]pyridine-8-carbaldehyde (2.0 g, 11.2 mmol) in 1,4-dioxane (0.2 L) was added 4-methyl-N'-(4-(o-tolyl)cyclohexylidene) benzenesulfono-hydrazide (4.0 g, 11.2 mmol) and $Cs_2CO_3$ (7.3 g, 22.4 mmol) at room temperature and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1) to give crude product as a solid (0.9 g in 22% yield), and which was used for next step without further purification.

Step 6: (7-cyclopropylimidazo[1,5-a]pyridin-8-yl)(4-(o-tolyl)cyclohexyl)methanol

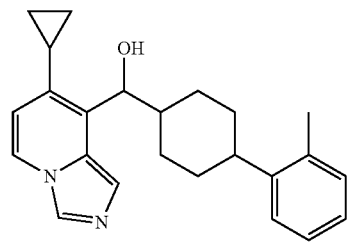 [SMILES: Cc1ccccc1C1CCC(C(O)c2c(C3CC3)ccn3cncc23)CC1]

To a solution of crude (7-cyclopropylimidazo[1,5-a]pyridin-8-yl)(4-(o-tolyl)cyclohexyl)methanone (0.9 g, 2.5 mmol) in methol (50 mL) was added $NaBH_4$ (0.5 g, 25 mol) at room temperature, and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was washed with methol to give product as a white solid (250 mg in 39% yield). $^1$H NMR (DMSO-$d_6$) $\delta_H$ 8.22 (s, 1H), 8.12 (d, J=7.2 Hz, 1H), 7.00-7.17 (m, 4H), 6.16 (d, J=7.6 Hz, 1H), 5.33 (d, J=3.2 Hz, 1H), 4.97-4.50 (m, 1H), 2.62-2.68 (m, 1H), 2.32-2.35 (m, 1H), 2.26 (s, 3H), 2.20 (s, 1H), 2.02-2.05 (m, 1H), 1.78-1.81 (m, 1H), 1.62-1.67 (m, 1H), 1.38-1.47 (m, 1H), 1.22-1.35 (m, 4H), 0.90-0.98 (m, 2H), 0.70-0.71 (m, 2H).

Example C112a and C112b: (S)-(7-cyclopropylimidazo[1,5-a]pyridin-8-yl)((1 r,4S)-4-(o-tolyl)cyclohexyl)methanol and (R)-(7-cyclopropylimidazo[1,5-a]pyridin-8-yl)((1 r,4R)-4-(o-tolyl)cyclohexyl)methanol

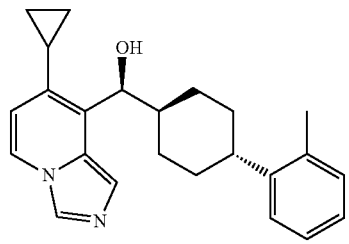

Fast isomer in CHIRALPAK IC HPLC
Eluting reagent: Hex(0.1% DEA):EtOH = 70:30

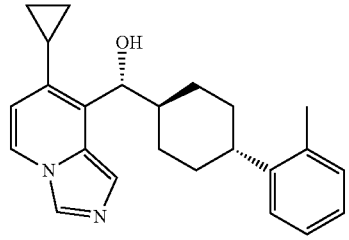

Slow isomer in CHIRALPAK IC HPLC
Eluting reagent: Hex(0.1% DEA):EtOH = 70:30

Each enantiomer of racemic C112a and C112b was separated using preparative HPLC on a CHIRALPAK IC Hex (0.1% DEA):EtOH=70:30 as an eluent. The enantiomeric excesses were determined by using HPLC on a CHIRAL IC with Hex (0.1% DEA):EtOH=70:30 as an eluent at a flow rate of 1.0 mL/min. The first one enantiomer eluted at the retention time of 1.407 min, which was dissolved in EA (4N HCl) and stirred for 0.5 h, filtered to give C112a as white solid, $^1$H NMR (DMSO-$d_6$) $\delta_H$ 9.43 (s, 1H), 8.37 (d, J=7.2 Hz, 1H), 8.04 (s, 1H), 7.01-7.14 (m, 4H), 6.61 (d, J=7.2 Hz, 1H), 5.40 (s, 1H), 5.07 (d, J=7.6 Hz, 1H), 2.62-2.68 (m, 1H), 2.22-2.25 (m, 4H), 1.96-1.98 (m, 1H), 1.78-1.81 (m, 1H), 1.62-1.65 (m, 1H), 1.23-1.35 (m, 5H), 1.04-1.07 (m, 2H), 0.75-0.76 (m, 2H); and the other enantiomer eluted at the retention time of 2.218 min, which was dissolved in EA (4N HCl) and stirred for 0.5 h, filtered to give C112b as white solid, $^1$H NMR (DMSO-$d_6$) $\delta_H$ 9.43 (s, 1H), 8.37 (d, J=7.2 Hz, 1H), 8.04 (s, 1H), 7.01-7.14 (m, 4H), 6.61 (d, J=7.2 Hz, 1H), 5.33 (s, 1H), 5.07 (d, J=7.6 Hz, 1H), 2.62-2.68 (m, 1H), 2.22-2.25 (m, 4H), 1.96-1.98 (m, 1H), 1.78-1.81 (m, 1H), 1.62-1.65 (m, 1H), 1.23-1.35 (m, 5H), 1.04-1.07 (m, 2H), 0.75-0.76 (m, 2H). The absolute configurations of chiral carbons in C112a and C112b are tentatively assigned as (S) and (R) respectively based on assumption that the binding model of the more potent isomer C112a is the same as that of C101a with IDO1 enzyme, and the relative stereochemistry on cyclohexane is assigned as trans configuration on the cyclohexane.

Compounds C113 and C114 were synthesized with the same procedure as example C102.

Example C113: (7-Cyclopropylimidazo[1,5-a]pyridin-8-yl)(4-(2-methoxyphenyl)cyclohexyl)methan

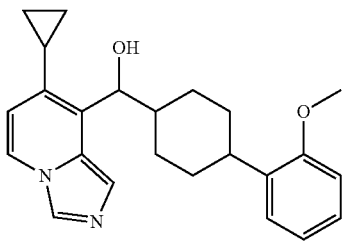

$^1$H NMR (DMSO-$d_6$) $\delta_H$ 8.21 (s, 1H), 8.11 (d, J=7.2 Hz, 1H), 7.43 (s, 1H), 7.10-7.14 (m, 2H), 6.83-6.92 (m, 2H), 6.15 (d, J=7.2 Hz, 1H), 5.30 (d, J=3.6 Hz, 1H), 4.96 (dd, J=3.6, 8.8 Hz, 1H), 3.75 (s, 3H), 2.82-2.85 (m, 1H), 2.31-2.35 (m, 1H), 2.18-2.20 (m, 1H), 1.98-2.01 (m, 1H), 1.77-1.81 (m, 1H), 1.62-1.64 (m, 1H), 1.15-1.45 (m, 5H), 0.92-0.98 (m, 2H) and 0.67-0.74 (m, 2H).

Example C113 a and C113b: (S)-(7-cyclopropylimidazo[1,5-a]pyridin-8-yl)((1r,4S)-4-(2-methoxyphenyl)cyclohexyl)methanol and (R)-(7-cyclopropylimidazo[1,5-a]pyridin-8-yl)(1r,4R)-4-(2-methoxyphenyl)cyclohexyl)methanol

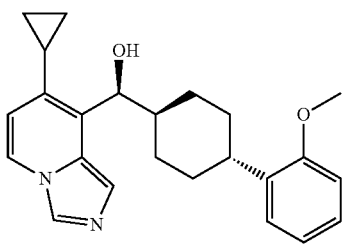

Fast isomer in chiral IC HPLC
Eluting reagent: Hex(0.1% DEA):EtOH = 70:30(v/v)

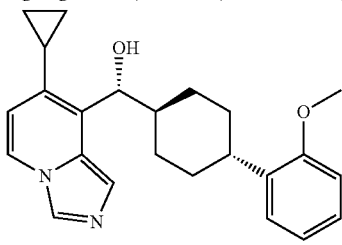

Slow isomer in chiral IC HPLC
Eluting reagent: Hex(0.1% DEA):EtOH = 70:30(v/v)

Each enantiomer of racemic C113a and C113b was separated using preparative HPLC on a CHIRAL PAK IC with Hex (0.1% DEA):EtOH=70:30 as an eluent. The enantiomeric excesses were determined by using HPLC on a CHIRAL PAK IC-3 with Hex (0.2% IPAmine):EtOH=70:30 as an eluent at a flow rate of 1 mL/min. The first one enantiomer eluted at the retention time of 3.53 min (C113a), which was dissolved in THF (10 mL), Ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid, $^1$H NMR (DMSO-$d_6$) $\delta$ 9.43 (s, 1H), 8.36 (d, 1H, J=7.6 Hz), 8.04 (s, 1H), 7.10-7.16 (m, 2H), 6.83-6.93 (m, 2H), 6.61 (d, 1H, J=7.6 Hz), 5.70 (brs, 1H), 5.06 (d, 1H, J=8.4 Hz), 3.76 (s, 3H), 2.83-2.89 (m, 1H), 2.21-2.33 (m, 2H), 1.91-1.97 (m, 1H), 1.78-1.82 (m, 1H), 1.64-1.68 (m, 5H), 1.03-1.06 (m, 2H) and 0.81-0.85 (m, 2H); and the other enantiomer eluted at the retention time of 6.62 min (C113b), which was dissolved in THF (10 mL), Ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid, $^1$H NMR (DMSO-$d_6$) $\delta$ 9.47 (s, 1H), 8.38 (d, 1H, J=7.2 Hz), 8.04 (s, 1H), 7.10-7.15 (m, 2H), 6.83-6.93 (m, 2H), 6.61 (d, 1H, J=8.0 Hz), 5.70 (brs, 1H), 5.06 (d, 1H, J=8.0 Hz), 3.76 (s, 3H), 2.83-2.89 (m, 1H), 2.21-2.33 (m, 2H), 1.91-1.97 (m, 1H), 1.78-1.82 (m, 1H), 1.64-1.68 (m, 5H), 1.03-1.06 (m, 2H) and 0.81-0.85 (m, 2H), MS (ESI) m/e [M+1]$^+$377. The absolute configurations of chiral carbons in C113a and C113b are tentatively assigned as (S) and (R) respectively based on assumption that the binding model of the more potent isomer C113a is the same as that of C101a with IDO1 enzyme, and the relative stereochemistry on cyclohexane is assigned as trans configuration on the cyclohexane.

Example C114: (7-cyclopropylimidazo[1,5-a]pyridin-8-yl)(4-(3-methoxyphenyl)cyclohexyl)methanol $^1$H NMR (DMSO-$d_6$) $\delta_H$ 8.22 (s, 1H), 8.11 (d, J=7.2 Hz, 1H), 7.43 (s, 1H), 7.13-7.17 (m, 1H), 6.69-6.78 (m, 3H), 6.16 (d, J=7.2 Hz, 1H), 6.16 (d, J=6.8 Hz, 1H), 5.32 (d, J=3.2 Hz, 1H), 4.96 (dd, J=3.2, 8.0 Hz, 1H), 3.71 (s, 3H), 2.28-2.45 (m, 3H), 2.17-2.18 (m, 1H), 1.96-2.02 (m, 1H), 1.83-1.87 (m, 1H), 1.66-1.70 (m, 1H), 1.15-1.49 (m, 4H), 0.88-0.98 (m, 2H) and 0.67-0.75 (m, 2H).

Example C114a and C114b: (S)-(7-cyclopropylimidazo[1,5-a]pyridin-8-yl)((1 r,4S)-4-(3-methoxyphenyl)cyclohexyl)methanol and (R)-(7-cyclopropylimidazo[1,5-a]pyridin-8-yl (1 r,4R)-4-(3-methoxyphenyl)cyclohexyl)methanol

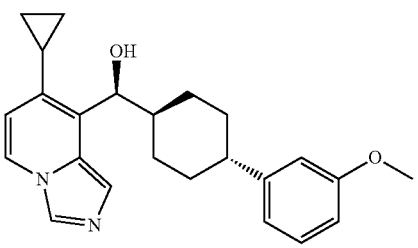

Fast isomer in chiral IC HPLC
Eluting reagent: Hex(0.1% DEA):EtOH = 70:30(v/v)

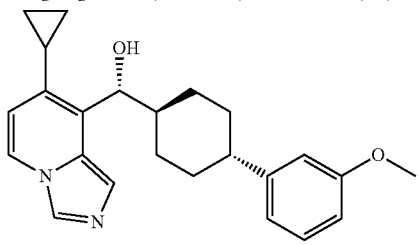

Slow isomer in chiral IC HPLC
Eluting reagent: Hex(0.1% DEA):EtOH = 70:30(v/v)

Each enantiomer of racemic C114a and C114b was separated using preparative HPLC on a CHIRAL PAK IC with Hex (0.1% DEA):EtOH=70:30 as an eluent. The enantiomeric excesses were determined by using HPLC on a CHIRAL PAK IC-3 with Hex (0.1% DEA):EtOH=70:30 as an eluent at a flow rate of 20 mL/min. The first one enantiomer eluted at the retention time of 3.46 min (C114a), which was dissolved in THF (10 mL), ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid, $^1$H NMR (DMSO-$d_6$) δ 9.34 (s, 1H), 8.35 (d, 1H, J=7.6 Hz), 7.98 (s, 1H), 7.16 (t, 1H, J=8.0 Hz), 6.70-6.77 (m, 3H), 6.58 (d, 1H, J=8.0 Hz), 5.69 (brs, 1H), 5.06 (d, 1H, J=7.6 Hz), 3.71 (s, 3H), 2.41-2.46 (m, 1H), 2.22-2.25 (m, 2H), 1.84-1.94 (m, 2H), 1.70-1.75 (m, 1H), 1.23-1.45 (m, 5H), 1.02-1.05 (m, 2H) and 0.79-0.83 (m, 2H), MS (ESI) m/e [M+1]$^+$377; and the other enantiomer eluted at the retention time of 4.60 min (C114b), which was dissolved in THF (10 mL), ethyl acetate solution of hydrochloric acid (0.5 mL, 4.0M) was added at room temperature, followed by addition of methol until the precipitate was dissolved, then the solvent was evaporated under reduced pressure and the residue was washed by PE to give the desired product as white solid, P2$^1$H NMR (DMSO-$d_6$) δ$_H$ 9.35 (s, 1H), 8.35 (d, 1H, J=7.6 Hz), 7.98 (s, 1H), 7.16 (t, 1H, J=8.0 Hz), 6.70-6.77 (m, 3H), 6.58 (d, 1H, J=7.6 Hz), 5.69 (brs, 1H), 5.06 (d, 1H, J=7.6 Hz), 3.71 (s, 3H), 2.41-2.46 (m, 1H), 2.22-2.25 (m, 2H), 1.84-1.94 (m, 2H), 1.70-1.75 (m, 1H), 1.23-1.45 (m, 5H), 1.02-1.05 (m, 2H) and 0.79-0.83 (m, 2H), MS (ESI) m/e [M+1]$^+$=377; The absolute configurations of chiral carbons in C114a and C114b are tentatively assigned as (S) and (R) respectively based on assumption that the binding model of the more potent isomer C114a is the same as that of C101a with IDO1 enzyme, and the relative stereochemistry on cyclohexane is assigned as trans configuration on the cyclohexane.

Example C115: (7-cyclopropylimidazo[1,5-a]pyridin-8-yl)(4-(4-trifluoromethyl)phenyl)cyclohexyl)methanol

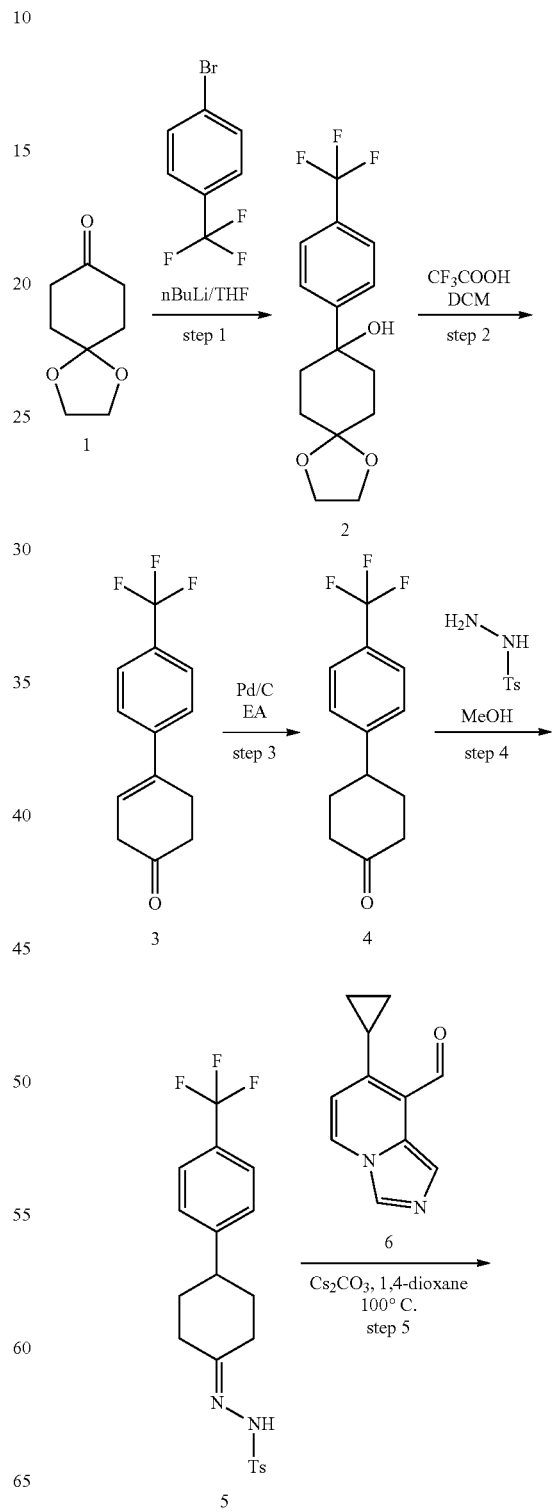

-continued

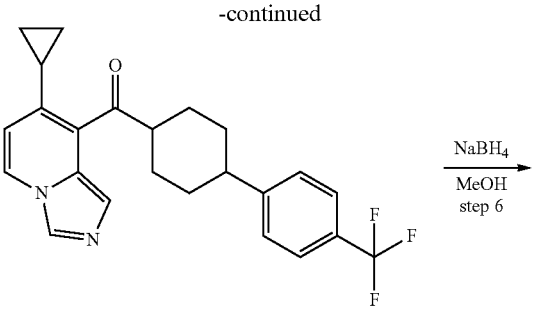

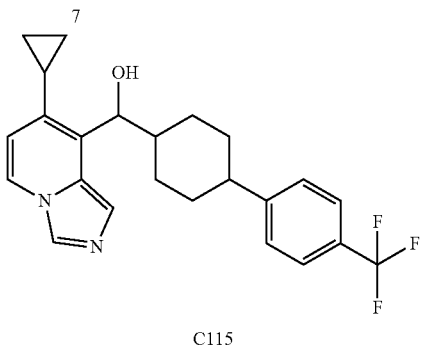

C115

Step 1: 8-(4-(trifluoromethyl)phenyl)-1,4-dioxaspiro[4.5]decan-8-ol

To a solution of n-Bu-Li (42 mL, 2.4 M) in dry THF (100 mL) was added a solution of 1-bromo-4-(trifluoromethyl)benzene (22.5 g, 100 mmol) in dry THF (30 mL) by dropwised at −70° C., the mixture was stirred for 0.5 h before a solution of 1,4-dioxaspiro[4.5]decan-8-one (10.5 g, 67 mmol) in dry THF (30 mL) was added at −70° C., and the mixture was stirred for 2 hours. Quenched with saturated aqueous of $NH_4Cl$ and extracted with ethyl acetate (100 mL×3), combined the organic layer and evaporated under reduced pressure to give crude product, which was used for next step without further purification.

Step 2: 4'-(trifluoromethyl)-2,5-dihydro-[1,1'-biphenyl]-4(3H)-one

To a solution of 8-(4-(trifluoromethyl)phenyl)-1,4-dioxaspiro[4.5]decan-8-ol (67 mmol) in dichloromethane (200 mL) was added trifluoroacetic acid (100 mL) at room temperature, and the mixture was stirred for overnight. The solvent was evaporated under reduced pressure and water (100 mL) was added, extracted with ethyl acetate (100 mL×3), combined the organic layer and washed with saturated aqueous of $NH_4Cl$ then the organic layer was evaporated under reduced pressure to give crude product, which was used for next step without further purification.

Step 3: 4-(4-(trifluoromethyl)phenyl)cyclohexan-1-one

To a solution of 4'-(trifluoromethyl)-2,5-dihydro-[1,1'-biphenyl]-4(3H)-one (67 mmol) in ethyl acetate (200 mL) was added Pd/C (2.0 g, 10%), and the mixture was stirred for 6 hours at room temperature under $H_2$ (0.4 Mpa). Then filtered to remove Pd/C and the filtrate was evaporated under reduced pressure to give a crude product, which was purified by column chromatography (PE as eluent) to give 18 g oil.

Step 4: 4-methyl-N'-(4-(4-(trifluoromethyl)phenyl)cyclohexylidene)-benzenesulfonohydrazide To a solution of 4-(4-(trifluoromethyl)phenyl)cyclohexan-1-one (18 g, 67 mmol) in methol (150 mL) was added 4-methylbenzenesulfonohydrazide (13.8 g, 67 mmol) at room temperature and the mixture was stirred for overnight. Evaporate half the solvent under reduced pressure and then filtered to give 7.5 g as a white solid. MS (ESI) m/e $[M+1]^+=411$.

Step 5: (7-cyclopropylimidazo[1,5-a]pyridin-8-yl)(4-(4-(trifluoromethyl)phenyl)cyclohexyl)methanone To a solution of 7-cyclopropylimidazo[1,5-a]pyridine-8-carbaldehyde (2.0 g, 11.2 mmol) in 1,4-dioxane (0.2 L) was added 4-methyl-N'-(4-(4-(trifluoromethyl)phenyl) cyclohexylidene)-benzenesulfonohydrazide (9.0 g, 22 mmol) and $Cs_2CO_3$ (7.3 g, 22.4 mmol) at room temperature [, and the mixture was heated at 100° C. for overnight. Evaporated the solvent under reduced pressure and water (100 mL) was added, extracted with ethyl acetate (50 mL×3) and combined the organic layer, the solvent was evaporated under reduced pressure and the residue was purified by column chromatography (PE:EA=1:1) to give crude product as a solid (1.5 g in 31% yield), which was used for next step without further purification. MS (ESI) m/e $[M+1]^+=413$.

Step 6: (7-cyclopropylimidazo[1,5-a]pyridin-8-yl)(4-(4-(trifluoromethyl)phenyl)cyclohexyl)methanol

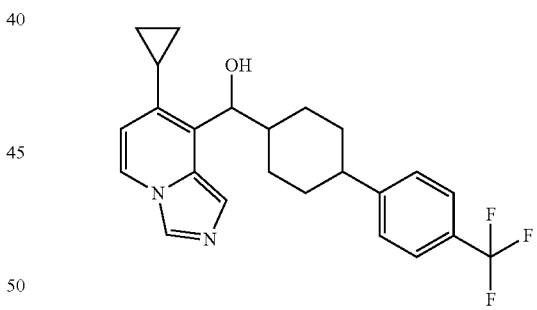

To a solution of crude (7-cyclopropylimidazo[1,5-a]pyridin-8-yl)(4-(4-(trifluoromethyl)phenyl)cyclohexyl)methanone (1.5 g, 3.6 mmol) in methanol (50 mL) was added $NaBH_4$ (1.4 g, 36 mol) at room temperature and the mixture was stirred for 0.5 h. Then the solvent was evaporated under reduced pressure and water (50 mL) was added, extracted with ethyl acetate (50 mL×3) and combined the organic layer, the solvent was evaporated and the residue was washed with methanol to give a mixture (250 mg in 17% yield). MS (ESI) m/e $[M+1]^+=415$.

Example C115a and C115b: (S)-(7-cyclopropylimidazo[1,5-a]pyridin-8-yl)((1 r,4S)-4-(4-(trifluoromethyl)phenyl)cyclohexyl)methanol and (R)-(7-cyclopropylimidazo[1,5-a]pyridin-8-yl)(1 r 4R)-4-(4-(trifluoromethyl)phenyl)cyclohexyl)methanol

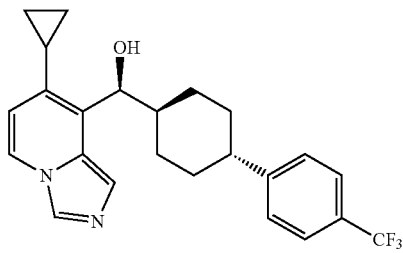

Fast isomer in CHIRALPAK IC HPLC
Eluting reagent: Hex(0.1% DEA):EtOH = 70:30

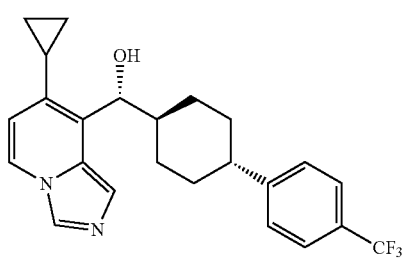

Slow isomer in CHIRALPAK IC HPLC
Eluting reagent: Hex(0.1% DEA):EtOH = 70:30

Each enantiomer of racemic C115a and C115b was separated using preparative HPLC on a CHIRALPAK IC Hex (0.1% DEA):EtOH=70:30 as an eluent. The enantiomeric excesses were determined by using HPLC on a CHIRALPAK IC with Hex (0.1% DEA):EtOH=70:30 as an eluent at a flow rate of 1.0 ml/min. The first one enantiomer eluted at the retention time of 2.852 min, which was dissolved in EA (HCl, 4N) and stirred for 0.5 h to give C115a as white solid, $^1$H NMR (DMSO-$d_6$) $\delta_H$ 9.44 (s, 1H), 8.37 (d, J=7.6 Hz, 1H), 8.03 (s, 1H), 7.61 (d, J=8.4 Hz, 2H), 7.43 (d, J=8.0 Hz, 1H), 6.62 (d, J=7.6 Hz, 1H), 5.72 (s, 1H), 5.07 (d, J=8.0 Hz, 1H), 2.51-2.58 (m, 1H), 2.23-2.26 (m, 2H), 1.87-1.94 (m, 2H), 1.74-1.76 (m, 1H), 1.30-1.49 (m, 5H), 1.04-1.06 (m, 2H), 0.80-0.84 (m, 2H); and the other enantiomer eluted at the retention time of 4.813 min, which was dissolved in EA (HCl, 4N) and stirred for 0.5 h to give C115b as white solid, $^1$H NMR (DMSO-$d_6$) $\delta_H$ 9.41 (s, 1H), 8.36 (d, J=7.6 Hz, 1H), 8.02 (s, 1H), 7.61 (d, J=8.4 Hz, 2H), 7.43 (d, J=8.0 Hz, 1H), 6.61 (d, J=7.6 Hz, 1H), 5.72 (s, 1H), 5.07 (d, J=8.0 Hz, 1H), 2.51-2.58 (m, 1H), 2.23-2.26 (m, 2H), 1.87-1.94 (m, 2H), 1.74-1.76 (m, 1H), 1.30-1.49 (m, 5H), 1.04-1.06 (m, 2H), 0.80-0.84 (m, 2H). The absolute configurations of chiral carbons in C115a and C115b are tentatively assigned as (S) and (R) respectively based on assumption that the binding model of the more potent isomer C115a is the same as that of C101a with IDO1 enzyme, and the relative stereochemistry on cyclohexane is assigned as trans configuration on the cyclohexane.

Example C116: (7-cyclopropylimidazo[1,5-a]pyridin-8-yl)(4-(2-trifluoromethyl)phenyl)cyclohexyl)methanol

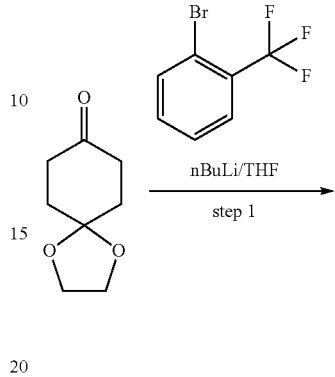

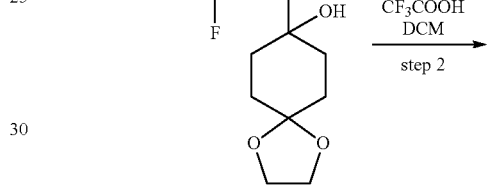

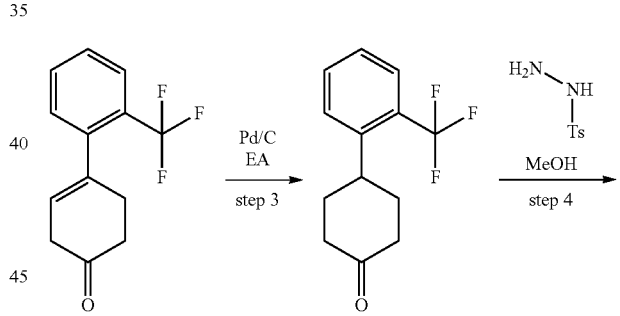

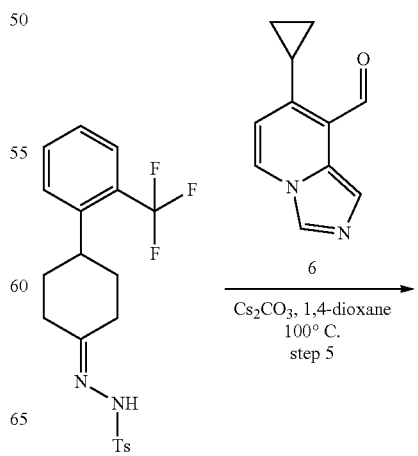

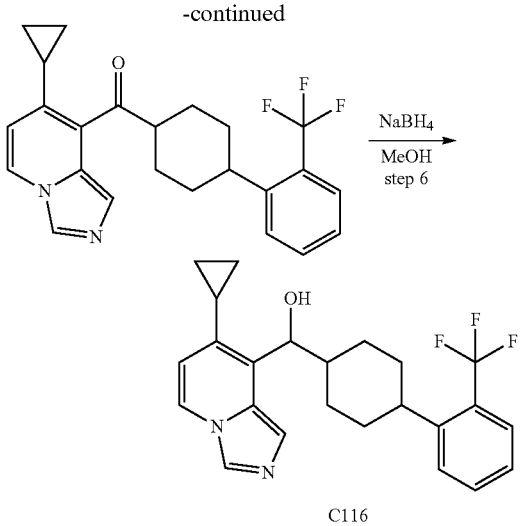

C116

Step 1: 8-(2-(trifluoromethyl)phenyl)-1,4-dioxaspiro[4.5]decan-8-ol

To a solution of n-BuLi (42 mL, 2.4 M) in dry THF (100 mL) was added a solution of 1-bromo-2-(trifluoromethyl)benzene (22.5 g, 100 mmol) by dropwised in dry THF (30 mL) at −70° C., and the mixture was stirred for 0.5 h before a solution of 1,4-dioxaspiro[4.5]decan-8-one (10.5 g, 67 mmol) was added in dry THF (30 mL) at −70° C. and the mixture was stirred for 2 hours. Quenched with saturated aqueous of NH$_4$Cl and extracted with ethyl acetate (100 mL×3), combined the organic layer and evaporated under reduced pressure to give crude product, which was used for next step without further purification.

Step 2: 2'-(trifluoromethyl)-2,5-dihydro-[1,1'-biphenyl]-4(3H)-one

To a solution of 8-(2-(trifluoromethyl)phenyl)-1,4-dioxaspiro[4.5]decan-8-ol (67 mmol) in dichloromethane (200 mL) was added trifluoroacetic acid (100 mL) at room temperature and the mixture was stirred for overnight. The solvent was evaporated under reduced pressure and water (100 mL) was added, extracted with ethyl acetate (100 mL; 3), combined the organic layer and washed with saturated aqueous of NaHCO$_3$, then the organic layer was evaporated under reduced pressure to give crude product, which was used for next step without further purification.

Step 3: 4-(2-(trifluoromethyl)phenyl)cyclohexan-1-one

To a solution of 2'-(trifluoromethyl)-2,5-dihydro-[1,1'-biphenyl]-4(3H)-one (67 mmol) in ethyl acetate (200 mL) was added Pd/C (2.0 g, 10%) and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give 22 g oil.

Step 4: 4-methyl-N'-(4-(2-(trifluoromethyl)phenyl)cyclohexylidene)-benzenesulfonohydrazide To a solution of 4-(2-(trifluoromethyl)phenyl)cyclohexan-1-one (22 g, 67 mmol) in methol (150 mL) was added 4-methylbenzenesulfonohydrazide (13.8 g, 67 mmol) at room temperature and the mixture was stirred for overnight. Evaporate half the solvent under reduced pressure and then filtered to give 17 g as a white solid. MS (ESI) m/e [M+1]$^+$=411.

Step 5: (7-cyclopropylimidazo[1,5-a]pyridin-8-yl)(4-(2-(trifluoromethyl)phenyl)cyclohexyl)methanone To a solution of 7-cyclopropylimidazo[1,5-a]pyridine-8-carbaldehyde (2.0 g, 11.2 mmol) in 1,4-dioxane (0.2 L) was added 4-methyl-N'-(4-(2-(trifluoromethyl)phenyl) cyclohexylidene)-benzenesulfonohydrazide (9.0 g, 22 mmol) and Cs$_2$CO$_3$ (7.3 g, 22.4 mmol) at room temperature, and the mixture was heated at 100° C. for overnight. The solvent was evaporated t and water (100 mL) was added, extracted with ethyl acetate (50 mL×3) and combined the organic layer, evaporated the solvent under reduced pressure and the residue was purified by column chromatography (PE:EA=1:1) to give crude product as a solid (1.2 g in 27% yield), which was used for next step without further purification. MS (ESI) m/e [M+1]$^+$=413.

Step 6: (7-cyclopropylimidazo[1,5-a]pyridin-8-yl)(4-(2-(trifluoromethyl)phenyl)cyclohexyl)methanol

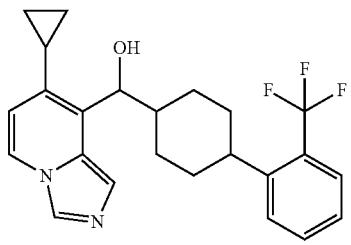 [SMILES: OC(c1c(C2CC2)ccn2cncc12)C1CCC(c2ccccc2C(F)(F)F)CC1]

To a solution of crude (7-cyclopropylimidazo[1,5-a]pyridin-8-yl)(4-(2-(trifluoromethyl)phenyl)cyclohexyl)methanone (1.2 g, 2.9 mmol) in methol (50 mL) was added NaBH$_4$ (0.6 g, 14.5 mol) at room temperature and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was purified by Pre-HPLC to give product as a white solid (550 mg in 46% yield). $^1$H NMR (DMSO-d$_6$) δ$_H$ 8.21 (s, 1H), 8.11 (d, J=7.2 Hz, 1H), 7.58-7.64 (m, 3H), 7.45 (s, 1H), 7.36 (t, J=7.6 Hz, 1H), 6.15 (d, J=7.2 Hz, 1H), 5.34 (d, J=3.6 Hz, 1H), 4.99 (dd, J=3.6, 8.4 Hz, 1H), 2.75-2.82 (m, 1H), 2.33-2.37 (m, 1H), 2.20 (s, 1H), 2.08-2.10 (m, 1H), 1.77-1.81 (m, 1H), 1.57-1.64 (m, 2H), 1.18-1.43 (m, 4H), 0.92-0.96 (m, 2H), 0.69-0.71 (m, 2H). MS (ESI) m/e [M+1]$^+$=415.

Example C116a and C116b: (S)-(7-cyclopropylimidazo[1,5-a]pyridin-8-yl)((1 r,4S)-4-(2-(trifluoromethyl)phenyl)cyclohexyl)methanol and (R)-(7-cyclopropylimidazo[1,5-a]pyridin-8-yl)(1 r,4R)-4-(2-(trifluoromethyl)phenyl)cyclohexyl)methanol Example C117: (7-cyclopropylimidazo[1,5-a]pyridin-8-yl)(4-(4-(oxetan-3-yloxy)phenyl)cyclohexyl)methanol

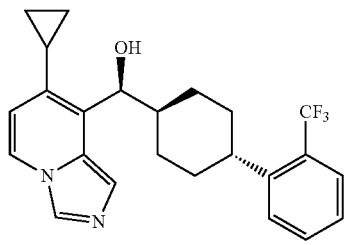

Fast isomer in CHIRALPAK IC HPLC
Eluting reagent: Hex(0.1% DEA):EtOH = 80:20

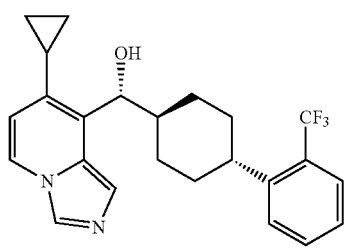

Slow isomer in CHIRALPAK IC HPLC
Eluting reagent: Hex(0.1% DEA):EtOH = 80:20

Each enantiomer of racemic C116a and C116b was separated using preparative HPLC on a CHIRALPAK IC Hex (0.1% DEA):EtOH=80:20 as an eluent. The enantiomeric excesses were determined by using HPLC on a CHIRALPAK IC-3 with Hex (0.1% DEA):EtOH=80:20 as an eluent at a flow rate of 1.0 mL/min. The first one enantiomer eluted at the retention time of 3.550 min, which was dissolved in EA (HCl, 4N) and stirred for 0.5 h to give C116a, $^1$H NMR (DMSO-d$_6$) $\delta_H$ 9.34 (s, 1H), 8.34 (d, J=7.6 Hz, 1H), 8.02 (s, 1H), 7.58-7.64 (m, 3H), 7.36 (t, J=7.6 Hz, 1H), 6.58 (d, J=7.6 Hz, 1H), 5.72 (s, 1H), 5.07 (d, J=8.0 Hz, 1H), 2.75-2.82 (m, 1H), 2.33-2.37 (m, 1H), 2.20 (s, 1H), 2.08-2.10 (m, 1H), 1.77-1.81 (m, 1H), 1.57-1.64 (m, 2H), 1.18-1.43 (m, 4H), 0.92-0.96 (m, 2H), 0.70-0.75 (m, 2H), and the other enantiomer eluted at the retention time of 5.704 min, which was dissolved in EA (HCl, 4N) and stirred for 0.5 h to give C116b, $^1$H NMR (DMSO-d$_6$) $\delta_H$ 9.44 (s, 1H), 8.36 (d, J=7.6 Hz, 1H), 8.05 (s, 1H), 7.58-7.64 (m, 3H), 7.36 (t, J=7.6 Hz, 1H), 6.61 (d, J=7.6 Hz, 1H), 5.72 (s, 1H), 5.07 (d, J=7.6 Hz, 1H), 2.75-2.83 (m, 1H), 2.33-2.37 (m, 1H), 2.20 (s, 1H), 2.08-2.10 (m, 1H), 1.77-1.81 (m, 1H), 1.57-1.64 (m, 2H), 1.18-1.43 (m, 4H), 0.92-0.96 (m, 2H), 0.70-0.75 (m, 2H). The absolute configurations of chiral carbons in C116a and C116b are tentatively assigned as (S) and (R) respectively based on assumption that the binding model of the more potent isomer C116a is the same as that of C101a with IDO1 enzyme, and the relative stereochemistry on cyclohexane is assigned as trans configuration on the cyclohexane.

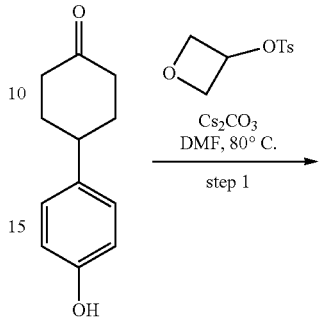

step 1

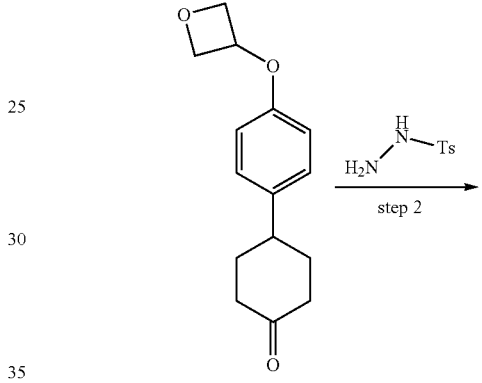

step 2

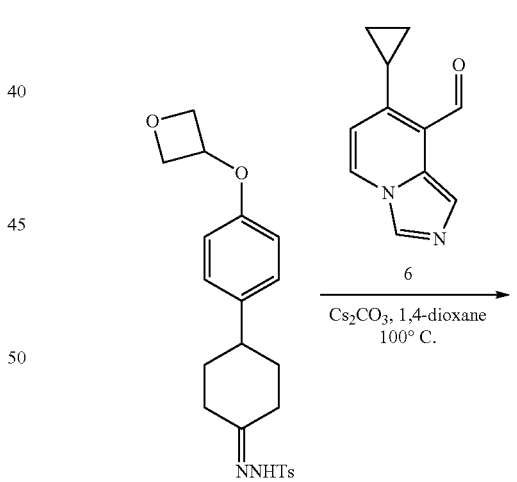

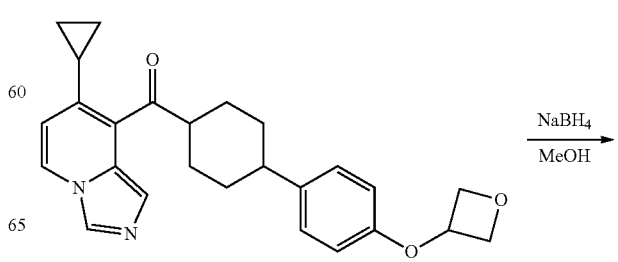

-continued

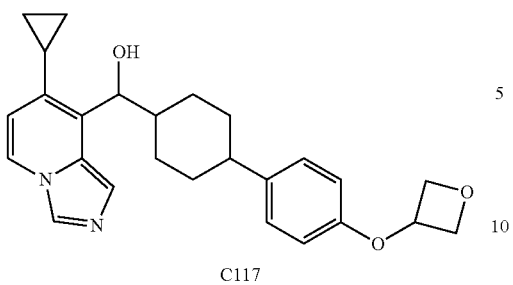

C117

Step 1: 4-(4-(oxetan-3-yloxy)phenyl)cyclohexan-1-one

To a solution of 4-(4-hydroxyphenyl)cyclohexan-1-one (19 g, 100 mmol) in DMF (100 mL) was added oxetan-3-yl 4-methylbenzenesulfonate (23 g, 100 mmol) and $Cs_2CO_3$ (33 g, 100 mmol) and the mixture was heated at 80° C. for 24 hours. Then the solvent was evaporated under reduced pressure, the crude product was purified by column chromatography (PE:EA=5:1) to give product as white solid (19 g in 70% yield). $^1$H NMR (DMSO-d$_6$) OH 7.21 (d, J=8.4 Hz, 2H), 6.72 (d, J=8.8 Hz, 2H), 5.21-5.26 (m, 1H), 4.91 (t, J=6.8 Hz, 2H), 4.53 (dd, J=4.8, 7.2 Hz, 2H), 2.97-3.02 (m, 1H), 2.50-2.60 (m, 2H), 2.23-2.27 (m, 2H), 2.00-2.04 (m, 2H), 1.77-1.88 (m, 2H).

Step 2: 4-methyl-N'-(4-(4-(oxetan-3-yloxy)phenyl)cyclohexylidene)benzene-sulfonohydrazide To a solution of 4-(4-(oxetan-3-yloxy)phenyl)cyclohexan-1-one (19 g, 77 mmol) in methol (100 mL) was added 4-methylbenzenesulfonohydrazide (14.3 g, 77 mmol) at room temperature, and the mixture was stirred for 30 min. Then the mixture was filtered to give product as a white solid (20 g in 63% yield). $^1$H NMR (DMSO-d) δ$_H$ 10.15 (s, 1H), 7.74 (d, J=8.4 Hz, 2H), 7.38 (d, J=8.0 Hz, 2H), 7.12 (d, J=8.4 Hz, 2H), 6.68 (d, J=8.4 Hz, 2H), 5.19-5.24 (m, 1H), 4.90 (t, J=6.4 Hz, 2H), 4.50-4.54 (m, 2H), 2.89-2.92 (m, 1H), 2.70-2.76 (m, 1H), 2.39 (s, 3H), 2.22-2.45 (m, 2H), 1.86-1.95 (m, 3H), 1.40-1.51 (m, 2H).

Step 3: (7-cyclopropylimidazo[1,5-a]pyridin-8-yl)(4-(4-(oxetan-3-yloxy)phenyl)cyclohexyl)methanone To a solution of 7-cyclopropylimidazo[1,5-a]pyridine-8-carbaldehyde (2.0 g, 11 mmol) in 1,4-dioxane (0.2 L) was added 4-methyl-N'-(4-(4-(oxetan-3-yloxy)phenyl) cyclohexylidene)-benzenesulfonohydrazide (9.1 g, 22 mmol) and $Cs_2CO_3$ (7.1 g, 22 mmol) at room temperature, and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1) to give crude product as a yellow solid (1.5 g in 33% yield), which was used for next step without further purification. MS (ESI) m/e $[M+1]^+$=417.

Step 4: (7-cyclopropylimidazo[1,5-a]pyridin-8-yl)(4-(4-(oxetan-3-yloxy)phenyl)cyclohexyl)methanol

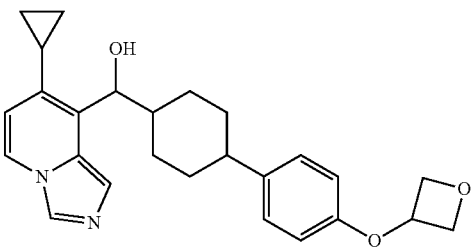 [SMILES: OC(c1c(C2CC2)ccn2cncc12)C1CCC(c2ccc(OC3COC3)cc2)CC1]

To a solution of crude (7-cyclopropylimidazo[1,5-a]pyridin-8-yl)(4-(4-(oxetan-3-yloxy)phenyl)cyclohexyl)methanone (1.5 g, 3.6 mmol) in methanol (100 mL) was added $NaBH_4$ (0.7 g, 18 mol) at room temperature, and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was purified by column chromatography (PE/EA=1:1) to give the product as a white solid (660 mg in 44% yield). $^1$H NMR (DMSO-d$_6$) δ$_H$ 8.22 (s, 1H), 8.11 (d, J=7.6 Hz, 1H), 7.43 (s, 1H), 7.10 (d, J=8.4 Hz, 2H), 6.65 (d, J=8.4 Hz, 2H), 6.16 (d, J=7.2 Hz, 1H), 5.32 (d, J=2.8 Hz, 1H), 5.19-5.22 (m, 1H), 4.96 (d, J=8.4 Hz, 1H), 4.88 (t, J=6.4 Hz, 2H), 4.51 (t, J=6.4 Hz, 2H), 2.30-2.39 (m, 2H), 2.16 (s, 1H), 1.98-2.00 (m, 1H), 1.81-1.84 (m, 1H), 1.65 (s, 1H), 1.34-1.43 (m, 1H), 1.20-1.29 (m, 4H), 0.92-0.94 (m, 2H), 0.70-0.71 (m, 2H).

Example C117a and C117b: (S)-(7-cyclopropylimidazo[1,5-a]pyridin-8-yl)((1r,4S)-4-(4-(oxetan-3-yloxy)phenyl)cyclohexyl)methanol and (R)-(7-cyclopropylimidazo[1,5-a]pyridin-8-yl(1 r,4R)-4-(4-(oxetan-3-yloxy)phenyl)cyclohexyl)methanol

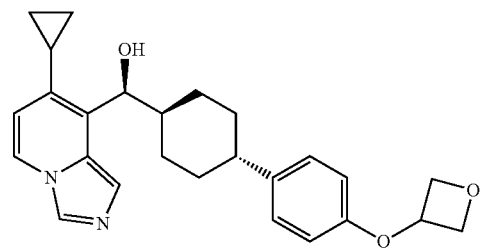

Fast isomer in CHIRALPAK IC HPLC
Eluting reagent: (Hex:DCM = 3:1):EtOH = 50:50

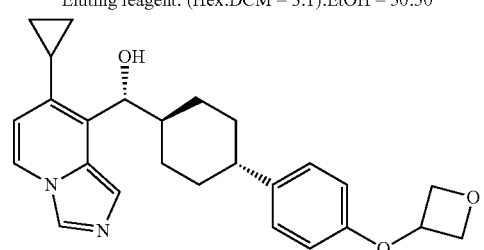

Slow isomer in CHIRALPAK IC HPLC
Eluting reagent: (Hex:DCM = 3:1):EtOH = 50:50

Each enantiomer of racemic C117a and C117b was separated using preparative HPLC on a CHIRALPAK IC (Hex:DCM=3:1):EtOH=50:50 as an eluent. The enantiomeric excesses were determined by using HPLC on a CHIRALPAK IC-3 with (Hex:DCM=5:1) (0.1% DEA):EtOH=50:50 as an eluent at a flow rate of 1.0 mL/min. The first one enantiomer eluted at the retention time of 2.099 min, and the other enantiomer eluted at the retention time of 4.041 min. To a solution of C117a (294 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (295 mg in 92% yield). $^1$H NMR (DMSO-d$_6$) $\delta_H$ 9.44 (s, 1H), 8.37 (d, J=7.2 Hz, 1H), 8.02 (s, 1H), 7.10 (d, J=8.4 Hz, 2H), 6.66 (d, J=8.4 Hz, 2H), 6.61 (d, J=7.2 Hz, 1H), 5.52 (s, 1H), 5.19-5.22 (m, 1H), 5.05 (d, J=7.6 Hz, 1H), 4.89 (t, J=6.4 Hz, 2H), 4.49-4.52 (m, 2H), 2.37-2.40 (m, 1H), 2.18-2.23 (m, 2H), 1.81-1.91 (m, 2H), 1.68-1.70 (m, 1H), 1.22-1.40 (m, 5H), 1.03-1.05 (m, 2H), 0.80-0.83 (m, 2H). To a solution of C117b (274 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (270 mg in 91% yield). $^1$H NMR (DMSO-d$_6$) $\delta_H$ 9.43 (s, 1H), 8.37 (d, J=7.2 Hz, 1H), 8.02 (s, 1H), 7.10 (d, J=8.4 Hz, 2H), 6.66 (d, J=8.4 Hz, 2H), 6.61 (d, J=7.2 Hz, 1H), 5.71 (s, 1H), 5.19-5.22 (m, 1H), 5.05 (d, J=7.6 Hz, 1H), 4.89 (t, J=6.4 Hz, 2H), 4.49-4.52 (m, 2H), 2.40-2.42 (m, 1H), 2.20-2.23 (m, 2H), 1.81-1.90 (m, 2H), 1.68-1.70 (m, 1H), 1.24-1.40 (m, 5H), 1.03-1.05 (m, 2H), 0.81-0.83 (m, 2H). The absolute configurations of chiral carbons in C117a and C117b are tentatively assigned as (S) and (R) respectively based on assumption that the binding model of the more potent isomer C117a is the same as that of C101a with IDO1 enzyme, and the relative stereochemistry on cyclohexane is assigned as trans configuration on the cyclohexane.

Examples C118 and C119 were synthesized using the same procedure as example C101.

Example C118: (4-(4-(cyclopentyloxy)phenyl)cyclohexyl)(7-cyclopropylimidazo[1,5-a]pyridin-8-yl)methanol

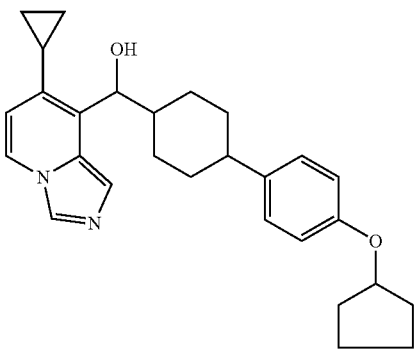 [SMILES: OC(c1c(C2CC2)ccn2cncc12)C1CCC(c2ccc(OC3CCCC3)cc2)CC1]

$^1$H NMR (DMSO-d$_6$) $\delta_H$ 8.21 (s, 1H), 8.11 (d, J=7.2 Hz, 1H) 7.43 (s, 1H), 7.07 (d, J=8.4 Hz, 2H), 6.75 (d, J=8.4 Hz, 2H), 6.16 (d, J=7.6 Hz, 1H), 5.30 (d, J=3.2 Hz, 1H), 4.96 (dd, J=8.0, 3.2 Hz, 1H), 4.73 (t, J=5.6 Hz, 1H), 2.31-2.37 (m, 2H), 2.25-2.10 (m, 1H), 2.05-1.93 (m, 1H), 1.92-1.78 (m, 3H), 1.67-1.66 (m, 5H), 1.58-1.50 (m, 2H), 1.43-1.34 (m, 1H), 1.26-1.16 (m, 5H), 0.94-0.92 (m, 2H), 0.75-0.65 (m, 2H). [M+H]$^+$=431.

Example C118a and C1118b: (S)-((1r,4S)-4-(4-(cyclopentyloxy)phenyl)cyclohexyl)-(7-cyclopropylimidazo[1,5-a]pyridin-8-yl)methanol and (R)-((1r,4R)-4-(4-(cyclopentyloxy)phenyl)cyclohexyl)(7-cyclopropylimidazo[1,5-a]pyridin-8-yl)methanol

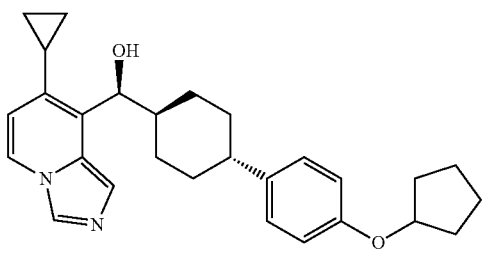

Fast isomer in CHIRALPAK IC-3
Eluting reagent: Hex (0.1% DEA):EtOH = 60:40

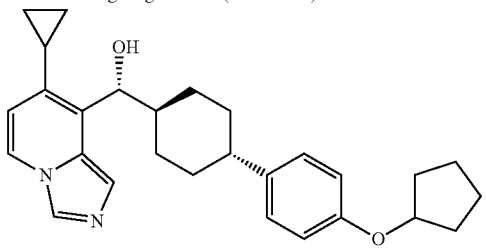

Slow isomer in CHIRALPAK IC-3
Eluting reagent: Hex (0.1% DEA):EtOH = 60:40

Each enantiomer of racemic C118a and C118b was separated using preparative HPLC on a CHIRAL PAK IC-3 with Hex (0.1% DEA):EtOH=60:40 as an eluent. The enantiomeric excesses were determined by using HPLC on a CHIRAL PAK IC-3 with Hex (0.1% DEA):EtOH=60:40 as an eluent at a flow rate of 1.0 mL/min. The first one enantiomer eluted at the retention time of 1.591 min (C118a), which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-d6) $\delta_H$ 9.42 (s, 1H), 8.36 (d, J=7.2 Hz, 1H), 8.02 (s, 1H), 7.06 (d, J=8.8 Hz, 2H), 6.76 (d, J=8.8 Hz, 2H), 6.61 (d, J=7.6 Hz, 1H), 5.70 (s, 1H), 5.05 (d, J=7.6 Hz, 1H), 4.73 (t, J=5.6 Hz, 1H), 2.401-2.32 (m, 3H), 2.23-2.20 (m, 3H), 1.87-1.83 (m, 5H), 1.75-1.60 (m, 6H), 1.57-1.55 (m, 3H), 1.40-1.22 (m, 6H), 1.06-1.03 (m, 2H), 0.85-0.75 (s, 3H). and the other enantiomer eluted at the retention time of 3.038 min (C118b), $^1$H NMR (DMSO-d6) $\delta_H$ 9.39 (s, 1H), 8.36 (d, J=7.6 Hz, 1H), 8.01 (s, 1H), 7.06 (d, J=8.8 Hz, 2H), 6.76 (d, J=8.8 Hz, 2H), 6.60 (d, J=7.6 Hz, 1H), 5.70 (s, 1H), 5.05 (d, J=8.0 Hz, 1H), 4.73 (t, J=5.8 Hz, 1H), 2.43-2.30 (m, 3H), 2.27-2.18 (m, 3H), 1.87-1.83 (m, 6H), 1.67-1.66 (m, 7H), 1.57-1.55 (m, 3H), 1.42-1.22 (m, 7H), 1.05-1.03 (m, 3H), 0.84-0.76 (m, 3H). The absolute configurations of chiral carbons in C118a and C118b are tentatively assigned as (S)

and (R) respectively based on assumption that the binding model of the more potent isomer C118a is the same as that of C101a with IDO1 enzyme, and the relative stereochemistry on cyclohexane is assigned as trans configuration on the cyclohexane.

Example C119: (7-cyclopropylimidazo[1,5-a]pyridin-8-yl)(4-(4-((tetrahydro-2H-pyran-4-yl)oxy)phenyl)cyclohexyl)methanol

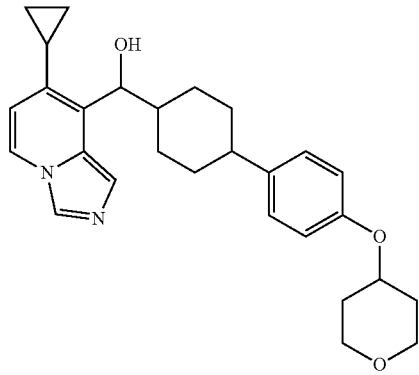 [SMILES: OC(c1c(C2CC2)ccn2cncc12)C1CCC(c2ccc(OC3CCOCC3)cc2)CC1]

$^1$H NMR (DMSO-d$_6$) δ$_H$ 8.23 (s, 1H), 8.12 (d, J=6.8 Hz, 1H), 7.44 (s, 1H), 7.08 (d, J=8.4 Hz, 2H), 6.84 (d, J=8.4 Hz, 2H), 6.17 (d, J=6.8 Hz, 1H), 5.32 (d, J=2.8 Hz, 1H), 4.96 (dd, J=2.8, 8.4 Hz, 1H), 4.45-4.49 (m, 1H), 3.79-3.85 (m, 2H), 3.41-3.85 (m, 2H), 2.29-2.39 (m, 2H), 2.12-2.20 (m, 1H), 1.81-1.99 (m, 4H), 1.65-1.68 (m, 1H), 1.48-1.58 (m, 2H), 1.17-1.41 (m, 5H), 0.90-0.96 (m, 2H), and 0.69-0.73 (m, 2H). MS (ESI) m/e [M+1]$^+$447;

Example C119a and C119b: (S)-(7-cyclopropylimidazo[1,5-a]pyridin-8-yl)((1r,4S)-4-(4-((tetrahydro-2H-pyran-4-yl)oxy)phenyl)cyclohexyl)methanol and (R)-(7-cyclopropylimidazo[1,5-a]pyridin-8-yl)((1r,4R)-4-(4-((tetrahydro-2H-pyran-4-yl)oxy)phenyl)cyclohexyl)methanol

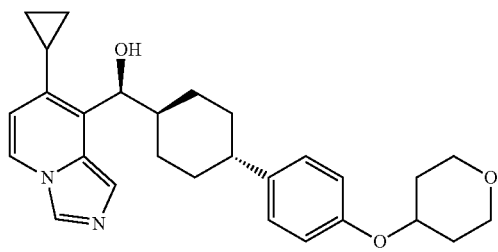

Fast isomer in CHIRALPAK IC HPLC
Eluting reagent: Hex (0.2% IPAmine):EtOH = 50:50

-continued

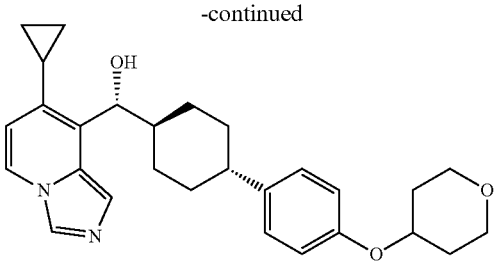

Slow isomer in CHIRALPAK IC HPLC
Eluting reagent: Hex (0.2% IPAmine):EtOH = 50:50

Each enantiomer of racemic C119a and C119b was separated using preparative HPLC on a CHIRALPAK IC with Hex (0.2% IPAmine):EtOH=50:50 as an eluent. The enantiomeric excesses were determined by using HPLC on a CHIRALPAK IC-3 with Hex (0.1% DEA):EtOH=50:50 as an eluent at a flow rate of 1.0 mL/min. The first one enantiomer eluted at the retention time of 4.099 min (C119a), and the other enantiomer eluted at the retention time of 8.162 min (C119b). To a solution of C119a (83.9 mg) in DCM (5 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (70.03 mg). $^1$H NMR (DMSO-d$_6$) δ$_H$ 9.43 (s, 1H), 8.37 (d, J=7.6 Hz, 1H), 8.02 (s, 1H), 7.08 (d, J=8.4 Hz, 2H), 6.85 (d, J=8.4 Hz, 2H), 6.61 (d, J=7.6 Hz, 1H), 5.71 (brs, 1H), 5.06 (d, J=7.6 Hz, 1H), 4.44-4.49 (m, 1H), 3.79-3.85 (m, 2H), 3.44-3.47 (m, 2H), 2.23-2.49 (m, 3H), 1.82-1.93 (m, 4H), 1.69-1.71 (m, 1H), 1.48-1.55 (m, 2H), 1.24-1.41 (m, 5H), 1.03-1.06 (m, 2H), and 0.79-0.85 (m, 2H). [M+H]$^+$=447. To a solution of C119b (82.4 mg) in DCM (6 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (66.67 mg). $^1$H NMR (DMSO-d$_6$) δ$_H$ 9.42 (s, 1H), 8.37 (d, J=7.6 Hz, 1H), 8.02 (s, 1H), 7.08 (d, J=8.8 Hz, 2H), 6.84 (d, J=8.8 Hz, 2H), 6.61 (d, J=7.6 Hz, 1H), 5.75 (brs, 1H), 5.06 (d, J=8.0 Hz, 1H), 4.44-4.49 (m, 1H), 3.79-3.85 (m, 2H), 3.41-3.48 (m, 2H), 2.20-2.42 (m, 3H), 1.84-1.93 (m, 4H), 1.66-1.71 (m, 1H), 1.48-1.58 (m, 2H), 1.25-1.35 (m, 5H), 1.03-1.08 (m, 2H), and 0.79-0.85 (m, 2H). [M+H]$^+$=447. The absolute configurations of chiral carbons in C119a and C119b are tentatively assigned as (S) and (R) respectively based on assumption that the binding model of the more potent isomer C119a is the same as that of C101a with IDO1 enzyme, and the relative stereochemistry on cyclohexane is assigned as trans configuration on the cyclohexane.

Example C120: (7-cyclopropylimidazo[1,5-a]pyridin-8-yl)(4-(6-(trifluoromethyl)pyridin-3-yl)cyclohexyl)methanol

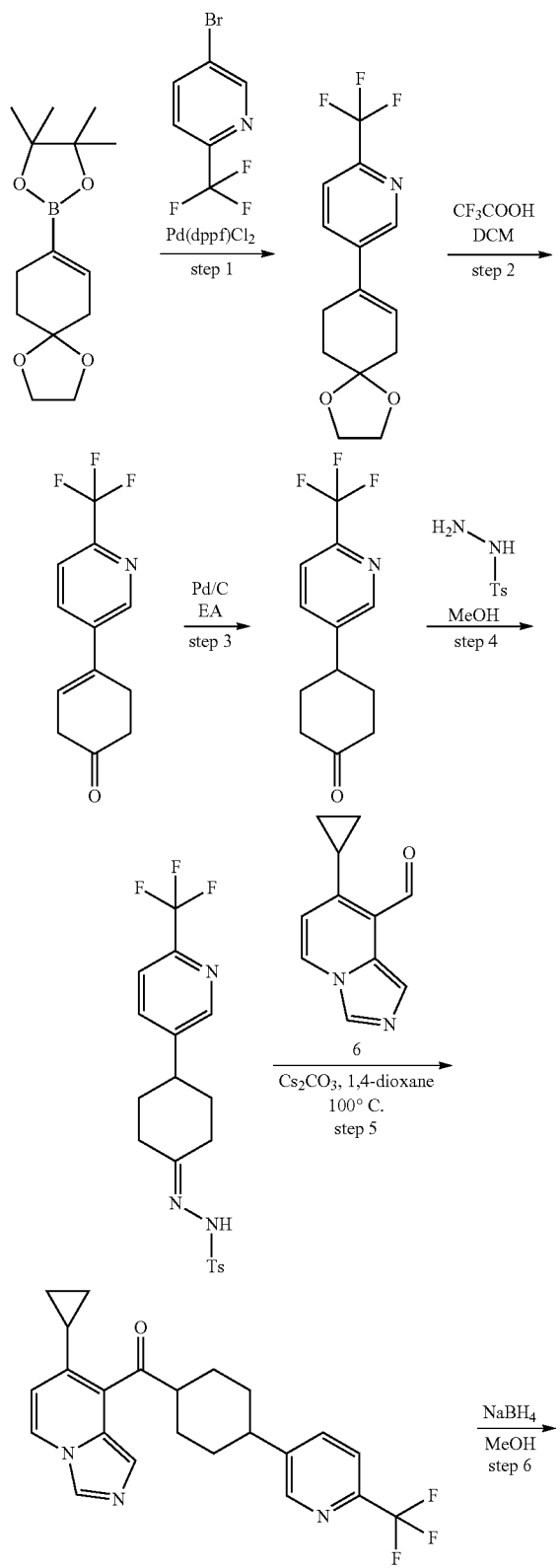

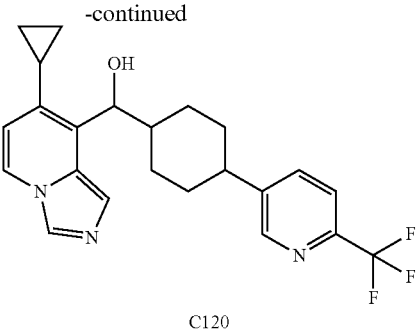

C120

Step 1: 5-(1,4-dioxaspiro[4.5]dec-7-en-8-yl)-2-(trifluoromethyl)pyridine

To a solution of 5-bromo-2-(trifluoromethyl)pyridine (15.3 g, 68 mmoL) in 1,4-dioxane (200 mL) was added 4,4,5,5-tetramethyl-2-(1,4-dioxaspiro[4.5]dec-7-en-8-yl)-1,3,2-dioxaborolane (18 g, 68 mmol), Pd(dppf)Cl$_2$ (8.0 g, 6.8 mmol) and Cs$_2$CO$_3$ (22 g, 68 mmol) and the mixture was heated at 70° C. for 5 hours. Then evaporated the solvent under reduced pressure and the residue was purified by column chromatography (PE:EA=5:1) to give product as an oil (12 g in 63% yield).

Step 2: 4-(6-(trifluoromethyl)pyridin-3-yl)cyclohex-3-en-1-one

To a solution of 5-(1,4-di oxaspiro[4.5]dec-7-en-8-yl)-2-(trifluoromethyl)pyridine (12 g, 42 mmol) in dichloromethane (100 mL) was added trifluoroacetic acid (50 mL) at room temperature and the mixture was stirred for overnight. The solvent was evaporated under reduced pressure and water (100 mL) was added, extracted with ethyl acetate (100 mL×3), combined the organic layer and washed with saturated aqueous of NaHCO$_3$, then the organic layer was evaporated in vacuo to give crude product, which was used for next step without further purification.

Step 3: 4-(6-(trifluoromethyl)pyridin-3-yl)cyclohexan-1-one

To a solution of 4-(6-(trifluoromethyl)pyridin-3-yl)cyclohex-3-en-1-one (42 mmol) in ethyl acetate (200 mL) was added Pd/C (2.0 g, 10%) and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give product (12 g, oil).

Step 4: 4-methyl-N'-(4-(6-(trifluoromethyl)pyridin-3-yl)cyclohexylidene)benzenesulfono-hydrazide To a solution of 4-(6-(trifluoromethyl)pyridin-3-yl)cyclohexan-1-one (12 g, 49 mmol) in methol (100 mL) was added 4-methylbenzenesulfonohydrazide (9.1 g, 49 mmol) at room temperature and the mixture was stirred for overnight. Evaporate half the solvent under reduced pressure and then filtered to give product as a white solid (9.0 g in 45% yield).
$^1$H NMR (DMSO-d6) δ$_H$ 10.23 (s, 1H), 8.68 (d, J=1.6 Hz, 1H), 7.95 (d, J=8.0 Hz, 1H), 7.81 (d, J=8.0 Hz, 1H), 7.74 (d, J=8.4 Hz, 2H), 7.40 (d, J=8.0 Hz, 2H), 2.92-3.02 (m, 2H), 2.39 (s, 3H), 2.27-2.30 (m, 2H), 1.94-2.00 (m, 3H), 1.55-1.67 (m, 2H).

Step 5: (7-cyclopropylimidazo[1,5-a]pyridin-8-yl)(4-(6-(trifluoromethyl)pyridin-3-yl)cyclohexyl)methanone To a solution of 7-cyclopropylimidazo[1,5-a]pyridine-8-carbaldehyde (2.0 g, 11 mmol) in 1,4-dioxane (0.2 L) was added 4-methyl-N'-(4-(6-(trifluoromethyl)pyridin-3-yl)cyclohexylidene)benzenesulfonohydrazide (9.0 g, 22 mmol) and $Cs_2CO_3$ (7.2 g, 22 mmol) at room temperature, and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1) to give crude product as a yellow solid (1.2 g in 27% yield), and this crude was used for next step without further purification. $[M+H]^+=414.2$.

Step 6: (7-cyclopropylimidazo[1,5-a]pyridin-8-yl)(4-(6-(trifluoromethyl)pyridin-3-yl)cyclohexyl)methanol

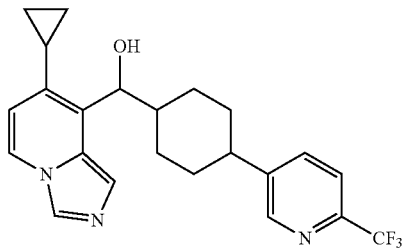 [SMILES: OC(c1c(C2CC2)ccn2cncc12)C1CCC(c2ccc(C(F)(F)F)nc2)CC1]

To a solution of crude (7-cyclopropylimidazo[1,5-a]pyridin-8-yl)(4-(6-(trifluoromethyl)pyridin-3-yl)cyclohexyl)methanone (1.2 g, 2.9 mmol) in methanol (50 mL) was added $NaBH_4$ (0.6 g, 15 mol) at room temperature, and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was purified by column chromatography (PE/EA=1:1) to give the product as a white solid (600 mg in 50% yield). $^1$H NMR (DMSO-$d_6$) $\delta_H$ 8.65 (s, 1H), 8.22 (s, 1H), 8.12 (d, J=7.6 Hz, 1H), 7.92 (d, J=7.6 Hz, 1H), 7.78 (d, J=8.4 Hz, 1H), 7.44 (s, 1H), 6.17 (d, J=7.2 Hz, 1H), 5.35 (d, J=3.6 Hz, 1H), 4.97 (dd, J=3.6, 8.4 Hz, 1H), 2.62-2.68 (m, 1H), 2.33-2.37 (m, 1H), 2.18 (s, 1H), 2.04-2.06 (m, 1H), 1.89-1.92 (m, 1H), 1.72-1.75 (m, 1H), 1.50-1.54 (m, 1H), 1.23-1.34 (m, 4H), 0.89-0.95 (m, 2H), and 0.70-0.75 (m, 2H).

Example C120a and C120b: (S)-(7-cyclopropylimidazo[1,5-a]pyridin-8-yl)((1r,4S)-4-(6-(trifluoromethyl)pyridin-3-yl)cyclohexyl)methanol and (R)-(7-cyclopropylimidazo[1,5-a]pyridin-8-yl)((1r,4R)-4-(6-(trifluoromethyl)pyridin-3-yl)cyclohexyl)methanol

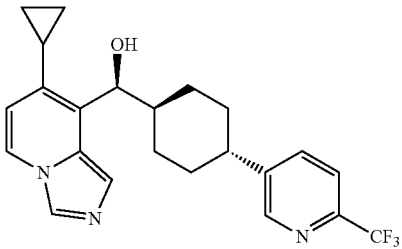

Fast isomer in Lux Cellulose-4 HPLC
Eluting reagent: Hex (0.1% DEA):EtOH = 60:40

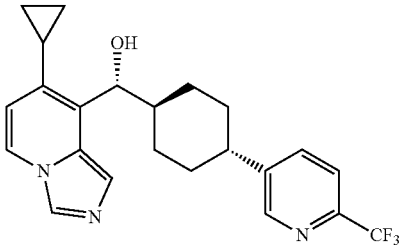

Slow isomer in Lux Cellulose-4 HPLC
Eluting reagent: Hex (0.1% DEA):EtOH = 60:40

Each enantiomer of racemic C120a and C120b was separated using preparative HPLC on a Phenomenex Lux 5u Cellulose-4 Hex (0.1% EDA):EtOH=73:27 as an eluent. The enantiomeric excesses were determined by using HPLC on a Lux Cellulose-4 with Hex (0.1% DEA):EtOH=60:40 as an eluent at a flow rate of 1.0 mL/min. The first one enantiomer eluted at the retention time of 4.696 min, and the other enantiomer eluted at the retention time of 5.452 min. To a solution of C120a (238 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (230 mg in 82% yield). $^1$H NMR (DMSO-$d_6$) $\delta_H$ 9.40 (s, 1H), 8.65 (s, 1H), 8.37 (d, J=7.2 Hz, 1H), 8.01 (s, 1H), 7.91 (d, J=8.4 Hz, 1H), 7.80 (d, J=8.4 Hz, 1H), 6.61 (d, J=7.6 Hz, 1H), 5.74 (s, 1H), 5.08 (d, J=8.0 Hz, 1H), 2.24-2.26 (m, 2H), 1.89-1.97 (m, 2H), 1.76-1.78 (m, 1H), 1.47-1.55 (m, 1H), 1.28-1.37 (m, 4H), 1.04-1.06 (m, 2H), and 0.80-0.88 (m, 2H). To a solution of C120b (260 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (250 mg in 82% yield). $^1$H NMR (DMSO-$d_6$) $\delta_H$ 9.40 (s, 1H), 8.65 (s, 1H), 8.37 (d, J=7.2 Hz, 1H), 8.01 (s, 1H), 7.91 (d, J=8.4 Hz, 1H), 7.80 (d, J=8.4 Hz, 1H), 6.61 (d, J=7.6 Hz, 1H), 5.74 (s, 1H), 5.08 (d, J=8.0 Hz, 1H), 2.24-2.26 (m, 2H), 1.89-1.97 (m, 2H), 1.76-1.78 (m, 1H), 1.47-1.55 (m, 1H), 1.28-1.37 (m, 4H), 1.04-1.06 (m, 2H), and 0.80-0.88 (m, 2H). The absolute configurations of chiral carbons in C120a and C120b are tentatively assigned as (S) and (R) respectively based on assumption that the binding model of the more potent isomer C120a is the same as that of C101a with IDO1 enzyme, and the relative stereochemistry on cyclohexane is assigned as trans configuration on the cyclohexane.

Example C121: (7-cyclopropylimidazo[1,5-a]pyridin-8-yl)(4-(naphthalen-1-yl)cyclohexyl)methanol

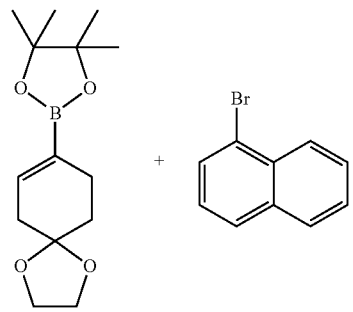

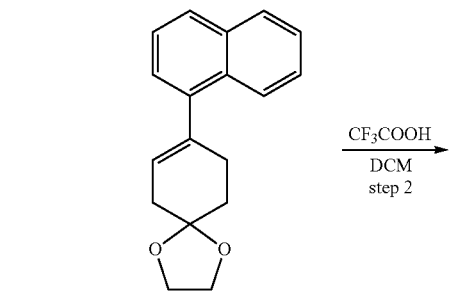

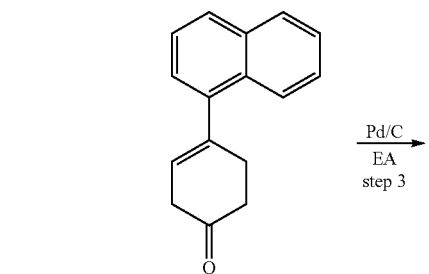

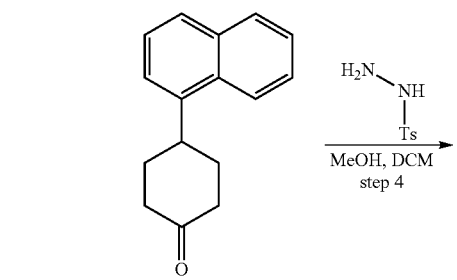

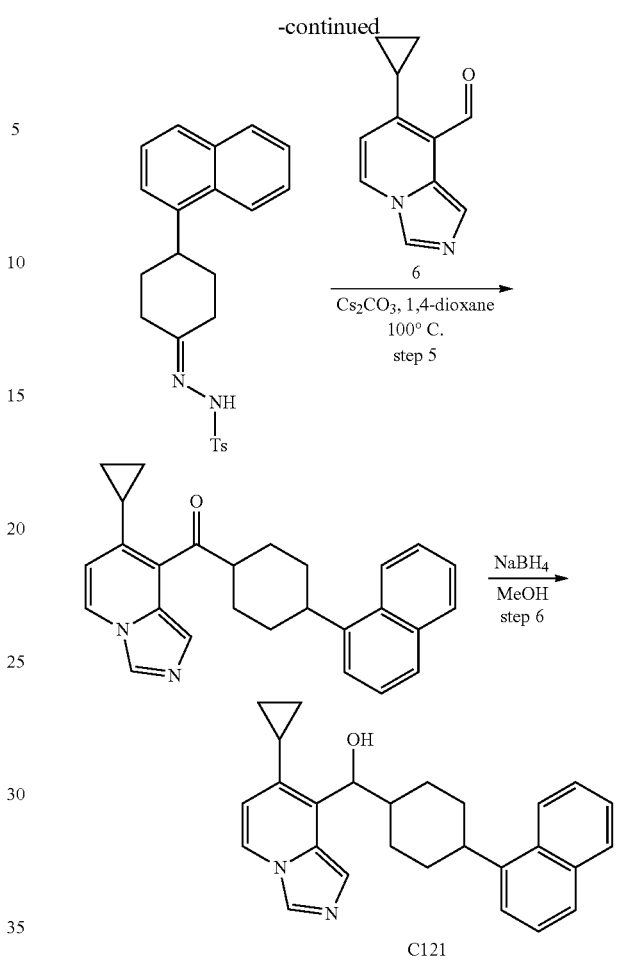

Step 1: 8-(naphthalen-1-yl)-1,4-dioxaspiro[4,5]dec-7-ene

To a solution of 4,4,5,5-tetramethyl-2-(1,4-dioxaspiro [4.5]dec-7-en-8-yl)-1,3,2-dioxaborolane (19.2 g, 72 mmol), 1-bromonaphthalene (15 g, 72 mmol), Pd(dppf)Cl$_2$ (5.26 g, 7.2 mmol) and C$_2$CO$_3$ (35.0 g, 108 mmol) in 1,4-dioxane (400 ml), the mixture was stirred at 90° C. under N$_2$ for over night. TLC (PE:EA=5:1, Rf=0.5) showed the reaction was completed. Filtered and concentrated, H$_2$O (100 ml) was added and extracted with ethyl acetate (50 ml×3). The combined organic layer was dried over Na$_2$SO$_4$, filtered and concentrated to give crude product, which was purified by silica gel chromatography (PE:EA=40:1-10:1) to give product (18.20 g, in 95% yield) as a yellow oil. $^1$H NMR (DMSO-d$_6$) δ$_H$ 7.91-7.95 (m, 2H), 7.82 (d, J=8.4 Hz, 1H), 7.50-7.53 (m, 2H), 7.45 (t, J=7.6 Hz, 1H), 7.27 (d, J=6.8 Hz, 1H), 5.58-5.60 (m, 1H), 3.98 (s, 4H), 3.86 (s, 2H), 2.48 (s, 2H), 2.43-2.48 (m, 2H), 1.91 (t, J=6.4 Hz, 2H). MS (ESI) m/e [M+1]$^+$=267.

Step 2: 4-(naphthalen-2-yl)cyclohex-3-en-1-one

To a solution of 8-(naphthalen-2-yl)-1,4-dioxaspiro[4.5] dec-7-ene (12.66 g, 47 mmol) in dichloromethane (15 mL) was added trifluoroacetic acid (15 mL) at room temperature, and the mixture was stirred for overnight. The solvent was evaporated under reduced pressure and water (100 mL) was added, extracted with ethyl acetate (100 ml×3), combined the organic layer and washed with saturated aqueous of NaHCO$_3$ then the organic layer was evaporated to give crude product, which was used for next step without further purification. $^1$H NMR (DMSO-d$_6$) $\delta_H$ 7.94-8.02 (m, 2H), 7.86 (d, J=8.4 Hz, 1H), 7.47-7.56 (m, 4H), 7.32-7.37 (m, 2H), 5.81-5.83 (m, 1H), 3.10-3.11 (m, 2H), 2.79-2.83 (m, 2H), 2.66-2.70 (m, 2H). MS (ESI) m/e [M+1]$^+$=223.

Step 3: 4-(naphthalen-1-yl)cyclohexan-1-one

To a solution of 4-(naphthalen-1-yl)cyclohex-3-en-1-one (12.2 g, 54.95 mmol) in ethyl acetate (100 mL) was added Pd/C (1.2 g, 10%) and the mixture was stirred for 6 hours at room temperature under H$_2$ (0.4 Mpa). Then filtered to remove Pd/C and the filtrate was evaporated under reduced pressure to give a crude product, which was purified by silica gel chromatography (PE:EA=40:1-10:1) to give product (3.99 g, in 32% yield as a yellow solid. $^1$H NMR (DMSO-d6) $\delta_H$ 8.31 (d, J=8.4 Hz, 1H), 7.94 (d, J=7.6 Hz, 1H), 7.79 (d, J=7.2 Hz, 1H), 7.43-7.61 (m, 4H), 3.91-3.97 (m, 1H), 2.75-2.84 (m, 2H), 2.32-2.36 (m, 2H), 2.17-2.21 (m, 2H), 1.93-2.03 (m, 2H). MS (ESI) m/e [M+1]$^+$=225.

Step 4: 4-methyl-N'-(4-(naphthalen-1-yl)cyclohexylidene)benzenesulfonohydrazide

To a solution of 4-(naphthalen-1-yl)cyclohexan-1-one (3.99 g, 17.80 mmol) in methanol (60 mL) was added 4-methylbenzenesulfonohydrazide (3.31 g, 17.80 mmol) at room temperature, and the mixture was stirred for overnight. The solvent was evaporated under reduced pressure and the residue was pulped with methanol 5 mL, filtered and washed with methanol 1 mL to give product 4.71 g in 67.50% yield as a white solid. $^1$H NMR (DMSO-d$_6$)$^{6H}$10.21 (s, 1H), 8.22 (d, J=8.4 Hz, 1H), 7.92 (d, J=7.6 Hz, 1H), 7.75-7.78 (m, 3H), 7.49-7.58 (m, 2H), 7.36-7.46 (m, 4H), 3.63-3.70 (m, 1H), 2.97-3.00 (m, 1H), 2.43-2.48 (m, 2H), 2.40 (s, 1H), 2.31-2.35 (m, 1H), 1.99-2.19 (m, 3H), 1.55-1.70 (m, 2H). MS (ESI) m/e [M+1]$^+$=393.

Step 5: (7-cyclopropylimidazo[1,5-a]pyridin-8-yl)(4-(naphthalen-1-yl)cyclohexyl)methanone To a solution of 7-cyclopropylimidazo[1,5-a]pyridine-8-carbaldehyde (2.23 g, 12 mmol) in 1,4-dioxane (70 mL) was added 4-methyl-N'-(4-(naphthalen-1-yl)cyclohexylidene)-benzenesulfonohydrazide (4.71 g, 12 mmol) and Cs$_2$CO$_3$ (5.85 g, 18 mmol) at room temperature, and the mixture was heated at 95° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1 to EA) to give crude product as a solid (1.54 g in 21.15% yield). MS (ESI) m/e [M+1]$^+$=363.

Step 6: (7-cyclopropylimidazo[1,5-a]pyridin-8-yl)(4-(naphthalen-1-yl)cyclohexyl)methanol

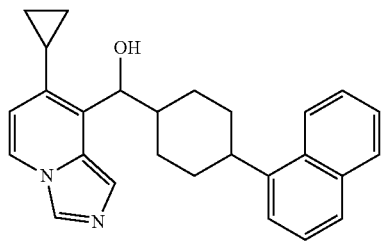 [SMILES: OC(c1c(C2CC2)ccn2cncc12)C1CCC(c2cccc3ccccc23)CC1]

To a solution of (7-cyclopropylimidazo[1,5-a]pyridin-8-yl)(4-(naphthalen-1-yl)cyclohexyl)methanone (1.54 g, 3.91 mmol) in methanol (30 mL) was added NaBH$_4$ (742 mg, 19.5 mmol) at room temperature and the mixture was stirred for 3 hours. Then the solvent was evaporated under reduced pressure and water (50 mL) was added, extracted with ethyl acetate (50 ml×3) and combined the organic layer, evaporated the solvent under reduced pressure and the residue was pulped with methanol 5 mL to give product as a white solid (515 mg, 33.26%). $^1$H NMR (DMSO-d$_6$) $\delta_H$ 8.21 (s, 1H), 8.11-8.14 (m, 2H), 7.89 (d, J=8.0 Hz, 1H), 7.72 (d, J=8.0 Hz, 1H), 7.37-7.55 (m, 5H), 6.18 (d, J=7.6 Hz, 1H), 5.35 (m, 1H), 5.03-5.06 (m, 1H), 1.99-2.42 (m, 5H), 1.84 (m, 1H), 1.35-1.63 (m, 5H), 0.92-0.98 (m, 2H), 0.72-0.73 (m, 2H). MS (ESI) m/e [M+1]$^+$=365.

Example C121a and C121b: (S)-(7-cyclopropylimidazo[1,5-a]pyridin-8-yl)((1r,4S)-4-(naphthalen-1-yl)cyclohexyl)methanol and (R)-(7-cyclopropylimidazo[1,5-a]pyridin-8-yl)(1r,4R)-4-naphthalen-1-yl)cyclohexyl)methanol

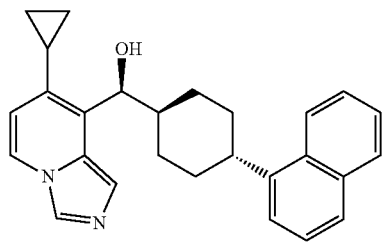

Fast isomer in CHIRALPAK IC
Eluting reagent: Hex:EtOH = 50:50

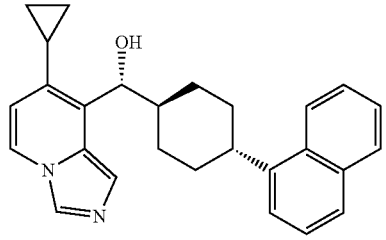

Slow isomer in CHIRALPAK IC
Eluting reagent: Hex:EtOH = 50:50

Each enantiomer of racemic C121a and C121b was separated using preparative HPLC on a CHIRAL PAK IC with Hex:EtOH=50:50 as an eluent. The enantiomer excesses were determined by using HPLC on a CHIRAL PAK IC with Hex:EtOH=50:50 as an eluent at a flow rate of 1.0 mL/min. The first one enantiomer eluted at the retention time of 2.448 min (C121a), which was dissolved in DCM (10 mL), and added ethyl acetate solution of hydrochloric acid (0.5 mL, 4.0M) at room temperature, followed by addition of methanol until the precipitate was dissolved, then the solvent was evaporated under reduced pressure and the residue was washed by PE to give the desired product as white solid, $^1$H NMR (DMSO-d6) $\delta_H$ 9.45 (s, 1H), 8.38 (d, J=6.8 Hz, 1H), 8.12 (d, J=7.6 Hz, 1H), 8.07 (s, 1H), 7.90 (d, J=7.2 Hz, 1H), 7.74 (d, J=7.2 Hz, 1H), 7.37-7.55 (m, 4H), 6.64 (d, J=6.8 Hz, 1H), 5.76 (s, 1H), 5.13 (s, 1H), 2.26-2.34 (m, 3H), 1.87-2.00 (m, 4H), 1.42-1.57 (m, 6H), 1.12-1.25 (m, 2H), 1.07-1.09 (m, 2H), and 0.80-0.90 (m, 2H); and the other enantiomer eluted at the retention time of 3.604 min (C121b), which was dissolved in DCM (10 mL), and added Ethyl acetate solution of hydrochloric acid (0.5 mL, 4.0M) at room temperature, followed by addition of methanol until the precipitate was dissolved, then the solvent was evaporated under reduced pressure and the residue was washed by PE to give the desired product as white solid, $^1$H NMR (DMSO-d$_6$) δ 9.45 (s, 1H), 8.38 (d, J=6.8 Hz, 1H), 8.12 (d, J=7.6 Hz, 1H), 8.07 (s, 1H), 7.90 (d, J=6.8 Hz, 1H), 7.74 (d, J=7.2 Hz, 1H), 7.37-7.55 (m, 4H), 6.64 (d, J=7.2 Hz, 1H), 5.76 (s, 1H), 5.13 (s, 1H), 2.26-2.35 (m, 2H), 1.95-2.05 (m, 2H), 1.85-1.89 (m, 1H), 1.42-1.57 (m, 4H), 1.20-1.25 (m, 2H), 1.06-1.10 (m, 2H), 0.80-0.90 (m, 2H). The absolute configurations of chiral carbons in C121a and C121b are tentatively assigned as (S) and (R) respectively based on assumption that the binding model of the more potent isomer C121a is the same as that of C101a with IDO1 enzyme, and the relative stereochemistry on cyclohexane is assigned as trans configuration on the cyclohexane.

Example C122: (7-cyclopropylimidazo[1,5-a]pyridin-8-yl)(4-(naphthalen-2-yl)cyclohexyl)methanol

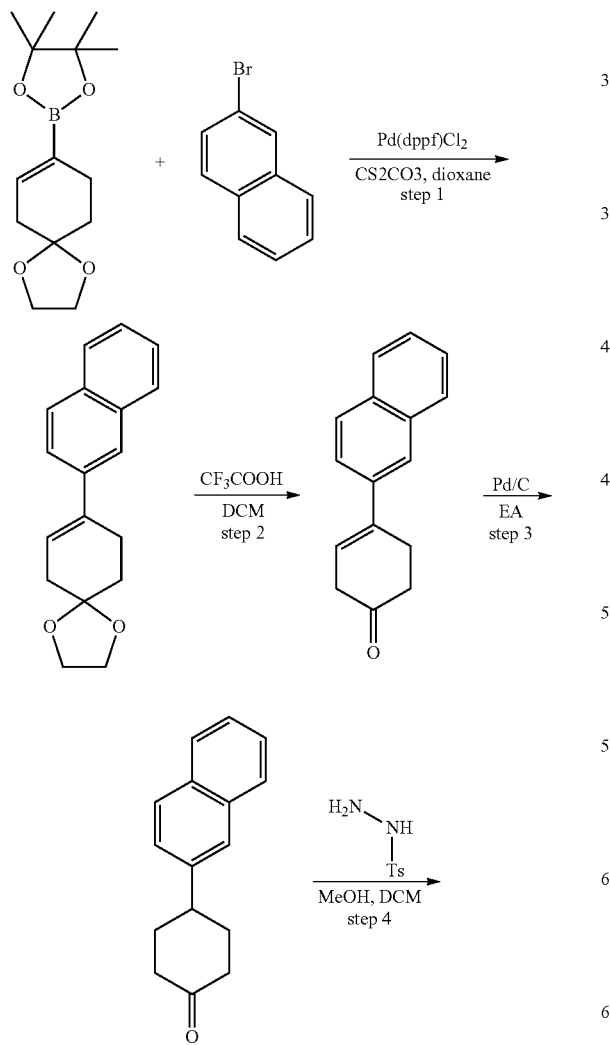

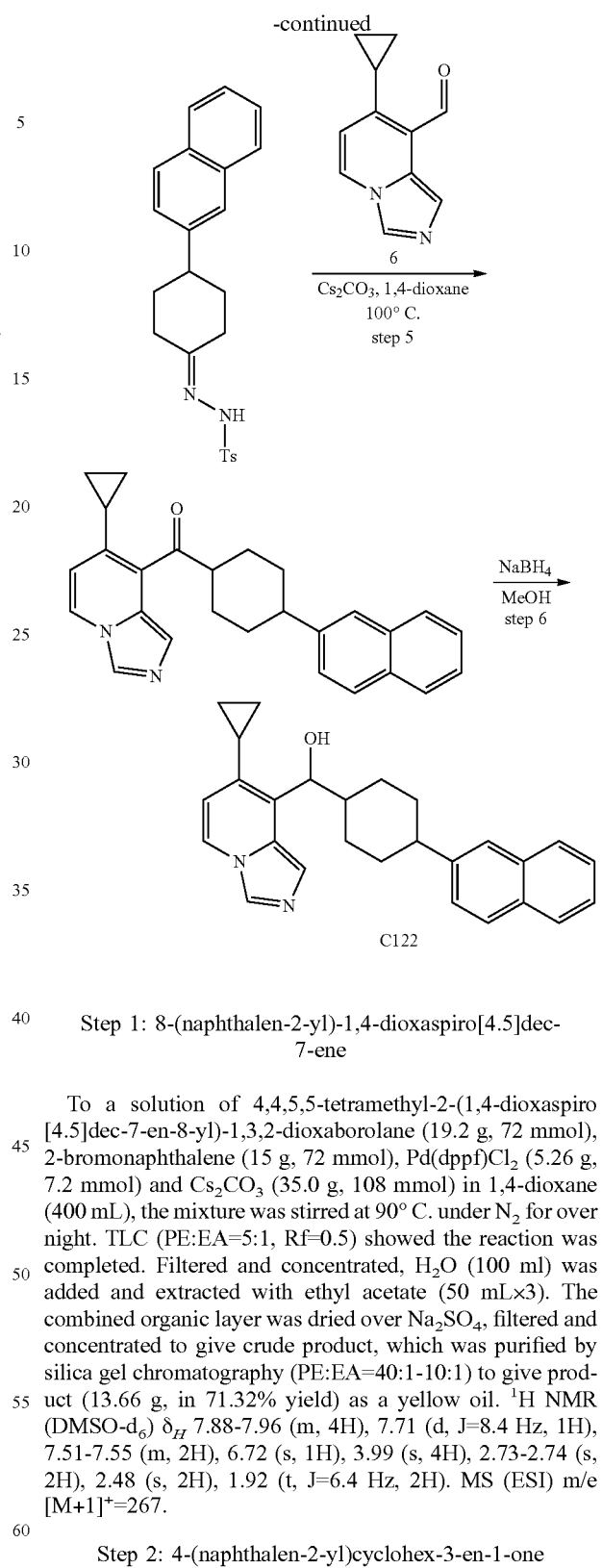

Step 1: 8-(naphthalen-2-yl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (19.2 g, 72 mmol), 2-bromonaphthalene (15 g, 72 mmol), Pd(dppf)Cl$_2$ (5.26 g, 7.2 mmol) and Cs$_2$CO$_3$ (35.0 g, 108 mmol) in 1,4-dioxane (400 mL), the mixture was stirred at 90° C. under N$_2$ for over night. TLC (PE:EA=5:1, Rf=0.5) showed the reaction was completed. Filtered and concentrated, H$_2$O (100 ml) was added and extracted with ethyl acetate (50 mL×3). The combined organic layer was dried over Na$_2$SO$_4$, filtered and concentrated to give crude product, which was purified by silica gel chromatography (PE:EA=40:1-10:1) to give product (13.66 g, in 71.32% yield) as a yellow oil. $^1$H NMR (DMSO-d$_6$) δ$_H$ 7.88-7.96 (m, 4H), 7.71 (d, J=8.4 Hz, 1H), 7.51-7.55 (m, 2H), 6.72 (s, 1H), 3.99 (s, 4H), 2.73-2.74 (s, 2H), 2.48 (s, 2H), 1.92 (t, J=6.4 Hz, 2H). MS (ESI) m/e [M+1]$^+$=267.

Step 2: 4-(naphthalen-2-yl)cyclohex-3-en-1-one

To a solution of 8-(naphthalen-2-yl)-1,4-dioxaspiro[4.5]dec-7-ene (12.66 g, 47 mmol) in dichloromethane (15 mL) was added trifluoroacetic acid (15 mL) at room temperature, and the mixture was stirred for overnight. The solvent was evaporated under reduced pressure and water (100 mL) was added, extracted with ethyl acetate (100 mL×3), combined the organic layer and washed with saturated aqueous of NaHCO₃ then the organic layer was evaporated to give crude product, which was used for next step without further purification. $^1$H NMR (DMSO-d₆) $\delta_H$ 7.88-7.94 (m, 4H), 7.44-7.53 (m, 4H), 7.15 (m, 1H), 2.97-3.10 (m, 2H), 2.57-2.67 (m, 2H), 2.32-2.42 (m, 2H), 2.02-2.10 (m, 2H). MS (ESI) m/e [M+1]⁺=223.

Step 3: 4-(naphthalen-2-yl)cyclohexan-1-one

To a solution of 4-(naphthalen-2-yl)cyclohex-3-en-1-one (7.28 g, 32.8 mmol) in ethyl acetate (100 mL) was added Pd/C (0.73 g, 10%) and the mixture was stirred for 6 hours at room temperature under H₂ (0.4 Mpa). Then filtered to remove Pd/C and the filtrate was evaporated under reduced pressure to give a crude product, which was purified by silica gel chromatography (PE:EA=40:1-10:1) to give product (4.26 g in 57.98% yield as a yellow oil. $^1$H NMR (DMSO-d₆) δ 7.88-7.94 (m, 4H), 7.44-7.53 (m, 4H), 7.15 (m, 1H), 2.97-3.10 (m, 2H), 2.57-2.67 (m, 2H), 2.32-2.42 (m, 2H), 2.02-2.10 (m, 2H). MS (ESI) m/e [M+1]⁺=225.

Step 4: 4-methyl-N'-(4-(naphthalen-2-yl)cyclohexylidene)benzenesulfonohydrazide

To a solution of 4-(naphthalen-2-yl)cyclohexan-1-one (4.26 g, 19.02 mmol) in methanol (60 mL) and DCM (20 mL) was added 4-methylbenzenesulfonohydrazide (3.54 g, 19.02 mmol) at room temperature, and the mixture was stirred for overnight. The solvent was evaporated under reduced pressure and the residue was pulped with methanol 5 mL, filtered and washed with methanol 1 mL to give product 2.74 g, in 36.75% yield as a white solid. MS (ESI) m/e [M+1]⁺=393.

Step 5: (7-cyclopropylimidazo[1,5-a]pyridin-8-yl)(4-(naphthalen-2-yl)cyclohexyl)methanone To a solution of 7-cyclopropylimidazo[1,5-a]pyridine-8-carbaldehyde (0.37 g, 2 mmol) in 1,4-dioxane (50 mL) was added 4-methyl-N'-(4-(naphthalen-2-yl)cyclohexylidene)-benzenesulfonohydrazide (0.78 g, 2 mmol) and Cs₂CO₃ (0.97 g, 3 mmol) at room temperature, and the mixture was heated at 95° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1 to EA) to give crude product as a solid (520 mg in 65.99% yield). MS (ESI) m/e [M+1]⁺=363.

Step 6: (7-cyclopropylimidazo[1,5-a]pyridin-8-yl)(4-(naphthalen-2-yl)cyclohexyl)methanol

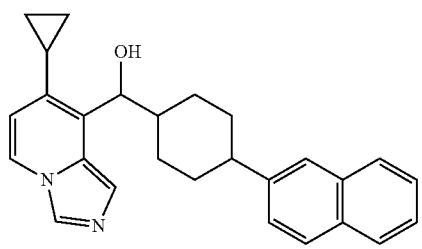 [SMILES: OC(c1c(C2CC2)ccn2cncc12)C1CCC(c2ccc3ccccc3c2)CC1]

To a solution of (7-cyclopropylimidazo[1,5-a]pyridin-8-yl)(4-(naphthalen-2-yl)cyclohexyl)methanone (510 mg, 1.29 mmol) in methanol (10 mL) was added NaBH₄ (245 mg, 6.45 mmol) at room temperature and the mixture was stirred for 2 hours. Then the solvent was evaporated under reduced pressure and water (50 mL) was added, extracted with ethyl acetate (50 ml×3) and combined the organic layer, evaporated the solvent under reduced pressure and the residue was slurried in methanol (2 mL) to give product as a pale yellow solid, which was purified with HPLC to give a white solid (210 mg, 41.00%). $^1$H NMR (DMSO-ds) $\delta_H$ 8.34 (s, 1H), 8.15 (d, J=7.6 Hz, 1H), 7.78-7.84 (m, 3H), 7.68 (s, 1H), 7.52 (s, 1H), 7.39-7.46 (m, 3H), 6.21 (d, J=7.2 Hz, 1H), 5.38 (s, 1H), 5.01 (d, J=4.8 Hz, 1H), 2.60-2.66 (m, 1H), 2.37 (m, 1H), 2.21 (m, 1H), 2.07 (m, 1H), 1.96 (m, 1H), 1.80 (m, 1H), 1.52-1.61 (m, 1H), 1.23-1.40 (m, 4H), 0.95-0.97 (m, 2H), 0.73 (m, 2H). MS (ESI) m/e [M+1]⁺=365.

Example C123: (4-(benzo[d][1,3]dioxol-5-yl)cyclohexyl)(7-cyclopropylimidazo[1,5-a]pyridin-8-yl)methanol

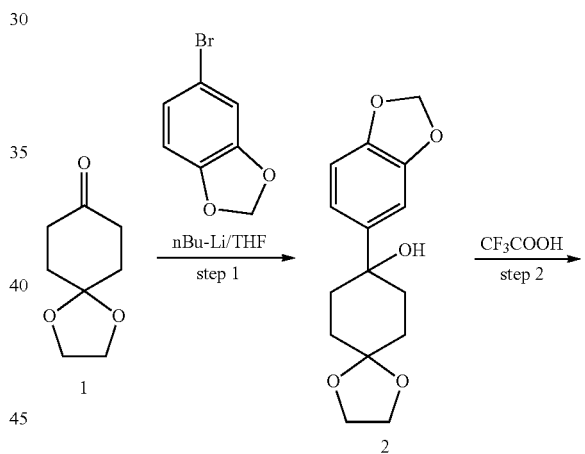

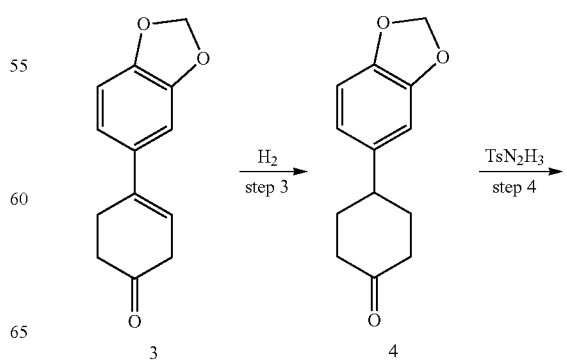

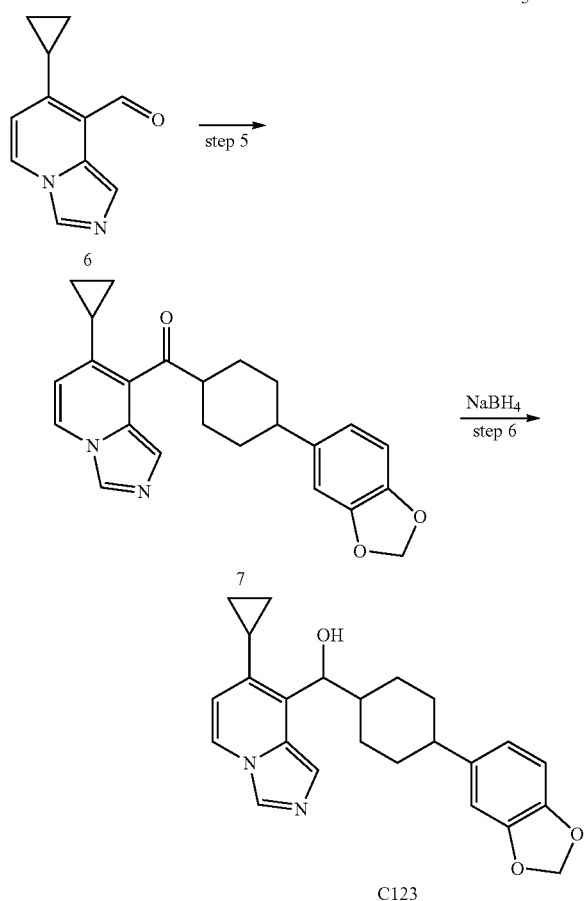

J=1.6 Hz, 8.0 Hz, 1H), 6.82 (d, J=8.0 Hz, 1H), 5.96 (s, 2H), 3.87 (s, 4H), 1.82-1.96 (m, 4H), 1.49-1.64 (m, 4H)

Step 2: 4-(benzo[d][1,3]dioxol-5-yl)cyclohex-3-en-1-one

A solution of 8-(benzo[d][,3]dioxol-5-yl)-1,4-dioxaspiro[4.5]decan-8-ol (9.9 g, 35.6 mmol) in TFA/DCM (50 mL/50 mL) was stirred for overnight at room temperature. The solvent was evaporated under reduced pressure and sat.NaHCO$_3$.aq was added, extracted with EA, the EA layer was washed with brine, dried over Na$_2$SO$_4$, concentrated to give crude product (11 g).

Step 3: 4-(benzo[d][1,3]dioxol-5-yl)cyclohexan-1-one

To a solution of 4-(benzo[d][1,3]dioxol-5-yl)cyclohex-3-en-1-one (11 g crude) in ethyl acetate (150 mL) was added Pd/C (1.7 g, 10%) and the mixture was stirred for 5 hours at room temperature under H$_2$ (0.4 Mpa). Then filtered to remove Pd/C and the filtrate was evaporated under reduced pressure to give a crude product, and this was purified by sili-gel to give 4.0 g.

Step 4: N'-(4-(benzo[d][1,3]dioxol-5-yl)cyclohex-ylidene)-4-methylbenzenesulfonohydrazide A solution of 4-(benzo[d][1,3]dioxol-5-yl)cyclohexan-1-one (4.5 g, 20.6 mmol) and 4-methylbenzenesulfonohydrazide (3.4 g, 18.3 mmol) in MeOH (400 mL) was stirred for 2 days at 50° C. The reaction mixture was concentrated and purified by sili-gel to give 2.3 g.

Step 5: (4-(benzo[d][1,3]dioxol-5-yl)cyclohexyl)(7-cyclopropylimidazo[1,5-a]pyridin-8-yl)methanone Under N$_2$, a mixture of 7-cyclopropylimidazo[1,5-a]pyridine-8-carbaldehyde (0.7 g, 3.76 mmol), N'-(4-(benzo[d][1,3]dioxol-5-yl)cyclohexylidene)-4-methylbenzenesulfonohydrazide (2.2 g, 5.7 mmol) and Cs$_2$CO$_3$ (2.1 g, 6.44 mmol) in 1,4-dioxane (50 mL) was heated at 90° C. for overnight. After cooled down, EA (50 mL) was added, the mixture was filtered, the filtrate was concentrated and purified by sili-gel to give 450 mg.

Step 6: (4-(benzo[d][1.3]dioxol-5-yl)cyclohexyl)(7-cyclopropylimidazo[1,5-a]pyridin-8-yl)methanol A solution of (4-(benzo[d][,3]dioxol-5-yl)cyclohexyl)(7-cyclopropylimidazo[1,5-a]pyridin-8-yl)methanone (450 mg, 1.16 mmol) and NaBH$_4$ (80 mg, 2.2 mmol) in MeOH (20 mL) was stirred for 2 hours at room temperature. Then the solvent was evaporated under reduced pressure and water (50 mL) was added, extracted with ethyl acetate (50 mL), the EA layer was washed with brine, dried over Na$_2$SO$_4$, concentrated and purified by sili-gel to give 160 mg. $^1$H NMR (DMSO-d$_6$) $\delta_H$ 8.21 (s, 1H), 8.11 (d, J=7.2 Hz, 1H), 7.42 (s, 1H), 6.74-6.80 (m, 2H), 6.63-6.65 (m, 1H), 6.16 (d, J=9.6 Hz, 1H), 5.92 (s, 2H), 5.30 (d, J=3.6 Hz, 1H), 4.94 (dd, J=3.6 Hz, 8.4 Hz, 1H), 2.27-2.42 (m, 2H), 1.94-2.03 (m, 1H), 1.78-1.86 (m, 1H), 1.61-1.68 (m, 1H), 1.33-1.45 (m, 1H), 1.14-1.31 (m, 5H), 0.89-0.96 (m, 2H), 0.65-0.74 (m, 2H), [M+H]$^+$=391.1.

Step 1: 8-(benzo[dl][1,3]dioxol-5-yl)-1,4-dioxaspiro[4.5]decan-8-ol

To a solution of 5-bromobenzo[d][1,3]dioxole (10.0 g, 49.8 mmol) in dry THF (80 mL) was added dropwise a solution of n-BuLi (2.4 M in hexane, 20.5 mL, 49.2 mmol) at −70° C. and the mixture was stirred for 0.5 h before a solution of 1,4-dioxaspiro[4.5]decan-8-one (5.1 g, 33 mmol) in dry THF (20 mL) was added dropwise at −70° C. and the mixture was stirred for 2 hours. The reaction mixture was quenched with sat.NH$_4$Cl.aq and extracted with ethyl acetate (100 mL×3), combined the organic layer and the solvent was evaporated and purified by sili-gel to give product (9.9 g). $^1$H NMR (DMSO-d6) $\delta_H$ 6.99 (d, J=1.6 Hz, 1H), 6.89 (dd, Example C124: 4-((1S,4r)-4-((S)-(7-cyclopropylimidazo[1,5-a]pyridin-8-yl)hydroxy)methyl)cyclohexyl)benzamide

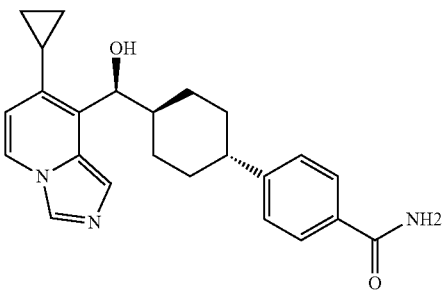 [SMILES: NC(=O)c1ccc([C@H]2CC[C@H]([C@H](O)c3c(C4CC4)ccn4cncc34)CC2)cc1]

To a solution of 4-((1 S,4r)-4-((S)-(7-cyclopropylimidazo[1,5-a]pyridin-8-yl)(hydroxy)methyl)cyclohexyl)benzonitrile (C106a, 50 mg, 0.13 mmol) in DMSO (4 mL) was added $K_2CO_3$ (40 mg, 0.26 mmol) at room temperature and followed by addition of $H_2O_2$ (0.5 mL, 30%) and the mixture was stirred at room temperature for 4 hours. Then water (40 mL) was added with stirring and filtered to give crude product, further purified by column chromatography (EA as eluent) to give product as a white solid (22 mg in 43% yield). $^1$H NMR (DMSO-$d_6$) 8.21 (s, 1H), 8.11 (d, J=7.2 Hz, 1H), 7.85 (s, 1H), 7.75 (d, J=8.0 Hz, 2H), 7.43 (s, 1H), 7.26 (d, J=8.0 Hz, 2H), 7.23 (s, 1H), 6.16 (d, J=7.6 Hz, 1H), 5.33 (d, J=3.6 Hz, 1H), 5.25 (dd, J=8.4 Hz, 1H), 2.33-2.35 (m, 1H), 2.18 (s, 1H), 2.01-2.03 (m, 1H), 1.85-1.91 (m, 1H), 1.64-1.68 (m, 1H), 1.42-1.52 (m, 1H), 1.15-1.28 (m, 5H), 0.93-0.94 (m, 2H), 0.70-0.72 (m, 2H). [M+H]$^+$=390.2.

Example C125: 1-(4-((1 S,4r)-4-((S)-(7-cyclopropylimidazo[1,5-a]pyridin-8-yl)(hydroxy)methyl)cyclohexyl)phenyl)ethan-1-one

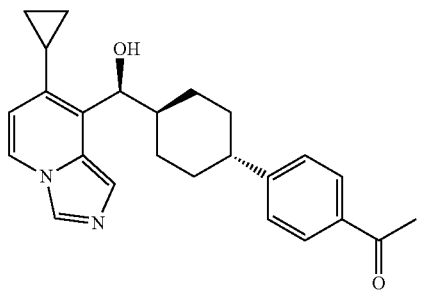 [SMILES: CC(=O)c1ccc([C@H]2CC[C@H]([C@H](O)c3c(C4CC4)ccn4cncc34)CC2)cc1]

To a solution of 4-((1 s,4s)-4-((7-cyclopropylimidazo[1,5-a]pyridin-8-yl)(hydroxy)methyl)cyclohexyl)benzonitrile (C106a, 60 mg, 0.16 mmol) in THF (10 mL) was added CuI (6 mg, 0.03 mmol) at room temperature and followed by addition of $CH_3MgBr$ (0.3 mL, 3.0 M) and the mixture was stirred at room temperature for 24 hours. Then saturated aqueous of $NH_4Cl$ was added and extracted with ethyl acetate (10 mL×3), combined the organic layer and washed with saturated aqueous of $NaHCO_3$, then the organic layer was evaporated in vacuo to give crude product, which was further purified by Pre-HPLC to give product as a white solid (15 mg in 24% yield). $^1$H NMR (400 MHz, DMSO-$d_6$) $\delta_H$ 8.21 (s, 1H), 8.12 (d, J=7.2 Hz, 1H), 7.85 (d, J=8.4 Hz, 2H), 7.44 (s, 1H), 7.35 (d, J=8.0 Hz, 2H), 6.16 (d, J=7.2 Hz, 1H), 5.34 (d, J=3.6 Hz, 1H), 4.98 (dd, J=3.6 Hz, J=8.4 Hz, 1H), 2.53 (s, 3H), 2.33-2.36 (m, 1H), 2.18 (s, 1H), 2.02-2.04 (m, 1H), 1.86-1.89 (m, 1H), 1.69-1.71 (m, 1H), 1.46-1.52 (m, 1H), 1.20-1.37 (m, 5H), 0.93-0.94 (m, 2H) and 0.70-0.72 (m, 2H), MS (ESI) m/e [M+1]$^+$=389.2;

Example C126: (7-cyclopropylimidazo[1,5-a]pyridin-8-yl)(4-(quinolin-5-yl)cyclohexyl)methanol

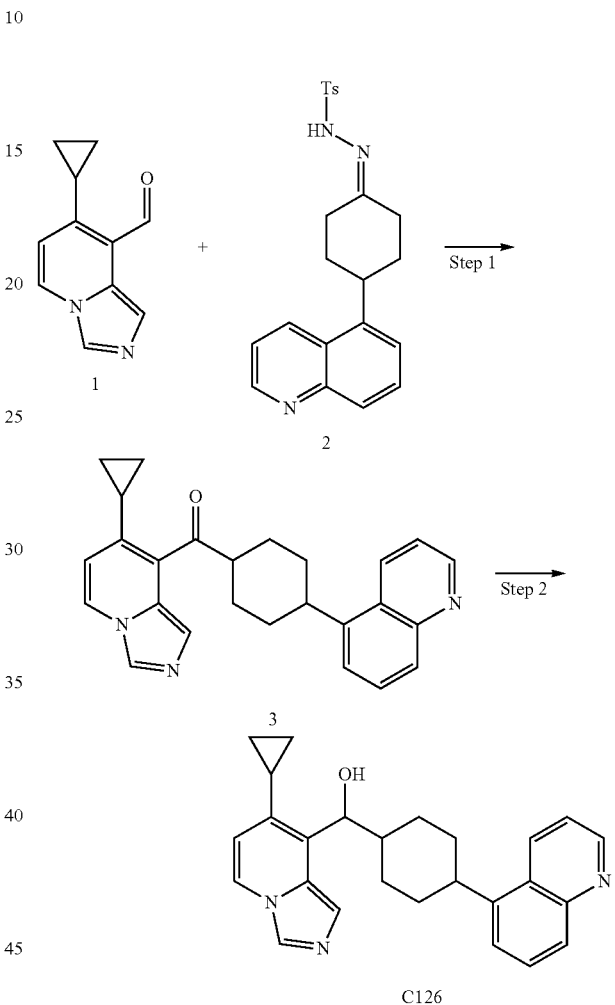

Step 1: (7-cyclopropylimidazo[1,5-a]pyridin-8-yl)(4-(quinolin-5-yl)cyclohexyl)methanone Under $N_2$, a mixture of 7-cyclopropylimidazo[1,5-a]pyridine-8-carbaldehyde (520 mg, 2.8 mmol), 4-methyl-N'-(4-(quinolin-5-yl)cyclohexylidene)benzenesulfonohydrazide (1.1 g, 2.8 mmol) and $Cs_2CO_3$ (2.0 g, 6.1 mmol) in 1,4-dioxane (30 mL) was heated at 90° C. for overnight. After cooled down, EA (50 mL) was added, the mixture was filtered, the filtrate was concentrated and purified by sili-gel to give product (1.0 g).

Step 2: (7-cyclopropylimidazo[1,5-a]pyridin-8-yl)(4-(quinolin-5-yl)cyclohexyl)methanol A solution of (7-cyclopropylimidazo[1,5-a]pyridin-8-yl)(4-(quinolin-5-yl)cyclohexyl)methanone (1.0 g, 2.53 mmol) and $NaBH_4$ (200 mg, 5.26 mmol) in MeOH (20 mL) was stirred for 2 hours at room temperature. Then the solvent was evaporated under reduced pressure and water (50 mL) was added, extracted with ethyl acetate (50 mL), the EA layer was washed with brine, dried over $Na_2SO_4$, concentrated and purified by sili-gel to give 300 mg, then purified by prep-HPLC to give product (60 mg). $^1$H NMR (DMSO-$d_6$) $\delta_H$ 8.88 (d, J=3.2 Hz, 1H), 8.59 (d, J=8.4 Hz, 1H), 8.22 (s, 1H), 8.12 (d, J=7.2 Hz, 1H), 7.84 (d, J=8.4 Hz, 1H), 7.67 (t, J=8.0 Hz, 1H), 7.45-7.56 (m, 3H), 6.18 (d, J=7.2 Hz, 1H), 5.37 (d, J=3.6 Hz, 1H), 5.00-5.07 (m, 1H), 2.34-2.43 (m, 1H), 2.04-2.25 (m, 2H), 1.93-2.00 (m, 1H), 1.77-1.84 (m, 1H), 1.32-1.66 (m, 5H), 0.91-1.01 (m, 2H), and 0.69-0.77 (m, 2H), $[M+H]^+$=398.2.

Example C126a and 126b: (S)-(7-cyclopropylimidazo[1,5-a]pyridin-8-yl)((1r,4S)-4-(quinolin-5-yl)cyclohexyl)methanol and (R)-(7-cyclopropylimidazo[1,5-a]pyridin-8-yl)((1r,4R)-4-(quinolin-5-yl)cyclohexyl)methanol

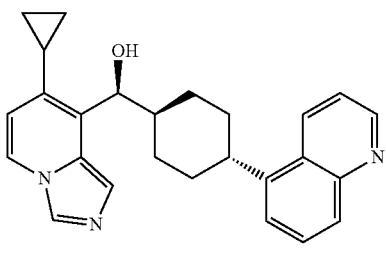

Fast isomer in CHIRALPAK IC
Eluting reagent: Hex (0.1% DEA):EtOH = 50:50

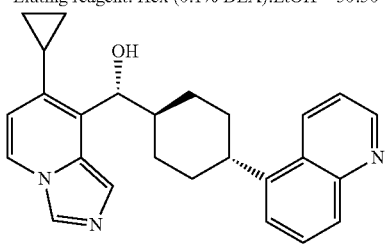

Slow isomer in CHIRALPAK IC
Eluting reagent: Hex (0.1% DEA):EtOH = 50:50

Each enantiomer of racemic C101a and C101b was separated using preparative HPLC on a CHIRALPAK IC with Hex (0.1% DEA):EtOH=50:50 as an eluent. The first one enantiomer eluted at the retention time of 2.626 min, which was dissolved in EA(5 ml), and HCl in EA(4N, 0.5 mL) was added and stirred at r.t for 1 h, the solvent was evaporated to give product as white solid, $^1$H NMR (DMSO-$d_6$) $\delta_H$ 9.52 (s, 1H), 9.18 (d, J=4.0 Hz, 1H), 8.41 (d, J=7.2 Hz, 1H), 8.13 (d, J=8.0 Hz, 1H), 8.06 (s, 1H), 7.88-8.01 (m, 2H), 7.71 (d, J=7.2 Hz, 1H), 6.67 (d, J=7.6 Hz, 1H), 5.15 (d, J=7.6 Hz, 1H), 2.23-2.33 (m, 2H), 1.94-2.09 (m, 2H), 1.81-1.89 (m, 1H), 1.41-1.67 (m, 5H), 1.08 (d, J=8.0 Hz, 2H), and 0.85 (s, 2H), $[M+H]^+$=398.2: and the other enantiomer eluted at the retention time of 4.133 min, which was dissolved in EA(5 ml), and HCl in EA(4N, 0.5 mL) was added and the solvent was evaporated to give product as white solid, $^1$H NMR (DMSO-$d_6$) $\delta_H$ 9.53 (s, 1H), 9.18 (d, J=4.4 Hz, 1H), 8.41 (d, J=7.2 Hz, 1H), 8.14 (d, J=8.4 Hz, 1H), 8.06 (s, 1H), 7.88-8.01 (m, 2H), 7.72 (d, J=7.2 Hz, 1H), 6.67 (d, J=7.6 Hz, 1H), 5.15 (d, J=7.6 Hz, 1H), 2.23-2.33 (m, 2H), 1.94-2.09 (m, 2H), 1.81-1.89 (m, 1H), 1.41-1.67 (m, 5H), 1.08 (d, J=8.0 Hz, 2H), and 0.85 (s, 2H), $[M+H]^+$=398.2. The absolute configurations of chiral carbons in C126a and C126b are tentatively assigned as (S) and (R) respectively based on assumption that the binding model of the more potent isomer C126a is the same as that of C101a with IDO1 enzyme, and the relative stereochemistry on cyclohexane is assigned as trans configuration on the cyclohexane.

Example C127: (7-cyclopropylimidazo[1,5-a]pyridin-8-yl)(4-(8-fluoroquinolin-5-yl)cyclohexyl)methanol

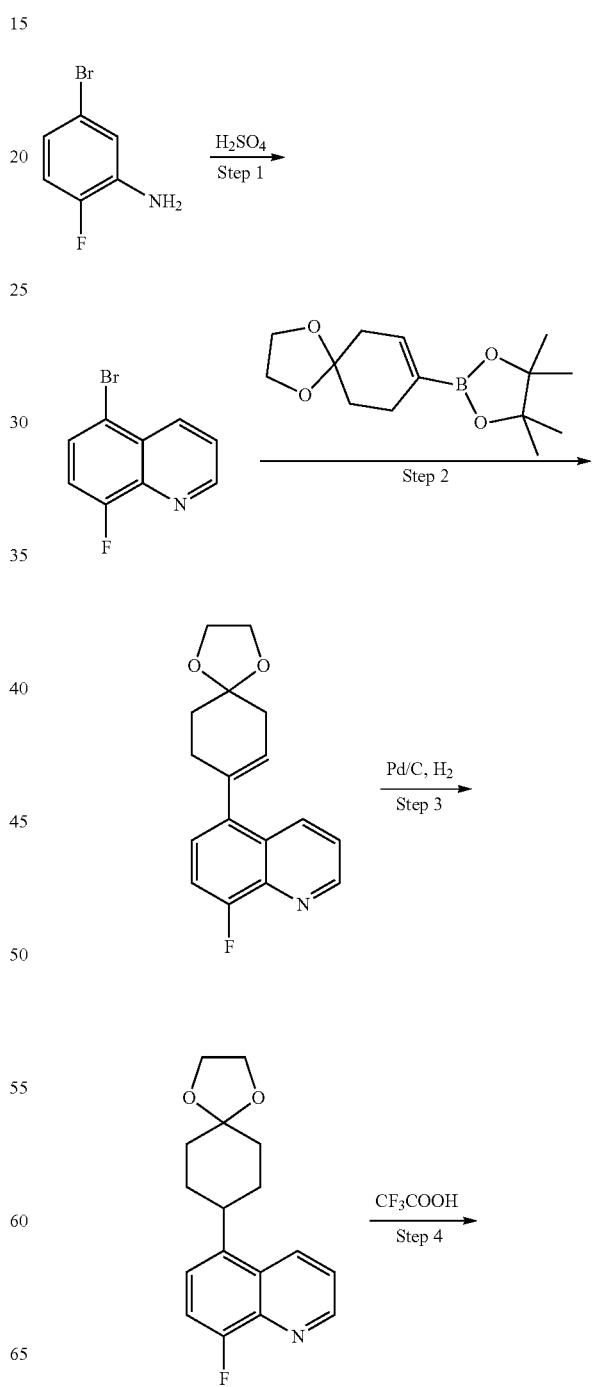

-continued
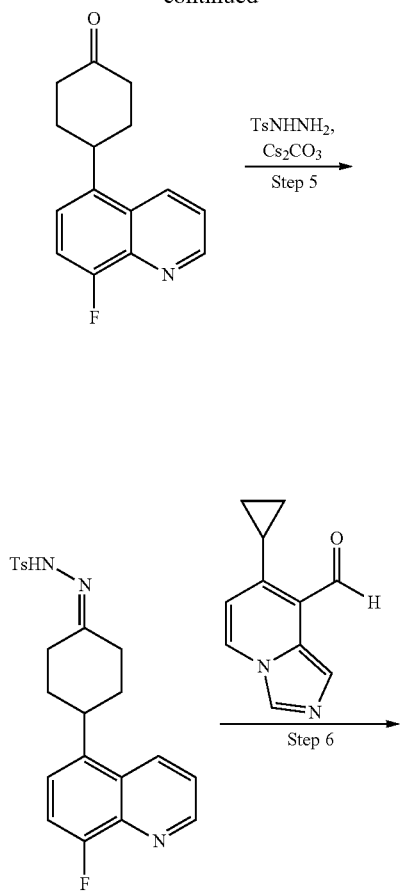
Example C127a and C127b: (S)-(7-cyclopropylimidazo[1,5-a]pyridin-8-yl)((1r,4S)-4-(8-fluoroquinolin-5-yl)cyclohexyl)methanol and (R)-7-cyclopropylimidazo[1,5-a]pyridin-8-yl)((1 r,4R)-4-(8-fluoroquinolin-5-yl)cyclohexyl)methanol
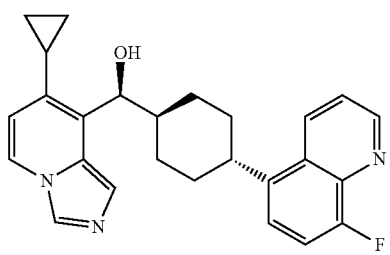
Fast isomer on chiral IC
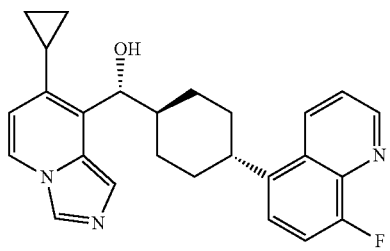
Slow isomer on chiral IC
Example C128: (7-cyclopropylimidazo[1,5-a]pyridin-8-yl)(4-(6-fluoroquinolin-4-yl)cyclohexyl)methanol
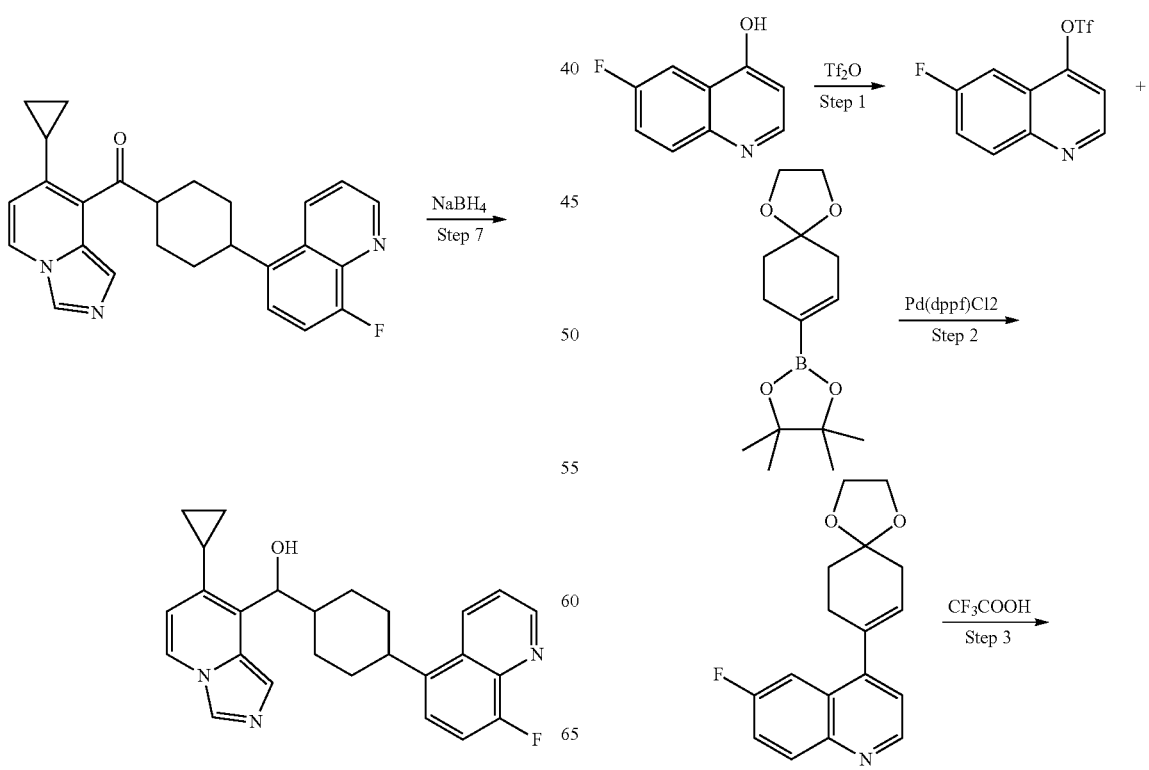

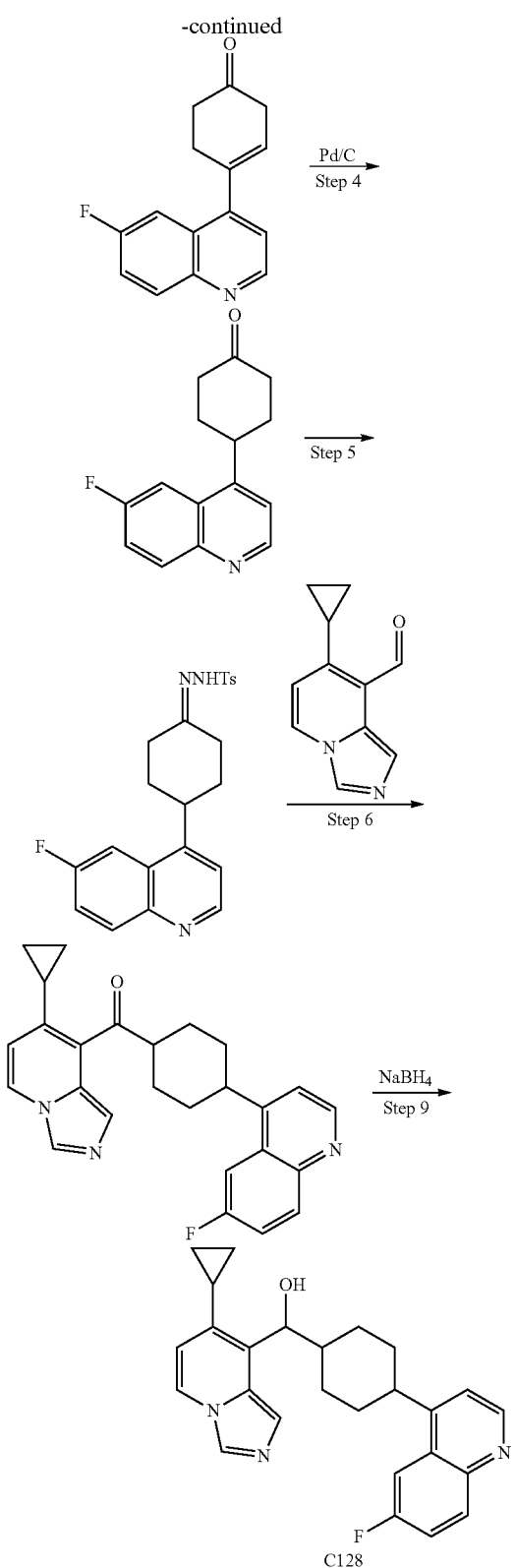

dropwised Tf$_2$O (21 g, 73.56 mmol) at 0° C. under N$_2$. The mixture was stirred overnight at r.t. The mixture was quenched by H$_2$O (30 mL) and extracted with DCM (50 mL×3). The organic layer was dried over with Na$_2$SO$_4$, filtered and concentrated to give crude product which was further purified by column chromatography, eluting with EA:PE=1:10 to give the product (8.56 g, 47%). [M+H]$^+$=296.

Step 2: 6-fluoro-4-(1,4-dioxaspiro[4.5]dec-7-en-8-yl)quinolone

To a solution of 6-fluoroquinolin-4-yl trifluoromethanesulfonate (8.56 g, 28.9 mmol) in 1,4-dioxane (60 mL) and H$_2$O (20 mL) was added 4,4,5,5-tetramethyl-2-(1,4-dioxaspiro[4.5]dec-7-en-8-yl)-1,3,2-dioxaborolane (7.7 g, 28.9 mmol), Pd(dppf)Cl$_2$ (3.1 g, 4.3 mmol) and Cs$_2$CO$_3$ (18.8 g, 57.8 mmol) and the mixture was heated at 80° C. overnight under N$_2$. Then evaporated the solvent under reduced pressure and the residue was purified by column chromatography (PE:EA=1:0-4:1) to give product as a brown solid (8.3 g, 85%). [M+H]$^+$=286.

Step 3: 4-(6-fluoroquinolin-4-yl)cyclohex-3-en-1-one

To a solution of 6-fluoro-4-(1,4-dioxaspiro[4.5]dec-7-en-8-yl)quinolone (8.3 g, 29 mmol) in dichloromethane (20 mL) was added trifluoroacetic acid (20 mL) at room temperature and the mixture was stirred for overnight. The solvent was evaporated under reduced pressure and water (100 mL) was added and adjusted the PH>7 by Na$_2$CO$_3$, extracted with ethyl acetate (50 mL×3), then the organic layer was further purified by column chromatography, on silica, eluting with EA:PE=0:1~1:5 to give the product (1.2 g, 17%) as a brown oil. [M+H]$^+$=242.

Step 4: 4-(6-fluoroquinolin-4-yl)cyclohexan-1-one

To a solution of 4-(6-fluoroquinolin-4-yl)cyclohex-3-en-1-one (1.2 g, 5.0 mmol) in MeOH (15 mL) was added Pd/C (0.24 g, 10%) and the mixture was stirred overnight at room temperature under H$_2$ (0.1 Mpa). Then filtered to remove Pd/C and the filtrate was evaporated under reduced pressure to give the product which was purified by column chromatography, on silica, eluting with EA:PE=1:5-1:1 to give the product (750 mg, 61%) as a yellow solid. [M+H]$^+$=244.

Step 5: N'-(4-(6-fluoroquinolin-4-yl)cyclohexylidene)-4-methylbenzenesulfonohydrazide To a solution of 4-(6-fluoroquinolin-4-yl)cyclohexan-1-one (750 mg, 3.07 mmol) in methol (10 mL) was added 4-methylbenzenesulfonohydrazide (628 mg, 3.38 mmol) at room temperature and the mixture was stirred for overnight. The solid was filtered and dried to give product (1 g, 77%) as a white solid. [M+H]$^+$=412.

Step 6: (7-cyclopropylimidazo[1,5-a]pyridin-8-yl)(4-(6-fluoroquinolin-4-yl)cyclohexyl)methanone To a solution of 7-cyclopropylimidazo[1,5-a]pyridine-8-carbaldehyde (452 mg, 2.43 mmol) in 1,4-dioxane (20 mL) was added N'-(4-(6-fluoroquinolin-4-yl)cyclohexylidene)-4-methylbenzenesulfonohydrazide (1.0 g, 2.43 mmol) and Cs$_2$CO$_3$ (1.6 g, 4.86 mmol) at room temperature, and the mixture was heated at 100° C. overnight under N$_2$. The Step 1: 6-fluoroquinolin-4-yl trifluoromethanesulfonate To a solution of 6-fluoroquinolin-4-ol (10 g, 61.3 mmol) in DCM (60 mL) and Et$_3$N (12.5 g, 122.6 mmol) was slowly mixture was purified by column chromatography (PE:EA=5:1) to give product as a brown oil (502 mg in 50% yield). [M+H]⁺=414.

Step 7: (7-cyclopropylimidazo[1,5-a]pyridin-8-yl)(4-(6-fluoroquinolin-4-yl)cyclohexyl)methanol

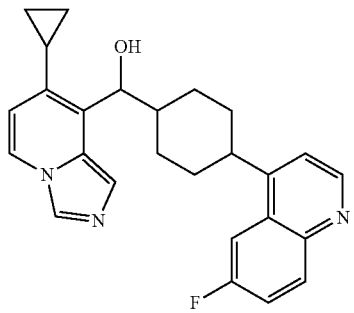 [SMILES: OC(c1c(C2CC2)ccn2cncc12)C1CCC(c2ccnc3ccc(F)cc23)CC1]

To a solution of (7-cyclopropylimidazo[1,5-a]pyridin-8-yl)(4-(6-fluoroquinolin-4-yl)cyclohexyl)methanone (413 mg, 1 mmol) in methol (30 mL) was added NaBH₄ (165 mg, 4.35 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product, which was further purified by Pre-HPLC to give the product (140 mg). ¹H NMR (DMSO-d₆) δ$_H$ 8.87-8.88 (d, J=3.2 Hz, 1H), 8.77-8.78 (d, J=4.8 Hz, 1H), 8.24 (s, 1H), 8.12-8.14 (d, J=7.2 Hz, 1H), 8.04-8.09 (m, 1H), 7.94-7.99 (m, 1H), 7.62-7.68 (m, 1H), 7.47 (s, 1H), 7.42-7.43 (d, J=4.8 Hz, 1H), 6.19-6.21 (d, J=7.6 Hz, 1H), 5.39 (d, J=3.2 Hz, 1H), 5.00-5.06 (m, 1H), 2.34-2.42 (m, 1H), 2.16-2.27 (m, 1H), 2.04-2.15 (m, 1H), 1.93-2.00 (m, 1H), 1.76-1.84 (m, 1H), 1.26-1.61 (m, 6H), 0.92-1.00 (m, 2H) and 0.69-0.72 (m, 2H). [M+H]⁺=416.2.

Example C128a and C128b: (S)-(7-cyclopropylimidazo[1,5-a]pyridin-8-yl)((1r,4S)-4-(6-fluoroquinolin-4-yl)cyclohexyl)methanol and (R)-(7-cyclopropylimidazo[1,5-a]pyridin-8-yl(1r,4R)-4-(6-fluoroquinolin-4-yl)cyclohexyl)methanol

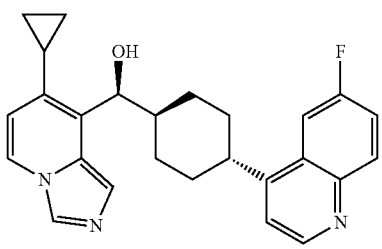

Fast isomer in CHIRALART Cellulose-SB
Eluting reagent: Hex:EtOH = 70:30

-continued

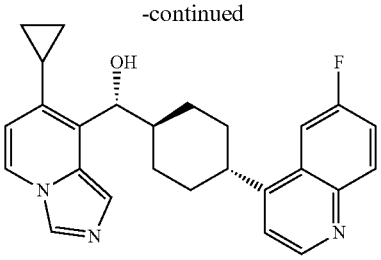

Slow isomer in CHIRALART Cellulose-SB
Eluting reagent: Hex:EtOH = 70:30

Each enantiomer of racemic C128a and C128b was separated using preparative HPLC on a CHIRALART Cellulose-SB with Hex:EtOH=70:30 as an eluent. The first one enantiomer eluted at the retention time of 4.337 min, which was dissolved in EA(5 ml), and HCl in EA(4N, 0.5 mL) was added and stirred at r.t for 1 h, the solvent was evaporated to give product as white solid, ¹H NMR (DMSO-d₆) δ$_H$ 9.57 (s, 1H), 9.07-9.13 (m, 1H), 8.42-8.44 (d, J=7.6 Hz, 2H), 8.30-8.33 (d, J=6.4 Hz, 1H), 8.06 (s, 1H), 7.95-8.04 (m, 1H), 7.81-7.86 (m, 1H), 6.67-6.69 (d, J=7.6 Hz, 1H), 5.14-5.16 (d, J=8.0 Hz, 1H), 3.47-3.57 (m, 1H), 2.22-2.32 (m, 2H), 1.94-2.10 (m, 2H), 1.80-1.90 (m, 1H), 1.41-1.71 (m, 5H), 1.05-1.12 (m, 2H) and 0.82-0.89 (m, 2H), [M+H]⁺=416.2; and the other enantiomer eluted at the retention time of 5.810 min, which was dissolved in EA(5 ml), and HCl in EA(4N, 0.5 mL) was added and the solvent was evaporated to give product as white solid, ¹H NMR (DMSO-d₆) δ 9.54 (d, J=1.2 Hz, 1H), 9.03-9.04 (d, J=5.2 Hz, 1H), 8.41-8.42 (d, J=7.2 Hz, 1H), 8.31-8.36 (m, 1H), 8.21-8.26 (m, 1H), 8.06 (m, 1H), 7.89-7.95 (m, 1H), 7.74-7.75 (d, J=5.2 Hz, 1H), 6.67-6.69 (d, J=7.6 Hz, 1H), 5.13-5.15 (d, J=8.0 Hz, 1H), 3.41-3.51 (m, 1H), 2.21-2.31 (m, 2H), 1.94-2.08 (m, 2H), 1.80-1.89 (m, 1H), 1.40-1.68 (m, 5H), 1.04-1.11 (m, 2H) and 0.82-0.89 (m, 2H), [M+H]⁺=416.2. The absolute configurations of chiral carbons in C128a and C128b are tentatively assigned as (S) and (R) respectively based on assumption that the binding model of the more potent isomer C128a is the same as that of C101a with IDO1 enzyme, and the relative stereochemistry on cyclohexane is assigned as trans configuration on the cyclohexane.

Example C129: (7-cyclopropylimidazo[1,5-a]pyridin-8-yl)(4-(8-fluoroquinolin-4-yl)cyclohexyl)methanol

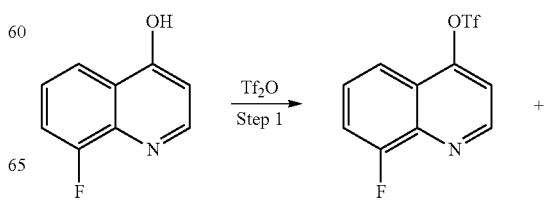

-continued

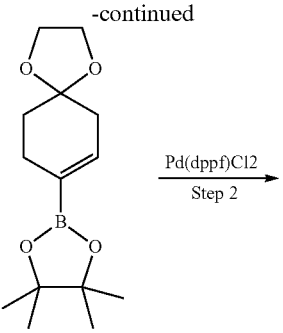

Pd(dppf)Cl2
Step 2

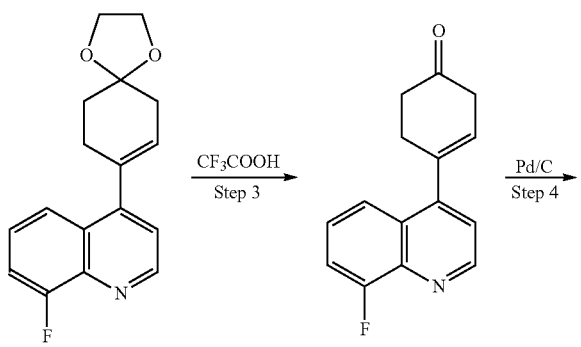

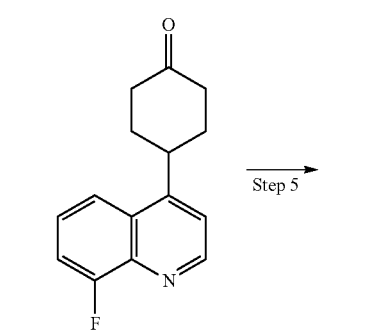

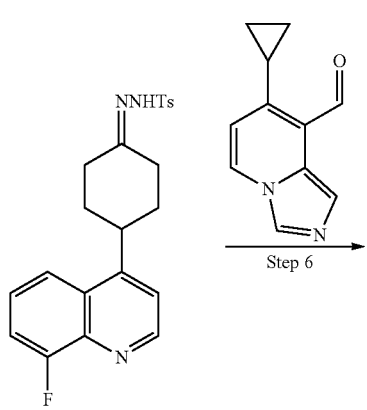

-continued

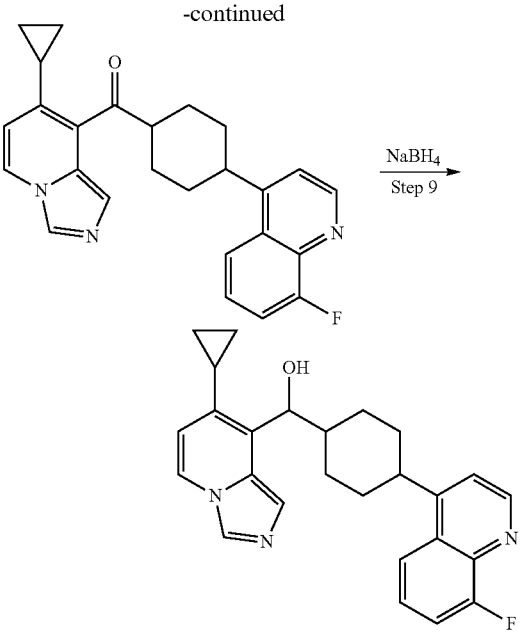

C129

Step 1: 8-fluoroquinolin-4-yl trifluoromethanesulfonate

To a solution of 8-fluoroquinolin-4-ol (20 g, 122 mmol) in DCM (100 mL) and Et$_3$N (25 g, 122.6 mmol) was slowly dropwised Tf$_2$O (42 g, 147 mmol) at 0° C. under N$_2$. The mixture was stirred overnight at r.t. The mixture was quenched by H$_2$O (30 mL) and extracted with DCM (100 mL×3). The organic layer was dried over with Na$_2$SO$_4$, filtered and concentrated to give crude product which was further purified by column chromatography, eluting with EA:PE=1:10 to give the product (16.1 g, 45%). [M+H]$^+$=296.

Step 2: 8-fluoro-4-(1,4-dioxaspiro[4.5]dec-7-en-8-yl)quinolone

To a solution of 8-fluoroquinolin-4-yl trifluoromethanesulfonate (16.1 g, 54 mmol) in 1,4-dioxane (100 mL) and H$_2$O (40 mL) was added 4,4,5,5-tetramethyl-2-(1,4-dioxaspiro[4.5]dec-7-en-8-yl)-1,3,2-dioxaborolane (15 g, 58 mmol), Pd(dppf)Cl$_2$ (6.2 g, 8.7 mmol) and Cs$_2$CO$_3$ (34 g, 116 mmol) and the mixture was heated at 80° C. overnight under N$_2$. Then evaporated the solvent under reduced pressure and the residue was purified by column chromatography (PE:EA=1:0-4:1) to give product as a brown solid (14.2 g, 81%). [M+H]$^+$=286.

Step 3: 4-(8-fluoroquinolin-4-yl)cyclohex-3-en-1-one

To a solution of 8-fluoro-4-(1,4-dioxaspiro[4.5]dec-7-en-8-yl)quinolone (14.2 g) in dichloromethane (40 mL) was added trifluoroacetic acid (40 mL) at room temperature and the mixture was stirred for overnight. The solvent was evaporated under reduced pressure and water (100 mL) was added and adjusted the PH>7 by Na$_2$CO$_3$, extracted with ethyl acetate (50 mL×3), then the organic layer was further purified by column chromatography, on silica, eluting with EA:PE=0:1~1:5 to give the product (2.2 g) as a brown oil. [M+H]$^+$=242.

Step 4: 4-(8-fluoroquinolin-4-yl)cyclohexan-1-one

To a solution of 4-(6-fluoroquinolin-4-yl)cyclohex-3-en-1-one (2.2 g, 9 mmol) in MeOH (15 mL) was added Pd/C (0.22 g, 10%) and the mixture was stirred overnight at room temperature under $H_2$ (0.1 Mpa). Then filtered to remove Pd/C and the filtrate was evaporated under reduced pressure to give the product which was purified by column chromatography, on silica, eluting with EA:PE=1:5-1:1 to give the product (1.35 g, 52%) as a yellow solid. $[M+H]^+=244$.

Step 5: N'-(4-(8-fluoroquinolin-4-yl)cyclohexylidene)-4-methylbenzenesulfonohydrazide To a solution of 4-(6-fluoroquinolin-4-yl)cyclohexan-1-one (1.2 g) in methanol (20 mL) was added 4-methylbenzenesulfonohydrazide (1.02 g) at room temperature and the mixture was stirred for overnight. The solid was filtered and dried to give product (1.8 g) as a white solid. $[M+H]^+=412$.

Step 6: (7-cyclopropylimidazo[1,5-a]pyridin-8-yl)(4-(8-fluoroquinolin-4-yl)cyclohexyl)methanone To a solution of 7-cyclopropylimidazo[1,5-a]pyridine-8-carbaldehyde (820 mg) in 1,4-dioxane (20 mL) was added N'-(4-(8-fluoroquinolin-4-yl)cyclohexylidene)-4-methyl-benzenesulfonohydrazide (1.6 g) and $Cs_2CO_3$ (2.6 g) at room temperature, and the mixture was heated at 100° C. overnight under $N_2$. The mixture was purified by column chromatography (PE:EA=5:1) to give product as a brown oil (0.82 g). $[M+H]^+=414$.

Step 7: (7-cyclopropylimidazo[1,5-a]pyridin-8-yl)(4-(8-fluoroquinolin-4-yl)cyclohexyl)methanol

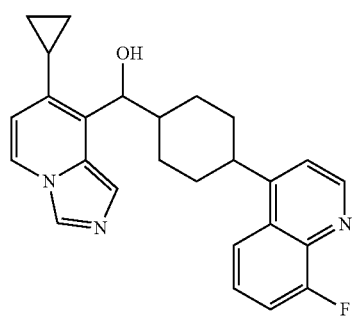 [SMILES: OC(c1c(C2CC2)ccn2cncc12)C1CCC(c2ccnc3c(F)cccc23)CC1]

To a solution of (7-cyclopropylimidazo[1,5-a]pyridin-8-yl)(4-(8-fluoroquinolin-4-yl)cyclohexyl)methanone (0.8 g) in methol (30 mL) was added $NaBH_4$ (350 mg) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product, which was further purified by Pre-HPLC to give the product (36 mg). $[M+H]^+=416$.

Example C129a and C129b: (S)-(7-cyclopropylimidazo[1,5-a]pyridin-8-yl)((1r,4S)-4-(8-fluoroquinolin-4-yl)cyclohexyl)methanol and (R)-(7-cyclopropylimidazo[1,5-a]pyridin-8-yl)((1r,4R)-4-(8-fluoroquinolin-4-yl)cyclohexyl)methanol

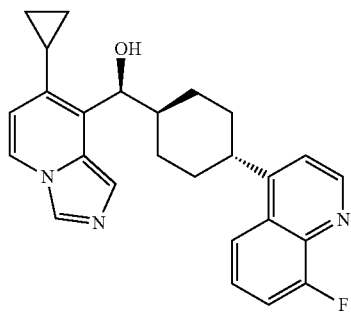

Fast isomer on chiral IC

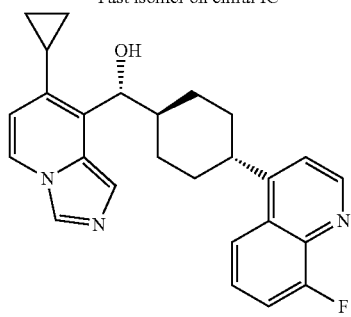

Slow isomer on chiral IC

Example C130: (7-cyclopropylimidazo[1,5-a]pyridin-8-yl)(4-(quinolin-4-yl)cyclohexyl)methanol

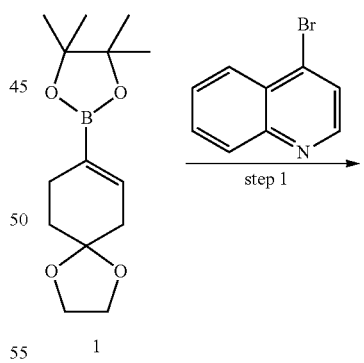

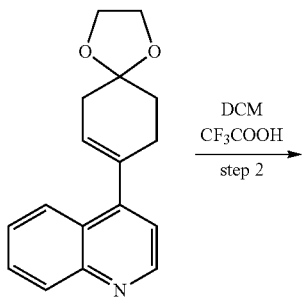

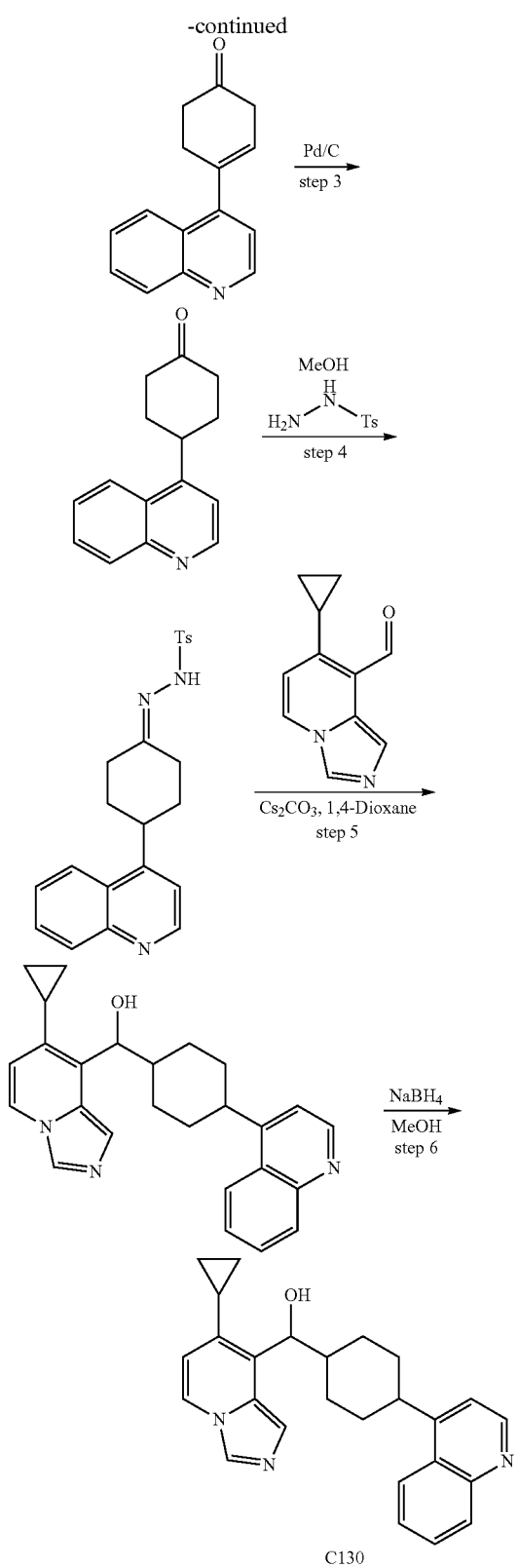

Step 1: 4-(1,4-dioxaspiro[4.5]dec-7-en-8-yl)quinoline

To a solution of 4-bromoquinoline (4.70 g, 22.67 mmol) in 1,4-dioxane (150 mL) was added 4,4,5,5-tetramethyl-2-(1,4-dioxaspiro[4.5]dec-7-en-8-yl)-1,3,2-dioxaborolane (6.00 g, 22.67 mmol), Pd(dppf)Cl$_2$ (2.47 g, 3.40 mmol) and Cs$_2$CO$_3$ (11.00 g, 34.0 mmol) and the mixture was heated at 95° C. for overnight. Then evaporated the solvent under reduced pressure and the residue was purified by column chromatography (PE:EA=4:1) to give product as a clear oil (4.41 g in 73% yield). $^1$H NMR (DMSO-d$_6$) δ$_H$ 8.83 (d, J=4.4 Hz, 1H), 8.01-8.05 (m, 2H), 7.74-7.78 (m, 1H), 7.59-7.64 (m, 1H), 7.31 (d, J=4.4 Hz, 1H), 5.70-5.72 (m, 1H), 3.99 (s, 4H), 2.51-2.56 (m, 2H), 2.45-2.46 (m, 2H), and 1.91 (t, J=6.4 Hz, 2H).

Step 2: 4-(quinolin-4-yl)cyclohex-3-en-1-one

To a solution of 4-(1,4-dioxaspiro[4.5]dec-7-en-8-yl)quinoline (4.41 g, 16.52 mmol) in dichloromethane (15 mL) was added trifluoroacetic acid (20 mL) at room temperature and the mixture was stirred for overnight. The solvent was evaporated under reduced pressure and water (100 mL) was added, extracted with EA (100 mL×3), combined the organic layer and washed with saturated aqueous of Na$_2$CO$_3$ then the organic layer was evaporated to give crude product, which was used for next step without further purification. MS (ESI) m/e [M+1]$^+$=224.

Step 3: 4-(quinolin-4-yl)cyclohexan-1-one

To a solution of 4-(quinolin-4-yl)cyclohex-3-en-1-one (4.66 g) in ethyl acetate (40 mL) and methanol (10 mL) was added Pd/C (0.5 g, 10%) and the mixture was stirred for 36 hours at room temperature under H$_2$ (0.4 Mpa). Then filtered to remove Pd/C and the filtrate was evaporated under reduced pressure to give a crude product, which was purified by silica gel chromatography (PE:EA=10:1-1:1) to give product (0.72 g in 15% yield) as a yellow oil. $^1$H NMR (DMSO-d$_6$) δ$_H$ 8.84 (d, J=4.4 Hz, 1H), 8.38 (d, J=8.4 Hz, 1H), 8.05 (d, J=8.4 Hz, 1H), 7.78 (t, J=7.6 Hz, 1H), 7.68 (t, J=7.6 Hz, 1H), 7.44 (d, J=4.4 Hz, 1H), 3.96-4.04 (m, 1H), 2.75-2.82 (m, 2H), 2.33-2.37 (m, 2H), 2.16-2.19 (m, 2H), and 1.95-2.05 (m, 2H).

Step 4: 4-methyl-N'-(4-(quinolin-4-yl)cyclohexylidene)benzenesulfonohydrazide

To a solution of 4-(quinolin-4-yl)cyclohexan-1-one (0.72 g 3.2 mmol) in methanol (10 mL) was added 4-methylbenzenesulfonohydrazide (0.60 g, 3.2 mmol) at room temperature, and the mixture was stirred for 2-3 hours. The solvent was evaporated under reduced pressure and the residue was pulped with methanol 5 mL, filtered and washed with methanol 2 mL to give product (0.86 g in 68% yield) as a white solid. $^1$H NMR (DMSO-d$_6$) δ$_H$ 10.24 (s, 1H), 8.81 (d, J=4.4 Hz, 1H), 8.30 (d, J=8.4 Hz, 1H), 8.02 (d, J=8.4 Hz, 1H), 7.74-7.78 (m, 3H), 7.62-7.67 (m, 1H), 7.37-7.43 (m, 3H), 3.70-3.76 (m, 1H), 2.96-3.00 (m, 1H), 2.43-2.48 (m, 1H), 2.40 (s, 3H), 2.32-2.35 (m, 1H), 2.12-2.21 (m, 1H), 2.02-2.05 (m, 2H), and 1.52-1.73 (m, 2H).

Step 5: (7-cyclopropylimidazo[1,5-a]pyridin-8-yl)(4-(quinolin-4-yl)cyclohexyl)methanone To a solution 7-cyclopropylimidazo[1,5-a]pyridine-8-carbaldehyde (400 mg) in 1,4-dioxane (30 mL) was added 4-methyl-N'-(4-(quinolin-4-yl)cyclohexylidene) benzenesulfonohydrazide (855 mg) and Cs$_2$CO$_3$ (1058 mg) at room temperature, and the mixture was heated at 95° C. for overnight. The solvent was cooled to room temperature, concentrated to dryness. The crude was purified by column chromatography (PE:EA=10:1-1:1) to give compound product as a pale yellow solid (581 mg in 55% yield). MS (ESI) m/e [M+1]+=396.

Step 6: (7-cyclopropylimidazo[1,5-a]pyridin-8-yl)(4-(quinolin-4-yl)cyclohexyl)methanol

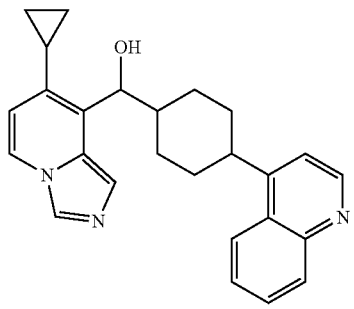

To a solution of (7-cyclopropylimidazo[1,5-a]pyridin-8-yl)(4-(quinolin-4-yl) cyclohexyl)methanone (360 mg, 0.91 mmol) in methanol (10 mL) was added NaBH$_4$ (173 mg, 4.55 mmol) at room temperature and the mixture was stirred for 2 hour. Then the solvent was evaporated under reduced pressure and water (10 mL) was added, extracted with ethyl acetate (20 ml×3) and combined the organic layer, evaporated the solvent under reduced pressure and the residue was purified by Pre-TLC (EA(0.2%):MeOH=50:1) to give compound product as a pale yellow solid (150 mg, in 42% yield). $^1$H NMR (DMSO-d$_6$) $\delta_H$ 8.78 (d, J=4.8 Hz, 1H), 8.24 (s, 1H), 8.21 (d, J=8.4 Hz, 1H), 8.13 (d, J=7.2 Hz, 1H), 8.00 (d, J=8.4 Hz, 1H), 7.73 (t, J=7.6 Hz, 1H), 7.62 (t, J=7.6 Hz, 1H), 7.47 (s, 1H), 7.38 (d, J=4.4 Hz, 1H), 6.19 (d, J=7.2 Hz, 1H), 5.36-5.43 (m, 1H), 5.00-5.05 (m, 1H), 3.35-3.40 (m, 1H), 2.35-2.45 (m, 1H), 2.15-2.30 (m, 1H), 2.06-2.13 (m, 1H), 1.95-2.05 (m, 1H), 1.79-1.85 (m, 1H), 1.30-1.65 (m, 5H), 0.92-1.02 (m, 2H), and 0.68-0.78 (m, 2H). MS (ESI) m/e [M+1]+=398.

Example C130a and C130b: (S)-(7-cyclopropylimidazo[1,5-a]pyridin-8-yl)((1r,4S)-4-(quinolin-4-yl)cyclohexyl)methanol and (R)-(7-cyclopropylimidazo[1,5-a]pyridin-8-yl)((1 r,4R)-4-(quinolin-4-yl)cyclohexyl)methanol

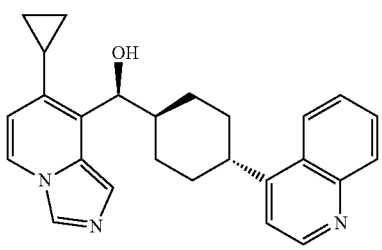

Fast isomer in CHIRALPAK IC-3 HPLC
Eluting reagent: Hex(0.1% DEA):EtOH = 80:20

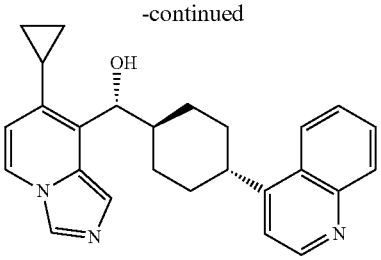

Slow isomer in CHIRALPAK IC-3 HPLC
Eluting reagent: Hex(0.1% DEA):EtOH = 80:20

Each enantiomer of racemic C130a and Cl$_{30}$b was separated using preparative HPLC on a CHIRALART Cellulose-SB with Hex:EtOH=80:20 as an eluent. The enantiomeric excesses were determined by using HPLC on a CHIRALART Cellulose-SB with Hex (0.1% DEA):EtOH=80:20 as an eluent at a flow rate of 1.0 ml/min. The first one enantiomer eluted at the retention time of 7.024 min (C130a), which was dissolved in DCM (10 mL), and added EA solution of hydrochloric acid (0.5 mL, 4.0 M) at room temperature, followed by addition of methanol until the precipitate was dissolved, then the solvent was evaporated under reduced pressure and the residue was washed by PE to give desired product as white solid. $^1$H NMR (DMSO-d6) $\delta_H$ 9.51 (s, 1H), 9.13 (d, J=5.2 Hz, 1H), 8.51 (d, J=8.4 Hz, 1H), 8.41 (d, J=7.6 Hz, 1H), 8.30 (d, J=8.4 Hz, 1H), 8.03-8.13 (m, 1H), 7.91 (t, J=7.6 Hz, 1H), 7.84 (d, J=4.4 Hz, 1H), 6.66 (d, J=7.2 Hz, 1H), 5.82 (m, 1H), 5.15 (d, J=7.6 Hz, 1H), 2.20-2.36 (m, 2H), 1.96-2.10 (m, 2H), 1.83-1.93 (m, 1H), 1.44-1.73 (m, 5H), 1.20-1.30 (m, 1H), 1.04-1.12 (m, 2H), and 0.82-0.89 (m, 2H); and the other enantiomer eluted at the retention time of 10.891 min (Cl$_{30}$b), $^1$H NMR (DMSO-d$_6$) $\delta_H$ 9.47 (s, 1H), 9.08 (br s, 1H), 8.46 (d, J=8.4 Hz, 1H), 8.39 (d, J=7.6 Hz, 1H), 8.22 (d, J=8.4 Hz, 1H), 7.98-8.07 (m, 2H), 7.86 (t, J=7.6 Hz, 1H), 7.76 (br s, 1H), 6.65 (d, J=7.2 Hz, 1H), 5.81 (m, 1H), 5.14 (d, J=7.6 Hz, 1H), 2.25-2.34 (m, 2H), 1.96-2.06 (m, 2H), 1.84-1.91 (m, 1H), 1.44-1.73 (m, 5H), 1.22-1.30 (m, 1H), 1.06-1.13 (m, 2H), and 0.82-0.93 (m, 2H).

Example C131: (7-cyclopropylimidazo[1,5-a]pyridin-8-yl)(4-(3,4-difluorophenyl)cyclohexyl)methanol

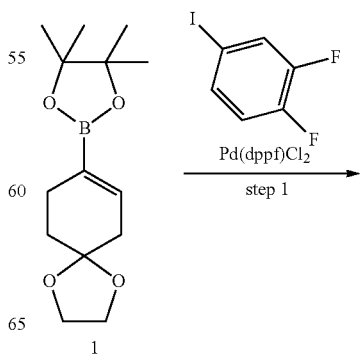

-continued

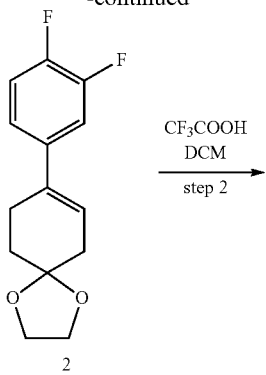

2

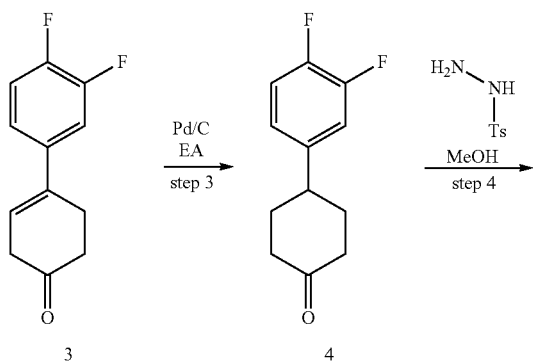

3 → 4

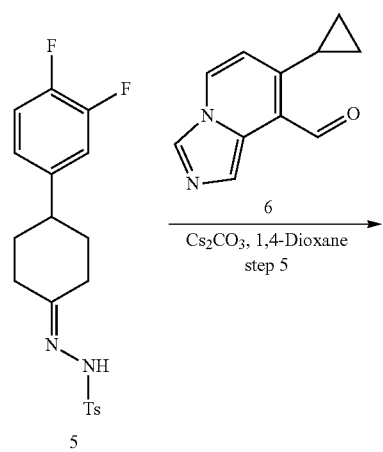

5

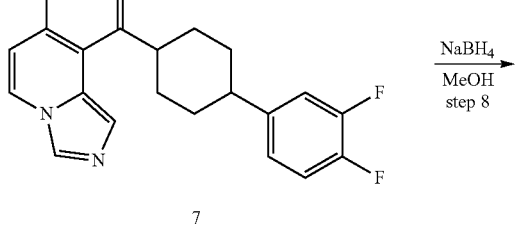

7

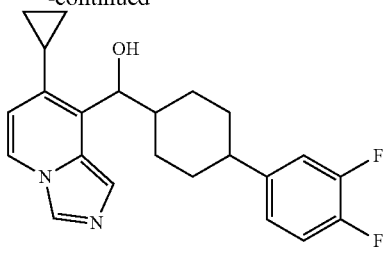

C131

Step 1: 8-(3,4-difluorophenyl)-1,4-dioxaspiro[4.5]dec-7-ene

To a solution of 1,2-difluoro-4-iodobenzene (9 g, 38 mmoL) in 1,4-dioxane (150 mL) was added 4,4,5,5-tetramethyl-2-(1,4-dioxaspiro[4.5]dec-7-en-8-yl)-1,3,2-dioxaborolane (10 g, 38 mmol), Pd(dppf)Cl$_2$ (1.4 g, 1.9 mmol) and Cs$_2$CO$_3$ (18.4 g, 56 mmol) and the mixture was heated at 90° C. overnight. Then evaporated the solvent under reduced pressure and the residue was purified by column chromatography (PE:EA=5:1) to give product as an yellow solid (8 g in 84% yield). $^1$H NMR (400 MHz, CDCl$_3$) δ 7.22-7.14 (m, 1H), 7.12-7.02 (m, 2H), 6.05-5.86 (m, 1H), 4.05-3.96 (m, 4H), 2.67-2.54 (m, 2H), 2.51-2.36 (m, 2H), 1.91 (t, J=6.5 Hz, 2H). [M+H]$^+$=253.1.

Step 2: 3′,4′-difluoro-2,5-dihydro-[1,1′-biphenyl]-4(3H)-one

To a solution of 8-(3,4-difluorophenyl)-1,4-dioxaspiro[4.5]dec-7-ene (8 g, 32 mmol) in dichloromethane (40 mL) was added trifluoroacetic acid (40 mL) at room temperature and the mixture was stirred for overnight. The solvent was evaporated under reduced pressure and water (100 mL) was added, extracted with ethyl acetate (100 mL×3), combined the organic layer and washed with saturated aqueous of NaHCO$_3$, then the organic layer was evaporated in vacuo to give crude product, which was used for next step without further purification.

Step 3: 4-(3,4-difluorophenyl)cyclohexan-1-one

To a solution of 3′,4′-difluoro-2,5-dihydro-[1,1′-biphenyl]-4(3H)-one (32 mmol) in ethyl acetate (150 mL) was added Pd/C (1.0 g, 10%) and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give product (4.8 g, oil). $^1$H NMR (400 MHz, CDCl$_3$) δ 7.17-7.01 (m, 2H), 7.01-6.94 (m, 1H), 3.16-2.85 (m, 1H), 2.57-2.42 (m, 4H), 2.30-2.14 (m, 2H), 1.99-1.75 (m, 2H). [M+H]$^+$=211.1.

Step 4: N′-(4-(3,4-difluorophenyl)cyclohexylidene)-4-methylbenzenesulfonohydrazide To a solution of 4-(3,4-difluorophenyl)cyclohexan-1-one (1 g, 4.8 mmol) in methol (15 mL) and DCM (5 mL) was added 4-methylbenzenesulfonohydrazide (0.89 g, 4.8 mmol) at room temperature and the mixture was stirred overnight. The solid was filtered to give product as a white solid (1.5 g in 83% yield). ¹H NMR (400 MHz, DMSO-d6) δ 10.20 (s, 1H), 7.74 (d, J=8.0 Hz, 2H), 7.40 (d, J=8.0 Hz, 2H), 7.35-7.26 (m, 2H), 7.13-6.99 (m, 1H), 2.99-2.74 (m, 2H), 2.39 (s, 3H), 2.32-2.16 (m, 2H), 2.02-1.82 (m, 3H), 1.63-1.36 (m, 2H). [M+H]⁺=379.1.

Step 5: (7-cyclopropylimidazo[1,5-a]pyridin-8-yl)(4-(3,4-difluorophenyl)cyclohexyl)methanone To a solution of 7-cyclopropylimidazo[1,5-a]pyridine-8-carbaldehyde (420 mg, 2.3 mmol) in 1,4-dioxane (20 mL) was added N'-(4-(3,5-difluorophenyl)cyclohexylidene)-4-methylbenzenesulfonohydrazide (860 mg, 2.3 mmol) and Cs₂CO₃ (1.11 g, 3.4 mmol) at room temperature, and the mixture was heated at 95° C. overnight. The solvent was evaporated in vacuo and water (30 mL) was added, extracted with ethyl acetate (20 mL×3) and combined the organic layer, the solvent was evaporated under reduced pressure and the residue was purified by column chromatography (EA=100%) to give product as a red oil (200 mg in 23% yield). [M+H]⁺=381.1

Step 6: (7-cyclopropylimidazo[1,5-a]pyridin-8-yl)(4-(3,4-difluorophenyl)cyclohexyl)methanol

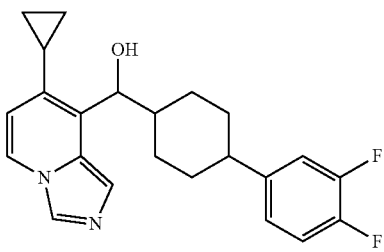 [SMILES: OC(c1c(C2CC2)ccn2cncc12)C1CCC(c2ccc(F)c(F)c2)CC1]

To a solution of (7-cyclopropylimidazo[1,5-a]pyridin-8-yl)(4-(3,4-difluorophenyl)cyclohexyl)methanone (200 mg, 0.53 mmol) in methanol (10 mL) was added NaBH₄ (100 mg, 2.63 mmol) at room temperature and the mixture was stirred for 2 h. Then the solvent was evaporated under reduced pressure and water (10 mL) was added, extracted with ethyl acetate (20 mL×3) and combined the organic layer, the solvent was evaporated under reduced pressure. The residue was purified by Prep-TLC (EA:PE=3:1) to afford the title compound as grey solid (50 mg in 25% yield). ¹H NMR (400 MHz, DMSO-d6) δ8.13 (s, 1H), 7.94 (d, J=7.2 Hz, 1H), 7.46 (s, 1H), 7.09-6.94 (m, 2H), 6.92-6.82 (m, 1H), 6.20 (d, J=7.2 Hz, 1H), 5.05 (d, J=8.8 Hz, 1H), 2.48-2.28 (m, 2H), 2.11-1.97 (m, 2H), 1.92-1.81 (m, 1H), 1.72-1.62 (m, 1H), 1.45-1.32 (m, 1H), 1.31-1.12 (m, 4H), 1.00-0.86 (m, 2H), 0.73-0.58 (m, 2H). [M+H]⁺=383.2

Example C31a and C131b: (S)-(7-cyclopropylimidazo[1,5-a]pyridin-8-yl)((1r,4S)-4-(3,4-difluorophenyl)cyclohexyl)methanol and (R)-(7-cyclopropylimidazo[1,5-a]pyridin-8-yl)(1 r,4R)-4-(3,4-difluorophenyl)cyclohexyl)methanol

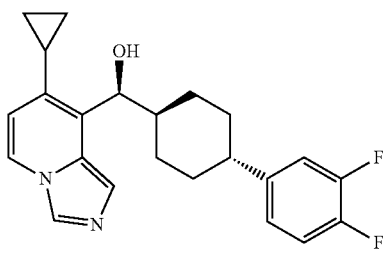

Fast isomer on chiral IC

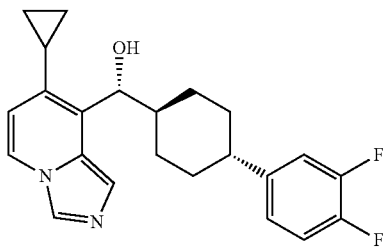

Slow isomer on chiral IC

Example C132: (4-(3-chloro-4-fluorophenyl)cyclohexyl)(7-cyclopropylimidazo[1,5-a]pyridin-8-yl)methanol

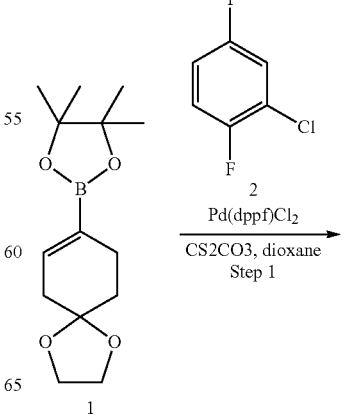

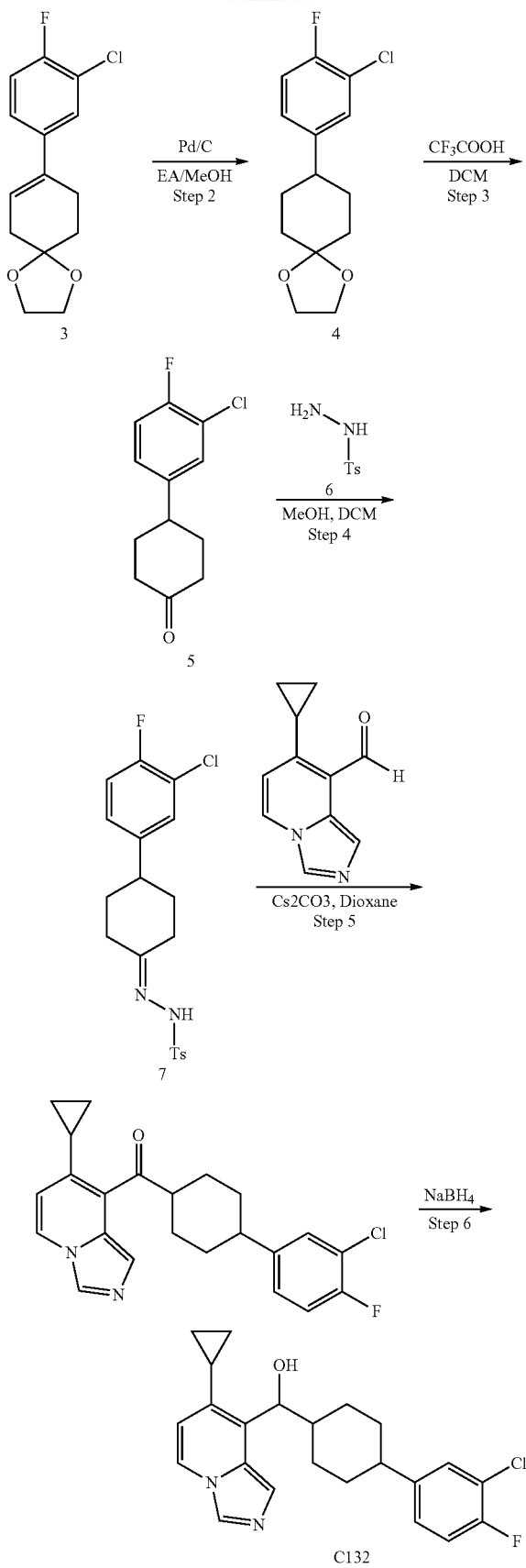

Step 1: 8-(3-chloro-4-fluorophenyl)-1,4-dioxaspiro[4.5]dec-7-ene

A mixture of 2-chloro-1-fluoro-4-iodobenzene (7.0 g, 27.3 mmol), 4,4,5,5-tetramethyl-2-(1,4-dioxaspiro[4.5]dec-7-en-8-yl)-1,3,2-dioxaborolane (7.2 g, 27.1 mmol), Pd(dppf)Cl$_2$ (1.0 g, 1.36 mmol) and Cs$_2$CO$_3$ (14.0 g, 42.9 mmol) in 1,4-dioxane (200 mL) was heated at 95° C. for 2 hours. The mixture was filtered and the filtrate was concentrated and the resulted residue was purified by column chromatography (PE:EA=50:1 to 20:1) to give product (3.8 g, crude) as a colorless oil.

Step 2: 8-(3-chloro-4-fluorophenyl)-1,4-dioxaspiro[4.5]decane

A mixture of 8-(3-chloro-4-fluorophenyl)-1,4-dioxaspiro[4.5]dec-7-ene (3.8 g, crude) and Pd/C (380 mg) in a mixed solvent (methanol/ethyl acetate: 60 mL/60 mL) was stirred at rt under H$_2$ for 2 hrs. The mixture was filtered and the filtrate was concentrated to give the title product (2.8 g, crude) as a colorless oil.

Step 3: 4-(3-chloro-4-fluorophenyl)cyclohexan-1-one

To a solution of 8-(3-chloro-4-fluorophenyl)-1,4-dioxaspiro[4.5]decane (2.8 g, 10.4 mmol) in dichloromethane (20 mL) was added trifluoroacetic acid (30 mL) at room temperature and the mixture was stirred for 2 days. The mixture was concentrated. Aqueous solution of NaHCO$_3$ (50 mL) and ethyl acetate (50 mL) were added, and the mixture was stirred for 20 min. Layers was separated and the organic layer was washed with brine (20 mL×2), dried over Na$_2$SO$_4$ and concentrated. The residue was purified by column chromatography (PE:EA=50:1 to 20:1) to give the title product (1.06 g, yield: 17% for 3 steps) as a colorless oil.

Step 4: N'-(4-(3-chloro-4-fluorophenyl)cyclohexylidene)-4-methylbenzenesulfonohydrazide To a stirred solution of 4-(3-chloro-4-fluorophenyl)cyclohexan-1-one (1.06 g, 4.7 mmol) in a mixed solvent (dichloromethane/ethanol: 10 mL/10 mL) was added 4-methylbenzenesulfonohydrazide (872 mg, 4.7 mmol) at room temperature and the mixture was stirred for 16 hrs. The mixture was concentrated and the residue was added 20 mL of 2-methoxy-2-methylpropane and the mixture was stirred at 50° C. for 2 hrs and cooled, and continued to stir for 1 hour. A white solid precipitated, which was filtered. The filter cake was dried under high vacuum to give the title product (1.12 g, yield: 60%) as a white solid.

Step 5: tert-butyl ((6-(4-(3-chloro-4-fluorophenyl)cyclohexane-1-carbonyl)-5-cyclopropylpyridin-2-yl)methyl)carbamate A mixture of 7-cyclopropylimidazo[1,5-a]pyridine-8-carbaldehyde (372 mg, 2 mmol), N'-(4-(3-chloro-4-fluorophenyl)cyclohexylidene)-4-methylbenzenesulfonohydrazide (790 mg, 2 mmol) and Cs$_2$CO$_3$ (1.2 g, 3.7 mmol) in 1,4-dioxane (20 mL) was heated at 100° C. for 16 hours. The mixture was cooled and treated with ethyl acetate (50 mL) and water (50 mL). The aqueous layer was extracted with ethyl acetate (50 mL×2). The combined organics was washed with brine (50 mL×2), dried over Na$_2$SO$_4$ and concentrated. The resulted residue was purified by column chromatography (PE:EA=10:1) to give the title product as a light yellow oil (600 mg, yield: 26%). [M+H]⁺=397.2

Step 8: (4-(3-chloro-4-fluorophenyl)cyclohexyl)(7-cyclopropylimidazo[1,5-a]pyridin-8-yl)methanol

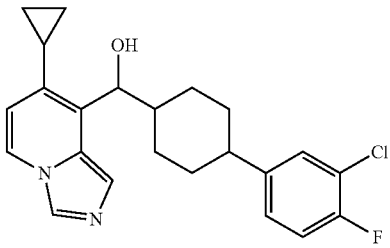 [SMILES: OC(c1c(C2CC2)ccn2cncc12)C1CCC(c2ccc(F)c(Cl)c2)CC1]

To a stirred solution of (4-(3-chloro-4-fluorophenyl)cyclohexyl)(7-cyclopropylimidazo[1,5-a]pyridin-8-yl)methanone (230 mg, 0.58 mmol) in methanol (5 mL) was added NaBH₄ (60 mg, 1.57 mmol) at room temperature. After the addition finished, the mixture was stirred for 1 hour. The mixture was diluted with EA (20 mL), washed with brine (20 mL×2), dried over Na₂SO₄, concentrated, and the residue was purified by prep-TLC (EA: 100%) to give product (107 mg, yield: 27% for 2 steps) as a white solid. ¹H NMR (400 MHz, DMSO-d₆) δ 8.33 (s, 1H), 8.16 (d, J=7.2 Hz, 1H), 7.53-7.37 (m, 2H), 7.35-7.17 (m, 2H), 6.21 (d, J=7.6 Hz, 1H), 5.38 (d, J=3.2 Hz, 1H), 4.97 (dd, J=8.0, 3.6 Hz, 1H), 2.49-2.41 (m, 1H), 2.30 (d, J=12.0 Hz, 1H), 2.16 (s, 1H), 2.04-1.91 (m, 1H), 1.84 (d, J=13.2 Hz, 1H), 1.72-1.62 (m, 1H), 1.50-1.36 (m, 1H), 1.35-1.11 (m, 4H), 1.05-0.85 (m, 2H), 0.78-0.63 (m, 2H). [M+H]⁺=399.1.

Example C132a and C132b: (S)-((1 r,4S)-4-(3-chloro-4-fluorophenyl)cyclohexyl)(7-cyclopropylimidazo[1,5-a]pyridin-8-yl)methanol and (R)-((r,4R)-4-(3-chloro-4-fluorophenyl)cyclohexyl)(7-cyclopropylimidazo[1,5-a]pyridin-8-yl)methanol

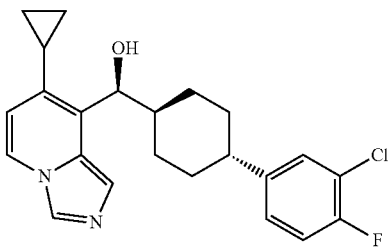

Fast isomer in CHIRALPAK IC HPLC
Eluting reagent: Hex(0.1% DEA):EtOH = 60:40

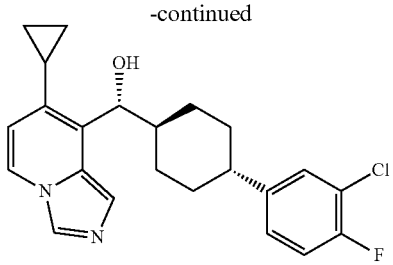

Slow isomer in CHIRALPAL IC HPLC
Eluting reagent: Hex(0.1% DEA):EtOH = 60:40

Each enantiomer of racemic C132a and Cl₃₂b was separated using preparative HPLC on a CHIRALART Cellulose-SB with Hex (0.1%):EtOH=60:40 as an eluent. The enantiomeric excesses were determined by using HPLC on a CHIRALART Cellulose-SB with Hex (0.1% DEA):EtOH=60:40 as an eluent at a flow rate of 1.0 mL/min. The first one enantiomer eluted at the retention time of 1.513 min (C132a), ¹H NMR (400 MHz, CDCl₃) δ 8.04 (s, 1H), 7.77 (d, J=7.2 Hz, 1H), 7.61 (s, 1H), 7.20 (d, J=6.8 Hz, 1H), 7.03 (d, J=7.2 Hz, 2H), 6.15 (d, J=7.2 Hz, 1H), 5.16 (d, J=8.8 Hz, 1H), 2.56-2.35 (m, 2H), 2.30-2.15 (m, 1H), 2.00 (d, J=12.8 Hz, 1H), 1.79 (d, J=12.8 Hz, 1H), 1.46 (d, J=12.1 Hz, 1H), 1.39-1.16 (m, 4H), 1.11-0.94 (m, 2H), 0.73 (d, J=4.8 Hz, 2H); and the other enantiomer eluted at the retention time of 2.494 min(C132b), ¹H NMR (400 MHz, CDCl₃) δ 8.05 (s, 1H), 7.76 (d, J=7.6 Hz, 1H), 7.61 (s, 1H), 7.20 (d, J=6.8 Hz, 1H), 7.03 (d, J=7.6 Hz, 2H), 6.16 (d, J=7.2 Hz, 1H), 5.16 (d, J=8.8 Hz, 1H), 2.53-2.37 (m, 2H), 2.25-2.15 (m, 1H), 2.12-2.06 (m, 1H), 2.04-1.95 (m, 1H), 1.82-1.73 (m, 1H), 1.48-1.42 (m, 1H), 1.42-1.15 (m, 4H), 1.08-0.93 (m, 2H), 0.73 (d, J=5.2 Hz, 2H). The absolute configurations of chiral carbons in C132a and C132b are tentatively assigned as (S) and (R) respectively based on assumption that the binding model of the more potent isomer C132a is the same as that of C101a with IDO1 enzyme, and the relative stereochemistry on cyclohexane is assigned as trans configuration on the cyclohexane.

Examples C133 to C135 were synthesized using the similar procedure as example C132.

Example C133: (4-(3-chlorophenyl)cyclohexyl)(7-cyclopropylimidazo[1,5-a]pyridin-8-yl)methanol

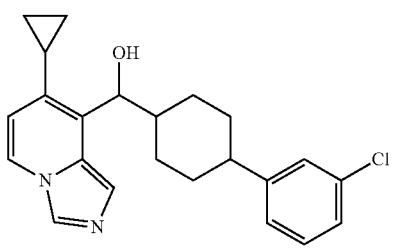

¹H NMR (400 MHz, DMSO-d₆) δ_H 8.27 (s, 1H), 7.13 (d, J=7.2 Hz, 1H), 7.45 (s, 1H), 7.16-7.29 (m, 4H), 6.18 (d, J=7.2 Hz, 1H), 5.36 (s, 1H), 4.96 (s, 1H), 2.29-2.33 (m, 1H), 2.17 (m, 1H), 1.99-2.01 (m, 1H), 1.83-1.86 (m, 1H), 1.64-1.67 (m, 1H), 1.46-1.49 (m, 1H), 1.21-1.28 (m, 4H), 0.83-0.95 (m, 3H), and 0.75-0.79 (m, 2H). [M+H]⁺=381.

Example C133a and C133b: (S)-((1r,4S)-4-(3-chlorophenyl)cyclohexyl)(7-cyclopropylimidazo[1,5-a]pyridin-8-yl)methanol and (R)-((1r,4R)-4-(3-chlorophenyl)cyclohexyl)(7-cyclopropylimidazo[1,5-a]pyridin-8-yl)methanol

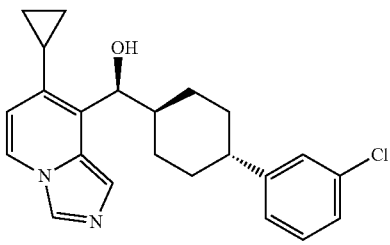

Fast isomer in CHIRALPAK OD HPLC
Eluting reagent: Hex:EtOH = 80:20

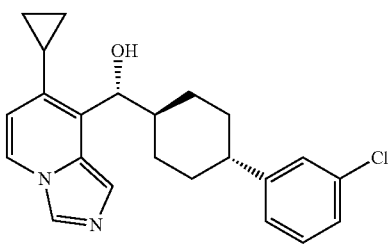

Slow isomer in CHIRALPAL OD HPLC
Eluting reagent: Hex:EtOH = 80:20

Each enantiomer of racemic C133a and C1₃₃b was were determined by using HPLC on a CHIRALPAK OD with Hex:EtOH=80:20 as an eluent at a flow rate of 1.0 mL/min. The first one enantiomer eluted at the retention time of 3.533 min, and the other enantiomer eluted at the retention time of 4.806 min.

Example C134: (7-cyclopropylimidazo[1,5-a]pyridin-8-yl)(4-(thiophen-3-yl)cyclohexyl)methanol

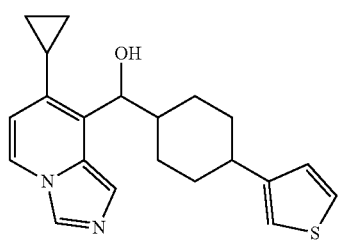 [SMILES: OC(c1c(C2CC2)ccn2cncc12)C1CCC(c2ccsc2)CC1]

Example C135: (7-cyclopropylimidazo[1,5-a]pyridin-8-yl)(4-furan-3-yl)cyclohexyl)methanol

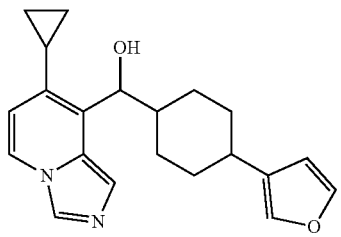 [SMILES: OC(c1c(C2CC2)ccn2cncc12)C1CCC(c2ccoc2)CC1]

Example C136: (7-cyclopropylimidazo[1,5-a]pyridin-8-yl)(1-phenylpiperidin-4-yl)methanol

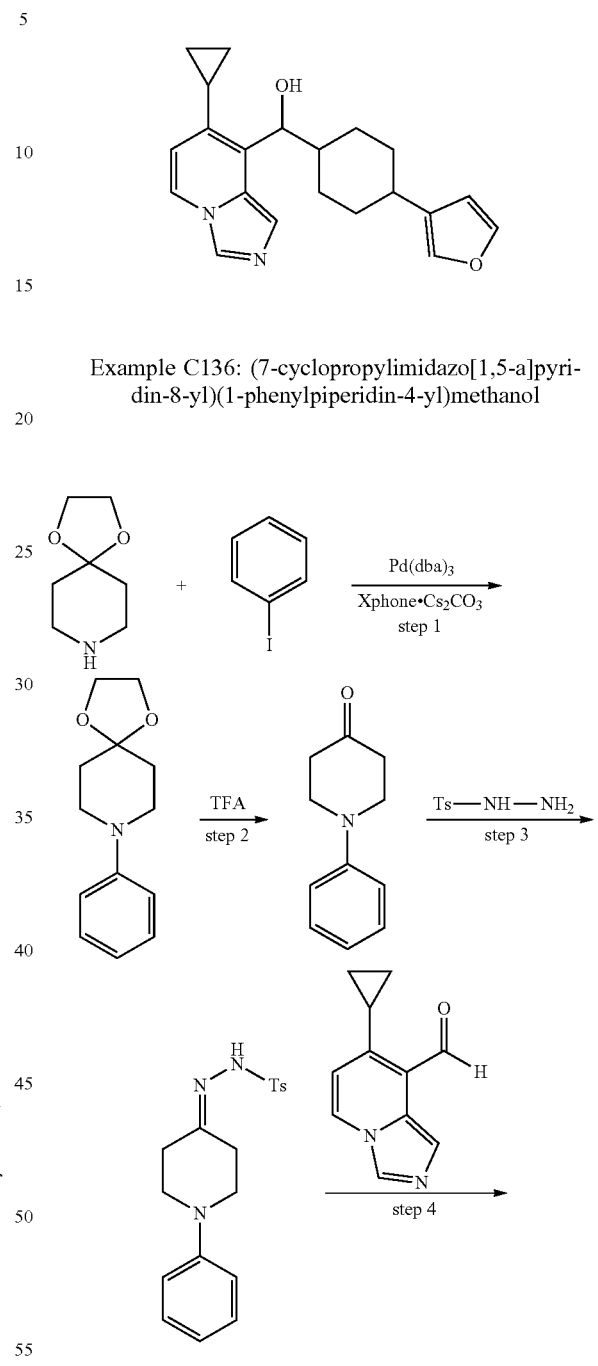

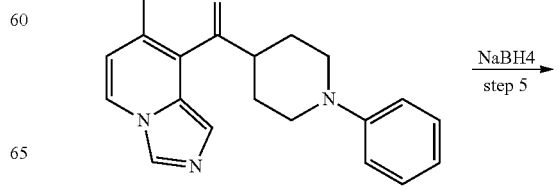

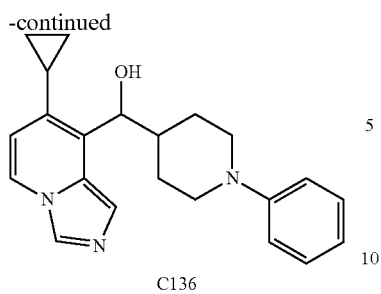

C136

Step 1: 8-phenyl-1,4-dioxa-8-azaspiro[4.5]decane

To a solution of 1,4-dioxa-8-azaspiro[4.5]decane (15 g, 105 mmol), was added 3-iodobenzene-1-ylium (31.2 g, 110 mmol), Pd(dba)$_3$ (9.6 g, 10.5 mmol), Xphone (9.6 g, 21 mmol) and Cs$_2$CO$_3$ (68.2 g, 210 mmol) in toluene (200 mL), the mixture was stirred at 90° C. under N$_2$ overnight. TLC (PE:EA=2:1, Rf=0.5) showed the reaction was completed. Filtered and concentrated, H$_2$O (100 ml) was was added and extracted with EA (50 ml×3). The combined organic layer was dried over Na$_2$SO$_4$, filtered and concentrated to give crude product, which was purified by silica gel chromatography (PE:EA=20:1-3:1) to give 8-phenyl-1,4-dioxa-8-azaspiro[4.5]decane (18 g, 78.2%) as a white solid.

Step 2: 1-phenylpiperidin-4-one

8-Phenyl-1,4-dioxa-8-azaspiro[4.5]decane (18 g, 82.2 mmol) was dissolved in TFA (100 ml), and the mixture was stirred for overnight. The solvent was evaporated under reduced pressure and water (100 mL) was added, extracted with ethyl acetate (100 mix 3), combined the organic layer and washed with saturated aqueous of NaHCO$_3$ then the organic layer was evaporated to give crude product, which was used for next step without further purification.

Step 3: 4-methyl-N'-(1-phenylpiperidin-4-ylidene)benzenesulfonohydrazide

To a solution of 1-phenylpiperidin-4-one (10 g, 56.8 mmol) in EtOH (100 mL) was added 4-methylbenzenesulfonohydrazide (10.56 g, 56.8 mmol) at room temperature, and the mixture was stirred for overnight. The solvent was evaporate under reduced pressure and the residue was purified by column chromatography (PE:EA=4:1) to give compound 7(9.5 g, 50%) g as a white solid. MS (ESI) m/e [M+1]$^+$=344. $^1$H NMR (DMSO-d$_6$) δ 10.26 (s, 1H), 7.74 (d, 2H, J=8.4 Hz), 7.39 (d, 2H, J=8.0 Hz), 7.20 (t, 2H, J=8.0 Hz), 6.91 (d, 2H, J=8.4 Hz), 6.74 (t, 1H, J=7.2 Hz), 3.31 (m, 4H), 2.47 (t, 2H, J=6.0 Hz), 2.31 (t, 2H, J=7.2 Hz).

Step 4: (7-cyclopropylimidazo[1,5-a]pyridin-8-yl)(1-phenylpiperidin-4-yl)methanone To a solution of 4-methyl-N'-(1-phenylpiperidin-4-ylidene)benzenesulfonohydrazide (5.4 g, 29.15 mmol) in 1,4-dioxane (100 ml) was added 7-cyclopropylimidazo[1,5-a]pyridine-8-carbaldehyde (10 g, 29.15 mmol) and Cs$_2$CO$_3$ (18.9 g, 58.3 mmol) at room temperature and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1 to EA) to give crude product as a solid (3.8 g), and which was used for next step without further purification. MS (ESI) m/e [M+1]$^+$=346.

Step 6: (7-cyclopropylimidazo[1,5-a]pyridin-8-yl)(1-phenylpiperidin-4-yl)methanol

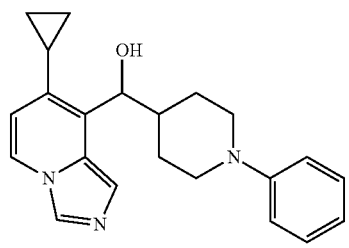

To a solution of crude (7-cyclopropylimidazo[1,5-a]pyridin-8-yl)(1-phenylpiperidin-4-yl)methanone (3.8 g, 11 mmol) in methanol (100 mL) was added NaBH$_4$ (0.84 g, 22 mmol) at room temperature, and the mixture was stirred overnight. Then the solvent was evaporated under reduced pressure and water (50 mL) was added, extracted with ethyl acetate (50 mL×3) and combined the organic layer, evaporated the solvent under reduced pressure and the residue was purified by column chromatography (PE:EA=1:1 to EA) to give crude product, which was stirred in EA to give product as a white solid (1.6 g in 42% yield). $^1$H NMR (DMSO-d6) δ 8.21 (s, 1H), 8.12 (d, J=7.6 Hz, 1H), 7.43 (s, 1H), 7.15 (t, J=7.8 Hz, 2H), 6.89 (d, J=8.8 Hz, 2H), 6.72 (t, J=7.4 Hz, 1H), 6.16 (d, J=7.6 Hz, 1H), 5.39 (d, J=3.6 Hz, 1H), 4.99 (m, 1H), 3.75 (d, J=12.4 Hz, 1H), 3.58 (d, J=12.4 Hz, 1H), 2.60 (t, J=11.4 Hz, 1H), 2.42 (m, 1H), 1.494-1.335 (m, 1H), 1.234-1.181 (m, 1H), 2.20 (m, 2H), 2.07 (m, 2H).

Examples C136a and C136b: ((S)-(7-cyclopropylimidazo[1,5-a]pyridin-8-yl)(1-phenylpiperidin-4-yl)methanol and (R)-(7-cyclopropylimidazo[1,5-a]pyridin-8-yl)(1-phenylpiperidin-4-yl)methanol

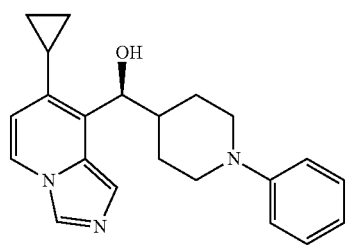

Fast isomer in Chiralpak AD-H
Eluting reagent: CO2:MeOH = 50:50

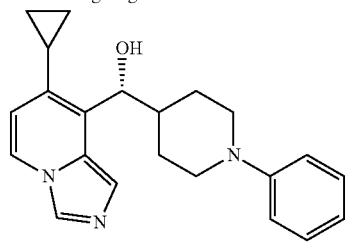

Slow isomer in Chiralpak AD-H
Eluting reagent: CO2:MeOH = 50:50

Each enantiomer of racemic C136a and C136b was separated using preparative HPLC on a Chiralpak AD-H with CO2:MeOH=50:50 as an eluent. The enantiomeric excesses were determined by using HPLC on a Chiralpak AD-H with CO2:MeOH=50:50 as an eluent at a flow rate of 40 mg/min. The first one enantiomer eluted at the retention time of 0.939 min, $^1$H NMR (DMSO-d6) δ 8.22 (s, 1H), 8.13 (d, J=7.2 Hz, 1H), 7.44 (s, 1H), 7.16 (t, J=7.8 Hz, 2H), 6.89 (d, J=8.4 Hz, 2H), 6.72 (t, J=7.2 Hz, 1H), 6.16 (d, J=7.2 Hz, 1H), 5.40 (d, J=3.2 Hz, 1H), 5.00 (dd, J=8.4, J=3.2 Hz, 1H), 3.75 (d, J=12.0 Hz, 1H), 3.58 (d, J=12.4 Hz, 1H), 3.17 (d, J=5.2 Hz, 1H), 2.63-2.57 (m, 1H), 2.45-2.39 (m, 1H), 2.22-2.19 (m, 2H), 2.11-2.03 (m, 1H), 1.53-1.40 (m, 2H), 1.24-1.18 (m, 1H), 0.93-0.91 (m, 2H), 0.71-0.070 (m, 2H). And the other enantiomer eluted at the retention time of 1.877 min. $^1$H NMR (DMSO-d6) δ 8.23 (s, 1H), 8.13 (d, J=7.6 Hz, 1H), 7.44 (s, 1H), 7.17 (dd, J=8.0, J=7.2 Hz, 2H), 6.89 (d, J=8.0 Hz, 2H), 6.72 (t, J=7.2 Hz, 1H), 6.17 (d, J=7.6 Hz, 1H), 5.40 (d, J=3.6 Hz, 1H), 5.00 (dd, J=8.4, J=3.2 Hz, 1H), 3.75 (d, J=12.0 Hz, 1H), 3.59 (d, J=12.0 Hz, 1H), 2.63-2.57 (m, 1H), 2.45-2.40 (m, 1H), 2.22-2.18 (m, 2H), 2.11-2.03 (m, 1H), 1.53-1.33 (m, 2H), 1.25-1.18 (m, 2H), 0.92-3-0.91 (m, 2H), 0.73-0.69 (m, 2H). The absolute configurations of chiral carbons in C136a and C136b are tentatively assigned as (S) and (R) respectively based on assumption that the binding model of the more potent isomer $Cl_{36}$a is the same as that of C101a Examples C137 to C156 were synthesized by using the similar procedure as Example C136.

Example C137: (7-cyclopropylimidazo[1,5-a]pyridin-8-yl)(1-(4-fluorophenyl)piperidin-4-yl)methanol

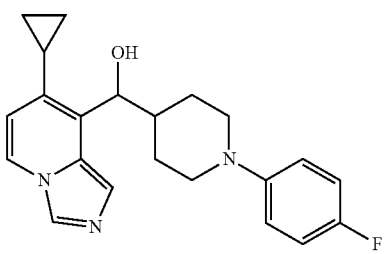 [SMILES: OC(c1c(C2CC2)ccn2cncc12)C1CCN(c2ccc(F)cc2)CC1]

$^1$H NMR (DMSO-d6) δ 8.21 (s, 1H), 8.12 (d, J=7.6 Hz, 1H), 7.43 (s, 1H), 7.02-6.98 (m, 2H), 6.92-6.88 (m, 2H), 6.16 (d, J=7.6 Hz, 1H), 5.39 (d, J=3.6 Hz, 1H), 5.00 (dd, J=8.8, 3.6 Hz, 1H), 3.65 (d, J=12.0 Hz, 1H), 3.48 (d, J=12.0 Hz, 1H), 2.59-2.51 (m, 1H), 2.41-2.33 (m, 1H), 2.21-2.18 (m, 2H), 2.05-2.03 (m, 1H), 1.53-1.44 (m, 1H), 1.40-1.35 (m, 2H), 1.24-1.18 (m, 2H), 0.93-0.91 (m, 2H), 0.71-0.69 (m, 2H).

Example C137a and C137b: (S)-(7-cyclopropylimidazo[1,5-a]pyridin-8-yl)(1-(4-fluorophenyl)piperidin-4-yl)methanol and (R)-(7-cyclopropylimidazo[1,5-a]pyridin-8-yl)(1-(4-fluorophenyl)piperidin-4-1 ylmethanol

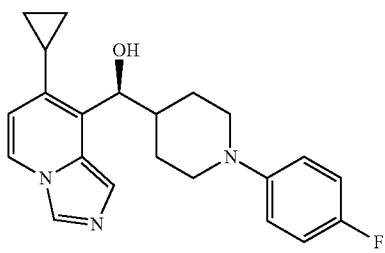

Fast isomer in CHIRALPAK IC
Eluting reagent: Hex:EtOH = 70:30

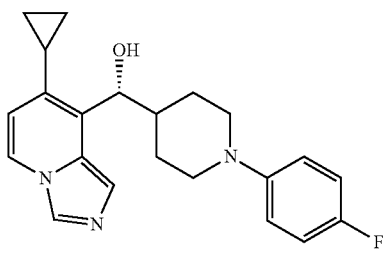

Slow isomer in CHIRALPAK IC
Eluting reagent: Hex:EtOH = 70:30

Each enantiomer of racemic C137a and C137b was separated using preparative HPLC on a Cellulose-SB with Hex:EtOH=70:30 as an eluent. The enantiomeric excesses were determined by using HPLC on a Cellulose-SB with Hex:EtOH=70:30 as an eluent at a flow rate of 20 mg/min. The first one enantiomer eluted at the retention time of 2.726 min, $^1$H NMR (DMSO-d6) δ8.40 (s, 1H), 8.16 (d, J=7.2 Hz, 1H), 7.52 (s, 1H), 7.00 (t, J=8.8 Hz, 2H), 6.93-6.89 (m, 2H), 6.23 (d, J=7.2 Hz, 1H), 5.45 (s, 1H), 5.01 (d, J=6.8 Hz, 1H), 3.65 (d, J=11.6 Hz, 1H), 3.49 (d, J=12.0 Hz, 1H), 2.67-2.57 (m, 1H), 2.42-2.33 (m, 2H), 2.20-2.17 (m, 2H), 2.04-2.02 (m, 1H), 1.54-1.36 (m, 2H), 1.23-1.19 (m, 2H), 0.95-0.93 (m, 2H), 0.75-0.65 (s, 2H). And the other enantiomer eluted at the retention time of 3.378 min. $^1$H NMR (DMSO-d6) δ 8.44 (s, 1H), 8.17 (d, J=7.2 Hz, 1H), 7.55 (s, 1H), 7.00 (t, J=8.8 Hz, 2H), 6.93-6.89 (m, 2H), 6.25 (d, J=7.6 Hz, 1H), 5.47 (s, 1H), 5.01 (d, J=7.2 Hz, 1H), 3.65 (d, J=12.0 Hz, 1H), 3.49 (d, J=12.0 Hz, 1H), 2.67-2.57 (m, 1H), 2.40-2.33 (m, 2H), 2.26-2.24 (m, 2H), 2.04-2.02 (m, 1H), 1.54-1.37 (m, 2H), 1.23-1.19 (m, 2H), 0.96-0.94 (m, 2H), 0.75-0.65 (m, 2H). The absolute configurations of chiral carbons in C137a and C137b are tentatively assigned as (S) and (R) respectively based on assumption that the binding model of the more potent isomer C137a is the same as that of C101a.

Example C138: (7-cyclopropylimidazo[1,5-a]pyridin-8-yl)(1-(3-fluorophenyl)piperidin-4-yl)methanol

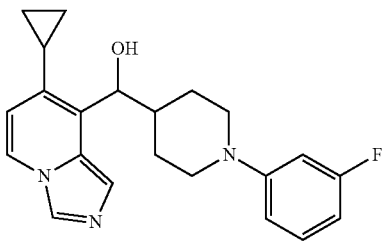 [SMILES: OC(c1c(C2CC2)ccn2cncc12)C1CCN(c2cccc(F)c2)CC1]

¹H NMR (DMSO-d6) δ8.21 (s, 1H), 8.13 (d, J=7.2 Hz, 1H), 7.43 (s, 1H), 7.16 (q, J=8 Hz 1H), 6.72-6.65 (m, 2H), 6.49-6.45 (m, 1H), 5.40 (d, J=3.2 Hz, 1H), 4.99-4.97 (m, 1H), 3.81 (d, J=12.4 Hz, 1H), 3.64 (d, J=12.4 Hz, 1H), 2.68-2.62 (m, 1H), 2.48-2.46 (m, 1H), 2.20-2.16 (m, 2H), 2.11-2.09 (m, 1H), 149-1.40 (m, 2H), 1.36-1.29 (m, 2H), 0.92-0.91 (m, 2H), 0.74-0.68 (m, 2H).

Example C138a and C138b: (S)-(7-cyclopropylimidazo[1,5-a]pyridin-8-yl)(1-(3-fluorophenyl)piperidin-4-yl)methanol and (R)-(7-cyclopropylimidazo[1,5-a]pyridin-8-yl)(1-(3-fluorophenyl)piperidin-4-yl)methanol

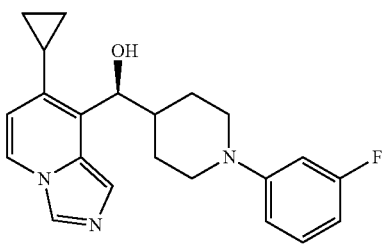

Fast isomer in CHIRALPAK IC
Eluting reagent: Hex:EtOH = 70:30

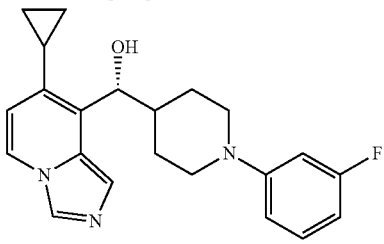

Slow isomer in CHIRALPAK IC
Eluting reagent: Hex:EtOH = 70:30

Each enantiomer of racemic C138a and C138b was separated using preparative HPLC on a CHIRALPAK IC with Hex:EtOH=70:30 as an eluent. The enantiomeric excesses were determined by using HPLC on CHIRALPAK IC with Hex:EtOH=70:30 as an eluent at a flow rate of 20 mL/min. The first one enantiomer eluted at the retention time of 1.251 min, ¹H NMR (DMSO-d6) δ 8.64 (s, 1H), 7.42 (d, J=9.2 Hz, 1H), 7.32 (s, 1H), 7.17 (q, J=7.8 Hz, 1H), 6.72-6.66 (m, 2H), 6.50-6.46 (m, 2H), 5.88 (d, J=3.6 Hz, 1H), 5.27 (dd, J=9.2, J=3.6 Hz, 1H), 3.84 (d, J=12.0 Hz, 1H), 3.63 (d, J=12.4 Hz, 1H), 2.71 (t, J=11.4 Hz, 1H), 2.48-2.45 (m, 1H), 2.32-2.26 (m, 2H), 2.21-1.95 (m, 1H), 1.50-1.31 (m, 2H), 1.09-1.06 (m, 1H), 0.93-0.89 (m, 2H), 0.78-0.74 (m, 1H), 0.66-0.62 (m, 1H). And the other enantiomer eluted at the retention time of 2.373 min, ¹H NMR (DMSO-d6) δ 8.64 (s, 1H), 7.42 (d, J=9.6 Hz, 1H), 7.32 (s, 1H), 7.16 (q, J=7.8 Hz, 1H), 6.72-6.66 (m, 2H), 6.50-6.46 (m, 2H), 5.88 (d, J=3.6 Hz, 1H), 5.27 (dd, J=9.6, J=4.0 Hz, 1H), 3.84 (d, J=12.8 Hz, 1H), 3.63 (d, J=12.4 Hz, 1H), 2.71 (t, J=11.6 Hz, 1H), 2.47-2.44 (m, 1H), 2.32-2.26 (m, 2H), 2.06-1.96 (m, 1H), 1.50-1.31 (m, 2H), 1.08-1.06 (m, 1H), 0.94-0.90 (m, 2H), 0.78-0.74 (m, 1H), 0.63-0.63 (m, 1H). Then the solvent was evaporated under reduced pressure and the residue was washed by PE to give desired product (141.2 mg) as white solid, The absolute configurations of chiral carbons in C138a and C138b are tentatively assigned as (S) and (R) respectively based on assumption that the binding model of the more potent isomer C138a is the same as that of C101a.

Example C139: (7-cyclopropylimidazo[1,5-a]pyridin-8-yl)(1-cyclopropylpiperidin-4-yl)methanol

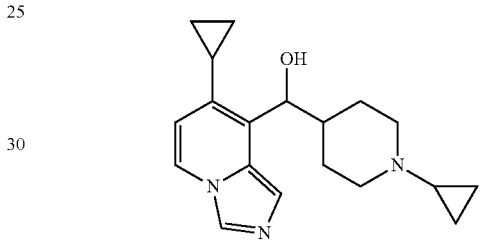

¹H NMR (DMSO-d6) δ_H 8.19 (s, 1H), 8.10 (d, J=7.2 Hz, 1H), 7.39 (s, 1H), 6.14 (d, J=7.2 Hz, 1H), 5.30 (d, J=3.2 Hz, 1H), 4.92 (dd, J=8.8, 3.2 Hz, 1H), 2.98 (d, J=10.8 Hz, 1H), 2.81 (d, J=10.8 Hz, 1H), 2.23-2.02 (m, 3H), 1.93-1.88 (m, 2H), 1.51 (s, 1H), 1.23-1.12 (m, 2H), 1.04 (d, J=12.8 Hz, 1H), 0.91-0.85 (m, 2H), 0.72-0.66 (m, 2H), 0.36-0.33 (m, 2H), 0.27-0.23 (m, 2H). [M+H]⁺=312.1.

Example C140: (1-(3-chlorophenyl)piperidin-4-yl)(7-cyclopropylimidazo[1,5-a]pyridin-8-yl)methanol

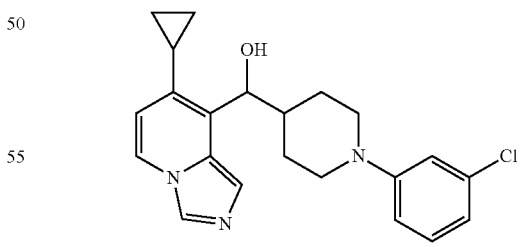

¹H NMR (DMSO-d6) δ 8.21 (s, 1H), 8.12 (d, J=7.6 Hz, 1H), 7.43 (s, 1H), 7.18-7.14 (m, 1H), 6.88-6.84 (m, 2H), 6.71 (d, J=8.8 Hz, 1H), 6.16 (d, J=7.2 Hz, 1H), 5.40 (d, J=3.2 Hz, 1H), 4.98 (dd, J=8.4 Hz, J=3.6 Hz 1H), 3.80 (d, J=12.8 Hz, 1H), 3.64 (d, J=12.4 Hz, 1H), 2.68-2.63 (m, 2H), 2.19-2.16 (m, 2H), 2.11-2.096 (m, 1H), 1.49-1.40 (m, 2H), 1.36-1.29 (m, 3H), 0.93-0.91 (m, 3H), 0.72-0.69 (m, 2H).

Example C141: (7-cyclopropylimidazo[1,5-a]pyridin-8-yl)(1-(3,4-difluorophenyl)piperidin-4-yl)methanol

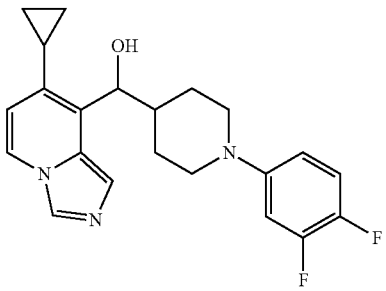 [SMILES: OC(c1c(C2CC2)ccn2cncc12)C1CCN(c2ccc(F)c(F)c2)CC1]

$^1$H NMR (DMSO-d6) δ 8.20 (s, 1H), 8.11 (d, J=7.2 Hz, 1H), 7.42 (s, 1H), 7.18-7.14 (m, 1H), 6.90 (dd, J=14.4 Hz, J=7.2 Hz, 1H), 6.66 (d, J=9.2 Hz, 1H), 6.15 (d, J=7.2 Hz, 1H), 5.41 (m, 1H), 4.97 (d, J=7.6 Hz, 1H), 3.70 (d, J=12 Hz, 1H), 3.54 (d, J=12 Hz, 1H), 2.58 (t, J=12 Hz, 1H), 2.40 (t, J=12 Hz, 1H), 2.18-2.15 (m, 2H), 2.06-2.04 (m, 1H), 1.48-1.30 (m, 3H), 1.18-1.15 (m, 1H), 0.91-0.89 (m, 2H), and 0.72-0.62 (m, 2H).

Example C142: (7-cyclopropylimidazo[1,5-a]pyridin-8-yl)(1-(4-methoxyphenyl)piperidin-4-yl)methanol

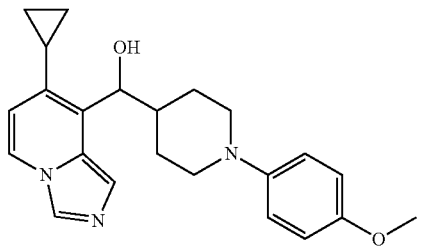 [SMILES: COc1ccc(N2CCC(C(O)c3c(C4CC4)ccn4cncc34)CC2)cc1]

$^1$H NMR (DMSO-d6) δ$_H$ 9.00 (s, 1H), 8.31 (d, J=7.6 Hz, 1H), 7.80 (s, 1H), 7.41 (s, 2H), 6.96 (d, J=8.0 Hz, 2H), 6.47 (d, J=7.2 Hz, 1H), 5.80 (s, 1H), 5.10 (d, J=7.2 Hz, 1H), 3.73 (s, 3H), 3.57-3.54 (m, 2H), 3.42-3.39 (m, 2H), 2.24-2.21 (m, 3H), 1.85-1.81 (m, 2H), 1.39-1.35 (m, 1H), 1.03-1.01 (m, 2H), 0.83-0.77 (m, 2H). [M+H]$^+$=378.

Example C143: 4-(4-((7-cyclopropylimidazo[1,5-a]pyridin-8-yl) hydroxy)methyl)piperidin-1-yl)phenol

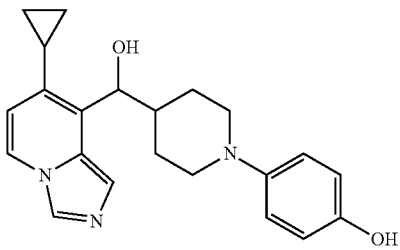

$^1$H NMR (DMSO-d6) δ$_H$ 8.81 (s, 1H), 8.21 (s, 1H), 8.13 (d, J=7.2 Hz, 1H), 7.42 (s, 1H), 6.67 (dd, J=5.2, 8.4 Hz, 4H), 6.16 (d, J=7.2 Hz, 1H), 5.38 (s, 1H), 5.00 (s, 1H), 3.478-3.45 (m, 1H), 2.33-2.18 (m, 4H), 2.0-1.98 (m, 1H), 1.50-1.35 (m, 2H). 1.23-1.15 (m, 2H), 0.94-0.92 (m, 2H), 0.71-0.69 (m, 2H). [M+H]$^+$=364.

Example C144: 4-(4-((7-cyclopropylimidazo[1,5-a]pyridin-8-yl)(hydroxy)methyl)piperidin-1-yl)benzonitrile

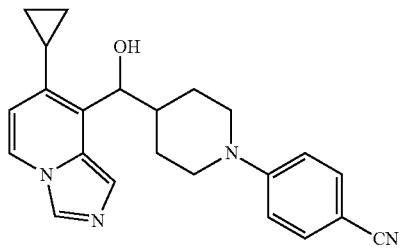

$^1$H NMR (DMSO-d$_6$) δ$_H$ 8.22 (s, 1H), 8.13 (d, J=7.6 Hz, 1H), 7.52 (d, J=8.8 Hz, 2H), 7.43 (s, 1H), 6.97 (d, J=8.8 Hz, 2H), 6.16 (d, J=7.2 Hz, 1H), 5.42 (d, J=3.2 Hz, 1H), 4.97 (d, J=3.2 Hz, 1H), 4.01 (d, J=12.8 Hz, 1H), 3.85 (d, J=12.8 Hz, 1H), 2.82 (t, J=12.2 Hz, 1H), 2.65 (t, J=11.4 Hz, 1H), 2.18-2.15 (m, 3H), 1.45-1.18 (m, 3H), 0.91-0.89 (m, 2H), 0.70-0.69 (m, 2H). [M+H]$^+$=373.

Example C144a and C144b: (S)-4-(4-((7-cyclopropylimidazo[1,5-a]pyridin-8-yl)(hydroxy)methyl)piperidin-1-yl)benzonitrile and (R)-4-(4-((7-cyclopropylimidazo[1,5-a]pyridin-8-yl)(hydroxy)methyl)piperidin-1-yl)benzonitrile

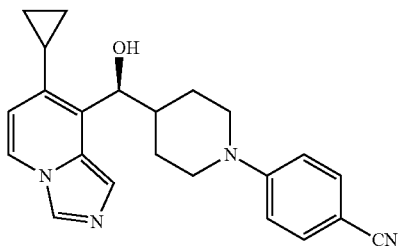

Fast isomer in CHIRAL ART Cellulose-SB
Eluting reagent: Hex:EtOH = 80:20

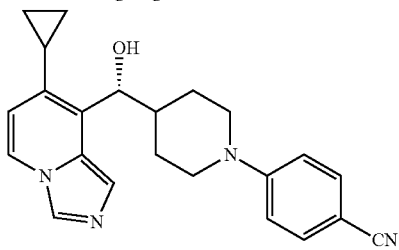

Slow isomer in CHIRAL ART Cellulose-SB
Eluting reagent: Hex:EtOH = 80:20

Each enantiomer of racemic C144a and C144b was separated using preparative HPLC on a CHIRAL ART Cellulose-SB with Hex:EtOH=80:20 as an eluent. The enantiomeric excesses were determined by using HPLC on a CHIRAL ART Cellulose-SB with Hex:EtOH=80:20 as an eluent at a flow rate of 20 mL/min. The first one enantiomer eluted at the retention time of 6.703 min, $^1$H NMR (DMSO-d$_6$) H 8.22 (s, 1H), 8.13 (d, J=7.2 Hz, 1H), 7.52 (d, J=8.8 Hz, 2H), 7.43 (s, 1H), 6.97 (d, J=8.8 Hz, 2H), 6.16 (d, J=7.6 Hz, 1H), 5.42 (d, J=3.2 Hz, 1H), 4.97 (d, J=4.4 Hz, 1H), 4.01 (d, J=12 Hz, 1H), 3.85 (d, J=13.2 Hz, 1H), 2.82 (t, J=12.2 Hz 1H), 2.65 (t, J=11.6 Hz, 1H), 2.18-2.15 (m, 3H), 1.42-1.18 (m, 3H), 0.91-0.90 (m, 2H), 0.70-0.69 (m, 2H). [M+H]$^+$=373. and the other enantiomer eluted at the retention time of 8.312 min, 8.26 (s, 1H), 8.14 (d, J=7.2 Hz, 1H), 7.52 (d, J=8.4 Hz, 2H), 7.46 (s, 1H), 6.97 (d, J=8.4 Hz, 2H), 6.18 (d, J=7.2 Hz, 1H), 5.43 (s, 1H), 4.97 (d, J=5.2 Hz, 1H), 4.01 (d, J=12.8 Hz, 1H), 3.86 (d, J=12.8 Hz, 1H), 2.82 (t, J=12.2 Hz, 1H), 2.66 (t, J=11.6 Hz, 1H), 2.17-2.16 (m, 3H), 1.42-1.18 (m, 3H), 0.92-0.84 (m, 2H), 0.70-0.69 (m, 2H). [M+H]$^+$=373. The absolute configurations of chiral carbons in C144a and C144b are tentatively assigned as (S) and (R) respectively based on assumption that the binding model of the more potent isomer C144a is the same as that of C101a with IDO1.

Example C145: 4-(4-((7-cyclopropylimidazo[1,5-a]pyridin-8-yl)(hydroxy)methyl)piperidin-1-yl)benzoic acid

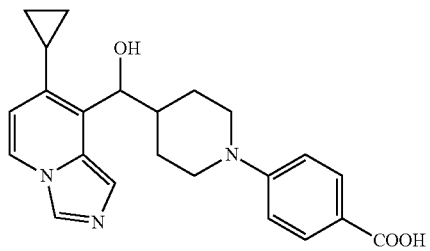 [SMILES: O=C(O)c1ccc(N2CCC(C(O)c3c(C4CC4)ccn4cncc34)CC2)cc1]

$^1$H NMR (DMSO-d$_6$) δ$_H$ 12.17 (s, 1H) 8.22 (s, 1H), 8.13 (d, J=7.2 Hz, 1H), 7.72 (d, J=8.8 Hz, 2H), 7.43 (s, 1H), 6.91 (d, J=8.4 Hz, 2H), 6.16 (d, J=7.2 Hz, 1H), 5.42 (d, J=2.4 Hz, 1H), 4.97 (d, J=5.2 Hz, 1H), 3.98 (d, J=12.4 Hz, 1H), 3.82 (d, J=12.8 Hz, 1H), 2.78 (t, J=12.2 Hz, 1H), 2.61 (t, J=11.6 Hz, 1H), 2.19-2.16 (m, 3H), 1.47-1.18 (m, 3H), 0.92-0.90 (m, 2H), 0.70-0.69 (m, 2H). [M+H]$^+$=392.

Example C146: (7-cyclopropylimidazo[1,5-a]pyridin-8-yl)(1-(pyridin-2-yl)piperidin-4-yl)methanol

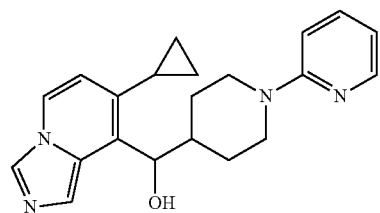 [SMILES: OC(c1c(C2CC2)ccn2cncc12)C1CCN(c2ccccn2)CC1]

$^1$H NMR (DMSO-d$_6$) δ$_H$ 8.29 (s, 2H), 8.11-8.14 (d, J=7.2 Hz, 1H), 8.05 (d, J=4.0 Hz, 1H), 7.41-7.50 (m, 2H), 6.77 (d, J=8.4 Hz, 1H), 6.52-6.58 (m, 1H), 6.15 (d, J=7.6 Hz, 1H), 5.36 (d, J=3.2 Hz, 1H), 4.93-5.00 (m, 1H), 4.36 (d, J=12.8 Hz, 1H), 4.24 (d, J=12.8 Hz, 1H), 2.50-2.80 (m, 2H), 2.10-2.23 (m, 3H), 1.19-1.39 (m, 2H), 0.96-0.97 (m, 2H), 0.63-0.75 (m, 2H), MS (ESI) m/e [M+1]$^+$349.

Example C147: (7-cyclopropylimidazo[1,5-a]pyridin-8-yl)(1-(pyridin-4-yl)piperidin-4-yl)methanol

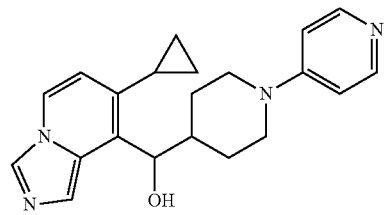 [SMILES: OC(c1c(C2CC2)ccn2cncc12)C1CCN(c2ccncc2)CC1]

$^1$H NMR (DMSO-d$_6$) δ$_H$ 8.21 (s, 2H), 8.08-8.13 (m, 3H), 7.43 (s, 1H), 6.75-6.76 (d, J=6.0 Hz, 1H), 6.14-6.16 (d, J=7.2 Hz, 1H), 5.41 (d, J=3.6 Hz, 1H), 4.93-5.00 (m, 1H), 3.95-4.02 (d, J=12.8 Hz, 1H), 3.80-3.88 (d, J=12.8 Hz, 1H), 2.72-2.84 (m, 1H), 2.56-2.65 (m, 1H), 2.10-2.23 (m, 3H), 1.18-1.42 (m, 4H), 0.86-0.96 (m, 2H), 0.66-0.74 (m, 2H), MS (ESI) m/e [M+1]$^+$349.

Example C148: (7-cyclopropylimidazo[1,5-a]pyridin-8-yl)(1-(pyridin-3-yl)piperidin-4-yl)methanol

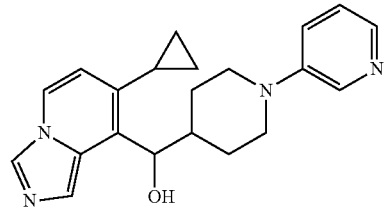 [SMILES: OC(c1c(C2CC2)ccn2cncc12)C1CCN(c2cccnc2)CC1]

$^1$H NMR (DMSO-d$_6$) δ$_H$ 8.26 (s, 2H), 8.12-8.15 (d, J=7.2 Hz, 1H), 7.93-7.95 (d, J=4.4 Hz, 1H), 7.46 (s, 1H), 7.28-7.33 (m, 1H), 7.17-7.22 (m, 1H), 6.17-6.19 (d, J=7.6 Hz, 1H), 5.43 (d, J=3.2 Hz, 1H), 4.97-5.02 (m, 1H), 3.80-3.86 (d, J=12 Hz, 1H), 3.64-3.71 (d, J=12 Hz, 1H), 2.63-2.71 (m, 1H), 2.06-2.24 (m, 3H), 1.32-1.53 (m, 2H), 1.17-1.25 (m, 1H), 0.89-0.96 (m, 2H), 0.66-0.74 (m, 2H), MS (ESI) m/e [M+1]$^+$349.

Example C149: (7-cyclopropylimidazo[1,5-a]pyridin-8-yl)(1-(8-fluoroquinolin-5-yl)piperidin-4-yl)methanol

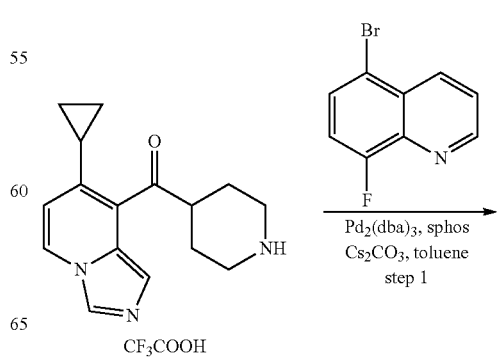

-continued

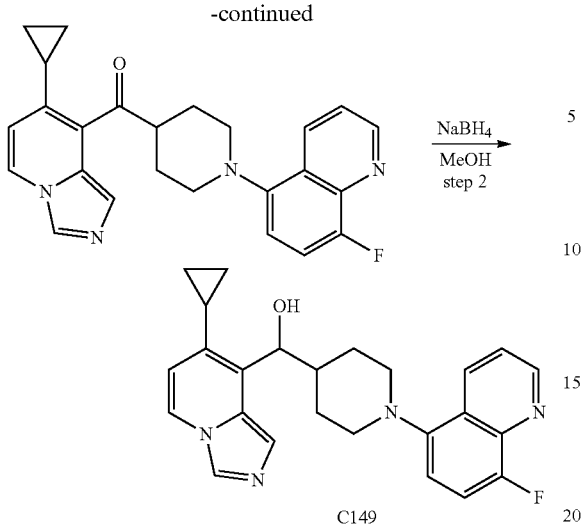

C149

Step 1: (7-cyclopropylimidazo[1,5-a]pyridin-8-yl)(1-(8-fluoroquinolin-5-yl)piperidin-4-yl)methanone To a solution of (7-cyclopropylimidazo[1,5-a]pyridin-8-yl)(piperidin-4-yl)methanone 2,2,2-trifluoroacetate (3.83 g, 10 mmol, 1.00 eq) dissolved in toluene (150 mL) was added 5-bromo-8-fluoroquinoline (2.25 g, 10 mmol, 1.00 eq), $Pd_2(dba)_3$ (0.915 g, 1 mmol, 0.10 eq), s-phos (0.952 g, 1 mmol, 0.20 eq) and $Cs_2CO_3$ (8.13 g, 25 mmol, 2.50 eq). Then the mixture was stirred at 95° C. for overnight. The solvent was evaporated under reduced pressure. The crude was purified by column chromatography on silica gel 50 g (PE/EA=1/2) to give compound 8 (907 mg, 22% yield) as a yellow solid. $^1$H NMR ($CDCL_3$) $\delta_H$ 8.96 (dd, J=1.6 Hz, J=4.4 Hz, 1H), 8.52 (d, J=8.8 Hz, 1H), 8.17 (s, 1H), 7.91 (d, J=7.6 Hz, 1H), 7.46-7.51 (m, 1H), 7.27-7.36 (m, 2H), 7.00-7.09 (m, 1H), 6.16 (d, J=7.6 Hz, 1H), 3.20-3.43 (m, 3H), 2.75-2.90 (m, 2H), 2.10-2.15 (m, 2H), 1.93-1.99 (m, 1H), 1.69-1.75 (m, 1H), 1.05-1.11 (m, 2H) and 0.77-0.85 (m, 2H).

Step 2: (7-cyclopropylimidazo[1,5-a]pyridin-8-yl)(1-(8-fluoroquinolin-5-yl)piperidin-4-yl)methanol

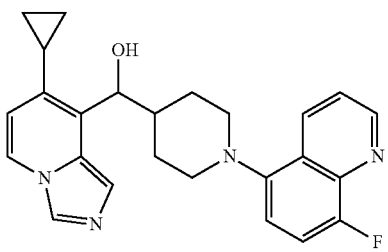 [SMILES: OC(c1c(C2CC2)ccn2cncc12)C1CCN(c2ccc(F)c3ncccc23)CC1]

To a solution of (7-cyclopropylimidazo[1,5-a]pyridin-8-yl)(1-(8-fluoroquinolin-5-yl)piperidin-4-yl)methanone (0.904 g, 2.1 mmol, 1.00 eq) dissolved in MeOH (20 mL) was added $NaBH_4$ (0.126 g, 3.15 mmol, 1.50 eq). Then the mixture was stirred at room temperature for 2 hours. The solvent was quenched with water 0.5 ml and concentrated to dryness. The crude was purified by column chromatography on silica gel 50 g (PE/EA=1/2) to give product (385 mg, 55% yield) as a yellow solid. $^1$H NMR (DMSO-d6) $\delta_H$ 8.93 (d, J=3.2 Hz, 1H), 8.49 (d, J=8.8 Hz, 1H), 8.24 (s, 1H), 8.14 (d, J=7.2 Hz, 1H), 7.62-7.72 (m, 1H), 7.41-7.51 (m, 2H), 7.05-7.14 (m, 1H), 6.19 (d, J=7.2 Hz, 1H), 5.40-5.52 (m, 1H), 5.04-5.17 (m, 1H), 3.26-3.31 (m, 1H), 3.11-3.19 (m, 1H), 2.68-2.78 (m, 1H), 2.53-2.60 (m, 1H), 2.20-2.33 (m, 2H), 2.08-2.17 (m, 1H), 1.59-1.78 (m, 2H), 1.24-1.32 (m, 1H), 0.94-1.01 (m, 2H) and 0.69-0.77 (m, 2H).

Example C149a and C149b: (S)-(6-cyclopropylimidazo[1,5-a]pyridin-5-yl)(1-(8-fluoroquinolin-5-yl)piperidin-4-yl)methanol and (R)-(6-cyclopropylimidazo[1,5-a]pyridin-5-yl 1-(8-fluoroquinolin-5-yl)piperidin-4-yl)methanol

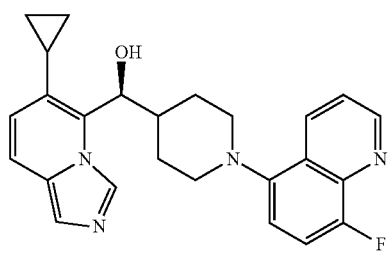

Fast isomer in CHIRALART Amylose-SB HPLC
Eluting reagent: Hex (0.2% IPAmine):EtOH = 70:30

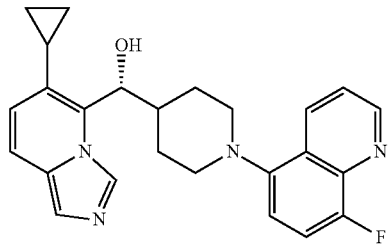

Slow isomer in CHIRALART Amylose-SB HPLC
Eluting reagent: Hex (0.2% IPAmine):EtOH = 70:30

Each enantiomer of racemic C149a and C149b was separated using preparative HPLC on a CHIRALART Amylose-SB with Hex:EtOH=70:30 as an eluent. The enantiomeric excesses were determined by using HPLC on a CHIRAL-ART Amylose-SB with Hex (0.2% IPAmine):EtOH=70:30 as an eluent at a flow rate of 1.0 ml/min. The first one enantiomer eluted at the retention time of 2.840 min, $^1$H NMR (DMSO-d6) $\delta_H$ 8.92 (d, J=3.6 Hz, 1H), 8.49 (d, J=8.4 Hz, 1H), 8.23 (s, 1H), 8.13 (d, J=7.6 Hz, 1H), 7.62 (q, J=4.0 Hz, 1H), 7.40-7.51 (m, 2H), 7.10 (q, J=4.0 Hz, 1H), 6.19 (d, J=7.2 Hz, 1H), 5.45 (d, J=2.8 Hz, 1H), 5.05-5.18 (m, 1H), 3.13 (d, J=11.2 Hz, 1H), 2.73 (t, J=11.2 Hz, 1H), 2.55 (t, J=11.2 Hz, 1H), 2.06-2.34 (m, 3H), 1.57-1.80 (m, 2H), 1.21-1.32 (m, 2H), 0.93-1.02 (m, 2H) and 0.69-0.79 (m, 2H); and the other enantiomer eluted at the retention time of 3.843 min, $^1$H NMR (DMSO-d6) $\delta_H$ 8.93 (d, J=2.8 Hz, 1H), 8.49 (d, J=8.4 Hz, 1H), 8.23 (s, 1H), 8.13 (d, J=7.2 Hz, 1H), 7.62 (q, J=4.0 Hz, 1H), 7.40-7.51 (m, 2H), 7.10 (q, J=4.0 Hz, 1H), 6.19 (d, J=7.6 Hz, 1H), 5.46 (d, J=2.8 Hz, 1H), 5.05-5.18 (m, 1H), 3.14 (d, J=11.2 Hz, 1H), 2.73 (t, J=11.2 Hz, 1H), 2.55 (t, J=11.2 Hz, 1H), 2.08-2.36 (m, 3H), 1.57-1.82 (m, 2H), 1.21-1.32 (m, 2H), 0.93-1.04 (m, 2H) and 0.69-0.90 (m, 2H). The absolute configurations of chiral carbons in C149a and C149b are tentatively assigned as (S) and (R) respectively based on assumption that the binding model of the more potent isomer C149a is the same as that of C101a with IDO1.

Example C150: (7-cyclopropylimidazo[1,5-a]pyridin-8-yl)(1-(quinolin-4-yl)piperidin-4-yl)methanol

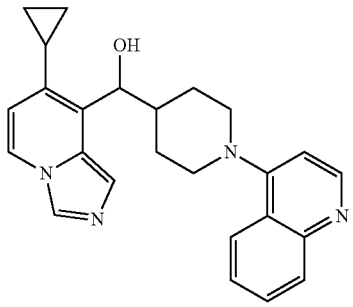 [SMILES: OC(c1c(C2CC2)ccn2cncc12)C1CCN(c2ccnc3ccccc23)CC1]

¹H NMR (CDCl₃) δ_H 8.65 (s, 1H), 8.06 (s, 1H), 7.98 (d, J=8.0 Hz, 1H), 7.79 (d, J=7.2 Hz, 1H), 7.60-7.72 (m, 2H), 7.48-7.54 (m, 1H), 6.83 (d, J=5.6 Hz, 1H), 6.17 (d, J=7.6 Hz, 1H), 5.31 (d, J=8.8 Hz, 1H), 3.40-3.90 (m, 5H), 2.75-3.06 (m, 2H), 2.35-2.53 (m, 2H), 1.83-1.95 (m, 1H), 1.60-1.75 (m, 2H), 1.01-1.12 (m, 2H), 0.69-0.81 (m, 2H).

Example C151: (7-cyclopropylimidazo[1,5-a]pyridin-8-yl)(1-(6-fluoroquinolin-4-yl)piperidin-4-yl)methanol

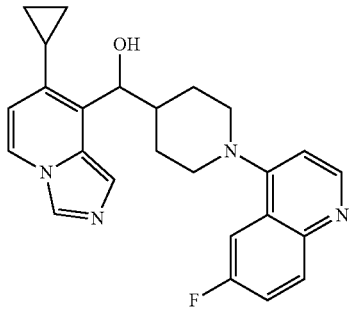 [SMILES: OC(c1c(C2CC2)ccn2cncc12)C1CCN(c2ccnc3ccc(F)cc23)CC1]

¹H NMR (DMSO-d₆) δ_H 8.65 (d, J=5.6 Hz, 1H), 8.34 (s, 1H), 8.16 (d, J=7.2 Hz, 1H), 8.01 (m, 1H), 7.62-7.72 (m, 2H), 7.54 (s, 1H), 7.03 (d, J=5.6 Hz, 1H), 6.23 (d, J=7.2 Hz, 1H), 5.52 (s, 1H), 5.11 (d, J=5.6 Hz, 1H), 3.72 (d, J=12.4 Hz, 1H), 3.54 (d, J=12.4 Hz, 1H), 2.94 (t, J=11.6 Hz, 1H), 2.76 (t, J=11.6 Hz, 1H), 2.17-2.36 (m, 3H), 1.58-1.80 (m, 2H), 1.26-1.36 (m, 1H), 0.92-1.03 (m, 2H), 0.69-0.79 (m, 2H).

Example C152: (7-cyclopropylimidazo[1,5-a]pyridin-8-yl)(1-(4-(1-methyl-1H-pyrazol-4-yl)phenyl)piperidin-4-yl)methanol

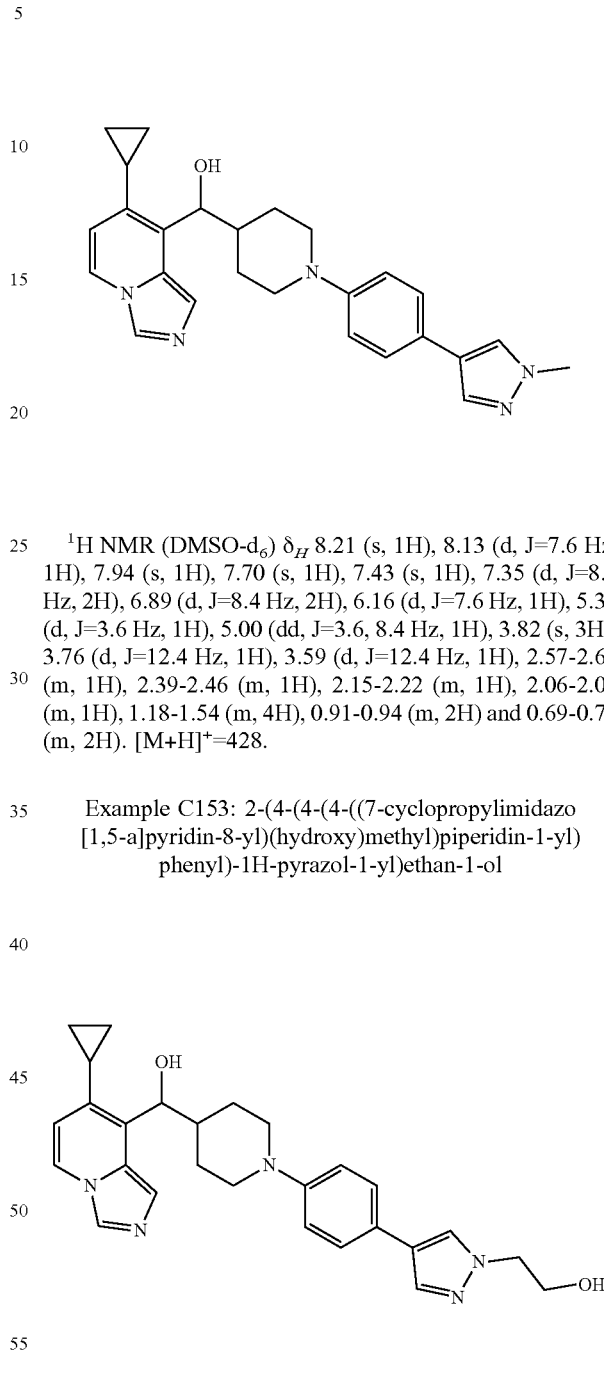

¹H NMR (DMSO-d₆) δ_H 8.21 (s, 1H), 8.13 (d, J=7.6 Hz, 1H), 7.94 (s, 1H), 7.70 (s, 1H), 7.43 (s, 1H), 7.35 (d, J=8.4 Hz, 2H), 6.89 (d, J=8.4 Hz, 2H), 6.16 (d, J=7.6 Hz, 1H), 5.39 (d, J=3.6 Hz, 1H), 5.00 (dd, J=3.6, 8.4 Hz, 1H), 3.82 (s, 3H), 3.76 (d, J=12.4 Hz, 1H), 3.59 (d, J=12.4 Hz, 1H), 2.57-2.67 (m, 1H), 2.39-2.46 (m, 1H), 2.15-2.22 (m, 1H), 2.06-2.09 (m, 1H), 1.18-1.54 (m, 4H), 0.91-0.94 (m, 2H) and 0.69-0.71 (m, 2H). [M+H]⁺=428.

Example C153: 2-(4-(4-(4-((7-cyclopropylimidazo[1,5-a]pyridin-8-yl)(hydroxy)methyl)piperidin-1-yl)phenyl)-1H-pyrazol-1-yl)ethan-1-ol ¹H NMR (DMSO-d₆) δ_H 8.21 (s, 1H), 8.13 (d, J=7.6 Hz, 1H), 7.96 (s, 1H), 7.72 (s, 1H), 7.43 (s, 1H), 7.35 (d, J=8.4 Hz, 2H), 6.88 (d, J=8.4 Hz, 2H), 6.16 (d, J=7.6 Hz, 1H), 5.39 (d, J=3.2 Hz, 1H), 5.00 (dd, J=3.2, 8.4 Hz, 1H), 4.89 (t, J=5.6 Hz, 1H), 4.11 (t, J=5.6 Hz, 2H), 3.71-3.76 (m, 3H), 3.57-3.61 (m, 1H), 2.60-2.61 (m, 1H), 2.42-2.46 (m, 1H), 2.18-2.22 (m, 2H), 2.05-2.09 (m, 1H), 1.46-1.53 (m, 3H), 0.91-0.94 (m, 2H), and 0.69-0.72 (m, 2H). [M+H]⁺=458.

Example C154: (1-(8-chloroquinolin-5-yl)piperidin-4-yl)(7-cyclopropylimidazo[1,5-a]pyridin-8-yl)methanol

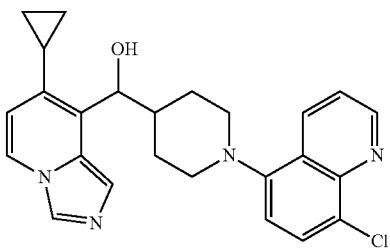

¹H NMR (DMSO-d₆) δ_H 8.98 (d, J=7.2 Hz, 1H), 8.51 (d, J=8.4 Hz, 1H), 8.23 (s, 1H), 8.13 (d, J=7.6 Hz, 1H), 7.80 (d, J=8.4 Hz, 1H), 7.63 (q, J=4.0 Hz, 1H), 7.48 (s, 1H), 7.11 (d, J=8.4 Hz, 1H), 6.19 (d, J=7.6 Hz, 1H), 5.46 (d, J=3.2 Hz, 1H), 5.11 (d, J=4.8 Hz, 1H), 3.19 (d, J=10.4 Hz, 1H), 2.75 (t, J=11.2 Hz, 1H), 2.54-2.60 (m, 2H), 2.24-2.30 (m, 2H), 2.13-2.16 (m, 1H), 1.63-1.77 (m, 2H), 1.23-1.30 (m, 1H), 0.96-0.99 (m, 2H), and 0.72-0.74 (m, 2H). [M+H]⁺=433.

Example C154a and C154b: (S)-(1-(8-chloroquinolin-5-yl)piperidin-4-yl)(7-cyclopropylimidazo[1,5-a]pyridin-8-yl)methanol and (R)-(1-(8-chloroquinolin-5-yl)piperidin-4-yl)(7-cyclopropylimidazo[1,5-a]pyridin-8-yl)methanol

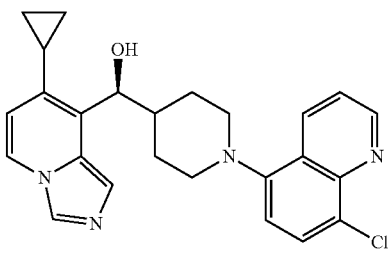

Fast isomer in CHIRALART Amylose-SB
Eluting reagent: Hex:EtOH = 70:30

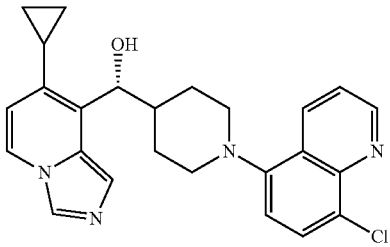 [SMILES: OC(c1c(C2CC2)ccn2cncc12)C1CCN(c2ccc(Cl)c3ncccc23)CC1]

Slow isomer in CHIRALART Amylose-SB
Eluting reagent: Hex:EtOH = 70:30

Each enantiomer of racemic C154a and C154b was separated using preparative HPLC on a CHIRALART Amylose-SB with Hex:EtOH=70:30 as an eluent. The enantiomeric excesses were determined by using HPLC on a Cellulose-SB with Hex (0.1% DEA):EtOH=70:30 as an eluent at a flow rate of 1.0 mL/min. The first one enantiomer eluted at the retention time of 4.162 min, ¹H NMR (DMSO-d₆) δ_H 8.98 (s, 1H), 8.51 (d, J=8.4 Hz, 1H), 8.22 (s, 1H), 8.13 (d, J=6.4 Hz, 1H), 7.80 (d, J=7.2 Hz, 1H), 7.61-7.64 (m, 1H), 7.47 (s, 1H), 7.11 (d, J=8.4 Hz, 1H), 6.19 (d, J=6.4 Hz, 1H), 5.46 (s, 1H), 5.09-5.12 (m, 1H), 3.17-3.20 (m, 1H), 2.74-2.78 (m, 1H), 2.53-2.60 (m, 1H), 2.26-2.33 (m, 2H), 2.10-2.19 (m, 1H), 1.63-1.77 (m, 2H), 1.23-1.30 (m, 2H), 0.96-0.98 (m, 2H), and 0.70-0.73 (m, 2H). [M+H]⁺=433; and the other enantiomer eluted at the retention time of 5.510 min, ¹H NMR (DMSO-d₆) δ_H 8.98 (s, 1H), 8.51 (d, J=8.0 Hz, 1H), 8.22 (s, 1H), 8.13 (d, J=7.6 Hz, 1H), 7.80 (d, J=8.0 Hz, 1H), 7.61-7.64 (m, 1H), 7.48 (s, 1H), 7.11 (d, J=8.0 Hz, 1H), 6.19 (d, J=7.6 Hz, 1H), 5.46 (s, 1H), 5.09-5.12 (m, 1H), 3.17-3.20 (m, 1H), 2.74-2.78 (m, 1H), 2.55-2.60 (m, 1H), 2.13-2.33 (m, 3H), 1.62-1.77 (m, 2H), 1.23-1.30 (m, 2H), 0.96-0.98 (m, 2H), and 0.72-0.74 (m, 2H). [M+H]⁺=433. The absolute configurations of chiral carbons in C154a and C154b are tentatively assigned as (S) and (R) respectively based on assumption that the binding model of the more potent isomer C154a is the same as that of C101a with IDO1.

Example C155: (7-cyclopropylimidazo[1,5-a]pyridin-8-yl)(1-(5-fluoroquinolin-8-yl)piperidin-4-yl)methanol

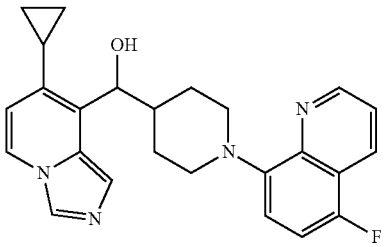 [SMILES: OC(c1c(C2CC2)ccn2cncc12)C1CCN(c2ccc(F)c3cccnc23)CC1]

¹H NMR (DMSO-d₆) δ_H 8.93 (d, J=2.8 Hz, 1H), 8.39 (d, J=8.4 Hz, 1H), 8.22 (s, 1H), 8.13 (d, J=7.2 Hz, 1H), 7.60 (q, J=4.0 Hz, 1H), 7.47 (s, 1H), 7.28 (t, J=9.2 Hz, 1H), 6.99-7.12 (m, 1H), 6.18 (d, J=7.2 Hz, 1H), 5.43 (s, 1H), 5.09 (d, J=8.4 Hz, 1H), 3.86 (d, J=11.2 Hz, 1H), 3.72 (d, J=11.2 Hz, 1H), 2.67 (t, J=11.2 Hz, 1H), 2.43-2.50 (m, 1H), 2.07-2.33 (m, 3H), 1.53-1.77 (m, 2H), 1.20-1.29 (m, 1H), 0.90-1.01 (m, 2H) and 0.67-0.77 (m, 2H).

Example C155a and C155b: (S)-(7-cyclopropylimidazo[1,5-a]pyridin-8-yl)(1-(5-fluoroquinolin-8-yl)piperidin-4-yl)methanol and (R)-(7-cyclopropylimidazo[1,5-a]pyridin-8-yl)(1-(5-fluoroquinolin-8-yl)piperidin-4-yl)methanol

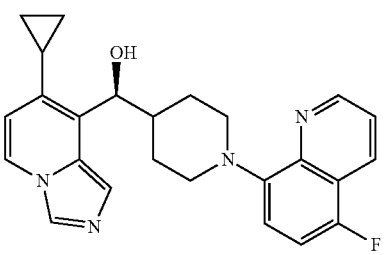

Fast isomer in CHIRALPAK AC-3 HPLC
Eluting reagent: Hex (0.2% IPAmine):EtOH = 50:50

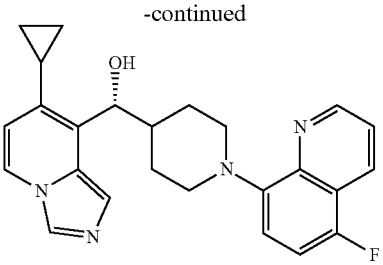

Slow isomer in CHIRALPAK AC-3 HPLC
Eluting reagent: Hex (0.2% IPAmine):EtOH = 50:50

Each enantiomer of racemic C155a and C155b was separated using preparative HPLC on a Chiralpak IA with Hex:EtOH=50:50 as an eluent. The enantiomeric excesses were determined by using HPLC on a Chiralpak IA-3 with Hex (0.2% IPAmine):EtOH=50:50 as an eluent at a flow rate of 1.0 mL/min. The first one enantiomer eluted at the retention time of 1.156 min, $^1$H NMR (DMSO-d6) $\delta_H$ 8.93 (d, J=2.8 Hz, 1H), 8.40 (d, J=8.0 Hz, 1H), 8.22 (s, 1H), 8.13 (d, J=7.6 Hz, 1H), 7.60 (q, J=4.0 Hz, 1H), 7.47 (s, 1H), 7.28 (t, J=8.8 Hz, 1H), 7.00-7.10 (m, 1H), 6.17 (d, J=7.6 Hz, 1H), 5.38-5.45 (m, 1H), 5.03-5.15 (m, 1H), 3.86 (d, J=11.2 Hz, 1H), 3.71 (d, J=11.2 Hz, 1H), 2.67 (t, J=11.2 Hz, 1H), 2.08-2.34 (m, 3H), 1.54-1.78 (m, 2H), 1.21-1.28 (m, 2H), 0.92-1.01 (m, 2H) and 0.68-0.77 (m, 2H): and the other enantiomer eluted at the retention time of 2.670 min, $^1$H NMR (DMSO-d$_6$) $\delta_H$ 8.93 (d, J=2.8 Hz, 1H), 8.40 (d, J=8.0 Hz, 1H), 8.22 (s, 1H), 8.13 (d, J=7.6 Hz, 1H), 7.60 (q, J=4.0 Hz, 1H), 7.47 (s, 1H), 7.28 (t, J=9.2 Hz, 1H), 6.99-7.12 (m, 1H), 6.18 (d, J=7.2 Hz, 1H), 5.41 (s, 1H), 5.09 (d, J=8.4 Hz, 1H), 3.86 (d, J=11.2 Hz, 1H), 3.72 (d, J=11.2 Hz, 1H), 2.67 (t, J=11.2 Hz, 1H), 2.07-2.33 (m, 3H), 1.56-1.75 (m, 2H), 1.20-1.26 (m, 2H), 0.91-1.01 (m, 2H) and 0.68-0.78 (m, 2H). The absolute configurations of chiral carbons in C155a and C155b are tentatively assigned as (S) and (R) respectively based on assumption that the binding model of the more potent isomer C155a is the same as that of C101a with IDO1.

Example C156: (7-cyclopropylimidazo[1,5-a]pyridin-8-yl 1-(8-fluoroisoquinoline-5-yl)piperidin-4-yl) methanol

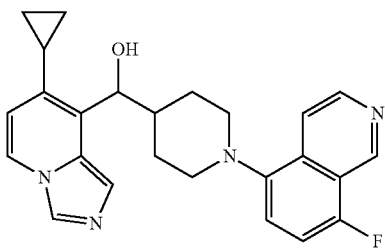

$^1$H NMR (DMSO-d6) $\delta_H$ 9.36 (s, 1H), 8.59 (d, J=6.0 Hz, 1H), 8.22 (s, 1H). 8.11 (d. J=7.2 Hz, 1H), 7.88 (d, J=5.6 Hz, 1H), 7.46 (s, 1H), 7.29-7.36 (m, 1H), 7.20-7.26 (m, 1H), 6.17 (d, J=6.8 Hz, 1H), 5.43 (s, 1H), 5.03-5.11 (m, 1H), 3.11-3.16 (m, 1H), 2.63-2.73 (m, 1H), 2.39-2.43 (m, 1H), 2.23-2.30 (m, 2H), 2.06-2.13 (m, 1H), 1.58-1.74 (m, 2H), 1.19-1.29 (m, 2H), 0.91-0.99 (m, 2H) and 0.67-0.74 (m, 2H).

Example D: Synthesis of 5-substituted imidazo[1,5-a]pyridines

Example D101: (6-cyclopropylimidazo[1,5-a]pyridin-5-yl)(4-phenylcyclohexyl)methanol

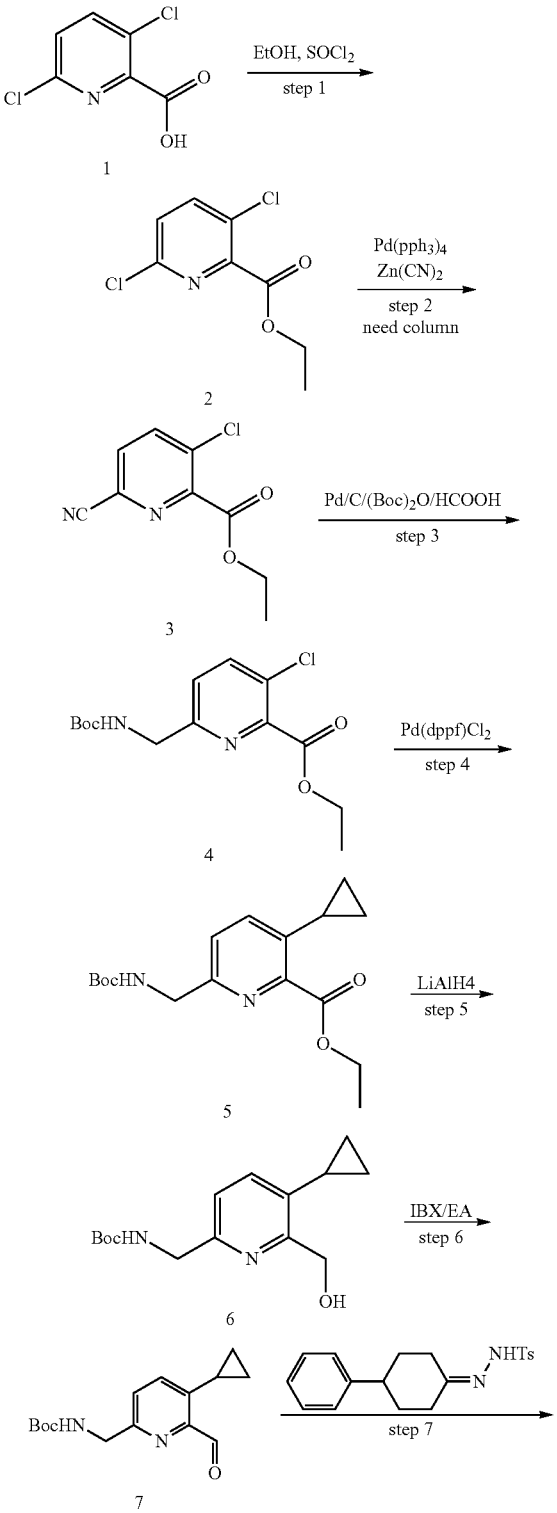

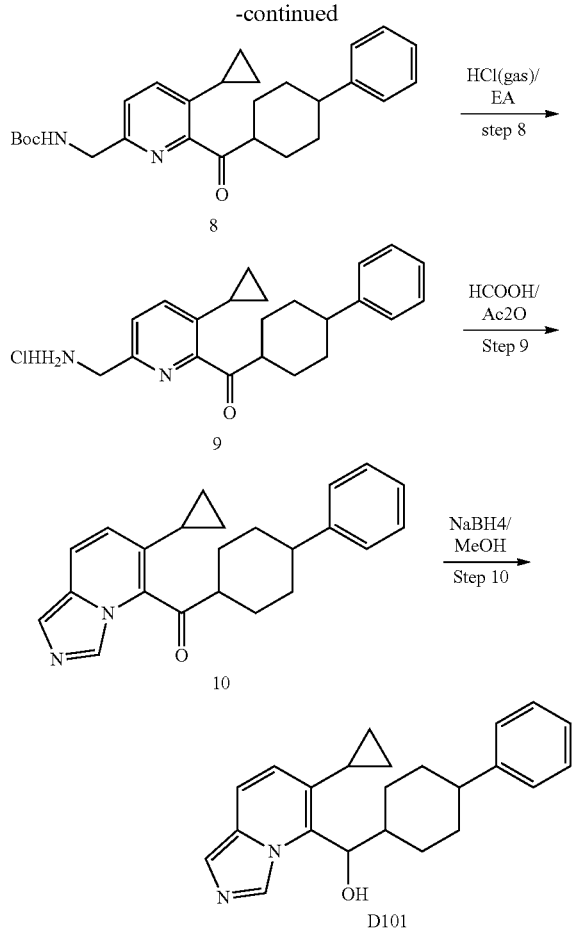

Step 1: Ethyl 3,6-dichloropicolinate

To a solution of 3,6-dichloropicolinic acid (100 g, 520.8 mmol) in EtOH (400 mL) was added SOCl₂ (155 g, 1.3 mol) by drop-wise at 0° C. Then the mixture was stirred at 90° C. for 2 h. TLC (PE:EA=3:1, Rf=0.5) showed the reaction was completed. The solvent was evaporated under reduced pressure and the crude product was added saturated NaHCO₃ solution adjusted PH=7 and extracted with EA (200 ml×3). The combined organic layer was dried with Na₂SO₄, filtered and concentrated to give compound (120 g, 100%) as yellow oil. LC-MS (M+H)$^+$=220.

Step 2: Ethyl 3-chloro-6-cyanopicolinate

A mixture of ethyl 3,6-dichloropicolinate (260 g, 1182 mmol) in DMF (300 mL) was added ZnCN₂ (91 g, 778 mmol) and Pd(pph₃)₄ (75 g, 65 mmol), then the mixture was stirred at 95° C. for 2 hours under N₂. TLC (PE:EA=3:1, Rf=0.5) showed the reaction was completed. H₂O (500 ml) was added, filtered to remove the white precipitate and extracted with EA (1000 ml×3). The combined organic layer was dried over Na₂SO₄, filtered and concentrated to give crude product. The crude product was purified by silica gel on chromatography (PE:EA=20:1-8:1) to give ethyl 3-chloro-6-cyanopicolinate (106 g, 43%) as yellow oil. ¹H NMR (DMSO-d6) δ 8.45 (d, J=8 Hz, 1H), 8.29 (d, J=8 Hz, 1H), 4.45 (q, J=7.2 Hz, 2H), 1.37 (t, J=7.2 Hz, 3H)

Step 3: Ethyl 6-(((tert-butoxycarbonyl)amino)methyl)-3-chloropicolinate

To a solution of ethyl 3-chloro-6-cyanopicolinate (80 g, 380 mmol) in HCOOH/thiophene (1000 mL/0.1 mL) was added Pd/C (12 g), the mixture was stirred at room temperature for 16 h under H₂ at 60 psi. Then filtration, the solvent was removed under vacuum. The residue was dissolved in water (1 L), and the mixture was extracted with EA/Pe=1:1 (500 mL×2), the water layer was neutralize with Na₂CO₃ (solid) to adjust PH=7-8, then added THF (300 mL), and (Boc)₂O (86.6 g, 380 mmol) inTHF (150 mL) was added by dropwised, the mixtures was stirred at RT for overnight. The mixture was extracted with EA (1.0 L), washed with brine (500 mL), dried with Na₂SO₄ and concentrated to give crude product was oil. Then PE (200 mL) was added to the oil and the mixture was stirred at 5-10° C. for 1-2 h, then the mixture was filtrated) to give white solid (60 g). LC-MS (M+H)$^+$=259, 315.

Step 4: Ethyl 6-(((tert-butoxycarbonyl)amino)methyl)-3-cyclopropylpicolinate

Ethyl 6-(((tert-butoxycarbonyl)amino)methyl)-3-chloropicolinate (37.8.0 g, 120 mmoL), Pd(dppf)₂Cl₂ (13.16 g, 18 mmol), Cs₂CO₃ (46.84 g, 144 mmol) and cyclopropylboronic acid (12.38 g, 144 mmol) were suspended on toluene (1.0 L), the mixture was heated to 90° C. for 7 hours under N₂ atmosphere. Then cooled to RT and EA/PE=1:2 (1.0 L) was added, the residue was filtered by a pad of silica, washed with EA/pet=1:1 (2.0 L), concentrated in vocuo and then PE (500 mL) was added, concentrated in vocuo again, and PE (500 mL) added to the mixture, stirred for 0.5 h, then filtrated to give product as yellow solid (73 g). ¹H NMR (DMSO-d₆) δ 7.46 (d, J=7.6 Hz, 1H), 7.29 (d, J=7.6 Hz, 1H), 4.36 (q, J=6.8 Hz, 2H), 4.17 (d, J=6.0 Hz, 2H), 2.11-2.13 (m, 1H), 1.40 (s, 9H), 1.30 (t, J=6.8 Hz, 3H), 0.95-0.99 (m, 2H), 0.67-0.71 (m, 2H). LC-MS (M+H)$^+$=321.

Step 5: Tert-butyl ((5-cyclopropyl-6-(hydroxymethyl)pyridin-2-yl)methyl)carbamate LiAlH₄ (5.85 g, 150 mmol) was suspended in THF (200 mL) under N₂ atmosphere at 0° C., then a solution of ethyl 6-(((tert-butoxycarbonyl)amino)methyl)-3-cyclopropylpicolinate (32.1 g, 100 mmol) in THF (300 mL) was added by dropwised at 0° C. for 0.5 hour, stirred 1 h at 0° C. The mixture was quenched with MeOH (200 mL), then EA (1200 mL) and water (1200 mL) were added, separated, the organic layer was dried over Na₂SO₄, filtered and concentrated to give crude product. The crude product was purified by silica gel on chromatography (PE:EA=20:1-1:1) to give tert-butyl ((5-cyclopropyl-6-(hydroxymethyl)pyridin-2-yl)methyl)carbamate (14.0 g) as an oil. LC-MS (M+H)$^+$=279.

Step 6: Tert-butyl ((5-cyclopropyl-6-formylpyridin-2-yl)methyl)carbamate

To a solution of tert-butyl ((5-cyclopropyl-6-(hydroxymethyl)pyridin-2-yl)methyl)carbamate (14.0 g, 50 mmol) in EA (500 mL) was added 2-Iodoxybenzoicacid (28.0 g, 0.1 mol) at RT, the mixture was heated to 90° C. for 7 hours under N₂ atmosphere, filtered and concentrated to give crude product. The crude product was purified by silica gel on chromatography (PE:EA=20:1-1:1) to give tert-butyl ((5-cyclopropyl-6-formylpyridin-2-yl)methyl)carbamate (7.5 g) as yellow oil. ¹H NMR (DMSO-d₆) $\delta_H$ 10.11 (s, 1H), 7.41-7.51 (m, 3H), 4.26-4.28 (m, 2H), 3.00 (m, 1H), 1.40 (s, 9H), 1.05-1.07 (m, 2H) 0.76-0.78 (m, 2H)

Step 7: Tert-butyl(5-cyclopropyl-6-(4-phenylcyclohexane-1-carbonyl)pyridin-2-yl)methyl) carbamate Tert-butyl ((5-cyclopropyl-6-formylpyridin-2-yl)methyl) carbamate (276 mg, 1.0 mmol), 4-methyl-N'-(4-phenylcyclohexylidene)benzenesulfonohydrazide (410 mg, 1.2 mmol) and Cs₂CO₃ (487 mg, 1.5 mmol) were suspended in 1,4-dioxane (20 mL), the mixture was heated to 100° C. for 7 hours under N₂ atmosphere. Then cooled to rt and EA/H₂O (50 mL/50 mL) was added, the organic layer was washed with brine (50 mL), dried with Na₂SO₄ and concentrated. The crude product was purified by silica gel on chromatography (PE:EA=20:1-8:1) to give tert-butyl((5-cyclopropyl-6-(4-phenylcyclohexane-1-carbonyl)pyridin-2-yl)methyl) carbamate (230 mg, 53%) as yellow solid. LC-MS (M+H)⁺=435.

Step 8: (6-(aminomethyl)-3-cyclopropylpyridin-2-yl)(4-phenylcyclohexyl)methanone hydrochloride Tert-butyl((5-cyclopropyl-6-(4-phenylcyclohexane-1-carbonyl)pyridin-2-yl)methyl) carbamate (220 mg, 0.507 mmol) was suspended in 4 M HCl(gas)/EA(20 mL), the mixture was stirred at rt for 4 hours. The solvent was removed by reduce pressure to give (6-(aminomethyl)-3-cyclopropylpyridin-2-yl)(4-phenylcyclohexyl)methanone hydrochloride (90 mg) as yellow solid. LC-MS (M+H)+=335.

Step 9: (6-cyclopropylimidazo[1,5-a]pyridin-5-yl)(4-phenylcyclohexyl)methanone (6-(Aminomethyl)-3-cyclopropylpyridin-2-yl)(4-phenylcyclohexyl)methanone hydrochloride (90 mg, 0.507 mmol) was suspended in HCOOH/Ac₂O (6 mL/9 mL), the mixture was stirred at 50° C. for overnight. The solvent was removed by reduce pressure. And EA/H₂O (50 mL/50 mL) was added, the organic layer was washed with brine (50 mL), dried with Na₂SO₄ and concentrated. The crude product was purified by silica gel on chromatography (PE:EA=20:1-8:1) to give (6-cyclopropylimidazo[1,5-a]pyridin-5-yl)(4-phenylcyclohexyl) methanone (90 mg) as yellow solid. LC-MS (M+H)⁺=345.

Step 10: (6-cyclopropylimidazo[1,5-a]pyridin-5-yl)(4-phenylcyclohexyl)methanol

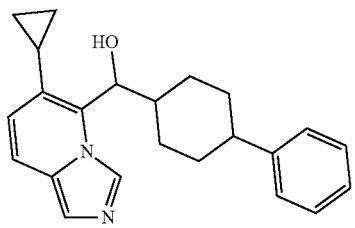 [SMILES: OC(c1c(C2CC2)ccc2cncn12)C1CCC(c2ccccc2)CC1]

To a solution of (6-cyclopropylimidazo[1,5-a]pyridin-5-yl)(4-phenylcyclohexyl) methanone (90 mg, 0.26 mmol) in MeOH (30 mL) was added NaBH₄ (20 mg, 0.52 mmol), the mixture was stirred at room temperature for 1 hour. Then EA/H₂O (100 mL/50 mL) was added, the organic layer was washed with brine (50 mL), dried with Na₂SO₄ and concentrated. The crude product was purified by silica gel on chromatography (PE:EA=20:1-1:1) to give (6-cyclopropylimidazo[1,5-a]pyridin-5-yl)(4-phenylcyclohexyl)methanol (80 mg) as yellow solid. ¹H NMR (DMSO-d₆) δ_H 8.62 (s, 1H), 7.40 (d, J=9.2 Hz, 1H), 7.31 (s, 1H), 7.12-7.26 (m, 5H), 6.47 (d, J=9.6 Hz, 1H), 5.80 (d, J=3.6 Hz, 1H), 5.26 (dd, J=3.6, 10.0 Hz, 1H), 2.41-2.49 (m, 2H), 2.20-2.23 (m, 1H), 1.87-2.01 (m, 2H), 1.10-1.52 (m, 2H), 0.64-0.67 (m, 8H). LC-MS (M+H)⁺=345.

Examples D101a and D101b: (S)-(6-cyclopropylimidazo[1,5-a]pyridin-5-yl)((1r,4S)-4-phenylcyclohexyl)methanol and (R)-(6-cyclopropylimidazo[1,5-a]pyridin-5-yl)((1r,4R)-4-phenylcyclohexyl) methanol

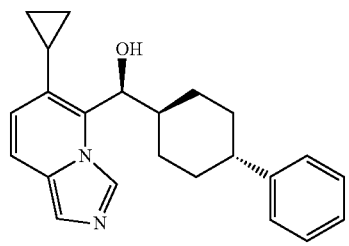

Fast isomer in chiral IC HPLC
Eluting reagent: Hex:EtOH = 70:30(V/V)

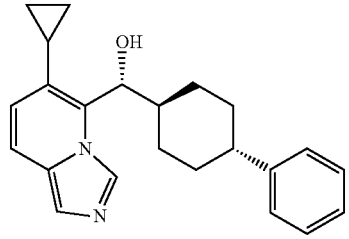

Slow isomer in chiral IC HPLC
Eluting reagent: Hex:EtOH = 70:30(V/V)

Each enantiomer of racemic D101a and D101b was separated using preparative HPLC on a Chiralpak IC with Hex:EtOH=70:30(V/V) as an eluent. The enantiomeric excesses were determined by using HPLC on a Chiralpak IC-3 with Hex (0.2% IPAmine):EtOH=70:30 as an eluent at a flow rate of 1.0 mL/min. The first one enantiomer eluted at the retention time of 2.1 min, and then was dissolved in 4 M HCl(gas)/EA and stirred for 0.5 h, concerned in vocuo to give a, ¹H NMR (DMSO-d₆) δ_H 9.64 (s, 1H), 8.07 (s, 1H), 7.71 (d, J=9.6 Hz, 1H), 7.13-7.27 (m, 5H), 6.84 (d, J=9.6 Hz, 1H), 6.20 (br s. 1H), 5.33 (d, J=9.6 Hz, 1H), 2.32-2.40 (m, 1H), 2.14-2.17 (m, 2H), 1.89-1.99 (m, 1H), 1.59-1.69 (m, 1H), 1.45-1.52 (m, 1H), 1.16-1.29 (m, 4H), 1.02-1.07 (m, 2H) 0.75-0.82 (m, 2H); and the other enantiomer eluted at the retention time of 3.8 min, and then was dissolved in 4 M HCl(gas)/EA and stirred for 0.5 h, concerned in vocuo to give b, ¹H NMR (DMSO-d₆) δ_H 9.63 (s, 1H), 8.06 (s, 1H), 7.70 (d, J=9.6 Hz, 1H), 7.13-7.24 (m, 5H), 6.83 (d, J=9.6 Hz, 1H), 6.19 (br s, 1H), 5.32 (d, J=9.6 Hz, 1H), 2.32-2.40 (m, 1H), 2.14-2.17 (m, 2H), 1.89-1.99 (m, 1H), 1.59-1.69 (m, 1H), 1.45-1.52 (m, 1H), 1.16-1.29 (m, 4H), 1.02-1.07 (m, 2H) 0.76-0.79 (m, 2H). The absolute configurations of chiral carbons in D101a and D11 b are tentatively assigned as (S) and (R) respectively based on assumption that the binding model of the more potent isomer D101a is the same as that of C101a with IDO1 enzyme, and the relative stereochemistry on cyclohexane is assigned as trans configuration on the cyclohexane.

Example D102: (6-cyclopropylimidazo[1,5-a]pyridin-5-yl)(4-(4-methoxyphenyl)cyclohexyl)methanol

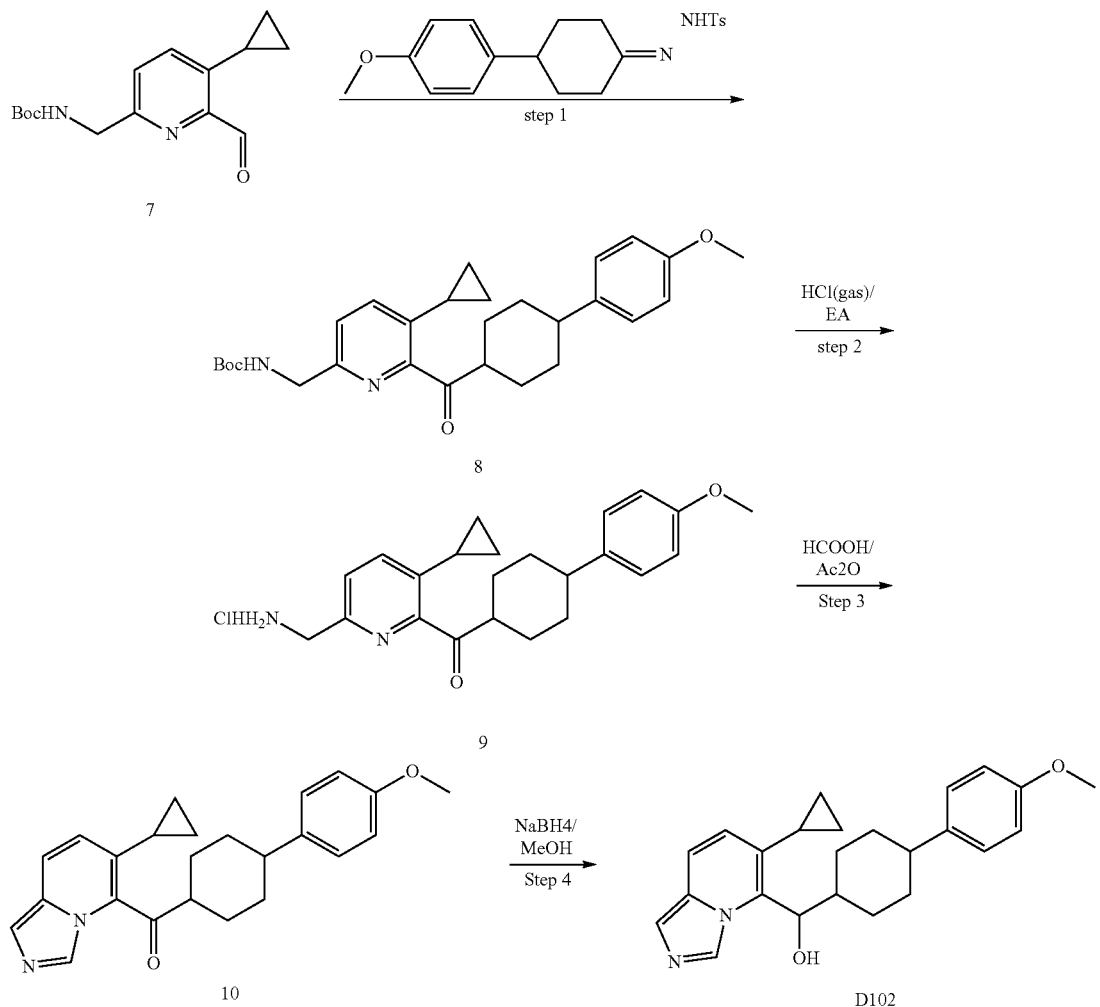

Step 1: Tert-butyl ((5-cyclopropyl-6-(4-(4-methoxyphenyl)cyclohexane-1-carbonyl) pyridin-2-yl) methyl)carbamate Tert-butyl ((5-cyclopropyl-6-formylpyridin-2-yl)methyl) carbamate (828 mg, 3.0 mmol), N'-(4-(4-methoxyphenyl) cyclohexylidene)-4-methylbenzenesulfonohydrazide (1.34 g, 3.6 mmol) and Cs$_2$CO$_3$ (1.46 g, 4.5 mmol) were suspended in 1,4-dioxane (50 mL), the mixture was heated to 100° C. for 7 hours under N$_2$ atmosphere. Then cooled to RT and EA/H$_2$O (50 mL/50 mL) was added, the organic layer was washed with brine (50 mL), dried with Na$_2$SO$_4$ and concentrated. The crude product was purified by silica gel on chromatography (PE:EA=20:1-8:1) to give tert-butyl ((5-cyclopropyl-6-(4-(4-methoxyphenyl)cyclohexane-1-carbonyl)pyridin-2-yl)methyl)-carbamate (800 mg) as yellow solid. LC-MS (M+H)$^+$-=465.

Step 2: (6-(aminomethyl)-3-cyclopropylpyridin-2-yl)(4-(4-methoxyphenyl)cyclohexyl) methanone hydrochloride Tert-butyl((5-cyclopropyl-6-(4-(4-methoxyphenyl)cyclohexane-1-carbonyl)pyridin-2-yl)methyl)carbamate (800 mg, 1.72 mmol) was suspended on 4 M HCl(gas)/EA(30 mL), the mixture was stirred at RT for 4 hours. The solvent was removed by reduce pressure to give (6-(aminomethyl)-3-cyclopropylpyridin-2-yl)(4-(4-methoxyphenyl)cyclohexyl) methanone hydrochloride (680 mg) as yellow solid. LC-MS (M+H)$^+$=365.

Step 3: (6-cyclopropylimidazo[1,5-a]pyridin-5-yl) (4-(4-methoxyphenyl)cyclohexyl) methanone (6-(Aminomethyl)-3-cyclopropylpyridin-2-yl)(4-(4-methoxyphenyl)cyclohexyl) methanone hydrochloride (680 mg, 1.70 mmol) was suspended in HCOOH/Ac$_2$O (10 mL/30 mL), the mixture was stirred at 50° C. for overnight. The solvent was removed by reduce pressure. EA/H$_2$O (50 mL/50 mL) was added, the organic layer was washed with brine (50 mL), dried with Na$_2$SO$_4$ and concentrated. The crude product was purified by silica gel on chromatography (PE:EA=20:1-8:1) to (6-cyclopropylimidazo[1,5-a]pyridin-5-yl)(4-(4-methoxyphenyl) cyclohexyl)methanone (540 mg) as yellow solid. LC-MS (M+H)$^+$=375.

Step 4: (6-cyclopropylimidazo[1,5-a]pyridin-5-yl)(4-(4-methoxyphenyl)cyclohexyl)methanol

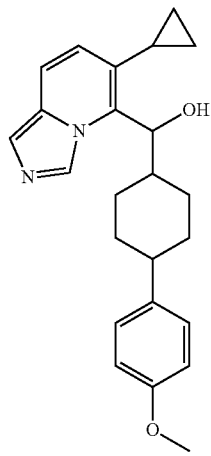 [SMILES: COc1ccc(C2CCC(C(O)c3c(C4CC4)ccc4cncn34)CC2)cc1]

(6-cyclopropylimidazo[1,5-a]pyridin-5-yl)(4-(4-methoxyphenyl)cyclohexyl) methanone (540 mg, 1.44 mmol) in MeOH (50 mL) was added NaBH$_4$ (109 mg, 2.88 mmol), the mixture was stirred at room temperature for 1 hour. The residue was quenched with EA/H$_2$O (100 ml/50 mL) was added, the organic layer was washed with brine (50 mL), dried with Na$_2$SO$_4$ and concentrated. The crude product was purified by silica gel on chromatography (PE:EA=20:1-1:1) to give (6-cyclopropylimidazo[1,5-a]pyridin-5-yl)(4-(4-methoxyphenyl)cyclohexyl)methanol (400 mg) as yellow solid. $^1$H NMR (DMSO-d$_6$) δ$_H$ 8.62 (s, 1H), 7.39 (d, J=9.6 Hz, 1H), 7.31 (s, 1H), 7.09 (d, J=8.8 Hz, 2H), 6.80 (d, J=8.8 Hz, 2H), 6.47 (d, J=9.6 Hz, 1H), 5.78 (d, J=4.0 Hz, 1H), 5.25 (dd, J=4.0, 10.0 Hz, 1H), 3.69 (s, 3H), 2.41-2.43 (m, 2H), 2.17-2.20 (m, 1H), 1.99-2.01 (m, 1H), 1.85-1.88 (m, 1H), 1.63-1.65 (m, 1H), 1.43-1.47 (m, 1H), 1.17-1.23 (m, 4H), 0.91-0.9 (m, 2H), 0.64-0.79 (m, 2H); LC-MS (M+H)$^+$=377.

Example D102a and D102b: (S)-(6-cyclopropylimidazo[1,5-a]pyridin-5-yl)((1r,4S)-4-(4-methoxyphenyl)cyclohexyl)methanol and (R)-(6-cyclopropylimidazo[1,5-a]pyridin-5-yl(1r,4R)-4-(4-methoxyphenyl)cyclohexyl)methanol

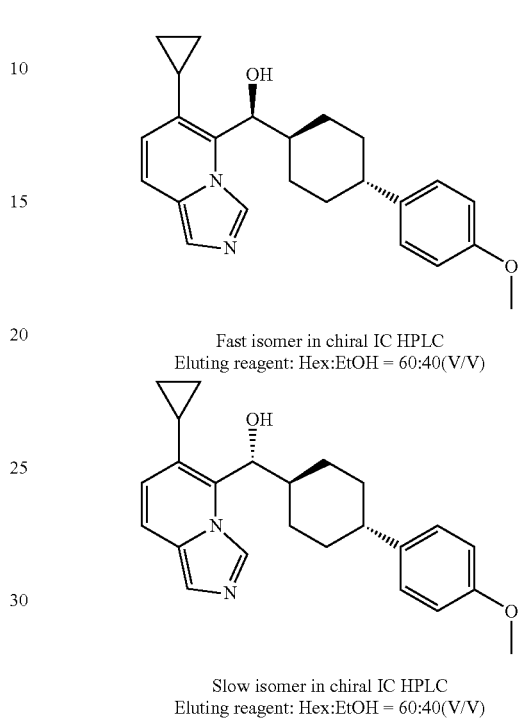

Fast isomer in chiral IC HPLC
Eluting reagent: Hex:EtOH = 60:40(V/V)

Slow isomer in chiral IC HPLC
Eluting reagent: Hex:EtOH = 60:40(V/V)

Each enantiomer of racemic D102a and D102b was separated using preparative HPLC on a Chiralpak IC with Hex:EtOH=60:40(V/V) as an eluent. The enantiomeric excesses were determined by using HPLC on a Chiralpak IC-3 with Hex (0.1% DEA):EtOH=80:20(V/V) as an eluent at a flow rate of 1.0 ml/min. The first one enantiomer eluted at the retention time of 1.8 min, and then was dissolved in 4 M HCl(gas)/EA and stirred for 0.5 h, concerned in vocuo to give D102a, $^1$H NMR (DMSO-d$_6$) δ 9.65 (s, 1H), 8.09 (s, 1H), 7.71 (d, 1H, J=9.2 Hz), 6.81-7.10 (m, 5H), 6.25 (s, 1H), 5.32 (d, J=9.6 Hz, 1H), 3.69 (s, 3H), 2.38-2.41 (m, 2H), 2.17-2.20 (m, 2H), 1.86-1.89 (m, 1H), 1.66-1.68 (m, 1H), 1.43-1.47 (m, 1H), 1.23-1.26 (m, 4H), 1.03-1.05 (m, 2H), 0.78-0.86 (m, 2H); and the other enantiomer eluted at the retention time of 5.0 min, and then was dissolved in 4 M HCl(gas)/EA and stirred for 0.5 h, concerned in vocuo to give D102b, $^1$H NMR (DMSO-d$_6$) δ 9.66 (s, 1H), 8.09 (s, 1H), 7.71 (d, 1H, J=9.2 Hz), 6.81-7.10 (m, 5H), 6.22 (s, 1H), 5.32 (d, J=10.0 Hz, 1H), 3.69 (s, 3H), 2.38-2.41 (m, 2H), 2.17-2.20 (m, 2H), 1.86-1.89 (m, 1H), 1.66-1.68 (m, 1H), 1.43-1.47 (m, 1H), 1.23-1.26 (m, 4H), 1.03-1.05 (m, 2H), 0.78-0.86 (m, 2H); The absolute configurations of chiral carbons in D102a and D102b are tentatively assigned as (S) and (R) respectively based on assumption that the binding model of the more potent isomer D102a is the same as that of C101a with IDO1 enzyme, and the relative stereochemistry on cyclohexane is assigned as trans configuration on the cyclohexane.

Example D103: (4-(4-chlorophenyl)cyclohexyl)(6-cyclopropylimidazo[1,5-a]pyridin-5-yl)methanol

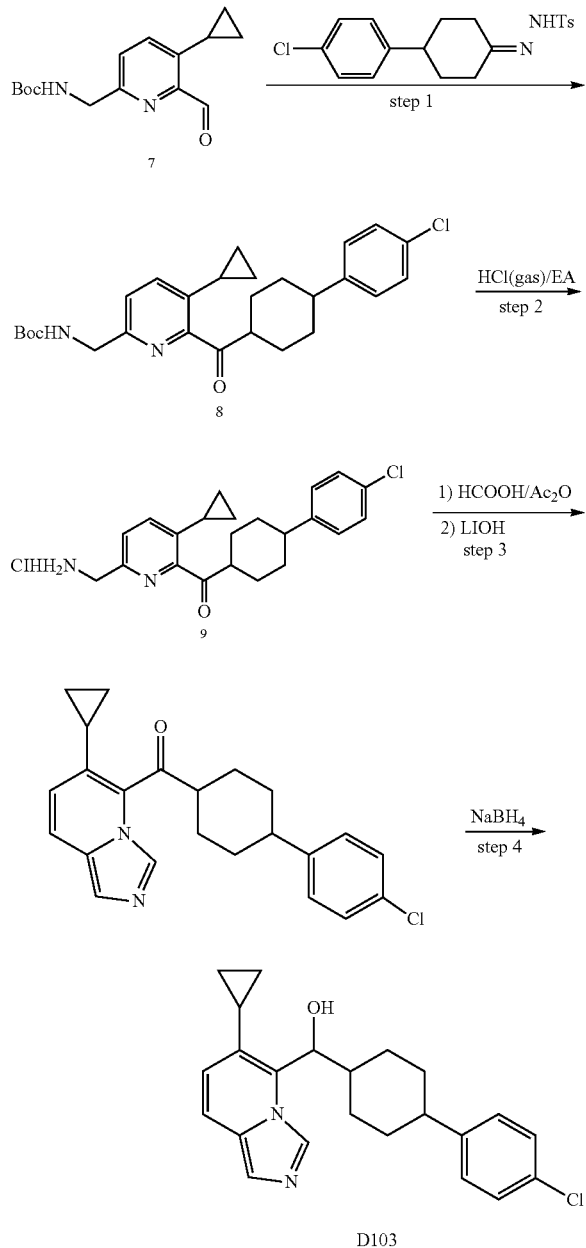

D103

Step 1: tert-butyl ((6-(4-(4-chlorophenyl)cyclohexane-1-carbonyl)-5-cyclopropylpyridin-2-yl)methyl)carbamate Tert-butyl ((5-cyclopropyl-6-formylpyridin-2-yl)methyl) carbamate (828 mg, 3.0 mmol), N'-(4-(4-chlorophenyl)cyclohexylidene)-4-methylbenzenesulfonohydrazide (1.470 g, 3.9 mmol) and Cs$_2$CO$_3$(1.46 g, 4.5 mmol) were suspended on 1,4-dioxane (20 mL), the mixture was heated to 100° C. for 7 hours under N$_2$ atmosphere. Then cooled to rt and EA/H$_2$O (50 mL/50 mL) was added, the organic layer was washed with brine (50 mL), dried with Na$_2$SO$_4$ and concentrated. The crude product was purified by silica gel on chromatography (PE:EA=20:1-8:1) to give tert-butyl ((6-(4-(4-chlorophenyl) cyclohexane-1-carbonyl)-5-cyclopropylpyridin-2-yl)methyl)-carbamate (860 mg, 61%) as yellow solid. LC-MS (M+H)$^+$=469.

Step 2: (6-(aminomethyl)-3-cyclopropylpyridin-2-yl)(4-(4-chlorophenyl)cyclohexyl)methanone hydrochloride Tert-butyl((6-(4-(4-chlorophenyl)cyclohexane-1-carbonyl)-5-cyclopropylpyridin-2-yl)methyl)carbamate (800 mg, 1.72 mmol) was suspended on 4 M HCl(gas)/EA(30 mL), the mixture was stirred at RT for 4 hours. The solvent was removed by reduce pressure to give (6-(aminomethyl)-3-cyclopropylpyridin-2-yl)(4-(4-chlorophenyl)cyclohexyl) methanone hydrochloride (680 mg) as yellow solid. LC-MS (M+H)$^+$=369.

Step 3: (4-(4-chlorophenyl)cyclohexyl)(6-cyclopropylimidazo[1,5-a]pyridin-5-yl)methanone A mixture of Ac$_2$O (150 mL) and HCOOH (50 mL) was heated at 50° C. for 1 hour and then a solution of (6-(aminomethyl)-3-cyclopropylpyridin-2-yl)(4-(4-fluoronaphthalen-1-yl)cyclohexyl)methanone hydrochloride (crude 10.5 g, 26 mmol) in HCOOH (10 mL) was added drop wise and the mixture was heated at 50° C. for 12 hours. The solvent was evaporated under reduced pressure and water (100 mL) was added, washed with saturated aqueous of NaHCO$_3$, then extracted with ethyl acetate (150 mL×3) and combined the organic layer, the solvent was evaporated under reduced pressure and the residue was suspended on MeOH (50 mL), then LiOH (5.0 g) was added, the mixtures was stirred at RT for 48 hours, the mixtures was quenched with EA(200 mL) and H$_2$O (100 mL), the organic layer was washed with brine (100 mL), dried over Na$_2$SO$_4$ and concentrated. The crude product was purified by silica gel on chromatography (PE:EA=20:1-8:1) to give (4-(4-chlorophenyl)cyclohexyl)(6-cyclopropylimidazo[1,5-a]pyridin-5-yl) methanone (7.4 g) as yellow solid. LC-MS (M+H)$^+$=379

Step 4: (4-(4-chlorophenyl)cyclohexyl)(6-cyclopropylimidazo[1,5-a]pyridin-5-yl)methanol To a solution of (4-(4-chlorophenyl)cyclohexyl)(6-cyclopropylimidazo[1,5-a]pyridin-5-yl)methanone (360 mg, 0.95 mmol) in methol (20 mL) was added NaBH$_4$ (76 mg, 2.0 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (160 mg in 42% yield). $^1$H NMR (400 MHz, DMSO-d6) δ$_H$ 8.62 (s, 1H), 7.40 (d, J=9.2 Hz, 1H), 7.31 (s, 1H), 7.21-7.28 (m, 5H), 6.47 (d, J=9.6 Hz, 1H), 5.80 (m, 1H), 5.24-5.27 (m, 1H), 2.41-2.49 (m, 2H), 2.20-2.23 (m, 1H), 1.87-2.01 (m, 2H), 1.64-1.67 (m, 1H), 1.46-1.52 (m, 1H), 1.15-1.26 (m, 5H), 0.89-0.97 (m, 2H), 0.75-0.79 (m, 1H), 0.63-0.68 (m, 1H). [M+H]$^+$=381.

Example D103a, D103b, D103c and D103d: (R)-((1s,4S)-4-(4-chlorophenyl)cyclohexyl)(6-cyclopropylimidazo[1,5-a]pyridin-5-yl)methanol and (R)-((1r,4R)-4-(4-chlorophenyl)cyclohexyl)(6-cyclopropylimidazo[1,5-a]pyridin-5-yl)methanol: (S)-((1r,4S)-4-(4-chlorophenyl)cyclohexyl)(6-cyclopropylimidazo[1,5-a]pyridin-5-yl)methanol and (S)-((1s,4R)-4-(4-chlorophenyl)cyclohexyl) 6-cyclopropylimidazo[1,5-a]pyridin-5-yl)methanol

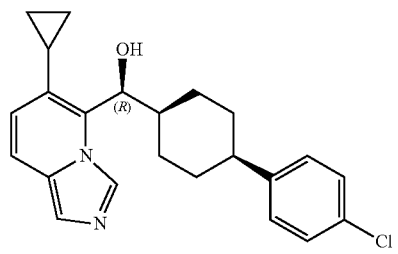

D103a

Fast isomer in CHIRALART Cellulose-SB
Eluting reagent: Hex(0.1% DEA):IPA = 70:30

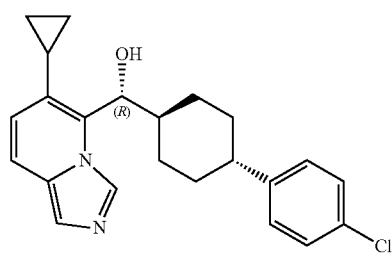

D103b

Slow isomer in CHIRALART Cellulose-SB
Eluting reagent: Hex(0.1% DEA):IPA = 70:30

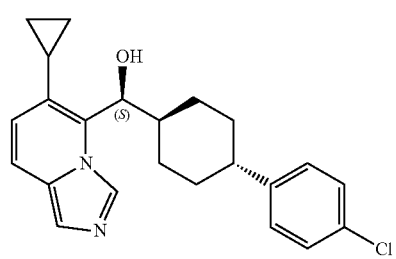

D103c

Fast isomer in CHIRALPAK IC HPLC
Eluting reagent: Hex (0.1% DEA):IPA = 90:10

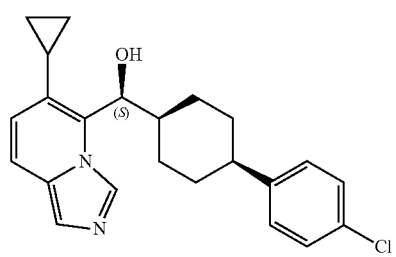

D103d

Slow isomer in CHIRALPAK IC HPLC
Eluting reagent: Hex (0.1% DEA):IPA = 90:10

Each enantiomer of racemic D103a and D103b was separated using preparative HPLC on a CHIRALART Cellulose-SB with Hex (0.1% DEA):IPA=70:30 as an eluent. The enantiomeric excesses were determined by using HPLC on a CHIRALART Cellulose-SB with Hex (0.1% DEA):IPA=70:30 as an eluent at a flow rate of 1.0 mL/min. The first one enantiomer eluted at the retention time of 4.089 min (14 mg, D103a), $^1$H NMR (400 MHz, DMSO-d6) δ 8.87 (s, 1H), 7.49-7.54 (m, 1H), 7.21-7.37 (m, 4H), 6.56 (d, J=9.2 Hz, 1H), 5.90 (s, 1H), 5.68 (d, J=8.8 Hz, 1H), 5.31-5.34 (m, 1H), 2.61-2.67 (m, 1H), 2.16-2.20 (m, 1H), 1.97-2.01 (m, 1H), 1.82-1.85 (m, 1H), 1.68-1.73 (m, 3H), 1.34-1.56 (m, 2H), 1.12-1.15 (m, 1H), 0.83-0.95 (m, 3H), 0.63-0.64 (m, 1H). [M+H]$^+$=381; and the other enantiomer eluted at the retention time of 5.315 min (49 mg, D103b), which was dissolved in THF (1.0 mL) was added drop wise of ethyl acetate solution of hydrochloric acid (5 mL, 4.0M) at room temperature, followed by addition of methanol until the precipitate was dissolved, then the solvent was evaporated under reduced pressure and the residue was washed by PE to give the desired product as white solid (38 mg in 72% yield). $^1$H NMR (400 MHz, DMSO-d$_6$) δ$_H$ 9.60 (s, 1H), 8.04 (s, 1H), 7.69 (d, J=9.6 Hz, 1H), 7.30 (d, J=8.0 Hz, 1H), 7.20 (d, J=8.0 Hz, 1H), 6.82 (d, J=9.6 Hz, 1H), 6.18 (s, 1H), 5.32 (d, J=6.0 Hz, 1H), 2.46-2.48 (m, 1H), 2.16-2.19 (m, 2H), 1.88-1.92 (m, 1H), 1.68-1.71 (m, 1H), 1.15-1.34 (m, 5H), 1.02-1.14 (m, 2H), and 0.76-0.82 (m, 2H), [M+H]$^+$=381. Each enantiomer of racemic D103c and D103d was separated using preparative HPLC on a CHIRALPAK IC with Hex (0.1% DEA):IPA=90:10 as an eluent. The enantiomeric excesses were determined by using HPLC on a CHIRALPAK IC with Hex (0.1% DEA):IPA=90:10 as an eluent at a flow rate of 1.0 mL/min. The first one enantiomer eluted at the retention time of 2.950 min (D103c, 49 mg), which was dissolved in THF (1.0 mL) was added drop wise of ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (44 mg in 81% yield). $^1$H NMR (DMSO-d$_6$) δ 9.54 (s, 1H), 8.99 (s, 1H), 7.68 (d, 1H, J=9.6 Hz), 7.21-7.32 (m, 4H), 6.81 (d, 1H, J=9.6 Hz), 6.14 (s, 1H), 5.31 (d, 1H, J=9.6 Hz), 2.40 (m, 1H), 2.16 (m, 2H), 1.89 (m, 1H), 1.68 (m, 1H), 1.45-1.52 (m, 1H), 1.16-1.29 (m, 4H), 1.03-1.05 (m, 2H), 0.77-0.84 (m, 2H). [M+H]$^+$=381, and the other enantiomer eluted at the retention time of 3.762 min (D103d), $^1$H NMR (400 MHz, DMSO-d$_6$) δ$_H$ 8.62 (s, 1H), 7.40 (d, J=9.2 Hz, 1H), 7.31 (s, 1H), 7.21-7.28 (m, 5H), 6.47 (d, J=9.6 Hz, 1H), 5.80 (m, 1H), 5.24-5.27 (m, 1H), 2.41-2.49 (m, 2H), 2.20-2.23 (m, 1H), 1.87-2.01 (m, 2H), 1.64-1.67 (m, 1H), 1.46-1.52 (m, 1H), 1.15-1.26 (m, 5H), 0.89-0.97 (m, 2H), 0.75-0.79 (m, 1H), 0.63-0.68 (m, 1H). [M+H]$^+$=381. The absolute configurations of chiral carbons in D103a, D103b, D103c and D103d are tentatively assigned as (R), (R), (S), and (S) respectively based on assumption that the binding model of the more potent isomer D103c and D103d are the same as that of C101a with IDO1 enzyme, and the relative stereochemistry on cyclohexane is assigned as cis, trans, trans and cis configuration on the cyclohexane respectively.

Example D104: (6-cyclopropylimidazo[1,5-a]pyridin-5-yl)(4-(4-fluorophenyl)cyclohexyl)methanol

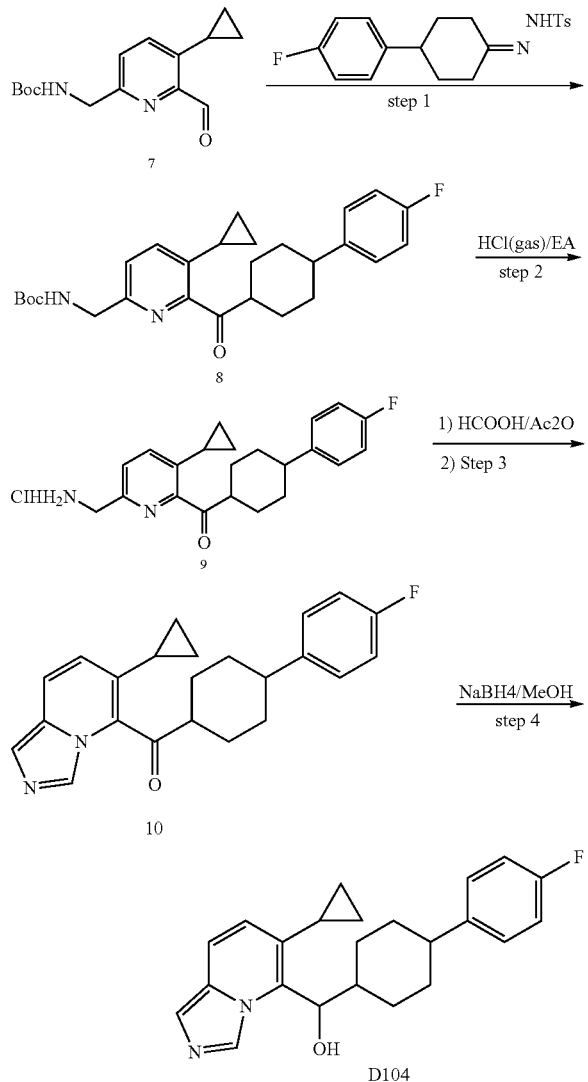

Step 1: tert-butyl ((5-cyclopropyl-6-(4-(4-fluorophenyl)cyclohexane-1-carbonyl)pyridin-2-yl)methyl)carbamate Tert-butyl ((5-cyclopropyl-6-formylpyridin-2-yl)methyl)carbamate (1.104 g, 4.0 mmol), N'-(4-(4-fluorophenyl)cyclohexylidene)-4-methylbenzenesulfonohydrazide (1.58 g, 4.4 mmol) and $Cs_2CO_3$ (1.95 g, 6.0 mmol) were suspended in 1,4-dioxane (50 mL), the mixture was heated to 100° C. for 7 hours under $N_2$ atmosphere. Then cooled to RT and $EA/H_2O$ (50 mL/50 mL) was added, the organic layer was washed with brine (50 mL), dried with $Na_2SO_4$ and concentrated. The crude product was purified by silica gel on chromatography (PE:EA=20:1-8:1) to give tert-butyl ((5-cyclopropyl-6-(4-(4-fluorophenyl)cyclohexane-1-carbonyl)pyridin-2-yl)methyl)-carbamate (760 mg) as yellow solid. LC-MS (M+H)+=453.

Step 2: (6-(aminomethyl)-3-cyclopropylpyridin-2-yl)(4-(4-fluorophenyl)cyclohexyl)methanone hydrochloride Tert-butyl ((5-cyclopropyl-6-(4-(4-fluorophenyl)cyclohexane-1-carbonyl)pyridin-2-yl)methyl)-carbamate (730 mg, 1.61 mmol) was suspended in 4 M HCl(gas)/EA (30 mL), the mixture was stirred at rt for 4 hours. The solvent was removed by reduce pressure to give (6-(aminomethyl)-3-cyclopropylpyridin-2-yl)(4-(4-fluorophenyl)cyclohexyl)methanone hydrochloride (615 mg) as yellow solid, which was used for the next step without further purification. LC-MS (M+H)+=353.

Step 3: (6-cyclopropylimidazo[1,5-a]pyridin-5-yl)(4-(4-fluorophenyl)cyclohexyl)methanone (6-(Aminomethyl)-3-cyclopropylpyridin-2-yl)(4-(4-fluorophenyl)cyclohexyl) methanone hydrochloride (610 mg, 1.56 mmol) was suspended in $HCOOH/Ac_2O$ (9 mL/27 mL), the mixture was stirred at 50° C. for overnight. The solvent was removed by reduce pressure. $EA/H_2O$ (50 mL/50 mL) was added, the organic layer was washed with brine (50 mL), dried with $Na_2SO_4$ and concentrated. The crude product was purified by silica gel on chromatography (PE:EA=20:1-8:1) to (6-cyclopropylimidazo[1,5-a]pyridin-5-yl)(4-(4-fluorophenyl)cyclohexyl) methanone (500 mg) as yellow solid. LC-MS (M+H)+=363.

Step 4: (6-cyclopropylimidazo[1,5-a]pyridin-5-yl)(4-(4-fluorophenyl)cyclohexyl)methanol

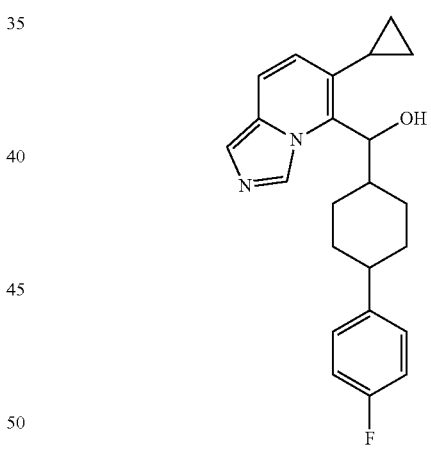

To a solution of (6-cyclopropylimidazo[1,5-a]pyridin-5-yl)(4-(4-fluorophenyl)cyclohexyl)methanone (450 mg, 1.24 mmol) in MeOH (50 mL) was added $NaBH_4$ (95 mg, 2.5 mmol), the mixture was stirred at room temperature for 1 hour. the residue was quenched with $EA/H_2O$ (100 mL/50 mL) was added, the organic layer was washed with brine (50 mL), dried with $Na_2SO_4$ and concentrated. The crude product was purified by silica gel on chromatography (PE:EA=20:1-1:1) to give (6-cyclopropylimidazo[1,5-a]pyridin-5-yl)(4-(4-fluorophenyl)cyclohexyl)methanol (240 mg) as yellow solid, which was suspended in in 4 M HCl(gas)/EA and stirred for 0.5 h, and concerned to give product. $^1H$ NMR (DMSO-$d_6$) $\delta_H$ 8.62 (s, 1H), 7.39 (d, 1H, J=9.2 Hz), 7.31 (s, 1H), 7.21-7.24 (m, 2H), 7.04-7.08 (m, 2H), 6.47 (d, 1H, J=9.2 Hz), 5.80 (d, J=3.6 Hz, 1H), 5.25 (dd, J=3.6, 9.2

Hz, 1H), 2.40-2.44 (m, 1H), 2.19-2.22 (m, 2H), 1.85-1.89 (m, 1H), 1.65-1.68 (m, 1H), 1.46-1.49 (m, 1H), 1.16-1.32 (m, 4H), 0.92-0.98 (m, 2H), and 0.64-0.78 (m, 2H); LC-MS (M+H)$^+$=365.

Example D104a and D104b: (S)-(6-cyclopropylimidazo[1,5-a]pyridin-5-yl)((1r,4S)-4-(4-fluorophenyl)cyclohexyl)methanol and (R)-(6-cyclopropylimidazo[1,5-a]pyridin-5-yl)(1,r4R)-4-(4-fluorophenyl)cyclohexyl)methanol

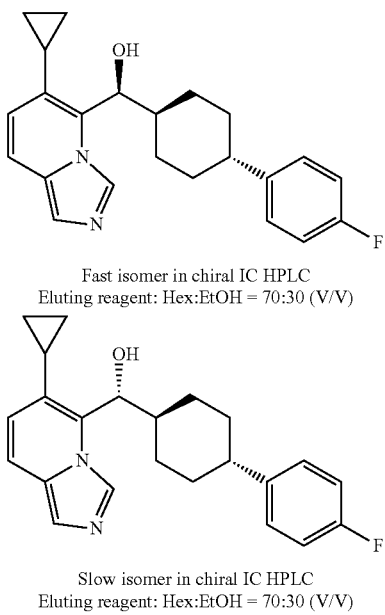

Fast isomer in chiral IC HPLC
Eluting reagent: Hex:EtOH = 70:30 (V/V)

Slow isomer in chiral IC HPLC
Eluting reagent: Hex:EtOH = 70:30 (V/V)

Each enantiomer of racemic D104a and D104b was separated using preparative HPLC on a Chiralpak IC with Hex:EtOH=70:30(V/V) as an eluent. The enantiomeric excesses were determined by using HPLC on a Chiralpak IC-3 with Hex (0.1% DEA):EtOH=70:30(V/V) as an eluent at a flow rate of 1.0 mL/min. The first one enantiomer eluted at the retention time of 2.1 min, and then was dissolved in 4 M HCl(gas)/EA and stirred for 0.5 h, concerned in vacuo to give D104a, $^1$H NMR (DMSO-d$_6$) δ 9.64 (s, 1H), 8.07 (s, 1H), 7.71 (d, 1H, J=9.6 Hz), 7.05-7.22 (m, 4H), 6.84 (d, 1H, J=9.6 Hz), 6.21 (s, 1H), 5.32 (d, 1H, J=9.6 Hz), 2.40 (m, 1H), 2.16 (m, 2H), 1.89 (m, 1H), 1.68 (m, 1H), 1.45-1.52 (m, 1H), 1.16-1.29 (m, 4H), 1.03-1.05 (m, 2H), 0.76-0.86 (m, 2H); and the other enantiomer eluted at the retention time of 3.9 min, and then was dissolved in 4 M HCl(gas)/EA and stirred for 0.5 h, concerned in vacuo to give D104b, $^1$H NMR (DMSO-d$_6$) δ9.63 (s, 1H), 8.06 (s, 1H), 7.71 (d, 1H, J=9.6 Hz), 7.05-7.22 (m, 4H), 6.84 (d, 1H, J=9.6 Hz), 6.19 (s, 1H), 5.32 (d, 1H, J=9.6 Hz), 2.40 (m, 1H), 2.16 (m, 2H), 1.89 (m, 1H), 1.68 (m, 1H), 1.45-1.52 (m, 1H), 1.16-1.29 (m, 4H), 1.03-1.05 (m, 2H), 0.76-0.86 (m, 2H). The absolute configurations of chiral carbons in D104a and D104b are tentatively assigned as (S) and (R) respectively based on assumption that the binding model of the more potent isomer D104a is the same as that of C101a with IDO1 enzyme, and the relative stereochemistry on cyclohexane is assigned as trans configuration on the cyclohexane.

Example D105: (6-cyclopropylimidazo[1,5-a]pyridin-5-yl)(4-(4-trifluoromethoxy)phenylcyclohexyl)methanol

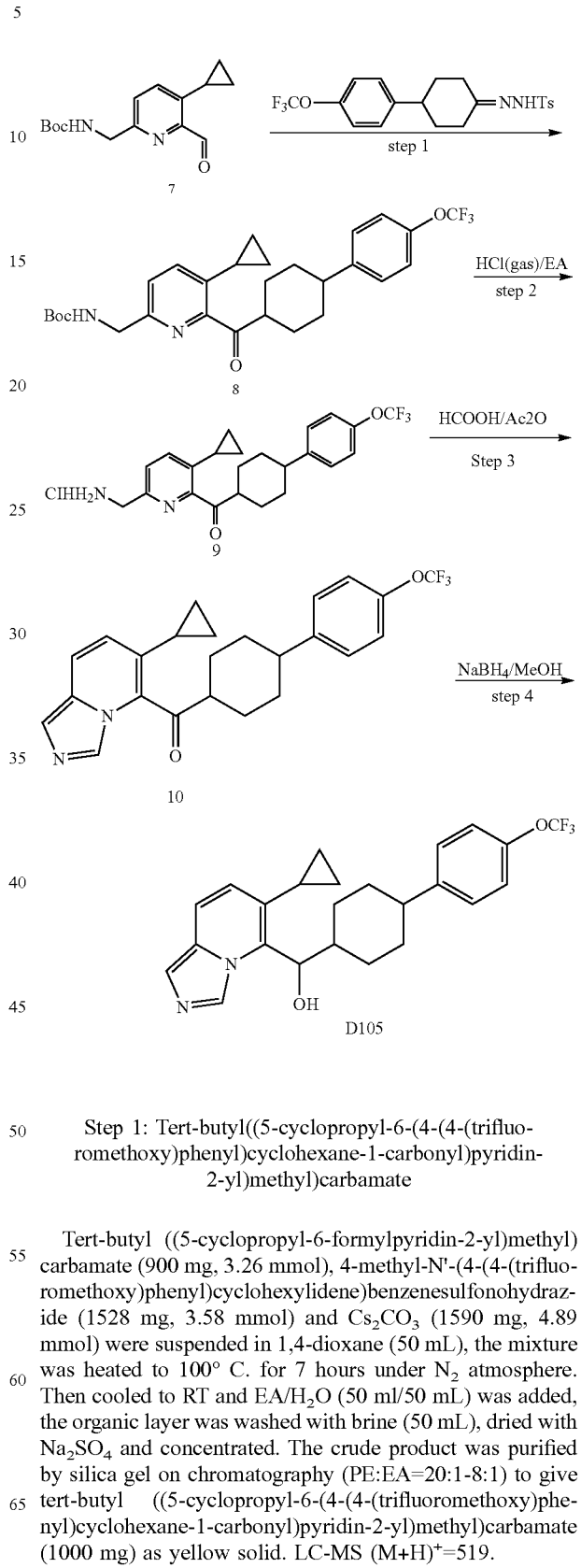

Step 1: Tert-butyl((5-cyclopropyl-6-(4-(4-(trifluoromethoxy)phenyl)cyclohexane-1-carbonyl)pyridin-2-yl)methyl)carbamate Tert-butyl ((5-cyclopropyl-6-formylpyridin-2-yl)methyl) carbamate (900 mg, 3.26 mmol), 4-methyl-N'-(4-(4-(trifluoromethoxy)phenyl)cyclohexylidene)benzenesulfonohydrazide (1528 mg, 3.58 mmol) and Cs$_2$CO$_3$ (1590 mg, 4.89 mmol) were suspended in 1,4-dioxane (50 mL), the mixture was heated to 100° C. for 7 hours under N$_2$ atmosphere. Then cooled to RT and EA/H$_2$O (50 ml/50 mL) was added, the organic layer was washed with brine (50 mL), dried with Na$_2$SO$_4$ and concentrated. The crude product was purified by silica gel on chromatography (PE:EA=20:1-8:1) to give tert-butyl ((5-cyclopropyl-6-(4-(4-(trifluoromethoxy)phenyl)cyclohexane-1-carbonyl)pyridin-2-yl)methyl)carbamate (1000 mg) as yellow solid. LC-MS (M+H)$^+$=519.

Step 2: (6-(aminomethyl)-3-cyclopropylpyridin-2-yl) (4-(4-methoxyphenyl)cyclohexyl)methanone hydrochloride Tert-butyl ((5-cyclopropyl-6-(4-(4-(trifluoromethoxy) phenyl)cyclohexane-1-carbonyl) pyridin-2-yl)methyl)carbamate (900 mg, 1.74 mmol) was suspended in 4 M HCl (gas)/EA (20 mL), the mixture was stirred at RT for 4 hours. The solvent was removed by reduce pressure to give (6-(aminomethyl)-3-cyclopropylpyridin-2-yl) (4-(4-(trifluoromethoxy) phenyl)cyclohexyl)methanone hydrochloride (680 mg) as yellow solid. LC-MS (M+H)$^+$=419

Step 3: (6-cyclopropylimidazo[1,5-a]pyridin-5-yl) (4-(4-(trifluoromethoxy)phenyl)cyclohexyl)methanone (6-(Aminomethyl)-3-cyclopropylpyridin-2-yl)(4-(4-(trifluoromethoxy)phenyl) cyclohexyl) methanone hydrochloride (680 mg, 1.49 mmol) was suspended in HCOOH/Ac$_2$O (9 mL/27 mL), the mixture was stirred at 50° C. for overnight. The solvent was removed by reduce pressure. The residue was quenched with EA/H$_2$O (50 mL/50 mL), the organic layer was washed with brine (50 mL), dried with Na$_2$SO$_4$ and concentrated. The crude product was purified by silica gel on chromatography (PE:EA=20:1-8:1) to give (6-cyclopropylimidazo[1,5-a]pyridin-5-yl) (4-(4-(trifluoromethoxy)phenyl)cyclohexyl)methanone (550 mg) as yellow solid. LC-MS (M+H)$^+$=429.

Step 4: (6-cyclopropylimidazo[1,5-a]pyridin-5-yl) (4-(4-(trifluoromethoxy)phenyl)cyclohexyl) methanol

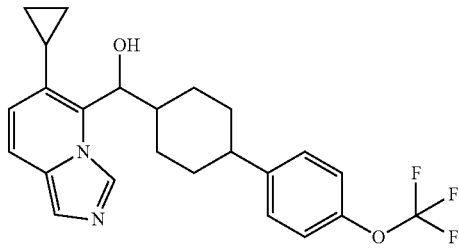 [SMILES: OC(c1c(C2CC2)ccc2cncn12)C1CCC(c2ccc(OC(F)(F)F)cc2)CC1]

(6-Cyclopropylimidazo[1,5-a]pyridin-5-yl)(4-(4-(trifluoromethoxy)phenyl) cyclohexyl) methanone (550 mg, 1.28 mmol) in MeOH (30 mL) was added NaBH$_4$ (97 mg, 2.56 mmol), the mixture was stirred at room temperature for 1 hour. The residue was quenched with EA/H$_2$O (100 mL/50 mL), the organic layer was washed with brine (50 mL), dried with Na$_2$SO$_4$ and concentrated. The crude product was purified by silica gel on chromatography (PE:EA=20:1-1:1) to give (6-cyclopropylimidazo[1,5-a]pyridin-5-yl)(4-(4-(trifluoromethoxy)phenyl) cyclohexyl)methanol (400 mg) as yellow solid. LC-MS (M+H)$^+$=431. $^1$H NMR (DMSO-d$_6$) $\delta_H$ 8.62 (s, 1H), 7.40 (d, J=9.2 Hz, 1H), 7.22-7.34 (m, 4H), 6.47 (d, J=9.6 Hz, 1H), 6.23 (s, 1H), 5.81 (d, J=3.6 Hz, 1H), 5.24-5.28 (m, 1H), 2.41-2.44 (m, 1H), 2.21-2.23 (m, 1H), 1.89-2.01 (m, 2H), 1.48-1.69 (m, 2H), 1.17-1.33 (m, 4H), 0.90-0.94 (m, 2H), 0.63-0.79 (m, 2H);

Example D105a and D105b: (S)-(6-cyclopropylimidazo[1,5-a]pyridin-5-yl)((1r,4S)-4-(4-(trifluoromethoxy)phenyl)cyclohexyl)methanol and (R)-(6-cyclopropylimidazo[1,5-a]pyridin-5-yl)((1r,4R)-4-(4-(trifluoromethoxy)phenyl)cyclohexyl)methanol

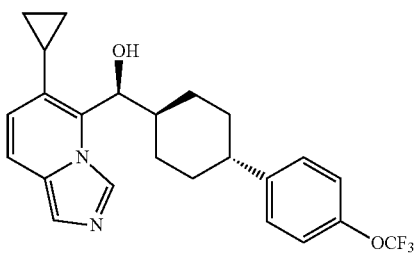

Fast isomer in chiral IC HPLC
Eluting reagent: Hex:EtOH = 70:30 (V/V)

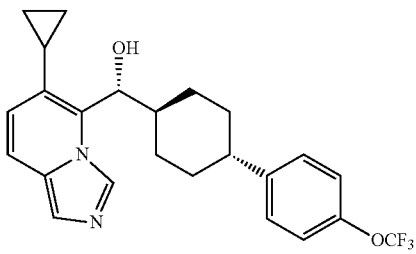

Slow isomer in chiral IC HPLC
Eluting reagent: Hex:EtOH = 70:30 (V/V)

Each enantiomer of racemic D105a and D105b was separated using preparative HPLC on a Chiralpak IC with Hex:EtOH=70:30(V/V) as an eluent. The enantiomeric excesses were determined by using HPLC on a Chiralpak IC-3 with Hex (0.1% DEA):EtOH=60:40(V/V) as an eluent at a flow rate of 1.0 ml/min. The first one enantiomer eluted at the retention time of 1.6 min, and then was dissolved in 4 M HCl(gas)/EA and stirred for 0.5 h, concerned in vocuo to give D105a, $^1$H NMR (DMSO-d$_6$) $\delta_H$ 9.65 (s, 1H), 8.08 (s, 1H), 7.71 (d, 1H, J=9.6 Hz), 7.24-7.31 (m, 4H), 6.84 (d, 1H, J=9.6 Hz), 6.23 (s, 1H), 5.32 (d, 1H, J=9.6 Hz), 2.40 (m, 1H), 2.16 (m, 2H), 1.89 (m, 1H), 1.68 (m, 1H), 1.45-1.52 (m, 1H), 1.24-1.29 (m, 4H), 1.01-1.07 (m, 2H), 0.76-0.86 (m, 2H); and the other enantiomer eluted at the retention time of 2.3 min, and then was dissolved in 4 M HCl(gas)/EA and stirred for 0.5 h, concerned in vocuo to give D105b, $^1$H NMR (DMSO-d$_6$) $\delta_H$ 9.66 (s, 1H), 8.09 (s, 1H), 7.71 (d, J=9.6 Hz, 1H), 7.24-7.31 (m, 4H), 6.84 (d, J=9.6 Hz, 1H), 6.25 (s, 1H), 5.32 (d, J=9.6 Hz, 1H), 2.40 (m, 1H), 2.16 (m, 2H), 1.89 (m, 1H), 1.68 (m, 1H), 1.45-1.52 (m, 1H), 1.16-1.29 (m, 4H), 1.03-1.05 (m, 2H), and 0.76-0.86 (m, 2H). The absolute configurations of chiral carbons in D105a and D105b are tentatively assigned as (S) and (R) respectively based on assumption that the binding model of the more potent isomer D105a is the same as that of C101a with IDO1 enzyme, and the relative stereochemistry on cyclohexane is assigned as trans configuration on the cyclohexane.

Example D106: 4-(4-((6-cyclopropylimidazo[1,5-a]pyridin-5-yl)(hydroxy)methyl) cyclohexyl)phenol

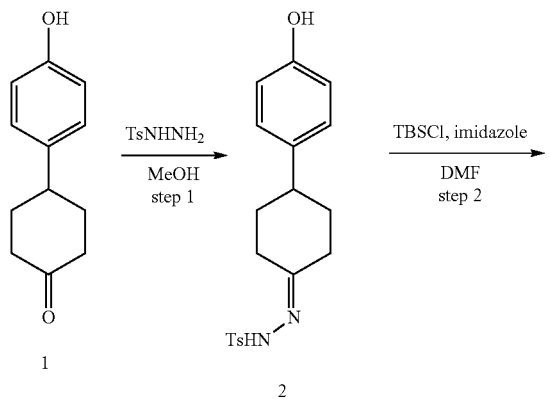

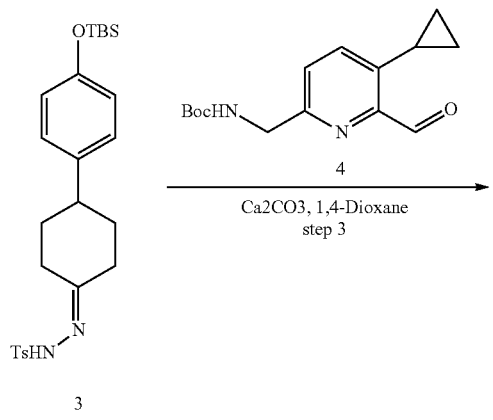

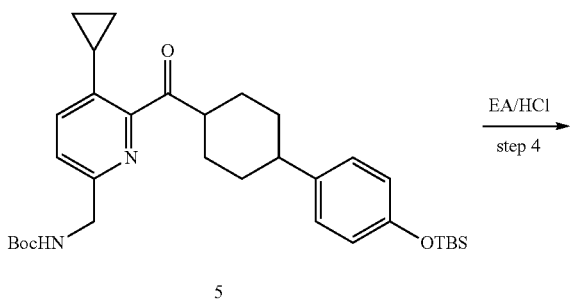

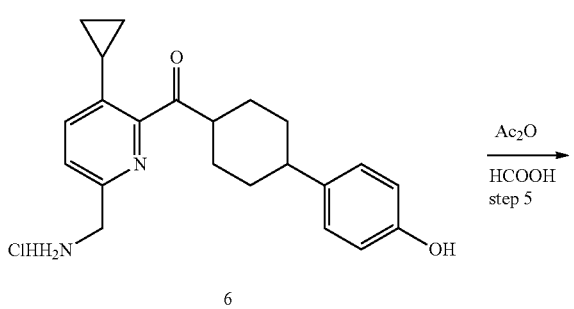

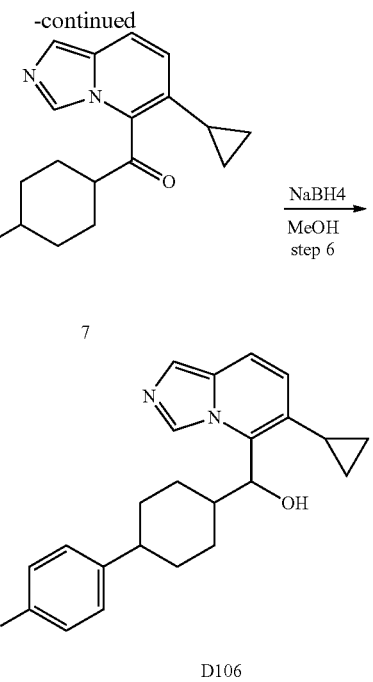

Step 1: N'-(4-(4-hydroxyphenyl)cyclohexylidene)-methylbenzenesulfonohydrazide To a solution of 4-(4-hydroxyphenyl)cyclohexan-1-one (10 g, 52.63 mmol) in methanol (200 mL) was added 4-methylbenzenesulfonohydrazide (9.79 g, 52.63 mmol) at room temperature, and the mixture was stirred for 5 hours, then filtered to give the product as a white solid (15 g in 79% yield). MS (ESI) m/e [M+1]$^+$=359.

Step 2: N'-(4-(4-((tert-butyldimethylsilyl)oxy)phenyl)cyclohexylidene)-4-methylbenzenesulfonohydrazide To a solution of N'-(4-(4-hydroxyphenyl)cyclohexylidene)-4-methylbenzenesulfonohydrazide (2 g in 20 mL DMF) was added TBSCl (1.09 g, 7.26 mmol) and imidazole (0.76 g, 11.18 mmol), the mixture was stirred at 70° C. overnight. TLC (PE:EA=3:1, Rf=0.5) showed the reaction was completed. H$_2$O (100 ml) was added to the mixture, extracted with EA (50 ml×3). The combined organic layer was dried over Na$_2$SO$_4$, filtered and concentrated to give crude product, which was purified by silica gel chromatography (PE:EA=20:1-6:1) to give N'-(4-(4-((tert-butyldimethylsilyl)oxy)phenyl)cyclohexylidene)-4-methylbenzenesulfonohydrazide (2.6 g, 99%) as a white solid.

Step 3: tert-butyl ((6-(4-(4-((tert-butyldimethylsilyl)oxy)phenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (1.0 g, 3.6 mmol) in 1,4-dioxane (0.2 L) was added N'-(4-(4-((tert-butyldimethylsilyl)oxy)phenyl)cyclohexylidene)-4-methylbenzenesulfonohydrazide (2.0 g, 4.3 mmol) and Cs$_2$CO$_3$ (1.8 g, 5.4 mmol) at room temperature, and the mixture was heated at 100° C. for 6 hours. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (1.1 g in 55% yield). $^1$H NMR (DMSO-d$_6$) $\delta_H$ 7.45 (d, J=8.0 Hz, 2H), 7.30 (d, J=8.0 Hz, 1H), 7.11 (d, J=8.0 Hz, 2H), 6.75 (d, J=8.4 Hz, 2H), 4.23 (d, J=6.4 Hz, 2H), 2.29-2.33 (m, 1H), 1.85-1.94 (m, 4H), 1.46-1.56 (m, 4H), 1.40 (s, 9H), 1.27 (s, 1H), 0.94-0.97 (m, 11H), 0.65-0.69 (m, 2H), 0.17 (s, 6H).

Step 4: (6-(aminomethyl)-3-cyclopropylpyridin-2-yl)(4-(4-hydroxyphenyl)cyclohexyl) methanone hydrochloride A mixture of ((6-(4-(4-((tert-butyldimethylsilyl)oxy)phenyl)cyclohexane-1-carbonyl)-5-cyclopropylpyridin-2-yl)methyl)carbamate (1.1 g, 1.9 mmol) and EA/HCl (10 mL, 4.0 M) was stirred at room temperature for two hours, the solvent was evaporated under reduced pressure to give crude product as solid. $^1$H NMR (DMSO-d$_6$) $\delta_H$ 8.43 (s, 2H), 7.53 (s, 2H), 7.02 (d, J=8.4 Hz, 2H), 6.68 (d, J=8.4 Hz, 2H), 4.19-4.23 (m, 2H), 3.72-3.78 (m, 1H), 2.41 (s, 1H), 2.30-2.33 (m, 1H), 1.83-1.93 (m, 3H), 1.44-1.54 (m, 3H), 1.04-1.07 (m, 1H), 0.97-1.02 (m, 2H), 0.71-0.74 (m, 2H).

Step 5: 4-(4-(6-cyclopropylimidazo[1,5-a]pyridine-5-carbonyl)cyclohexyl)phenyl acetate A mixture of Ac$_2$O (30 mL) and HCOOH (30 mL) was heated at 50° C. for 1 hour, then the solution of (6-(aminomethyl)-3-cyclopropylpyridin-2-yl)(4-(4-hydroxyphenyl) cyclohexyl)methanone hydrochloride (crude, 1.9 mmol) in HCOOH (20 mL) was added by dropwised, and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give crude product as a solid (0.5 g in 65% yield). $^1$H NMR (DMSO-d$_6$) $\delta_H$ 8.10 (s, 1H), 7.61 (d, J=9.6 Hz, 1H), 7.44 (s, 1H), 7.26 (d, J=8.4 Hz, 2H), 7.02 (d, J=8.4 Hz, 2H), 6.50 (d, J=8.4 Hz, 1H), 2.54-2.59 (m, 1H), 2.24 (s, 3H), 2.03-2.06 (m, 2H), 1.86-1.90 (m, 3H), 1.52-1.66 (m, 4H), 0.98-1.01 (m, 2H), 0.75-0.78 (m, 2H).

Step 6: 4-(4-((6-cyclopropylimidazo[1,5-a]pyridin-5-yl)(hydroxy methyl)cyclohexyl)phenol

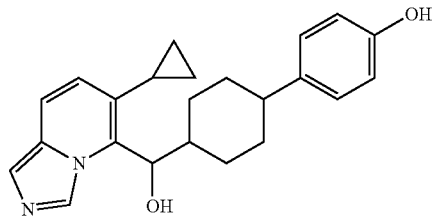 [SMILES: Oc1ccc(C2CCC(C(O)c3c(C4CC4)ccc4cncn34)CC2)cc1]

To a solution of 4-(4-(6-cyclopropylimidazo[1,5-a]pyridine-5-carbonyl) cyclohexyl)-phenyl acetate (1.063 g, 2.6 mmol) in methanol (100 mL) was added NaBH$_4$ (0.6 g, 15 mol) at room temperature, and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (810 mg in 86% yield). $^1$H NMR (DMSO-d$_6$) $\delta_H$ 9.07 (s, 1H), 8.61 (s, 1H), 7.39 (d, J=9.2 Hz, 1H), 7.31 (s, 1H), 6.97 (d, J=8.4 Hz, 2H), 6.62 (d, J=8.4 Hz, 2H), 6.47 (d, J=9.6 Hz, 1H), 5.78 (d, J=3.6 Hz, 1H), 5.24 (dd, J=4.0, 9.2 Hz, 1H), 2.33-2.38 (m, 2H), 2.14-2.20 (m, 1H), 2.00 (s, 1H), 1.82-1.86 (m, 1H), 1.62-1.65 (m, 1H), 1.38-1.48 (m, 1H), 1.12-1.30 (m, 4H), 0.92-0.98 (m, 2H), 0.73-0.79 (m, 1H), and 0.63-0.67 (m, 1H).

Example D106a and D106b: 4-((1S,4r)-4-((S)-(6-cyclopropylimidazo[1,5-a] pyridin-5-yl)(hydroxy)methyl)cyclohexyl)phenol and 4-((1R,4r)-4-((R)-(6-cyclopropylimidazo [1,5-a]pyridin-5-yl)(hydroxy)methyl)cyclohexyl)phenol

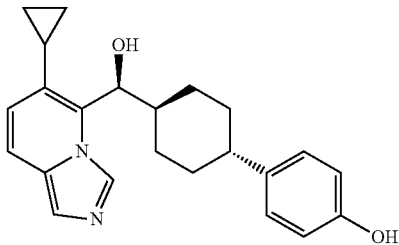

Fast isomer in CHIRALCEL OD-3 HPLC
Eluting reagent: CO$_2$:MeOH = 50:50

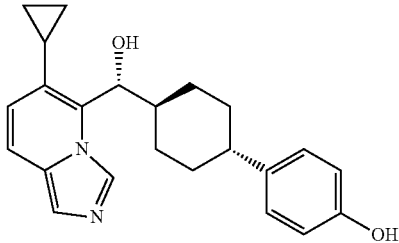

Slow isomer in CHIRALCEL OD-3 HPLC
Eluting reagent: CO$_2$:MeOH = 50:50

Each enantiomer of racemic D106a and D106b was separated using preparative HPLC on a CHIRALCEL OD-3 CO$_2$:MeOH=50:50 as an eluent. The enantiomeric excesses were determined by using HPLC on a CHIRALCEL OD-3 with MeOH (20 mM NH$_3$) as an eluent at a flow rate of 1.0 mL/min. The first one enantiomer eluted at the retention time of 2.237 min, $^1$H NMR (DMSO-d$_6$) $\delta_H$ 9.07 (s, 1H), 8.61 (s, 1H), 7.39 (d, J=9.2 Hz, 1H), 7.31 (s, 1H), 6.97 (d, J=8.4 Hz, 2H), 6.63 (d, J=8.4 Hz, 2H), 6.47 (d, J=9.2 Hz, 1H), 5.78 (d, J=3.6 Hz, 1H), 5.25 (dd, J=4.0, 9.2 Hz, 1H), 2.32-2.42 (m, 2H), 2.13-2.22 (m, 1H), 1.98-2.00 (m, 1H), 1.83-1.86 (m, 1H), 1.62-1.64 (m, 1H), 1.38-1.47 (m, 1H), 1.13-1.30 (m, 4H), 0.92-0.98 (m, 2H), 0.75-0.79 (m, 1H), and 0.63-0.66 (m, 1H): and the other enantiomer eluted at the retention time of 2.630 min, $^1$H NMR (DMSO-d$_6$) $\delta_H$ 9.07 (s, 1H), 8.61 (s, 1H), 7.39 (d, J=9.2 Hz, 1H), 7.31 (s, 1H), 6.97 (d, J=8.4 Hz, 2H), 6.63 (d, J=8.4 Hz, 2H), 6.47 (d, J=9.2 Hz, 1H), 5.78 (d, J=3.6 Hz, 1H), 5.25 (dd, J=4.0, 9.2 Hz, 1H), 2.32-2.42 (m, 2H), 2.13-2.22 (m, 1H), 1.98-2.00 (m, 1H), 1.83-1.86 (m, 1H), 1.62-1.64 (m, 1H), 1.38-1.47 (m, 1H), 1.13-1.30 (m, 4H), 0.92-0.98 (m, 2H), and 0.64-0.75 (m, 2H). The absolute configurations of chiral carbons in D106a and D106b are tentatively assigned as (S) and (R)

respectively based on assumption that the binding model of the more potent isomer D106a is the same as that of C101a with IDO1 enzyme, and the relative stereochemistry on cyclohexane is assigned as trans configuration on the cyclohexane.

Example D107: (6-cyclopropylimidazo[1,5-a]pyridin-5-yl)(4-(6-(trifluoromethyl) pyridin-3-yl)cyclohexyl)methanol

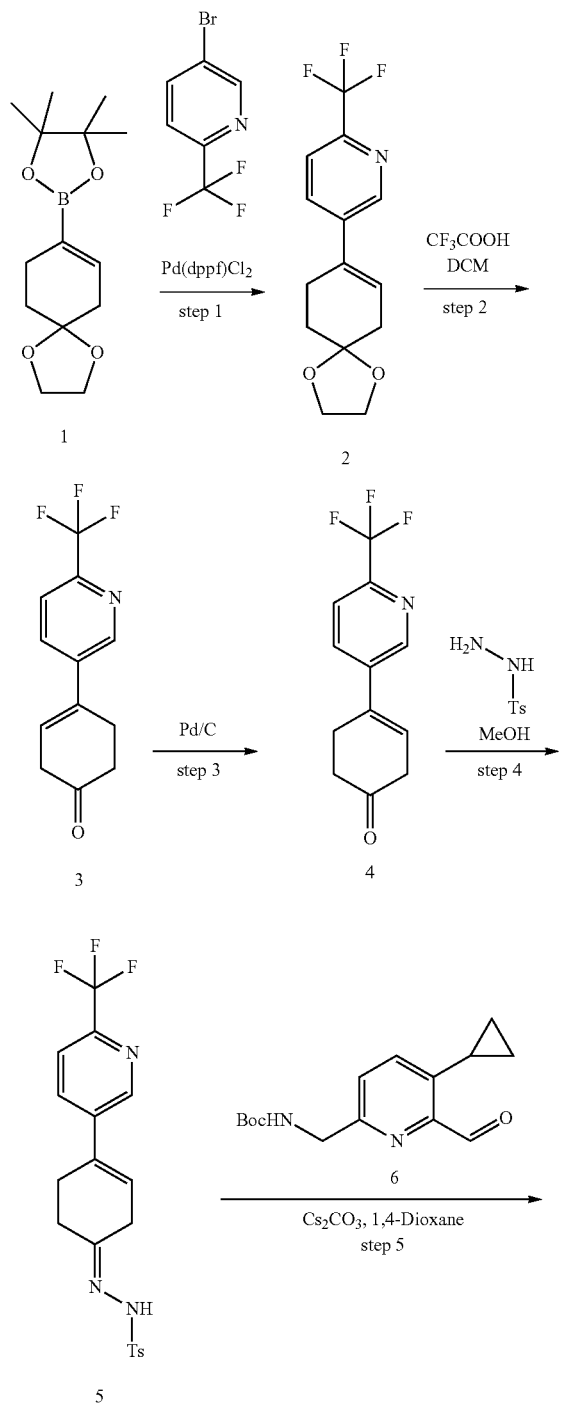

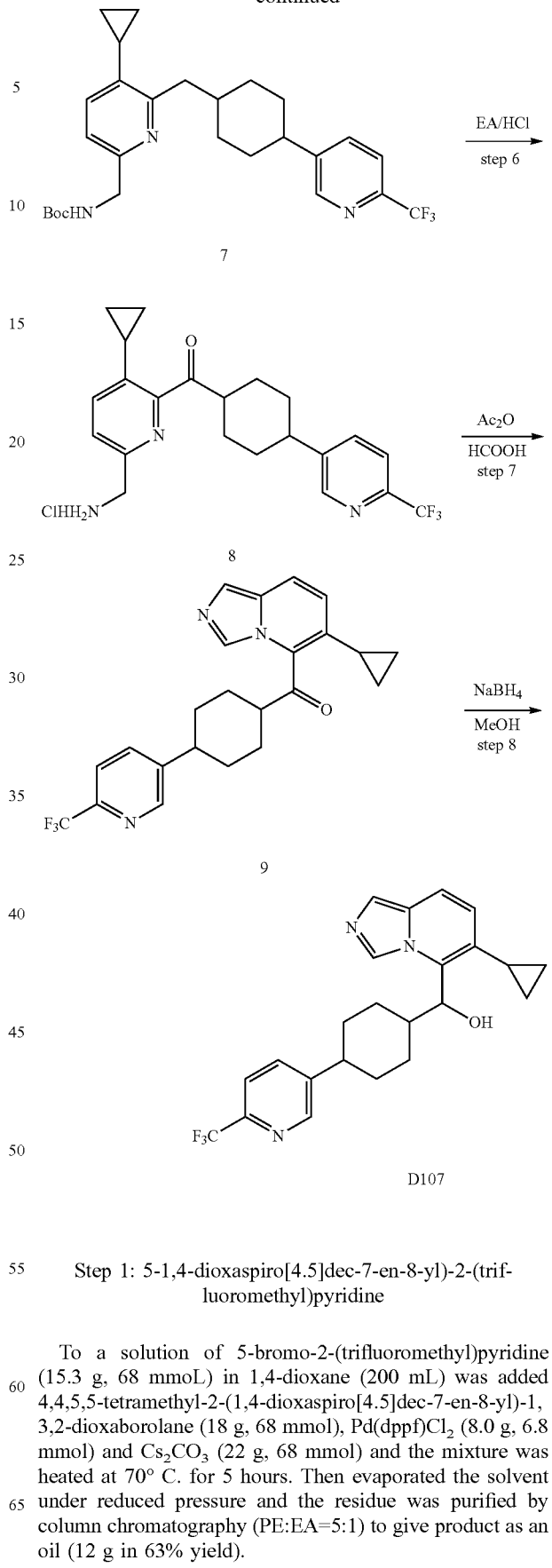

Step 1: 5-1,4-dioxaspiro[4.5]dec-7-en-8-yl)-2-(trifluoromethyl)pyridine

To a solution of 5-bromo-2-(trifluoromethyl)pyridine (15.3 g, 68 mmoL) in 1,4-dioxane (200 mL) was added 4,4,5,5-tetramethyl-2-(1,4-dioxaspiro[4.5]dec-7-en-8-yl)-1,3,2-dioxaborolane (18 g, 68 mmol), Pd(dppf)Cl$_2$ (8.0 g, 6.8 mmol) and Cs$_2$CO$_3$ (22 g, 68 mmol) and the mixture was heated at 70° C. for 5 hours. Then evaporated the solvent under reduced pressure and the residue was purified by column chromatography (PE:EA=5:1) to give product as an oil (12 g in 63% yield).

Step 2: 4-(6-(trifluoromethyl)pyridin-3-yl)cyclohex-3-en-1-one

To a solution of 5-(1,4-dioxaspiro[4.5]dec-7-en-8-yl)-2-(trifluoromethyl)pyridine (12 g, 42 mmol) in dichloromethane (100 mL) was added trifluoroacetic acid (50 mL) at room temperature and the mixture was stirred for overnight. The solvent was evaporated under reduced pressure and water (100 mL) was added, extracted with ethyl acetate (100 mL×3), combined the organic layer and washed with saturated aqueous of $NaHCO_3$, then the organic layer was evaporated in vacuo to give crude product, which was used for next step without further purification.

Step 3: 4-(6-(trifluoromethyl)pyridin-3-yl)cyclohexan-1-one

To a solution of 4-(6-(trifluoromethyl)pyridin-3-yl)cyclohex-3-en-1-one (42 mmol) in ethyl acetate (200 mL) was added Pd/C (2.0 g, 10%) and the mixture was stirred for 6 hours at room temperature under $H_2$ (0.4 Mpa). Then filtered to remove Pd/C and the filtrate was evaporated under reduced pressure to give a crude product, and then purified by column chromatography (PE as eluent) to give product (12 g, oil).

Step 4: 4-methyl-N'-(4-(6-(trifluoromethyl)pyridin-3-yl)cyclohexylidene)benzenesulfonohydrazide To a solution of 4-(6-(trifluoromethyl)pyridin-3-yl)cyclohexan-1-one (12 g, 49 mmol) in methol (100 mL) was added 4-methylbenzenesulfonohydrazide (9.1 g, 49 mmol) at room temperature and the mixture was stirred for overnight. Evaporate half the solvent under reduced pressure and then filtered to give product as a white solid (9.0 g in 45% yield). $^1$H NMR (DMSO-$d_6$) $\delta_H$ 10.23 (s, 1H), 8.68 (d, J=1.6 Hz, 1H), 7.95 (d, J=8.0 Hz, 1H), 7.81 (d, J=8.0 Hz, 1H), 7.74 (d, J=8.4 Hz, 2H), 7.40 (d, J=8.0 Hz, 2H), 2.92-3.02 (m, 2H), 2.39 (s, 3H), 2.27-2.30 (m, 2H), 1.94-2.00 (m, 3H), 1.55-1.67 (m, 2H).

Step 5: tert-butyl ((5-cyclopropyl-6-(4-(6-(trifluoromethyl)pyridin-3-yl)cyclohexane-1-carbonyl)pyridin-2-yl)methyl)carbamate To a solution of tert-butyl ((5-cyclopropyl-6-formylpyridin-2-yl)methyl)carbamate (1.0 g, 3.6 mmol) in 1,4-dioxane (0.1 L) was added 4-methyl-N'-(4-(6-(trifluoromethyl)pyridin-3-yl)cyclohexylidene)benzenesulfonohydrazide (1.8 g, 4.3 mmol) and $Cs_2CO_3$ (1.8 g, 5.4 mmol) at room temperature, and the mixture was heated at 100° C. for 6 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (0.4 g in 27% yield). [M+H]$^+$=504.2

Step 6: (6-(aminomethyl)-3-cyclopropylpyridin-2-yl)(4-(6-(trifluoromethyl)pyridin-3-yl) cyclohexyl) ethanone Trifluoracetic acid To a solution of tert-butyl ((5-cyclopropyl-6-(4-(6-(trifluoromethyl)pyridin-3-yl)cyclohexane-1-carbonyl)pyridin-2-yl)methyl)carbamate (0.4 g, 0.8 mmol) in DCM (40 mL) was added trifluoroacetic acid (10 mL) and the mixture was stirred at room temperature for overnight. The solvent was evaporated under reduced pressure to give crude product as solid. [M+H]$^+$=404.1.

Step 7: (6-cyclopropylimidazo[1,5-a]pyridin-5-yl)(4-(6-(trifluoromethyl)pyridin-3-yl) cyclohexyl) methanone A mixture of $Ac_2O$ (30 mL) and HCOOH (10 mL) was heated at 50° C. for 1 hour and then a solution of (6-(aminomethyl)-3-cyclopropylpyridin-2-yl)(4-(6-(trifluoromethyl) pyridin-3-yl)cyclohexyl)methanone Trifluoracetic acid (crude, 0.8 mmol) in HCOOH (5 mL) was added drop wise and the mixture was heated at 50° C. for 2 hours. The solvent was evaporated under reduced pressure and water (100 mL) was added, washed with saturated aqueous of $NaHCO_3$, then extracted with ethyl acetate (50 mL×3) and combined the organic layer, the solvent was evaporated under reduced pressure and the residue was purified by column chromatography (PE:EA=4:1) to give crude product as a solid (0.1 g in 30% yield). $^1$H NMR (DMSO-$d_6$) $\delta_H$ 8.68 (s, 1H), 8.11 (s, 1H), 7.95 (d, J=8.0 Hz, 1H), 7.83 (d, J=8.0 Hz, 1H), 7.62 (d, J=9.6 Hz, 1H), 7.45 (s, 1H), 6.50 (d, J=7.2 Hz, 1H), 2.73-2.75 (m, 1H), 2.07-2.09 (m, 2H), 1.87-1.93 (m, 3H), 1.58-1.72 (m, 4H), 0.98-1.03 (m, 2H), 0.74-0.78 (m, 2H). [M+H]$^+$=414.1.

Step 8: (6-cyclopropylimidazo[1,5-a]pyridin-5-yl)(4-(6-(trifluoromethyl)pyridin-3-yl) cyclohexyl) methanol

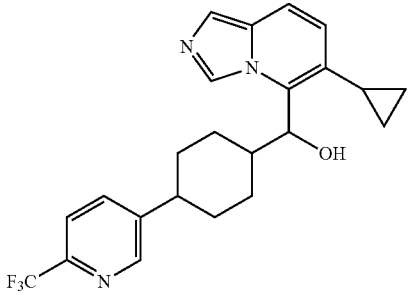 [SMILES: OC(c1c(C2CC2)ccc2cncn12)C1CCC(c2ccc(C(F)(F)F)nc2)CC1]

To a solution of (6-cyclopropylimidazo[1,5-a]pyridin-5-yl)(4-(6-(trifluoromethyl) pyridin-3-yl)cyclohexyl)methanone (0.1 g, 0.24 mmol) in methol (10 mL) was added $NaBH_4$ (50 mg, 1.2 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (60 mg in 60% yield). $^1$H NMR (DMSO-$d_6$) $\delta_H$ 8.65 (s, 1H), 8.63 (s, 1H), 7.92 (d, J=8.0 Hz, 1H), 7.79 (d, J=8.0 Hz, 1H), 7.41 (d, J=9.2 Hz, 1H), 7.32 (s, 1H), 6.48 (d, J=9.6 Hz, 1H), 5.84 (d, J=3.6 Hz, 1H), 5.27 (d, J=9.2 Hz, 1H), 2.64-2.70 (m, 1H), 2.44-2.47 (m, 1H), 2.14-2.20 (m, 1H), 2.21-2.29 (m, 1H), 1.99-2.08 (m, 1H), 1.92-1.95 (m, 1H), 1.69-1.72 (m, 1H), 1.54-1.63 (m, 1H), 1.16-1.41 (m, 4H), 0.90-1.01 (m, 2H), 0.77-0.81 (m, 1H), 0.63-0.67 (m, 1H). [M+H]$^+$=416.2.

Example D107a and D107b: (S)-(6-cyclopropylimidazo[1,5-a]pyridin-5-yl) ((1r,4S)-4-(6-(trifluoromethyl)pyridin-3-yl)cyclohexyl)methanol and (R)-(6-cyclopropylimidazo [1,5-a]pyridin-5-yl)((1 r,4R)-4-(6-(trifluoromethyl)pyridin-3-yl)cyclohexyl)methanol

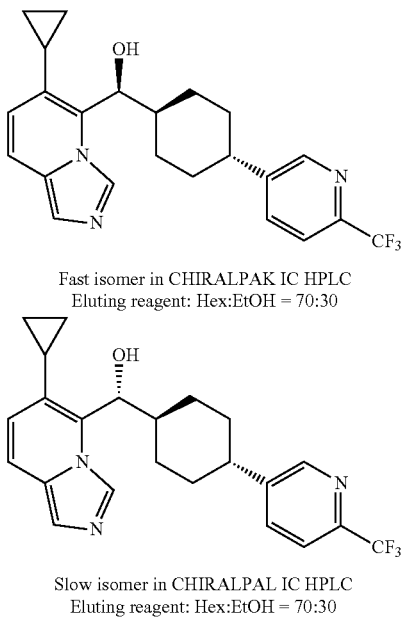

Fast isomer in CHIRALPAK IC HPLC
Eluting reagent: Hex:EtOH = 70:30

Slow isomer in CHIRALPAL IC HPLC
Eluting reagent: Hex:EtOH = 70:30

Each enantiomer of racemic D107a and D107b was separated using preparative HPLC on a CHIRALPAK IC with Hex:EtOH=70:30 as an eluent. The enantiomeric excesses were determined by using HPLC on a CHIRALPAK IC-3 with Hex (0.2% IPAmine):EtOH=50:50 as an eluent at a flow rate of 1.0 ml/min. The first one enantiomer eluted at the retention time of 2.024 min, and the other enantiomer eluted at the retention time of 3.606 min. To a solution of D107a (34 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (38 mg in 92% yield). $^1$H NMR (DMSO-$d_6$) $\delta_H$ 9.48 (s, 1H), 8.65 (s, 1H), 7.95 (s, 1H), 7.91 (d, J=8.4 Hz, 1H), 7.80 (d, J=8.0 Hz, 1H), 7.66 (d, J=9.6 Hz, 1H), 6.78 (d, J=9.6 Hz, 1H), 6.18 (s, 1H), 5.33 (d, J=9.6 Hz, 1H), 2.65-2.71 (m, 1H), 2.42-2.45 (m, 1H), 2.16-2.23 (m, 2H), 1.94-1.97 (m, 1H), 1.73-1.76 (m, 1H), 1.52-1.61 (m, 1H), 1.26-1.40 (m, 4H), 0.99-1.05 (m, 2H), 0.85-0.87 (m, 1H), and 0.75-0.78 (m, 1H). [M+H]$^+$=416.1. To a solution of D107b (31 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (32 mg in 84% yield). $^1$H NMR (DMSO-$d_6$) $\delta_H$ 9.49 (s, 1H), 8.65 (s, 1H), 7.95 (s, 1H), 7.91 (d, J=8.4 Hz, 1H), 7.80 (d, J=8.0 Hz, 1H), 7.66 (d, J=9.6 Hz, 1H), 6.78 (d, J=9.6 Hz, 1H), 6.15 (s, 1H), 5.33 (d, J=9.6 Hz, 1H), 2.65-2.71 (m, 1H), 2.42-2.45 (m, 1H), 2.16-2.23 (m, 2H), 1.94-1.97 (m, 1H), 1.73-1.76 (m, 1H), 1.52-1.61 (m, 1H), 1.26-1.40 (m, 4H), 0.99-1.05 (m, 2H), 0.85-0.87 (m, 1H), and 0.75-0.78 (m, 1H). [M+H]$^+$=416.1. The absolute configurations of chiral carbons in D107a and D107b are tentatively assigned as (S) and (R) respectively based on assumption that the binding model of the more potent isomer D107a is the same as that of C101a with IDO1 enzyme, and the relative stereochemistry on cyclohexane is assigned as trans configuration on the cyclohexane.

Example D108: 3-chloro-2-(4-(4-((6-cyclopropylimidazo[1,5-a]pyridin-5-yl) (hydroxy)methyl)cyclohexyl)phenoxy)propan-1-ol

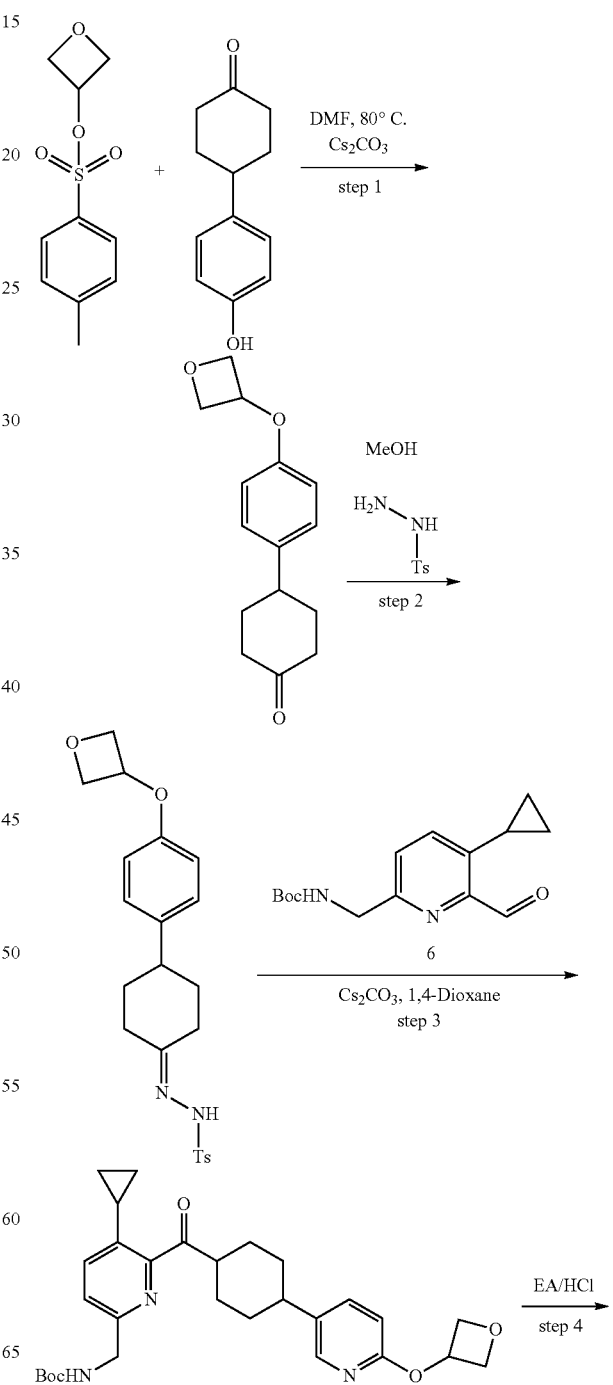

-continued

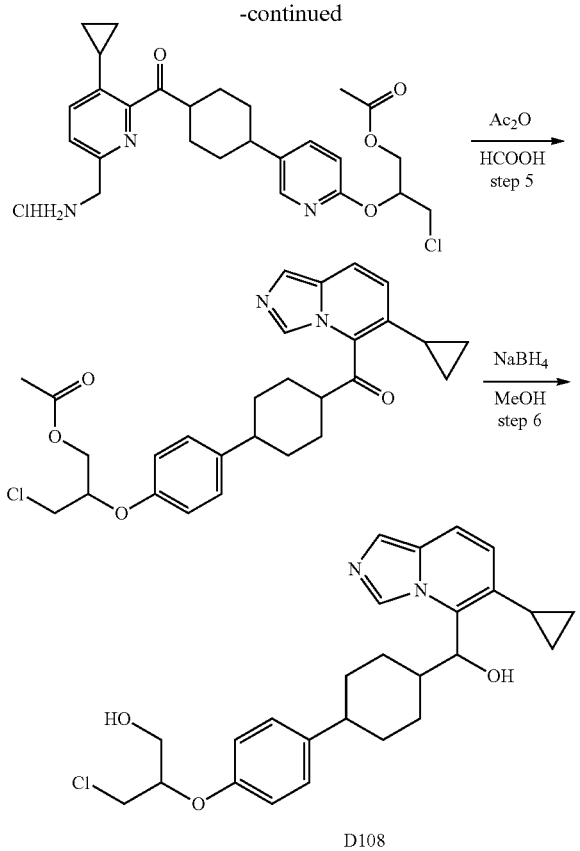

To a solution of 4-(4-hydroxyphenyl)cyclohexan-1-one (19 g, 100 mmol) in DMF (100 mL) was added oxetan-3-yl 4-methylbenzenesulfonate (23 g, 100 mmol) and Cs$_2$CO$_3$ (33 g, 100 mmol) and the mixture was heated at 80° C. for 24 hours. Then the solvent was evaporated under reduced pressure, the crude product was purified by column chromatography (PE:EA=5:1) to give product as white solid (19 g in 7063% yield). $^1$H NMR (DMSO-d$_6$) δ$_H$ 7.21 (d, J=8.4 Hz, 2H), 6.72 (d, J=8.8 Hz, 2H), 5.21-5.26 (1H), 4.91 (t, J=6.8 Hz, 2H), 4.53 (dd, J=7.2 Hz, 2H), 2.97-3.02 (m, 1H), 2.50-2.60 (m, 2H), 2.23-2.27 (m, 2H), 2.00-2.04 (m, 2H), and 1.77-1.88 (m, 2H).

Step 2: 4-methyl-N'-(4-(4-(oxetan-3-yloxy)phenyl) cyclohexylidene)benzenesulfonohydrazide To a solution of 4-(4-(oxetan-3-yloxy)phenyl)cyclohexan-1-one (19 g, 77 mmol) in methanol (100 mL) was added 4-methylbenzenesulfonohydrazide (14.3 g, 77 mmol) at room temperature and the mixture was stirred for 30 min. Then the mixture was filtered to give product as a white solid (20 g in 63% yield). $^1$H NMR (DMSO-d$_6$) δ$_H$ 10.15 (s, 1H), 7.74 (d, J=8.4 Hz, 2H), 7.39 (d, J=8.0 Hz, 2H), 7.12 (d, J=8.4 Hz, 2H), 6.68 (d, J=8.4 Hz, 2H), 5.19-5.24 (m, 1H), 4.90 (t, J=6.4 Hz, 2H), 4.50-4.54 (m, 2H), 2.89-2.92 (m, 1H), 2.70-2.76 (m, 1H), 2.39 (s, 3H), 2.22-2.45 (m, 2H), 1.86-1.95 (m, 3H), and 1.40-1.51 (m, 2H).

Step 3: tert-butyl ((5-cyclopropyl-6-(4-(4-(oxetan-3-yloxy)phenyl)cyclohexane-1-carbonyl) pyridin-2-yl) methyl)carbamate To a solution of tert-butyl ((5-cyclopropyl-6-formylpyridin-2-yl)methyl)carbamate (1.0 g, 3.6 mmol) in 1,4-dioxane (0.1 L) was added 4-methyl-N'-(4-(4-(oxetan-3-yloxy)phenyl)cyclohexylidene)benzenesulfonohydrazide (2.0 g, 4.3 mmol) and Cs$_2$CO$_3$ (2.0 g, 5.4 mmol) at room temperature and the mixture was heated at 100° C. for 6 hours. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=1:1) to give crude product as a yellow oil (1.5 g in 83% yield). $^1$H NMR (DMSO-d$_6$) δ$_H$ 7.45 (d, J=8.4 Hz, 2H), 7.30 (d, J=8.0 Hz, 1H), 7.16 (d, J=8.4 Hz, 2H), 6.70 (d, J=8.8 Hz, 2H), 5.20-5.25 (m, 1H), 4.90 (t, J=7.2 Hz, 2H), 4.51-4.54 (m, 2H), 4.23 (d, J=6.0 Hz, 1H), 3.58 (s, 1H), 2.26-2.33 (m, 1H), 1.91-1.93 (m, 2H), 1.83-1.85 (m, 2H), 1.63-1.65 (m, 1H), 1.46-1.56 (m, 4H), 1.40 (s, 9H), 1.27-1.32 (m, 1H), 0.93-0.97 (m, 2H), and 0.65-0.69 (m, 2H). [M+H]$^+$=507.2

Step 4: 2-(4-(4-(6-(aminomethyl)-3-cyclopropylpicolinoyl)cyclohexyl)phenoxy)-3-chloropropyl acetate hydrochloride A mixture of ((5-cyclopropyl-6-(4-(4-(oxetan-3-yloxy)phenyl)cyclohexane-1-carbonyl)pyridin-2-yl)methyl)carbamate (1.5 g, 3.0 mmol) and EA/HCl (10 mL, 4M) was stirred for 4 hours. The solvent was evaporated under reduced pressure to give crude product, which was used for next step without purification. [M+H]$^+$=485.2.

Step 5: 3-chloro-2-(4-(4-(6-cyclopropylimidazo[1,5-a]pyridine-5-carbonyl)cyclohexyl)-phenoxy) propyl acetate A mixture of Ac$_2$O (30 mL) and HCOOH (10 mL) was heated at 50° C. for 1 hour and then a solution of 2-(4-(4-(6-(aminomethyl)-3-cyclopropylpicolinoyl)cyclohexyl)phenoxy)-3-chloropropyl acetate hydrochloride (crude, 3.0 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give crude product as a solid (1.0 g in 67% yield). $^1$H NMR (DMSO-d$_6$) δ$_H$ 8.15 (s, 1H), 7.67 (d, J=9.2 Hz, 1H), 7.50 (s, 1H), 7.21 (d, J=8.8 Hz, 2H), 6.99 (d, J=8.8 Hz, 2H), 6.55 (d, J=9.6 Hz, 1H), 4.78-4.83 (m, 1H), 4.27-4.34 (m, 2H), 3.87-3.98 (m, 2H), 2.52 (s, 1H), 2.07-2.11 (m, 4H), 1.89-1.96 (m, 2H), 1.52-1.73 (m, 4H), 1.03-1.08 (m, 2H), and 0.79-0.83 (m, 2H). [M+H]$^+$=495.2.

Step 6: 3-chloro-2-(4-(4-((6-cyclopropylimidazo[1,5-a]pyridin-5-yl)hydroxy)methyl)cyclohexyl) phenoxy)propan-1-ol

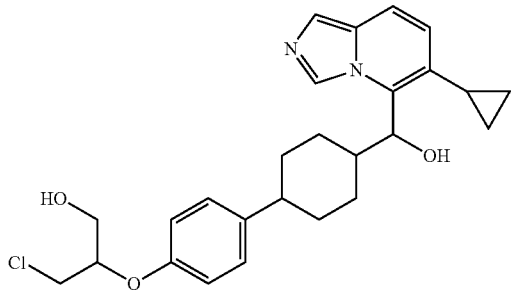 [SMILES: OCC(CCl)Oc1ccc(C2CCC(C(O)c3c(C4CC4)ccc4cncn34)CC2)cc1]

To a solution of 3-chloro-2-(4-(4-(6-cyclopropylimidazo[1,5-a]pyridine-5-carbonyl)cyclohexyl)phenoxy)propyl acetate (1.0 g, 2.0 mmol) in methanol (50 mL) was added NaBH₄ (0.4 mg, 10 mmol) at room temperature and the mixture was stirred for overnight. Then the solvent was evaporated under reduced pressure and water (50 mL) was added, extracted with ethyl acetate (50 mL×3) and combined the organic layer, the solvent was evaporated under reduced pressure to give product as a white solid (0.7 g in 77% yield). ¹H NMR (DMSO-d₆) δ$_H$ 8.66 (s, 1H), 7.44 (d, J=9.6 Hz, 1H), 7.35 (s, 1H), 7.15 (d, J=8.4 Hz, 2H), 6.92 (d, J=8.4 Hz, 2H), 6.51 (d, J=7.2 Hz, 1H), 5.84 (d, J=8.0 Hz, 1H), 5.29 (dd, J=9.6 Hz, 1H), 5.05 (t, J=5.6 Hz, 1H), 4.47 (t, J=4.8 Hz, 1H), 3.91 (d, J=8.0 Hz, 1H), 3.81 (d, J=8.0 Hz, 1H), 3.60-3.67 (m, 2H), 2.45-2.47 (m, 2H), 2.23-2.25 (m, 1H), 2.03-2.04 (m, 1H), 1.89-1.92 (m, 1H), 1.68 (s, 1H), 1.46-1.55 (m, 1H), 1.15-1.36 (m, 4H), 0.94-1.02 (m, 2H), 0.79-0.82 (m, 1H), and 0.68-0.71 (m, 1H). [M+H]⁺=455.2.

Example D109: (6-cyclopropylimidazo[1,5-a]pyridin-5-yl)(4-(4-(oxetan-3-yloxy)phenyl)cyclohexyl)methanol

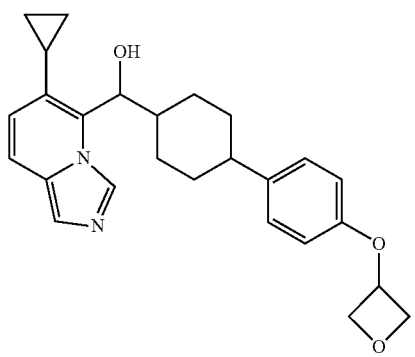 [SMILES: OC(c1c(C2CC2)ccc2cncn12)C1CCC(c2ccc(OC3COC3)cc2)CC1]

To a solution of 3-chloro-2-(4-(4-((6-cyclopropylimidazo[1,5-a]pyridin-5-yl)(hydroxy)methyl)cyclohexyl)phenoxy)propan-1-ol (100 mg, 0.22 mmol) in dry DMF (10 mL) was added NaH (38 mg. 5 eq) at room temperature and the mixture was stirred overnight. Quenched with saturated aqueous of NH₄Cl and extracted with ethyl acetate (50 mL×3) and combined the organic layer, the solvent was evaporated under reduced pressure to give crude product, further purified by Pre-HPLC to give product as a white solid (20 mg in 20% yield). ¹H NMR (DMSO-d₆) δ$_H$ 8.83 (s, 1H), 7.45-7.47 (m, 2H), 7.10 (d, J=8.4 Hz, 2H), 6.66 (d, J=8.4 Hz, 2H), 6.54-6.56 (m, 1H), 5.88 (s, 1H), 5.18-5.28 (m, 2H), 4.88 (t, J=6.4 Hz, 2H), 4.49-4.52 (m, 2H), 2.39-2.42 (m, 2H), 2.17-2.19 (m, 1H), 2.04 (s, 1H), 1.40-1.49 (m, 1H), 1.15-1.24 (m, 4H), 0.96-0.98 (m, 2H), and 0.69-0.80 (m, 2H). [M+H]⁺=419.2.

Example D110: 4-(4-((6-cyclopropylimidazo[1,5-a]pyridin-5-yl)(hydroxy)methyl) cyclohexyl)benzonitrile

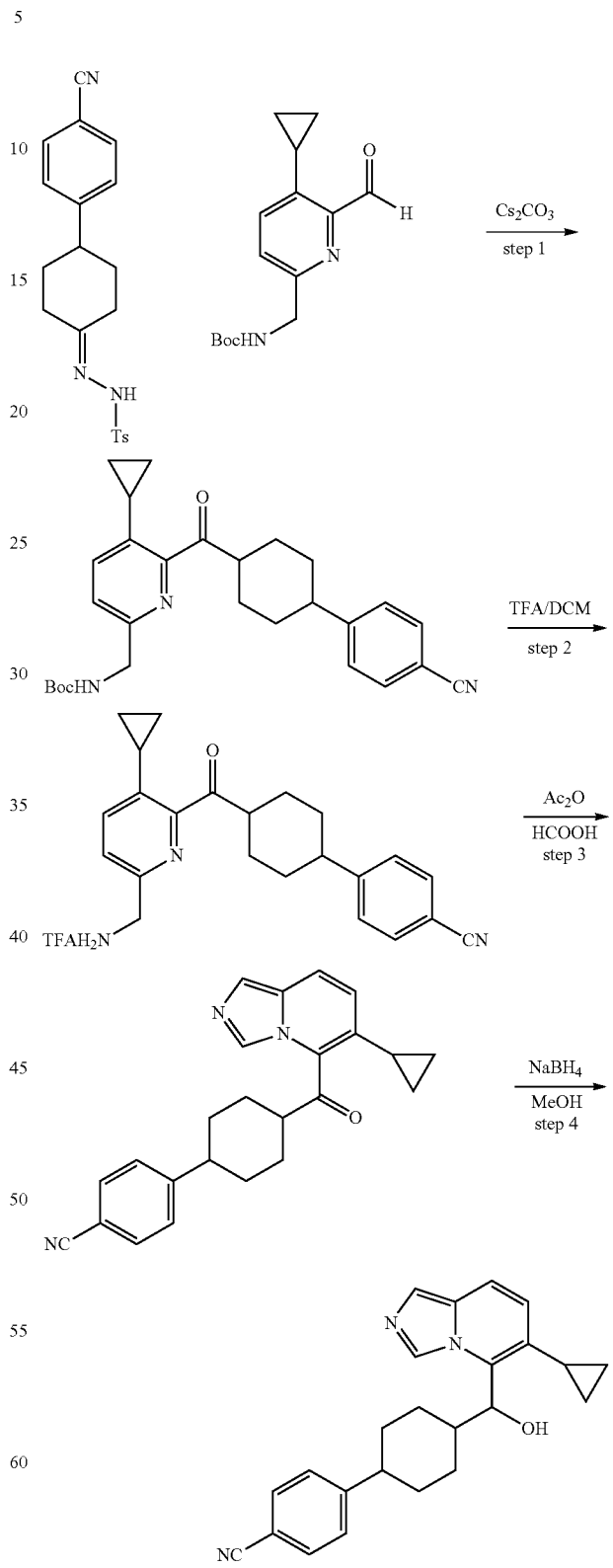

Step 1: tert-butyl ((6-(4-(4-cyanophenyl)cyclo-hexane-1-carbonyl)-5-cyclopropylpyridin-2-yl) methyl)carbamate To a solution of tert-butyl ((5-cyclopropyl-6-formylpyridin-2-yl)methyl) carbamate (0.6 g, 2.2 mmol) in 1,4-dioxane (0.1 L) was added N'-(4-(4-cyanophenyl) cyclohexylidene)-4-methylbenzenesulfonohydrazide (1.6 g, 4.4 mmol) and $Cs_2CO_3$ (1.4 g, 4.4 mmol) at room temperature, and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=5:1) to give crude product as a yellow oil (0.42 g in 42% yield). $[M+H]^+$=460.2

Step 2: 4-(4-(6-(aminomethyl)-3-cyclopropylpicolinoyl)cyclohexyl)benzonitrile To a solution of tert-butyl ((6-(4-(4-cyanophenyl)cyclo-hexane-1-carbonyl)-5-cyclopropylpyridin-2-yl)methyl)carbamate (0.42 g, 0.9 mmol) in DCM (40 mL) was added TFA (10 mL) at room temperature and the mixture was stirred overnight. The solvent was evaporated under reduced pressure and the residue was dissolved in DCM (100 mL), washed with saturated aqueous of $NaHCO_3$ and isolated the organic layer, the solvent was evaporated under reduced pressure and the residue was used for next step without further purification. $[M+H]^+$=360.2.

Step 3: 4-(4-(6-cyclopropylimidazo[1,5-a]pyridine-5-carbonyl)cyclohexyl)benzonitrile A mixture of $Ac_2O$ (30 mL) and HCOOH (10 mL) was heated at 50° C. for 1 hour and then a solution of 4-(4-(6-(aminomethyl)-3-cyclopropylpicolinoyl)cyclohexyl)benzo-nitrile (crude, 0.9 mmol) in HCOOH (5 mL) was added drop wise and the mixture was heated at 50° C. for 2 hours. The solvent was evaporated under reduced pressure and water (100 mL) was added, washed with saturated aqueous of $NaHCO_3$, then extracted with ethyl acetate (50 mL×3) and combined the organic layer, the solvent was evaporated under reduced pressure and the residue was purified by column chromatography (PE:EA=4:1) to give crude product as a solid (0.19 g in 57% yield). $^1$H NMR (DMSO-$d_6$) $\delta_H$ 8.11 (s, 1H), 7.75 (d, J=8.4 Hz, 2H), 7.62 (d, J=8.4 Hz, 1H), 7.46 (d, J=8.4 Hz, 3H), 6.50 (d, J=9.6 Hz, 1H), 2.63-2.69 (m, 1H), 2.04-2.07 (m, 2H), 1.86-1.91 (m, 3H), 1.52-1.70 (m, 4H), 0.97-1.02 (m, 2H), and 0.74-0.78 (m, 2H). $[M+H]^+$=370.2.

Step 4: 4-(4-((6-cyclopropylimidazo[1,5-a]pyridin-5-yl)(hydroxy)methyl)cyclohexyl) benzonitrile

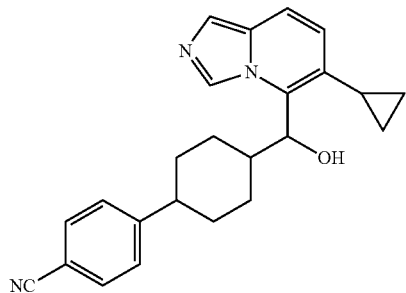 [SMILES: N#Cc1ccc(C2CCC(C(O)c3c(C4CC4)ccc4cncn34)CC2)cc1]

To a solution of 4-(4-(6-cyclopropylimidazo[1,5-a]pyridine-5-carbonyl) cyclohexyl)benzonitrile (0.19 g, 0.51 mmol) in methol (50 mL) was added $NaBH_4$ (100 mg, 2.5 mmol) at room temperature and the mixture was stirred for overnight. Then the solvent was evaporated under reduced pressure and water (50 mL) was added, extracted with ethyl acetate (50 mL×3) and combined the organic layer, the solvent was evaporated under reduced pressure to give product as a white solid (0.14 g in 74% yield). $^1$H NMR (DMSO-$d_6$) $\delta_H$ 8.62 (s, 1H), 7.72 (d, J=8.4 Hz, 2H), 7.42 (d, J=8.4 Hz, 2H), 7.40 (d, J=8.4 Hz, 1H), 7.31 (s, 1H), 6.47 (d, J=9.2 Hz, 1H), 5.82 (d, J=3.6 Hz, 1H), 5.26 (dd, J=9.6 Hz, 1H), 2.55-2.58 (m, 1H), 2.42-2.44 (m, 1H), 2.22-2.24 (m, 1H), 1.99-2.01 (m, 1H), 1.87-1.90 (m, 1H), 1.62-1.68 (m, 1H), 1.49-1.57 (m, 1H), 1.24-1.38 (m, 4H), 0.91-1.00 (m, 2H), 0.76-0.79 (m, 1H), and 0.63-0.67 (m, 1H). $[M+H]^+$=372.2.

Example D110 and D110b: 4-((1S,4r)-4-((S)-(6-cyclopropylimidazo[1,5-a]pyridin-5-yl)(hydroxy)methyl)cyclohexyl)benzonitrile and 4-((1R,4r)-4-((R)-(6-cyclopropylimidazo[1,5-a]pyridin-5-yl)(hydroxy)methyl)cyclohexyl)benzonitrile

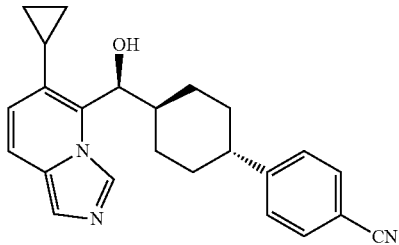

Fast isomer in CHIRALART Cellulose-SB HPLC
Eluting reagent: Hex:EtOH = 80:20

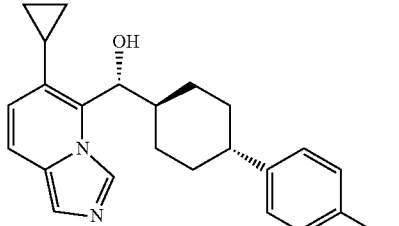

Slow isomer in CHIRALART Cellulose-SB HPLC
Eluting reagent: Hex:EtOH = 80:20

Each enantiomer of racemic D110a and D110b was separated using preparative HPLC on a CHIRALART Cellulose-SB with Hex:EtOH=80:20 as an eluent. The enantiomeric excesses were determined by using HPLC on a CHIRAL Cellulose-SB with Hex (0.2% IPAmine):EtOH=80:20 as an eluent at a flow rate of 1.0 mL/min. The first one enantiomer eluted at the retention time of 4.598 min (D110a), which was dissolved in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-$d_6$) $\delta_H$ 9.63 (s, 1H), 8.07 (s, 1H), 7.70-7.74 (m, 3H), 7.41 (d, 2H, J=8.4 Hz), 6.84 (d, 2H, J=9.6 Hz), 6.24 (s, 1H), 5.33 (d, 1H, J=9.6 Hz), 2.57-2.62 (m, 1H), 2.40-2.43 (m, 1H), 2.18

(s, 2H), 1.90-1.93 (m, 1H), 1.69 (s, 1H), 1.47-1.55 (m, 1H), 1.27-1.40 (m, 4H), 1.00-1.09 (m, 2H), 0.85-0.88 (m, 1H), 0.76-0.79 (m, 1H); and the other enantiomer eluted at the retention time of 8.431 min (D110b), which was dissolved in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid. $^1$H NMR (DMSO-d$_6$) $\delta_H$ 9.63 (s, 1H), 8.07 (s, 1H), 7.70-7.74 (m, 3H), 7.41 (d, J=8.4 Hz, 2H), 6.84 (d, J=9.6 Hz, 2H), 6.23 (s, 1H), 5.33 (d, J=8.4 Hz, 1H), 2.57-2.62 (m, 1H), 2.40-2.43 (m, 1H), 2.18 (s, 2H), 1.90-1.93 (m, 1H), 1.69 (s, 1H), 1.46-1.55 (m, 1H), 1.25-1.39 (m, 4H), 1.00-1.09 (m, 2H), 0.85-0.88 (m, 1H), 0.76-0.79 (m, 1H). The absolute configurations of chiral carbons in D110a and D110b are tentatively assigned as (S) and (R) respectively based on assumption that the binding model of the more potent isomer D110a is the same as that of C101a with IDO1 enzyme, and the relative stereochemistry on cyclohexane is assigned as trans configuration on the cyclohexane.

Example D111: 4-(4-((6-cyclopropylimidazo[1,5-a]pyridin-5-yl)(hydroxy)methyl) cyclohexyl)benzoic acid

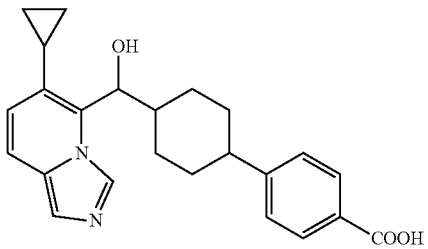 [SMILES: O=C(O)c1ccc(C2CCC(C(O)c3c(C4CC4)ccc4cncn34)CC2)cc1]

To a solution of 4-(4-((6-cyclopropylimidazo[1,5-a]pyridin-5-yl) (hydroxy)methyl)cyclohexyl)benzonitrile (200 mg, 0.54 mmoL) in a mixture of MeOH (10 mL) and H$_2$O (10 mL) was added KOH (124 mg, 2.2 mmol) at room temperature and the mixture was heated at 80° C. for 48 hours. The organic solvent was evaporated under reduced pressure and the residue was adjust pH=7 with HCl (aq, 1.0 M), the white precipitate was filtered to give crude product as white solid. Further purified by Pre-HPLC to give product as white solid (90 mg in 43% yield). $^1$H NMR (400 MHz. DMSO-d$_6$) $\delta_H$ 9.47 (s, 1H), 7.94 (s, 1H), 7.84 (d, J=8.0 Hz, 2H), 7.66 (d, J=8.4 Hz, 1H), 7.32 (d, J=8.4 Hz, 2H), 6.78 (d, J=8.8 Hz, 1H), 6.12 (s, 1H), 5.32 (d, J=9.6 Hz, 1H), 2.54-2.57 (m, 1H), 2.40-2.43 (m, 1H), 2.16-2.21 (m, 2H), 1.91-1.94 (m, 1H), 1.70 (s, 1H), 1.47-1.56 (m, 1H), 1.24-1.38 (m, 4H), 0.99-1.05 (m, 2H), 0.83-0.86 (m, 1H) and 0.75-0.78 (m, 1H). MS (ESI) m/e [M+1]$^+$=391.2.

Example D111a and D111b: 4-((1S,4r)-4-((S)-(6-cyclopropylimidazo[1,5-a]pyridin-5-yl)(hydroxy)methyl)cyclohexyl)benzoic acid and 4-((1R,4r)-4-((R)-(6-cyclopropylimidazo[1,5-a]pyridin-5-yl)(hydroxy)methyl)cyclohexyl)benzoic acid

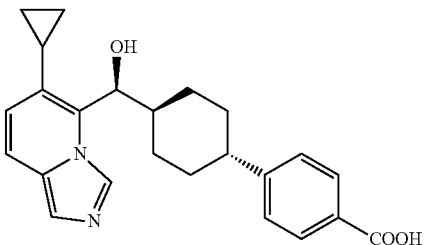

Fast isomer in CHIRALPAK AS-3 HPLC
Eluting reagent: MeOH (20 mM NH$_3$)

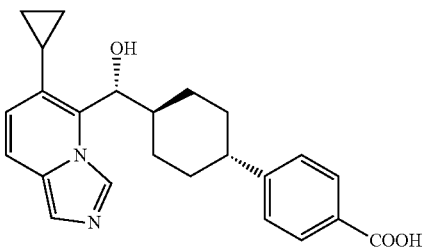

Slow isomer in CHIRALPAK AS-3 HPLC
Eluting reagent: MeOH (20 mM NH$_3$)

Each enantiomer of racemic D111a and D111b was separated using preparative HPLC on a CHIRALPAK AS-H with CO$_2$:MeOH=60:40 as an eluent. The enantiomeric excesses were determined by using HPLC on a CHIRALPAK AS-3 with MeOH (20 Mm NH$_3$) as an eluent at a flow rate of 1.0 mL/min. The first one enantiomer eluted at the retention time of 1.880 min, and the other enantiomer eluted at the retention time of 2.493 min. D111a (7.8 mg). $^1$H NMR (400 MHz, DMSO-d$_6$) $\delta_H$ 12.55 (brs, 1H), 8.62 (s, 1H), 7.82 (d, J=8.0 Hz, 2H), 7.40 (d, J=9.2 Hz, 1H), 7.31 (d, J=8.0 Hz, 3H), 6.47 (d, J=9.6 Hz, 1H), 5.81 (d, J=4.0 Hz, 1H), 5.26 (dd, J=3.6 Hz, J=9.6 Hz, 1H), 2.56-2.58 (m, 1H), 2.42-2.45 (m, 1H), 2.21-2.24 (m, 1H), 2.01 (s, 1H), 1.89-1.92 (m, 1H), 1.67-1.70 (m, 1H), 1.49-1.54 (m, 1H), 1.15-1.34 (m, 4H), 0.94-0.96 (m, 2H), 0.76-0.78 (m, 1H) and 0.65-0.67 (m, 1H). MS (ESI) m/e [M+1]$^+$=391.2. D111b (19.2 mg). $^1$H NMR (400 MHz, DMSO-d$_6$) $\delta_H$ 12.68 (brs, 1H), 8.62 (s, 1H), 7.83 (d, J=8.0 Hz, 2H), 7.40 (d, J=9.2 Hz, 1H), 7.32 (d, J=8.0 Hz, 3H), 6.47 (d, J=9.6 Hz, 1H), 5.81 (d, J=4.0 Hz, 1H), 5.26 (dd, J=3.6 Hz, J=9.6 Hz, 1H), 2.56-2.58 (m, 1H), 2.42-2.45 (m, 1H), 2.22-2.25 (m, 1H), 2.02 (s, 1H), 1.89-1.92 (m, 1H), 1.67-1.70 (m, 1H), 1.49-1.58 (m, 1H), 1.18-1.35 (m, 4H), 0.92-0.99 (m, 2H), 0.76-0.79 (m, 1H) and 0.63-0.67 (m, 1H). MS (ESI) m/e [M+1]$^+$=391.2. The absolute configurations of chiral carbons in D111a and D111b are tentatively assigned as (S) and (R) respectively based on assumption that the binding model of the more potent isomer D111a is the same as that of C101a with IDO1 enzyme, and the relative stereochemistry on cyclohexane is assigned as trans configuration on the cyclohexane.

Example D112 to D114 were synthesized using the same procedure was discriped in Example D101

Example D112: 2-(4-((6-cyclopropylimidazo[1,5-a]pyridin-5-yl)(hydroxy)methyl) cyclohexyl)phenol

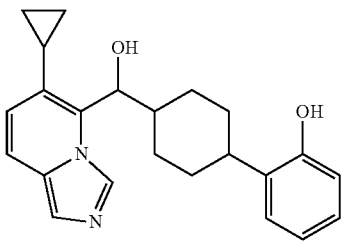 [SMILES: Oc1ccccc1C1CCC(C(O)c2c(C3CC3)ccc3cncn23)CC1]

$^1$H NMR (DMSO-d$_6$) δ$_H$ 9.17 (s, 1H), 8.62 (s, 1H), 7.39-7.41 (d, J=9.2 Hz, 1H), 7.31 (s, 1H), 7.03-7.05 (d, J=7.2 Hz, 1H), 6.92-6.95 (t, J=7.2 Hz, 1H), 6.66-6.78 (m, 2H), 6.46-6.48 (d, J=9.2 Hz, 1H), 5.77-5.78 (d, J=4.0 Hz, 1H), 5.25-5.28 (dd, J=9.6 Hz, J$_2$=4.0 Hz, 1H), 2.76-2.88 (m, 1H), 2.38-2.46 (m, 1H), 2.13-2.26 (m, 1H), 1.96-2.09 (m, 1H), 1.78-1.87 (m, 1H), 1.57-1.67 (m, 1H), 1.40-1.52 (m, 1H), 1.14-1.33 (m, 4H), 0.90-1.02 (m, 2H), and 0.62-0.79 (m, 2H). [M+H]$^+$=363.2.

Example D112a and D112b: 2-((1S,4r)-4-((S)-(6-cyclopropylimidazo[1,5-a]pyridin-5-yl)(hydroxy)methyl)cyclohexyl)phenol and 2-((1R,4r)-4-((R)-(6-cyclopropylimidazo[1,5-a]pyridin-5-yl)hydroxy)methyl)cyclohexyl)phenol

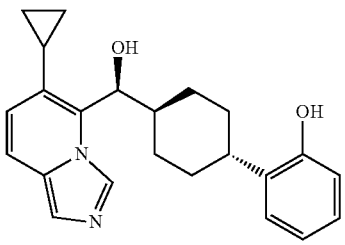

Fast isomer in CHIRALART Cellulose-SB
Eluting reagent: Hex:EtOH = 80:20

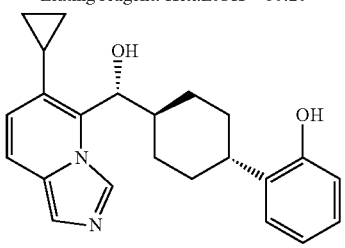

Slow isomer in CHIRALART Cellulose-SB
Eluting reagent: Hex:EtOH = 80:20

Each enantiomer of racemic D112a and D112b was separated using preparative HPLC on a CHIRALART Cellulose-SB with Hex:EtOH=80:20 as an eluent. The first one enantiomer eluted at the retention time of 3.549 min (D112a), which was dissolved in EA(5 ml), and HCl in EA(4N, 0.5 mL) was added and stirred at r.t for 1 h, the solvent was evaporated to give product as white solid, $^1$H NMR (DMSO-d$_6$) δ$_H$ 9.61 (s, 1H), 9.22 (s, 1H), 8.03 (s, 1H), 7.69 (d, J=7.6 Hz, 1H), 7.02 (d, J=7.6 Hz, 1H), 6.94 (t, J=7.6 Hz, 1H), 6.82 (d, J=9.6 Hz, 1H), 6.76 (d, J=8.0 Hz, 1H), 6.69 (t, J=7.2 Hz, 1H), 6.14 (s, 1H), 5.32 (d, J=9.6 Hz, 1H), 2.77-2.89 (m, 1H), 2.36-2.44 (m, 1H), 2.12-2.33 (m, 2H), 1.81-1.90 (m, 1H), 1.62-1.70 (m, 1H), 1.40-1.51 (m, 1H), 1.24-1.38 (m, 4H), 1.02-1.08 (m, 2H), and 0.74-0.89 (m, 2H). [M+H]$^+$=363.2; and the other enantiomer eluted at the retention time of 5.543 min (D112b), which was dissolved in EA(5 ml), and HCl in EA(4N, 0.5 mL) was added and the solvent was evaporated to give product as white solid, $^1$H NMR (DMSO-d$_6$) δ$_H$ 9.63 (s, 1H), 9.22 (s, 1H), 8.05 (s, 1H), 7.69-7.71 (d, J=7.6 Hz, 1H), 7.00-7.03 (dd, J$_1$=7.6 Hz, J$_2$=1.2 Hz, 1H), 6.92-6.97 (dt, J$_1$=7.6 Hz, J$_2$=1.2 Hz, 1H), 6.82-6.85 (d, J=10.0 Hz, 1H), 6.75-6.77 (d, J=8.0 Hz, 1H), 6.67-6.71 (t, J=7.2 Hz, 1H), 6.16 (s, 1H), 5.31-5.34 (d, J=9.6 Hz, 1H), 2.77-2.89 (m, 1H), 2.36-2.44 (m, 1H), 2.12-2.33 (m, 2H), 1.81-1.90 (m, 1H), 1.62-1.70 (m, 1H), 1.40-1.51 (m, 1H), 1.24-1.38 (m, 4H), 1.02-1.08 (m, 2H), and 0.74-0.89 (m, 2H). [M+H]$^+$=363.2. The absolute configurations of chiral carbons in D112a and D112b are tentatively assigned as (S) and (R) respectively based on assumption that the binding model of the more potent isomer D112a is the same as that of C1101a with IDO1 enzyme, and the relative stereochemistry on cyclohexane is assigned as trans configuration on the cyclohexane.

Example D113: (6-cyclopropylimidazo[1,5-a]pyridin-5-yl)(4-(2-methoxyphenyl) cyclohexyl)methanol

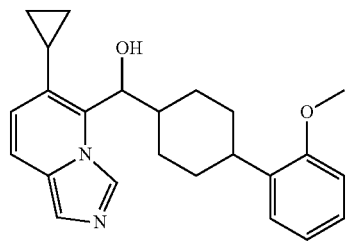 [SMILES: COc1ccccc1C1CCC(C(O)c2c(C3CC3)ccc3cncn23)CC1]

$^1$H NMR (DMSO-d$_6$) δ$_H$ 8.64 (s, 1H), 7.39-7.42 (d, J=9.2 Hz, 1H), 7.33 (s, 1H), 7.09-7.16 (m, 2H), 6.83-6.93 (m, 2H), 6.47-6.49 (d, J=9.2 Hz, 1H), 5.78-5.79 (d, J=3.6 Hz, 1H), 5.25-5.28 (dd, J$_1$=9.2 Hz, J$_2$=3.6 Hz, 1H), 3.75 (s, 3H), 2.82-2.92 (m, 1H), 2.38-2.46 (m, 1H), 2.15-2.27 (m, 1H), 1.96-2.09 (m, 1H), 1.77-1.87 (m, 1H), 1.57-1.65 (m, 1H), 1.40-1.52 (m, 1H), 1.14-1.33 (m, 4H), 0.90-1.02 (m, 2H), and 0.63-0.79 (m, 2H). [M+H]$^+$=377.2.

259

Example D114: (6-cyclopropylimidazo[1,5-a]pyridin-5-yl)(4-(4-((tetrahydro-2H-pyran-4-yl)oxy)phenyl)cyclohexyl)methanol

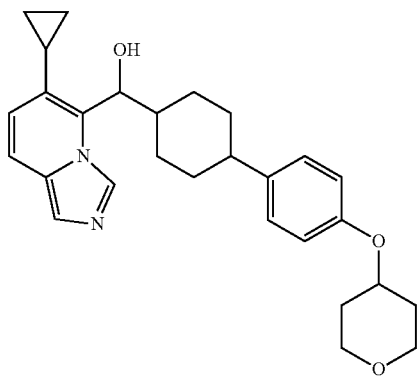 [SMILES: OC(c1c(C2CC2)ccc2cncn12)C1CCC(c2ccc(OC3CCOCC3)cc2)CC1]

MS (ESI) m/e [M+1]$^+$447; $^1$H NMR (DMSO-d$_6$) δ8.66 (s, 1H), 7.42 (d, J=9.6 Hz, 1H), 7.34 (s, 1H), 7.08 (d, J=8.4 Hz, 2H), 6.83 (d, J=8.4 Hz, 2H), 6.49 (d, J=9.6 Hz, 1H), 5.82 (d, J=2.8 Hz, 1H), 5.25 (dd, J=4.0, 9.6 Hz, 1H), 4.43-4.51 (m, 1H), 3.79-3.85 (m, 2H), 3.41-3.48 (m, 2H), 2.39-2.42 (m, 2H), 2.15-2.19 (m, 1H), 2.00-2.02 (m, 1H), 1.84-1.94 (m, 3H), 1.40-1.65 (m, 5H), 1.14-1.32 (m, 5H), 0.90-0.99 (m, 2H), and 0.64-0.69 (m, 2H).

Example D114a, D114b, D114c and D114c: (R)-(6-cyclopropylimidazo[1,5-a]pyridin-5-yl)((1 s,4S)-4-(4-((tetrahydro-2H-pyran-4-yl)oxy)phenyl)cyclohexyl)methanol. (R)-(6-cyclopropylimidazo[1,5-a]pyridin-5-yl)((r,4R)-4-(4-((tetrahydro-2H-pyran-4-yl)oxy)phenyl) cyclohexyl)methanol, (S)-(6-cyclopropylimidazo[1,5-a]pyridin-5-yl)((1r,4S)-4-(4-((tetrahydro-2H-pyran-4-yl)oxy)phenyl)cyclohexyl) methanol and (S)-(6-cyclopropylimidazo[1,5-a]pyridin-5-yl)((1 s,4R)-4-(4-((tetrahydro-2H-pyran-4-yl)oxy)phenyl)cyclohexyl)methanol D114a

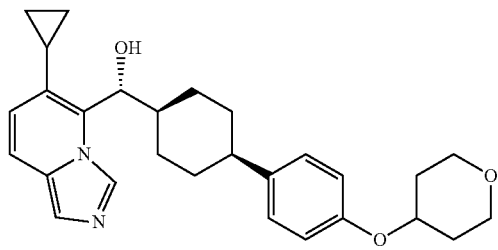

Fast isomer in CHIRALART Cellulose-SB
Eluting reagent: Hex(0.2% IPAmine):EtOH = 70:30

260

-continued

D114b

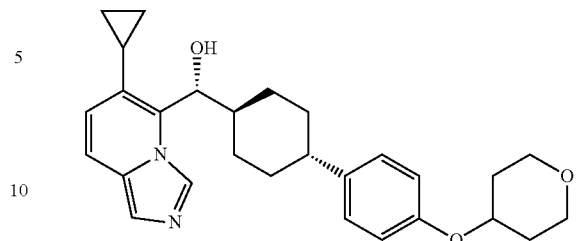

Slow isomer in CHIRALART Cellulose-SB
Eluting reagent: Hex(0.2% IPAmine):EtOH = 70:30

D114c

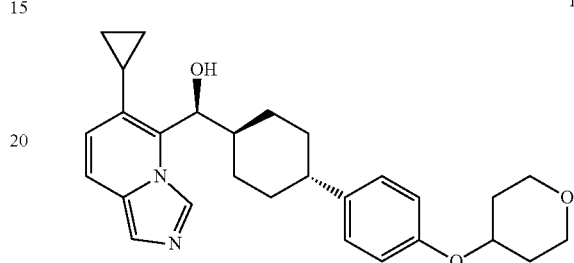

Fast isomer in CHIRALPAK IC
Eluting reagent: Hex(0.2% IPAmine):EtOH = 75:25

D114d

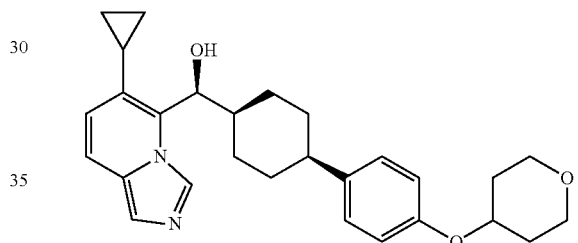

Slow isomer in CHIRALPAK IC
Eluting reagent: Hex(0.2% IPAmine):EtOH = 75:25

Each enantiomer of racemic D114a and D114b was separated using preparative HPLC on a CHIRALART Cellulose-SB with Hex (0.2% IPAmine):EtOH=70:30 as an eluent. The enantiomeric excesses were determined by using HPLC on a CHIRALART Cellulose-SB with Hex (0.2% IPAmine):EtOH=70:30 as an eluent at a flow rate of 1.0 mL/min. The first one enantiomer eluted at the retention time of 4.104 min (D114a), To a solution of D114a (18.1 mg) in DCM (3 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give the desired product as white solid (8.68 mg). $^1$H NMR (DMSO-d$_6$) δ$_H$ 9.53 (s, 1H), 8.03 (s, 1H), 7.69 (d, J=10.0 Hz, 1H), 7.18 (d, J=8.4 Hz, 2H), 6.90 (d, J=8.4 Hz, 2H), 6.81 (d, J=10.0 Hz, 1H) 6.15 (brs, 1H), 5.73 (d, J=10.8 Hz, 1H), 4.49-4.52 (m, 1H), 3.81-3.87 (m, 2H), 3.44-3.50 (m, 2H), 2.16-2.23 (m, 2H), 1.93-2.03 (m, 2H), 1.69-1.75 (m, 3H), 1.52-1.61 (m, 3H), 0.96-1.17 (m, 7H), and 0.73-0.87 (m, 2H). [M+H]$^+$=447. and the other enantiomer eluted at the retention time of 4.917 min (D114b), To a solution of D114b (99.5 mg) in DCM (5 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (81.79 mg). $^1$H NMR (DMSO-d$_6$) $\delta_H$ 9.67 (s, 1H), 8.11 (s, 1H), 7.72 (d, J=7.2 Hz, 1H), 7.08 (d, J=8.8 Hz, 2H), 6.84-6.87 (m, 3H), 6.23 (brs, 1H), 5.32 (d, J=9.6 Hz, 1H), 4.44-4.51 (m, 1H), 3.80-3.85 (m, 2H), 3.42-3.48 (m, 2H), 2.38-2.42 (m, 2H), 2.15-2.18 (m, 2H), 1.89-1.94 (m, 3H), 1.66-1.68 (m, 1H), 1.49-1.56 (m, 3H), 1.15-1.19 (m, 4H), 1.03-1.10 (m, 2H), and 0.76-0.88 (m, 2H). [M+H]$^+$=447. Each enantiomer of racemic D114c and D114d was separated using preparative HPLC on a CHIRALPAK IC with Hex (0.2% IPAmine):EtOH=75:25 as an eluent. The enantiomeric excesses were determined by using HPLC on a CHIRALPAK IC-3 with Hex (0.2% IPAmine):EtOH=80:20 as an eluent at a flow rate of 1.0 mL/min. The first one enantiomer eluted at the retention time of 5.200 min. To a solution of D114a (88.7 mg) in DCM (5 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (80.35 mg), $^1$H NMR (DMSO-d$_6$) $\delta_H$ 9.63 (s, 1H), 8.07 (s, 1H), 7.70 (d, J=9.2 Hz, 1H), 7.08 (d, J=8.8 Hz, 2H), 6.82-6.87 (m, 3H), 6.18 (brs, 1H), 5.31 (d, J=9.6 Hz, 1H), 4.48-4.50 (m, 1H), 3.81-3.84 (m, 2H), 3.42-3.51 (m, 2H), 2.32-2.44 (m, 2H), 2.15-2.18 (m, 2H), 1.93-1.99 (m, 3H), 1.66-1.68 (m, 1H), 1.26-1.66 (m, 7H), 1.02-1.06 (m, 2H), and 0.78-0.88 (m, 2H). [M+H]$^+$=447, and the other enantiomer eluted at the retention time of 7.268 min (D114d), to a solution of D114d (15.5 mg) in DCM (3 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give the desired product as white solid (9.19 mg). $^1$H NMR (DMSO-d$_6$) $\delta_H$ 9.47 (s, 1H), 7.99 (s, 1H), 7.67 (d, J=9.6 Hz, 1H), 7.18 (d, J=8.4 Hz, 2H), 6.91 (d, J=8.4 Hz, 2H), 6.79 (d, J=9.6 Hz, 1H), 6.12 (brs, 1H), 5.72 (d, J=10.8 Hz, 1H), 4.52-4.54 (m, 1H), 3.84-3.87 (m, 2H), 3.44-3.50 (m, 2H), 2.40-2.46 (m, 2H), 2.15-2.26 (m, 2H), 1.93-1.97 (m, 2H), 1.48-1.84 (m, 7H), 1.35-1.39 (m, 1H), 0.99-1.07 (m, 2H), and 0.69-0.74 (m, 2H). [M+H]$^+$=447. The absolute configurations of chiral carbons in D114a, D114b, D114c and D114d are tentatively assigned as (R), (R), (S) and (S) respectively based on assumption that the binding model of the more potent isomer D114c and D114d are the same as that of C101a with IDO1 enzyme, and the relative stereochemistry on cyclohexane is assigned as trans configuration on the cyclohexane.

Example D115: (4-(4-chlorophenyl)cyclohexyl)(6-isopropylimidazo[1,5-a]pyridin-5-yl)methanol

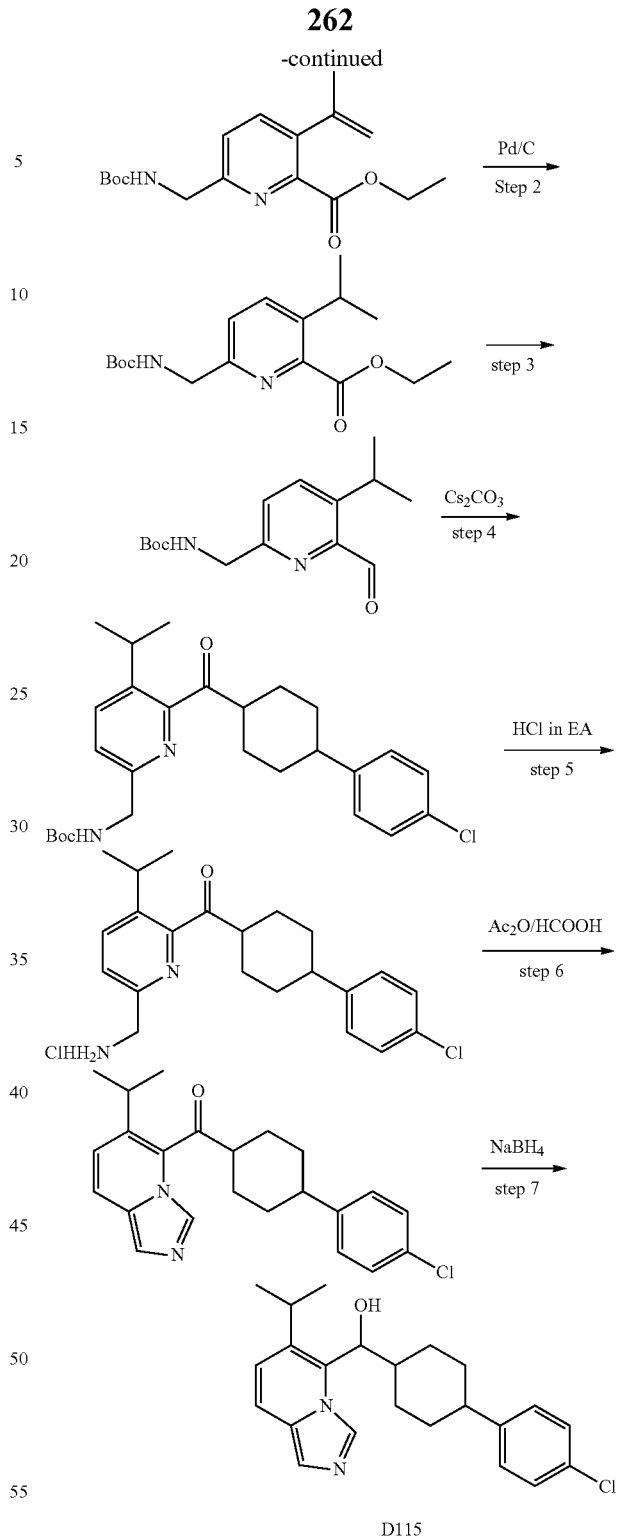

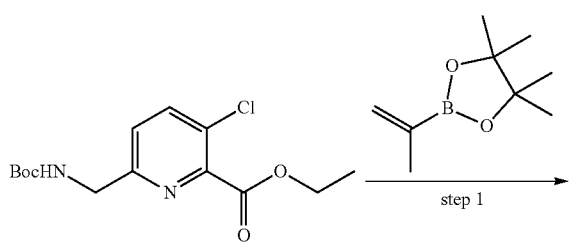

Step 1: ethyl 6-(((tert-butoxycarbonyl)amino)methyl)-3-(prop-1-en-2-yl)picolinate To a solution of ethyl 6-(((tert-butoxycarbonyl)amino)methyl)-3-chloropicolinate (3.15 g, 10 mmoL) in Toluene (60 mL) was added 4,4,5,5-tetramethyl-2-(prop-1-en-2-yl)-1,3,2-dioxaborolane (2.5 g, 15 mmol), Pd(dppf)Cl$_2$ (1.1 g, 1.5 mmol) and Cs$_2$CO$_3$ (6.5 g, 20 mmol) and the mixture was heated at 100° C. overnight under N₂. The mixture was purified by column chromatography (PE:EA=10:1~5:1) to give product (2 g in 62.5% yield).

Step 2: ethyl 6-(((tert-butoxycarbonyl)amino)methyl)-3-isopropylpicolinate

To a solution of ethyl 6-(((tert-butoxycarbonyl)amino)methyl)-3-(prop-1-en-2-yl)picolinate (2.0 g, 6.3 mmol) in MeOH (50 mL) was added Pd/C (400 mg) and the mixture was stirred overnight at room temperature under H₂(4 atm). The solid was filtered and the filtrate was concentrated under vacuo to give the product (1.2 g, 60%), which was used for next step without further purification. [M+H]⁺=323.

Step 3: tert-butyl ((6-formyl-5-isopropylpyridine-2-yl)methyl)carbamate

To a solution of ethyl 6-(((tert-butoxycarbonyl)amino)methyl)-3-isopropylpicolinate (1.2 g, 3.7 mmol) in THF (30 mL) was slowly dropwised DIBA-H (11.1 mmol) at −78° C. under N₂. The mixture was stirred for 1 h at −78° C. under N₂. The mixture was quenched by H₂O (50 mL). The mixture was extracted with EA(30 mL×2). The organic layer was further purified by column chromatography, on silica, eluting with EA:PE=1:10 to give the product (0.53 g, 53%) as a brown oil. [M+H]⁺=279.

Step 4: tert-butyl ((6-(4-(4-chlorophenyl)cyclohexane-1-carbonyl)-5-isopropylpyridin-2-yl)methyl)carbamate To a solution of tert-butyl ((6-formyl-5-isopropylpyridin-2-yl)methyl)carbamate (530 mg, 1.9 mmol) in 1,4-dioxane (50 mL) was added N'-(4-(4-chlorophenyl)cyclohexylidene)-4-methylbenzenesulfonohydrazide (716 mg, 1.9 mmol) and Cs₂CO₃(929 mg, 2.85 mmol). The mixture was stirred overnight at 100° C. under N₂. The resulting mixture was further purified by column chromatography, on silica, eluting with PE:EA=0~4:1 to give the product (600 mg, 67%) as a brown oil.

Step 5: (6-(aminomethyl)-3-isopropylpyridin-2-yl)(4-(4-chlorophenyl)cyclohexyl)methanone hydrochloride A solution of tert-butyl ((6-(4-(4-chlorophenyl)cyclohexane-1-carbonyl)-5-isopropylpyridin-2-yl)methyl)carbamate (600 mg, 1.3 mmol) in HCl in EA(4N, 15 mL) was stirred for 3 h at room temperature. The mixture was concentrated to give the product (700 mg, crude) as brown oil, which was used next step without further purification.

Step 6: (4-(4-chlorophenyl)cyclohexyl)(6-isopropylimidazo[1,5-a]pyridin-5-yl)methanone A solution of (6-(aminomethyl)-3-isopropylpyridin-2-yl)(4-(4-chlorophenyl)cyclohexyl)methanone hydrochloride (700 mg) in Ac₂O/HCOOH (3:1(vol), 30 mL) was stirred overnight at room temperature under N₂. The solvent was removed under vacuo. To the residue was added Na₂CO₃ (aq, 30 ml) and extracted with EA(30 mL×3). The organic layer was dried over with Na₂SO₄, filtered and concentrated to give the product (750 mg, crude) as brown oil.

Step 7: (4-(4-chlorophenyl)cyclohexyl)(6-isopropylimidazo[1,5-a]pyridin-5-yl)methanol To a solution of (4-(4-chlorophenyl)cyclohexyl)(6-isopropylimidazo[1,5-a]pyridin-5-yl)methanone (750 mg, 1.97 mmol) in MeOH was added NaBH₄(374 mg, 9.85 mmol). The mixture was stirred for 1 h at room temperature. The solvent was removed under vacuo. To the residue was added H₂O (20 mL) and extracted with EA (30 mL×3). The organic layer was dried over with Na₂SO₄, filtered and concentrated to give crude product which was further purified by prepare TLC to give the product (150 mg) as white solid. ¹H NMR (DMSO-d₆) δ_H 8.62 (s, 1H), 7.47 (d, J=9.6 Hz, 1H), 7.21-7.31 (m, 5H), 6.83 (d, J=9.6 Hz, 1H), 5.78 (d, J=3.6 Hz, 1H), 4.99-5.01 (m, 1H), 3.15-3.27 (m, 1H), 2.28-2.42 (m, 2H), 2.14-2.19 (m, 1H), 1.85-1.88 (m, 1H), 1.64-1.67 (m, 1H), 1.43-1.53 (m, 1H), and 1.12-1.22 (m, 10H). [M+H]⁺=383.

Example D115a and D115b: (S)-((1r,4S)-4-(4-chlorophenyl)cyclohexyl)(6-isopropylimidazo[1,5-a]pyridin-5-yl)methanol and (R-((1 r,4R)-4-(4-chlorophenyl)cyclohexyl)(6-isopropylimidazo[1,5-a]pyridin-5-yl)methanol

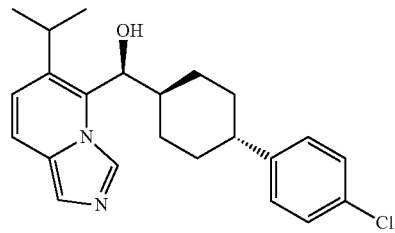

Fast isomer in CHIRALART Cellulose-SB
Eluting reagent: Hex(0.2% IPAmine):EtOH = 70:30

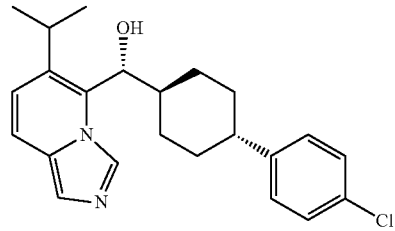

Slow isomer in CHIRALART Cellulose-SB HPLC
Eluting reagent: Hex(0.2% IPAmine):EtOH = 70:30

Each enantiomer of racemic D115a and D115b was separated using preparative HPLC on a CHIRALART Cellulose-SB with Hex (0.2% IPAmine):EtOH=70:30 as an eluent. The enantiomeric excesses were determined by using HPLC on a CHIRALART Cellulose-SB with Hex (0.2% IPAmine):EtOH=70:30 as an eluent at a flow rate of 1.0 mL/min. The first one enantiomer eluted at the retention time of 2.488 min (D115a), and the other enantiomer eluted at the retention time of 3.635 min (D115b). To a solution of D115a (80.6 mg) in DCM (5 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (59.43 mg). ¹H NMR (DMSO-d₆) δ_H 9.63 (s, 1H), 8.07 (s, 1H), 7.78 (d, J=10.0 Hz, 1H), 7.20-7.32 (m, 5H), 6.19 (brs, 1H), 5.10 (d, J=9.6 Hz, 1H), 3.38-3.41 (m, 1H), 2.37-2.41 (m, 1H), 2.09-2.14 (m, 1H), 1.87-1.91 (m, 1H), 1.67-1.71 (m, 1H), and 1.14-1.52 (m, 12H). [M+H]⁺=383. To a solution of D115b (71.8 mg) in DCM (5 mL) was added drop wise of Ethyl acetate solution of hydrochloric acid (2.0 mL, 4.0M) at room temperature, followed by addition of methol until the precipitate was dissolved, then the solvent was evaporated under reduced pressure and the residue was washed by PE to give the desired product as white solid (62.60 mg). $^1$H NMR (DMSO-$d_6$) $\delta_H$ 9.65 (s, 1H), 8.08 (s, 1H), 7.78 (d, J=10.0 Hz, 1H), 7.20-7.32 (m, 5H), 6.22 (brs, 1H), 5.10 (d, J=9.6 Hz, 1H), 3.21-3.41 (m, 1H), 2.33-2.41 (m, 1H), 2.14-2.15 (m, 1H), 1.87-1.91 (m, 1H), 1.67-1.71 (m, 1H), and 1.18-1.52 (m, 12H). [M+H]$^+$=383. The absolute configurations of chiral carbons in D115a and D115b are tentatively assigned as (S) and (R) respectively based on assumption that the binding model of the more potent isomer D115a is the same as that of C101a with IDO1 enzyme, and the relative stereochemistry on cyclohexane is assigned as trans configuration on the cyclohexane.

Example D116: (4-(3-chlorophenyl)cyclohexyl)(6-cyclopropylimidazo[1,5-a]pyridin-5-yl)methanol

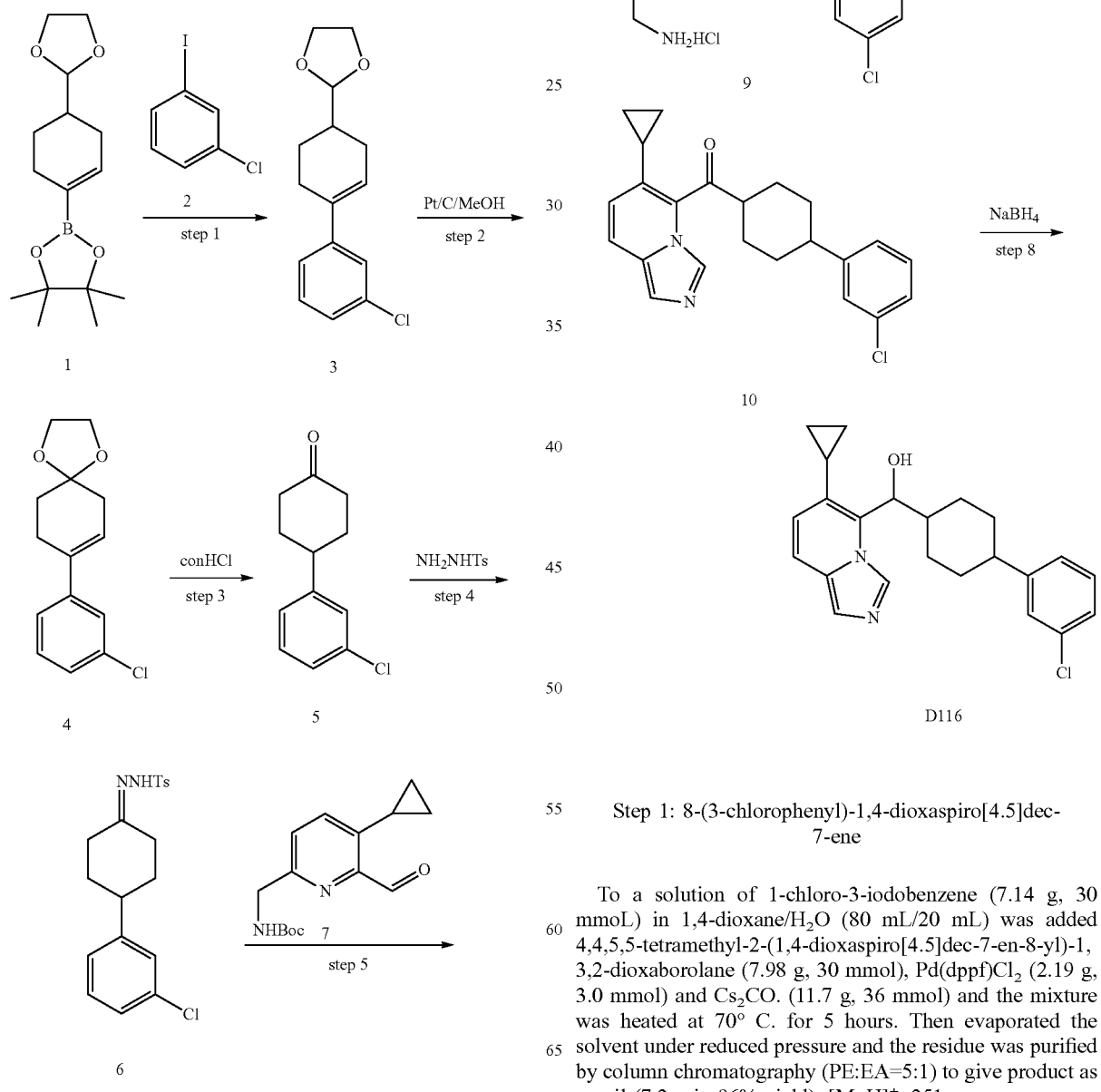

Step 1: 8-(3-chlorophenyl)-1,4-dioxaspiro[4.5]dec-7-ene

To a solution of 1-chloro-3-iodobenzene (7.14 g, 30 mmoL) in 1,4-dioxane/H$_2$O (80 mL/20 mL) was added 4,4,5,5-tetramethyl-2-(1,4-dioxaspiro[4.5]dec-7-en-8-yl)-1,3,2-dioxaborolane (7.98 g, 30 mmol), Pd(dppf)Cl$_2$ (2.19 g, 3.0 mmol) and Cs$_2$CO. (11.7 g, 36 mmol) and the mixture was heated at 70° C. for 5 hours. Then evaporated the solvent under reduced pressure and the residue was purified by column chromatography (PE:EA=5:1) to give product as an oil (7.2 g in 96% yield). [M+H]$^+$=251

Step 2: 8-(3-chlorophenyl)-1,4-dioxaspiro[4.5]decane

To a solution of 8-(3-chlorophenyl)-1,4-dioxaspiro[4.5]dec-7-ene (2.51 g, 10.0 mmol) in MeOH (30 mL) was added Pd/C (400 mg, 10%) and the mixture was stirred for 6 hours at room temperature under H$_2$ (0.1 Mpa). Then filtered to remove Pd/C and the filtrate was evaporated under reduced pressure to give a crude product (2.53 g, oil). [M+H]$^+$=253

Step 3: 4-(3-chlorophenyl)cyclohexan-1-one

To a solution of 8-(3-chlorophenyl)-1,4-dioxaspiro[4.5]decane (2.53 g, 10.0 mmol) in 1,4-dioxane/H$_2$O (20 mL/15 mL) was added con HCl (5.0 mL) at room temperature and the mixture was stirred for overnight. The mixture was quench with EA(200 mL) and H$_2$O (200 mL), the organic layer was washed with saturated aqueous of NaHCO$_3$, then the organic layer was evaporated in vacuo to give crude product (1.8 g), which was used for next step without further purification. [M+H]$^+$=209

Step 4: N'-(4-(3-chlorophenyl)cyclohexylidene)-4-methylbenzenesulfonohydrazide To a solution of 4-(3-chlorophenyl)cyclohexan-1-one (1.7 g, 8.1 mmol) in methol (30 mL) was added 4-methylbenzenesulfonohydrazide (1.5 g, 8.1 mmol) at room temperature and the mixture was stirred for overnight. Evaporate half the solvent under reduced pressure and then filtered to give product as a white solid (1.6 g in 52% yield). [M+H]$^+$=377

Step 5: tert-butyl ((6-(4-(3-chlorophenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (828 mg, 3.0 mmol) in 1,4-dioxane (0.1 L) was added N'-(4-(3-chlorophenyl)cyclohexylidene)-4-methylbenzenesulfonohydrazide (1.134 g, 3.0 mmol) and Cs$_2$CO$_3$ (1.462 g, 4.5 mmol) at room temperature, and the mixture was heated at 100° C. for 6 hours. The solvent was evaporated in vacuo and water (100 m L) was added, extracted with ethyl acetate (50 mL×3) and combined the organic layer, the solvent was evaporated under reduced pressure and the residue was purified by column chromatography (PE:EA=10:1) to give product as a light yellow oil (700 mg in 49.8% yield). [M+H]$^+$=469

Step 6: (6-(aminomethyl)-3-cyclopropylpyridin-2-yl)(4-(3-chlorophenyl)cyclohexyl) methanone hydrochloride Tert-butyl ((6-(4-(3-chlorophenyl)cyclohexane-1-carbonyl)-5-cyclopropylpyridin-2-yl)methyl)carbamate (650 mg, 1.38 mmol) was suspended in HCl (gas)/EA (20 mL, 4.0M in EA), the mixture was stirred at room temperature for overnight. The solvent was evaporated under reduced pressure to give crude product as solid (560 mg). [M+H]$^+$=369.

Step 7: (4-(3-chlorophenyl)cyclohexyl)(6-cyclopropylimidazo[1,5-a]pyridin-5-yl)meth anone A mixture of Ac$_2$O (30 mL) and HCOOH (10 mL) was heated at 50° C. for 1 hour and then a solution of (6-(aminomethyl)-3-cyclopropylpyridin-2-yl)(4-(3-chlorophenyl)cyclohexyl) methanone hydrochloride (crude 560 mg, 1.38 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give the product as a solid (410 mg in 78% yield). [M+H]$^+$=379.

Step 8: (4-(3-chlorophenyl)cyclohexyl)(6-cyclopropylimidazo[1,5-a]pyridin-5-yl)methanol To a solution of (4-(3-chlorophenyl)cyclohexyl)(6-cyclopropylimidazo[1,5-a]pyridin-5-yl)methanone (379 mg, 1.0 mmol) in methol (20 mL) was added NaBH$_4$ (76 mg, 2.0 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (340 mg in 89% yield). $^1$H NMR (400 MHz, DMSO-d$_6$) $\delta_H$ 8.62 (s, 1H), 7.40 (d, J=9.2 Hz, 1H), 7.16-7.21 (m, 5H), 6.47 (d, J=9.6 Hz, 1H), 5.81 (d, J=4.0 Hz, 1H), 5.25 (dd, J=9.2 Hz, J=3.6 Hz, 1H), 2.40-2.50 (m, 1H), 2.21-2.24 (m, 1H), 1.99-2.01 (m, 1H), 1.86-1.89 (m, 1H), 1.64-1.67 (m, 1H), 1.46-1.49 (m, 1H), 1.15-1.26 (m, 5H), 0.89-0.97 (m, 2H), 0.75-0.79 (m, 1H), 0.63-0.68 (m, 1H). [M+H]$^+$=381.

Example D116a and D116b: (S)-((1r,4S)-4-(3-chlorophenyl)cyclohexyl)(6-cyclopropylimidazo[1,5-a]pyridin-5-yl)methanol and (R)-((1 r,4R)-4-(3-chlorophenyl)cyclohexyl)(6-cyclopropylimidazo[1,5-a]pyridin-5-yl)methanol

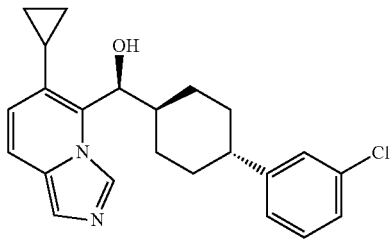

Fast isomer in CHIRALPAK IC HPLC
Eluting reagent: Hex:EtOH = 70:30

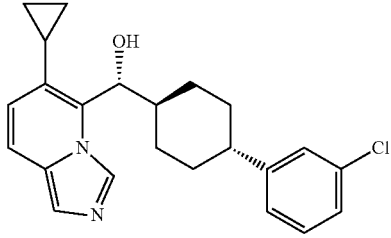

Slow isomer in CHIRALPAL IC HPLC
Eluting reagent: Hex:EtOH = 70:30

Each enantiomer of racemic D116a and D116b was separated using preparative HPLC on a CHIRALPAK IC with Hex:EtOH=70:30 as an eluent. The enantiomeric excesses were determined by using HPLC on a CHIRALPAK IC-3 with Hex (0.1% DEA):EtOH=70:30 as an eluent at a flow rate of 1.0 mL/min. The first one enantiomer (D116a) eluted at the retention time of 2.114 min, and the other enantiomer (D116b) eluted at the retention time of 4.258 min, To a solution of D116a (140 mg) in THF (10 mL) was added drop wise of Ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (120 mg in 78% yield). $^1$H NMR (400 MHz, DMSO-d$_6$) $\delta_H$ 9.69 (s, 1H), 8.1 (s, 1H), 7.73 (d, J=9.6 Hz, 1H), 7.15-7.31 (m, 1H), 6.86 (dd, J=9.6 Hz, J=2.4 Hz, 1H), 6.21 (s, 1H), 5.33 (d, J=9.6 Hz, 1H), 2.38-2.41 (m, 1H), 2.16-2.23 (m, 2H), 1.89-1.92 (m, 1H), 1.68-1.70 (m, 1H), 1.47-1.52 (m, 1H), 1.24-1.37 (m, 4H), 1.02-1.05 (m, 2H), 0.86-0.89 (m, 1H) and 0.77-0.80 (m, 1H). [M+H]$^+$=381. To a solution of D116b (140 mg) in THF (10 mL) was added drop wise of ethyl acetate solution of hydrochloric acid (5 mL, 4.0M) at room temperature, followed by addition of methol until the precipitate was dissolved, then the solvent was evaporated under reduced pressure and the residue was washed with PE to give the desired product as white solid (132 mg in 85% yield). $^1$H NMR (400 MHz, DMSO-d$_6$) $\delta_H$ 9.67 (s, 1H), 8.10 (s, 1H), 7.72 (d, J=9.6 Hz, 1H), 7.15-7.29 (m, 1H), 6.86 (d, J=9.6 Hz, 1H), 6.21 (s, 1H), 5.33 (d, J=9.6 Hz, 1H), 2.38-2.41 (m, 1H), 2.16-2.18 (m, 2H), 1.89-1.92 (m, 1H), 1.68-1.70 (m, 1H), 1.47-1.51 (m, 1H), 1.24-1.33 (m, 4H), 1.02-1.07 (m, 2H), 0.86-0.87 (m, 1H) and 0.76-0.80 (m, 1H). [M+H]$^+$=381. The absolute configurations of chiral carbons in D116a and D116b are tentatively assigned as (S) and (R) respectively based on assumption that the binding model of the more potent isomer D116a is the same as that of C101a with IDO1 enzyme, and the relative stereochemistry on cyclohexane is assigned as trans configuration on the cyclohexane.

Example D117: 4-(2-chlorophenyl)cyclohexyl)(6-cyclopropylimidazo[1,5-a]pyridin-5-yl)methanol

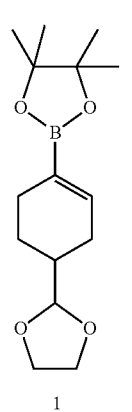

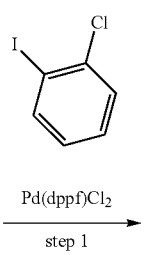

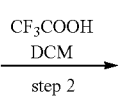

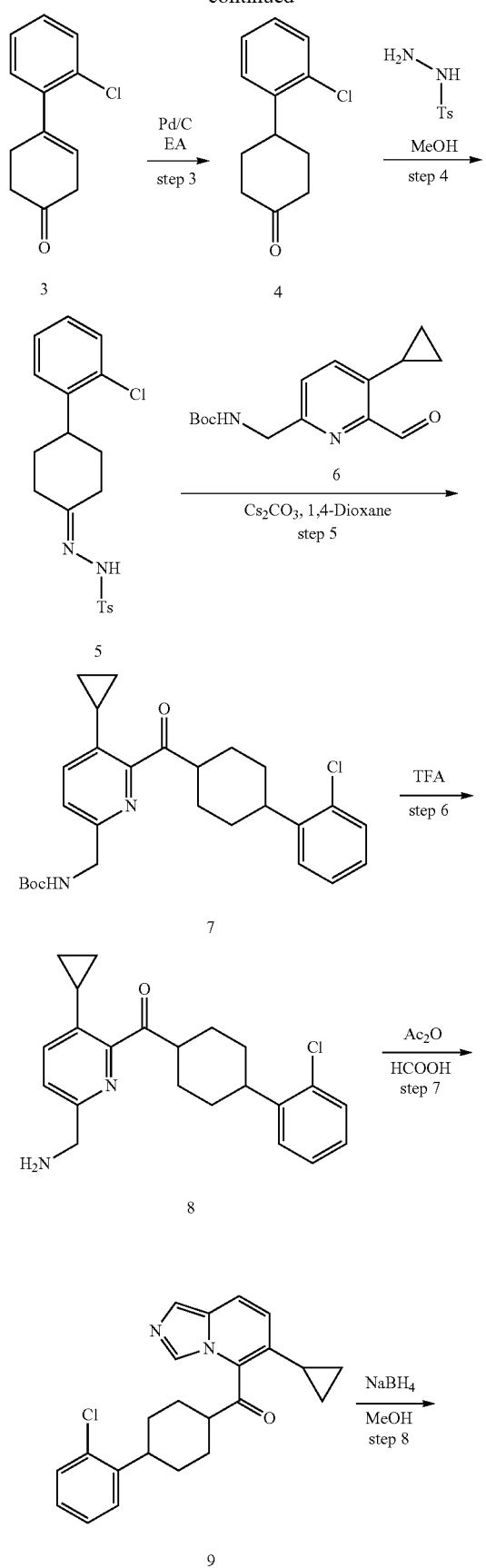

-continued

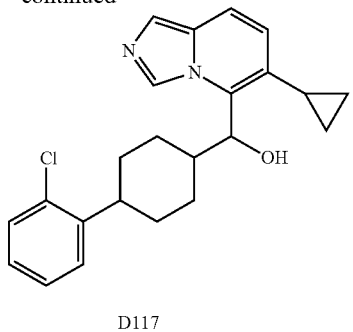

D117

Step 1: 8-(2-chlorophenyl)-1,4-dioxaspiro[4.5]dec-7-ene

To a solution of 1-chloro-2-iodobenzene (13.4 g, 56 mmoL) in 1,4-dioxane (200 mL) was added 4,4,5,5-tetramethyl-2-(1,4-dioxaspiro[4.5]dec-7-en-8-yl)-1,3,2-dioxaborolane (15 g, 56 mmol), Pd(dppf)$_2$Cl$_2$ (4.1 g, 5.6 mmol) and Cs$_2$CO$_3$ (27.6 g, 85 mmol) and the mixture was heated at 90° C. overnight. After evaporated the solvent under reduced pressure, the residue was added with water (100 mL), extracted with ethyl acetate (100 mL). The organic layer was dried, concentrated and purified by column chromatography (PE:EA=100:1) to give product as an oil (10.3 g in 73% yield). $^1$H NMR (CDCl$_3$) $\delta_H$ 7.35-7.33 (m, 1H), 7.21-7.16 (m, 3H), 5.59-5.57 (m, 1H), 4.05-4.01 (m, 4H), 2.57-2.54 (m, 2H), 2.46-2.45 (m, 2H), 1.91 (t, J=4.0 Hz, 2H). [M+H]$^+$=251.1.

Step 2: 2'-chloro-2,5-dihydro-[1,1'-biphenyl]-4(3H)-one

To a solution of 8-(2-chlorophenyl)-1,4-dioxaspiro[4.5]dec-7-ene (3 g, 12 mmol) in dichloromethane (15 mL) was added trifluoroacetic acid (5 mL) and the mixture was stirred at room temperature overnight. The solvent was evaporated under reduced pressure and water (20 mL) was added, extracted with ethyl acetate (20 mL×2), combined the organic layers and washed with saturated aqueous of NaHCO$_3$(20 mL), then the organic layer was evaporated in vacuo to give crude product (about 2.5 g), which was used in the next step without further purification.

Step 3: 4-(2-chlorophenyl)cyclohexan-1-one

To a solution of 2'-chloro-2,5-dihydro-[1,1'-biphenyl]-4(3H)-one (2.5 g, 12 mmol) in ethyl acetate (50 mL) was added with Pd/C (250 mg, 10%) and the mixture was stirred at room temperature under H$_2$ balloon overnight. Then filtered to remove Pd/C and the filtrate was evaporated under reduced pressure to give a crude product, which was purified by column chromatography (PE:EA=25:1) to give product (0.9 g in 36% yield) as a white solid. $^1$H NMR (CDCl$_3$-d) $\delta_H$ 7.40-7.38 (m, 1H), 7.25-7.23 (m, 2H), 7.19-7.16 (m, 1H), 3.57-3.49 (m, 1H), 2.61-2.50 (m, 4H), 2.28-2.22 (m, 2H), 1.93-1.82 (m, 2H). [M+H]$^+$=209.1

Step 4: N'-(4-(2-chlorophenyl)cyclohexylidene)-4-methylbenzenesulfonohydrazide To a solution of 4-(2-chlorophenyl)cyclohexan-1-one (615 mg, 3 mmol) in methol (10 mL) was added with 4-methylbenzenesulfonohydrazide (550 mg, 3 mmol) and the mixture was stirred at room temperature overnight. After concentrated under reduced pressure, the residue was redissolved in PE/EA solvent (v/v=10:1, 20 mL), and then filtered to give product as a white solid (1 g in 91% yield).

Step 5: tert-butyl ((6-(4-(2-chlorophenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (600 mg, 2.2 mmol) in 1,4-dioxane (40 mL) was added with N'-(4-(2-chlorophenyl)cyclohexylidene)-4-methylbenzenesulfonohydrazide (817 mg, 2.2 mmol) and Cs$_2$CO$_3$ (1.1 g, 3.3 mmol) at room temperature, and the mixture was heated at 95° C. overnight. The solvent was evaporated in vacuo and water (20 mL) was added, extracted with ethyl acetate (20 mL×2) and combined the organic layers, the solvent was evaporated under reduced pressure to give the crude product, which was used in the next step directly (1 g, crude).

Step 6: (6-(aminomethyl)-3-cyclopropylpyridin-2-yl)(4-(2-chlorophenyl)cyclohexyl) methanone To a solution of tert-butyl ((6-(4-(2-chlorophenyl)cyclohexane-1-carbonyl)-5-cyclopropylpyridin-2-yl)methyl)carbamate (1 g, 2.1 mmol) in DCM (50 mL) was added with trifluoracetic acid (5 mL) and the mixture was stirred at room temperature for 2 hours. The solvent was evaporated under reduced pressure to give the crude product, which was used in the next step directly.

Step 7: (4-(2-chlorophenyl)cyclohexyl)(6-cyclopropylimidazo[1,5-a]pyridin-5-yl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(2-chlorophenyl)cyclohexyl) methanone (780 mg, 2.1 mmol) in HCOOH (5 mL) was added drop wise and the mixture was heated at 70° C. for 2 hours. The solvent was evaporated under reduced pressure and water (20 mL) was added, washed with saturated aqueous of NaHCO$_3$ (20 mL), then extracted with ethyl acetate (20 mL×2) and combined the organic layers, the solvent was evaporated under reduced pressure and the residue was purified by column chromatography (PE:EA=15:1 to 8:1) to give the product as a yellow oil (382 mg in 48% yield). $^1$H NMR (CDCl$_3$) $\delta_H$ 8.03 (s, 1H), 7.45 (t, J=8.0 Hz, 2H), 7.35 (d, J=4.0 Hz, 1H), 7.21 (d, J=4.0 Hz, 2H), 7.15-7.11 (m, 1H), 6.43 (d, J=8.0 Hz, 1H), 3.35-3.27 (m, 1H), 3.14-3.06 (m, 1H), 2.15-2.05 (m, 4H), 1.94-1.74 (m, 3H), 1.53-1.42 (m, 2H), 1.06-1.01 (m, 2H), 0.80-0.76 (m, 2H). [M+H]$^+$=379.1.

Step 8: (4-(2-chlorophenyl)cyclohexyl)(6-cyclopropylimidazo[1,5-a]pyridin-5-yl)methanol

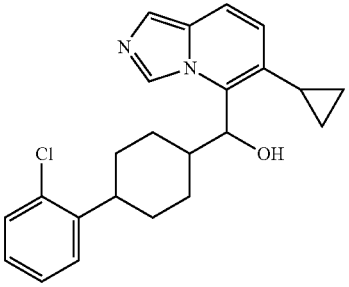 [SMILES: OC(c1c(C2CC2)ccc2cncn12)C1CCC(c2ccccc2Cl)CC1]

To a solution of (4-(2-chlorophenyl)cyclohexyl)(6-cyclopropylimidazo[1,5-a]pyridin-5-yl)methanone (380 mg, 1 mmol) in methol (10 mL) was added with NaBH$_4$ (190 mg, 5 mmol) at room temperature and the mixture was stirred for 2 hours. Then the solvent was evaporated under reduced pressure and water (10 mL) was added, extracted with ethyl acetate (10 mL×2) and combined the organic layer, the solvent was evaporated under reduced pressure to give the residue, which was purified by column chromatography (PE:EA=10:1 to 5:1) to get the product as a white solid (270 mg in 71% yield). $^1$H NMR (DMSO-d$_6$) $\delta_H$ 8.63 (s, 1H), 7.41-7.31 (m, 4H), 7.28-7.25 (m, 1H), 7.20-7.16 (m, 1H), 6.47 (d, J=8.0 Hz, 1H), 5.81 (d, J=4.0 Hz, 1H), 5.30-5.26 (m, 1H), 2.94-2.89 (m, 1H), 2.50-2.43 (m, 1H), 2.26-2.23 (m, 1H), 2.05-2.03 (m, 1H), 1.88 (d, J=12.0 Hz, 1H), 1.67-1.65 (m, 1H), 1.56-1.47 (m, 1H), 1.37-1.24 (m, 4H), 1.01-0.89 (m, 2H), 0.78-0.74 (m, 1H), 0.69-0.64 (m, 1H). [M+H]$^+$=381.1.

Example D117a and D117b: (S)-((1r,4S)-4-(2-chlorophenyl)cyclohexyl)(6-cyclopropylimidazo[1,5-a]pyridin-5-yl)methanol and (R)-((1 r,4R)-4-(2-chlorophenyl)cyclohexyl)(6-cyclopropylimidazo[1,5-a]pyridin-5-yl)methanol

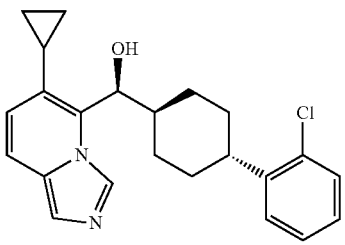

Fast isomer in CHIRALPAK IC HPLC
Eluting reagent: Hex:EtOH = 80:20

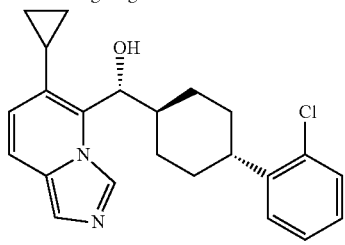

Slow isomer in CHIRALPAL IC HPLC
Eluting reagent: Hex:EtOH = 80:20

Each enantiomer of racemic Example D117a and D117b was separated using preparative HPLC on a CHIRALPAK IC with Hex:EtOH=80:20 as an eluent. The enantiomeric excesses were determined by using HPLC on a CHIRALPAK IC-3 with Hex (0.1% IPAmine):EtOH=80:20 as an eluent at a flow rate of 1.0 mL/min. The first one enantiomer eluted at the retention time of 1.361 min, and the other enantiomer eluted at the retention time of 2.313 min. To a solution of D117a (111 mg) in DCM (5 mL) was added dropwise of 1,4-dioxane solution of hydrochloric acid (0.5 mL, 4.0M) at room temperature. After stirred at r.t for 30 mins, the solvent was evaporated under reduced pressure and the residue was added with water (5 mL), lyophilized to give the desired product of HCl salt as a white solid (107 mg in 88% yield). $^1$H NMR (DMSO-d$_6$) $\delta_H$ 9.62 (s, 1H), 8.05 (s, 1H), 7.70 (d, J=8.0 Hz, 1H), 7.39 (d, J=8.0 Hz, 1H), 7.32-7.26 (m, 2H), 7.22-7.18 (m, 1H), 6.83 (d, J=8.0 Hz, 1H), 6.19 (br, 1H), 5.35 (d, J=12.0 Hz, 1H), 2.94-2.92 (m, 1H), 2.43 (d, J=12.0 Hz, 1H), 2.22-2.18 (m, 2H), 1.91 (d, J=12.0 Hz, 1H), 1.71-1.69 (m, 1H), 1.54-1.42 (m, 1H), 1.39-1.25 (m, 4H), 1.05 (d, J=8.0 Hz, 2H), 0.82 (dd, J$_1$=16.0 Hz, J$_2$=4.0 Hz, 2H). [M+H]$^+$=381.1. To a solution of D117b (104 mg) in DCM (5 mL) was added dropwise of 1,4-dioxane solution of hydrochloric acid (0.5 mL, 4.0M) at room temperature. After stirred at r.t for 30 mins, the solvent was evaporated under reduced pressure and the residue was added with water (5 mL), lyophilized to give the desired product of HCl salt as a white solid (108 mg in 95% yield). $^1$H NMR (DMSO-d$_6$) $\delta_H$ 9.55 (s, 1H), 7.99 (s, 1H), 7.68 (d, J=12.0 Hz, 1H), 7.39 (d, J=8.0 Hz, 1H), 7.32-7.26 (m, 2H), 7.22-7.18 (m, 1H), 6.80 (d, J=8.0 Hz, 1H), 6.15 (br, 1H), 5.34 (d, J=8.0 Hz, 1H), 2.95-2.91 (m, 1H), 2.43 (d, J=16.0 Hz, 1H), 2.22-2.18 (m, 2H), 1.91 (d, J=12.0 Hz, 1H), 1.71-1.69 (m, 1H), 1.54-1.42 (m, 1H), 1.39-1.24 (m, 4H), 1.05 (d, J=12.0 Hz, 2H), 0.85-0.77 (m, 2H). [M+H]$^+$=381.1. The absolute configurations of chiral carbons in D117a and D117b are tentatively assigned as (S) and (R) respectively based on assumption that the binding model of the more potent isomer D117a is the same as that of C101a with IDO1 enzyme, and the relative stereochemistry on cyclohexane is assigned as trans configuration on the cyclohexane.

Example D118: (4-(4-bromophenyl)cyclohexyl)(6-cyclopropylimidazo[1,5-a]pyridin-5-yl)methanol

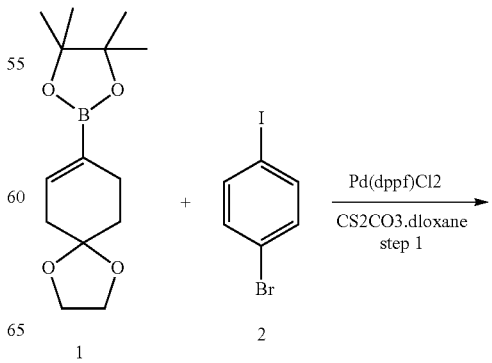

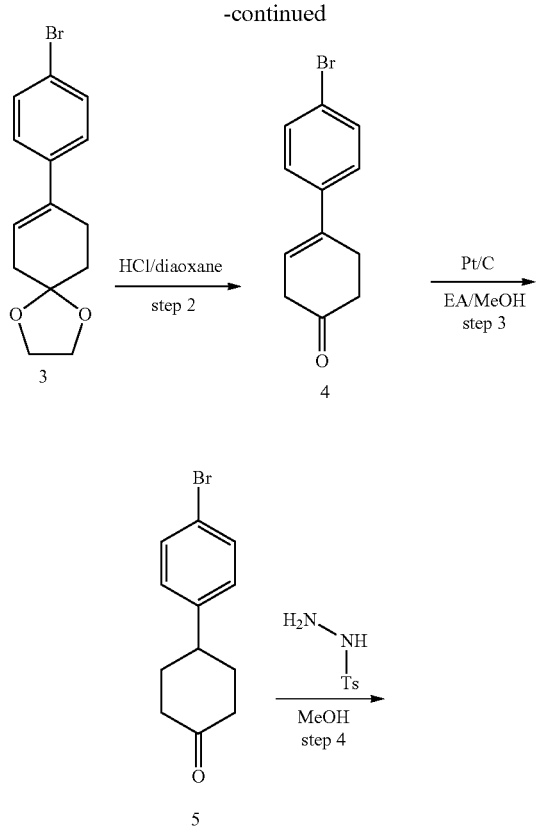
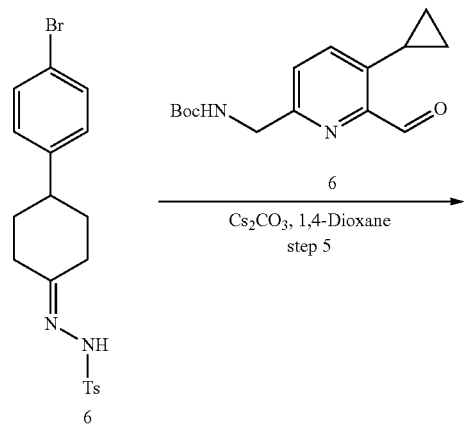
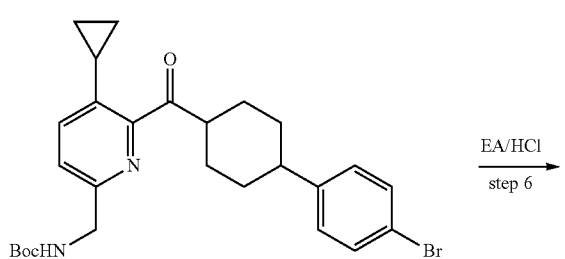
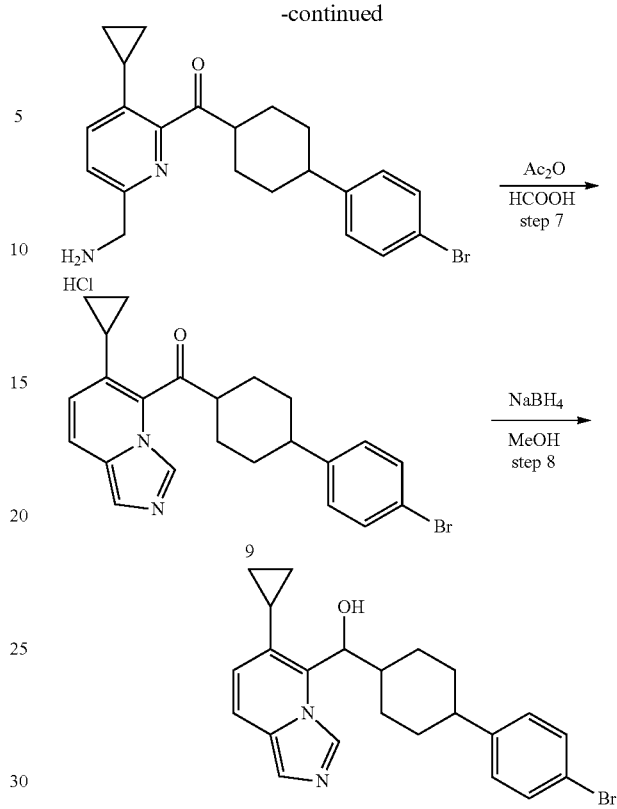

Step 1: 8-(4-bromophenyl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (20 g, 75.15 mmol), 1-bromo-4-iodobenzene (32 g, 112.7 mmol), Pd(dppf)Cl$_2$ (5.5 g, 7.5 mmol) and Cs$_2$CO$_3$ (36.6 g, 112.5 mmol) in dioxane (200 mL), the mixture was stirred at 90° C. under N$_2$ for 3 h. TLC (PE:EA=5:1, Rf=0.5) showed the reaction was completed. Filtered and concentrated, H$_2$O (100 ml) was was added and extracted with EA (50 ml×3). The combined organic layer was dried over Na$_2$SO$_4$, filtered and concentrated to give crude product, which was purified by silica gel chromatography (PE:EA=20:1-6:1) to give product (18 g, 81%) as a red solid.

Step 2: 4'-bromo-2,5-dihydro-[1,1'-biphenyl]-4(3H)-one

To a solution of 8-(4-bromophenyl)-1,4-dioxaspiro[4.5]dec-7-ene (9 g, 30.6 mmol) in 1,4-Dioxane (50 mL) was added 3N hydrochloric acid (50 mL) at room temperature, and the mixture was stirred for overnight. The solvent was evaporated under reduced pressure and water (100 mL) was added, extracted with ethyl acetate (100 mL×3), combined the organic layer and washed with saturated aqueous of NaHCO$_3$ then the organic layer was evaporated to give crude product, which was used for next step without further purification.

Step 3: 4-(4-bromophenyl)cyclohexan-1-one

To a solution of 4'-bromo-2,5-dihydro-[1,1'-biphenyl]-4(3H)-one (2.8 g, 11.2 mmol) in ethyl acetate:EA=1:1 (100 mL) was added Pt/C (0.28 g, 10%) and the mixture was stirred for 6 hours at room temperature under $H_2$ (0.4 Mpa). Then filtered to remove Pt/C and the filtrate was evaporated under reduced pressure to give a crude product, which was used for next step without further purification.

Step 4: N'-(4-(4-bromophenyl)cyclohexylidene)-4-methylbenzenesulfonohydrazide To a solution of 4-(4-bromophenyl)cyclohexan-1-one (2.4 g, 9.52 mmol) in methol (50 mL) was added 4-methylbenzenesulfonohydrazide (1.77 g, 9.52 mmol) at room temperature, and the mixture was stirred for overnight. The solvent was evaporate under reduced pressure and the residue was purified by column chromatography (PE:EA=4:1) to give product (7 g) as a white solid. MS (ESI) m/e $[M+1]^+$=421.

Step 5: tert-butyl ((6-(4-(4-bromophenyl)cyclohexane-1-carbonyl)-5-cyclopropylpyridin-2-yl)methyl)carbamate To a solution of N'-(4-(4-bromophenyl)cyclohexylidene)-4-methylbenzenesulfonohydrazide (1.0 g, 2.38 mmol) in 1,4-dioxane (50 mL) was added compound 6 (0.66 g, 2.38 mmol) and $Cs_2CO_3$ (0.93 g, 21.4 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE:EA=1:1 to EA) to give crude product as a solid (0.4 g in 38.98% yield), which was used for next step without further purification. MS (ESI) m/e $[M+1]^+$=514.

Step 6: (6-(aminomethyl)-3-cyclopropylpyridin-2-yl)(4-(6-bromopyridin-3-yl)cyclo hexyl)methanone hydrochloride To a solution of tert-butyl ((6-(4-(4-bromophenyl)cyclohexane-1-carbonyl)-5-cyclopropylpyridin-2-yl)methyl)carbamate (0.4 g, 0.8 mmol) in 1.4 dioxane (10 mL)_was added 3N HCl (10 mL) and the mixture was stirred at room temperature for overnight. The solvent was evaporated under reduced pressure to give crude product as solid. $[M+H]^+$=414.

Step 7: (4-(4-bromophenyl)cyclohexyl)(6-cyclopropylimidazo[1,5-a]pyridin-5-yl)methanone A mixture of $Ac_2O$ (30 mL) and HCOOH (10 mL) was heated at 50° C. for 1 hour and then a solution of (6-(aminomethyl)-3-cyclopropylpyridin-2-yl)(4-(6-bromopyridin-3-yl)cyclo hexyl)methanone hydrochloride (crude, 0.8 mmol) in HCOOH (5 mL) was added drop wise and the mixture was heated at 50° C. for 2 hours. The solvent was evaporated under reduced pressure and water (100 mL) was added, washed with saturated aqueous of $NaHCO_3$, then extracted with ethyl acetate (50 mL×3) and combined the organic layer, the solvent was evaporated under reduced pressure and the residue was purified by column chromatography (PE:EA=4:1) to give crude product as a solid (0.28 g in 40% yield). $[M+H]^+$=424

Step 8: (4-(4-bromophenyl)cyclohexyl)(6-cyclopropylimidazo[1,5-a]pyridin-5-yl)methanol To a solution of (4-(4-bromophenyl)cyclohexyl)(6-cyclopropylimidazo[1,5-a]pyridin-5-yl)methanone (0.28 g, 0.62 mmol) in methol (10 mL) was added $NaBH_4$ (47 mg, 2 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (0.2 g in 71.74% yield). $^1$H NMR (DMSO-$d_6$) $\delta_H$ 8.62 (s, 1H), 7.44-7.39 (t, J=9.2 Hz, 3H), 7.31 (s, 1H), 7.17 (d, J=8.4 Hz, 2H), 6.47 (d, J=9.2 Hz, 1H), 5.81 (d, J=3.6 Hz, 1H), 5.25 (dd, J=9.6, 3.6 Hz, 1H), 2.46-2.40 (m, 2H), 2.22-2.20 (m, 1H), 2.06-1.96 (m, 1H), 1.88-1.85 (m, 1H), 1.72-1.62 (m, 2H), 1.52-1.44 (m, 1H), 1.32-1.16 (m, 5H), 0.98-0.62 (m, 2H), 0.79-0.76 (m, 1H). 0.67-0.63 (m, 1H). $[M+H]^+$=425.

Example D118a and D118b: (S)-((1r,4S)-4-(4-bromophenyl)cyclohexyl)(6-cyclopropylimidazo[1,5-a]pyridin-5-yl)methanol and (R)-((1 r,4R)-4-(4-bromophenyl)cyclohexyl)(6-cyclopropylimidazo[1,5-a]pyridin-5-yl)methanol

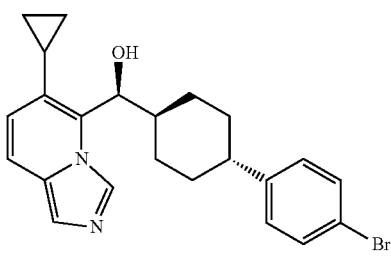

Fast isomer in CHIRALPAK IC-3
Eluting reagent: Hex(0.1% DEA):EtOH = 70:30

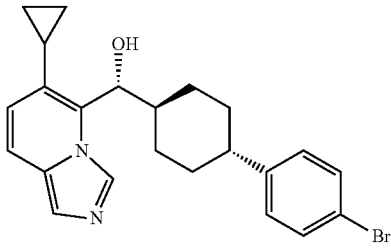

Slow isomer in CHIRALPAK IC-3
Eluting reagent: Hex(0.1% DEA):EtOH = 70:30

Each enantiomer of racemic D118a and D118b was separated using preparative HPLC on a CHIRAL PAK IC-3 with Hex (0.1% DEA):EtOH=70:30 as an eluent. The enantiomeric excesses were determined by using HPLC on a CHIRAL PAK IC-3 with Hex (0.1% DEA):EtOH=70:30 as an eluent at a flow rate of 1.0 mL/min. The first one enantiomer eluted at the retention time of 2.239 min (D118a), which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-$d_6$) $\delta_H$ 9.54 (s, 1H), 8.00 (s, 1H), 7.68 (d, J=9.6 Hz, 1H), 7.44 (d, J=8.0 Hz, 2H), 7.16 (d, J=8.4 Hz, 2H), 6.80 (d, J=9.6 Hz, 1H), 6.15 (s, 1H), 5.31 (d, J=9.6 Hz, 1H), 2.67-2.55 (m, 1H), 2.42-2.33 (m, 2H), 2.25-2.10 (m, 2H), 1.90-1.88 (m, 1H), 1.73-1.65 (min, 1H), 1.51-1.42 (min, 1H), 1.34-1.24 (m, 4H), 1.05-1.03 (m, 2H), 0.86-0.82 (m, 1H), 0.79-0.75 (m, 1H). and the other enantiomer eluted at the retention time of 4.450 min (D118b), 9.69 (s, 1H), 8.13 (s, 1H), 7.77 (d, J=9.6 Hz, 1H), 7.51 (d, J=8.4 Hz, 2H), 7.23 (d, J=8.4 Hz, 2H), 6.90 (d, J=10 Hz, 1H), 6.27 (s, 1H), 5.39 (d, J=9.6 Hz, 1H), 2.49-2.45 (m, 1H), 2.30-2.16 (m, 2H), 1.98-1.95 (m, 1H), 1.78-1.70 (m, 1H), 1.55-1.49 (m, 1H), 1.41-1.30 (m, 5H), 1.13-1.10 (m, 2H), 0.96-0.90 (m, 1H), 0.87-0.83 (m, 1H). The absolute configurations of chiral carbons in D118a and D118b are tentatively assigned as (S) and (R) respectively based on assumption that the binding model of the more potent isomer D118a is the same as that of C101a with IDO1 enzyme, and the relative stereochemistry on cyclohexane is assigned as trans configuration on the cyclohexane.

Example D119: (4-([1,1'-biphenyl]-4-yl)cyclohexyl) (6-cyclopropylimidazo[1,5-a]pyridin-5-yl)methanol

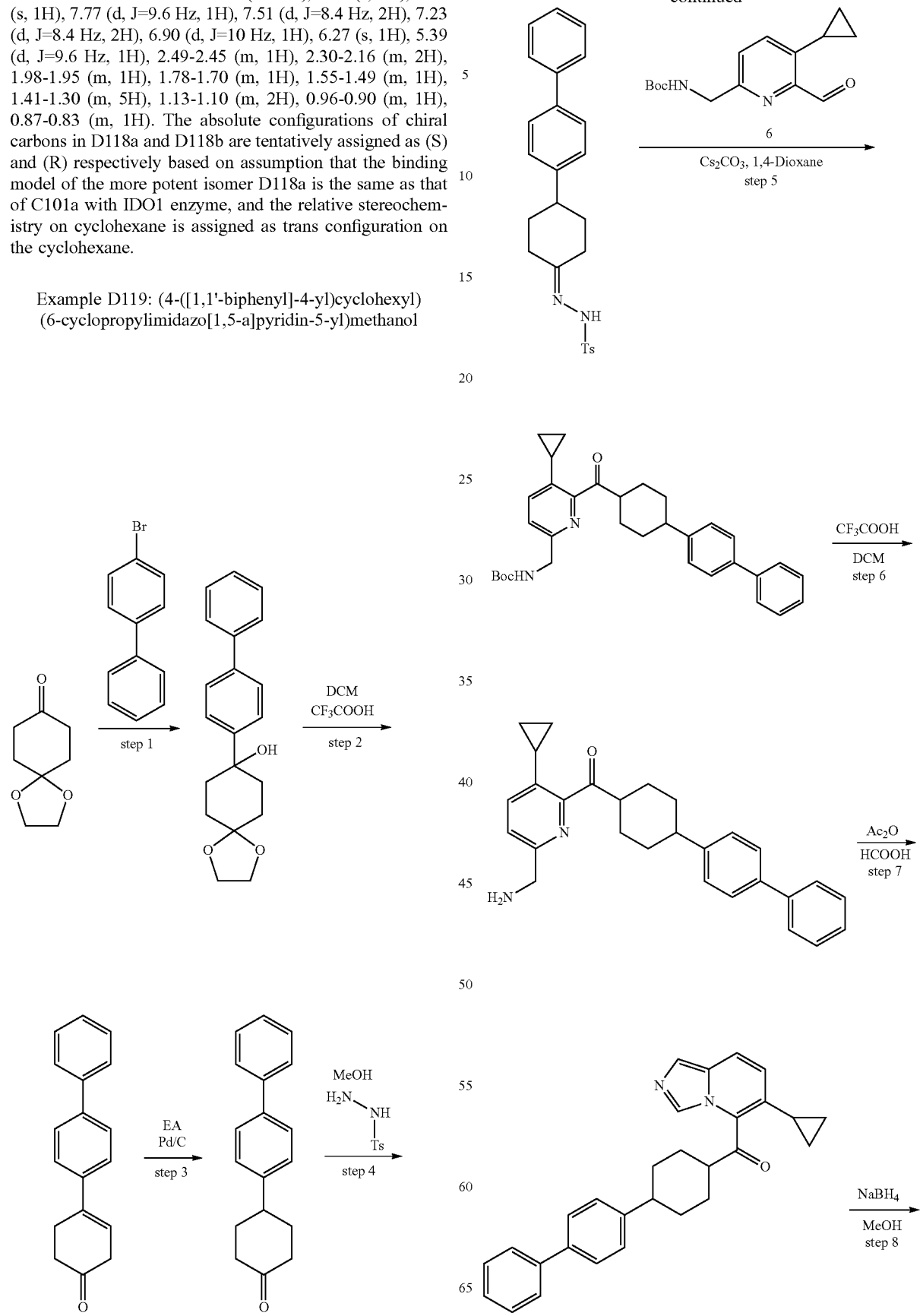

-continued

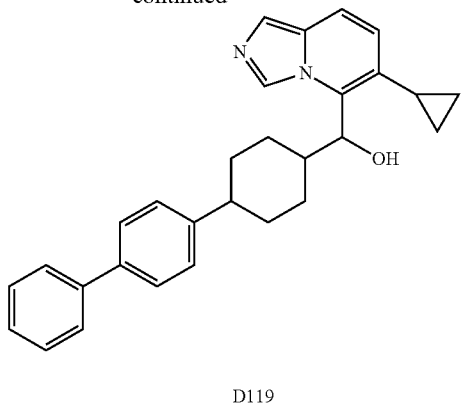

D119

Step 1: 8-([1,1'-biphenyl]-4-yl)-1,4-dioxaspiro[4.5]decan-8-ol

To a solution of n-Bu-Li (42 mL, 2.4 M) in dry THF (300 mL) was added drop wise a solution of 4-bromo-1,1'-biphenyl (23.3 g, 100 mmol) in dry THF (30 mL) at −70° C. and the mixture was stirred for 0.5 h before a solution of 1,4-dioxaspiro[4.5]decan-8-one (13 g, 83 mmol) in dry THF (30 mL) was added drop wise at −70° C. and the mixture was stirred for 2 hours. Quenched with saturated aqueous of $NH_4Cl$ and extracted with ethyl acetate (100 mL×3), combined the organic layer and the solvent was evaporated to give crude product, which was used for next step without further purification. $[M+H–H_2O]^+=293.1$.

Step 2: 2,5-dihydro-[1,1':4',1''-terphenyl]-4(3H)-one

To a solution of 8-([1,1'-biphenyl]-4-yl)-1,4-dioxaspiro[4.5]decan-8-ol (83 mmol) in dichloromethane (200 mL) was added trifluoroacetic acid (100 mL) at room temperature and the mixture was stirred for overnight. The solvent was evaporated under reduced pressure and water (100 mL) was added, extracted with ethyl acetate (100 mL×3), combined the organic layer and washed with saturated aqueous of $NaHCO_3$ then the organic layer was evaporated to give crude product, which was used for the next step without further purification. $[M+H]^+=249.1$.

Step 3: 4-([1,1'-biphenyl]-4-yl)cyclohexan-1-one

To a solution of 2,5-dihydro-[1,1':4',1''-terphenyl]-4(3H)-one (42 mmol) in ethyl acetate (200 mL) was added Pd/C (2.0 g, 10%) and the mixture was stirred for 6 hours at room temperature under $H_2$ (0.4 Mpa). Then filtered to remove Pd/C and the filtrate was evaporated under reduced pressure to give a crude product, which was washed with PE/EA=5:1 to give 4.4 g (42% yield for three steps) product as white solid. $[M+H]^+=251.1$.

Step 4: N'-(4-([1,1'-biphenyl]-4-yl)cyclohexylidene)-4-methylbenzenesulfonohydrazide To a solution of 4-([1,1'-biphenyl]-4-yl)cyclohexan-1-one (4.4 g, 18 mmol) in methanol (100 mL) was added 4-methylbenzenesulfonohydrazide (3.4 g, 18 mmol) at room temperature, and the mixture was stirred for overnight. Then half of the solvent was evaporated under reduced pressure and then filtered to give 5.0 g (yield: 67%) as a white solid.

$^1$H NMR (DMSO-$d_6$) $\delta_H$10.19 (s, 1H), 7.75 (d, J=8.0 Hz, 2H), 7.63 (d, J=7.6 Hz, 2H), 7.57 (d, J=8.0 Hz, 2H), 7.40-7.46 (m, 4H), 7.30-7.36 (m, 3H), 2.92-2.95 (m, 1H), 2.81-2.87 (m, 1H), 2.40 (s, 3H), 2.27-2.30 (m, 2H), 1.94-2.00 (m, 3H). $[M+H]^+=419.1$.

Step 5: tert-butyl ((6-(4-([1,1'-biphenyl]-4-yl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (0.8 g, 2.9 mmol) in 1,4-dioxane (0.1 L) was added N'-(4-([1,1'-biphenyl]-4-yl)cyclohexylidene)-4-methylbenzenesulfonohydrazide (2.5 g, 5.8 mmol) and $Cs_2CO_3$ (1.8 g, 5.8 mmol) at room temperature and the mixture was heated at 100° C. for overnight. The solvent was evaporated under reduced pressure and water (100 mL) was added, extracted with ethyl acetate (50 mL×3) and combined the organic layer, the solvent was evaporated under reduced pressure and the residue was purified by column chromatography (PE:EA=10:1) to give crude product as a yellow oil (0.9 g in 61% yield). $[M+H]^+=511.2$.

Step 6: (4-([1,1'-biphenyl]-4-yl)cyclohexyl)(6-(aminomethyl)-3-cyclopropylpyridin-2-yl)methanone To a solution of tert-butyl ((6-(4-([1,1'-biphenyl]-4-yl)cyclohexane-1-carbonyl)-5-cyclopropylpyridin-2-yl)methyl)carbamate (0.9 g, 1.76 mmol) in DCM (60 mL) was added TFA (30 mL) at room temperature and the mixture was stirred overnight. The solvent was evaporated under reduced pressure and the residue was used for next step without further purification. $[M+H]^+=411.2$.

Step 7: (4-([1,1'-biphenyl]-4-yl)cyclohexyl)(6-cyclopropylimidazo[1,5-a]pyridin-5-yl)methanone A mixture of $Ac_2O$ (30 mL) and HCOOH (10 mL) was heated at 50° C. for 1 hour and then a solution of (4-([1,1'-biphenyl]-4-yl)cyclohexyl)(6-(aminomethyl)-3-cyclopropylpyridin-2-yl)methanone (crude, 1.76 mmol) in HCOOH (5 mL) was added drop wise and the mixture was heated at 50° C. for 2 hours. The solvent was evaporated under reduced pressure and water (100 mL) was added, washed with saturated aqueous of $NaHCO_3$, then extracted with ethyl acetate (50 mL×3) and combined the organic layer, the solvent was evaporated under reduced pressure to give crude product as a an oil. $[M+H]^+=421.2$.

Step 8: (4-([1,1'-biphenyl]-4-yl)cyclohexyl)(6-cyclopropylimidazo[1,5-a]pyridin-5-yl)methanol

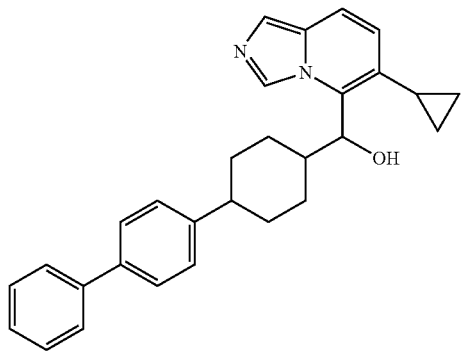 [SMILES: OC(c1c(C2CC2)ccc2cncn12)C1CCC(c2ccc(-c3ccccc3)cc2)CC1]

To a solution of (4-([1,1'-biphenyl]-4-yl)cyclohexyl)(6-cyclopropylimidazo[1,5-a]pyridin-5-yl)methanone (crude, 1.76 mmol) in methol (50 mL) was added NaBH$_4$ (333 mg, 8.8 mmol) at room temperature and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure and the residue was washed with MeOH to give product, further purified by column chromatography (PE:EA=4:1) to give product as a white solid (0.3 g in 40% yield). $^1$H NMR (DMSO-d$_6$) $\delta_H$ 8.64 (s, 1H), 7.61 (d, J=7.6 Hz, 2H), 7.54 (d, J=8.4 Hz, 2H), 7.40-7.45 (m, 3H), 7.28-7.34 (m, 4H), 6.48 (d, J=9.6 Hz, 1H), 5.81 (d, J=3.6 Hz, 1H), 5.27 (dd, J=8.0, 4.0 Hz, 1H), 2.43-2.48 (m, 2H), 2.20-2.27 (m, 1H), 2.03 (s, 1H), 1.91-1.95 (m, 1H), 1.69-1.73 (m, 1H), 1.50-1.61 (m, 1H), 1.16-1.36 (m, 4H), 0.92-0.99 (m, 2H), 0.74-0.80 (m, 1H), 0.64-0.70 (m, 1H). [M+H]$^+$=423.2.

Example D119a and D119b: (S)-((1r,4S)-4-([1,1'-biphenyl]-4-yl)cyclohexyl)(6-cyclopropylimidazo[1,5-a]pyridin-5-yl)methanol and (R)-((1r,4R)-4-([1,1'-biphenyl]-4-ylcyclohexyl)(6-cyclopropylimidazo[1,5-a]pyridin-5-yl)methanol

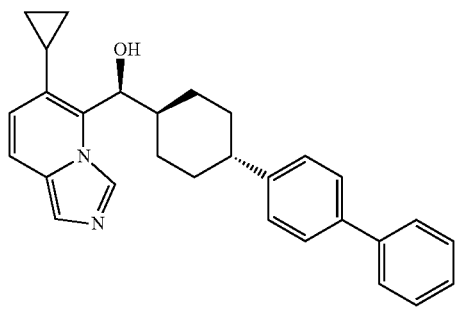

Fast isomer in CHIRALART Cellulose-SB
Eluting reagent: Hex:EtOH = 70:30

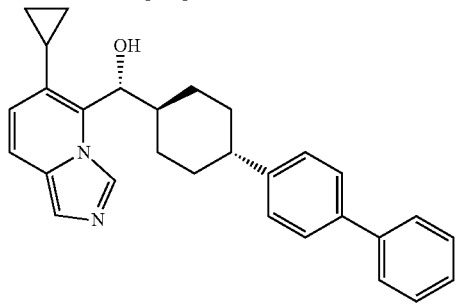

Slow isomer in CHIRALART Cellulose-SB
Eluting reagent: Hex:EtOH = 70:30

Each enantiomer of racemic D119a and D119b was separated using preparative HPLC on a CHIRALART Cellulose-SB with Hex:EtOH=70:30 as an eluent. The enantiomeric excesses were determined by using HPLC on a CHIRAL Cellulose-SB with Hex (0.1% DEA):EtOH=70:30 as an eluent at a flow rate of 1.0 mL/min. The first one enantiomer eluted at the retention time of 2.823 min, and the other enantiomer eluted at the retention time of 4.820 min. To a solution of D119a (137 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (115 mg in 77% yield). $^1$H NMR (400 MHz, DMSO-d$_6$) $\delta_H$ 9.67 (s, 1H), 8.09 (s, 1H), 7.72 (d, J=9.6 Hz, 1H), 7.61 (d, J=7.6 Hz, 2H), 7.55 (d, J=8.0 Hz, 2H), 7.44 (t, J=7.6 Hz, 2H), 7.33 (t, J=7.6 Hz, 1H), 7.28 (d, J=8.0 Hz, 2H), 6.86 (d, J=9.6 Hz, 1H), 6.23 (brs, 1H), 5.34 (d, J=9.6 Hz, 1H), 2.42-2.45 (m, 1H), 2.20 (s, 2H), 1.94-1.97 (m, 1H), 1.73-1.76 (m, 1H), 1.49-1.58 (m, 1H), 1.23-1.42 (m, 4H), 1.05-1.07 (m, 2H), 0.85-0.87 (m, 1H), and 0.77-0.81 (m, 1H). MS (ESI) m/e [M+1]$^+$=423.2. To a solution of D119b (111 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (81 mg in 67% yield). $^1$H NMR (400 MHz, DMSO-d$_6$) $\delta_H$ 9.66 (s, 1H), 8.08 (s, 1H), 7.71 (d, J=9.6 Hz, 1H), 7.61 (d, J=7.6 Hz, 2H), 7.55 (d, J=8.0 Hz, 2H), 7.44 (t, J=7.6 Hz, 2H), 7.33 (t, J=7.6 Hz, 1H), 7.28 (d, J=8.0 Hz, 2H), 6.85 (d, J=9.6 Hz, 1H), 6.21 (brs, 1H), 5.34 (d, J=9.6 Hz, 1H), 2.42-2.45 (m, 1H), 2.20 (s, 2H), 1.94-1.97 (m, 1H), 1.73-1.76 (m, 1H), 1.49-1.58 (m, 1H), 1.24-1.40 (m, 4H), 1.05-1.07 (m, 2H), 0.85-0.89 (m, 1H), and 0.77-0.81 (m, 1H). MS (ESI) m/e [M+1]$^+$=423.2. The absolute configurations of chiral carbons in D119a and D119b are tentatively assigned as (S) and (R) respectively based on assumption that the binding model of the more potent isomer D119a is the same as that of C101a with IDO1 enzyme, and the relative stereochemistry on cyclohexane is assigned as trans configuration on the cyclohexane.

Example D120 was prepared with the same procedure as example D119

Example D120: (6-cyclopropylimidazo[1,5-a]pyridin-5-yl)(4-(4-phenoxyphenyl)cyclohexyl)methanol

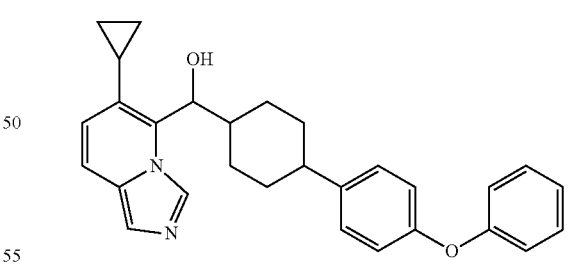

$^1$H NMR (DMSO-d$_6$) $\delta_H$ 8.62 (s, 1H), 7.29-7.41 (m, 4H), 7.21 (d, J=8.4 Hz, 2H), 7.10 (t, J=7.6 Hz, 1H), 6.96 (d, J=8.0 Hz, 2H), 6.89 (d, J=8.4 Hz, 2H), 6.47 (d, J=9.2 Hz, 1H), 5.80 (d, 1H, J=4.0 Hz), 5.26 (dd, J=9.6, 3.2 Hz, 1H), 2.41-2.44 (m, 2H), 2.20-2.22 (m, 1H), 1.99-2.01 (m, 1H), 1.88-1.91 (m, 1H), 1.62-1.74 (m, 1H), 1.45-1.54 (m, 1H), 1.16-1.30 (m, 4H), 0.89-0.98 (m, 2H), 0.75-0.79 (m, 1H), 0.64-0.67 (m, 1H). [M+H]$^+$=439.2.

Example D120a and D120b: (S)-(6-cyclopropylimidazo[1,5-a]pyridin-5-yl)((1r,4S)-4-(4-phenoxyphenyl)cyclohexyl)methanol and (R)-(6-cyclopropylimidazo[1,5-a]pyridin-5-yl)(1r,4R)-4-(4-phenoxyphenyl)cyclohexyl)methanol

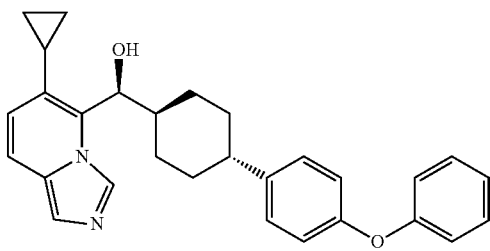

Fast isomer in chiral IC HPLC
Eluting reagent: Hex(0.2% IPAmine):IPA = 60:40 (v/v)

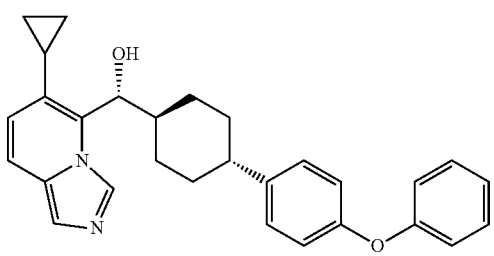

Slow isomer in chiral IC HPLC
Eluting reagent: Hex(0.2% IPAmine):IPA = 60:40 (v/v)

Each enantiomer of racemic D120a and D120b was separated using preparative HPLC on a Phenomenex Lux 5u Cellulose-4 with Hex:EtOH=80:20 as an eluent. The first one enantiomer eluted at the retention time of 3.178 min (D120a), which was dissolved in THF (5 ml), and HCl in EA(4N, 0.5 mL) was added and stirred at r.t for 1 h, the solvent was evaporated to give product as white solid, $^1$H NMR (DMSO-$d_6$) δ 9.64 (s, 1H), 8.07 (s, 1H), 7.71 (d, J=9.6 Hz, 1H), 7.37 (t, J=8.0 Hz, 2H), 7.20 (d, J=8.4 Hz, 2H), 7.11 (t, J=7.6 Hz, 1H), 6.96 (d, J=8.4 Hz, 2H), 6.91 (d, J=8.4 Hz, 2H), 6.85 (d, J=8.4 Hz, 1H), 6.21 (brs, 1H), 5.33 (d, J=9.6 Hz, 1H), 2.40-2.43 (m, 1H), 2.17 (s, 2H), 1.91-1.94 (m, 1H), 1.70-1.76 (m, 1H), 1.44-1.52 (m, 1H), 1.24-1.38 (m, 4H), 1.04-1.06 (m, 2H), 0.85-0.88 (m, 1H) and 0.77-0.80 (m, 1H), MS (ESI) m/e [M+1]$^+$439; and the other enantiomer eluted at the retention time of 7.499 min(D120b), which was dissolved in THF (5 ml), and HCl in EA(4N, 0.5 mL) was added and the solvent was evaporated to give product as white solid, $^1$H NMR (DMSO-$d_6$) δ 9.63 (s, 1H), 8.07 (s, 1H), 7.71 (d, J=9.6 Hz, 1H), 7.37 (t, J=8.0 Hz, 2H), 7.20 (d, J=8.4 Hz, 2H), 7.11 (t, J=7.6 Hz, 1H), 6.96 (d, J=8.4 Hz, 2H), 6.91 (d, J=8.4 Hz, 2H), 6.84 (d, J=8.4 Hz, 1H), 6.20 (brs, 1H), 5.33 (d, J=9.6 Hz, 1H), 2.40-2.42 (m, 1H), 2.17 (s, 2H), 1.91-1.94 (m, 1H), 1.70-1.76 (m, 1H), 1.43-1.52 (m, 1H), 1.24-1.35 (m, 4H), 1.00-1.10 (m, 2H), 0.84-0.87 (m, 1H) and 0.77-0.80 (m, 1H), MS (ESI) m/e [M+1]$^+$=439; The absolute configurations of chiral carbons in D120a and D120b are tentatively assigned as (S) and (R) respectively based on assumption that the binding model of the more potent isomer D120a is the same as that of C101a with IDO1 enzyme, and the relative stereochemistry on cyclohexane is assigned as trans configuration on the cyclohexane.

Example D121: benzyl (4-(4-((6-cyclopropylimidazo[1,5-a]pyridin-5-yl)hydroxy)methyl)cyclohexyl)phenyl)carbamate

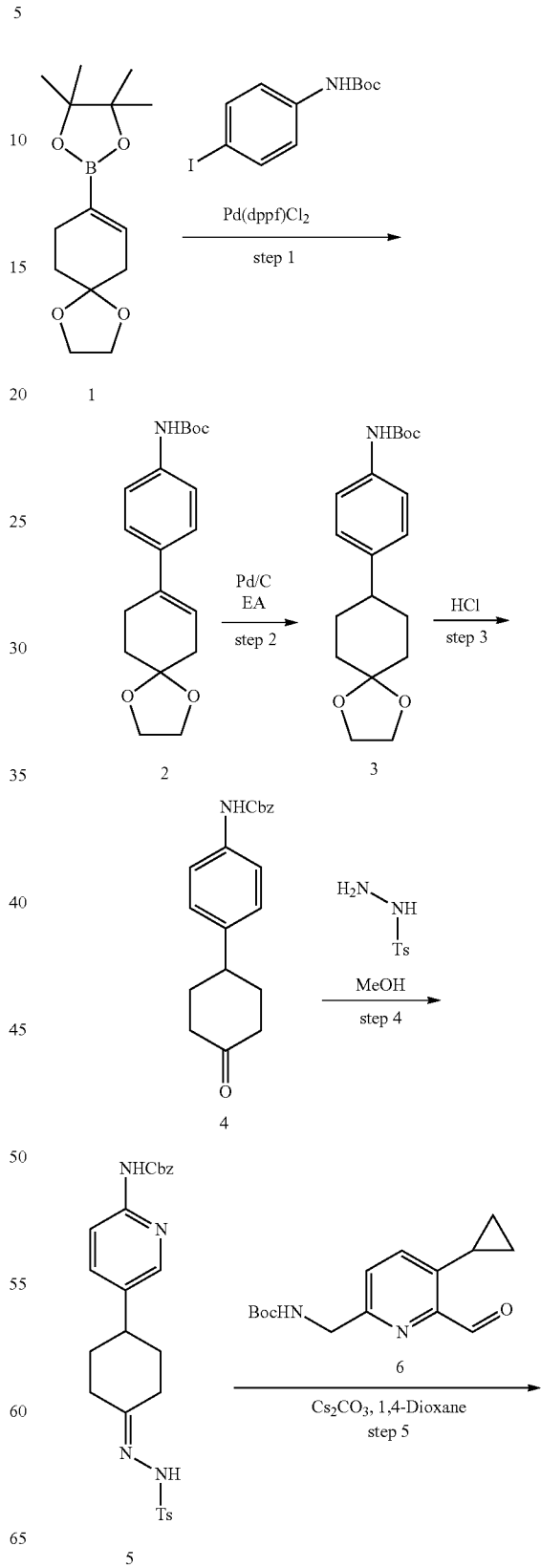

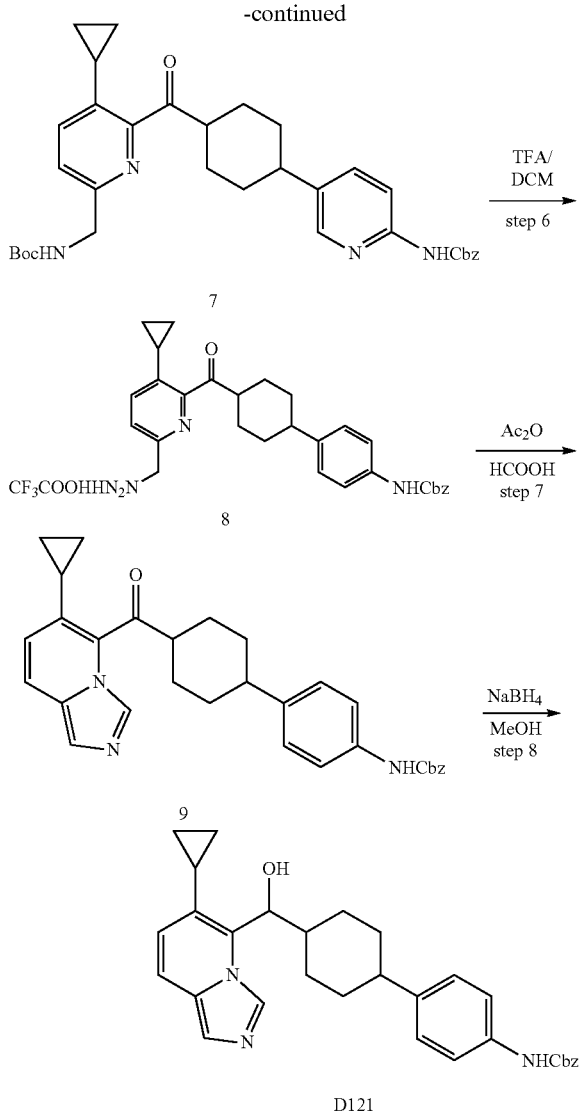

Step 1: tert-butyl (4-(1,4-dioxaspiro[4.5]dec-7-en-8-yl)phenyl)carbamate

To a solution of tert-butyl (4-iodophenyl)carbamate (7.2 g, 22.6 mmoL) in 1,4-dioxane (100 mL) was added 4,4,5,5-tetramethyl-2-(1,4-dioxaspiro[4.5]dec-7-en-8-yl)-1,3,2-dioxaborolane (6.0 g, 22.6 mmol), Pd(dppf)Cl$_2$ (1.6 g, 2.2 mmol) and Cs$_2$CO$_3$ (11.0 g, 33.9 mmol) and the mixture was heated at 80° C. for 20 hours. Then filter off the solid, the filtrate was evaporated under reduced pressure and the residue was purified by column chromatography (PE:EA=4:1) to give product as yellow solid (2.9 g in 38.7% yield). [M+H]$^+$=332.2.

Step 2: tert-butyl (4-(1,4-dioxaspiro[4.5]decan-8-yl)phenyl)carbamate

To a solution of tert-butyl (4-(1,4-dioxaspiro[4.5]dec-7-en-8-yl)phenyl)carbamate (2.9 g, 8.8 mmol) in ethyl acetate (100 mL) was added Pd/C (0.5 g, 10%) and the mixture was stirred for 2 days at room temperature under H$_2$ (0.4 Mpa). Then filtered to remove Pd/C and the filtrate was evaporated under reduced pressure to give a crude product (3.0 g) for next step directly without further purification. [M+H−56]$^+$=278.1.

Step 3: benzyl (4-(4-oxocyclohexyl)phenyl)carbamate

To a solution of tert-butyl (4-(1,4-dioxaspiro[4.5]decan-8-yl)phenyl)carbamate (2.7 g, 8.1 mmol) in DCM (40 mL) was added TFA (30 mL). The mixture was stirred for 2 hours at room temperature. Evaporated the solvent under reduce pressure. To the oil residue was added saturated NaHCO$_3$ solution (80 mL) and ethyl acetate (80 mL). Stirred for 1 hour at room temperature. Added CbzCl (2.7 g, 16.2 mmol) to the mixture and stirred for 18 hours. Separated the organic phase, concentrated and purified by column chromatography (PE/EA=3:1) to give product (1.8 g in 69.2% yield) as white solid. $^1$H NMR (400 MHz, DMSO-d$_6$) $\delta_H$ 9.69 (s, 1H), 7.43-7.32 (m, 7H), 7.20 (d, J=8.4 Hz, 2H), 5.14 (s, 2H), 2.99 (t, J=12.0 Hz, 1H), 2.60-2.50 (m, 2H), 2.25 (d, J=14.0 Hz, 2H), 2.05-1.99 (m, 2H), and 1.87-1.78 (m, 2H).

Step 4: benzyl (4-(4-(2-tosylhydrazono)cyclohexyl)phenyl)carbamate

To a solution of benzyl (4-(4-oxocyclohexyl)phenyl)carbamate (0.96 g, 3.0 mmol) in methol (50 mL) was added 4-methylbenzenesulfonohydrazide (0.56 g, 3.0 mmol) at room temperature and the mixture was stirred for 20 hours. Filtered and washed with methol (3 mL) to give product as a white solid (1.3 g in 88.4% yield). $^1$HNMR (400 MHz, DMSO-d6) OH 10.17 (s, 1H), 9.67 (s, 1H), 7.74 (d, J=8.2 Hz, 2H), 7.47-7.30 (m, 9H), 7.12 (d, J=8.4 Hz, 2H), 5.13 (s, 2H), 2.99-2.82 (m, 1H), 2.71 (t, J=12.0 Hz, 1H), 2.39 (s, 3H), 2.25-2.22 (m, 2H), 1.96-1.86 (m, 3H), 1.57-1.35 (m, 2H).

Step 5: tert-butyl ((6-(4-(4-(((benzyloxy)carbonyl)amino)phenyl)cyclohexane-1-carbonyl)-5-cyclopropylpyridin-2-yl)methyl)carbamate To a solution of benzyl (4-(4-(2-tosylhydrazono)cyclohexyl)phenyl)carbamate (1.3 g, 2.6 mmol) in 1,4-dioxane (50 mL) was added tert-butyl ((5-cyclopropyl-6-formylpyridin-2-yl)methyl)carbamate (0.7 g, 2.6 mmol) and Cs$_2$CO$_3$ (1.3 g, 4.0 mmol) at room temperature, and the mixture was heated at 85° C. for 20 hours. Water (100 mL) was added, extracted with ethyl acetate (100 mL×2) and combined the organic layer, the solvent was evaporated under reduced pressure and the residue was purified by column chromatography (PE:EA=5:1) to give product. (0.55 g in 36.7% yield). [M+H]$^+$=584.3

Step 6: benzyl (4-(4-(6-(aminomethyl)-3-cyclopropylpicolinoyl)cyclohexyl)phenyl)carbamate 2,2,2-trifluoroacetate To a solution of tert-butyl ((6-(4-(4-(((benzyloxy)carbonyl)amino)phenyl)cyclohexane-1-carbonyl)-5-cyclopropylpyridin-2-yl)methyl)carbamate (0.5 g, 0.9 mmol) in DCM (20 mL) was added trifluoracetic acid (10 mL) and the mixture was stirred at room temperature for 1 hour. The solvent was evaporated under reduced pressure to give crude product for next step directly without further purification.

Step 7: benzyl (4-(4-(6-cyclopropylimidazo[1,5-a]pyridine-5-carbonyl)cyclohexyl)phenyl)-carbamate A mixture of Ac$_2$O (20 mL) and HCOOH (5 mL) was heated at 55° C. for 1 hour and then a solution of benzyl (4-(4-(6-(aminomethyl)-3-cyclopropylpicolinoyl)cyclohexyl)phenyl)-carbamate 2,2,2-trifluoroacetate (crude, 0.9 mmol) in HCOOH (5 mL) was added drop wise and the mixture was heated at 55° C. for 18 hours. The solvent was evaporated under reduced pressure and saturated aqueous of NaHCO$_3$(50 mL) was added, then extracted with ethyl acetate (50 mL) and separated the organic layer, the solvent was evaporated under reduced pressure and the residue was purified pre-TLC (PE:EA=1:2) to give crude product as a solid (0.3 g). [M+H]$^+$=494.2.

Step 8: benzyl (4-(4-((6-cyclopropylimidazo[1,5-a]pyridin-5-yl)(hydroxy)methyl)cyclohexyl)phenyl) carbamate

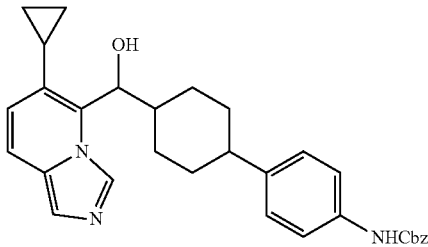 [SMILES: O=C(Nc1ccc(C2CCC(C(O)c3c(C4CC4)ccc4cncn34)CC2)cc1)OCc1ccccc1]

To a solution of benzyl (4-(4-(6-cyclopropylimidazo[1,5-a]pyridine-5-carbonyl)cyclohexyl)phenyl)carbamate (0.3 g, 0.6 mmol) in MeOH (30 mL) was added NaBH$_4$ (2.0 g, 52.6 mmol) at room temperature in portions. The mixture was stirred at 25° C. for 20 hours. Then quenched the reaction with water (100 mL) and extracted with EA (100 mL). Concentrated the organic phase and purified by pre-TLC (PE/EA=1:1) (140.0 mg in 46.4% yield). $^1$H NMR (DMSO-d6) $\delta_H$ 9.69 (s, 1H), 8.71 (s, 1H), 7.49-7.38 (m, 9H), 7.16 (d, J=8.8 Hz, 2H), 6.55 (d, J=9.2 Hz, 1H), 5.88 (s, 1H), 5.32 (dd, J=9.6, 4.0 Hz, 1H), 5.18 (s, 2H), 2.48-2.39 (m, 2H), 2.23 (m, 1H), 2.07 (m, 1H), 1.92 (m, 1H), 1.69 (m, 1H), 1.56-1.47 (m, 1H), 1.37-1.21 (m, 4H), 1.05-0.96 (m, 2H), 0.84-0.82 (m, 1H), and 0.74-0.71 (m, 1H). [M+H]$^+$=496.2.

Example D122: (4-(4-aminophenyl)cyclohexyl)(6-cyclopropylimidazo[1,5-a]pyridin-5-yl)methanol

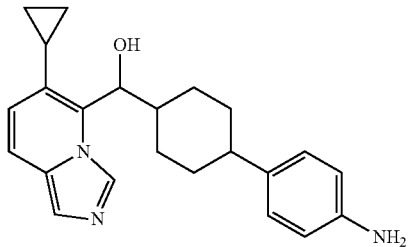 [SMILES: Nc1ccc(C2CCC(C(O)c3c(C4CC4)ccc4cncn34)CC2)cc1]

To a solution of benzyl (4-(4-((6-cyclopropylimidazo[1,5-a]pyridin-5-yl)(hydroxy)methyl)cyclohexyl)phenyl)carbamate (0.2 g, 0.4 mmol) in MeOH (30 mL) was added Pd/C (0.1 g, 10%), and stirred at room temperature for 3 hours under H$_2$. Filtered, concentrated to give crude product, which was purified by pre-HPLC to give product. $^1$H NMR (DMSO-d6) $\delta_H$ 8.61 (s, 1H), 7.39 (d, J=9.6 Hz, 1H), 7.31 (s, 1H), 6.83 (d, J=8.4 Hz, 2H), 6.48-6.43 (m, 3H), 5.77 (d, J=4.0 Hz, 1H), 5.24 (dd, J=9.6, 3.6 Hz, 1H), 4.80 (s, 2H), 2.41-2.38 (m, 1H), 2.29-2.25 (m, 1H), 2.20-2.15 (m, 1H), 1.99 (m, 1H), 1.82 (d, J=12.4 Hz, 1H), 1.61 (m, 1H), 1.42-1.35 (m, 1H), 1.25-1.14 (m, 4H), 0.98-0.89 (m, 2H), 0.78-0.74 (m, 1H), 0.66-0.64 (m, 1H). [M+H]$^+$=362.2.

Examples D122a and D122b: (S)-((1r,4S)-4-(4-aminophenyl)cyclohexyl)(6-cyclopropylimidazo[1,5-a]pyridin-5-yl)methanol and (R)-((1r,4R)-4-(4-aminophenyl)cyclohexyl)(6-cyclopropylimidazo[1,5-a]pyridin-5-yl)methanol

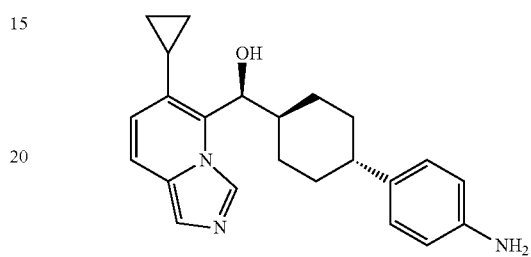

Fast isomer in CHIRALPAK IC HPLC
Eluting reagent: MeOH = 100%

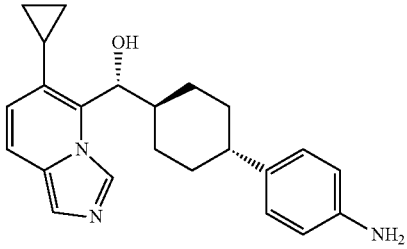

Slow isomer in CHIRALPAL IC HPLC
Eluting reagent: MeOH = 100%

Each enantiomer of racemic D122a and D122b was separated using preparative HPLC on a CHIRALPAK IC with MeOH=100% as an eluent. The enantiomeric excesses were determined by using HPLC on a CHIRALPAK IC with MeOH (0.1% DEA)=100% as an eluent at a flow rate of 1.0 mL/min. The first one enantiomer eluted at the retention time of 1.145 min, and the other enantiomer eluted at the retention time of 2.166 min. To a solution of D122a (29.3 mg) in MeOH (5 mL) was added drop wise of Ethyl acetate solution of hydrochloric acid (2 mL, 4.0M) at room temperature, stirred at room temperature for 10 min, then the solvent was evaporated under reduced pressure to give the desired product as white solid (24.6 mg in 70.0% yield). $^1$H NMR (DMSO-d$_6$) $\delta_H$ 9.64 (s, 1H), 8.07 (s, 1H), 7.71 (d, J=9.6 Hz, 1H), 7.30-7.23 (m, 4H), 6.84 (d, J=9.6 Hz, 1H), 6.21 (s, 1H), 5.32 (d, J=9.6 Hz, 1H), 2.50-2.39 (m, 2H), 2.17 (b, 2H), 1.90 (d, J=12.0 Hz, 1H), 1.68 (b, 1H), 1.53-1.2 (m, 5H), 1.06-1.04 (m, 2H), 0.86 (b, 1H), and 0.79 (b, 1H). [M+H]$^+$=362.2. To a solution of D122b (29.1 mg) in MeOH (5 mL) was added drop wise of ethyl acetate solution of hydrochloric acid (2 mL, 4.0M) at room temperature, stirred at room temperature for 10 min, then the solvent was evaporated under reduced pressure to give the desired product as white solid (22.0 mg in 62.8% yield). $^1$H NMR (DMSO-d$_6$) $\delta_H$ 9.62 (s, 1H), 8.06 (s, 1H), 7.70 (d, J=9.6 Hz, 1H), 7.30-7.22 (m, 4H), 6.83 (d, J=9.6 Hz, 1H), 6.21 (s, 1H), 5.32 (d, J=9.6 Hz, 1H), 2.50-2.3 (m, 2H), 2.17 (b, 2H), 1.90 (d, J=12.4 Hz, 1H), 1.68 (b, 1H), 1.53-1.23 (m, 5H), 1.05-1.00 (m, 2H), 0.86 (b, 1H), and 0.78 (b, 1H). [M+H]⁺=362.2. The absolute configurations of chiral carbons in D122a and D122b are tentatively assigned as (S) and (R) respectively based on assumption that the binding model of the more potent isomer D122a is the same as that of C101a with IDO1 enzyme, and the relative stereochemistry on cyclohexane is assigned as trans configuration on the cyclohexane.

Example D123: 4-(4-((6-cyclopropylimidazo[1,5-a]pyridin-5-yl)(hydroxy)methyl)cyclohexyl)benzaldehyde

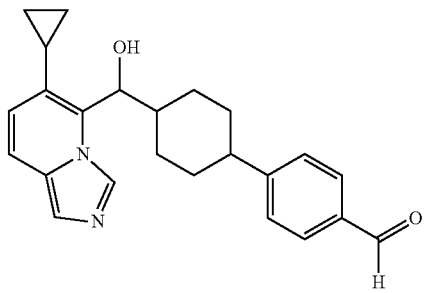 [SMILES: O=Cc1ccc(C2CCC(C(O)c3c(C4CC4)ccc4cncn34)CC2)cc1]

To a solution of 4-(4-((6-cyclopropylimidazo[1,5-a]pyridin-5-yl)(hydroxy)methyl)cyclohexyl)benzonitrile (100 mg, 0.26 mmoL) in dry THF (20 mL) was added drop wise of DIBAL-H (0.6 mL, 1.5 M) at −70° C. and the mixture was stirred for 3 hours. Quenched with saturated aqueous of N H₄Cl and extracted with ethyl acetate (20 mL×3), combined the organic layer, the solvent was evaporated under reduced pressure and the residue was purified by column chromatography (PE:EA=1:1) to give product as white solid (30 mg in 31% yield). ¹H NMR (400 MHz, DMSO-d₆) δ_H 9.93 (s, 1H), 8.62 (s, 1H), 7.80 (d, J=8.0 Hz, 2H), 7.45 (d, J=8.0 Hz, 2H), 7.40 (d, J=9.2 Hz, 1H), 7.31 (s, 1H), 6.48 (d, J=8.4 Hz, 1H), 5.82 (d, J=3.6 Hz, 1H), 5.27 (dd, J=3.6 Hz, J=9.6 Hz, 1H), 2.57-2.63 (m, 1H), 2.23-2.25 (m, 1H), 2.02 (s, 1H), 1.90-1.93 (m, 1H), 1.68-1.76 (m, 1H), 1.51-1.60 (m, 1H), 1.19-1.33 (m, 4H), 0.89-0.95 (m, 2H), 0.76-0.79 (m, 1H) and 0.65-0.67 (m, 1H). MS (ESI) m/e [M+1]⁺=375.1.

Example D124: 4-(4-((6-cyclopropylimidazo[1,5-a]pyridin-5-yl)(hydroxy)methyl)cyclohexyl)-N-methylbenzamide

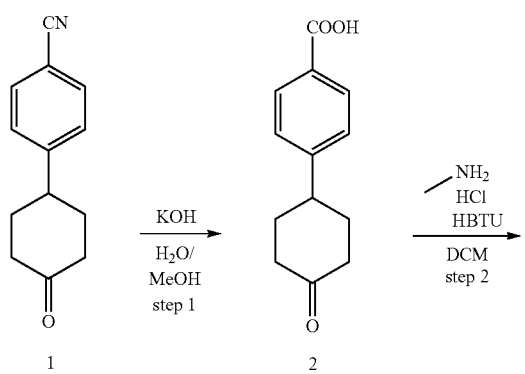

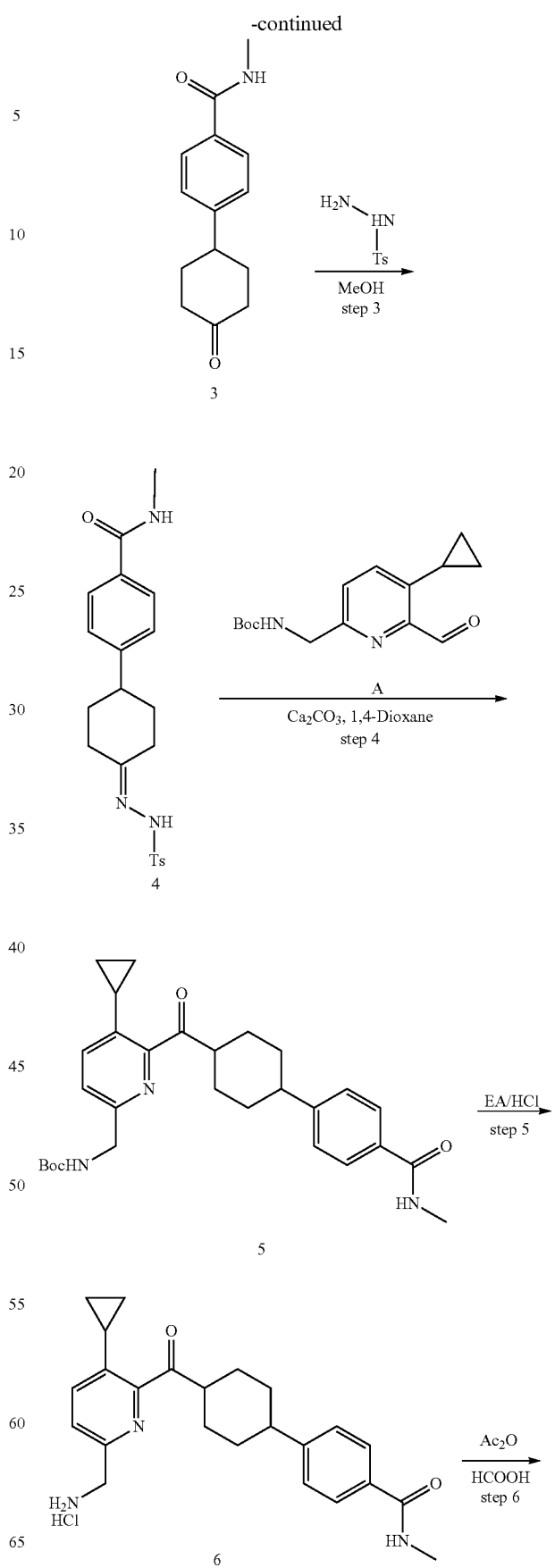

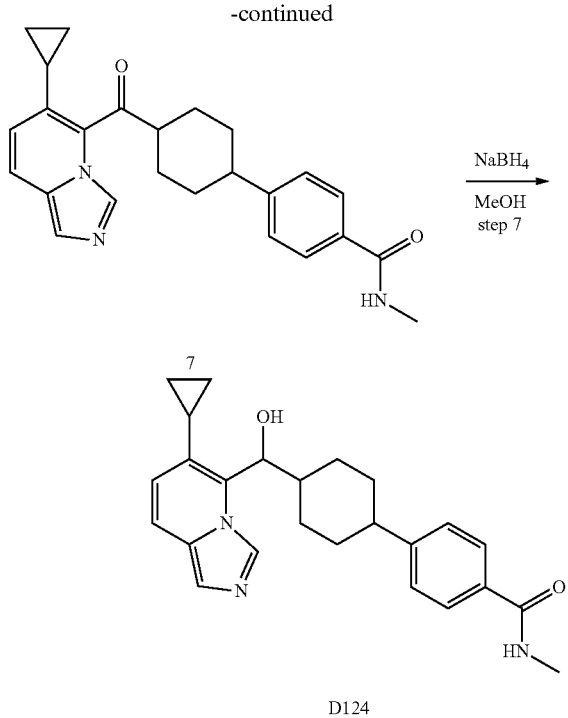

D124

Step 1: 4-(4-oxocyclohexyl)benzoic acid

To a solution of 4-(4-oxocyclohexyl)benzonitrile (5 g, 25.1 mmol) and KOH (5.6 g, 100.4 mmol) in MeOH:H$_2$O=20:1 (100 mL), the mixture was stirred at 70° C. for 3 h. TLC (EA, Rf=0.5) showed the reaction was completed. Filtered and concentrated, H$_2$O (100 ml) was was added and extracted with DCM (50 ml×3). The combined organic layer was dried over Na$_2$SO$_4$, filtered and concentrated to give product (4.5 g, 81.8%) as a white solid.

Step 2: N-methyl-4-(4-oxocyclohexyl)benzamide

To a solution of 4-(4-oxocyclohexyl)benzoic acid (1 g, 4.6 mmol), HBTU (2.1 g, 5.52 mmol) and Methylamine hydrochloride (0.34 g, 5.04 mmol) in DCM (50 mL) was added Et$_3$N (0.7 g, 6.9 mmol) at room temperature, and the mixture was stirred for overnight. The solvent was evaporated under reduced pressure and aqueous NH$_4$Cl (50 mL) was added, extracted with ethyl acetate (50 ml×3), combined the organic layer was evaporated to give crude product, The solvent was evaporate under reduced pressure and the residue was purified by column chromatography (PE:EA=1:1) to give product (0.62 g, 58.5%) as a white solid. MS (ESI) m/e [M+1]$^+$=232.

Step 3: N-methyl-4-(4-(2-tosylhydrazono)cyclohexyl)benzamide

To a solution of N-methyl-4-(4-oxocyclohexyl)benzamide (0.62 g, 2.68 mmol) in methol (50 mL) was added 4-methylbenzenesulfonohydrazide (0.55 g, 2.95 mmol) at room temperature, and the mixture was stirred for overnight. Evaporate half the solvent under reduced pressure and then filtered to give product as a white solid (0.99 g in 89% yield). MS (ESI) m/e [M+1]$^+$=400.

Step 4: tert-butyl ((5-cyclopropyl-6-(4-(4-(methylcarbamoyl)phenyl)cyclohexane-1-carbonyl)pyridin-2-yl)methyl)carbamate To a solution of N-methyl-4-(4-(2-tosylhydrazono)cyclohexyl)benzamide (0.96 g, 2.4 mmol) in 1,4-dioxane (50 mL) was added compound A (0.6 g, 2.18 mmol) and Cs$_2$CO$_3$ (0.85 g, 2.616 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE:EA=1:1 to EA) to give crude product as a solid (0.6 g in 55.56% yield), which was used for next step without further purification. MS (ESI) m/e [M+1]$^+$=492.

Step 5: 4-(4-(6-(aminomethyl)-3-cyclopropylpicolinoyl)cyclohexyl)-N-methylbenzamide hydrochloride To a solution of tert-butyl ((5-cyclopropyl-6-(4-(4-(methylcarbamoyl)phenyl)cyclohexane-1-carbonyl)pyridin-2-yl)methyl)carbamate (0.6 g, 1.22 mmol) in 1.4 dioxane (10 mL) was added 3N HCl (10 mL) and the mixture was stirred at room temperature for overnight. The solvent was evaporated under reduced pressure to give crude product as solid. [M+H]$^+$=392.

Step 6: 4-(4-(6-cyclopropylimidazo[1,5-a]pyridine-5-carbonyl)cyclohexyl)-N-methylbenzamide A mixture of Ac$_2$O (30 mL) and HCOOH (10 mL) was heated at 50° C. for 1 hour and then a solution of 4-(4-(6-(aminomethyl)-3-cyclopropylpicolinoyl)cyclohexyl)-N-methylbenzamide hydrochloride (crude, 1.22 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give crude product as a solid (270 mg in 55.2% yield). [M+H]$^+$=402

Step 7: 4-(4-(4(6-cyclopropylimidazo[1,5-a]pyridin-5-yl)(hydroxy)methyl)cyclohexyl)-N-methylbenzamide To a solution of 4-(4-(6-cyclopropylimidazo[1,5-a]pyridine-5-carbonyl)cyclohexyl)-N-methylbenzamide (0.27 g, 0.73 mmol) in methol (10 mL) was added NaBH$_4$ (55 mg, 1.46 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (200 mg in 74% yield). $^1$H NMR (DMSO-d$_6$) δ$_H$ 8.66 (s, 1H), 8.31 (d, J=4.4 Hz, 1H), 7.71 (d, J=8.0 Hz, 2H), 7.42 (d, J=9.2 Hz, 1H), 7.34 (s, 1H), 7.27 (d, J=8 Hz, 2H), 6.49 (d, J=9.6 Hz, 1H), 5.84 (d, J=3.2 Hz, 1H), 5.7 (dd, J=9.2, 3.6 Hz, 1H), 2.75 (d, J=4.0 Hz, 3H), 2.65-2.55 (m, 1H), 2.45-2.41 (m, 1H), 2.23-2.20 (m, 1H), 2.22-1.96 (m, 1H), 1.91-1.88 (m, 1H), 1.69-1.66 (m, 1H), 1.54-

1.51 (m, 1H), 1.31-1.18 (m, 4H), 0.97-0.95 (m, 2H), 0.79-0.76 (m, 1H), 0.67-0.65 (m, 1H). [M+H]+=404.

Example D124a and D124b: 4-((1S,4r)-4-((S)-(6-cyclopropylimidazo[1,5-a]pyridin-5-yl)(hydroxy)methyl)cyclohexyl)-N-methylbenzamide and 4-((1R,4r)-4-((R)-(6-cyclopropylimidazo[1,5-a]pyridin-5-yl)(hydroxy)methyl)cyclohexyl)-N-methylbenzamide

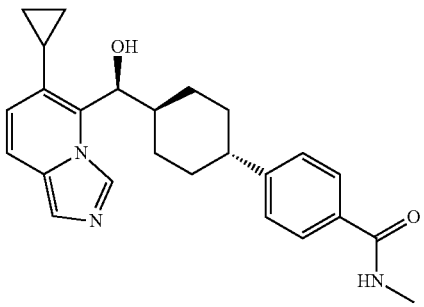

Fast isomer in CHIRALPAK IB-3
Eluting reagent: MeOH(20 mM NH₃)

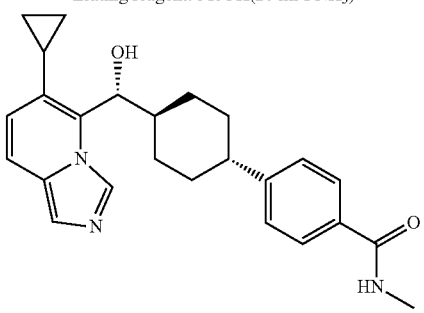

Slow isomer in CHIRALPAK IB-3
Eluting reagent: MeOH(20 mM NH₃)

Each enantiomer of racemic D124a and D124b was separated using preparative HPLC on a CHIRALPAK IB-3 100*3 mm, 3 um with MeOH (20 mM NH₃) as an eluent. The enantiomeric excesses were determined by using HPLC on a CHIRALPAK IB-3 100*3 mm, 3 um with MeOH (20 mM NH₃) as an eluent at a flow rate of 50 mL/min. The first one enantiomer eluted at the retention time of 2.684 min (D124a), which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, ¹H NMR (DMSO-d6) δ$_H$ 9.70 (s, 1H). 8.36 (d, J=4.4 Hz, 2H), 8.12 (s, 1H), 7.74-7.72 (m, 3H), 7.26 (d, J=8.4 Hz, 3H), 6.87 (d, J=9.6 Hz, 1H), 5.34 (d, J=9.6 Hz, 1H), 2.75 (d, J=4.4 Hz, 3H), 2.60-2.52 (m, 1H), 2.43-2.40 (m, 1H), 2.25-2.15 (m, 2H), 1.93-1.90 (m, 1H), 1.75-1.68 (m, 1H), 1.53-1.47 (m, 1H), 1.32-1.23 (m, 5H), 1.07-1.04 (m, 2H), 0.87-0.86 (m, 1H), 0.80-0.77 (m, 1H); and the other enantiomer eluted at the retention time of 3.834 min (D124b), ¹H NMR (DMSO-d₆) δ$_H$ 9.71 (s, 1H), 8.36 (d, J=4.8 Hz, 1H), 8.14 (s, 1H), 7.74 (d, J=8.8 Hz, 3H), 7.26 (d, J=8.0 Hz, 2H), 6.87 (d, J=9.6 Hz, 1H), 5.34 (d, J=10 Hz, 1H), 2.75 (d, J=4.0 Hz, 3H), 2.53 (m, 1H), 2.43-2.40 (m, 1H), 2.25-2.10 (m, 2H), 1.9-1.90 (m, 1H), 1.75-1.65 (m, 1H), 1.52-1.50 (m, 1H), 1.37-1.23 (m, 5H), 1.07-1.05 (m, 2H), 0.90-0.84 (m, 1H), 0.82-0.74 (m, 1H). The absolute configurations of chiral carbons in D124a and D124b are tentatively assigned as (S) and (R) respectively based on assumption that the binding model of the more potent isomer D124a is the same as that of C101a with IDO11 enzyme, and the relative stereochemistry on cyclohexane is assigned as trans configuration on the cyclohexane.

Example D125: 4-(4-((6-cyclopropylimidazo[1,5-a]pyridin-5-yl)(hydroxy)methyl)cyclohexyl)-N,N-dimethylbenzamide

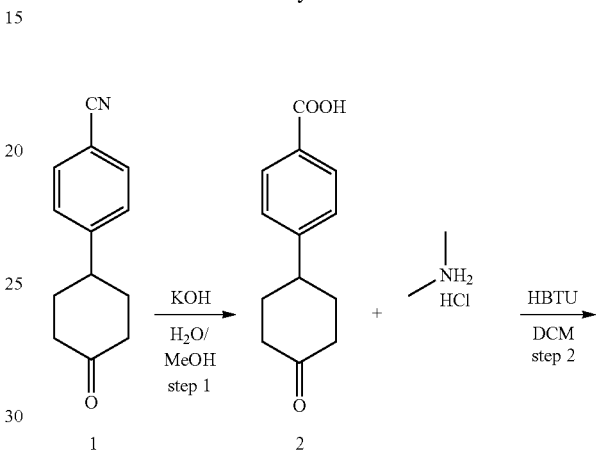

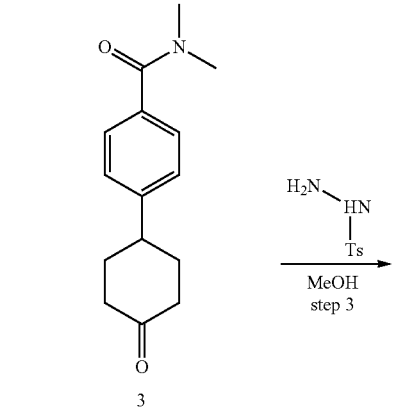

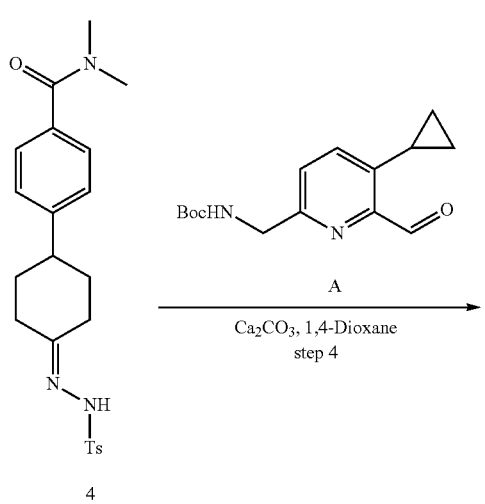

-continued

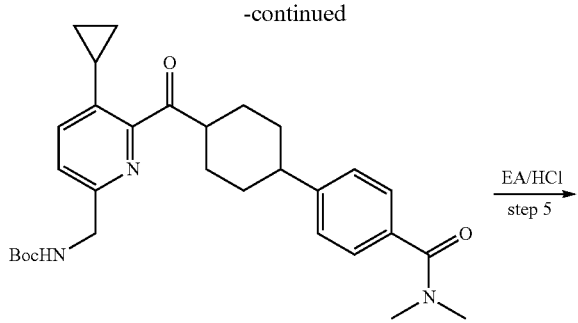

5

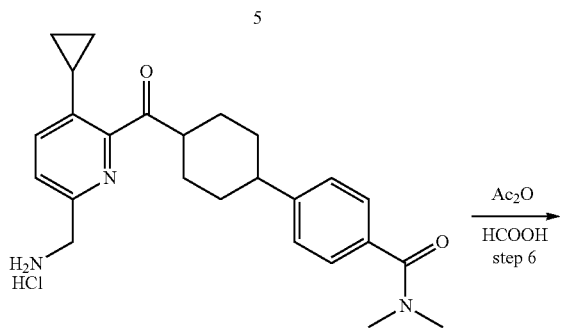

6

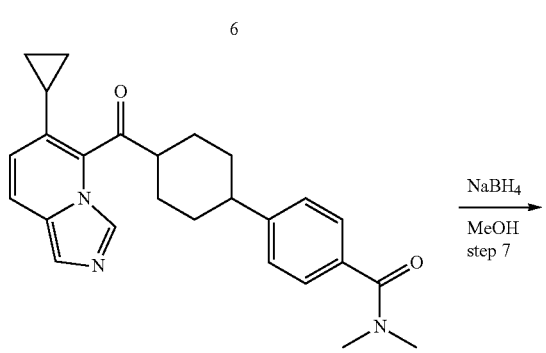

7

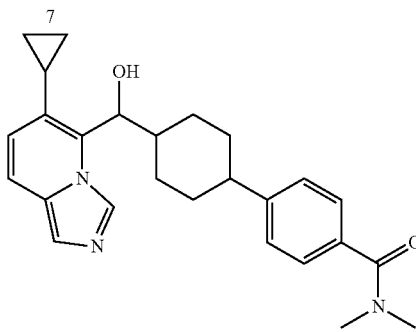

D125

Step 1: 4-(4-oxocyclohexyl)benzoic acid

To a solution of 4-(4-oxocyclohexyl)benzonitrile (5 g, 25.1 mmol) and KOH (5.6 g, 100.4 mmol) in MeOH:H₂O=20:1 (100 mL), the mixture was stirred at 70° C. for 3 h. TLC (EA, Rf=0.5) showed the reaction was completed. Filtered and concentrated, H₂O (100 ml) was was added and extracted with DCM (50 ml×3). The combined organic layer was dried over Na₂SO₄, filtered and concentrated to give compound 2 (4.5 g, 81.8%) as a white solid.

Step 2: N,N-dimethyl-4-(4-oxocyclohexyl)benzamide

To a solution of 4-(4-oxocyclohexyl)benzoic acid (1.5 g, 6.9 mmol), HBTU (3.13 g, 8.28 mmol) and dimethylamine hydrochloride (0.62 g, 7.57 mmol) in DCM (50 mL) was added Et₃N (1 g, 9.9 mmol) at room temperature, and the mixture was stirred for overnight. The solvent was evaporated under reduced pressure and aqueous NH₄Cl (50 mL) was added, extracted with ethyl acetate (50 ml×3), combined the organic layer was evaporated to give crude product, The solvent was evaporate under reduced pressure and the residue was purified by column chromatography (PE:EA=1:1) to give product (0.62 g, 58.5%) as a white solid. MS (ESI) m/e [M+1]⁺=245.

Step 3: N,N-dimethyl-4-(4-(2-tosylhydrazono)cyclohexyl)benzamide

To a solution of N,N-dimethyl-4-(4-oxocyclohexyl)benzamide (1.1 g, 4.5 mmol) in methol (50 mL) was added 4-methylbenzenesulfonohydrazide (0.92 g, 4.94 mmol) at room temperature, and the mixture was stirred for overnight. Evaporate half the solvent under reduced pressure and then filtered to give product as a white solid (1.4 g in 76% yield). MS (ESI) m/e [M+1]⁺=414.

Step 4: tert-butyl ((5-cyclopropyl-6-(4-(4-(dimethylcarbamoyl)phenyl)cyclohexane-1-carbonyl)pyridin-2-yl)methyl)carbamate To a solution of N,N-dimethyl-4-(4-(2-tosylhydrazono)cyclohexyl)benzamide (1 g, 2.4 mmol) in 1,4-dioxane (50 mL) was added compound A (0.6 g, 2.18 mmol) and Cs₂CO₃ (0.85 g, 2.616 mmol) at room temperature, and the mixture was heated at 100° C. for overnight. The solvent was evaporated under reduced pressure and water (100 mL) was added, extracted with ethyl acetate (50 ml×3) and combined the organic layer, the solvent was evaporated under reduced pressure and the residue was purified by column chromatography (PE:EA=1:1 to EA) to give crude product as a solid (0.8 g in 72.7% yield), which was used for next step without further purification. MS (ESI) m/e [M+1]⁺=506.

Step 5: 4-(4-(6-(aminomethyl)-3-cyclopropylpicolinoyl)cyclohexyl)-N,N-dimethylbenzamide To a solution of tert-butyl ((5-cyclopropyl-6-(4-(4-(dimethylcarbamoyl)phenyl)-cyclohexane-1-carbonyl)pyridin-2-yl)methyl)carbamate (0.6 g, 1.22 mmol) in 1.4 dioxane (10 mL was added 3N HCl (10 mL) and the mixture was stirred at room temperature for overnight. The solvent was evaporated under reduced pressure to give crude product as solid. [M+H]⁺=406.

Step 6: 4-(4-(6-cyclopropylimidazo[1,5-a]pyridine-5-carbonyl)cyclohexyl)-N,N-dimethylbenzamide A mixture of Ac₂O (30 mL) and HCOOH (10 mL) was heated at 50° C. for 1 hour and then a solution of 4-(4-(6-(aminomethyl)-3-cyclopropylpicolinoyl)cyclohexyl)-N,N-dimethylbenzamide (crude, 1.22 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give crude product as a solid (400 mg in 44.44% yield). [M+H]$^+$=416

Step 7: 4-(4-((6-cyclopropylimidazo[1,5-a]pyridin-5-yl)(hydroxy)methyl)cyclohexyl)-N,N-dimethylbenzamide To a solution of 4-(4-(6-cyclopropylimidazo[1,5-a]pyridine-5-carbonyl)cyclohexyl)-N-methylbenzamide (0.27 g, 0.73 mmol) in methol (10 mL) was added NaBH$_4$ (55 mg, 1.46 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (200 mg in 74% yield). $^1$H NMR (DMSO-d$_6$) $\delta_H$ 8.64 (s, 1H), 7.41 (d, J=9.2 Hz, 1H), 7.32 (s, 1H), 7.30-7.24 (m, 3H), 6.48 (d, J=9.2 Hz, 1H), 5.82 (d, J=3.6 Hz, 1H), 5.27 (dd, J=9.6, 3.6 Hz, 1H), 2.92 (d, J=15.2 Hz, 6H), 2.60-2.52 (m, 1H), 2.44-2.41 (m, 1H), 2.23-2.20 (m, 1H), 2.02-1.99 (m, 1H), 1.92-1.89 (m, 1H), 1.70-1.68 (m, 1H), 1.56-1.48 (m, 1H), 1.34-1.18 (m, 5H), 0.99-0.93 (m, 2H), 0.78-0.76 (m, 1H), 0.68-0.65 (m, 1H). [M+H]$^+$=418.

Example D125a and D125b: 4-((1S,4r)-4-((S)-(6-cyclopropylimidazo[1,5-a]pyridin-5-yl)(hydroxy)methyl)cyclohexyl)-N,N-dimethylbenzamide and 4-((1R,4r)-4-((R)-(6-cyclopropylimidazo[1,5-a]pyridin-5-yl)hydroxy)methyl)cyclohexyl-N,N-dimethylbenzamide Each enantiomer of racemic D125a and D125b was separated using preparative HPLC on a CHIRAL Cellulose-SB with Hex (0.1% IPAmine):EtOH=70:30 as an eluent. The enantiomeric excesses were determined by using HPLC on a CHIRAL Cellulose-SB with Hex (0.1% IPAmine):EtOH=70:30 as an eluent at a flow rate of 1.0 mL/min. The first one enantiomer eluted at the retention time of 3.536 min, which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-d6) $\delta_H$ 9.64 (s, 1H), 8.07 (s, 1H), 7.71 (d, J=9.6 Hz, 1H), 7.27 (dd, J=23.2, 8.0 Hz, 4H), 6.84 (d, J=9.6 Hz, 1H), 6.20 (s, 1H), 5.33 (d, J=9.6 Hz, 1H), 2.92 (d, J=16.8 Hz, 7H), 2.43-2.40 (m, 1H), 2.30-2.18 (m, 2H), 1.96-1.91 (m, 1H), 1.78-1.64 (m, 1H), 1.52-1.46 (m, 1H), 1.30-1.24 (m, 6H), 1.06-1.04 (m, 2H), 0.90-0.82 (m, 1H), 0.80-0.79 (m, 1H); and the other enantiomer eluted at the retention time of 6.477 min, 1H NMR (DMSO-d6) $\delta_H$ 9.56 (s, 1H), 8.01 (s, 1H), 7.70-7.66 (m, 1H), 7.27 (dd, J=22.8, 8.0 Hz, 4H), 6.81 (t, J=8.2 Hz, 1H), 6.15 (s, 1H), 5.32 (d, J=9.6 Hz, 1H), 2.92 (d, J=16.4 Hz, 6H), 2.43-2.40 (m, 2H), 2.25-2.10 (m, 2H), 1.94-1.91 (m, 1H), 1.76-1.65 (m, 1H), 1.55-1.46 (m, 1H), 1.36-1.24 (m, 4H), 1.06-1.04 (m, 2H), 0.85-0.78 (m, 2H). The absolute configurations of chiral carbons in D125a and D125b are tentatively assigned as (S) and (R) respectively based on assumption that the binding model of the more potent isomer D125a is the same as that of C101a with IDO11 enzyme, and the relative stereochemistry on cyclohexane is assigned as trans configuration on the cyclohexane.

Example D126: (6-cyclopropylimidazo[1,5-a]pyridin-5-yl)(4-(3,4-difluorophenyl)cyclohexyl)methanol

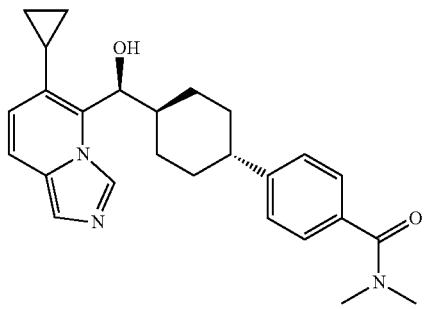

Fast isomer in CHIRAL Cellulose-SB
Eluting reagent: Hex(0.1% IPAmine):EtOH = 70:30

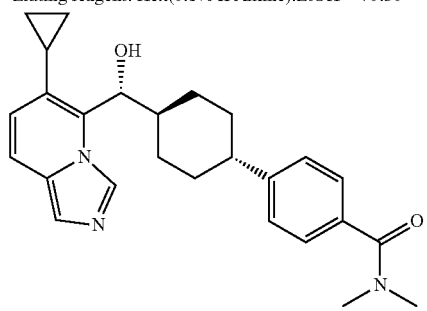

Slow isomer in CHIRAL Cellulose-SB
Eluting reagent: Hex(0.1% IPAmine):EtOH = 70:30

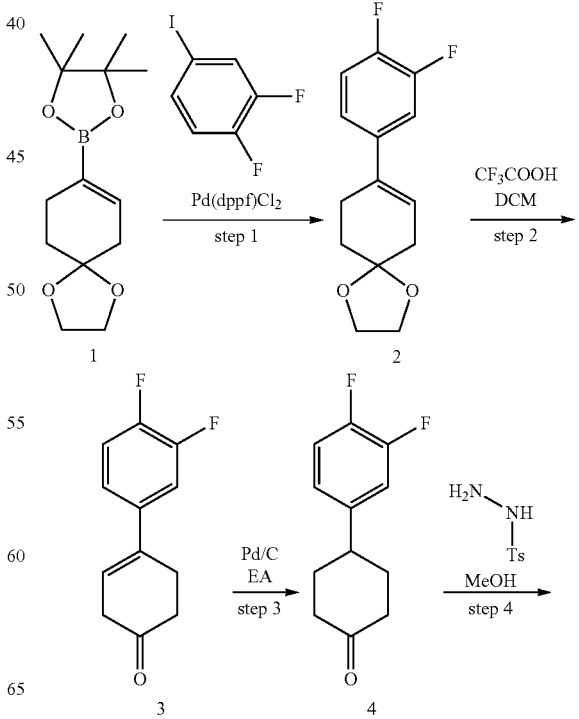

-continued

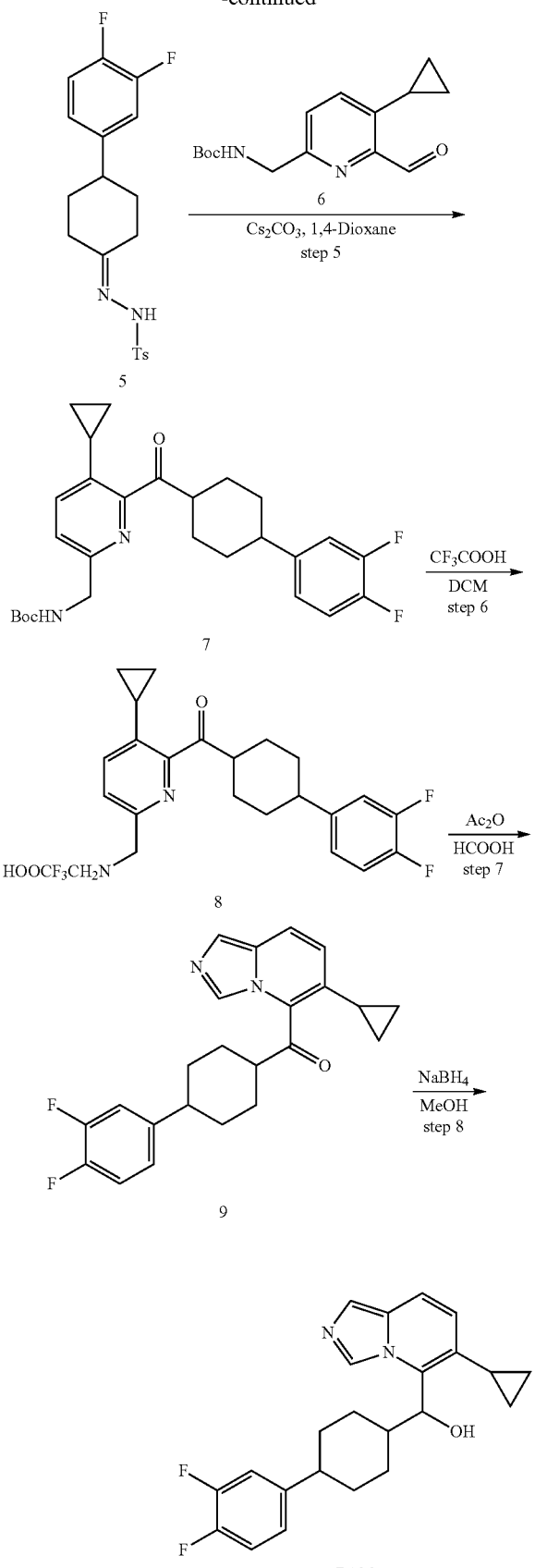

Step 1: 8-(3,4-difluorophenyl)-1,4-dioxaspiro[4.5]dec-7-ene

To a solution of 1,2-difluoro-4-iodobenzene (9 g, 38 mmoL) in 1,4-dioxane (150 mL) was added 4,4,5,5-tetramethyl-2-(1,4-dioxaspiro[4.5]dec-7-en-8-yl)-1,3,2-dioxaborolane (10 g, 38 mmol), Pd(dppf)Cl$_2$ (1.4 g, 1.9 mmol) and Cs$_2$CO$_3$ (18.4 g, 56 mmol) and the mixture was heated at 90° C. overnight. Then evaporated the solvent under reduced pressure and the residue was purified by column chromatography (PE:EA=5:1) to give product as an yellow solid (8 g in 84% yield). $^1$H NMR (400 MHz, CDCl$_3$) δ 7.22-7.14 (m, 1H), 7.12-7.02 (min, 2H), 6.05-5.86 (m, 1H), 4.05-3.96 (min, 4H), 2.67-2.54 (min, 2H), 2.51-2.36 (min, 2H), 1.91 (t, J=6.5 Hz, 2H). [M+H]$^+$=253.1.

Step 2: 3',4'-difluoro-2,5-dihydro-[1,1'-biphenyl]-4(3H)-one

To a solution of 8-(3,4-difluorophenyl)-1,4-dioxaspiro[4.5]dec-7-ene (8 g, 32 mmol) in dichloromethane (40 mL) was added trifluoroacetic acid (40 mL) at room temperature and the mixture was stirred for overnight. The solvent was evaporated under reduced pressure and water (100 mL) was added, extracted with ethyl acetate (100 mL×3), combined the organic layer and washed with saturated aqueous of NaHCO$_3$, then the organic layer was evaporated in vacuo to give crude product, which was used for next step without further purification.

Step 3: 4-(3,4-difluorophenyl)cyclohexan-1-one

To a solution of 3',4'-difluoro-2,5-dihydro-[1,1'-biphenyl]-4(3H)-one (32 mmol) in ethyl acetate (150 mL) was added Pd/C (1.0 g, 10%) and the mixture was stirred for 6 hours at room temperature under H$_2$ (0.4 Mpa). Then filtered to remove Pd/C and the filtrate was evaporated under reduced pressure to give a crude product, and then purified by column chromatography (PE as eluent) to give product (4.8 g, oil). $^1$H NMR (400 MHz, CDCl$_3$) δ 7.17-7.01 (m, 2H), 7.01-6.94 (m, 1H), 3.16-2.85 (m, 1H), 2.57-2.42 (m, 4H), 2.30-2.14 (m, 2H), 1.99-1.75 (m, 2H). [M+H]$^+$=211.1.

Step 4: N'-(4-(3,4-difluorophenyl)cyclohexylidene)-4-methylbenzenesulfonohydrazide To a solution of 4-(3,4-difluorophenyl)cyclohexan-1-one (1 g, 4.8 mmol) in methol (15 mL) and DCM (5 mL) was added 4-methylbenzenesulfonohydrazide (0.89 g, 4.8 mmol) at room temperature and the mixture was stirred overnight. The solid was filtered to give product as a white solid (1.5 g in 83% yield). $^1$H NMR (400 MHz, DMSO-d6) δ 10.20 (s, 1H), 7.74 (d, J=8.0 Hz, 2H), 7.40 (d, J=8.0 Hz, 2H), 7.35-7.26 (m, 2H), 7.13-6.99 (m, 1H), 2.99-2.74 (m, 2H), 2.39 (s, 3H), 2.32-2.16 (m, 2H), 2.02-1.82 (m, 3H), 1.63-1.36 (m, 2H). [M+H]$^+$=379.1.

Step 5: tert-butyl ((5-cyclopropyl-6-(4-(3,4-difluorophenyl)cyclohexane-1-carbonyl)pyridin-2-yl)methyl)carbamate To a solution of tert-butyl ((5-cyclopropyl-6-formylpyridin-2-yl)methyl)carbamate (400 mg, 1.4 mmol) in 1,4-dioxane (30 mL) was added N'-(4-(3,4-difluorophenyl)cyclohexylidene)-4-methylbenzenesulfonohydrazide (547 mg, 1.4 mmol) and Cs$_2$CO$_3$ (473 mg, 5.4 mmol) at room temperature, and the mixture was heated at 95° C. overnight.

The solvent was evaporated in vacuo and water (100 mL) was added, extracted with ethyl acetate (50 mL×3) and combined the organic layer, the solvent was evaporated under reduced pressure and the residue was purified by column chromatography (PE:EA=5:1) to give product as a light yellow oil (0.4 g in 59% yield). [M+H]⁺=471.2

Step 6: (3-cyclopropyl-6-((methyleneamino)methyl)pyridin-2-yl)(4-(3,4-difluorophenyl)cyclohexyl)methanone Trifluoracetic acid To a solution of tert-butyl ((5-cyclopropyl-6-(4-(3,4-difluorophenyl)cyclohexane-1-carbonyl)pyridin-2-yl)methyl)carbamate (0.4 g, 0.85 mmol) in DCM (40 mL) was added trifluoracetic acid (4 mL) and the mixture was stirred at room temperature overnight. The solvent was evaporated under reduced pressure to give crude product as oil.

Step 7: (6-cyclopropylimidazo[1,5-a]pyridin-5-yl)(4-(3,4-difluorophenyl)cyclohexyl)methanone A mixture of Ac₂O (30 mL) and HCOOH (10 mL) was heated at 50° C. for 1 hour and then a solution of (3-cyclopropyl-6-((methyleneamino)methyl)pyridin-2-yl)(4-(3,4-difluorophenyl)cyclohexyl)methanone Trifluoracetic acid (crude, 0.85 mmol) in HCOOH (5 mL) was added drop wise and the mixture was heated at 50° C. overnight. The solvent was evaporated under reduced pressure and water (50 mL) was added, washed with saturated aqueous of NaHCO₃, then extracted with ethyl acetate (30 mL×3) and combined the organic layer, the solvent was evaporated under reduced pressure and the residue was purified by column chromatography (PE:EA=4:1) to give crude product as a solid (210 mg in 65% yield). [M+H]⁺=381.1.

Step 8: (6-cyclopropylimidazo[1,5-a]pyridin-5-yl)(4-(3,4-difluorophenyl)cyclohexyl)methanol

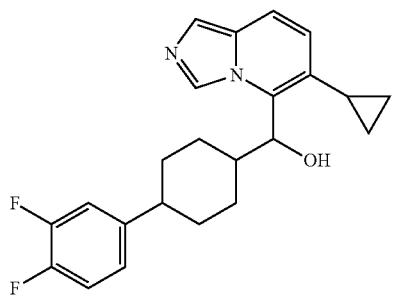

To a solution of (6-cyclopropylimidazo[1,5-a]pyridin-5-yl)(4-(3,4-difluorophenyl)cyclohexyl)methanone (210 mg, 0.55 mmol) in methanol (10 mL) was added NaBH₄ (105 mg, 2.76 mmol) at room temperature and the mixture was stirred for 4 h. Then the solvent was evaporated under reduced pressure and water (20 mL) was added, extracted with ethyl acetate (20 mL×3) and combined the organic layer, the solvent was evaporated under reduced pressure to give product as a white solid (169 mg in 72% yield). 1H NMR (400 MHz, DMSO-d6) δ 8.63 (s, 1H), 7.41 (d, J=9.2 Hz, 1H), 7.33-7.24 (m, 3H), 7.09-7.00 (m, 1H), 6.48 (d, J=9.2 Hz, 1H), 5.81 (d, J=4.0 Hz, 1H), 5.25 (dd, J=9.6, 4.0 Hz, 1H), 2.41 (d, J=12.0 Hz, 1H), 2.29-2.15 (m, 1H), 2.08-1.97 (m, 1H), 1.88 (d, J=13.2 Hz, 1H), 1.75-1.62 (m, 1H), 1.55-1.43 (m, 1H), 1.35-1.10 (m, 5H), 1.01-0.89 (m, 2H), 0.81-0.71 (m, 1H), 0.70-0.58 (m, 1H). [M+H]⁺=383.2.

Example D126a and D126b: (S)-(6-cyclopropylimidazo[1,5-a]pyridin-5-yl)((1r,4S)-4-(3,4-difluorophenyl)cyclohexyl)methanol and (R)-(6-cyclopropylimidazo[1,5-a]pyridin-5-yl)((1r 4R)-4-(3,4-difluorophenyl)cyclohexyl)methanol

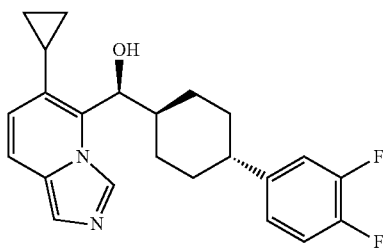

Fast isomer in CHIRAL Cellulose-SB
Eluting reagent: Hex:EtOH = 80:20

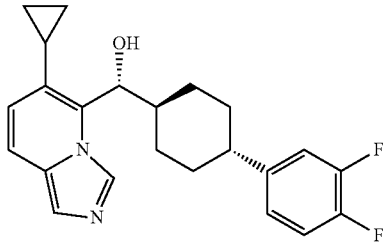

Slow isomer in CHIRAL Cellulose-SB
Eluting reagent: Hex:EtOH = 80:20

Each enantiomer of racemic D126a and D126b was separated using preparative HPLC on a CHIRAL Cellulose-SB with Hex:EtOH=80:20 as an eluent. The enantiomeric excesses were determined by using HPLC on a CHIRAL Cellulose-SB with Hex (0.1% IPAmine):EtOH=80:20 as an eluent at a flow rate of 1.0 mL/min. The first one enantiomer eluted at the retention time of 3.099 min (D126a), and the other enantiomer eluted at the retention time of 5.601 min (D126b). To a solution of D126a (63 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (54 mg in 78% yield). ¹H NMR (400 MHz, DMSO-d6) δ 9.65 (s, 1H), 8.09 (s, 1H), 7.72 (d, J=9.6 Hz, 1H), 7.38-7.20 (m, 2H), 7.08-6.98 (m, 1H), 6.85 (d, J=9.6 Hz, 1H), 6.26 (s, 1H), 5.32 (d, J=9.6 Hz, 1H), 2.39 (d, J=12.0 Hz, 1H), 2.26-2.10 (m, 2H), 1.90 (d, J=12.4 Hz, 1H), 1.77-1.63 (m, 1H), 1.56-1.39 (m, 1H), 1.37-1.18 (m, 4H), 1.11-0.99 (m, 2H), 0.91-0.71 (m, 2H). [M+H]⁺=383.2. To a solution of D126b (65 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (59 mg in 83% yield). 1H NMR (400 MHz, DMSO-d6) δ 9.64 (s, 1H), 8.09 (s, 1H), 7.71 (d, J=9.6 Hz, 1H), 7.38-7.20 (m, 2H), 7.10-6.98 (m, 1H), 6.85 (d, J=9.6 Hz, 1H), 6.25 (s, 1H), 5.32 (d, J=9.6 Hz, 1H), 2.39 (d, J=10.8 Hz, 1H), 2.25-2.08

(m, 2H), 1.98-1.83 (m, 1H), 1.78-1.61 (m, 1H), 1.57-1.40 (m, 1H), 1.39-1.14 (m, 4H), 1.14-0.98 (m, 2H), 0.96-0.72 (m, 2H). [M+H]⁺=383.2. The absolute configurations of chiral carbons in D126a and D126b are tentatively assigned as (S) and (R) respectively based on assumption that the binding model of the more potent isomer D126a is the same as that of C101a with IDO1 enzyme, and the relative stereochemistry on cyclohexane is assigned as trans configuration on the cyclohexane.

Example D127: (6-cyclopropylimidazo[1,5-a]pyridin-5-yl)(4-(2,4-difluorophenyl)cyclohexyl)methanol

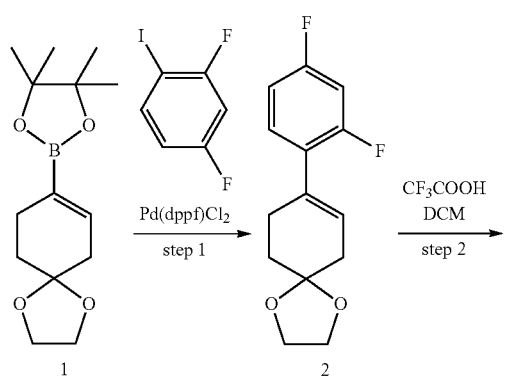

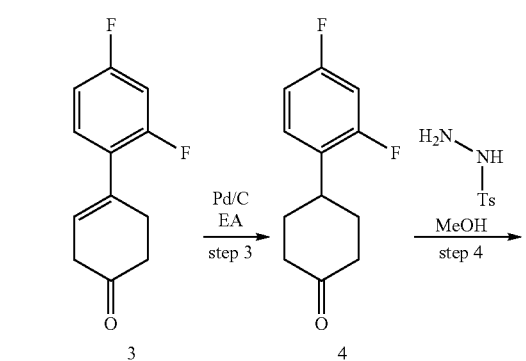

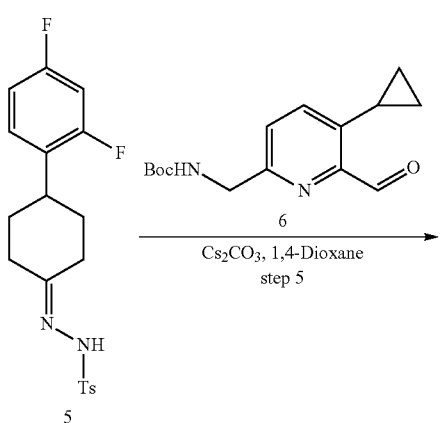

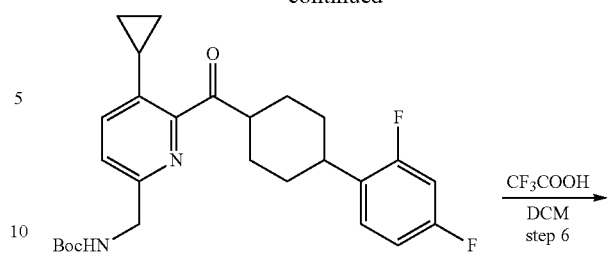

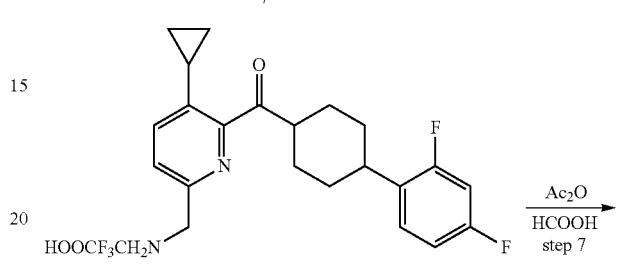

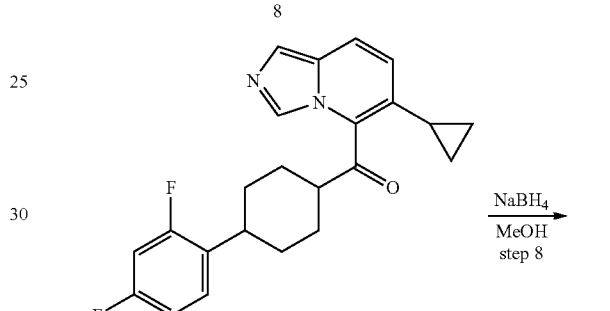

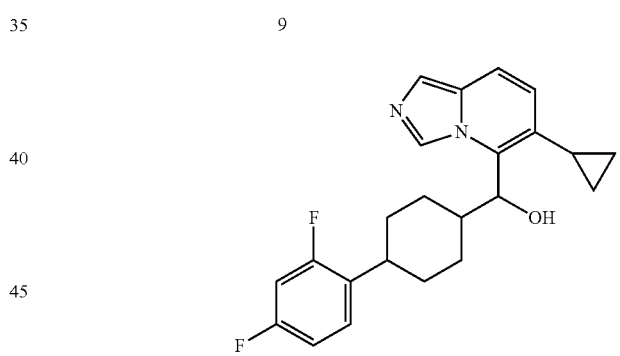

Step 1: 8-(2,4-difluorophenyl)-1,4-dioxaspiro[4.5]dec-7-ene

To a solution of 2,4-difluoro-1-iodobenzene (9 g, 38 mmoL) in 1,4-dioxane (150 mL) was added 4,4,5,5-tetramethyl-2-(1,4-dioxaspiro[4.5]dec-7-en-8-yl)-1,3,2-dioxaborolane (10 g, 38 mmol), Pd(dppf)Cl₂ (1.4 g, 1.9 mmol) and Cs₂CO₃ (18.4 g, 56 mmol) and the mixture was heated at 90° C. overnight. Then evaporated the solvent under reduced pressure and the residue was purified by column chromatography (PE:EA=5:1) to give product as an yellow solid (7 g in 74% yield). ¹H NMR (400 MHz, CDCl₃) δ 7.25-7.14 (m, 1H), 6.87-6.70 (m, 2H), 5.87-5.70 (m, 1H), 4.02 (t, J=1.5 Hz, 4H), 2.68-2.55 (m, 2H), 2.50-2.36 (m, 2H), 1.89 (t, J=6.4 Hz, 2H). [M+H]⁺=253.1.

Step 2: 2',4'-difluoro-2,5-dihydro-[1,1'-biphenyl]-4(3H)-one

To a solution of 8-(2,4-difluorophenyl)-1,4-dioxaspiro[4.5]dec-7-ene (7 g, 28 mmol) in dichloromethane (40 mL) was added trifluoroacetic acid (40 mL) at room temperature and the mixture was stirred overnight. The solvent was evaporated under reduced pressure and water (100 mL) was added, extracted with ethyl acetate (100 mL×3), combined the organic layer and washed with saturated aqueous of NaHCO₃, then the organic layer was evaporated in vacuo to give crude product, which was used for next step without further purification. [M+H]⁺=209.1.

Step 3: 4-(2,4-difluorophenyl)cyclohexan-1-one

To a solution of 2',4'-difluoro-2,5-dihydro-[1,1'-biphenyl]-4(3H)-one (28 mmol) in methanol (150 mL) was added Pd/C (1.0 g, 10%) and the mixture was stirred for 16 hours at room temperature under H₂ (0.4 Mpa). Then filtered to remove Pd/C and the filtrate was evaporated under reduced pressure to give a crude product, and then purified by column chromatography (PE as eluent) to give product (3.5 g, oil). [M+H]⁺=211.1.

Step 4: N'-(4-(2,4-difluorophenyl)cyclohexylidene)-4-methylbenzenesulfonohydrazide To a solution of 4-(2,4-difluorophenyl)cyclohexan-1-one (2.1 g, 10 mmol) in methol (30 mL) and DCM (10 mL) was added 4-methylbenzenesulfonohydrazide (1.86 g, 10 mmol) at room temperature and the mixture was stirred overnight. The solid was filtered to give product as a white solid (2 g in 53% yield). ¹H NMR (400 MHz, DMSO-d6) δ 10.23 (s, 1H), 7.77 (d, J=8.0 Hz, 2H), 7.40 (d, J=8.0 Hz, 2H), 7.37-7.28 (m, 1H), 7.23-7.10 (m, 1H), 7.05-6.94 (m, 1H), 3.44-3.30 (m, 1H), 3.18-2.87 (m, 2H), 2.34-2.24 (m, 2H), 1.98 (s, 3H), 1.94-1.83 (m, 2H), 1.70-1.45 (m, 2H). [M+H]⁺=379.1.

Step 5: tert-butyl ((5-cyclopropyl-6-(4-(2,4-difluorophenyl)cyclohexane-1-carbonyl)pyridin-2-yl)methyl)carbamate To a solution of tert-butyl ((5-cyclopropyl-6-formylpyridin-2-yl)methyl)carbamate (600 mg, 2.2 mmol) in 1,4-dioxane (40 mL) was added N'-(4-(2,4-difluorophenyl)cyclohexylidene)-4-methylbenzenesulfonohydrazide (823 mg, 2.2 mmol) and Cs₂CO₃ (1.06 g, 3.3 mmol) at room temperature, and the mixture was heated at 95° C. overnight. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=3:1) to give product as a light yellow oil (0.75 g in 74% yield). [M+H]⁺=471.2

Step 6: (3-cyclopropyl-6-((methyleneamino)methyl)pyridin-2-yl)(4-(2,4-difluorophenyl)cyclohexyl)methanone Trifluoracetic acid To a solution of tert-butyl ((5-cyclopropyl-6-(4-(2,4-difluorophenyl)cyclohexane-1-carbonyl)pyridin-2-yl)methyl)carbamate (0.75 g, 1.6 mmol) in DCM (40 mL) was added trifluoracetic acid (4 mL) and the mixture was stirred at room temperature overnight. The solvent was evaporated under reduced pressure to give crude product as oil.

Step 7: (6-cyclopropylimidazo[1,5-a]pyridin-5-yl)(4-(2,4-difluorophenyl)cyclohexyl)methanone A mixture of Ac₂O (30 mL) and HCOOH (10 mL) was heated at 50° C. for 1 hour and then a solution of (3-cyclopropyl-6-((methyleneamino)methyl)pyridin-2-yl)(4-(2,4-difluorophenyl)cyclohexyl)methanone Trifluoracetic acid (crude, 1.6 mmol) in HCOOH (5 mL) was added drop wise and the mixture was heated at 50° C. overnight. The solvent was evaporated under reduced pressure and water (50 mL) was added, washed with saturated aqueous of NaHCO₃, then extracted with ethyl acetate (30 mL×3) and combined the organic layer, the solvent was evaporated under reduced pressure and the residue was purified by column chromatography (PE:EA=3:1) to give crude product as a solid (320 mg in 53% yield). [M+H]⁺=381.1.

Step 8: (6-cyclopropylimidazo[1,5-a]pyridin-5-yl)(4-(2,4-difluorophenyl)cyclohexyl)methanol

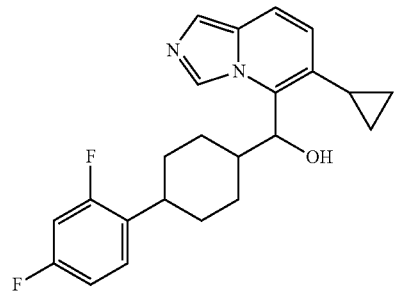

To a solution of (6-cyclopropylimidazo[1,5-a]pyridin-5-yl)(4-(2,4-difluorophenyl)cyclohexyl)methanone (320 mg, 0.84 mmol) in methanol (10 mL) was added NaBH₄ (160 mg, 4.21 mmol) at room temperature and the mixture was stirred for 4 h. Then the solvent was evaporated under reduced pressure and water (20 mL) was added, extracted with ethyl acetate (20 mL×3) and combined the organic layer, the solvent was evaporated under reduced pressure to give product as a white solid (190 mg in 59% yield). ¹H NMR (400 MHz, DMSO-d6) δ 8.63 (s, 1H), 7.46-7.27 (m, 3H), 7.19-7.07 (m, 1H), 7.06-6.92 (m, 1H), 6.47 (d, J=9.2 Hz, 1H), 5.82 (d, J=3.9 Hz, 1H), 5.26 (dd, J=9.6, 4.0 Hz, 1H), 2.82-2.63 (m, 1H), 2.43 (d, J=12.8 Hz, 1H), 2.27-2.15 (m, 1H), 2.11-1.96 (m, 1H), 1.85 (d, J=12.4 Hz, 1H), 1.70-1.47 (m, 2H), 1.40-1.09 (m, 4H), 1.04-0.88 (m, 2H), 0.84-0.72 (m, 1H), 0.71-0.60 (m, 1H). [M+H]⁺=383.2.

Example D127a and D127b: (S)-(6-cyclopropylimidazo[1,5-a]pyridin-5-yl)((r,4S)-4-(2,4-difluorophenyl)cyclohexyl)methanol and (R)-(6-cyclopropylimidazo[1,5-a]pyridin-5-yl)((1r,4R)-4-(2,4-difluorophenyl)cyclohexyl)methanol

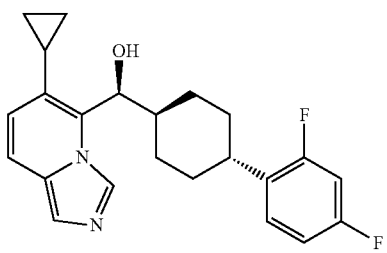

Fast isomer in CHIRALPAK IC HPLC
Eluting reagent: Hex:EtOH = 80:20

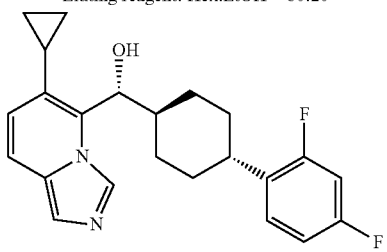

Slow isomer in CHIRALPAL IC HPLC
Eluting reagent: Hex:EtOH = 80:20

Each enantiomer of racemic D127a and D127b was separated using preparative HPLC on a CHIRALPAK IC with Hex:EtOH=80:20 as an eluent. The enantiomeric excesses were determined by using HPLC on a CHIRALPAK IA-3 with Hex (0.1% IPAmine):EtOH=80:20 as an eluent at a flow rate of 1.0 mL/min. The first one enantiomer eluted at the retention time of 1.346 min (D127a), and the other enantiomer eluted at the retention time of 2.244 min (D127b). To a solution of D127a (71.2 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (60 mg in 77% yield). $^1$H NMR (400 MHz, DMSO-d6) δ 9.60 (s, 1H), 8.04 (s, 1H), 7.67 (d, J=9.6 Hz, 1H), 7.27 (dd, J=15.6, 8.8 Hz, 1H), 7.16-7.06 (m, 1H), 7.04-6.91 (m, 1H), 6.81 (d, J=9.6 Hz, 1H), 6.20 (s, 1H), 5.30 (d, J=9.6 Hz, 1H), 2.72 (t, J=10.0 Hz, 1H), 2.38 (d, J=11.6 Hz, 1H), 2.24-2.09 (m, 2H), 1.83 (d, J=12.4 Hz, 1H), 1.69-1.59 (m, 1H), 1.57-1.42 (m, 1H), 1.39-1.15 (m, 4H), 1.08-0.95 (m, 2H), 0.89-0.68 (m, 2H). [M+H]$^+$=383.1. To a solution of D127b (72 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (59 mg in 75% yield). 1H NMR (400 MHz, DMSO-d6) δ 9.61 (s, 1H), 8.05 (s, 1H), 7.68 (d, J=9.6 Hz, 1H), 7.27 (dd, J=15.6, 8.4 Hz, 1H), 7.16-7.05 (m, 1H), 7.04-6.92 (m, 1H), 6.81 (d, J=9.6 Hz, 1H), 6.22 (s, 1H), 5.30 (d, J=9.6 Hz, 1H), 2.82-2.64 (m, 1H), 2.38 (d, J=12.6 Hz, 1H), 2.23-2.07 (m, 2H), 1.83 (d, J=12.0 Hz, 1H), 1.71-1.57 (m, 1H), 1.56-1.41 (m, 1H), 1.40-1.14 (m, 4H), 1.10-0.94 (m, 2H), 0.91-0.70 (m, 2H). [M+H]$^+$=383.1. The absolute configurations of chiral carbons in D127a and D127b are tentatively assigned as (S) and (R) respectively based on assumption that the binding model of the more potent isomer D127a is the same as that of C101a with IDO1 enzyme, and the relative stereochemistry on cyclohexane is assigned as trans configuration on the cyclohexane.

Example D128: (4-(4-chloro-3-fluorophenyl)cyclohexyl)(6-cyclopropylimidazo[1,5-a]pyridin-5-yl)methanol

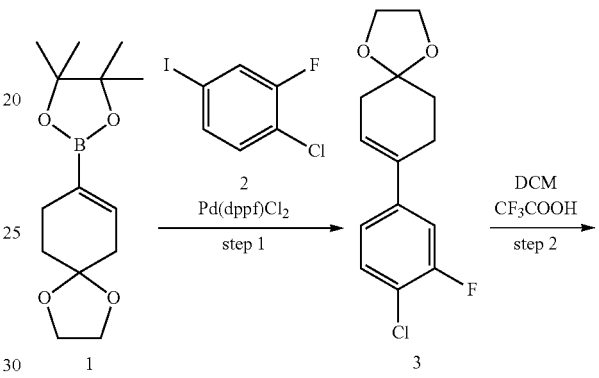

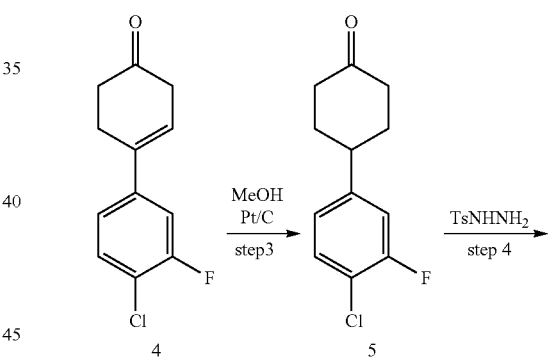

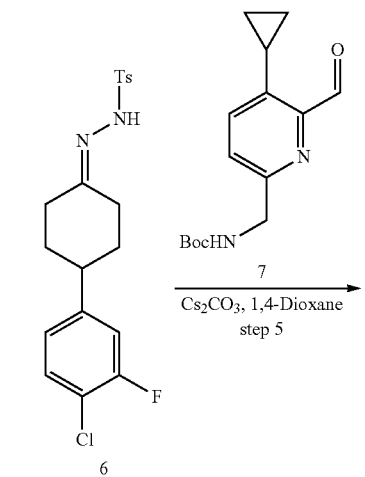

-continued

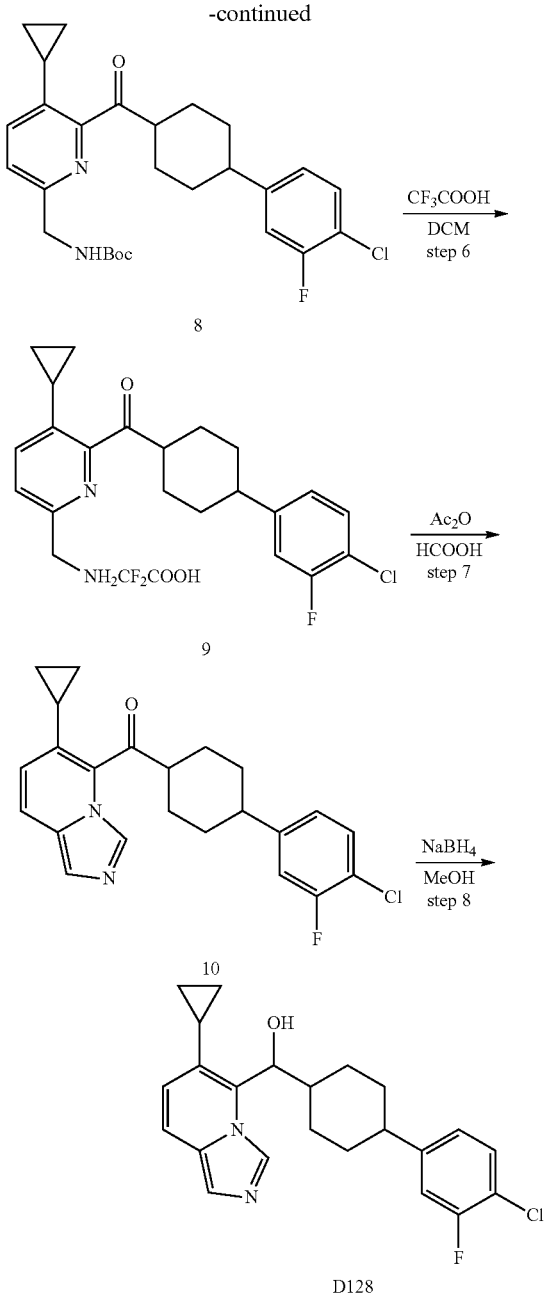

Step 1: 8-(4-chloro-3-fluorophenyl)-1,4-dioxaspiro[4.5]dec-7-ene

To a solution of 1-chloro-2-fluoro-4-iodobenzene (5.72 g, 22.67 mmol) in 1,4-dioxane (150 mL) was added 4,4,5,5-tetramethyl-2-(1,4-dioxaspiro[4.5]dec-7-en-8-yl)-1,3,2-dioxaborolane (6.00 g, 22.67 mmol), Pd(dppf)Cl$_2$ (2.47 g, 3.38 mmol) and Cs$_2$CO$_3$ (11.00 g, 33.83 mmol) and the mixture was heated at 80° C. for overnight. Then evaporated the solvent under reduced pressure and the residue was purified by column chromatography (PE:EA=20:1) to give product as a clear oil (4.06 g in 67% yield). $^1$H NMR (DMSO-d$_6$) $\delta_H$ 7.51 (t, J=8.0 Hz, 1H), 7.46 (m, 1H), 7.28 (m, 1H), 7.12-7.20 (m, 1H), 3.91 (s, 4H), 2.51-2.56 (m, 2H), 2.34-2.40 (m, 2H), and 1.80 (t, J=6.8 Hz, 2H).

Step 2: 4'-chloro-3'-fluoro-2,5-dihydro-[1,1'-biphenyl]-4(3H)-one

To a solution of 4-(1,4-dioxaspiro[4.5]dec-7-en-8-yl)quinoline (4.07 g, 15.19 mmol) in 1,4-dioxane (50 mL) was added concentrated hydrochloric acid (5 mL) at room temperature and the mixture was stirred for overnight. The solvent was evaporated under reduced pressure and water (100 mL) was added, extracted with EA (100 ml 3), combined the organic layer and washed with saturated aqueous of Na$_2$CO$_3$ then the organic layer was evaporated to give crude product. The crude was purified by column chromatography (PE:EA=20:1-5:1) to give product as a clear oil (0.75 g in 15% yield). $^1$H NMR (DMSO-d$_6$) $\delta_H$ 7.50-7.60 (m, 2H), 7.30-7.35 (m, 1H), 6.26-6.31 (m, 1H), 3.00-3.08 (m, 2H), 2.82 (t, J=6.8 Hz, 2H), and 2.54 (t, J=6.8 Hz, 2H).

Step 3: 4-(4-chloro-3-fluorophenyl)cyclohexan-1-one

To a solution of 4'-chloro-3'-fluoro-2,5-dihydro-[1,1'-biphenyl]-4(3H)-one (0.75 g 3.35 mmol) in ethyl acetate (40 mL) and methanol (10 mL) was added Pt/C (0.23 g, 30%) and the mixture was stirred for 18 hours at room temperature under H$_2$ in balloon. Then filtered to remove Pt/C and the filtrate was evaporated under reduced pressure to give a crude product, which was purified by silica gel chromatography (PE:EA=5:1) to give the product (0.46 g in 61% yield) as a yellow oil. MS (ESI) m/e [M+1]$^+$=227.

Step 4: N'-(4-(4-chloro-3-fluorophenyl)cyclohexylidene)-4-methylbenzenesulfonohydrazide To a solution of 4-(4-chloro-3-fluorophenyl)cyclohexan-1-one (0.46 g 2.04 mmol) in methanol (10 mL) was added 4-methylbenzenesulfonohydrazide (0.39 g, 2.04 mmol) at room temperature, and the mixture was stirred for 2-3 hours. The solvent was evaporated under reduced pressure and the residue was pulped with methanol 5 mL, filtered and washed with methanol (2 mL) to give product (0.36 g in 45% yield) as a white solid. $^1$H NMR (DMSO-d$_6$) $\delta_H$10.20 (s, 1H), 7.73 (d, J=8.0 Hz, 1H), 7.47 (t, J=8.0 Hz, 1H), 7.39 (d, J=8.0 Hz, 1H), 7.25-7.35 (m, 1H), 7.05-7.15 (m, 1H), 2.80-2.95 (m, 2H), 2.39 (s, 3H), 2.20-2.30 (m, 2H), 1.80-2.00 (m, 3H), and 1.40-1.50 (m, 2H).

Step 5: tert-butyl ((6-(4-(4-chloro-3-fluorophenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (255 mg, 0.93 mmol) in 1,4-dioxane (15 mL) was added N'-(4-(4-chloro-3-fluorophenyl)cyclohexylidene)-4-methylbenzenesulfonohydrazide (365 mg, 0.93 mmol) and Cs$_2$CO$_3$ (457 mg, 1.40 mmol) at room temperature, and the mixture was heated at 90° C. for overnight. The solvent was cooled to room temperature, concentrated to dryness. The crude was purified by column chromatography (PE:EA=10:1-4:1) to give compound product as a clear oil (182 mg in 40% yield). MS (ESI) m/e [M+1]$^+$=487.

Step 6: (6-(aminomethyl)-3-cyclopropylpyridin-2-yl)(4-(4-chloro-3-fluorophenyl)cyclohexyl)methanone To a solution of tert-butyl ((6-(4-(4-chloro-3-fluorophenyl)cyclohexane-1-carbonyl)-5-cyclopropylpyridin-2-yl)

methyl)carbamate (180 mg 0.37 mmol) in DCM (10 mL) was added CF₃COOH (15 mL) and the mixture was stirred at room temperature for overnight. The solvent was concentrated to dryness, which was used for next step without further purification.

Step 7: (4-(4-chloro-3-fluorophenyl)cyclohexyl)(6-cyclohexyl)(6-cycloropylimidazo[1,5-a]pyridin-5-yl)-methanone To a solution of acetic anhydride (15 mL) and formic acid (10 mL) was stirred at 60° C. for 1 hour, after was added (6-(aminomethyl)-3-cyclopropylpyridin-2-yl)(4-(4-chloro-3-fluorophenyl)cyclohexyl)methanone (201 mg, 0.37 mmol) in formic acid 5 mL. Then the mixture was stirred at 60° C. for 2 hours. After cooled to room temperature, the solvent was concentrated to dryness. The crude was added EA 50 mL, extracted with saturated sodium bicarbonate (50 mL×3). The organic layer was dried over Na₂SO₄, filtered and concentrated to dryness. And the crude was purified by column chromatography (PE:EA=5:1) to give compound product as a yellow solid (105 mg in 71% yield). ¹H NMR (DMSO-d₆) δ$_H$ 8.10 (s, 1H), 7.61 (d, J=9.6 Hz, 1H), 7.40-7.55 (m, 2H), 7.30 (d, J=11.2 Hz, 1H), 7.12 (t, J=8.4 Hz, 1H), 6.50 (d, J=9.6 Hz, 2H), 2.55-2.61 (m, 1H), 2.00-2.10 (2, 1H), 1.80-1.95 (m, 3H), 1.45-1.75 (m, 5H), 0.90-1.05 (m, 2H), and 0.70-0.80 (m, 2H).

Step 8: (4-(4-chloro-3-fluorophenyl)cyclohexyl)(6-cyclopropylimidazo[1,5-a]pyridin-5-yl)methanol

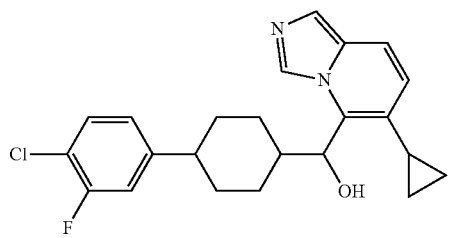 [SMILES: OC(c1c(C2CC2)ccc2cncn12)C1CCC(c2ccc(Cl)c(F)c2)CC1]

To a solution of (4-(4-chloro-3-fluorophenyl)cyclohexyl)(6-cyclopropylimidazo[1,5-a]pyridin-5-yl)methanone (105 mg, 0.27 mmol) in methanol (10 mL) was added NaBH₄ (50 mg, 1.32 mmol) at room temperature and the mixture was stirred for 1 hour. Then the solvent was evaporated under reduced pressure and water (50 mL) was added, extracted with ethyl acetate (50 mL×3) and combined the organic layer, evaporated the solvent under reduced pressure and the residue was pulped in methanol 3 mL and filtered to get a white solid (55 mg, in 51% yield). ¹H NMR (DMSO-d₆) δ$_H$ 8.61 (S, 1H), 7.44 (t, J=8.0 Hz, 1H), 7.40 (d, J=9.6 Hz, 1H), 7.31 (s, 1H), 7.23-7.29 (m, 1H), 7.06-7.12 (m, 1H), 6.47 (d, J=9.6 Hz, 1H), 5.81 (d, J=3.6 Hz, 1H), 5.20-5.30 (dd, J=3.6 Hz, 9.6 Hz, 1H), 2.38-2.46 (m, 1H), 2.15-2.25 (m, 1H), 1.93-1.96 (m, 1H), 1.61-1.69 (m, 1H), 1.43-1.55 (m, 1H), 1.13-1.35 (m, 4H), 0.88-1.00 (m, 2H), and 0.61-0.90 (m, 2H).

Example D128a and D128b: (S)-((1r,4S)-4-(4-chloro-3-fluorophenyl)cyclohexyl)(6-cyclopropylimidazo[1,5-a]pyridin-5-yl)methanol and (R)-((1r,4R)-4-(4-chloro-3-fluorophenyl)cyclohexyl)(6-cyclopropylimidazo[1,5-a]pyridin-5-yl)methanol

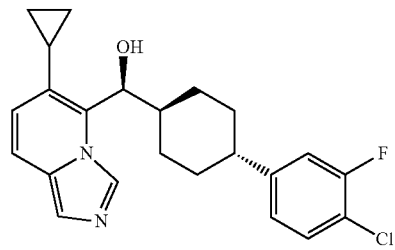

Fast isomer in CHIRALPAK IC-3 HPLC
Eluting reagent: Hex(0.1% IPAmine):EtOH = 80:20

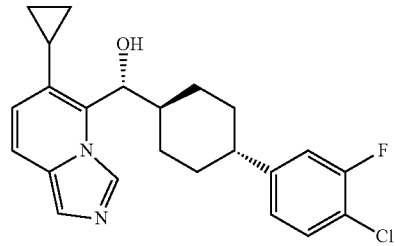

Slow isomer in CHIRALPAK IC-3 HPLC
Eluting reagent: Hex(0.1% IPAmine):EtOH = 80:20

Each enantiomer of racemic D128a and D128b was separated using preparative HPLC on a CHIRAL PAK IC with Hex:EtOH=80:20 as an eluent. The enantiomeric excesses were determined by using HPLC on a CHIRAL PAK IC with Hex (0.1% IPAmine):EtOH=80:20 as an eluent at a flow rate of 1.0 mL/min. The first one enantiomer eluted at the retention time of 1.646 min (D128a), which was dissolved in DCM (10 mL), and added EA solution of hydrochloric acid (0.5 mL, 4.0 M) at room temperature, followed by addition of methanol until the precipitate was dissolved, then the solvent was evaporated under reduced pressure and the residue was washed by PE to give the desired product as white solid. ¹H NMR (DMSO-d6) δ$_H$ 9.55 (s, 1H), 8.00 (s, 1H), 7.68 (d, J=9.6 Hz, 1H), 7.46 (t, J=8.4 Hz, 1H), 7.24 (dd, J=8.0 Hz, J=8.4 Hz, 1H), 7.07 (d, J=8.4 Hz, 1H), 6.80 (d, J=9.6 Hz, 1H), 6.15 (s, 1H), 5.31 (d, J=9.6 Hz, 1H), 3.40-3.46 (m, 2H), 2.35-2.54 (m, 1H), 2.10-2.20 (m, 2H), 1.85-1.95 (m, 1H), 1.65-1.75 (m, 1H), 1.44-1.53 (m, 1H), 1.25-1.38 (m, 3H), 0.98-1.09 (m, 2H), and 0.70-0.90 (m, 2H). and the other enantiomer eluted at the retention time of 3.364 min (D128b), ¹H NMR (DMSO-d₆) δ$_H$ 9.59 (s, 1H), 8.03 (s, 1H), 7.69 (d, J=9.6 Hz, 1H), 7.46 (t, J=8.4 Hz, 1H), 7.25 (dd, J=8.0 Hz, J=8.4 Hz, 1H), 7.07 (d, J=8.4 Hz, 1H), 6.82 (d, J=9.6 Hz, 1H), 6.18 (s, 1H), 5.31 (d, J=9.6 Hz, 1H), 3.40-3.46 (m, 2H), 2.35-2.45 (m, 1H), 2.10-2.24 (m, 2H), 1.85-1.96 (m, 1H), 1.65-1.75 (m, 1H), 1.40-1.53 (m, 1H), 1.25-1.38 (m, 3H), 0.97-1.09 (m, 2H), and 0.72-0.90 (m, 2H). The absolute configurations of chiral carbons in D128a and D128b are tentatively assigned as (S) and (R) respectively based on assumption that the binding model of the more potent isomer D128a is the same as that of C101a with IDO1 enzyme, and the relative stereochemistry on cyclohexane is assigned as trans configuration on the cyclohexane.

Example D129: (4-(3-chloro-4-fluorophenyl)cyclohexyl)(6-cyclopropylimidazo[1,5-a]pyridin-5-yl)methanol

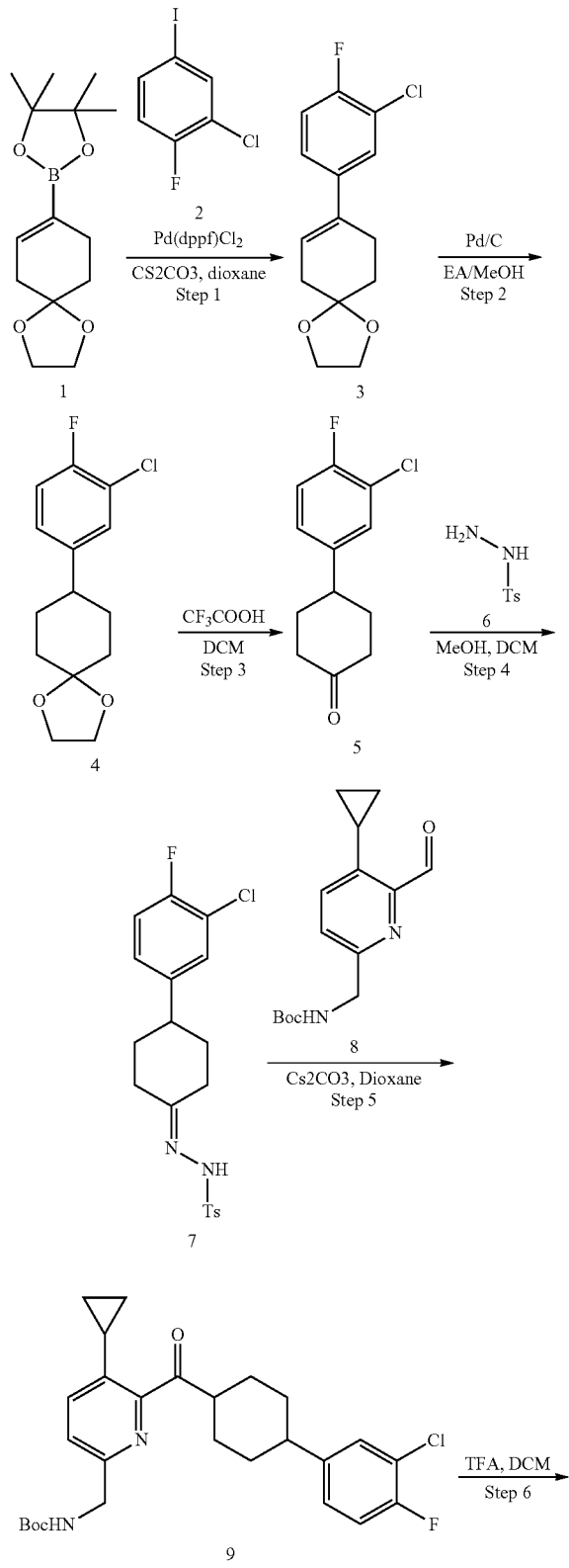

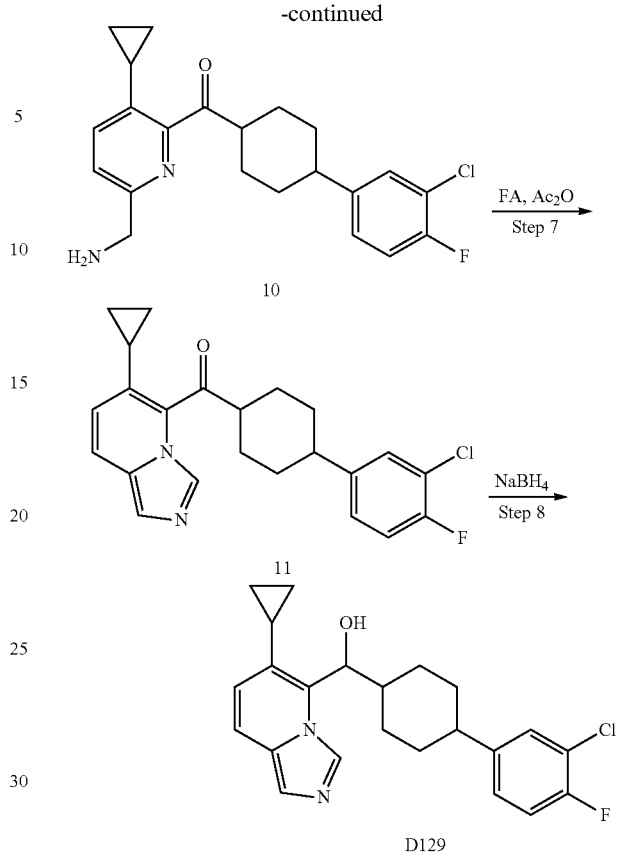

Step 1: 8-(3-chloro-4-fluorophenyl)-1,4-dioxaspiro[4.5]dec-7-ene

A mixture of 2-chloro-1-fluoro-4-iodobenzene (7.0 g, 27.3 mmol), 4,4,5,5-tetramethyl-2-(1,4-dioxaspiro[4.5]dec-7-en-8-yl)-1,3,2-dioxaborolane (7.2 g, 27.1 mmol), Pd(dppf)Cl$_2$ (1.0 g, 1.36 mmol) and Cs$_2$CO$_3$ (14.0 g, 42.9 mmol) in 1,4-dioxane (200 mL) was heated at 95° C. for 2 hours. The mixture was filtered and the filtrate was concentrated and the resulted residue was purified by column chromatography (PE:EA=50:1 to 20:1) to give product (3.8 g, crude) as a colorless oil.

Step 2: 8-(3-chloro-4-fluorophenyl)-1,4-dioxaspiro[4.5]decane

A mixture of 8-(3-chloro-4-fluorophenyl)-1,4-dioxaspiro[4.5]dec-7-ene (3.8 g, crude) and Pd/C (380 mg) in a mixed solvent (methanol/ethyl acetate: 60 mL/60 mL) was stirred at rt under H$_2$ for 2 hrs. The mixture was filtered and the filtrate was concentrated to give the title product (2.8 g, crude) as a colorless oil.

Step 3: 4-(3-chloro-4-fluorophenyl)cyclohexan-1-one

To a solution of 8-(3-chloro-4-fluorophenyl)-1,4-dioxaspiro[4.5]decane (2.8 g, 10.4 mmol) in dichloromethane (20 mL) was added trifluoroacetic acid (30 mL) at room temperature and the mixture was stirred for 2 days. The mixture was concentrated. Aqueous solution of NaHCO$_3$ (50 mL) and ethyl acetate (50 mL) were added, and the mixture was stirred for 20 min. Layers was separated and the organic layer was washed with brine (20 mL×2), dried over $Na_2SO_4$ and concentrated. The residue was purified by column chromatography (PE:EA=50:1 to 20:1) to give the title product (1.06 g, yield: 17% for 3 steps) as a colorless oil.

Step 4: N'-(4-(3-chloro-4-fluorophenyl)cyclohexylidene)-4-methylbenzenesulfonohydrazide To a stirred solution of 4-(3-chloro-4-fluorophenyl)cyclohexan-1-one (1.06 g, 4.7 mmol) in a mixed solvent (dichloromethane/ethanol: 10 mL/10 mL) was added 4-methylbenzenesulfonohydrazide (872 mg, 4.7 mmol) at room temperature and the mixture was stirred for 16 hrs. The mixture was concentrated and the residue was added 20 mL of 2-methoxy-2-methylpropane and the mixture was stirred at 50° C. for 2 hrs and cooled, and continued to stir for 1 hour. A white solid precipitated, which was filtered. The filter cake was dried under high vacuum to give the title product (1.12 g, yield: 60%) as a white solid.

Step 5: tert-butyl ((6-(4-(3-chloro-4-fluorophenyl)cyclohexane-1-carbonyl)-5-cyclopropylpyridin-2-yl)methyl)carbamate A mixture of tert-butyl ((5-cyclopropyl-6-formylpyridin-2-yl)methyl)carbamate (510 mg, 1.85 mmol), N'-(4-(3-chloro-4-fluorophenyl)cyclohexylidene)-4-methylbenzenesulfonohydrazide (730 mg, 1.85 mmol) and $Cs_2CO_3$ (1.2 g, 3.7 mmol) in 1,4-dioxane (20 mL) was heated at 100° C. for 16 hours. The mixture was cooled and treated with ethyl acetate (50 mL) and water (50 mL). The aqueous layer was extracted with ethyl acetate (50 mL×2). The combined organics was washed with brine (50 mL×2), dried over $Na_2SO_4$ and concentrated. The resulted residue was purified by column chromatography (PE:EA=10:1) to give the title product as a light yellow oil (580 mg, yield: 27%). $[M+H]^+$=487.2

Step 6: (6-(aminomethyl)-3-cyclopropylpyridin-2-yl)(4-(3-chloro-4-fluorophenyl)cyclohexyl)methanone To a solution of tert-butyl ((6-(4-(3-chloro-4-fluorophenyl)cyclohexane-1-carbonyl)-5-cyclopropylpyridin-2-yl)methyl)carbamate (520 mg, 1.07 mmol) in DCM (10 mL) was added trifluoracetic acid (10 mL) and the mixture was stirred at room temperature for 2 hrs. The solvent was evaporated under reduced pressure to give the title product as a dark brown oil. $[M+H]^+$=387.1.

Step 7: (4-(3-chloro-4-fluorophenyl)cyclohexyl)(6-cyclopropylimidazo[1,5-a]pyridin-5-yl)methanone A mixture of $Ac_2O$ (30 mL) and HCOOH (10 mL) was heated at 50° C. for 1 hour and then a solution of (6-(aminomethyl)-3-cyclopropylpyridin-2-yl)(4-(3-chloro-4-fluorophenyl)cyclohexyl)methanone trifluoracetic acid (crude, 1.07 mmol) in HCOOH (5 mL) was added drop wise and the mixture was heated at 50° C. for 1 hour. The solvent was evaporated under reduced pressure, aqueous solution of $NaHCO_3$(50 mL) and ethyl acetate (50 mL) were added. The layers were separated and the organic layer was washed with brine (50 mL×2), dried over $Na_2SO_4$ and concentrated. The resulted residue was purified by column chromatography (PE:EA=10:1-4:1) to give the title product as a yellow solid (380 g, crude). $[M+H]^+$=397.1.

Step 8: (4-(3-chloro-4-fluorophenyl)cyclohexyl)(6-cyclopropylimidazo[1,5-a]pyridin-5-yl)methanol

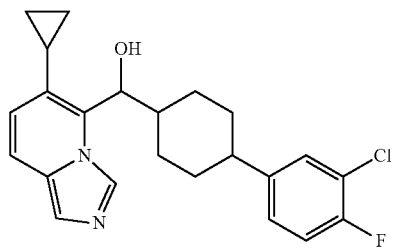 [SMILES: OC(c1c(C2CC2)ccc2cncn12)C1CCC(c2ccc(F)c(Cl)c2)CC1]

To a stirred solution of (4-(3-chloro-4-fluorophenyl)cyclohexyl)(6-cyclopropylimidazo[1,5-a]pyridin-5-yl)methanone (380 mg, 0.96 mmol) in methanol (20 mL) was added $NaBH_4$ (400 mg, 42 mmol, 100 mg per hour) at room temperature. After the addition finished, the mixture was concentrated. 20 mL of water was added, and the mixture was extracted with ethyl acetate (20 mL×3). The combined organics was washed with brine (20 mL×2), dried over $Na_2SO_4$, and concentrated. The residue was purified by prep-TLC (PE/EA=1:1) to give the title product as a gray solid (290 mg, yield: 68% for 3 steps). $^1$H NMR (400 MHz, DMSO-$d_6$) δ 8.77 (s, 1H), 7.47-7.39 (m, 3H), 7.28 (t, J=8.8 Hz, 1H), 7.24-7.18 (m, 1H), 6.53 (d, J=9.2 Hz, 1H), 5.87 (d, J=3.6 Hz, 1H), 5.26 (dd, J=9.6, 3.2 Hz, 1H), 2.57-2.51 (m, 1H), 2.41 (d, J=12.4 Hz, 1H), 2.27-2.12 (m, 1H), 1.99-1.95 (m, 1H), 1.87 (d, J=12.4 Hz, 1H), 1.66 (d, J=11.2 Hz, 1H), 1.55-1.40 (m, 1H), 1.35-1.10 (m, 4H), 1.05-0.85 (m, 2H), 0.84-0.73 (m, 1H), 0.71-0.64 (m, 1H). $[M+H]^+$=399.1.

Example 129a and D129b: (S)-((1r,4S)-4-(3-chloro-4-fluorophenyl)cyclohexyl)(6-cyclopropylimidazo[1,5-a]pyridin-5-yl)methanol and (R)-((1 r,4R)-4-(3-chloro-4-fluorophenyl)cyclohexyl)(6-cyclopropylimidazo[1,5-a]pyridin-5-yl)methanol

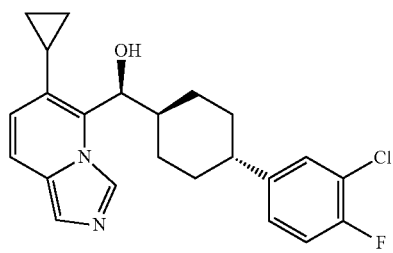

Fast isomer in CHIRALPAK IC HPLC
Eluting reagent: Hex(0.1% DEA):EtOH = 80:20

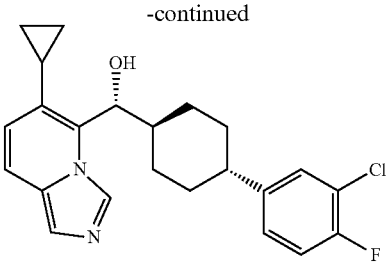

Slow isomer in CHIRALPAL IC HPLC
Eluting reagent: Hex(0.1% DEA):EtOH = 80:20

Each enantiomer of racemic D129a and D129b was separated using preparative HPLC on a CHIRALPAK IC with Hex (0.1% DEA):EtOH=80:20 as an eluent. The enantiomeric excesses were determined by using HPLC on a CHIRALPAK IC-3 with Hex (0.1% IPAmine):EtOH=80:20 as an eluent at a flow rate of 1.0 mL/min. The first one enantiomer eluted at the retention time of 1.493 min (D129a), $^1$H NMR (400 MHz, DMSO-$d_6$) δ 9.64 (s, 1H), 8.09 (s, 1H), 7.72 (d, J=9.6 Hz, 1H), 7.40 (dd, J=7.2, 2.0 Hz, 1H), 7.30 (t, J=9.2 Hz, 1H), 7.24-7.16 (m, 1H), 6.85 (d, J=9.6 Hz, 1H), 6.26 (s, 1H), 5.32 (d, J=9.6 Hz, 1H), 2.59-2.52 (m, 1H), 2.39 (d, J=11.6 Hz, 1H), 2.25-2.10 (m, 2H), 1.90 (d, J=12.8 Hz, 1H), 1.68 (s, 1H), 1.55-1.40 (m, 1H), 1.40-1.15 (m, 4H), 1.11-0.97 (m, 2H), 0.95-0.72 (m, 2H). and the other enantiomer eluted at the retention time of 3.334 min (D129b), $^1$H NMR (400 MHz, DMSO-$d_6$) δ 9.63 (s, 1H), 8.08 (s, 1H), 7.73 (d, J=9.6 Hz, 1H), 7.40 (dd, J=7.2, 2.0 Hz, 1H), 7.30 (t, J=9.2 Hz, 1H), 7.24-7.16 (m, 1H), 6.85 (d, J=10.0 Hz, 1H), 6.26 (s, 1H), 5.32 (d, J=9.6 Hz, 1H), 2.59-2.52 (m, 1H), 2.39 (d, J=11.6 Hz, 1H), 2.25-2.10 (m, 2H), 1.90 (d, J=12.4 Hz, 1H), 1.68 (s, 1H), 1.55-1.40 (m, 1H), 1.40-1.15 (m, 4H), 1.11-0.97 (m, 2H), 0.95-0.72 (m, 2H). The absolute configurations of chiral carbons in D1129a and D129b are tentatively assigned as (S) and (R) respectively based on assumption that the binding model of the more potent isomer D129a is the same as that of C101a with IDO1 enzyme, and the relative stereochemistry on cyclohexane is assigned as trans configuration on the cyclohexane.

Example D130: (4-(2-chloro-4-fluorophenyl)cyclohexyl)(6-cyclopropylimidazo[1,5-a]pyridin-5-yl)methanol

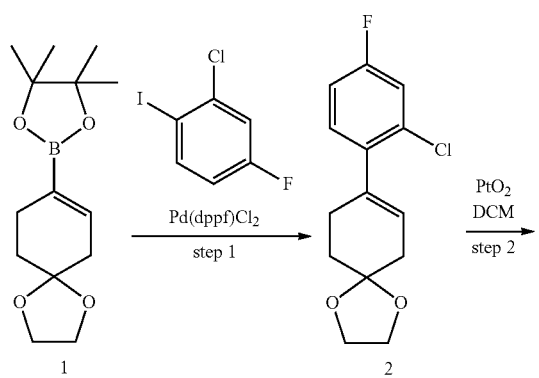

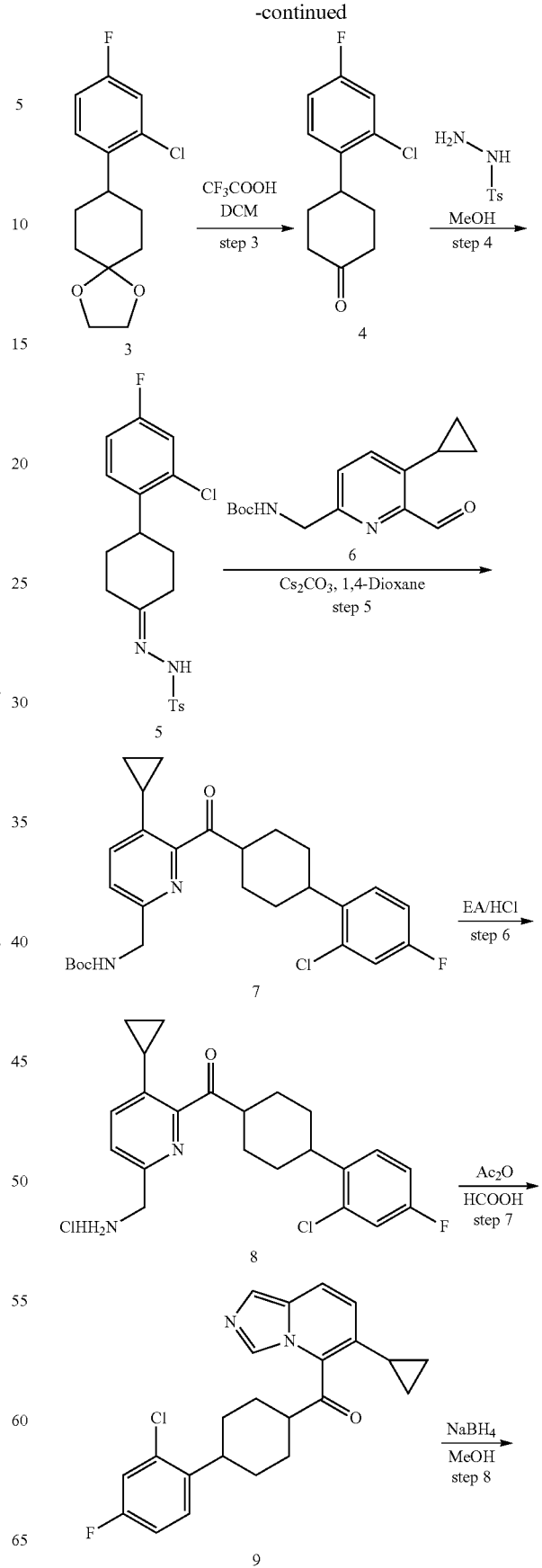

-continued

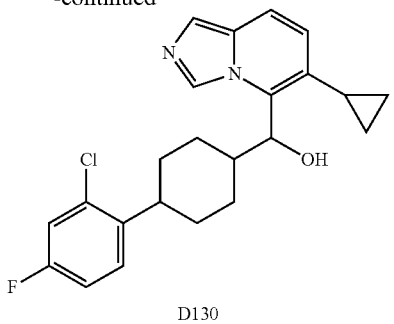

D130

Step 1: 8-(2-chloro-4-fluorophenyl)-1,4-dioxaspiro[4.5]dec-7-ene

To a solution of 2-chloro-4-fluoro-1-iodobenzene (7.7 g, 30 mmoL) in 1,4-dioxane (150 mL) was added 4,4,5,5-tetramethyl-2-(1,4-dioxaspiro[4.5]dec-7-en-8-yl)-1,3,2-dioxaborolane (8 g, 30 mmol), Pd(dppf)Cl$_2$(2.2 g, 3 mmol) and Cs$_2$CO$_3$ (14.7 g, 45 mmol) and the mixture was heated at 95° C. overnight. The mixture was cooled to room temperature, diluted with water (100 mL), extracted with ethyl acetate (80 mL×3), washed with brine, dried over Na$_2$SO$_4$, filtered and filtrate was evaporated under reduced pressure. The residue was purified by column chromatography (PE:EA=100:1) to give product as a solid (3.2 g in 39.8% yield).

Step 2: 8-(2-chloro-4-fluorophenyl)-1,4-dioxaspiro[4.5]decane

To a solution of 8-(2-chloro-4-fluorophenyl)-1,4-dioxaspiro[4.5]dec-7-ene (3 g, 11.2 mmol) in dichloromethane (60 mL) was added PtO$_2$ (0.6 g). The reaction was stirred at room temperature overnight under H$_2$ (balloon). Then filtered to remove PtO$_2$ and the filtrate was evaporated under reduced pressure to give product as oil (3 g, crude).

Step 3: 4-(2-chloro-4-fluorophenyl)cyclohexan-1-one

To a solution of 8-(2-chloro-4-fluorophenyl)-1,4-dioxaspiro[4.5]decane (3 g, 11.2 mmol) in dichloromethane (10 mL) was added trifluoroacetic acid (3 mL) at room temperature and the mixture was stirred for overnight. The reaction was quenched with saturated NaHCO$_3$ solution, extracted with dichloromethane (50 mL×2), then the organic layer was evaporated in vacuo. The residue was was purified by column chromatography (PE:EA=10:1) to give product as a white solid (1.12 g in 44% yield for two steps). $^1$H NMR (CDCl$_3$-d) δ$_H$ 7.24-7.17 (m, 1H), 7.15 (dd, J=2.8, 8.8 Hz, 1H), 7.02-6.94 (m, 1H), 3.54-3.42 (m, 1H), 2.62-2.48 (m, 4H), 2.28-2.16 (m, 2H), 1.92-1.77 (m, 2H).

Step 4: N'-(4-(2-chloro-4-fluorophenyl)cyclohexylidene)-4-methylbenzenesulfonohydrazide To a solution of 4-(2-chloro-4-fluorophenyl)cyclohexan-1-one (1.12 g, 4.95 mmol) in dichloromethane:methanol (10:20 mL) was added 4-methylbenzenesulfonohydrazide (0.92 g, 4.95 mmol) at room temperature and the mixture was stirred for overnight. The mixture was concentrated to dryness and to the residue was added PE:EA (20 mL:5 mL).

A suspension was formed and filtered. The solid was collected and dried to give product as a white solid (1.8 g in 92% yield).

Step 5: tert-butyl ((6-(4-(2-chloro-4-fluorophenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (0.6 g, 2.17 mmol) in 1,4-dioxane (30 mL) was added N'-(4-(2-chloro-4-fluorophenyl)cyclohexylidene)-4-methylbenzenesulfonohydrazide (0.85 g, 2.17 mmol) and Cs$_2$CO$_3$ (1.06 g, 3.25 mmol) at room temperature, and the mixture was heated at 90° C. for 16 hours. The solvent was evaporated in vacuo and water (50 mL) was added, extracted with ethyl acetate (50 mL×3) and combined the organic layer, the solvent was evaporated under reduced pressure to give product as an oil (1.3 g, crude). [M+H]$^+$=487

Step 6: (6-(aminomethyl)-3-cyclopropylpyridin-2-yl)(4-(2-chloro-4-fluorophenyl)cyclohexyl)methanone Trifluoracetic acid To a solution of tert-butyl ((6-(4-(2-chloro-4-fluorophenyl)cyclohexane-1-carbonyl)-5-cyclopropylpyridin-2-yl)methyl)carbamate (1.3 g, crude) in DCM (10 mL) was added trifluoracetic acid (4 mL) and the mixture was stirred at room temperature for 3 hours. The solvent was evaporated under reduced pressure to give crude product as solid. [M+H]$^+$=387.

Step 7: (4-(2-chloro-4-fluorophenyl)cyclohexyl)(6-cyclopropylimidazo[1,5-a]pyridin-5-yl)methanone A mixture of Ac$_2$O (9 mL) and HCOOH (3 mL) was heated at 50° C. for 1 hour and then (6-(aminomethyl)-3-cyclopropylpyridin-2-yl)(4-(2-chloro-4-fluorophenyl)cyclohexyl)methanone Trifluoracetic acid (crude, 0.8 mmol) was added. The mixture was heated at 70° C. for 2 hours. The solvent was evaporated under reduced pressure and treated with saturated aqueous of NaHCO$_3$, then extracted with ethyl acetate (40 mL×3) and combined the organic layer, the solvent was evaporated under reduced pressure and the residue was purified by column chromatography (PE:EA=4:1) to give product as a solid (260 mg in 30% yield for three steps). [M+H]$^+$=397.

Step 8: (4-(2-chloro-4-fluorophenyl)cyclohexyl)(6-cyclopropylimidazo[1,5-a]pyridin-5-yl)methanol

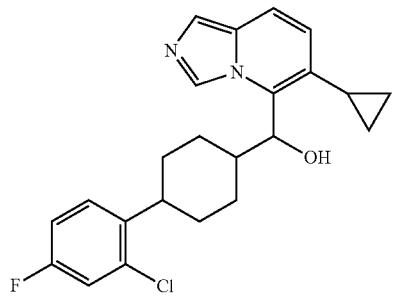 [SMILES: OC(c1c(C2CC2)ccc2cncn12)C1CCC(c2ccc(F)cc2Cl)CC1]

To a solution of (4-(2-chloro-4-fluorophenyl)cyclohexyl)(6-cyclopropylimidazo[1,5-a]pyridin-5-yl)methanone (0.26 g, 0.656 mmol) in methol (10 mL) was added NaBH$_4$ (125 mg, 3.28 mmol) at room temperature and the mixture was stirred for 2 h. The mixture was quenched with acetone (20 mL) and the solvent was evaporated under reduced pressure. The residue was purified by column chromatography (PE: EA=3:2) to give product as a solid (180 mg in 69% yield). $^1$H NMR (DMSO-d$_6$) δ$_H$ 8.62 (s, 1H), 7.44-7.33 (m, 3H), 7.31 (s, 1H), 7.18-7.10 (m, 1H), 6.47 (d, J=9.2 Hz, 1H), 5.82 (d, J=4.0 Hz, 1H), 5.26 (dd, J=4.0, 9.6 Hz, 1H), 2.95-2.81 (m, 1H), 2.48-2.40 (m, 1H), 2.30-2.15 (m, 1H), 2.10-2.01 (m, 1H), 1.91-1.82 (m, 1H), 1.68-1.61 (m, 1H), 1.57-1.43 (m, 1H), 1.39-1.14 (m, 4H), 1.02-0.89 (m, 2H), 0.80-0.72 (m, 1H), 0.70-0.61 (m, 1H). [M+H]$^+$=399.

Example D130a and D130b: (S)-((1r,4S)-4-(2-chloro-4-fluorophenyl)cyclohexyl)(6-cyclopropylimidazo[1,5-a]pyridin-5-yl)methanol and (R)-((1r,4R)-4-(2-chloro-4-fluorophenyl)cyclohexyl)(6-cyclopropylimidazo[1,5-a]pyridin-5-yl)methanol

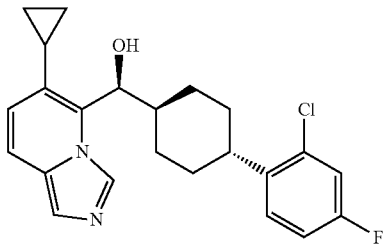

Fast isomer in CHIRALPAK IC HPLC
Eluting reagent: Hex:EtOH = 70:30

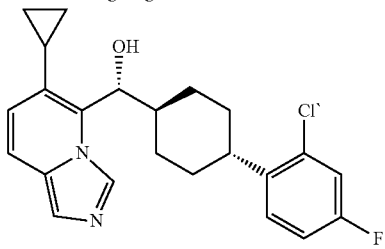

Slow isomer in CHIRALPAL IC HPLC
Eluting reagent: Hex:EtOH = 70:30

Each enantiomer of racemic D130a and D130b was separated using preparative HPLC on a CHIRALPAK IC with Hex:EtOH=70:30 as an eluent. The enantiomeric excesses were determined by using HPLC on a CHIRALPAK IC-3 with Hex (0.1% IPAmine):EtOH=70:30 as an eluent at a flow rate of 1.0 mL/min. The first one enantiomer eluted at the retention time of 1.099 min, and the other enantiomer eluted at the retention time of 1.567 min. To a solution of D130a (74 mg) in DCM (10 mL) was added drop wise of dioxane solution of hydrochloric acid (0.5 mL, 4.0M) at room temperature and stirred for 0.5 hour. Then the solvent was evaporated under reduced pressure and the residue was treated with distilled water (10 mL). The resulting mixture was lyophilized to give the desired product as white solid (67 mg in 83.1% yield). $^1$H NMR (DMSO-d$_6$) δ$_H$ 9.64 (s, 1H), 8.07 (s, 1H), 7.71 (d, J=9.6 Hz, 1H), 7.40-7.31 (m, 2H), 7.20-7.12 (m, 1H), 6.84 (d, J=9.2 Hz, 1H), 6.21 (s, 1H), 5.34 (d, J=10.4 Hz, 1H), 2.95-2.84 (m, 1H), 2.46-2.37 (m, 1H), 2.26-2.14 (m, 2H), 1.95-1.84 (m, 1H), 1.73-1.62 (m, 1H), 1.55-1.19 (m, 5H), 1.11-1.00 (m, 2H), 0.90-0.74 (m, 2H). [M+H]$^+$=399. To a solution of D130b (77 mg) in DCM (10 mL) was added drop wise of dioxane solution of hydrochloric acid (0.5 mL, 4.0M) at room temperature, and stirred for 0.5 hour. Then the solvent was evaporated under reduced pressure and the residue was treated with distilled water (10 mL). The resulting mixture was lyophilized to give the desired product as white solid (70 mg in 83.3% yield). $^1$H NMR (DMSO-d$_6$) δ$_H$ 9.64 (s, 1H), 8.07 (s, 1H), 7.71 (d, J=9.2 Hz, 1H), 7.40-7.32 (m, 2H), 7.21-7.13 (m, 1H), 6.84 (d, J=10.0 Hz, 1H), 6.23 (s, 1H), 5.34 (d, J=10.0 Hz, 1H), 2.95-2.84 (m, 1H), 2.46-2.37 (m, 1H), 2.26-2.14 (m, 2H), 1.95-1.84 (m, 1H), 1.72-1.62 (m, 1H), 1.55-1.20 (m, 5H), 1.11-1.00 (m, 2H), 0.90-0.74 (m, 2H). [M+H]$^+$=399. The absolute configurations of chiral carbons in D130a and D130b are tentatively assigned as (S) and (R) respectively based on assumption that the binding model of the more potent isomer D130a is the same as that of C101a with IDO1 enzyme, and the relative stereochemistry on cyclohexane is assigned as trans configuration on the cyclohexane.

Example D131: (4-(4-chloro-2-fluorophenyl)cyclohexyl)(6-cyclopropylimidazo[1,5-a]pyridin-5-yl)methanol

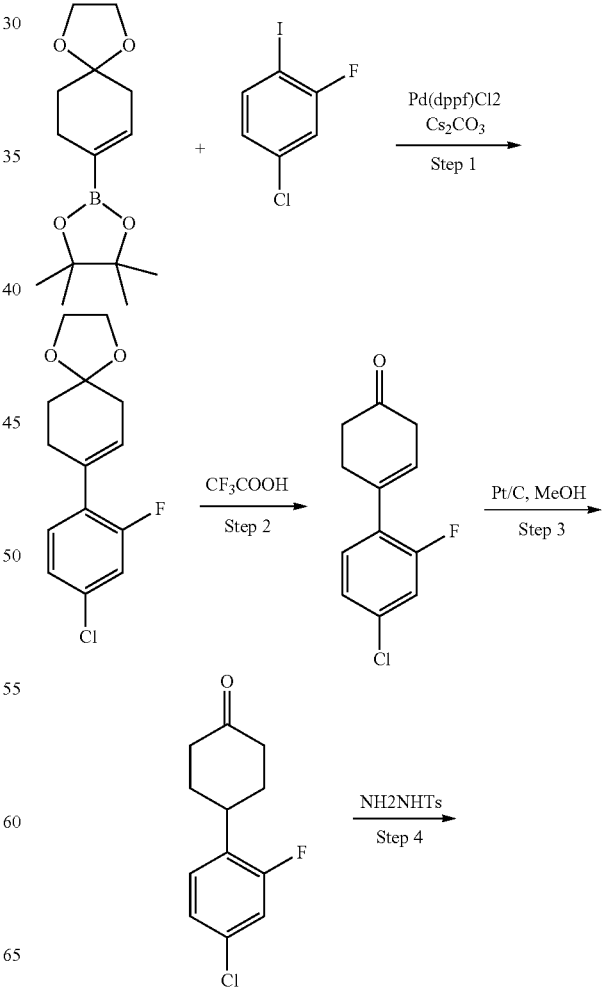

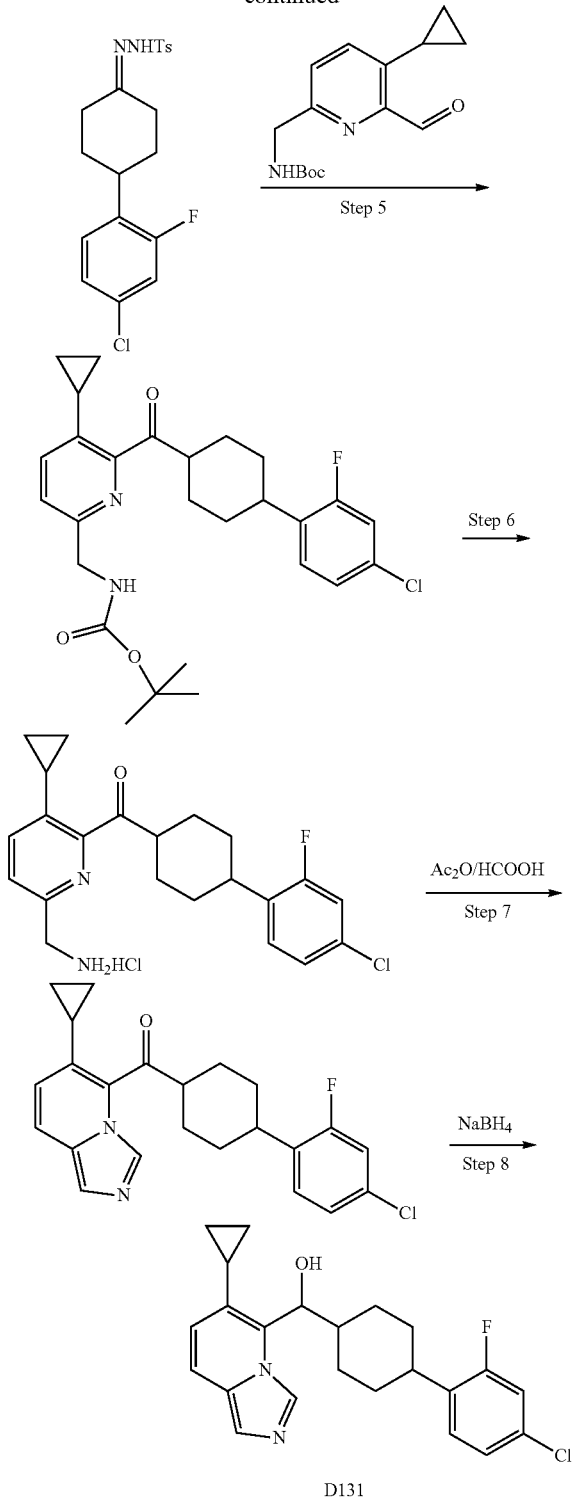

Step 1: 8-(4-chloro-2-fluorophenyl)-1,4-dioxaspiro[4.5]dec-7-ene

To a solution of 4-chloro-2-fluoro-1-iodobenzene (11.5 g, 45 mmoL) in 1,4-dioxane (100 mL) and H₂O (10 mL) was added 4,4,5,5-tetramethyl-2-(1,4-dioxaspiro[4.5]dec-7-en-8-yl)-1,3,2-dioxaborolane (7.98 g, 30 mmol), Pd(dppf)Cl₂ (3.3 g, 4.5 mmol) and Cs₂CO₃ (19.6 g, 60 mmol) and the mixture was heated at 80° C. overnight under N₂. Then evaporated the solvent under reduced pressure and the residue was purified by column chromatography (PE:EA=1:0-50:1) to give product as a brown solid (6.9 g, 85%). [M+H]⁺=269.

Step 2: 4'-chloro-2'-fluoro-2,5-dihydro-[1,1'-biphenyl]-4(3H)-one

To a solution of 8-(4-chloro-2-fluorophenyl)-1,4-dioxaspiro[4.5]dec-7-ene (6.9 g, 25.7 mmol) in dichloromethane (20 mL) was added trifluoroacetic acid (20 mL) at room temperature and the mixture was stirred for overnight. The solvent was evaporated under reduced pressure and water (100 mL) was added, extracted with ethyl acetate (20 mL×3), combined the organic layer and washed with saturated aqueous of NaHCO₃, then the organic layer was further purified by column chromatography, on silica, eluting with EA:PE=0:1-1:5 to give the product (3.8 g, 66%) as a brown oil.

Step 3: 4-(4-chloro-2-fluorophenyl)cyclohexan-1-one

To a solution of 4'-chloro-2'-fluoro-2,5-dihydro-[1,1'-biphenyl]-4(3H)-one (1.8 g, 8.0 mmol) in MeOH (30 mL) was added Pt/C (0.36 g, 10%) and the mixture was stirred overnight at room temperature under H₂ (0.1 Mpa). Then filtered to remove Pt/C and the filtrate was evaporated under reduced pressure to give the product (1.7 g, crude) which was used next step without further purification.

Step 4: N'-(4-(4-chloro-2-fluorophenyl)cyclohexylidene)-4-methylbenzenesulfonohydrazide To a solution of 4-(4-chloro-2-fluorophenyl)cyclohexan-1-one (1.7 g, 7.49 mmol) in methanol (30 mL) was added 4-methylbenzenesulfonohydrazide (1.4 g, 7.49 mmol) at room temperature and the mixture was stirred for overnight. The mixture was purified by column chromatography on silica, eluting eith EA:PE=1:4 to give the product (670 mg, 23%) as a white solid. [M+H]⁺=395.

Step 5: tert-butyl ((6-(4-(4-chloro-2-fluorophenyl)cyclohexane-1-carbonyl)-5-cyclopropyl-pyridin-2-yl)methyl)carbamate To a solution of tert-butyl ((5-cyclopropyl-6-formylpyridin-2-yl)methyl)carbamate (471 mg, 1.7 mmol) in 1,4-dioxane (20 mL) was added N'-(4-(4-chloro-2-fluorophenyl)cyclohexylidene)-4-methylbenzenesulfonohydrazide (670 mg, 1.7 mmol) and Cs₂CO₃ (831 mg, 2.55 mmol) at room temperature, and the mixture was heated at 100° C. overnight under N₂. The mixture was purified by column chromatography (PE:EA=5:1) to give product as a brown oil (540 mg in 65% yield).

Step 6: (6-(aminomethyl)-3-cyclopropylpyridin-2-yl)(4-(4-chloro-2-fluorophenyl)cyclohexyl)methanone hydrochloride A solution of tert-butyl ((6-(4-(4-chloro-2-fluorophenyl)cyclohexane-1-carbonyl)-5-cyclopropylpyridin-2-yl)methyl)carbamate (540 mg, 1.1 mmol) in HCl in EA (30 mL) was stirred at room temperature for overnight. The solvent was evaporated under reduced pressure to give crude product as solid (700 mg, crude).

Step 7: (4-(4-chloro-2-fluorophenyl)cyclohexyl)(6-cyclopropylimidazo[1,5-a]pyridin-5-yl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(4-chloro-2-fluorophenyl)cyclohexyl)methanone hydrochloride (700 mg, crude) in HCOOH (5 mL) was added drop wise and the mixture was heated at 50° C. for 2 hours. The solvent was evaporated under reduced pressure and water (70 mL) was added, washed with saturated aqueous of NaHCO$_3$, then extracted with ethyl acetate (50 mL×3) and combined the organic layer, the solvent was evaporated to give crude product as a solid (470 mg).

Step 8: (4-(4-chloro-2-fluorophenyl)cyclohexyl)(6-cyclopropylimidazo[1,5-a]pyridin-5-yl)methanol To a solution of (4-(4-chloro-2-fluorophenyl)cyclohexyl)(6-cyclopropylimidazo[1,5-a]pyridin-5-yl)methanone (470 mg, 1.2 mmol) in methanol (10 mL) was added NaBH$_4$ (228 mg, 6.0 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid which was washed with EA(10 mL) (200 mg). $^1$H NMR (DMSO-d$_6$) $\delta_H$ 8.62 (s, 1H), 7.41 (d, J=9.2 Hz, 1H), 7.29-7.35 (m, 3H), 7.18-7.21 (m, 1H), 6.47 (d, J=10.8 Hz, 1H), 5.81 (d, J=4.0 Hz, 1H), 5.26 (dd, J=4.0, 9.2 Hz, 1H), 2.73-2.79 (m, 1H), 2.41-2.51 (m, 1H), 2.20-2.24 (m, 1H), 2.02-2.08 (m, 1H), 1.83-1.87 (m, 1H), 1.52-1.64 (m, 2H), 1.14-1.35 (m, 4H), 0.92-0.97 (m, 2H) and, 0.64-0.78 (m, 2H). [M+H]$^+$=399.

Example D131a and D131b: (S)-((1 r,4S)-4-(4-chloro-2-fluorophenyl)cyclohexyl)(6-cyclopropylimidazo[1,5-a]pyridin-5-yl)methanol and (R)-((1r,4R)-4-(4-chloro-2-fluorophenyl)cyclohexyl)(6-cyclopropylimidazo[1,5-a]pyridin-5-yl)methanol hydrochloride

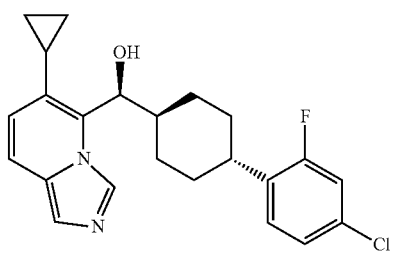

Fast isomer in CHIRALART Cellulose-SB
Eluting reagent: Hex:EtOH = 80:20

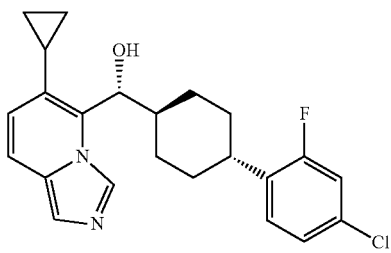

Slow isomer in CHIRALART Cellulose-SB
Eluting reagent: Hex:EtOH = 80:20

Each enantiomer of racemic D131a and D131b was separated using preparative HPLC on a CHIRALART Cellulose-SB with Hex:EtOH=80:20 as an eluent. The enantiomeric excesses were determined by using HPLC on a CHIRALART Cellulose-SB with Hex (0.1% IPAmine):EtOH=80:20 as an eluent at a flow rate of 1.0 mL/min. The first one enantiomer eluted at the retention time of 2.974 min, and the other enantiomer eluted at the retention time of 5.295 min. To a solution of D131a (85.2 mg) in DCM (5 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give the desired product as white solid (74.84 mg). $^1$H NMR (DMSO-d$_6$) $\delta_H$ 9.60 (s, 1H), 8.05 (s, 1H), 7.69 (d, J=10.0 Hz, 1H), 7.20-7.35 (m, 3H), 6.82 (d, J=9.2 Hz, 1H), 6.20 (brs, 1H), 5.32 (d, J=9.6 Hz, 1H), 2.76-2.79 (m, 1H), 2.39-2.43 (m, 1H), 2.17-2.20 (m, 2H), 1.85-1.89 (m, 1H), 1.51-1.65 (m, 2H), 1.23-1.40 (m, 4H), 1.03-1.06 (m, 2H), and 0.77-0.87 (m, 2H). [M+H]$^+$=399. To a solution of D131b (81.3 mg) in DCM (5 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give the desired product as white solid (84.26 mg). $^1$H NMR (DMSO-d$_6$) $\delta_H$ 9.62 (s, 1H), 8.06 (s, 1H), 7.70 (d, J=10.0 Hz, 1H), 7.20-7.35 (m, 3H), 6.83 (d, J=10.0 Hz, 1H), 6.19 (brs, 1H), 5.32 (d, J=9.6 Hz, 1H), 2.76-2.80 (m, 1H), 2.41-2.43 (m, 1H), 2.17-2.20 (m, 2H), 1.85-1.89 (m, 1H), 1.64-1.66 (m, 1H), 1.51-1.55 (m, 1H), 1.23-1.38 (m, 4H), 1.02-1.06 (m, 2H), and 0.77-0.87 (m, 2H). [M+H]$^+$=399. The absolute configurations of chiral carbons in D131a and D131b are tentatively assigned as (S) and (R) respectively based on assumption that the binding model of the more potent isomer D131a is the same as that of C101a with IDO1 enzyme, and the relative stereochemistry on cyclohexane is assigned as trans configuration on the cyclohexane.

Example D132: (6-cyclopropylimidazo[1,5-a]pyridin-5-yl)(4-(2,3-difluorophenyl)cyclohexyl)methanol

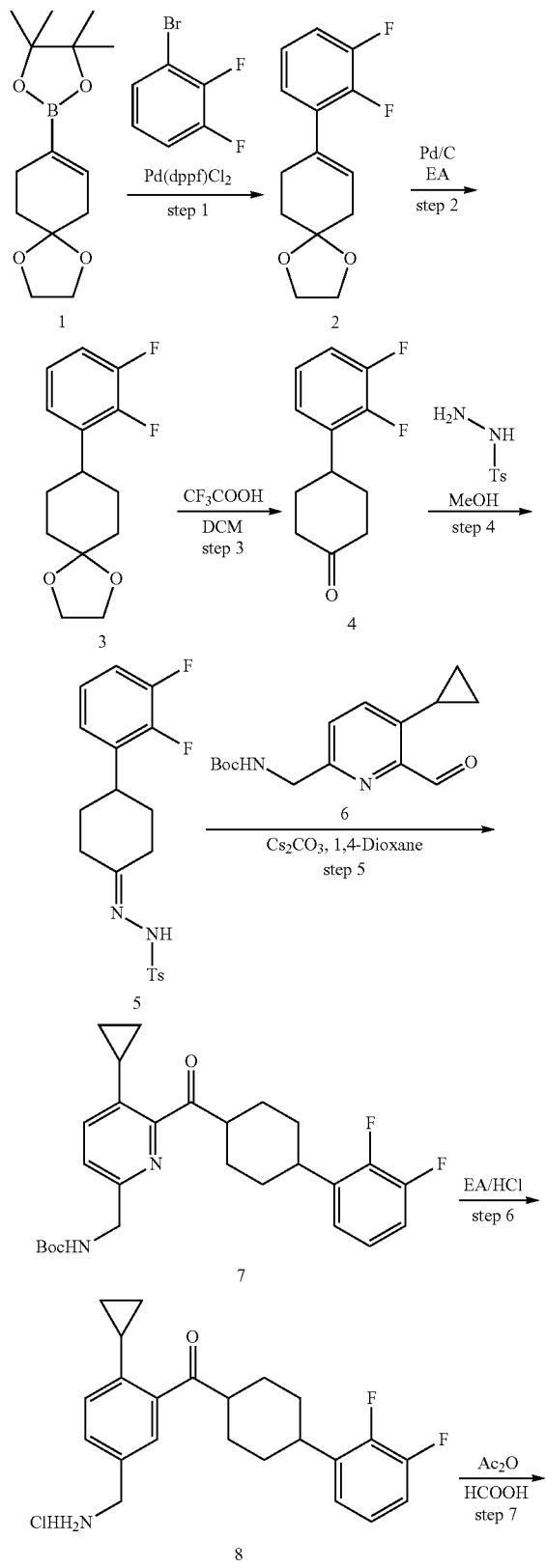

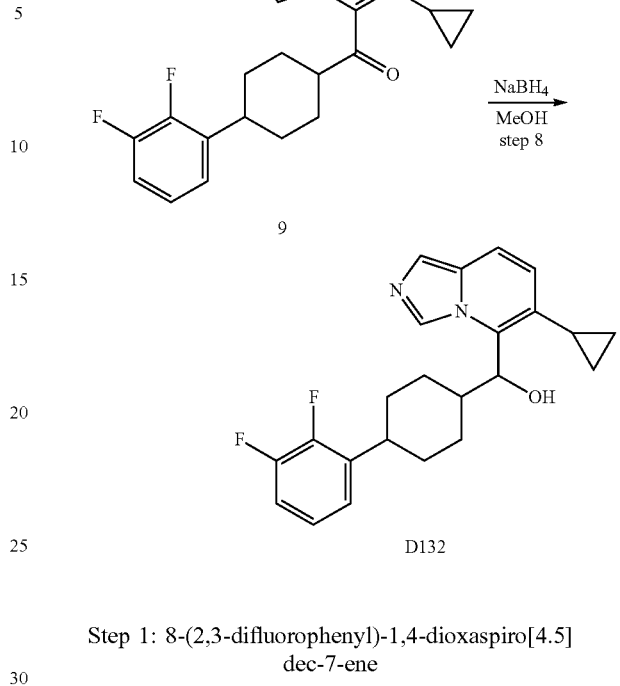

Step 1: 8-(2,3-difluorophenyl)-1,4-dioxaspiro[4.5]dec-7-ene

To a solution of 1-bromo-2,3-difluorobenzene (5 g, 26 mmol) in 1,4-dioxane (150 mL) was added 4,4,5,5-tetramethyl-2-(1,4-dioxaspiro[4.5]dec-7-en-8-yl)-1,3,2-dioxaborolane (7 g, 68 mmol), Pd(dppf)Cl$_2$ (1.9 g, 2.6 mmol) and Cs$_2$CO$_3$ (12.5 g, 26 mmol) and the mixture was heated at 70° C. for 5 hours. Then evaporated the solvent under reduced pressure and the residue was purified by column chromatography (PE:EA=5:1) to give product as an oil (5 g in 76% yield).

Step 2: 8-(2,3-difluorophenyl)-1,4-dioxaspiro[4.5]decane

To a solution of 8-(2,3-difluorophenyl)-1,4-dioxaspiro[4.5]dec-7-ene (5 g, 19.8 mmol) in methanol (200 mL) was added Pd/C (500 mg, 10%, wet) and the mixture was stirred for 2 hours at room temperature under H$_2$ (1 atm). Then filtered to remove Pd/C and the filtrate was evaporated under reduced pressure to give a crude product, and then purified by column chromatography (PE as eluent) to give the product (5.0 g, oil).

Step 3: 4-(2,3-difluorophenyl)cyclohexan-1-one

To a solution of 8-(2,3-difluorophenyl)-1,4-dioxaspiro[4.5]decane (5.0 g, 19.7 mmol) in dichloromethane (50 mL) was added trifluoroacetic acid (25 mL) at room temperature and the mixture was stirred for overnight. The solvent was evaporated under reduced pressure and water (50 mL) was added, extracted with ethyl acetate (50 mL×3), combined the organic layer and washed with saturated aqueous of NaHCO$_3$, then the organic layer was evaporated in vacuo to give crude product and the residue was purified by column chromatography (PE:EA=10:1) to give product as a light yellow oil (3.7 g in 88% yield). $^1$H NMR (CDCl$_3$) $\delta_H$ 7.14-6.88 (m, 3H), 3.39 (tt, J=12.2, 3.3 Hz, 1H), 2.63-2.47 (m, 4H), 2.29-2.17 (m, 2H), 2.01-1.91 (m, 2H). [M+H]⁺=211.2

Step 4: N'-(4-(2,3-difluorophenyl)cyclohexylidene)-4-methylbenzenesulfonohydrazide To a solution of 4-(6-(trifluoromethyl)pyridin-3-yl)cyclohexan-1-one (3.7 g, 17.5 mmol) in DCM/methol (30 mL/10 mL) was added 4-methylbenzenesulfonohydrazide (3.26 g, 17.5 mmol) at room temperature and the mixture was stirred for overnight. Evaporate half the solvent under reduced pressure and then filtered to give crude product, this residue was recycled with 2-methoxy-2-methylpropane (30 mL) and then got the target compound as a white solid (2.6 g in 39% yield).

Step 5: tert-butyl ((5-cyclopropyl-6-(4-(2,3-difluorophenyl)cyclohexane-1-carbonyl)pyridin-2-yl)methyl)carbamate To a solution of tert-butyl ((5-cyclopropyl-6-formylpyridin-2-yl)methyl)carbamate (600 mg, 2.2 mmol) in 1,4-dioxane (50 mL) was added N'-(4-(2,3-difluorophenyl)cyclohexylidene)-4-methylbenzenesulfonohydrazide (820 mg, 4.3 mmol) and Cs₂CO₃ (700 m g, 3.3 mmol) at room temperature, and the mixture was heated at 100° C. for 16 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (400 mg in 38% yield). [M+H]⁺=471.5

Step 6: (5-(aminomethyl)-2-cyclopropylphenyl)(4-(2,3-difluorophenyl)cyclohexyl) methanone Trifluoracetic acid To a solution of tert-butyl ((5-cyclopropyl-6-(4-(2,3-difluorophenyl)cyclohexane-1-carbonyl)pyridin-2-yl)methyl) carbamate (0.4 g, 0.85 mmol) in DCM (40 mL) was added trifluoracetic acid (10 mL) and the mixture was stirred at room temperature for overnight. The solvent was evaporated under reduced pressure to give crude product as solid. [M+H]⁺=370.4.

Step 7: (6-cyclopropylimidazo[1,5-a]pyridin-5-yl)(4-(2,3-difluorophenyl)cyclohexyl)methanone A mixture of Ac₂O (30 mL) and HCOOH (10 mL) was heated at 50° C. for 1 hour and then a solution of (5-(aminomethyl)-2-cyclopropylphenyl)(4-(2,3difluorophenyl) cyclohexyl) methanone Trifluoracetic acid (crude, 0.85 mmol) in HCOOH (5 mL) was added drop wise and the mixture was heated at 50° C. for 2 hours. The solvent was evaporated under reduced pressure and water (100 mL) was added, washed with saturated aqueous of NaHCO₃, then extracted with ethyl acetate (50 mL×3) and combined the organic layers, the solvent was evaporated under reduced pressure and the residue was purified by column chromatography (PE:EA=4:1) to give crude product as a solid (260 mg in 80% yield).

Step 8: (6-cyclopropylimidazo[1,5-a]pyridin-5-yl)(4-(2,3-difluorophenyl)cyclohexyl)methanol

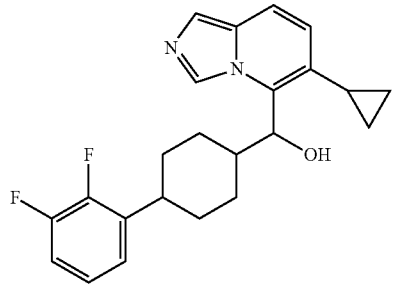

To a solution of (6-cyclopropylimidazo[1,5-a]pyridin-5-yl)(4-(6-(trifluoromethyl)pyridin-3-yl)cyclohexyl)methanone (260 g, 0.68 mmol) in methol (10 mL) was added NaBH₄ (130 mg, 3.4 mmol) at room temperature and the mixture was stirred for 4 h. Then the solvent was evaporated under reduced pressure and water (100 mL) was added, extracted with ethyl acetate (100 mL×3) and combined the organic layers, the solvent was evaporated under reduced pressure and the residue was purified by column chromatography (PE:EA=3:1) to give product as a white solid (140 mg in 54% yield). ¹H NMR (DMSO-d₆) δ_H 8.62 (s, 1H), 7.45-7.37 (m, 1H), 7.31 (s, 1H), 7.27-7.16 (m, 1H), 7.15-7.05 (m, 2H), 6.47 (d, J=9.4 Hz, 1H), 5.85-5.80 (m, 1H), 5.27 (dd, J=9.7, 3.9 Hz, 1H), 2.83 (d, J=11.7 Hz, 1H), 2.44 (d, J=13.2 Hz, 1H), 2.30-2.17 (m, 1H), 2.05 (s, 1H), 1.88 (d, J=12.7 Hz, 1H), 1.74-1.50 (m, 2H), 1.40-1.12 (m, 4H), 1.02-0.88 (m, 2H), 0.80-0.73 (m, 1H), 0.70-0.59 (m, 1H). [M+H]⁺=383.4.

Example D132a and D132b: (S)-(6-cyclopropylimidazo[1,5-a]pyridin-5-yl)((1r,4S)-4-(2,3-difluorophenyl)cyclohexyl)methanol and (R)-(6-cyclopropylimidazo[1,5-a]pyridin-5-yl)(1r,4R)-4-(2,3-difluorophenyl)cyclohexyl)methanol

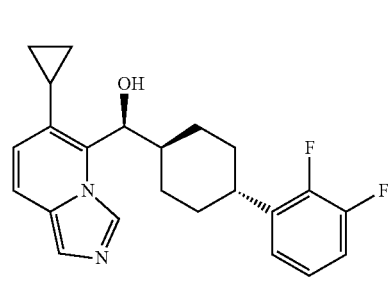

Fast isomer in CHIRALPAK IC HPLC
Eluting reagent: Hex:EtOH = 70:30

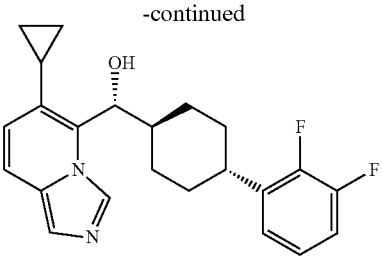

Slow isomer in CHIRALPAL IC HPLC
Eluting reagent: Hex:EtOH = 70:30

Each enantiomer of racemic D132a and D132b was separated using preparative HPLC on a CHIRALPAK IC with Hex:EtOH=85:15 as an eluent. D132a: $^1$H NMR (DMSO-d$_6$) δ 9.64 (s, 1H), 8.08 (s, 1H), 7.71 (d, J=9.6 Hz, 1H), 7.30-7.17 (m, 1H), 7.18-7.01 (m, 2H), 6.84 (d, J=9.6 Hz, 1H), 6.23 (s, 1H), 5.33 (d, J=9.6 Hz, 1H), 2.84 (t, J=11.2 Hz, 1H), 2.42 (d, J=12.0 Hz, 1H), 2.27-2.10 (m, 2H), 1.90 (d, J=12.4 Hz, 1H), 1.75-1.65 (m, 1H), 1.64-1.46 (m, 1H), 1.46-1.18 (m, 4H), 1.13-0.99 (m, 2H), 0.90-0.73 (m, 2H); D132b: $^1$H NMR (DMSO-d$_6$) δ 9.61 (s, 1H), 8.05 (s, 1H), 7.70 (d, J=9.6 Hz, 1H), 7.28-7.19 (m, 1H), 7.18-7.05 (m, 2H), 6.83 (d, J=9.6 Hz, 1H), 6.19 (s, 1H), 5.33 (d, J=9.6 Hz, 1H), 2.90-2.76 (m, 1H), 2.42 (d, J=12.8 Hz, 1H), 2.27-2.10 (m, 2H), 1.90 (d, J=12.0 Hz, 1H), 1.75-1.65 (m, 1H), 1.56 (dd, J=24.0, 12.0 Hz, 1H), 1.45-1.22 (m, 4H), 1.11-0.98 (m, 2H), 0.92-0.73 (m, 2H). The absolute configurations of chiral carbons in D132a and D132b are tentatively assigned as (S) and (R) respectively based on assumption that the binding model of the more potent isomer D132a is the same as that of C101 with IDO1 enzyme, and the relative stereochemistry on cyclohexane is assigned as trans configuration on the cyclohexane.

Example D133: (4-(benzo[b]thiophen-5-yl)cyclohexyl)(6-cyclopropylimidazo[1,5-a]pyridin-5-yl)methanol

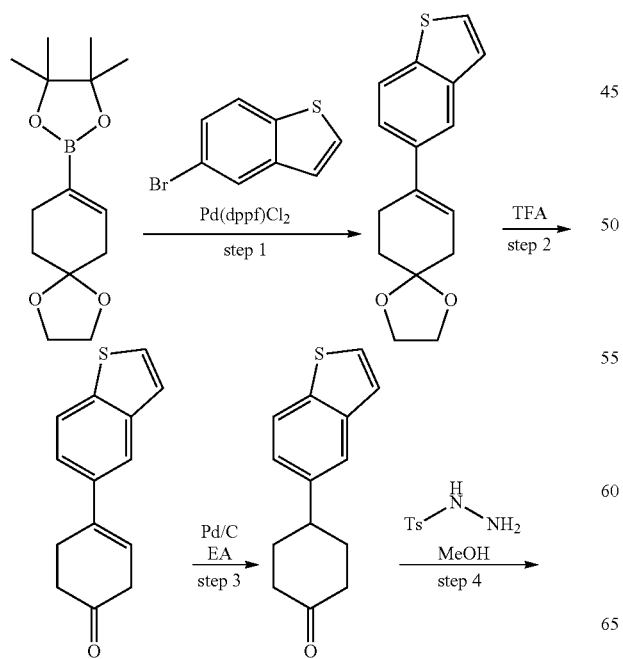

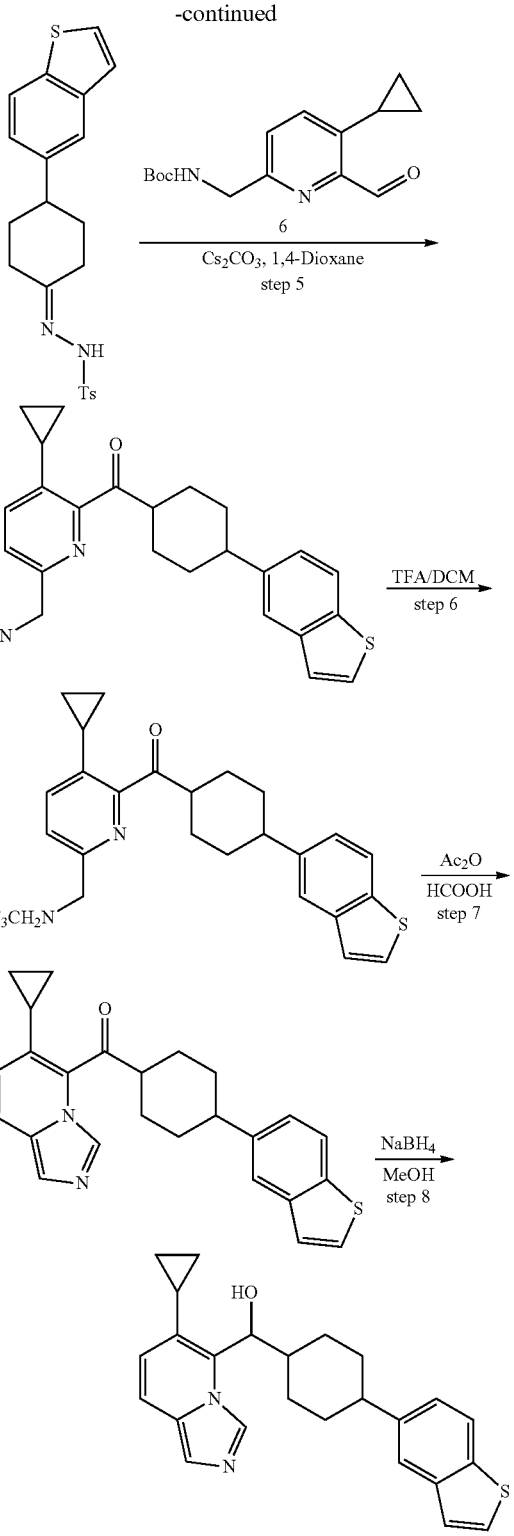

Step 1: 8-(benzo[b]thiophen-5-yl)-1,4-dioxaspiro[4.5]dec-7-ene

To a solution of 5-bromobenzo[b]thiophene (8.5 g, 40 mmoL) in 1,4-dioxane (150 mL) was added 4,4,5,5-tetramethyl-2-(1,4-dioxaspiro[4.5]dec-7-en-8-yl)-1,3,2-dioxaborolane (10.6 g, 40 mmol), Pd(dppf)Cl$_2$ (4.4 g, 6 mmol) and Cs$_2$CO$_3$ (19.5 g, 60 mmol) and the mixture was heated at 80° C. for 2 hours. Then filter off the solid, the filtrate was evaporated under reduced pressure and the residue was purified by column chromatography (PE:EA=25:1) to give product as yellow solid (6.6 g in 61% yield). $^1$HNMR (400 MHz, DMSO-d$_6$) δ$_H$ 7.92 (d, J=8.8 Hz, 1H), 7.89 (s, 1H), 7.74 (d, J=5.2 Hz, 1H), 7.46 (dd, J=8.8 Hz, 1.6 Hz, 1H), 7.43 (d, J=5.6 Hz, 1H), 6.09 (t, J=3.6 Hz 1H), 3.93 (s, 4H), 2.63 (t, J=5.6 Hz, 2H), 2.40 (s, 2H), and 1.85 (t, J=6.4 Hz, 2H). [M+H]$^+$=273.0.

Step 2: 4-(benzo[b]thiophen-5-yl)cyclohex-3-en-1-one

To a solution of 8-(benzo[b]thiophen-5-yl)-1,4-dioxaspiro [4.5]dec-7-ene (6.6 g, 24 mmol) in DCM (50 mL) was added TFA (50 mL). The mixture was stirred for 20 hours at room temperature. The solvent was evaporated under reduced pressure and DCM (100 mL) was added, followed by sat. NaHCO$_3$ solution (100 mL). Separated the organic layer and purified by column chromatography on silica gel to give product (700 mg) with PE/EA=25:1. $^1$H NMR (400 MHz, CDCl$_3$) δ$_H$ 7.84 (d, J=8.4 Hz, 1H), 7.82 (d, J=1.2 Hz, 1H), 7.46 (d, J=5.2 Hz, 1H), 7.43-7.40 (dd, J=8.4 Hz, 1.6 Hz, 1H), 7.33 (d, J=5.6 Hz, 1H), 6.16-6.14 (m, 1H), 3.10 (t, J=1.6 Hz, 2H), 3.00-2.96 (m, 2H), 2.69 (t, J=6.8 Hz, 2H). [M+H]$^+$=229.1.

Step 3: 4-(benzo[b]thiophen-5-yl)cyclohexan-1-one

To a solution of 4-(benzo[b]thiophen-5-yl)cyclohex-3-en-1-one (0.7 g, 3 mmol) in ethyl acetate (25 mL) was added Pd/C (0.1 g, 10%) and the mixture was stirred for 20 hours at room temperature under H$_2$ (0.4 Mpa). Then filtered to remove Pd/C and the filtrate was evaporated under reduced pressure to give a crude product (4.2 g) for next step directly without further purification. [M+H]$^+$=231.0.

Step 4: N'-(4-(benzo[b]thiophen-5-yl)cyclohexylidene)-4-methylbenzenesulfonohydrazide To a solution of 4-(benzo[b]thiophen-5-yl)cyclohexan-1-one (0.64 g, 2.8 mmol) in methol (10 mL) was added 4-methylbenzenesulfonohydrazide (0.52 g, 2.8 mmol) at room temperature and the mixture was stirred for overnight. Filtered and washed the filter cake with MeOH (2 mL) to give product as a white solid (0.8 g in 72.7% yield).

Step 5: tert-butyl ((6-(4-(benzo[b]thiophen-5-yl) cyclohexane-1-carbonyl)-5-cyclopropylpyridin-2-yl) methyl)carbamate To a solution of N'-(4-(benzo[b]thiophen-5-yl)cyclohexylidene)-4-methylbenzenesulfonohydrazide (0.80 g, 2.0 mmol) in 1,4-dioxane (30 mL) was added tert-butyl ((5-cyclopropyl-6-formylpyridin-2-yl)methyl)carbamate (0.55 g, 2.0 mmol) and Cs$_2$CO$_3$ (0.98 g, 3.0 mmol) at room temperature, and the mixture was heated at 80° C. for 20 hours. Water (100 mL) was added, extracted with ethyl acetate (100 mL×2) and combined the organic layer, the solvent was evaporated under reduced pressure and the residue was purified by column chromatography (PE:EA=8:1) to give product as a white solid (0.5 g in 51.0% yield). [M+H]$^+$=491.2.

Step 6: (6-(aminomethyl)-3-cyclopropylpyridin-2-yl)(4-(benzo[b]thiophen-5-yl)cyclohexyl)methanone 2,2,2-trifluoroacetate To a solution of tert-butyl ((6-(4-(benzo[b]thiophen-5-yl) cyclohexane-1-carbonyl)-5-cyclopropylpyridin-2-yl) methyl)carbamate (0.5 g, 1.2 mmol) in DCM (20 mL) was added trifluoracetic acid (20 mL) and the mixture was stirred at room temperature for 2 hours. The solvent was evaporated under reduced pressure to give crude product for next step directly without further purification. [M+H]$^+$=391.1.

Step 7: (4-(benzo[b]thiophen-5-yl)cyclohexyl)(6-cyclopropylimidazo[1,5-a]pyridin-5-yl)methanone A mixture of Ac$_2$O (15 mL) and HCOOH (5 mL) was heated at 55° C. for 2 hours and then a solution of (6-(aminomethyl)-3-cyclopropylpyridin-2-yl)(4-(benzo[b]thiophen-5-yl)cyclohexyl)methanone 2,2,2-trifluoroacetate (crude) in HCOOH (5 mL) was added drop wise and the mixture was heated at 55° C. for 1 hour. The solvent was evaporated under reduced pressure and saturated aqueous of NaHCO$_3$(50 mL) was added, then extracted with ethyl acetate (50 mL) and separated the organic layer, the solvent was evaporated under reduced pressure and the residue was purified pre-TLC (PE:EA=2:1) to give crude product as a solid (0.25 g). [M+H]$^+$=401.1.

Step 8: (4-(benzo[b]thiophen-5-yl)cyclohexyl)(6-cyclopropylimidazo[1,5-a]pyridin-5-yl)methanol

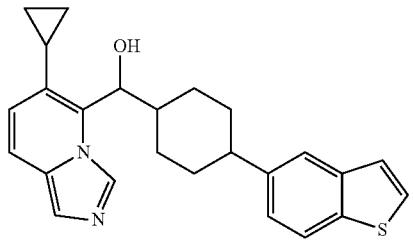 [SMILES: OC(c1c(C2CC2)ccc2cncn12)C1CCC(c2ccc3sccc3c2)CC1]

To a solution of (4-(benzo[b]thiophen-5-yl)cyclohexyl) (6-cyclopropylimidazo[1,5-a]pyridin-5-yl)methanone (0.25 g, 0.6 mmol) in methanol (50 mL) was added NaBH$_4$ (0.24 g, 6 mmol) at room temperature and the mixture was stirred for 18 hours. Then quenched the reaction with water (100 mL). Extracted with ethyl acetate (100 mL×2) and combined the organic layer, the solvent was evaporated under reduced pressure and the residue was purified by pre-TLC (DCM/MeOH=20:1) to give product (179 mg in 71.3% yield). $^1$H NMR (DMSO-d$_6$) δ$_H$ 8.72 (d, J=4.4 Hz, 1H), 7.92 (dd, J=8.0 Hz, 4.8 Hz, 1H), 7.75 (b, 2H), 7.47 (dd, J=9.2 Hz, 4.8 Hz, 1H),7.42-7.39 (m, 2H), 7.30-7.28 (m, 1H), 6.55 (dd, J=9.2 Hz, 4.8 Hz, 1H), 5.89 (s, 1H), 5.37-5.32 (m, 1H), 2.66-2.56 (m, 1H), 2.56-2.50 (m, 1H), 2.29 (b, 1H), 2.09-2.00 (m, 2H), 1.78 (d, J=10.8 Hz, 1H), 1.69-1.60 (m, 1H), 1.38-1.26 (m, 4H), 1.03 (b, 2H), 0.83 (b, 1H), and 0.74 (b, 1H). [M+H]$^+$=403.1.

Example D133a and D133b: (S)-((1r,4S)-4-(benzo[b]thiophen-5-yl)cyclohexyl)(6-cyclopropylimidazo[1,5-a]pyridin-5-yl)methanol and (R)-((1r,4R)-4-(benzo[b]thiophen-5-yl)cyclohexyl)(6-cyclopropylimidazo[1,5-a]pyridin-5-yl)methanol

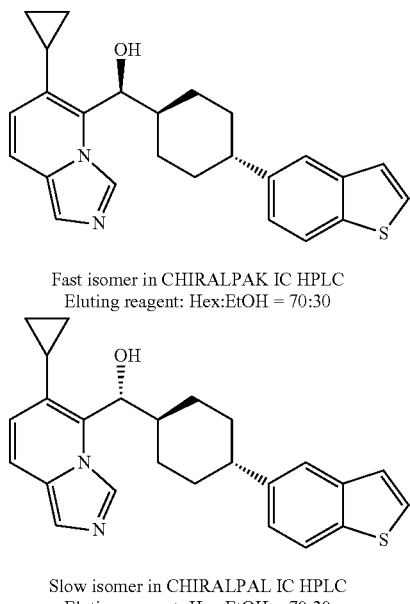

Fast isomer in CHIRALPAK IC HPLC
Eluting reagent: Hex:EtOH = 70:30

Slow isomer in CHIRALPAL IC HPLC
Eluting reagent: Hex:EtOH = 70:30

Each enantiomer of racemic D133a and D133b was separated using preparative HPLC on a CHIRALPAK IC with Hex:EtOH=70:30 as an eluent. The enantiomeric excesses were determined by using HPLC on a CHIRALPAK IC with Hex (0.1% DEA):EtOH=70:30 as an eluent at a flow rate of 20 mL/min. The first one enantiomer eluted at the retention time of 2.451 min (D133a), and the other enantiomer eluted at the retention time of 6.345 min (D133b). To a solution of D133a (53.4 mg) in DCM (5 mL) was added drop wise of Ethyl acetate solution of hydrochloric acid (2 mL, 4.0M) at room temperature, stirred at room temperature for 10 min, then the solvent was evaporated under reduced pressure to give the desired product as white solid (47.9 mg in 82.2% yield). $^1$H NMR (400 MHz, DMSO-d$_6$) δ$_H$9.64 (s, 1H), 8.06 (s, 1H), 7.87 (d, J=8.4 Hz, 1H), 7.77-7.68 (m, 3H), 7.37 (d, J=5.6 Hz, 1H), 7.22 (d, J=8.4 Hz, 1H), 6.84 (d, J=9.6 Hz, 1H), 6.21 (s, 1H), 5.35 (d, J=9.6 Hz, 1H), 2.65-2.59 (m, 1H), 2.45-2.42 (m, 1H), 2.20 (b, 2H), 1.98 (d, J=11.2 Hz, 1H), 1.76 (d, J=10.4 Hz, 1H), 1.62-1.53 (m, 1H), 1.42-1.23 (m, 4H), 1.10-1.01 (m, 2H), 0.88-0.85 (m, 1H), and 0.80-0.77 (m, 1H). [M+H]$^+$=403.1. To a solution of D133b (59.3 mg) in DCM (5 mL) was added drop wise of ethyl acetate solution of hydrochloric acid (2 mL, 4.0M) at room temperature, stirred at room temperature for 10 min, then the solvent was evaporated under reduced pressure to give the desired product as white solid (49.0 mg in 75.6% yield). $^1$H NMR (DMSO-d$_6$) δ$_H$ 9.67 (s, 1H), 8.09 (s, 1H), 7.87 (d, J=8.4 Hz, 1H), 7.73-7.68 (m, 3H), 7.37 (d, J=5.2 Hz, 1H), 7.22 (d, J=8.4 Hz, 1H), 6.85 (d, J=9.6 Hz, 1H), 6.23 (s, 1H), 5.35 (d, J=10.0 Hz, 1H), 2.67-2.59 (m, 1H), 2.50-2.42 (m, 1H), 2.21 (b, 2H), 1.98 (d, J=11.6 Hz, 1H), 1.77 (d, J=10.4 Hz, 1H), 1.62-1.53 (m, 1H), 1.42-1.24 (m, 4H), 1.06 (d, J=8.4 Hz, 2H), 0.87-0.83 (m, 1H), and 0.83-0.79 (m, 1H). [M+H]$^+$=403.1. The absolute configurations of chiral carbons in D133a and D133b are tentatively assigned as (S) and (R) respectively based on assumption that the binding model of the more potent isomer D133a is the same as that of C101a with IDO1 enzyme, and the relative stereochemistry on cyclohexane is assigned as trans configuration on the cyclohexane.

Example D134: (4-(benzo[b]thiophen-6-yl)cyclohexyl)(6-cyclopropylimidazo[1,5-a]pyridin-5-yl)methanol

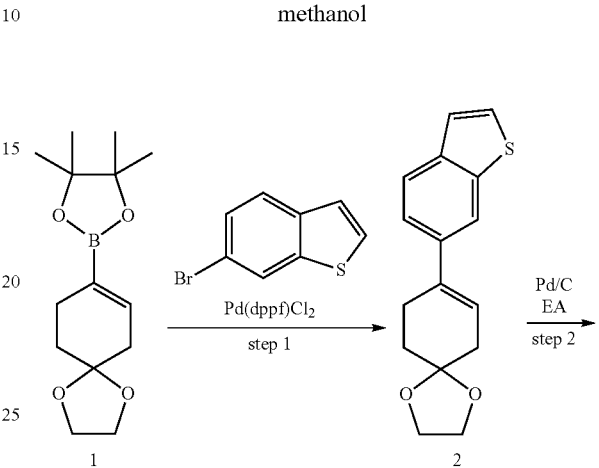

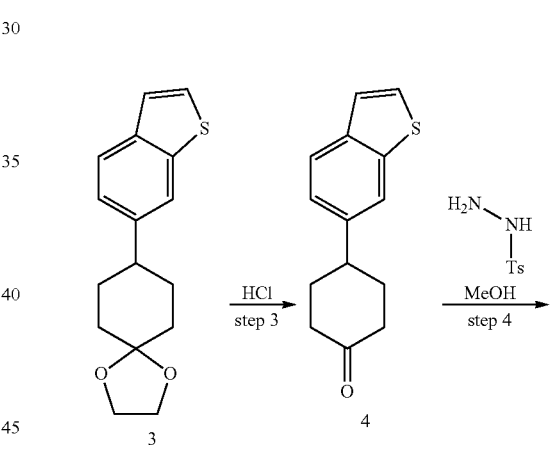

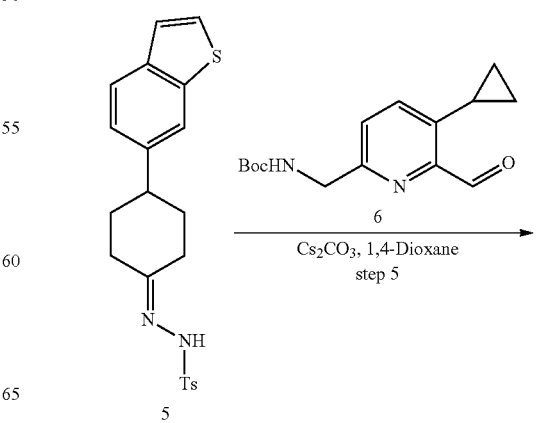

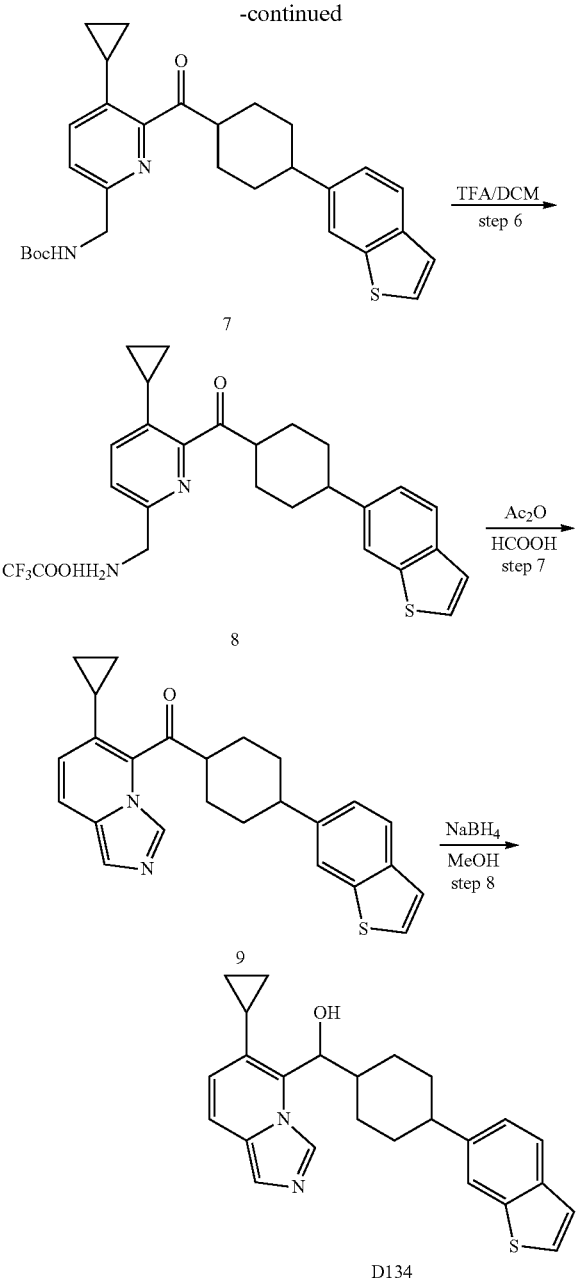

Step 1: 8-(benzo[b]thiophen-6-yl)-1,4-dioxaspiro[4.5]dec-7-ene

To a solution of 6-bromobenzo[b]thiophene (5.3 g, 25 mmol) in 1,4-dioxane (150 mL) was added 4,4,5,5-tetramethyl-2-(1,4-dioxaspiro[4.5]dec-7-en-8-yl)-1,3,2-dioxaborolane (6.6 g, 25 mmol), Pd(dppf)Cl$_2$ (2.2 g, 3.8 mmol) and Cs$_2$CO$_3$ (12 g, 38 mmol) and the mixture was heated at 80° C. for 2 hours. Then filtered off the solid, the filtrate was evaporated under reduced pressure and the residue was purified by column chromatography (PE:EA=5:1) to give product as an oil (3.8 g in 55.8% yield). $^1$HNMR (400 MHz, DMSO-d$_6$) $\delta_H$ 8.01 (s, 1H), 7.80 (d, J=8.4 Hz, 2H), 7.71 (d, J=5.6 Hz, 1H), 7.48 (d, J=8.4 Hz, 2H), 7.41 (d, J=5.6 Hz, 2H), 6.11 (s, 1H), 3.93 (s, 4H), 2.63 (s, 2H), 2.40 (s, 2H), and 1.84 (t, J=6.4 Hz, 2H). [M+H]$^+$=273.0.

Step 2: 8-(benzo[b]thiophen-6-yl)-1,4-dioxaspiro[4.5]decane

To a solution of 8-(benzo[b]thiophen-6-yl)-1,4-dioxaspiro[4.5]dec-7-ene (5.2 g, 19 mmol) in ethyl acetate (100 mL) was added Pd/C (0.75 g, 10%) and the mixture was stirred for 5 days at room temperature under H$_2$ (0.4 Mpa). Then filtered to remove Pd/C and the filtrate was evaporated under reduced pressure to give a crude product (4.2 g) for next step directly without further purification. $^1$H NMR (400 MHz, DMSO-d$_6$) $\delta_H$ 7.88 (s, 1H), 7.84 (d, J=8.4 Hz, 1H), 7.71 (dd, J=5.6 Hz, 1.2 Hz, 1H), 7.44 (d, J=5.2 Hz, 1H), 7.30 (dd, J=8.4 Hz, 1.2 Hz, 1H), 3.95 (t, J=3.2 Hz, 4H), 2.79-2.73 (m, 1H), and 1.89-1.68 (m, 8H). [M+H]$^+$=275.1.

Step 3: 4-(benzo[b]thiophen-6-yl)cyclohexan-1-one

To a solution of 8-(benzo[b]thiophen-6-yl)-1,4-dioxaspiro[4.5]decane (4.2 g, 15 mmol) in dioxane (40 mL) was added H$_2$O (30 mL) and conc. HCl (10 mL). The mixture was stirred for 0.5 hour at room temperature. Then added H$_2$O (50 mL) and extracted with ethyl acetate (100 mL). Separated the organic phase and concentrated for next step without further purification. [M+H]$^+$=231.1.

Step 4: N'-(4-(benzo[b]thiophen-6-yl)cyclohexylidene)-4-methylbenzenesulfonohydrazide To a solution of 4-(benzo[b]thiophen-6-yl)cyclohexan-1-one (4.0 g, 17 mmol) in methol (60 mL) was added 4-methylbenzenesulfonohydrazide (3.2 g, 17 mmol) at room temperature and the mixture was stirred for overnight. Evaporate half the solvent under reduced pressure and then filtered to give product as a white solid (4.2 g in 60.9% yield). $^1$H NMR (DMSO-d6) $\delta_H$ 10.20 (s, 1H), 7.82 (s, 1H), 7.79-7.70 (m, 3H), 7.66 (d, J=5.6 Hz, 1H), 7.44-7.35 (m, 3H), 7.25 (d, J=8.4 Hz, 1H), 2.92 (t, J=12.8 Hz, 2H), 2.39 (s, 3H), 2.30-2.28 (m, 2H), 2.00-1.94 (m, 3H), and 1.64-1.52 (m, 2H).

Step 5: tert-butyl ((6-(4-(benzo[b]thiophen-6-yl)cyclohexane-1-carbonyl)-5-cyclopropylpyridin-2-yl)methyl)carbamate To a solution of N'-(4-(benzo[b]thiophen-6-yl)cyclohexylidene)-4-methylbenzenesulfonohydrazide (0.86 g, 2.2 mmol) in 1,4-dioxane (25 mL) was added tert-butyl ((5-cyclopropyl-6-formylpyridin-2-yl)methyl)carbamate (0.6 g, 2.2 mmol) and Cs$_2$CO$_3$ (1.1 g, 3.3 mmol) at room temperature, and the mixture was heated at 100° C. for 18 hours. Water (100 mL) was added, extracted with ethyl acetate (100 mL×2) and combined the organic layer, the solvent was evaporated under reduced pressure and the residue was purified by column chromatography (PE:EA=8:1) to give product as a light yellow oil (0.6 g in 56.6% yield). [M+H]$^+$=491.2

Step 6: (6-(aminomethyl)-3-cyclopropylpyridin-2-yl)(4-(benzo[b]thiophen-6-yl)cyclohexyl)methanone Trifluoracetic acid To a solution of tert-butyl ((6-(4-(benzo[b]thiophen-6-yl)cyclohexane-1-carbonyl)-5-cyclopropylpyridin-2-yl)methyl)carbamate (0.6 g, 1.2 mmol) in DCM (12 mL) was added trifluoracetic acid (12 mL) and the mixture was stirred at room temperature for 2 hours. The solvent was evaporated under reduced pressure to give crude product for next step directly without further purification. [M+H]⁺=391.1.

Step 7: (4-(benzo[b]thiophen-6-yl)cyclohexyl)(6-cyclohexyl)(6-cyclopropylimidazo[1,5-a]pyridin-5-yl)methanone A mixture of Ac₂O (15 mL) and HCOOH (5 mL) was heated at 55° C. for 1.5 hours and then a solution of (6-(aminomethyl)-3-cyclopropylpyridin-2-yl)(4-(benzo[b]thiophen-6-yl)cyclohexyl)methanone trifluoracetic acid (crude, 0.8 mmol) in HCOOH (5 mL) was added drop wise and the mixture was heated at 55° C. for 1 hour. The solvent was evaporated under reduced pressure and saturated aqueous of NaHCO₃ (50 mL) was added, then extracted with ethyl acetate (50 mL) and separated the organic layer, the solvent was evaporated under reduced pressure and the residue was purified pre-TLC (PE:EA=2:1) to give crude product as a solid (0.3 g). [M+H]⁺=401.1.

Step 8: (4-(benzo[b]thiophen-6-yl)cyclohexyl)(6-cyclopropylimidazo[1,5-a]pyridin-5-yl)methanol

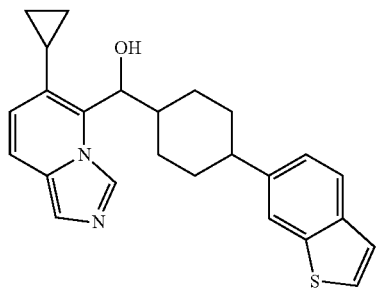 [SMILES: OC(c1c(C2CC2)ccc2cncn12)C1CCC(c2ccc3ccsc3c2)CC1]

To a solution of (4-(benzo[b]thiophen-6-yl)cyclohexyl)(6-cyclopropylimidazo[1,5-a]pyridin-5-yl)methanone (0.3 g, 0.24 mmol) in methol (35 mL) was added NaBH₄ (180 mg, 4.7 mmol) at room temperature and the mixture was stirred for 6 hours. Then quenched the reaction with water (100 mL), filtered and filter cake was purified by pre-TLC (DCM/MeOH=20:1) to give product (179 mg). ¹H NMR (DMSO-d6) δ_H 8.71 (s, 1H), 7.86 (s, 1H), 7.81 (d, J=8.4 Hz, 1H), 7.70 (d, J=5.6 Hz, 1H), 7.47 (d, J=9.6 Hz, 1H), 7.43 (d, J=5.6 Hz, 1H), 7.39 (s, 1H), 7.30 (d, J=8.4 Hz, 1H), 6.55 (d, J=9.6 Hz, 1H), 5.90 (d, J=3.6 Hz, 1H), 5.34 (dd, J=9.6, 3.6 Hz, 1H), 2.73-2.64 (m, 1H), 2.50-2.48 (m, 1H), 2.35-2.25 (m, 1H), 2.15-2.00 (m, 2H), 1.79 (d, J=12.0 Hz, 1H), 1.68-1.58 (m, 1H), 1.42-1.24 (m, 4H), 1.07-0.97 (m, 2H), 0.86-0.83 (m, 1H), and 0.77-0.71 (m, 1H). [M+H]⁺=403.1.

Example D134a and D134b: (S)-((1r,4S)-4-(benzo[b]thiophen-6-yl)cyclohexyl)(6-cyclopropylimidazo[1,5-a]pyridin-5-yl)methanol and (R)-((1r,4R)-4-(benzo[b]thiophen-6-yl)cyclohexyl)(6-cyclopropylimidazo[1,5-a]pyridin-5-yl)methanol

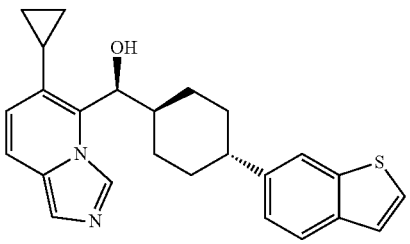

Fast isomer in CHIRALPAK IC HPLC
Eluting reagent: Hex:EtOH = 70:30

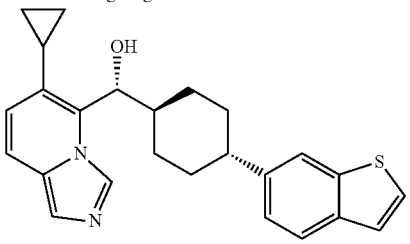

Slow isomer in CHIRALPAL IC HPLC
Eluting reagent: Hex:EtOH = 70:30

Each enantiomer of racemic D134a and D134b was separated using preparative HPLC on a CHIRALPAK IC with Hex:EtOH=70:30 as an eluent. The enantiomeric excesses were determined by using HPLC on a CHIRALPAK IC with Hex (0.1% DEA):EtOH=70:30 as an eluent at a flow rate of 20 mL/min. The first one enantiomer eluted at the retention time of 2.427 min, and the other enantiomer eluted at the retention time of 6.242 min. To a solution of D134a (53.4 mg) in DCM (5 mL) was added drop wise of Ethyl acetate solution of hydrochloric acid (2 mL, 4.0M) at room temperature, stirred at room temperature for 10 min, then the solvent was evaporated under reduced pressure to give the desired product as white solid (47.9 mg in 82% yield). ¹H NMR (DMSO-d₆) δ_H δ_H 9.72 (s, 1H), 8.14 (s, 1H), 7.85 (s, 1H), 7.82 (d, J=8.4 Hz, 1H), 7.77 (d, J=9.6 Hz, 1H), 7.71 (d, J=5.2 Hz, 1H), 7.44 (d, J=5.2 Hz, 1H), 7.30 (d, J=8.0 Hz, 1H), 6.91 (d, J=9.6 Hz, 1H), 6.29 (s, 1H), 5.41 (d, J=9.6 Hz, 1H), 2.71-2.66 (m, 1H), 2.51-2.48 (m, 1H), 2.26 (b, 2H), 2.04 (d, J=12.8 Hz, 1H), 1.82 (d, J=10.8 Hz, 1H), 1.68-1.60 (m, 1H), 1.48-1.30 (m, 4H), 1.13-1.11 (m, 2H), and 0.95-0.85 (m, 2H). [M+H]⁺=403.1. To a solution of D134b (59 mg) in DCM (5 mL) was added drop wise of ethyl acetate solution of hydrochloric acid (2 mL, 4.0M) at room temperature, stirred at room temperature for 10 min, then the solvent was evaporated under reduced pressure to give the desired product as white solid (49 mg in 75% yield). ¹H NMR (DMSO-d₆) δ 9.65 (s, 1H), 8.07 (s, 1H), 7.79 (s, 1H), 7.76 (d, J=8.4 Hz, 1H), 7.71 (d, J=9.6 Hz, 1H), 7.65 (d, J=5.6 Hz, 1H), 7.37 (d, J=5.2 Hz, 1H), 7.23 (d, J=8.0 Hz, 1H), 6.85 (d, J=9.6 Hz, 1H), 6.22 (s, 1H), 5.35 (d, J=9.6 Hz, 1H), 2.67-2.57 (m, 1H), 2.45-2.42 (m, 1H), 2.20 (b, 2H), 1.97 (d, J=12.4 Hz, 1H), 1.76 (d, J=10.8 Hz, 1H), 1.62-1.53 (m, 1H), 1.42-1.16 (m, 4H), 1.10-1.01 (m, 2H), and 0.88-0.77 (m, 2H). [M+H]⁺=403.1. The absolute configurations of chiral carbons in D134a and D134b are tentatively assigned as (S) and (R) respectively based on assumption that the binding model of the more potent isomer D134a is the same as that of C101a with IDO1 enzyme, and the relative stereochemistry on cyclohexane is assigned as trans configuration on the cyclohexane.

Example D135: (6-cyclopropylimidazo[1,5-a]pyridin-5-yl)(4-(naphthalen-1-yl)cyclohexyl)methanol

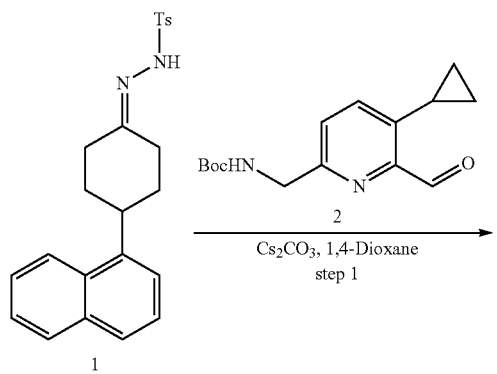

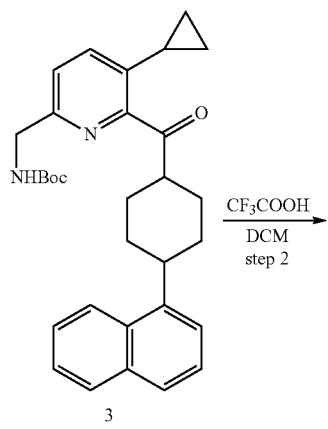

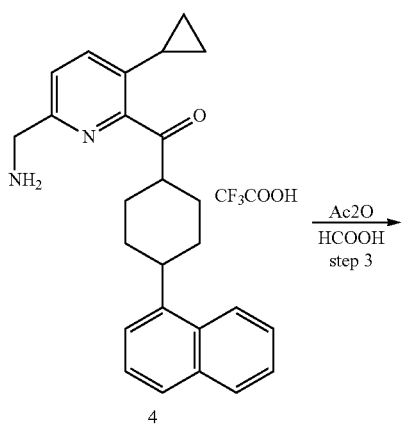

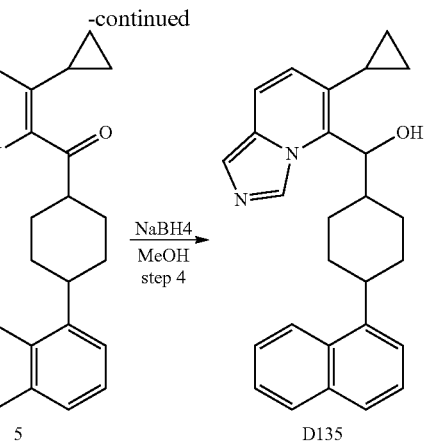

Step 1: (7-cyclopropylimidazo[1,5-a]pyridin-8-yl) (4-(naphthalen-2-yl)cyclohexyl)methanone To a solution of tert-butyl ((5-cyclopropyl-6-formylpyridin-2-yl)methyl)carbamate (600 mg) in 1,4-dioxane (25 mL) was added 4-methyl-N'-(4-(naphthalen-2-yl)cyclohexylidene)-benzenesulfonohydrazide (852 mg) and Cs$_2$CO$_3$ (1058 mg) at room temperature, and the mixture was heated at 95° C. for overnight. The solvent was cooled to room temperature, concentrated to dryness, which was purified by column chromatography (PE:EA=20:1 to PE:EA=10:1) to give product as a pale yellow solid (481 mg in 45.8% yield). $^1$H NMR (DMSO-d$_6$) $\delta_H$ 8.19 (d, J=8.0 Hz, 1H), 7.91 (d, J=8.0 Hz, 1H), 7.76 (d, J=8.0 Hz, 1H), 7.43-7.52 (m, 6H), 7.31 (d, J=8.0 Hz, 1H), 4.24 (d, J=6.0 Hz, 2H), 3.63-3.90 (m, 1H), 2.32-2.36 (m, 1H), 1.91-2.12 (m, 4H), 1.65-1.77 (m, 3H), 1.21-1.56 (m, 10H), 0.92-1.04 (m, 2H), 0.65-0.74 (min, 2H). MS (ESI) m/e [M+1]$^+$=485.

Step 2: (6-(aminomethyl)-3-cyclopropylpyridin-2-yl)(4-(naphthalen-1-yl)cyclohexyl)methanone 2,2,2-trifluoroacetate To a solution of tert-butyl ((5-cyclopropyl-6-(4-(naphthalen-1-yl)cyclohexane-1-carbonyl)pyridin-2-yl)methyl)carbamate (481 mg) in DCM (10 mL) was added CF$_3$COOH (10 mL) and the mixture was stirred at room temperature for overnight. The solvent was concentrated to dryness, which was used for the next step without further purification.

Step 3: (6-cyclopropylimidazo[1,5-a]pyridin-5-yl) (4-(naphthalen-1-yl)cyclohexyl)methanone To a solution of acetic anhydride (15 m L) and formic acid (10 m L) was stirred at 60° C. for 1 hour, after was added (6-(aminomethyl)-3-cyclopropylpyridin-2-yl)(4-(naphthalen-1-yl)cyclohexyl)methanone (526 mg) in formic acid 5 mL. Then the mixture was stirred at 60° C. for 2 hours. After cooled to room temperature, the solvent was concentrated to dryness. The crude was added EA 50 mL, extracted with saturated sodium bicarbonate (50 mL×3). The organic layer was dried over Na$_2$SO$_4$, filtered and concentrated to dryness, which was purified by column chromatography (PE:EA=5:1 to 1:1) to give product as a yellow solid (306 mg in 78.5% yield). $^1$H NMR (DMSO-d$_6$) $\delta_H$ 8.18 (d, J=8.0 Hz, 1H), 8.11 (s, 1H), 7.91 (d, J=8.0 Hz, 1H), 7.75 (d, J=8.0 Hz, 1H), 7.74 (d, J=9.6 Hz, 1H), 7.40-7.57 (m, 5H), 6.51 (d, J=8.0 Hz, 1H), 3.37-3.43 (m, 3H), 2.10-2.13 (m, 2H), 1.98-2.03 (m, 3H), 1.92-1.94 (m, 3H), 1.64-1.73 (m, 2H), 0.99-1.04 (m, 2H), 0.75-0.79 (m, 2H). MS (ESI) m/e [M+1]$^+$=395.

Step 4: (6-cyclopropylimidazo[1,5-a]pyridin-5-yl)(4-(naphthalen-1-yl)cyclohexyl)methanol

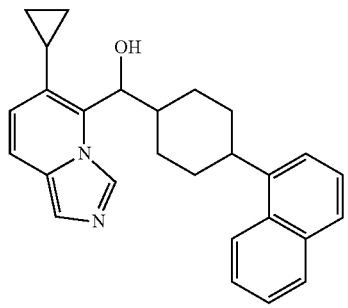 [SMILES: OC(c1c(C2CC2)ccc2cncn12)C1CCC(c2cccc3ccccc23)CC1]

To a solution of (6-cyclopropylimidazo[1,5-a]pyridin-5-yl)(4-(naphthalen-1-yl)cyclohexyl)methanone (306 mg) in methanol (10 mL) was added NaBH$_4$ (148 mg) at room temperature and the mixture was stirred for 1 hour. Then the solvent was evaporated under reduced pressure and water (50 mL) was added, extracted with ethyl acetate (50 ml×3) and combined the organic layer, evaporated the solvent under reduced pressure and the residue was pulped with methanol 2 mL to give product as a white solid (206 mg, 66.9%). $^1$H NMR (DMSO-d6) $\delta_H$ 8.74 (s, 1H), 8.31 (d, J=8.0 Hz, 1H), 7.84 (d, J=8.0 Hz, 1H), 7.69 (d, J=8.0 Hz, 1H), 6.48 (d, J=9.6 Hz, 1H), 5.53 (d, J=10.0 Hz, 1H), 3.30-3.35 (m, 1H), 2.62-2.65 (m, 1H), 2.45-2.48 (m, 1H), 2.20-2.23 (m, 1H), 1.94-1.97 (m, 2H), 1.65-1.75 (m, 1H), 1.35-1.57 (m, 4H), 1.00-1.31 (m, 2H), and 0.73-0.76 (m, 2H). MS (ESI) m/e [M+1]$^+$=397.

Examples: D135a and D135b: (S)-(6-cyclopropylimidazo[1,5-a]pyridin-5-yl)((1 r,4S)-4-(naphthalen-1-yl)cyclohexyl)methanol and (R)-(6-cyclopropylimidazo[1,5-a]pyridin-5-yl)((r,4R)-4-(naphthalen-1-yl)cyclohexyl)methanol

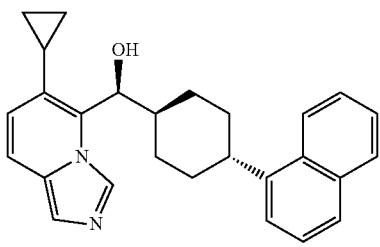

Fast isomer in CHIRALPAK IC
Eluting reagent: Hex:IPA = 70:30

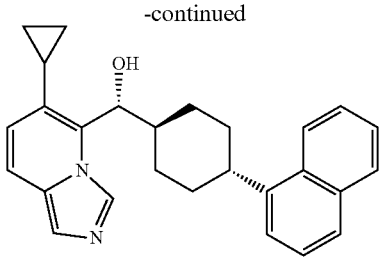

Slow isomer in CHIRALPAK IC
Eluting reagent: Hex:IPA = 70:30

Each enantiomer of racemic D135a and D135b was separated using preparative HPLC on a CHIRAL PAK IC with Hex:IPA=70:30 as an eluent. The enantiomeric excesses were determined by using HPLC on a CHIRAL PAK IC with Hex:IPA=70:30 as an eluent at a flow rate of 1.0 mL/min. The first one enantiomer eluted at the retention time of 3.821 min (D135a), which was dissolved in DCM (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid. $^1$H NMR (DMSO-d$_6$) $\delta_H$ 9.65 (s, 1H), 8.13 (d, J=8.0 Hz, 1H), 8.06 (s, 1H), 7.90 (d, J=8.0 Hz, 1H), 7.70-7.76 (m, 2H), 7.35-7.57 (m, 4H), 6.86 (d, J=9.6 Hz, 1H), 6.21 (s, 1H), 5.40 (d, J=9.6 Hz, 1H), 3.31-3.37 (m, 1H), 2.21-2.33 (m, 2H), 1.83-2.07 (m, 2H), 1.38-1.69 (m, 4H), 1.23-1.31 (m, 2H), 1.05-1.10 (m, 2H), 0.82-0.87 (m, 2H). MS (ESI) m/e [M+1]$^+$=397: and the other enantiomer eluted at the retention time of 8.221 min (D135b), $^1$H NMR (DMSO-d$_6$) $\delta_H$ 9.66 (s, 1H), 8.13 (d, J=8.0 Hz, 1H), 8.07 (s, 1H), 7.90 (d, J=8.0 Hz, 1H), 7.70-7.76 (m, 2H), 7.34-7.57 (m, 4H), 6.87 (d, J=8.0 Hz, 1H), 6.23 (s, 1H), 5.40 (d, J=9.6 Hz, 1H), 3.31-3.37 (m, 1H), 2.21-2.33 (m, 2H), 1.83-2.07 (m, 2H), 1.38-1.69 (m, 4H), 1.23-1.31 (m, 2H), 1.05-1.10 (m, 2H), 0.82-0.87 (m, 2H). MS (ESI) m/e [M+1]$^+$=397. The absolute configurations of chiral carbons in D135a and D135b are tentatively assigned as (S) and (R) respectively based on assumption that the binding model of the more potent isomer D135a is the same as that of C101a with IDO1 enzyme, and the relative stereochemistry on cyclohexane is assigned as trans configuration on the cyclohexane.

Example D136: (6-cyclopropylimidazo[1,5-a]pyridin-5-yl)(4-(naphthalen-2-yl)cyclohexyl)methanol

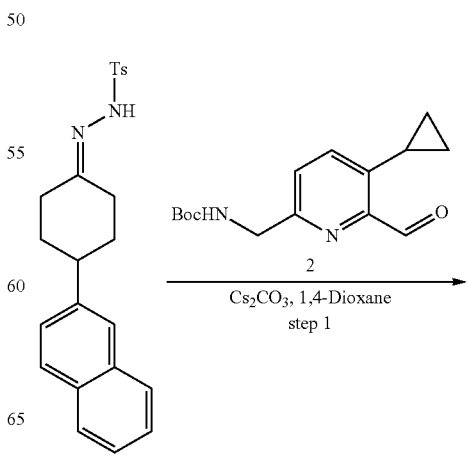

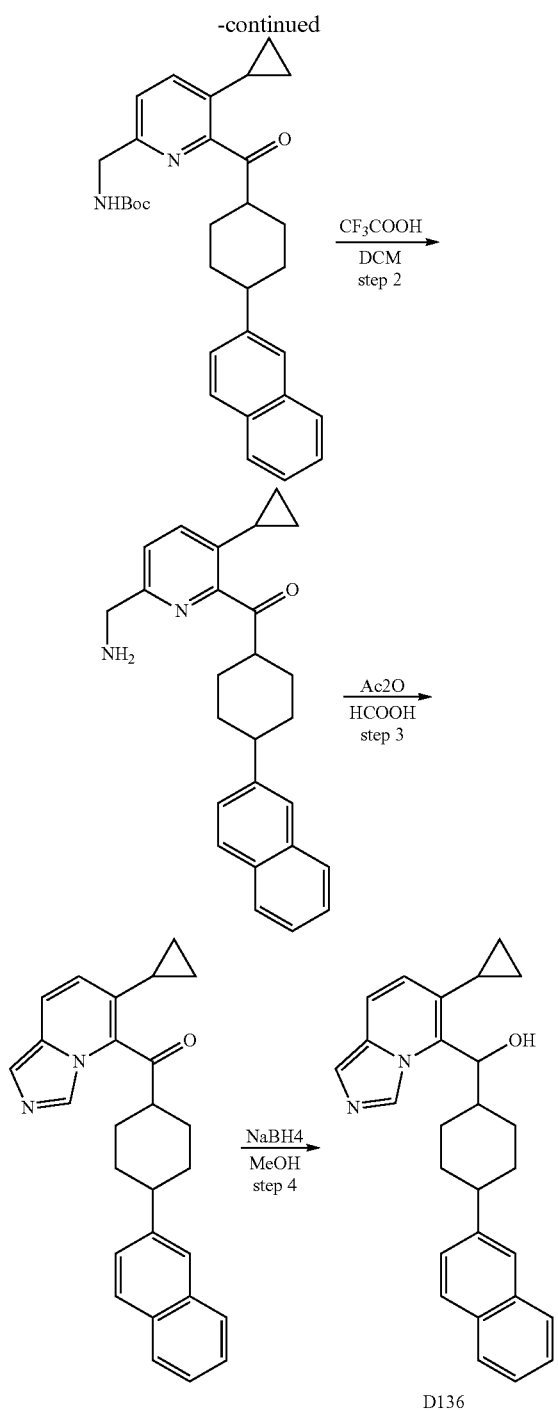

Step 1: tert-butyl ((5-cyclopropyl-6-(4-(naphthalen-2-yl)cyclohexane-1-carbonyl)pyridin-2-yl)methyl)carbamate To a solution of tert-butyl ((5-cyclopropyl-6-formylpyridin-2-yl)methyl)carbamate (600 mg) in 1,4-dioxane (25 mL) was added 4-methyl-N'-(4-(naphthalen-2-yl)cyclohexylidene)-benzenesulfonohydrazide (852 mg) and Cs$_2$CO$_3$ (1058 mg) at room temperature, and the mixture was heated at 95° C. for overnight. The solvent was cooled to room temperature, concentrated to dryness. The crude was purified by column chromatography (PE:EA=20:1 to 5:1) to give product as a pale yellow oil (475 mg in 45.2% yield). $^1$H NMR (DMSO-d$_6$) $\delta_H$ 7.83-7.87 (m, 3H), 7.73 (s, 1H), 7.42-7.49 (m, 5H), 7.31 (d, J=6.0 Hz, 1H), 4.24 (d, J=6.0 Hz, 2H), 3.63-3.90 (m, 1H), 2.68-2.74 (m, 1H), 2.32-2.35 (m, 1H), 1.97-2.00 (m, 4H), 1.51-1.77 (m, 4H), 1.41 (s, 9H), 0.94-0.99 (m, 2H), 0.67-0.71 (m, 2H). MS (ESI) m/e [M+1]$^+$=485.

Step 2: (6-(aminomethyl)-3-cyclopropylpyridin-2-yl)(4-(naphthalen-2-yl)cyclohexyl)methanone To a solution of tert-butyl ((5-cyclopropyl-6-(4-(naphthalen-2-yl)cyclohexane-1-carbonyl)pyridin-2-yl)methyl)carbamate (475 mg) in DCM (10 mL) was added CF$_3$COOH (10 mL) and the mixture was stirred at room temperature for 2 hours. The solvent was concentrated to dryness, which was used for next step without further purification.

Step 3: (6-cyclopropylimidazo[1,5-a]pyridin-5-yl)(4-(naphthalen-2-yl)cyclohexyl)methanone To a solution of acetic anhydride (15 m L) and formic acid (10 m L) was stirred at 60° C. for 1 hour, after was added (6-(aminomethyl)-3-cyclopropylpyridin-2-yl)(4-(naphthalen-2-yl)cyclohexyl)methanone (530 mg) in formic acid 5 mL. Then the mixture was stirred at 60° C. for 2 hours. After cooled to room temperature, the solvent was concentrated to dryness. The crude was added EA 50 mL, extracted with saturated sodium bicarbonate (50 mL×3). The organic layer was dried over Na$_2$SO$_4$, filtered and concentrated to dryness. And the crude was purified by column chromatography (PE:EA=5:1 to 1:1) to give product as a yellow solid (328 mg in 84.73% yield). $^1$H NMR (DMSO-d$_6$) δ 8.12 (s, 1H), 7.82-7.86 (m, 3H), 7.71 (s, 1H), 7.62 (d, J=9.2 Hz, 1H), 7.41-7.48 (m, 4H), 6.51 (d, J=9.6 Hz, 1H), 3.37-3.40 (m, 1H), 2.70-2.72 (m, 1H), 2.31-2.10 (m, 2H), 1.97-1.99 (m, 2H), 1.89-1.93 (m, 1H), 1.64-1.72 (m, 4H), 0.99-1.05 (m, 2H), 0.75-0.79 (m, 2H). MS (ESI) m/e [M+1]$^+$=395.

Step 4: (6-cyclopropylimidazo[1,5-a]pyridin-5-yl)(4-(naphthalen-2-yl)cyclohexyl)methanol

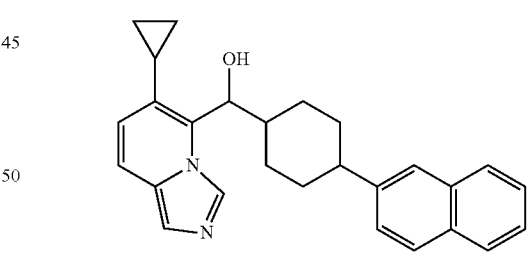

To a solution of (6-cyclopropylimidazo[1,5-a]pyridin-5-yl)(4-(naphthalen-1-yl)cyclohexyl)methanone (328 mg) in methanol (10 mL) was added NaBH$_4$ (157 mg) at room temperature and the mixture was stirred for 1 hour. Then the solvent was evaporated under reduced pressure and water (50 mL) was added, extracted with ethyl acetate (50 ml×3) and combined the organic layer, evaporated the solvent under reduced pressure and the residue was pulped with methanol 2 mL to give product as a white solid (222 mg, 55.92%). $^1$H NMR (DMSO-d$_6$) $\delta_H$ 8.67 (s, 1H), 7.78-7.84 (m, 3H), 7.68 (s, 1H), 7.40-7.48 (m, 4H), 7.33 (s, 1H), 6.48 (d, J=9.2 Hz, 1H), 5.83 (d, J=3.6 Hz, 1H), 5.29 (dd, J=9.2 Hz, 1H), 2.61-2.67 (m, 1H), 2.45-2.48 (m, 1H), 2.25-2.28

(m, 1H), 1.97-2.01 (m, 2H), 1.61-1.78 (m, 2H), 1.21-1.39 (m, 4H), 0.94-1.00 (m, 2H), 0.66-0.79 (m, 2H). MS (ESI) m/e [M+1]$^+$=397.

Examples D136a and D136b: (S)-(6-cyclopropylimidazo[1,5-a]pyridin-5-yl)((1r,4S)-4-(naphthalen-2-yl)cyclohexyl)methanol and (R)-(6-cyclopropylimidazo[1,5-a]pyridin-5-yl)(1r,4R)-4-(naphthalen-2-yl)cyclohexyl)methanol

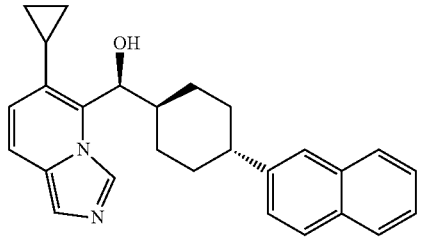

Fast isomer in CHIRALPAK IC
Eluting reagent: Hex:EtOH = 70:30

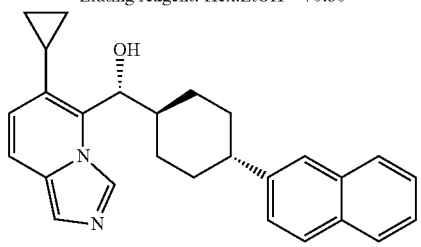

Slow isomer in CHIRALPAK IC
Eluting reagent: Hex:EtOH = 70:30

Each enantiomer of racemic D136a and D136b was separated using preparative HPLC on a CHIRAL PAK IC with Hex:EtOH=70:30 as an eluent. The enantiomeric excesses were determined by using HPLC on a CHIRAL PAK IC with Hex:EtOH=70:30 as an eluent at a flow rate of 1.0 mL/min. The first one enantiomer eluted at the retention time of 2.753 min (D136a), which was dissolved in DCM (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid, $^1$H NMR (DMSO-d6) $\delta_H$ 9.66 (s, 1H), 8.31 (s, 1H), 7.80-7.85 (m, 3H), 7.72 (d, J=9.6 Hz, 1H), 7.67 (s, 1H), 7.38-7.47 (m, 3H), 6.85 (d, J=9.6 Hz, 1H), 6.24 (s, 1H), 5.35 (d, J=9.6 Hz, 1H), 2.63-2.69 (m, 1H), 2.41-2.43 (m, 1H), 2.20-2.28 (m, 2H), 2.00-2.03 (m, 1H), 1.78-1.81 (m, 1H), 1.57-1.66 (m, 1H), 1.32-1.46 (m, 3H), 1.23-1.29 (m, 1H), 1.02-1.11 (m, 2H), 0.77-0.89 (m, 2H). MS (ESI) m/e [M+1]$^+$=397; and the other enantiomer eluted at the retention time of 4.539 min (D136b), $^1$H NMR (DMSO-d$_6$) $\delta_H$ 9.65 (s, 1H), 8.06 (s, 1H), 7.80-7.85 (m, 3H), 7.67-7.72 (m, 3H), 7.38-7.47 (m, 3H), 6.85 (d, J=9.2 Hz, 1H), 6.21 (s, 1H), 5.35 (d, J=9.6 Hz, 1H), 2.60-2.66 (m, 1H), 2.41-2.43 (m, 1H), 2.19-2.25 (m, 2H), 1.99-2.03 (m, 1H), 1.78-1.81 (m, 1H), 1.57-1.66 (m, 1H), 1.32-1.43 (m, 3H), 1.23-1.29 (m, 1H), 1.05-1.07 (m, 2H), 0.79-0.86 (m, 2H). MS (ESI) m/e [M+1]$^+$=397. The absolute configurations of chiral carbons in D136a and D136b are tentatively assigned as (S) and (R) respectively based on assumption that the binding model of the more potent isomer D136a is the same as that of C101a with IDO1 enzyme, and the relative stereochemistry on cyclohexane is assigned as trans configuration on the cyclohexane.

Example D137: (6-cyclopropylimidazo[1,5-a]pyridin-5-yl)(4-(4-fluoronaphthalen-1-yl)cyclohexyl)methanol

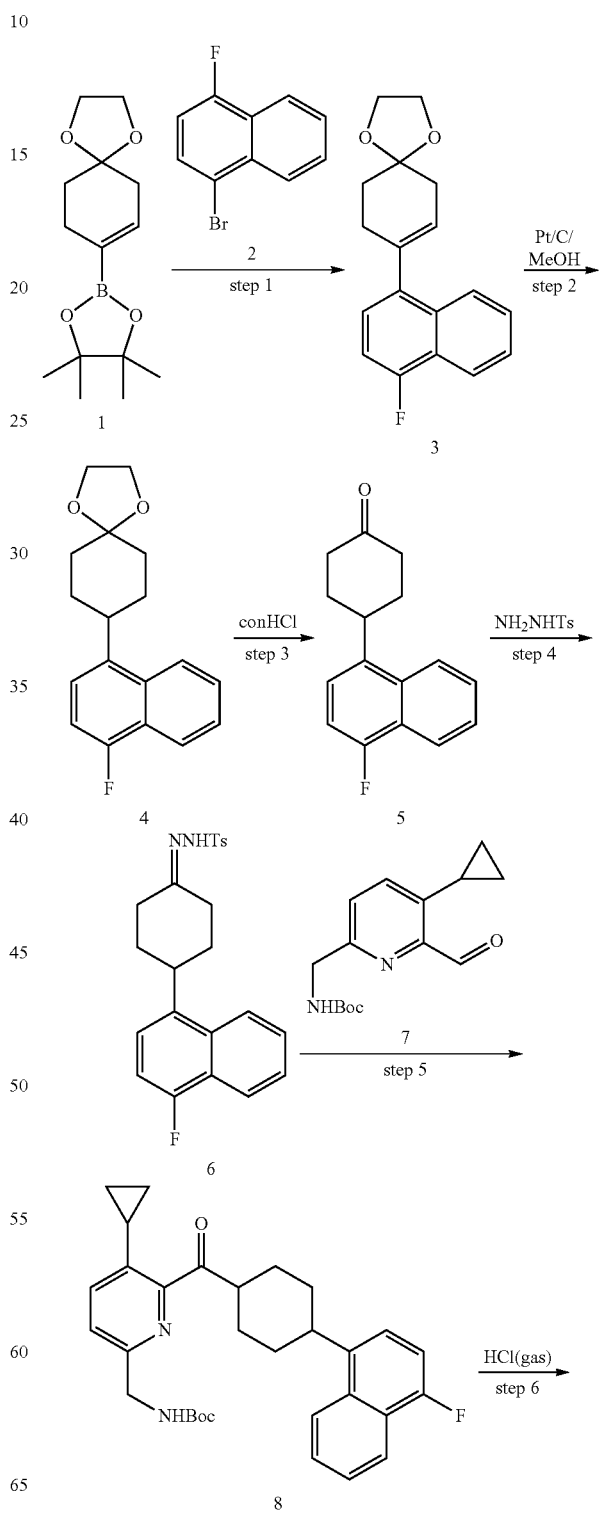

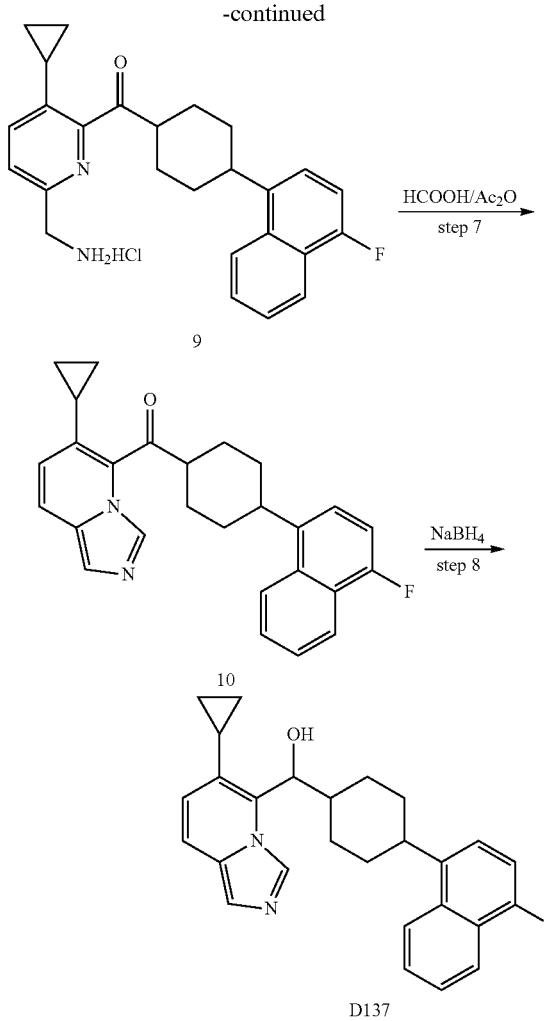

Step 1: 8-(3-chlorophenyl)-1,4-dioxaspiro[4.5]dec-7-ene

To a solution of 1-bromo-4-fluoronaphthalene (2.25 g, 10 mmoL) in 1,4-dioxane/H₂O (80 ml/20 mL) was added 4,4,5,5-tetramethyl-2-(1,4-dioxaspiro[4.5]dec-7-en-8-yl)-1,3,2-dioxaborolane (2.66 g, 10 mmol), Pd(dppf)Cl₂ (731 mg, 1.0 mmol) and Cs₂CO₃ (4.88 g, 1.5 mmol) and the mixture was heated at 70° C. for 5 hours. Then evaporated the solvent under reduced pressure and the residue was purified by column chromatography (PE:EA=5:1) to give product as an oil (2.1 g in 74% yield). [M+H]⁺=285

Step 2: 8-(4-fluoronaphthalen-1-yl)-1,4-dioxaspiro[4.5]decane

To a solution of 8-(4-fluoronaphthalen-1-yl)-1,4-dioxaspiro[4.5]dec-7-ene (2.0 g, 7.0 mmol) in MeOH (20 mL) was added Pd/C (400 mg, 10%) and the mixture was stirred for 6 hours at room temperature under H₂ (0.1 Mpa). Then filtered to remove Pd/C and the filtrate was evaporated under reduced pressure to give a crude product (1.9 g, oil). [M+H]⁺=287

Step 3: 4-(4-fluoronaphthalen-1-yl)cyclohexan-1-one

To a solution of 8-(4-fluoronaphthalen-1-yl)-1,4-dioxaspiro[4.5]decane (1.9 g, 6.6 mmol) in 1,4-dioxane/H₂O (20 mL/15 mL) was added con HCl (5.0 mL) at room temperature and the mixture was stirred for overnight. The mixture was quench with EA(100 mL) and H₂O (100 mL), the organic layer was washed with saturated aqueous of NaHCO₃, then the organic layer was evaporated in vacuo to give crude product (1.4 g), which was used for next step without further purification. [M+H]⁺=243

Step 4: N'-(4-(4-fluoronaphthalen-1-yl)cyclohexylidene)-4-methylbenzenesulfonohydrazide To a solution of 4-(3-chlorophenyl)cyclohexan-1-one (1.21 g, 5.0 mmol) in methol (20 mL) was added 4-methylbenzenesulfonohydrazide (930 mg, 5.0 mmol) at room temperature and the mixture was stirred for overnight. Evaporate half the solvent under reduced pressure and then filtered to give product as a white solid (1.9 g in 92% yield). [M+H]⁺=411

Step 5: tert-butyl ((5-cyclopropyl-6-(4-(4-fluoronaphthalen-1-yl)cyclohexane-1-carbonyl)-pyridin-2-yl)methyl)carbamate To a solution of tert-butyl ((5-cyclopropyl-6-formylpyridin-2-yl)methyl)carbamate (552 mg, 2.0 mmol) in 1,4-dioxane (0.1 L) was added N'-(4-(3-chlorophenyl)cyclohexylidene)-4-methylbenzenesulfonohydrazide (0.82 g, 2.0 mmol) and Cs₂CO₃ (975 mg, 3.0 mmol) at room temperature, and the mixture was heated at 100° C. for 6 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (810 mg in 80% yield). [M+H]⁺=503

Step 6: (6-(aminomethyl)-3-cyclopropylpyridin-2-yl)(4-(4-fluoronaphthalen-1-yl)cyclohexyl)methanone hydrochloride Tert-butyl ((5-cyclopropyl-6-(4-(4-fluoronaphthalen-1-yl)cyclohexane-1-carbonyl)-pyridin-2-yl)methyl)carbamate (800 mg, 1.6 mmol) was suspended in HCl (gas)/EA (20 mL, 4.0M in EA), the mixture was stirred at room temperature for overnight. The solvent was evaporated under reduced pressure to give crude product as solid (670 mg). [M+H]⁺=403

Step 7: (6-cyclopropylimidazo[1,5-a]pyridin-5-yl)(4-(4-fluoronaphthalen-1-yl)cyclohexyl) methanone A mixture of Ac₂O (30 mL) and HCOOH (10 mL) was heated at 50° C. for 1 hour and then a solution of (6-(aminomethyl)-3-cyclopropylpyridin-2-yl)(4-(4-fluoronaphthalen-1-yl)cyclohexyl)methanone hydrochloride (crude 670 mg, 1.52 mmol) in HCOOH (5 mL) was added drop wise and the mixture was heated at 50° C. for 2 hours. The solvent was evaporated under reduced pressure and water (100 mL) was added, washed with saturated aqueous of NaHCO₃, then extracted with ethyl acetate (50 mL×3) and combined the organic layer, the solvent was evaporated under reduced pressure and the residue was purified by column chromatography (PE:EA=4:1) to give the product as a solid (460 mg in 70% yield). [M+H]⁺=413.

Step 8: (6-cyclopropylimidazo[1,5-a]pyridin-5-yl)(4-(4-fluoronaphthalen-1-yl)cyclohexyl)methanol To a solution of (6-cyclopropylimidazo[1,5-a]pyridin-5-yl)(4-(4-fluoronaphthalen-1-yl)cyclohexyl)methanone (413 mg, 1.0 mmol) in methol (20 mL) was added NaBH$_4$ (76 mg, 2.0 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (310 mg in 74% yield). $^1$H NMR (400 MHz, DMSO-d$_6$) $\delta_H$ 8.65 (s, 1H), 8.20 (d, J=8.0 Hz, 1H), 8.04-8.07 (m, 1H), 7.63-7.67 (m, 2H), 7.41 (d, J=8.0 Hz, 1H), 7.21-7.35 (m, 3H), 6.50 (d, J=9.6 Hz, 1H), 5.84 (d, J=3.6 Hz, 1H), 5.33 (dd, J=9.6 Hz, J=4.0 Hz, 1H), 2.62-2.67 (m, 1H), 2.28-2.33 (m, 1H), 1.99-2.01 (m, 1H), 1.78-1.81 (m, 1H), 1.46-1.64 (m, 2H), 1.19-1.26 (m, 4H), 0.85-0.97 (m, 2H), 0.77-0.79 (m, 1H), 0.67-0.69 (m, 1H). [M+H]$^+$=415

Example D137a and D137b: (S)-(6-cyclopropylimidazo[1,5-a]pyridin-5-yl)((1r,4S)-4-(4-fluoronaphthalen-1-yl)cyclohexyl)methanol and (R)-(6-cyclopropylimidazo[1,5-a]pyridin-5-yl)(1r,4R)-4-(4-fluoronaphthalen-1-yl)cyclohexyl)methanol

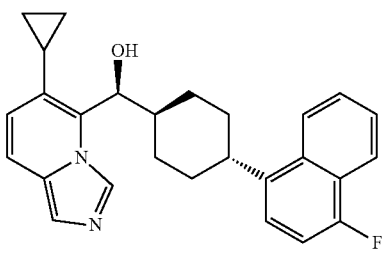

Fast isomer in CHIRALART Cellulose-SB
Eluting reagent: Hex:IPA = 70:30

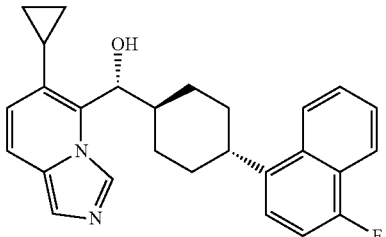

Slow isomer in CHIRALART Cellulose-SB
Eluting reagent: Hex:IPA = 70:30

Each enantiomer of racemic D137a and D137b was separated using preparative HPLC on a CHIRALART Cellulose-SB, Eluting reagent: Hex:IPA=70:30 as an eluent. The enantiomeric excesses were determined by using HPLC on a CHIRALART Cellulose-SB with Hex (0.1% DEA):IPA=70:30 as an eluent at a flow rate of 1.0 mL/min. The first one enantiomer eluted at the retention time of 2.969 min (D137a), and the other enantiomer eluted at the retention time of 6.005 min (D137b). To a solution of D137a (80 mg) in THF (10 mL) was added drop wise of Ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (70 mg in 80% yield). $^1$H NMR (400 MHz, DMSO-d$_6$) $\delta_H$ 9.68 (d, J=7.6 Hz, 1H), 8.19 (s, J=8.0 Hz, 1H), 8.06 (d, J=7.6 Hz, 1H), 7.61-7.67 (m, 3H), 7.23-7.34 (m, 2H), 6.87 (d, J=9.6 Hz, 1H), 6.23 (s, 1H), 5.39 (d, J=9.6 Hz, 1H), 3.27-3.30 (m, 1H), 2.20-2.33 (m, 2H), 2.05-2.05 (m, 1H), 1.81-1.84 (m, 1H), 1.42-1.58 (m, 4H), 1.27-1.30 (m, 1H), 1.04-1.09 (m, 2H), and 0.83-0.87 (m, 2H) [M+H]$^+$=415. To a solution of D137b (80 mg) in THF (10 mL) was added drop wise of ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (72 mg in 80% yield). $^1$H NMR (400 MHz, DMSO-d$_6$) $\delta_H$ 9.69 (s, 1H), 8.19 (s, J=8.0 Hz, 1H), 8.06-8.10 (m, 2H), 7.60-7.74 (m, 3H), 7.23-7.34 (m, 2H), 6.88 (d, J=9.6 Hz, 1H), 6.23 (s, 1H), 5.39 (d, J=9.6 Hz, 1H), 3.74-3.81 (m, 1H), 2.20-2.33 (m, 2H), 2.01-2.05 (m, 1H), 1.81-1.84 (m, 1H), 1.42-1.58 (m, 4H), 1.27-1.30 (m, 1H), 1.04-1.09 (m, 2H), and 0.83-0.87 (m, 2H) [M+H]$^+$=415. The absolute configurations of chiral carbons in D137a and D137b are tentatively assigned as (S) and (R) respectively based on assumption that the binding model of the more potent isomer D137a is the same as that of C101a with IDO1 enzyme, and the relative stereochemistry on cyclohexane is assigned as trans configuration on the cyclohexane.

Example D138: (6-cyclopropylimidazo[1,5-a]pyridin-5-yl)(4-(4-hydroxynaphthalen-1-yl)cyclohexyl)methanol

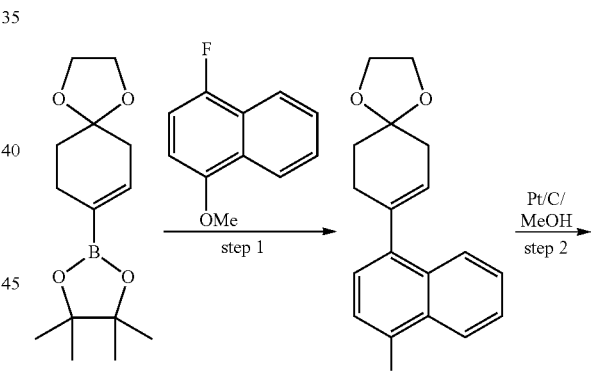

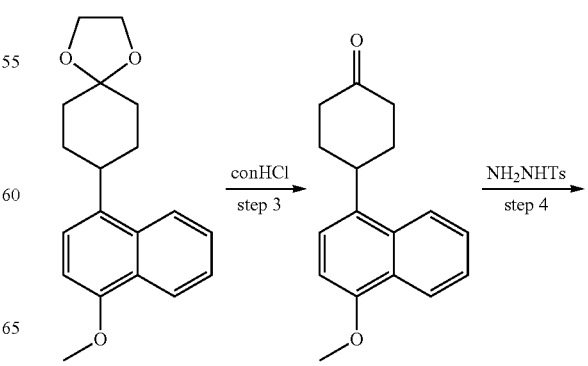

355

-continued

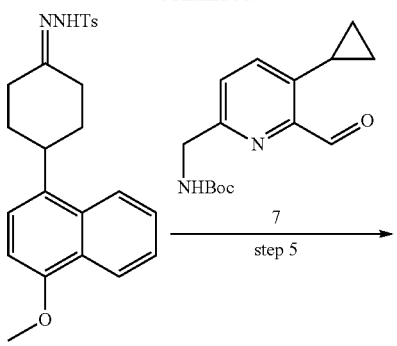

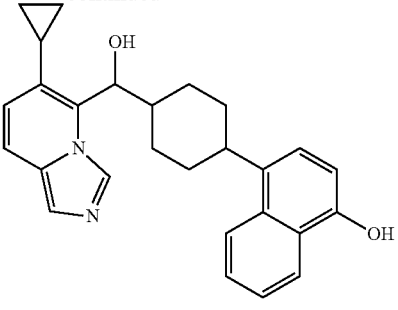

→ step 5

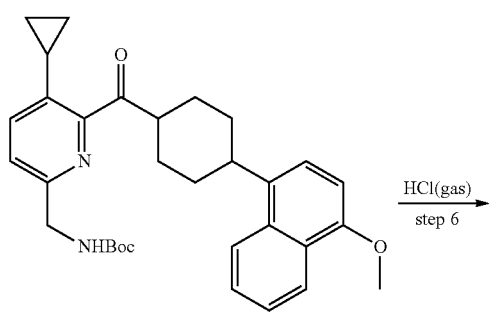

→ step 6 HCl(gas)

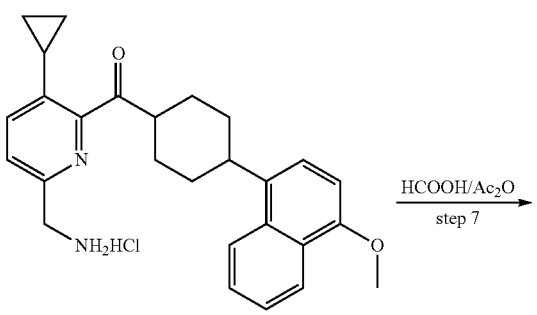

→ step 7 HCOOH/Ac₂O

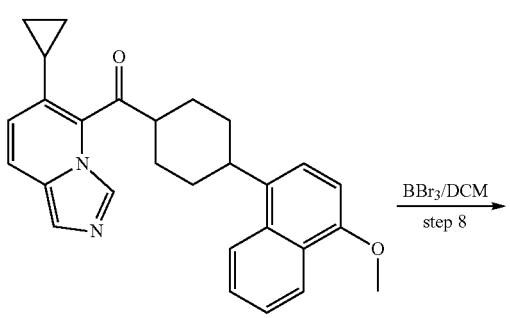

→ step 8 BBr₃/DCM

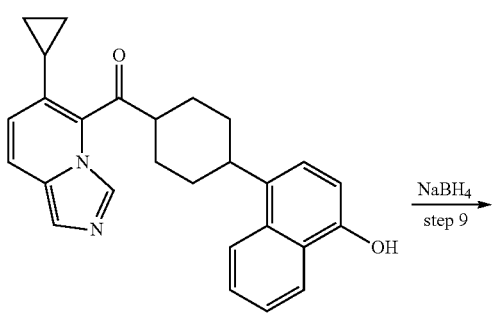

→ step 9 NaBH₄

356

-continued

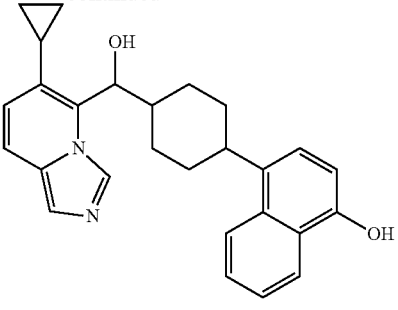

D138

Step 1: 8-(4-methoxynaphthalen-1-yl)-1,4-dioxas-piro[4.5]dec-1-ene

To a solution of 1-bromo-4-methoxynaphthalene (4.72 g, 20 mmoL) in 1,4-dioxane/H₂O (80 m/20 mL) was added 4,4,5,5-tetramethyl-2-(1,4-dioxaspiro[4.5]dec-7-en-8-yl)-1,3,2-dioxaborolane (5.32 g, 10 mmol), Pd(dppf)Cl₂ (1462 mg, 2.0 mmol) and Cs₂CO₃ (9.75 g, 30 mmol) and the mixture was heated at 70° C. for 5 hours. Then evaporated the solvent under reduced pressure and the residue was purified by column chromatography (PE:EA=5:1) to give product as an oil (4.1 g in 69% yield). [M+H]⁺=297.

Step 2: 8-(4-methoxynaphthalen-1-yl)-1,4-dioxas-piro[4.5]decane

To a solution of 8-(4-methoxynaphthalen-1-yl)-1,4-dioxaspiro[4.5]dec-7-ene (2.96 g, 10 mmol) in MeOH (20 mL) was added Pd/C (500 mg, 10%) and the mixture was stirred for 6 hours at room temperature under H₂ (0.1 Mpa). Then filtered to remove Pd/C and the filtrate was evaporated under reduced pressure to give a crude product (2.5 g, oil). [M+H]⁺=299.

Step 3: 4-(4-methoxynaphthalen-1-yl)cyclohexan-1-one

To a solution of 8-(4-methoxynaphthalen-1-yl)-1,4-dioxaspiro[4.5]decane (2.5 g, 8.4 mmol) in 1,4-dioxane/H₂O (20 mL/15 mL) was added con HCl (5.0 mL) at room temperature and the mixture was stirred for overnight. The mixture was quench with EA(100 mL) and H₂O (100 mL), the organic layer was washed with saturated aqueous of NaHCO₃, then the organic layer was evaporated in vacuo to give crude product (1.9 g), which was used for next step without further purification. [M+H]⁺=255

Step 4: N'-(4-(4-methoxynaphthalen-1-yl)cyclohex-ylidene)-4-methylbenzenesulfonohydrazide To a solution of 4-(4-methoxynaphthalen-1-yl)cyclo-hexan-1-one (1.9 g, 7.4 mmol) in methol (20 mL) was added 4-methylbenzenesulfonohydrazide (1.53 mg, 58.1 mmol) at room temperature and the mixture was stirred for overnight. Evaporate half the solvent under reduced pressure and then filtered to give product as a white solid (1.9 g in 61% yield). [M+H]⁺=423

Step 5: tert-butyl ((5-cyclopropyl-6-(4-(4-methoxynaphthalen-1-yl)cyclohexane-1-carbonyl)pyridin-2-yl)methyl)carbamate To a solution of tert-butyl ((5-cyclopropyl-6-formylpyri-din-2-yl)methyl)carbamate (552 mg, 2.0 mmol) in 1,4- dioxane (0.1 L) was added N'-(4-(4-methoxynaphthalen-1-yl)cyclohexylidene)-4-methylbenzenesulfonohydrazide (0.845 g, 2.0 mmol) and Cs$_2$CO$_3$ (780 mg, 2.4 mmol) at room temperature, and the mixture was heated at 100° C. for 6 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (750 mg in 73% yield). [M+H]$^+$=515

Step 6: (6-(aminomethyl)-3-cyclopropylpyridin-2-yl)(4-(4-methoxynaphthalen-1-yl)cyclohexyl)methanone hydrochloride tert-butyl ((5-cyclopropyl-6-(4-(4-methoxynaphthalen-1-yl)cyclohexane-1-carbonyl)pyridin-2-yl)methyl)carbamate (700 mg, 1.35 mmol) was suspended in HCl (gas)/EA (10 mL, 4.0M in EA), the mixture was stirred at room temperature for overnight. The solvent was evaporated under reduced pressure to give crude product as solid (610 mg). [M+H]$^+$=415.

Step 7: (6-cyclopropylimidazo[1,5-a]pyridin-5-yl)(4-(4-methoxynaphthalen-1-yl)cyclohexyl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(4-methoxynaphthalen-1-yl)cyclohexyl)methanone hydrochloride (crude 610 mg, 1.3 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give the product as a solid (350 mg in 61% yield). [M+H]$^+$=425.

Step 8: (6-cyclopropylimidazo[1,5-a]pyridin-5-yl)(4-(4-hydroxynaphthalen-1-yl)cyclohexyl)methanone To a solution of (6-cyclopropylimidazo[1,5-a]pyridin-5-yl)(4-(4-methoxynaphthalen-1-yl)cyclohexyl)methanone (130 mg, 0.28 mmol) in DCM (5 mL) was added drop wise tribromoborane (700 mg, 2.8 mmol) at 0° C. for 0.2 hour. The mixtures was quenched with saturated aqueous of NaHCO$_3$ (50 mL), then extracted with ethyl acetate (50 mL×3) and combined the organic layer, the solvent was evaporated under reduced pressure and the residue was purified by column chromatography (PE:EA=3:1) to give the product as a solid (115 mg, 91%). [M+H]$^+$=411.

Step 9: 4-(4-((6-cyclopropylimidazo[1,5-a]pyridin-5-yl)(hydroxy)methyl)cyclohexyl)naphthalen-1-ol To a solution of (6-cyclopropylimidazo[1,5-a]pyridin-5-yl)(4-(4-hydroxynaphthalen-1-yl)cyclohexyl)methanone (115 mg, 0.28 mmol) in methol (10 mL) was added NaBH$_4$ (21.4 mg, 0.56 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (110 mg in 90% yield). $^1$H NMR (400 MHz, DMSO-d$_6$) δ$_H$ 9.85 (s, 1H), 8.65 (s, 1H), 8.14 (d, J=8.4 Hz, 1H), 8.01 (d, J=8.4 Hz, 1H), 7.39-7.51 (m, 3H), 7.32 (s, 1H), 7.14 (d, J=8.0 Hz, 1H), 6.77 (d, J=8.0 Hz, 1H), 6.50 (d, J=9.6 Hz, 1H), 5.82 (d, J=3.6 Hz, 1H), 5.33 (dd, J=9.6 Hz, J=3.6 Hz, 1H), 3.14-3.21 (m, 1H), 2.25-2.29 (m, 1H), 1.99-2.01 (m, 1H), 1.78-1.81 (m, 1H), 1.46-1.64 (m, 2H), 1.21-1.26 (m, 4H), 0.95-0.99 (m, 2H), 0.77-0.79 (m, 1H), 0.67-0.69 (m, 1H). [M+H]$^+$=413

Example D139: (6-cyclopropylimidazo[1,5-a]pyridin-5-yl)(4-(4-methoxynaphthalen-1-yl)cyclohexyl)methanol

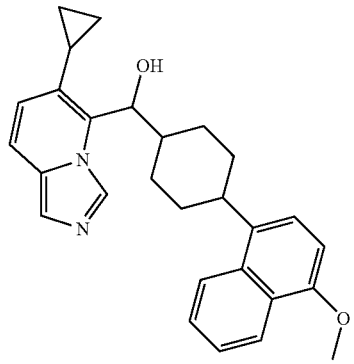 [SMILES: COc1ccc(C2CCC(C(O)c3c(C4CC4)ccc4cncn34)CC2)c2ccccc12]

To a solution of (6-cyclopropylimidazo[1,5-a]pyridin-5-yl)(4-(4-methoxynaphthalen-1-yl)cyclohexyl)methanone (120 mg, 0.28 mmol) in methanol (10 m L) was added NaBH$_4$ (21.4 mg, 0.56 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product as a white solid (110 mg in 90% yield). $^1$H NMR (400 MHz, DMSO-d$_6$) δ$_H$ 8.65 (s, 1H), 8.17 (d, J=8.4 Hz, 1H), 8.07 (d, J=8.4 Hz, 1H), 7.45-7.57 (m, 2H), 7.41 (d, J=9.2 Hz, 1H), 7.26-7.32 (m, 3H), 6.88 (d, J=8.4 Hz, 1H), 6.50 (d, J=9.2 Hz, 1H), 5.84 (d, J=4.0 Hz, 1H), 5.33 (dd, J=9.6 Hz, 4.0 Hz, 1H), 3.91 (s, 3H), 3.17-3.21 (m, 1H), 2.27-2.29 (m, 1H), 1.99-2.01 (m, 1H), 1.78-1.81 (m, 1H), 1.46-1.64 (m, 2H), 1.19-1.26 (m, 4H), 0.95-0.99 (m, 2H), 0.77-0.79 (m, 1H), and 0.67-0.69 (m, 1H). [M+H]$^+$=427

Example D139a and D139b: (S)-(6-cyclopropylimidazo[1,5-a]pyridin-5-yl)((1r,4S)-4-(4-methoxynaphthalen-1-yl)cyclohexyl)methanol and (R)-(6-cyclopropylimidazo[1,5-a]pyridin-5-yl)((1r,4R)-4-(4-methoxynaphthalen-1-yl)cyclohexyl)methanol

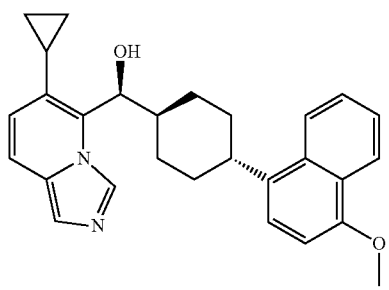

Fast isomer in CHIRALPAK IC
Eluting reagent: Hex:EtOH = 80:20

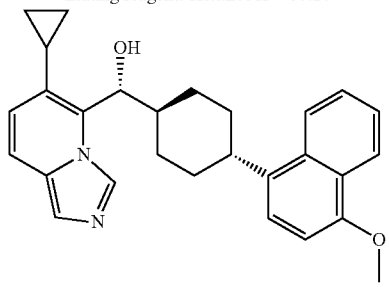

Slow isomer in CHIRALPAK IC
Eluting reagent: Hex:EtOH = 80:20

Each enantiomer of racemic D139a and D139b was separated using preparative HPLC on a CHIRALPAK IC, Eluting reagent: Hex:EtOH=80:20 as an eluent. The enantiomeric excesses were determined by using HPLC on a CHIRALART IC with Hex (0.1% IPAmine):EtOH=80:20 as an eluent at a flow rate of 1.0 mL/min. The first one enantiomer eluted at the retention time of 1.755 min, and the other enantiomer eluted at the retention time of 3.848 min. To a solution of D139a (40 mg) in THF (10 mL) was added drop wise of Ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (38 mg in 88% yield). $^1$H NMR (400 MHz, DMSO-d$_6$) $\delta_H$ 9.65 (s, 1H), 8.18 (d, J=8.0 Hz, 1H), 8.06 (m, 1H), 7.72 (d, J=9.6 Hz, 1H), 7.46-7.58 (m, 2H), 7.25 (d, J=9.6 Hz, 1H), 6.86-6.90 (m, 2H), 6.23 (s, 1H), 5.39 (d, J=9.6 Hz, 1H), 3.90 (s, 3H), 3.22-3.25 (m, 1H), 2.20-2.33 (m, 2H), 1.99-2.05 (m, 1H), 1.81-1.84 (m, 1H), 1.42-1.58 (m, 4H), 1.27-1.30 (m, 1H), 1.04-1.09 (m, 2H), and 0.83-0.87 (m, 2H) [M+H]$^+$=427. To a solution of D139b (40 mg) in THF (10 mL) was added drop wise of ethyl acetate solution of hydrochloric acid (5 mL, 4.0M) at room temperature, followed by addition of methol until the precipitate was dissolved, then the solvent was evaporated under reduced pressure and the residue was washed by PE to give the desired product as white solid (36 mg in 85% yield). $^1$H NMR (400 MHz, DMSO-d) $\delta_H$ 9.68 (s, 1H), 8.18 (d, J=8.0 Hz, 1H), 8.06 (m, J=9.2 Hz, 1H), 7.72 (d, J=9.6 Hz, 1H), 7.46-7.58 (m, 2H), 7.25 (d, J=9.6 Hz, 1H), 6.86-6.90 (m, 2H), 6.23 (s, 1H), 5.39 (d, J=9.6 Hz, 1H), 3.90 (s, 3H), 3.22-3.25 (m, 1H), 2.20-2.33 (m, 2H), 1.99-2.05 (m, 1H), 1.81-1.84 (m, 1H), 1.42-1.58 (m, 4H), 1.27-1.30 (m, 1H), 1.04-1.09 (m, 2H), and 0.83-0.87 (m, 2H) [M+H]$^+$=427. The absolute configurations of chiral carbons in D139a and D139b are tentatively assigned as (S) and (R) respectively based on assumption that the binding model of the more potent isomer D139a is the same as that of C101a with IDO1 enzyme, and the relative stereochemistry on cyclohexane is assigned as trans configuration on the cyclohexane.

Example D140: (6-cyclopropylimidazo[1,5-a]pyridin-5-yl)(4-(quinolin-4-yl)cyclohexyl)methanol

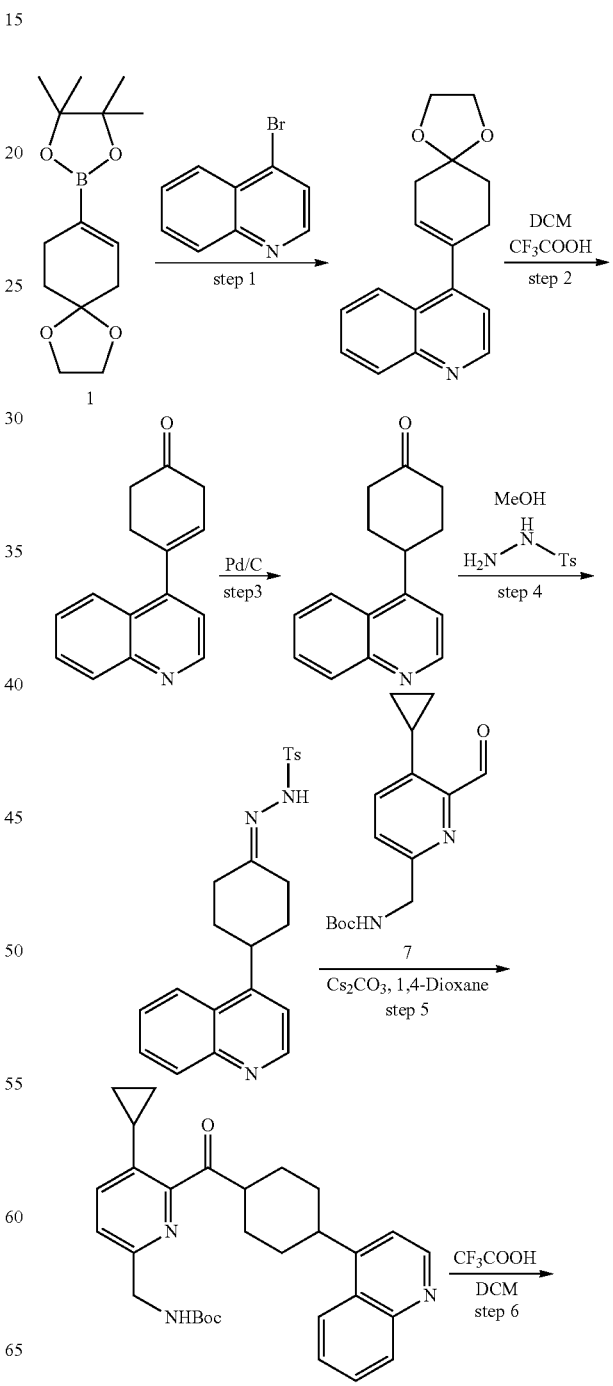

-continued

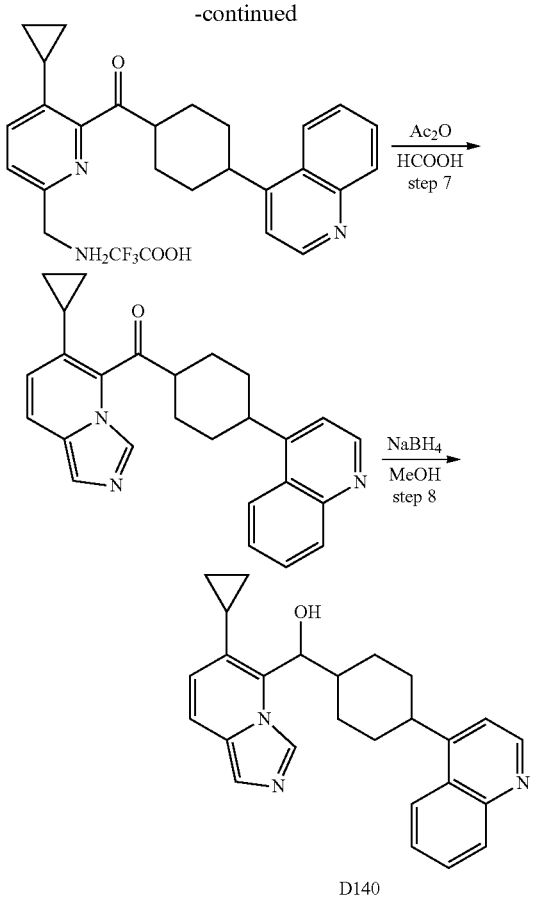

D140

Step 1: 4-(1,4-dioxaspiro[4.5]dec-7-en-8-yl)quinoline

To a solution of 4-bromoquinoline (4.70 g, 22.67 mmol) in 1,4-dioxane (150 mL) was added 4,4,5,5-tetramethyl-2-(1,4-dioxaspiro[4.5]dec-7-en-8-yl)-1,3,2-dioxaborolane (6.00 g, 22.67 mmol), Pd(dppf)Cl$_2$ (2.47 g, 3.40 mmol) and Cs$_2$CO$_3$ (11.00 g, 34.0 mmol) and the mixture was heated at 95° C. for overnight. Then evaporated the solvent under reduced pressure and the residue was purified by column chromatography (PE:EA=4:1) to give product as a clear oil (4.41 g in 73% yield). $^1$H NMR (DMSO-d$_6$) $\delta_H$ 8.83 (d, J=4.4 Hz, 1H), 8.01-8.05 (m, 2H), 7.74-7.78 (m, 1H), 7.59-7.64 (m, 1H), 7.31 (d, J=4.4 Hz, 1H), 5.70-5.72 (m, 1H), 3.99 (s, 4H), 2.51-2.56 (m, 2H), 2.45-2.46 (m, 2H), and 1.91 (t, J=6.4 Hz, 2H).

Step 2: 4-(quinolin-4-yl)cyclohex-3-en-1-one

To a solution of 4-(1,4-dioxaspiro[4.5]dec-7-en-8-yl)quinoline (4.41 g, 16.52 mmol) in dichloromethane (15 mL) was added trifluoroacetic acid (20 mL) at room temperature and the mixture was stirred for overnight. The solvent was evaporated under reduced pressure and water (100 mL) was added, extracted with EA (100 ml×3), combined the organic layer and washed with saturated aqueous of Na$_2$CO$_3$ then the organic layer was evaporated to give crude product, which was used for next step without further purification. MS (ESI) m/e [M+1]$^+$=224.

Step 3: 4-(quinolin-4-yl)cyclohexan-1-one

To a solution of 4-(quinolin-4-yl)cyclohex-3-en-1-one (4.66 g) in ethyl acetate (40 mL) and methanol (10 mL) was added Pd/C (0.5 g, 10%) and the mixture was stirred for 36 hours at room temperature under H$_2$ (0.4 Mpa). Then filtered to remove Pd/C and the filtrate was evaporated under reduced pressure to give a crude product, which was purified by silica gel chromatography (PE:EA=10:1-1:1) to give product (0.72 g in 15% yield) as a yellow oil. $^1$H NMR (DMSO-d$_6$) $\delta_H$ 8.84 (d, J=4.4 Hz, 1H), 8.38 (d, J=8.4 Hz, 1H), 8.05 (d, J=8.4 Hz, 1H), 7.78 (t, J=7.6 Hz, 1H), 7.68 (t, J=7.6 Hz, 1H), 7.44 (d, J=4.4 Hz, 1H), 3.96-4.04 (m, 1H), 2.75-2.82 (m, 2H), 2.33-2.37 (m, 2H), 2.16-2.19 (m, 2H), and 1.95-2.05 (m, 2H).

Step 4: 4-methyl-N'-(4-(quinolin-4-yl)cyclohexylidene)benzenesulfonohydrazide To a solution of 4-(quinolin-4-yl)cyclohexan-1-one (0.72 g 3.2 mmol) in methanol (10 mL) was added 4-methylbenzenesulfonohydrazide (0.60 g, 3.2 mmol) at room temperature, and the mixture was stirred for 2-3 hours. The solvent was evaporated under reduced pressure and the residue was pulped with methanol 5 mL, filtered and washed with methanol 2 mL to give product (0.86 g in 68% yield) as a white solid. $^1$H NMR (DMSO-d$_6$) $\delta_H$ 10.24 (s, 1H), 8.81 (d, J=4.4 Hz, 1H), 8.30 (d, J=8.4 Hz, 1H), 8.02 (d, J=8.4 Hz, 1H), 7.74-7.78 (m, 3H), 7.62-7.67 (m, 1H), 7.37-7.43 (m, 3H), 3.70-3.76 (m, 1H), 2.96-3.00 (m, 1H), 2.43-2.48 (m, 1H), 2.40 (s, 3H), 2.32-2.35 (m, 1H), 2.12-2.21 (m, 1H), 2.02-2.05 (m, 2H), and 1.52-1.73 (m, 2H).

Step 5: tert-butyl ((5-cyclopropyl-6-(4-(quinolin-4-yl)cyclohexane-1-carbonyl)pyridin-2-yl)methyl)carbamate To a solution of tert-butyl ((5-cyclopropyl-6-formylpyridin-2-yl)methyl)carbamate (600 mg, 2.17 mmol) in 1,4-dioxane (30 mL) was added 4-methyl-N'-(4-(quinolin-4-yl)cyclohexylidene)benzenesulfonohydrazide (855 mg, 2.17 mmol) and Cs$_2$CO$_3$ (1058 mg, 3.26 mmol) at room temperature, and the mixture was heated at 95° C. for overnight. The solvent was cooled to room temperature, concentrated to dryness. The crude was purified by column chromatography (PE:EA=10:1-1:1) to give compound product as a pale yellow solid (581 mg in 55% yield). $^1$H NMR (DMSO-d$_6$) $\delta_H$ 8.84 (d, J=4.4 Hz, 1H), 8.28 (d, J=8.4 Hz, 1H), 8.03 (d, J=8.4 Hz, 1H), 7.75 (t, J=8.4 Hz, 1H), 7.63 (t, J=8.4 Hz, 1H), 7.43-7.48 (m, 3H), 7.31 (d, J=8.4 Hz, 1H), 4.24 (d, J=6.4 Hz, 2H), 3.65-3.70 (m, 1H), 3.43-3.55 (m, 1H), 2.32-2.38 (m, 1H), 1.91-2.05 (m, 4H), 1.72-1.78 (m, 4H), 1.21-1.43 (m, 10H), 0.95-1.00 (m, 2H), and 0.68-0.72 (m, 2H).

Step 6: (6-(aminomethyl)-3-cyclopropylpyridin-2-yl)(4-(quinolin-4-yl)cyclohexyl)methanone 2,2,2-trifluoroacetate To a solution of tert-butyl ((5-cyclopropyl-6-(4-(quinolin-4-yl)cyclohexane-1-carbonyl)pyridin-2-yl)methyl)carbamate (581 mg 1.20 mmol) in DCM (10 mL) was added CF$_3$COOH (15 mL) and the mixture was stirred at room temperature for overnight. The solvent was concentrated to give crude product, which was used for next step without further purification.

Step 7: (6-cyclopropylimidazo[1,5-a]pyridin-5-yl) (4-(quinolin-4-yl)cyclohexyl)methanone To a solution of acetic anhydride (15 mL) and formic acid (10 mL) was stirred at 60° C. for 1 hour, after was added (6-(aminomethyl)-3-cyclopropylpyridin-2-yl)(4-(naphthalen-1-yl)cyclohexyl)methanone (611 mg, 1.20 mmol) in formic acid 5 mL. Then the mixture was stirred at 60° C. for 2 hours. After cooled to room temperature, the solvent was concentrated to dryness. The crude was added EA 50 mL, extracted with saturated sodium bicarbonate (50 mL×3). The organic layer was dried over $Na_2SO_4$, filtered and concentrated to dryness. And the crude was purified by column chromatography (PE:EA=5:1-1:1) to give product as a yellow solid (331 mg in 71% yield). $^1$H NMR (DMSO-$d_6$) $\delta_H$ 8.83 (d, J=4.4 Hz, 1H), 8.26 (d, J=8.4 Hz, 1H), 8.11 (s, 1H), 8.02 (d, J=8.4 Hz, 1H), 7.75 (t, J=8.0 Hz, 1H), 7.61-7.65 (m, 2H), 7.45 (s, 1H), 7.39 (d, J=4.4 Hz, 1H), 6.51 (d, J=9.6 Hz, 1H), 3.39-3.49 (m, 2H), 2.10-2.13 (m, 2H), 1.98-2.04 (m, 2H), 1.82-1.94 (m, 3H), 1.68-1.74 (m, 2H), 0.96-1.04 (m, 2H), and 0.77-0.79 (m, 2H).

Step 6: (6-cyclopropylimidazo[1,5-a]pyridin-5-yl) (4-(quinolin-4-yl)cyclohexyl)methanol To a solution of (6-cyclopropylimidazo[1,5-a]pyridin-5-yl)(4-(quinolin-4-yl)cyclohexyl)methanone (331 mg, 0.84 mmol) in methanol (10 mL) was added $NaBH_4$ (160 mg, 4.12 mmol) at room temperature and the mixture was stirred for 1 hour. Then the solvent was evaporated under reduced pressure and water (50 mL) was added, extracted with ethyl acetate (50 ml×3) and combined the organic layer, evaporated the solvent under reduced pressure and the residue was purified by Per-HPLC get a white solid (201 mg, in 67% yield). $^1$H NMR (DMSO-$d_6$) $\delta_H$ 8.78 (d, J=4.4 Hz, 1H), 8.66 (s, 1H), 8.22 (d, J=8.4 Hz, 1H), 8.00 (d, J=8.4 Hz, 1H), 7.74 (t, J=8.0 Hz, 1H), 7.62 (t, J=8.0 Hz, 1H), 7.37-7.42 (m, 2H), 7.33 (s, 1H), 6.50 (d, J=9.6 Hz, 1H), 5.86 (d, J=4.0 Hz, 1H), 5.30-5.35 (m, 1H), 3.39-3.41 (m, 1H), 3.16 (d, J=4.8 Hz, 1H), 2.29-2.32 (m, 2H), 2.00-2.04 (m, 2H), 1.62-1.82 (m, 2H), 1.36-1.55 (m, 3H), 1.21-1.24 (m, 1H), 0.94-1.04 (m, 2H), and 0.69-0.80 (m, 2H).

Example D140a and D140b: (S)-(6-cyclopropylimidazo[1,5-a]pyridin-5-yl)((1r,4S)-4-(quinolin-4-yl)cyclohexyl)methanol and (R)-(6-cyclopropylimidazo[1,5-a]pyridin-5-yl)((1 r,4R)-4-(quinolin-4-yl)cyclohexyl)methanol

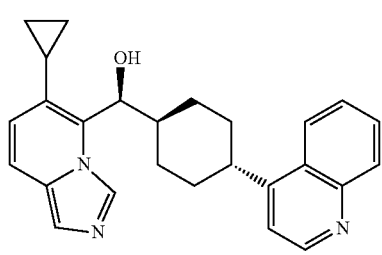

Fast isomer in CHIRALPAK IC-3 HPLC
Eluting reagent: Hex (0.1% DEA):EtOH = 50:50

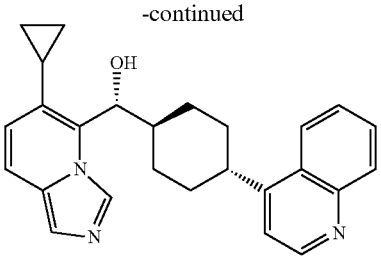

Slow isomer in CHIRALPAK IC-3 HPLC
Eluting reagent: Hex (0.1% DEA):EtOH = 50:50

Each enantiomer of racemic D140a and D140b was separated using preparative HPLC on a CHIRAL PAK IC with Hex:EtOH=50:50 as an eluent. The enantiomeric excesses were determined by using HPLC on a CHIRAL PAK IC with Hex (0.1%):EtOH=50:50 as an eluent at a flow rate of 1.0 mL/min. The first one enantiomer eluted at the retention time of 4.245 min (D140a), which was dissolved in DCM (10 mL), and added EA solution of hydrochloric acid (0.5 mL, 4.0M) at room temperature, followed by addition of methanol until the precipitate was dissolved, then the solvent was evaporated under reduced pressure and the residue was washed by PE to give the desired product as white solid. $^1$H NMR (DMSO-$d_6$) $\delta_H$ 9.71 (s, 1H), 9.17 (d, J=5.6 Hz, 1H), 8.55 (d, J=8.8 Hz, 1H), 8.35 (d, J=8.4 Hz, 1H), 8.09-8.13 (m, 2H), 7.94 (t, J=8.0 Hz, 1H), 7.85 (d, J=5.2 Hz, 1H), 7.74 (d, J=9.6 Hz, 1H), 6.90 (d, J=9.6 Hz, 1H), 6.33 (s, 1H), 5.40 (d, J=9.6 Hz, 1H), 3.55-3.74 (m, 2H), 2.25-2.34 (m, 1H), 2.14-2.22 (m, 1H), 2.02-2.12 (m, 1H), 1.80-1.90 (m, 1H), 1.69-1.78 (m, 1H), 1.48-1.64 (m, 3H), 1.30-1.38 (m, 1H), 1.07-1.14 (m, 2H), and 0.81-0.92 (m, 2H); and the other enantiomer eluted at the retention time of 5.933 min (D140b), $^1$H NMR (DMSO-$d_6$) $\delta_H$ 9.70 (s, 1H), 9.15 (d, J=5.6 Hz, 1H), 8.54 (d, J=8.8 Hz, 1H), 8.34 (d, J=8.4 Hz, 1H), 8.07-8.12 (m, 2H), 7.93 (t, J=8.0 Hz, 1H), 7.83 (d, J=5.2 Hz, 1H), 7.74 (d, J=9.6 Hz, 1H), 6.90 (d, J=9.6 Hz, 1H), 6.33 (s, 1H), 5.41 (d, J=9.6 Hz, 1H), 3.57-3.74 (m, 2H), 2.25-2.33 (m, 1H), 2.15-2.23 (m, 1H), 2.03-2.10 (m, 1H), 1.82-1.88 (m, 1H), 1.67-1.78 (m, 1H), 1.50-1.62 (m, 3H), 1.30-1.37 (m, 1H), 1.06-1.14 (m, 2H), and 0.81-0.92 (m, 2H). The absolute configurations of chiral carbons in D140a and D140b are tentatively assigned as (S) and (R) respectively based on assumption that the binding model of the more potent isomer D140a is the same as that of C101a with IDO1 enzyme, and the relative stereochemistry on cyclohexane is assigned as trans configuration on the cyclohexane.

Example D141: (6-cyclopropylimidazo[1,5-a]pyridin-5-yl)(4-(quinolin-5-yl)cyclohexyl)methanol

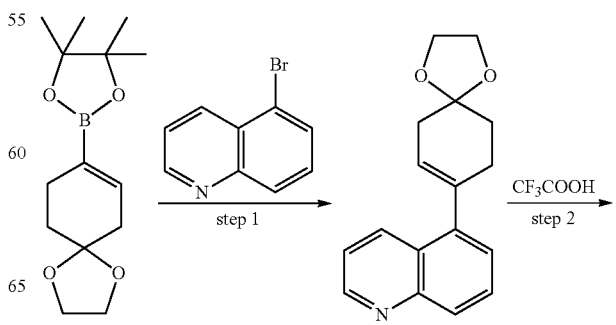

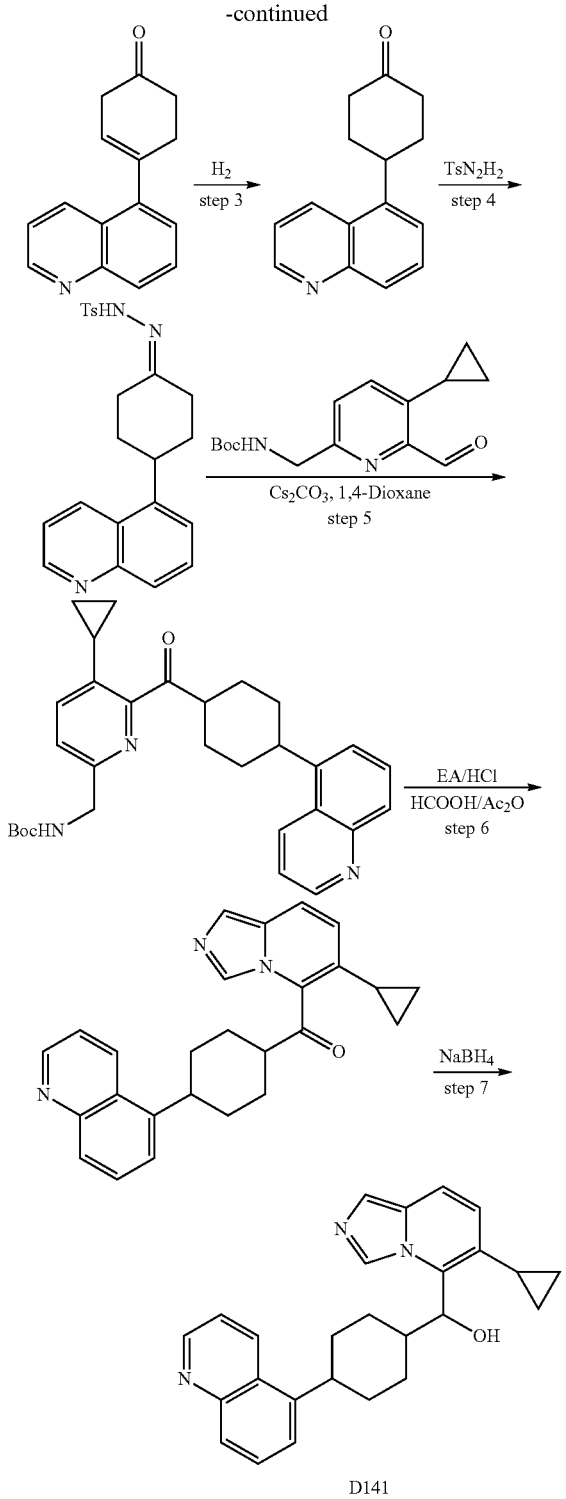

Step 1: 5-(1,4-Dioxaspiro[4.5]dec-7-en-8-yl)quinoline

Under N₂, a mixture of 5-bromoquinoline (8.0 g, 38.5 mmoL), 4,4,5,5-tetramethyl-2-(1,4-dioxaspiro[4.5]dec-7-en-8-yl)-1,3,2-dioxaborolane (10 g, 37.6 mmol), Pd(dppf)Cl₂ (4.0 g, 5.5 mmol) and Cs₂CO₃ (18 g, 55.2 mmol) in dioxane/H₂O (80 mL/20 mL) was heated to 90° C. for 3 hours. After cooling to rt, the solvent was evaporated under reduced pressure and the residue was purified by column chromatography on silica gel to give product (16 g) as oil. [M+H]⁺=268

Step 2: 4-(quinolin-5-yl)cyclohex-3-en-1-one

A solution of 5-(1,4-dioxaspiro[4.5]dec-7-en-8-yl)quinoline (16 g, 60 mmol) in TFA/DCM (100 mL/100 mL) was stirred for overnight at room temperature. The solvent was evaporated under reduced pressure and sat.NaHCO₃.aq (100 mL) was added, extracted with ethyl acetate (100 mL), the organic layer was washed with water and brine, dried over Na₂SO₄, concentrated and purified by sili-gel to give product (3.5 g).

Step 3: 4-(quinolin-5-yl)cyclohexan-1-one

A mixture of 4-(quinolin-5-yl)cyclohex-3-en-1-one (3.5 g, 15.7 mmol) and Pd/C (500 mg) in MeOH (150 mL) was stirred for overnight at room temperature under H₂ (1 atm). Then filtered to remove Pd/C and the filtrate was evaporated and then purified by column chromatography on silica gel to give product (1.75 g).

Step 4: 4-Methyl-N'-(4-(quinolin-5-yl)cyclohexylidene)benzenesulfonohydrazide

A solution of 4-(quinolin-5-yl)cyclohexan-1-one (1.75 g, 7.77 mmol) and 4-methylbenzenesulfonohydrazide (1.4 g, 7.52 mmol) in MeOH (50 mL) was stirred for 1 hour at room temperature, TLC shows starting material was disappeared, then filtered to give product (2.3 g).

Step 5: tert-butyl ((5-cyclopropyl-6-(4-(quinolin-5-yl)cyclohexane-1-carbonyl)pyridin-2-yl)methyl)carbamate A mixture of tert-butyl ((5-cyclopropyl-6-formylpyridin-2-yl)methyl)carbamate (0.6 g, 2.17 mmol), 4-methyl-N'-(4-(quinolin-5-yl)cyclohexylidene)benzenesulfonohydrazide (1.0 g, 2.54 mmol) and Cs₂CO₃ (2.0 g, 6.13 mmol) in 1,4-dioxane (20 mL) was heated at 90° C. for overnight. After cooling to rt, EA (30 mL) was added, filtered, and the filtrate was evaporated under reduced pressure to give crude product, which was purified by column chromatography to give product (520 mg). [M+H]⁺=486.2

Step 6: (6-cyclopropylimidazo[1,5-a]pyridin-5-yl)(4-(quinolin-5-yl)cyclohexyl)methanone A mixture of tert-butyl ((5-cyclopropyl-6-(4-(quinolin-5-yl)cyclohexane-1-carbonyl)pyridin-2-yl)methyl)carbamate (520 mg, 1.07 mmol) in HCl/EA (4M) was stirred for 30 min at room temperature, TLC show starting material disappeared, concentrated in vacuo to give crude product, which was dissolved in a solution of HCOOH/Ac₂O (15 mL/40 mL). The reaction mixture was stirred for overnight at 60° C. Then the solvent was concentrated in vacuo, sat.NaHCO₃.aq was added, extracted with EA, the EA layer was washed with brine, dried over Na₂SO₄, concentrated and purified by sili-gel to give product (350 mg). [M+H]⁺=396.2

Step 7: (6-cyclopropylimidazo[1,5-a]pyridin-5-yl)(4-(quinolin-5-yl)cyclohexyl)methanol A solution of (6-cyclopropylimidazo[1,5-a]pyridin-5-yl)(4-(quinolin-5-yl)cyclohexyl)methanone (350 mg, 0.88 mmol) and NaBH₄ (100 mg, 2.63 mmol) in MeOH (30 mL) was stirred for 1 hour at room temperature. Then the solvent was evaporated under reduced pressure and water (50 mL) was added, extracted with ethyl acetate (50 mL), the EA layer was washed with brine, dried over Na₂SO₄, concentrated and purified by sili-gel to give 210 mg. ¹H NMR (DMSO-d₆) $\delta_H$ 8.87-8.89 (d, J=3.6 Hz, 1H), 8.66 (s, 1H), 8.59-8.61 (d, J=8.8 Hz, 1H), 7.83-7.86 (d, J=8.4 Hz, 1H), 7.65-7.69 (t, J=8.0 Hz, 1H), 7.52-7.56 (dd, J₁=4.4 Hz, J₂=8.8 Hz, 1H), 7.46-7.48 (d, J=7.2 Hz, 1H), 7.40-7.43 (d, J=9.2 Hz, 1H), 7.33 (s, 1H), 6.50-6.52 (d, J=9.6 Hz, 1H), 5.84-5.85 (d, J=3.6 Hz, 1H), 5.31-5.36 (dd, J=3.6 Hz, J₂=9.6 Hz, 1H), 2.23-2.36 (m, 1H), 1.95-2.11 (m, 2H), 1.60-1.82 (m, 2H), 1.40-1.56 (m, 2H), 0.92-1.05 (m, 2H), 0.66-0.88 (m, 3H). [M+H]⁺=398.2.

Example D141a and D141b: (S)-(6-cyclopropylimidazo[, 5-a]pyridin-5-yl)((1r,4S)-4-(quinolin-5-yl)cyclohexyl)methanol and (R)-(6-cyclopropylimidazo[1,5-a]pyridin-5-yl)((1 r,4R)-4-(quinolin-5-yl)cyclohexyl)methanol

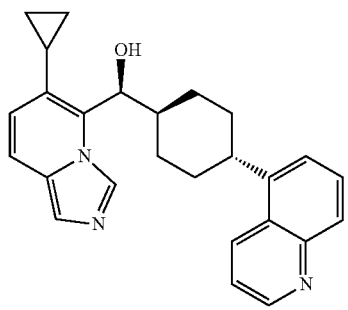

Fast isomer in CHIRALPAK IC
Eluting reagent: Hex:EtOH = 70:30

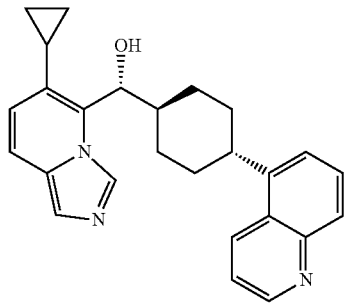

Slow isomer in CHIRALPAK IC
Eluting reagent: Hex:EtOH = 70:30

Each enantiomer of racemic D141a and D141b was separated using preparative HPLC on a CHIRALART CHIRALPAK IC with Hex:EtOH=70:30 as an eluent. The first one enantiomer eluted at the retention time of 2.927 min (D141a), which was dissolved in THF (5 ml), and HCl in EA(4N, 0.5 mL) was added and stirred at r.t for 1 h, the solvent was evaporated to give product as white solid, ¹H NMR (DMSO-d₆) $\delta_H$ 9.72 (s, 1H), 9.21 (d, J=4.8 Hz, 2H), 8.10-8.20 (m, 2H), 7.92-8.01 (m, 2H), 7.67-7.78 (m, 2H), 6.90 (d, J=9.6 Hz, 1H), 5.40 (d, J=9.6 Hz, 1H), 3.41-3.50 (m, 1H), 2.13-2.35 (m, 2H), 2.00-2.05 (m, 1H), 1.77-1.86 (m, 1H), 1.43-1.73 (m, 4H), 1.27-1.36 (m, 1H), 1.04-1.11 (m, 2H), and 0.80-0.94 (m, 2H), MS (ESI) m/e [M+1]⁺398.2; and the other enantiomer eluted at the retention time of 5.722 min (D141b), which was dissolved in THF (5 ml), and HCl in EA(4N, 0.5 mL) was added and the solvent was evaporated to give product as white solid, ¹H NMR (DMSO-d₆) $\delta_H$ 9.71 (s, 1H), 9.20 (d, J=4.8 Hz, 2H), 8.13-8.15 (m, 2H), 7.91-8.00 (m, 2H), 7.68-7.78 (m, 2H), 6.90 (d, J=9.6 Hz, 1H), 5.40 (d, J=9.6 Hz, 1H), 3.42-3.51 (m, 1H), 2.13-2.35 (m, 2H), 2.00-2.05 (m, 1H), 1.77-1.86 (m, 1H), 1.43-1.73 (m, 4H), 1.27-1.36 (m, 1H), 1.04-1.11 (m, 2H), and 0.80-0.94 (m, 2H), MS (ESI) m/e [M+1]⁺398.2. The absolute configurations of chiral carbons in D141a and D141b are tentatively assigned as (S) and (R) respectively based on assumption that the binding model of the more potent isomer D141a is the same as that of C1101a with IDO1 enzyme, and the relative stereochemistry on cyclohexane is assigned as trans configuration on the cyclohexane.

Example D142 and D143 were synthesized using the same procedure as example D139

Example D142: 3-(4-((6-cyclopropylimidazo[1,5-a]pyridin-5-yl)(hydroxy)methyl)cyclohexyl)phenol

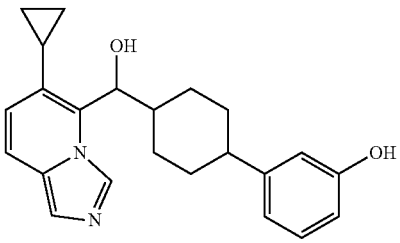 [SMILES: Oc1cccc(C2CCC(C(O)c3c(C4CC4)ccc4cncn34)CC2)c1]

¹H NMR (DMSO-d₆) $\delta_H$ 9.47 (s, 1H), 9.20 (s, 1H), 7.93 (s, 1H), 7.64-7.66 (d, J=9.6 Hz, 1H), 7.01-7.05 (t, J=7.6 Hz, 1H), 6.76-6.79 (d, J=9.6 Hz, 1H), 6.53-6.60 (m, 3H), 6.09 (s, 1H), 5.29-5.31 (d, J=9.6 Hz, 1H), 2.32-2.41 (m, 2H), 2.07-2.23 (m, 2H), 1.82-1.93 (m, 1H), 1.61-1.74 (m, 1H), 1.23-1.51 (m, 5H), 0.99-1.10 (m, 2H), and 0.71-0.88 (m, 2H)

Example D142a and D142b: 3-((1S,4r)-4-((S)-(6-cyclopropylimidazo[1,5-a]pyridin-5-yl)hydroxy)methyl)cyclohexyl)phenol and 3-((1R,4r)-4-((R)-(6-cyclopropylimidazo[1,5-a]pyridin-5-yl)(hydroxy)methyl)cyclohexyl)phenol

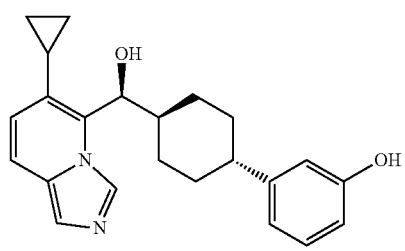

Fast isomer on Chiral OD-H
Eluting reagent:
n-Hexane/EtOH (0.1%DEA) = 80/20(v/v)

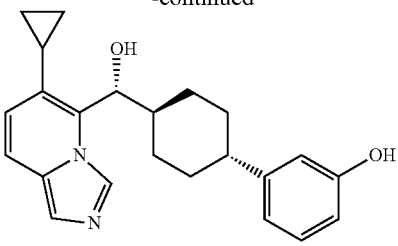

Slow isomer on Chiral OD-H
Eluting reagent:
n-Hexane/EtOH (0.1%DEA) = 80/20(v/v)

Example D143: (6-cyclopropylimidazo[1,5-a]pyridin-5-yl)(4-(3-methoxyphenyl)cyclohexyl)methanol

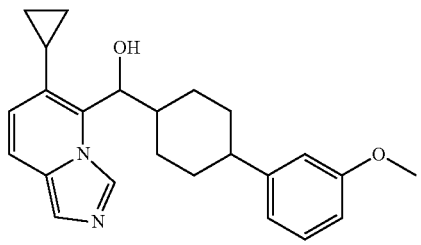 [SMILES: COc1cccc(C2CCC(C(O)c3c(C4CC4)ccc4cncn34)CC2)c1]

$^1$H NMR (DMSO-$d_6$) $\delta_H$ 8.63 (s, 1H), 7.40 (d, J=9.2 Hz, 1H), 7.32 (s, 1H), 7.15 (t, J=8.0 Hz, 1H), 6.69-6.77 (m, 3H), 6.47 (d, J=9.2 Hz, 1H), 5.0 (d, J=3.6 Hz, 1H), 5.25 (dd, J$_1$=9.6 Hz, J: =4.0 Hz, 1H), 3.70 (s, 3H), 2.37-2.47 (m, 2H), 2.14-2.27 (m, 1H), 1.97-2.06 (m, 1H), 1.84-1.92 (m, 1H), 1.62-1.69 (m, 1H), 1.44-1.57 (m, 1H). 1.20-1.33 (m, 4H), 0.89-1.00 (m, 2H), and 0.63-0.79 (m, 2H)

Example D143a and D143b: (S)-(6-cyclopropylimidazo[1,5-a]pyridin-5-yl)((1r,4S)-4-(3-methoxyphenyl)cyclohexyl)methanol and (R)-(6-cyclopropylimidazo[1,5-a]pyridin-5-yl) (1 r,4R)-4-(3-methoxyphenyl)cyclohexyl)methanol

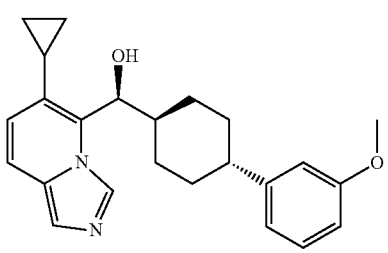

Fast isomer on Chiral OD-H
Eluting reagent:
n-Hexane/EtOH (0.1%DEA) = 80/20(v/v)

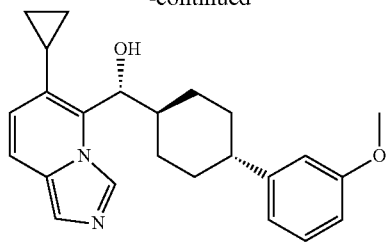

Slow isomer on Chiral OD-H
Eluting reagent:
n-Hexane/EtOH (0.1%DEA) = 80/20 (v/v)

Example D144: (6-cyclopropylimidazo[1,5-a]pyridin-5-yl)(4-(3,5-difluorophenyl)cyclohexyl)methanol

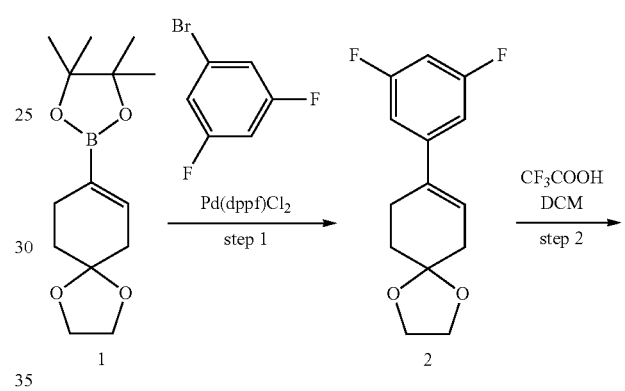

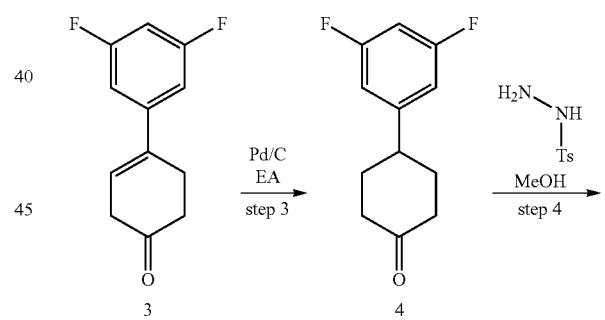

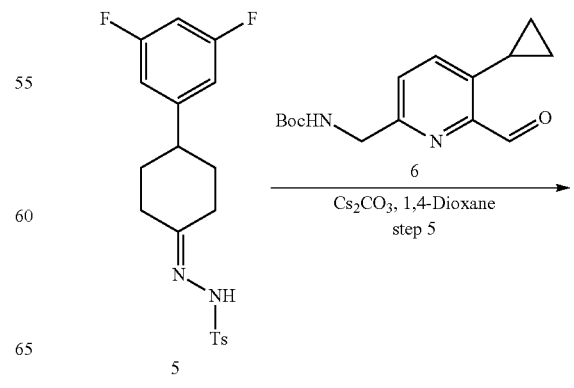

Step 2: 3',5'-difluoro-2,5-dihydro-[1,1'-biphenyl]-4(3H)-one

To a solution of 8-(3,5-difluorophenyl)-1,4-dioxaspiro[4.5]dec-7-ene (7 g, 28 mmol) in dichloromethane (40 mL) was added trifluoroacetic acid (40 mL) at room temperature and the mixture was stirred overnight. The solvent was evaporated under reduced pressure and water (100 mL) was added, extracted with ethyl acetate (100 mL×3), combined the organic layer and washed with saturated aqueous of NaHCO$_3$, then the organic layer was evaporated in vacuo to give crude product, which was used for next step without further purification. [M+H]$^+$=209.1.

Step 3: 4-(3,5-difluorophenyl)cyclohexan-1-one

To a solution of 3',5'-difluoro-2,5-dihydro-[1,1'-biphenyl]-4(3H)-one (28 mmol) in EA (150 mL) was added Pd/C (1.0 g, 10%) and the mixture was stirred for 16 hours at room temperature under H$_2$ (0.4 Mpa). Then filtered to remove Pd/C and the filtrate was evaporated under reduced pressure to give a crude product, and then purified by column chromatography (PE as eluent) to give product (3.4 g, oil). [M+H]$^+$=211.1.

Step 4: N'-(4-(3,5-difluorophenyl)cyclohexylidene)-4-methylbenzenesulfonohydrazide To a solution of 4-(3,5-difluorophenyl)cyclohexan-1-one (2.1 g, 10 mmol) in methol (30 mL) and DCM (10 mL) was added 4-methylbenzenesulfonohydrazide (1.86 g, 10 mmol) at room temperature and the mixture was stirred overnight. The solid was filtered to give product as a white solid (993 mg in 26% yield). $^1$H NMR (400 MHz, DMSO-d6) δ 10.21 (s, 1H), 7.74 (d, J=8.0 Hz, 2H), 7.40 (d, J=8.0 Hz, 2H), 7.06-6.94 (m, 3H), 3.00-2.78 (m, 2H), 2.39 (s, 3H), 2.30-2.17 (m, 2H), 2.02-1.86 (m, 3H), 1.64-1.39 (m, 2H). [M+H]$^+$=379.1.

Step 5: tert-butyl ((5-cyclopropyl-6-(4-(3,5-difluorophenyl)cyclohexane-1-carbonyl)pyridin-2-yl)methyl)carbamate To a solution of tert-butyl ((5-cyclopropyl-6-formylpyridin-2-yl)methyl)carbamate (725 mg, 2.6 mmol) in 1,4-dioxane (30 mL) was added N'-(4-(3,5-difluorophenyl)cyclohexylidene)-4-methylbenzenesulfonohydrazide (993 mg, 2.6 mmol) and Cs$_2$CO$_3$ (1.28 g, 3.9 mmol) at room temperature, and the mixture was heated at 95° C. overnight. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=3:1) to give product as a light yellow oil (0.85 g in 69% yield). [M+H]$^+$=471.2

Step 6: (3-cyclopropyl-6-((methyleneamino)methyl)pyridin-2-yl)(4-(3,5-difluorophenyl)cyclohexyl)methanone Trifluoracetic acid To a solution of tert-butyl ((5-cyclopropyl-6-(4-(3,5-difluorophenyl)cyclohexane-1-carbonyl)pyridin-2-yl)methyl)carbamate (0.85 g, 1.8 mmol) in DCM (40 mL) was added trifluoracetic acid (4 mL) and the mixture was stirred at room temperature overnight. The solvent was evaporated under reduced pressure to give crude product as oil.

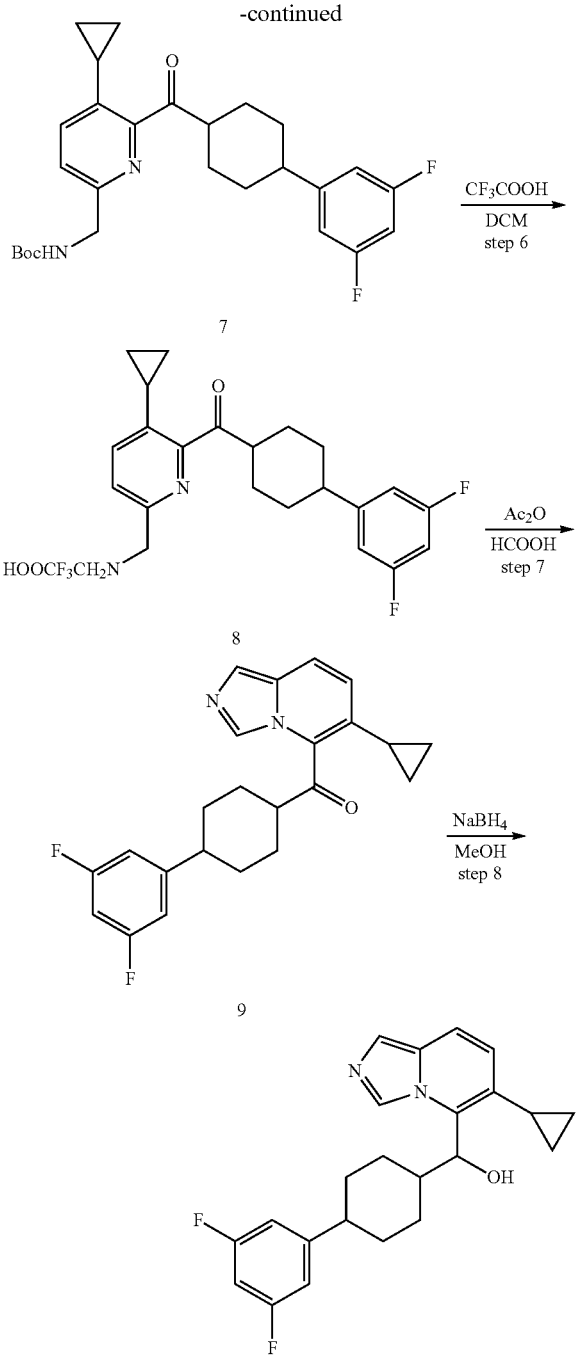

Step 1: 8-(3,5-difluorophenyl)-1,4-dioxaspiro[4.5]dec-7-ene

To a solution of 1-bromo-3,5-difluorobenzene (5 g, 26 mmoL) in 1,4-dioxane (50 mL) was added 4,4,5,5-tetramethyl-2-(1,4-dioxaspiro[4.5]dec-7-en-8-yl)-1,3,2-dioxaborolane (6.2 g, 26 mmol), Pd(dppf)Cl$_2$ (1.9 g, 2.6 mmol) and Cs$_2$CO$_3$ (12.7 g, 39 mmol) and the mixture was heated at 90° C. overnight. Then evaporated the solvent under reduced pressure and the residue was purified by column chromatography (PE:EA=5:1) to give product as an yellow solid (7 g in 74% yield). [M+H]$^+$=253.1.

Step 7: (6-cyclopropylimidazo[1,5-a]pyridin-5-yl) (4-(3,5-difluorophenyl)cyclohexyl)methanone A mixture of Ac₂O (30 mL) and HCOOH (10 mL) was heated at 50° C. for 1 hour and then a solution of (3-cyclopropyl-6-((methyleneamino)methyl)pyridin-2-yl)(4-(3,5-difluorophenyl)cyclohexyl)methanone Trifluoracetic acid (crude, 1.8 mmol) in HCOOH (5 mL) was added drop wise and the mixture was heated at 50° C. overnight. The solvent was evaporated under reduced pressure and water (50 mL) was added, washed with saturated aqueous of NaHCO₃, then extracted with ethyl acetate (30 mL×3) and combined the organic layer, the solvent was evaporated under reduced pressure and the residue was purified by column chromatography (PE:EA=3:1) to give crude product as a solid (510 mg in 75% yield). [M+H]⁺=381.1.

Step 8: (6-cyclopropylimidazo[1,5-a]pyridin-5-yl) (4-(3,5-difluorophenyl)cyclohexyl)methanol

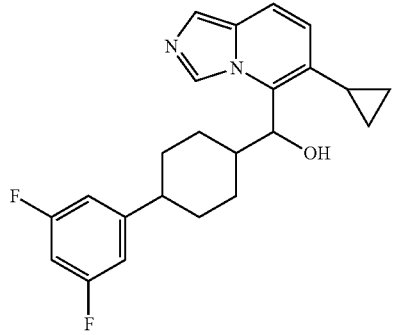 [SMILES: OC(c1c(C2CC2)ccc2cncn12)C1CCC(c2cc(F)cc(F)c2)CC1]

To a solution of (6-cyclopropylimidazo[1,5-a]pyridin-5-yl)(4-(3,5-difluorophenyl)cyclohexyl)methanone (510 mg, 1.34 mmol) in methanol (10 mL) was added NaBH₄ (255 mg, 6.7 mmol) at room temperature and the mixture was stirred for 4 h. Then the solvent was evaporated under reduced pressure and water (20 mL) was added, extracted with ethyl acetate (20 mL×3) and combined the organic layer, the solvent was evaporated under reduced pressure to give product as a white solid (230 mg in 45% yield). ¹H NMR (400 MHz, DMSO-d6) δ 8.61 (s, 1H), 7.40 (d, J=9.6 Hz, 1H), 7.31 (s, 1H), 6.98-6.89 (m, 3H), 6.47 (d, J=9.6 Hz, 1H), 5.82 (d, J=4.0 Hz, 1H), 5.25 (dd, J=9.6, 4.0 Hz, 1H), 2.41 (d, J=11.6 Hz, 1H), 2.28-2.16 (m, 1H), 2.05-1.96 (m, 1H), 1.88 (d, J=12.8 Hz, 1H), 1.71-1.63 (m, 1H), 1.58-1.44 (m, 1H), 1.35-1.10 (m, 5H), 1.02-0.89 (m, 2H), 0.81-0.73 (m, 1H), 0.71-0.60 (m, 1H). [M+H]⁺=383.2.

Example D144a and D144b: (S)-(6-cyclopropylimidazo[1,5-a]pyridin-5-yl)((1r,4S)-4-(3,5-difluorophenyl)cyclohexyl)methanol and (R)-(6-cyclopropylimidazo[1,5-a]pyridin-5-yl)((1r,4R)-4-(3,5-difluorophenyl)cyclohexyl)methanol

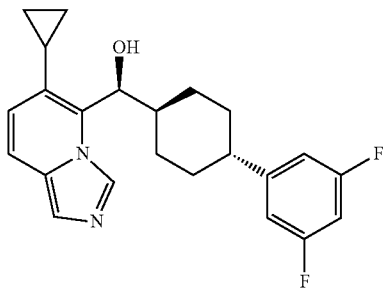

Fast isomer in CHIRALPAK IC HPLC
Eluting reagent: Hex:EtOH = 80:20

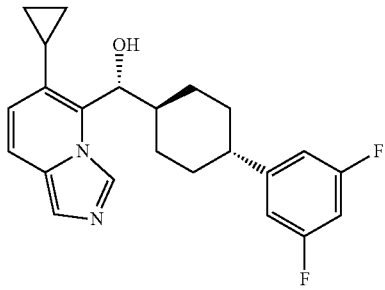

Slow isomer in CHIRALPAL IC HPLC
Eluting reagent: Hex:EtOH = 80:20

Each enantiomer of racemic D144a and D144b was separated using preparative HPLC on a CHIRAL IC with Hex:EtOH=80:20 as an eluent. The enantiomeric excesses were determined by using HPLC on a IC-H with Hex (0.1% DEA):EtOH=85:15 as an eluent at a flow rate of 1.0 mL/min. The first one enantiomer eluted at the retention time of 3.467 min (D144a), and the other enantiomer eluted at the retention time of 7.003 min (D144b). To a solution of D144a (102.5 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give desired product as white solid (99 mg in 88% yield). ¹H NMR (400 MHz, DMSO-d6) δ 9.64 (s, 1H), 8.08 (s, 1H), 7.71 (d, J=9.6 Hz, 1H), 7.30 (dd, J=15.6, 8.4 Hz, 1H), 7.19-7.09 (m, 1H), 7.06-6.93 (m, 1H), 6.84 (d, J=9.6 Hz, 1H), 6.23 (s, 1H), 5.33 (d, J=9.6 Hz, 1H), 2.76 (t, J=10.0 Hz, 1H), 2.41 (d, J=11.6 Hz, 1H), 2.26-2.11 (m, 2H), 1.87 (d, J=12.4 Hz, 1H), 1.71-1.61 (m, 1H), 1.59-1.45 (m, 1H), 1.44-1.16 (m, 4H), 1.15-0.97 (m, 2H), 0.93-0.73 (m, 2H). [M+H]⁺=383.2. To a solution of D144b (95.6 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give desired product as white solid (89 mg in 85% yield). 1H NMR (400 MHz, DMSO-d6) δ9.64 (s, 1H), 8.08 (s, 1H), 7.71 (d, J=9.6 Hz, 1H), 7.30 (dd, J=15.6, 8.4 Hz, 1H), 7.19-7.07 (m, 1H), 7.06-6.95 (m, 1H), 6.84 (d, J=9.6 Hz, 1H), 6.25 (s, 1H), 5.33

(d, J=9.6 Hz, 1H), 2.86-2.70 (m, 1H), 2.41 (d, J=12.4 Hz, 1H), 2.28-2.14 (m, 2H), 1.86 (d, J=12.0 Hz, 1H), 1.74-1.61 (m, 1H), 1.59-1.44 (m, 1H), 1.42-1.14 (m, 4H), 1.12-0.98 (m, 2H), 0.93-0.68 (m, 2H). [M+H]⁺=383.2. The absolute configurations of chiral carbons in D144a and D144b are tentatively assigned as (S) and (R) respectively based on assumption that the binding model of the more potent isomer D144a is the same as that of C101a with IDO11 enzyme, and the relative stereochemistry on cyclohexane is assigned as trans configuration on the cyclohexane.

Example D145: (6-cyclopropylimidazo[1,5-a]pyridin-5-yl)(4-(2,3,4-trifluorophenyl)cyclohexyl)methanol

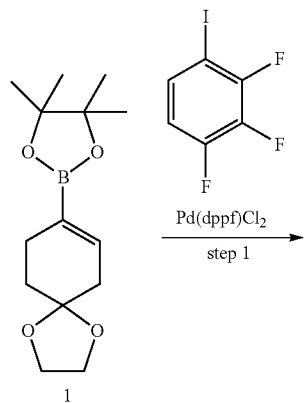

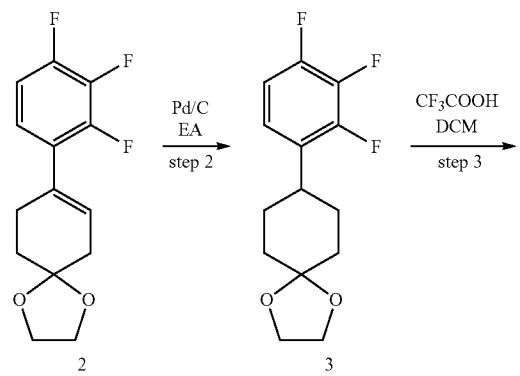

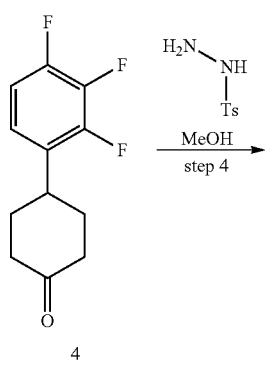

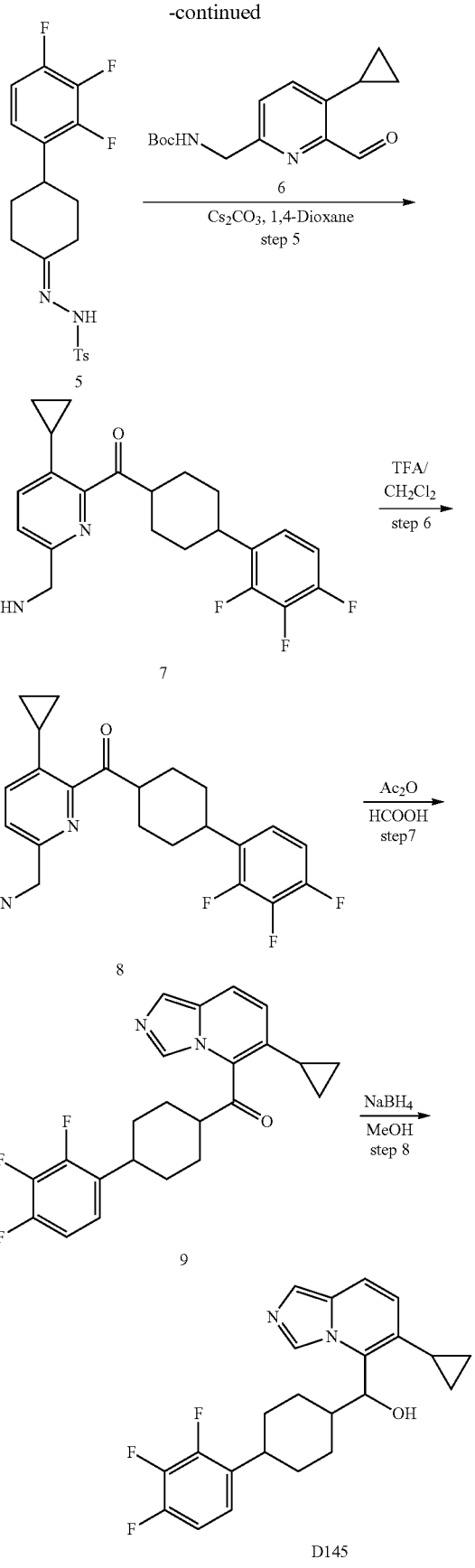

Step 1: 8-(2,3,4-trifluorophenyl)-1,4-dioxaspiro[4.5]dec-7-ene

To a solution of 1,2,3-trifluoro-4-iodobenzene (3.3 g, 18.8 mmoL) in 1,4-dioxane (100 mL) was added 4,4,5,5-tetramethyl-2-(1,4-dioxaspiro[4.5]dec-7-en-8-yl)-1,3,2-dioxaborolane (5 g, 18.8 mmol), Pd(dppf)Cl$_2$ (1.3 g, 1.88 mmol) and Cs$_2$CO$_3$ (9.2 g, 28.2 mmol) and the mixture was heated at 70° C. for 5 hours. Then evaporated the solvent under reduced pressure and the residue was purified by column chromatography (PE:EA=5:1) to give product as an oil (4.5 g in 88.6% yield).

Step 2: 8-(2,3,4-trifluorophenyl)-1,4-dioxaspiro[4.5]decane

To a solution of 8-(2,3,4-trifluorophenyl)-1,4-dioxaspiro[4.5]dec-7-ene (4.5 g, 16.7 mmol) in EtOAc (40 mL) was added Pd/C (1 g). The mixture was stirred overnight under H$_2$ (4 atm). The reaction mixture was filtered and the filtrate was concentrated to give target compound (4.6 g, 100%) as a white solid.

Step 3: 4-(2,3,4-trifluorophenyl)cyclohexan-1-one

To a solution of 8-(2,3,4-trifluorophenyl)-1,4-dioxaspiro[4.5]decane (4.6 g, 16.9 mmol) in CH$_2$Cl$_2$ (30 mL) was added TFA (10 mL). After the addition, the reaction mixture was stirred overnight. The reaction mixture was concentrated to give the residue, treated with EtOAc (100 mL), washed with aq.K$_2$CO$_3$, brine, dried over Na$_2$SO$_4$, concentrated and purified by column chromatography (petroleum ether/EtOAc=20:1-5:1) to give target compound (1.9 g, 49.3%) as a white solid.

Step 4: 4-methyl-N'-(4-(2,3,4-trifluorophenyl)cyclohexylidene)benzenesulfonohydrazide To a solution of 4-(2,3,4-trifluorophenyl)cyclohexan-1-one (1.9 g, 8.33 mmol) in CH$_2$Cl$_2$/methol (30 mL/10 mL) was added 4-methylbenzenesulfonohydrazide (1.55 g, 8.33 mmol) at room temperature and the mixture was stirred for overnight. Evaporate half the solvent under reduced pressure and then filtered to give product as a white solid (2.8 g in 84.9% yield). $^1$H NMR (DMSO-d$_6$) δ 10.21 (s, 1H), 7.73 (d, J=8.0 Hz, 2H), 7.40 (d, J=8.0 Hz, 2H), 7.29-7.10 (m, 2H), 3.15-3.05 (m, 1H), 2.92 (d, J=14.4 Hz, 1H), 2.39 (s, 3H), 2.31-2.22 (m, 2H), 2.05-1.81 (m, 3H), 1.68-1.46 (m, 2H) ppm.

Step 5: tert-butyl ((5-cyclopropyl-6-(4-(2,3,4-trifluorophenyl)cyclohexane-1-carbonyl)pyridin-2-yl)methyl)carbamate To a solution of tert-butyl ((5-cyclopropyl-6-formylpyridin-2-yl)methyl)carbamate (400 mg, 1.45 mmol) in 1,4-dioxane (50 mL) was added 4-methyl-N'-(4-(2,3,4-trifluorophenyl)cyclohexylidene)benzenesulfonohydrazide (574 mg, 1.45 mmol) and Cs$_2$CO$_3$ (709 mg, 2.18 mmol) at room temperature, and the mixture was heated at 90° C. overnight. The solvent was evaporated in vacuo and water (100 mL) was added, extracted with ethyl acetate (50 mL×3) and combined the organic layer, the solvent was evaporated under reduced pressure to give crude target compound as light yellow oil (800 mg in 100% yield). [M+H]$^+$=489

Step 6: (6-(aminomethyl)-3-cyclopropylpyridin-2-yl)(4-(2,3,4-trifluorophenyl)cyclohexyl)methanone Trifluoracetic acid To a solution of tert-butyl ((5-cyclopropyl-6-(4-(2,3,4-trifluorophenyl)cyclohexane-1-carbonyl)pyridin-2-yl)methyl)carbamate (0.8 g, 1.45 mmol) in DCM (40 mL) was added trifluoracetic acid (10 mL) and the mixture was stirred at room temperature overnight. The solvent was evaporated under reduced pressure to give crude product as yellow oil. [M+H]$^+$=389.

Step 7: (6-cyclopropylimidazo[1,5-a]pyridin-5-yl)(4-(2,3,4-trifluorophenyl)cyclohexyl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(6-(trifluoromethyl)pyridin-3-yl)cyclohexyl)methanone Trifluoracetic acid (crude, 1.45 mmol) in HCOOH (5 mL) was added dropwise and the mixture was heated at 50° C. overnight. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=5:1-2:1) to give crude product as a solid (178 mg in 30.8% yield over 3 steps). [M+H]$^+$=399.

Step 8: (6-cyclopropylimidazo[1,5-a]pyridin-5-yl)(4-(2,3,4-trifluorophenyl)cyclohexyl)methanol

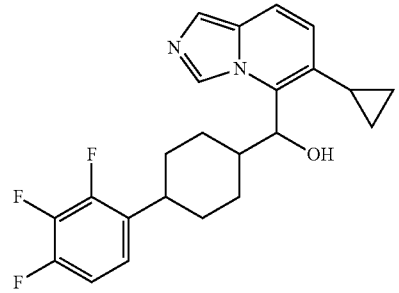 [SMILES: OC(c1c(C2CC2)ccc2cncn12)C1CCC(c2ccc(F)c(F)c2F)CC1]

To a solution of (6-cyclopropylimidazo[1,5-a]pyridin-5-yl)(4-(2,3,4-trifluorophenyl)cyclohexyl)methanone (178 g, 0.45 mmol) in methol (10 mL) was added NaBH$_4$ (50 mg, 1.2 mmol) at room temperature and the mixture was stirred for 20 min. Then the reaction was quenched with acetone and concentrated and purified by column chromatography (petroleum ether/EtOAc=4:1-100% EtOAc) to give product as a white solid (148 mg in 82.2% yield). $^1$H NMR (DMSO-d$_6$) δ 8.62 (s, 1H), 7.40 (d, J=9.6 Hz, 1H), 7.31 (s, 1H), 7.27-7.09 (m, 2H), 6.47 (d, J=9.6 Hz, 1H), 5.81 (d, J=3.6 Hz, 1H), 5.25 (dd, J=9.6, 3.6 Hz, 1H), 2.79 (m, 1H), 2.43 (m, 1H), 2.24-2.21 (m, 1H), 2.02 (s, 1H), 1.88-1.84 (m, 1H), 1.65-1.62 (m, 2H), 1.33-1.12 (m, 4H), 1.03-0.89 (m, 2H), 0.83-0.81 (m, 1H), 0.80-0.62 (m, 2H). [M+H]$^+$=401.

Example D145a and D145b: (S)-(6-cyclopropylimi-
dazo[1,5-a]pyridin-5-yl)((1r,4S)-4-(2,3,4-trifluoro-
phenyl)cyclohexyl)methanol and (R)-(6-cyclopropy-
limidazo[1,5-a]pyridin-5-yl)((1 r,4R)-4-(2,3,4-
trifluorophenyl)cyclohexyl)methanol D145b are tentatively assigned as (S) and (R) respectively based on assumption that the binding model of the more potent isomer D145a is the same as that of C101a with IDO1 enzyme, and the relative stereochemistry on cyclohexane is assigned as trans configuration on the cyclohexane.

Example D146: (6-cyclopropylimidazo[1,5-a]pyri-
din-5-yl)(4-(2-fluoro-4-methoxyphenyl)cyclohexyl)
methanol

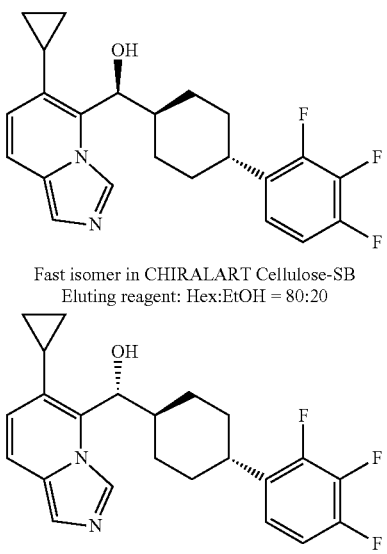

Fast isomer in CHIRALART Cellulose-SB
Eluting reagent: Hex:EtOH = 80:20

Slow isomer in CHIRALART Cellulose-SB
Eluting reagent: Hex:EtOH = 80:20

Each enantiomer of racemic D145a and D145b was separated using preparative HPLC on a CHIRALART Cellulose-SB with Hex:EtOH=80:20 as an eluent. The enantiomeric excesses were determined by using HPLC on a CHIRAL Cellulose-SB with Hex (0.1% IPAmine): EtOH=80:20 as an eluent at a flow rate of 1.0 mL/min. The first one enantiomer eluted at the retention time of 3.152 min (D145a), and the other enantiomer eluted at the retention time of 5.617 min (D145b). To a solution of D145a (64.2 mg) in $CH_2Cl_2$ (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (58 mg in 82.7% yield). $^1$H NMR (DMSO-$d_6$) δ 9.63 (s, 1H), 8.07 (s, 1H), 7.70 (d, J=9.6 Hz, 1H), 7.31-7.05 (m, 2H), 6.83 (d, J=9.6 Hz, 1H), 6.21 (s, 1H), 5.31 (d, J=9.6 Hz, 1H), 2.81-2.76 (m, 1H), 2.43-2.39 (m, 1H), 2.18 (m, 2H), 1.88 (d, J=12.4 Hz, 1H), 1.66 (m, 1H), 1.62-1.47 (m, 1H), 1.45-1.21 (m, 4H), 1.13-0.99 (m, 2H), 0.87-0.76 (m, 2H). [M+H]$^+$=401. To a solution of D145b (65.9 mg) in $CH_2Cl_2$ (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (57 mg in 79.2% yield). $^1$H NMR (DMSO-$d_6$) δ 9.61 (s, 1H), 8.05 (s, 1H), 7.70 (d, J=9.6 Hz, 1H), 7.33-7.05 (m, 2H), 6.83 (d, J=9.6 Hz, 1H), 6.20 (s, 1H), 5.32 (d, J=9.6 Hz, 1H), 2.79 (m, 1H), 2.41 (d, J=12.8 Hz, 1H), 2.18 (m, 2H), 1.90 (d, J=12.8 Hz, 1H), 1.66 (m, 1H), 1.58-1.50 (m, 1H), 1.43-1.20 (m, 4H), 1.10-0.99 (m, 2H), 0.90-0.74 (m, 2H). [M+H]$^+$=401. The absolute configurations of chiral carbons in D145a and

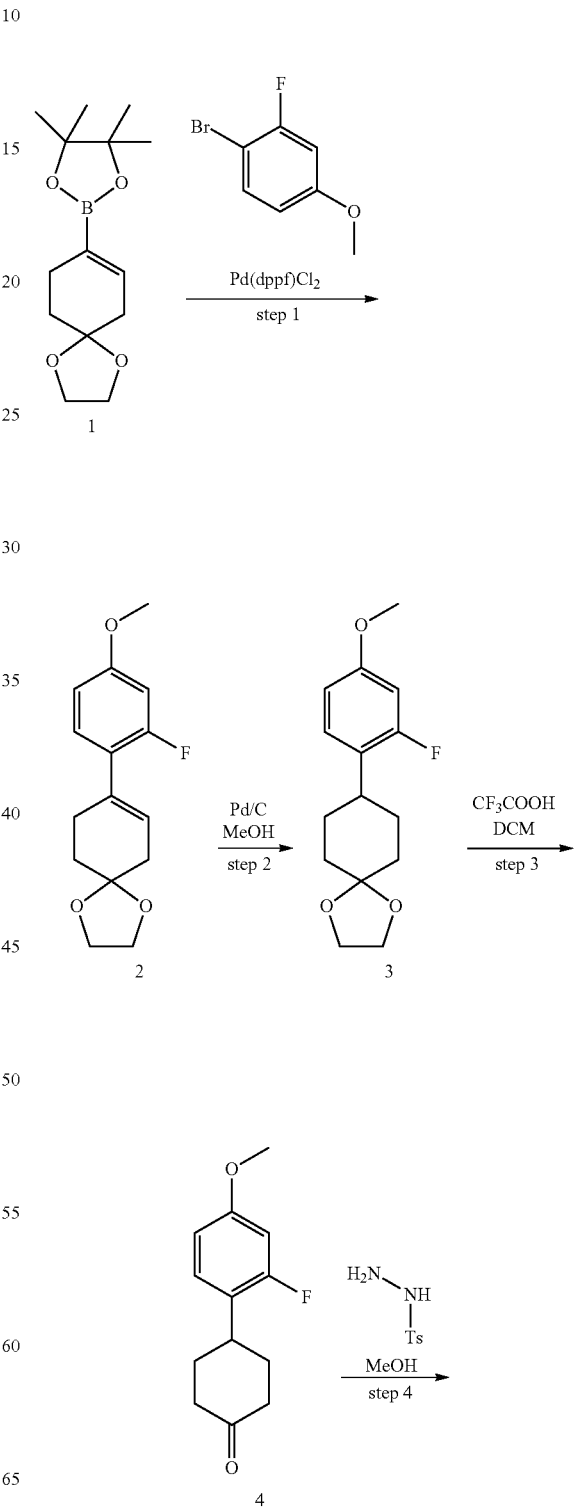

-continued

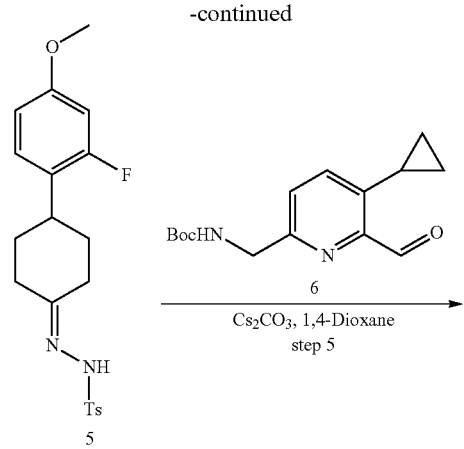

5

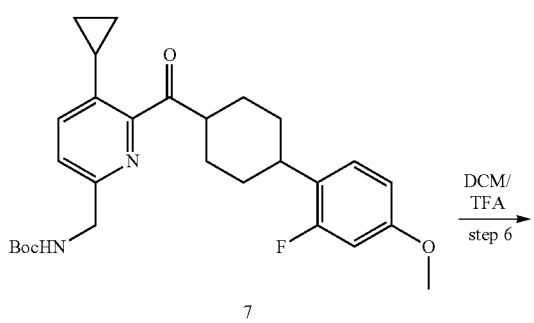

7

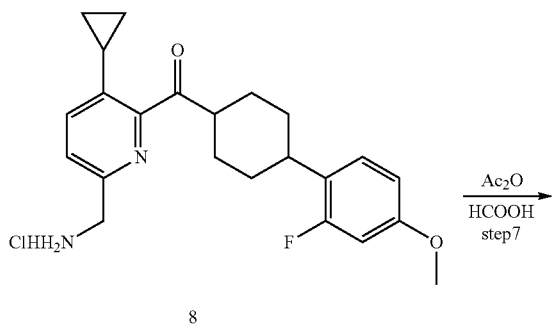

8

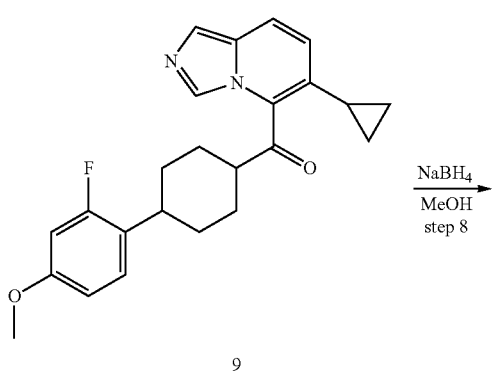

9

-continued

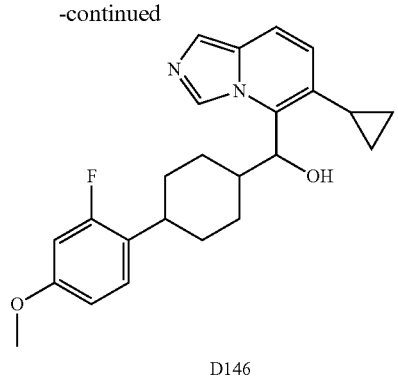

D146

Step 1: 8-(2-fluoro-4-methoxyphenyl)-1,4-dioxaspiro[4.5]dec-7-ene

To a solution of 1-bromo-2-fluoro-4-methoxybenzene (4.1 g, 20 mmoL) in 1,4-dioxane (60 mL) was added 4,4,5,5-tetramethyl-2-(1,4-dioxaspiro[4.5]dec-7-en-8-yl)-1,3,2-dioxaborolane (5.32 g, 20 mmol), Pd(dppf)Cl2 (731 mg, 1 mmol) and Cs$_2$CO$_3$ (9.7 g, 30 mmol) and the mixture was heated at 90° C. overnight. The mixture was cooled to room temperature, diluted with water (100 mL), extracted with ethyl acetate (75 mL×2), washed with brine, dried over Na$_2$SO$_4$, filtered and filtrate was evaporated under reduced pressure. The residue was purified by column chromatography (PE:EA=50:1) to give product as an oil (4 g in 75.7% yield).

Step 2: 8-(2-fluoro-4-methoxyphenyl)-1,4-dioxaspiro[4.5]decane

To a solution of 8-(2-fluoro-4-methoxyphenyl)-1,4-dioxaspiro[4.5]dec-7-ene (4 g, 15.15 mmol) in methanol (40 mL) was added Pd/C (0.4 g). The reaction was stirred at room temperature overnight under H$_2$ (balloon). Then filtered to remove Pd/C and the filtrate was evaporated under reduced pressure to give product as an oil (4 g, crude).

Step 3: 4-(2-fluoro-4-methoxyphenyl)cyclohexan-1-one

To a solution of 8-(2-fluoro-4-methoxyphenyl)-1,4-dioxaspiro[4.5]decane (4 g, crude) in dichloromethane (30 mL) was added trifluoroacetic acid (4 mL) at room temperature and the mixture was stirred for overnight. The reaction was quenched with saturated NaHCO$_3$ solution, extracted with dichloromethane (50 mL×2), then the organic layer was evaporated in vacuo. The residue was was purified by column chromatography (PE:EA=20:1) to give product (1.68 g in 50% yield for two steps). $^1$H NMR (DMSO-d$_6$) $\delta_H$ 7.26 (t, J=8.4 Hz, 1H), 6.85-6.70 (m, 2H), 3.73 (s, 3H), 3.31-3.21 (m, 1H), 2.66-2.54 (m, 2H), 2.30-2.21 (m, 2H), 2.06-1.95 (m, 2H), 1.93-1.78 (m, 2H).

Step 4: N'-(4-(2-fluoro-4-methoxyphenyl)cyclohexylidene)-4-methylbenzenesulfonohydrazide To a solution of 4-(2-fluoro-4-methoxyphenyl)cyclohexan-1-one (1.68 g, 7.56 mmol) in dichloromethane:methanol (10:30 mL) was added 4-methylbenzenesulfonohydrazide (1.4 g, 7.56 mmol) at room temperature and the mixture was stirred for overnight. The mixture was concentrated to dryness and to the residue was added PE:EA (30 mL:5 mL). A suspension was formed and filtered. The solid was collected and dried to give product as a white solid (2.1 g in 71.4% yield).

Step 5: tert-butyl ((5-cyclopropyl-6-(4-(2-fluoro-4-methoxyphenyl)cyclohexane-1-carbonyl)pyridin-2-yl)methyl)carbamate To a solution of tert-butyl ((5-cyclopropyl-6-formylpyridin-2-yl)methyl)carbamate (0.6 g, 2.17 mmol) in 1,4-dioxane (30 mL) was added N'-(4-(2-fluoro-4-methoxyphenyl)cyclohexylidene)-4-methylbenzenesulfonohydrazide (0.85 g, 2.17 mmol) and $Cs_2CO_3$ (1.06 g, 3.25 mmol) at room temperature, and the mixture was heated at 90° C. for 16 hours. The solvent was evaporated in vacuo and water (50 mL) was added, extracted with ethyl acetate (50 mL×3) and combined the organic layer, the solvent was evaporated under reduced pressure to give product as an oil (1.3 g, crude). $[M+H]^+=483$ Step 6: (6-(aminomethyl)-3-cyclopropylpyridin-2-yl)(4-(2-fluoro-4-methoxyphenyl)cyclohexyl)methanone Trifluoracetic acid To a solution of tert-butyl ((5-cyclopropyl-6-(4-(2-fluoro-4-methoxyphenyl)cyclohexane-1-carbonyl)pyridin-2-yl)methyl)carbamate (1.3 g, crude) in DCM (10 mL) was added trifluoracetic acid (5 mL) and the mixture was stirred at room temperature for 3 hours. The solvent was evaporated under reduced pressure to give crude product as solid. $[M+H]^+=383$.

Step 7: (6-cyclopropylimidazo[1,5-a]pyridin-5-yl)(4-(2-fluoro-4-methoxyphenyl)cyclohexyl)methanone A mixture of $Ac_2O$ (9 mL) and HCOOH (3 mL) was heated at 50° C. for 1 hour and then (6-(aminomethyl)-3-cyclopropylpyridin-2-yl)(4-(2-fluoro-4-methoxyphenyl)cyclohexyl)methanone Trifluoracetic acid (crude, 0.8 mmol) was added. The mixture was heated at 70° C. for 2 hours. The solvent was evaporated under reduced pressure and treated with saturated aqueous of $NaHCO_3$, then extracted with ethyl acetate (50 mL×3) and combined the organic layer, the solvent was evaporated under reduced pressure and the residue was purified by column chromatography (PE:EA=3:1) to give product as a solid (330 mg in 38.8% yield for three steps). $[M+H]^+=393$.

Step 8: (6-cyclopropylimidazo[1,5-a]pyridin-5-yl)(4-(2-fluoro-4-methoxyphenyl)cyclohexyl)methanol

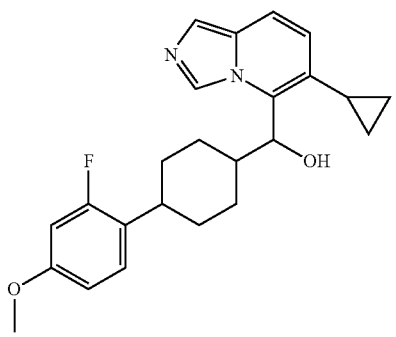 [SMILES: COc1ccc(C2CCC(C(O)c3c(C4CC4)ccc4cncn34)CC2)c(F)c1]

To a solution of (6-cyclopropylimidazo[1,5-a]pyridin-5-yl)(4-(2-fluoro-4-methoxyphenyl)cyclohexyl)methanone (0.33 g, 0.842 mmol) in methol (10 mL) was added $NaBH_4$ (160 mg, 4.2 mmol) at room temperature and the mixture was stirred for 2 h. The mixture was quenched with acetone (20 mL) and the solvent was evaporated under reduced pressure. The residue was purified by column chromatography (PE:EA=1:1) to give product as a solid (205 mg in 61.9% yield). $^1H$ NMR (DMSO-$d_6$) $\delta_H$ 8.64 (d, J=10.8 Hz, 1H), 7.44-7.37 (m, 1H), 7.35-7.30 (m, 1H), 7.17 (d, J=8.8 Hz, 1H), 6.76-6.64 (m, 2H), 6.48 (dd, J=4.0, 9.6 Hz, 1H), 5.84-5.78 (m, 1H), 5.26 (dd, J=3.2, 8.8 Hz, 1H), 3.71 (s, 3H), 2.75-2.64 (m, 1H), 2.46-2.38 (m, 1H), 2.26-2.14 (m, 1H), 2.10-1.99 (m, 1H), 1.89-1.78 (m, 1H), 1.66-1.45 (m, 2H), 1.37-1.10 (m, 4H), 1.02-0.90 (m, 2H), 0.80-0.72 (m, 1H), 0.70-0.61 (m, 1H). $[M+H]^+=395$.

Example D146a and D146b: (S)-(6-cyclopropylimidazo[1,5-a]pyridin-5-yl)((1r,4S)-4-(2-fluoro-4-methoxyphenyl)cyclohexyl)methanol and (R)-(6-cyclopropylimidazo[1,5-a]pyridin-5-yl)((1r,4R)-4-(2-fluoro-4-methoxyphenyl)cyclohexyl)methanol

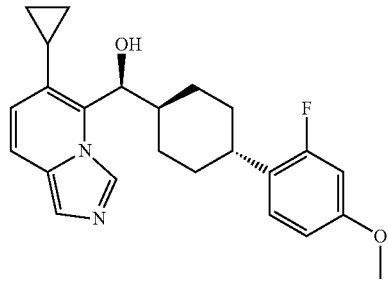

Fast isomer in CHIRALPAK IC HPLC
Eluting reagent: Hex(0.1%iPAmine):EtOH = 80:20

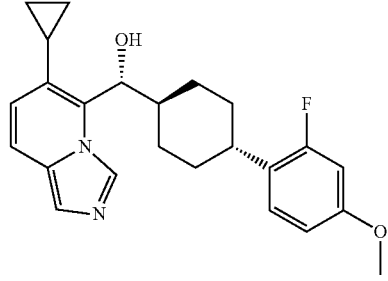

Slow isomer in CHIRALPAL IC HPLC
Eluting reagent: Hex(0.1%iPAmine):EtOH = 80:20

Each enantiomer of racemic D146a and D146b was separated using preparative HPLC on a CHIRALPAK IC with Hex (0.1% DEA):EtOH=80:20 as an eluent. The enantiomeric excesses were determined by using HPLC on a CHIRALPAK IC-3 with Hex (0.1% IPAmine):EtOH=80:20 as an eluent at a flow rate of 1.0 mL/min. The first one enantiomer eluted at the retention time of 1.608 min, and the other enantiomer eluted at the retention time of 3.139 min. To a solution of D146a (90 mg) in DCM (10 mL) was added drop wise of dioxane solution of hydrochloric acid (0.5 mL, 4.0M) at room temperature and stirred for 0.5 hour. Then the solvent was evaporated under reduced pressure and the residue was treated with distilled water (10 mL). The resulting mixture was lyophilized to give the desired product as white solid (86 mg in 87.7% yield). $^1H$ NMR (DMSO-$d_6$)

δ_H 9.63 (s, 1H), 8.07 (s, 1H), 7.70 (d, J=9.2 Hz, 1H), 7.15 (t, J=9.2 Hz, 1H), 6.84 (d, J=9.6 Hz, 1H), 6.76-6.67 (m, 2H), 6.21 (s, 1H), 5.32 (d, J=9.2 Hz, 1H), 3.72 (s, 3H), 2.76-2.64 (m, 1H), 2.45-2.36 (m, 1H), 2.25-2.13 (m, 2H), 1.90-1.80 (m, 1H), 1.70-1.61 (m, 1H), 1.58-1.45 (m, 1H), 1.40-1.15 (m, 4H), 1.10-0.99 (m, 2H), 0.90-0.74 (m, 2H). [M+H]⁺=395. To a solution of D146b (97 mg) in DCM (10 mL) was added drop wise of dioxane solution of hydrochloric acid (0.5 mL, 4.0M) at room temperature, and stirred for 0.5 hour. Then the solvent was evaporated under reduced pressure and the residue was treated with distilled water (10 mL). The resulting mixture was lyophilized to give the desired product as white solid (93 mg in 87.9% yield). ¹H NMR (DMSO-d₆) δ_H 9.56 (s, 1H), 8.01 (s, 1H), 7.68 (d, J=9.6 Hz, 1H), 7.15 (t, J=9.2 Hz, 1H), 6.81 (d, J=9.6 Hz, 1H), 6.76-6.65 (m, 2H), 6.15 (s, 1H), 5.32 (d, J=9.2 Hz, 1H), 3.71 (s, 3H), 2.76-2.64 (m, 1H), 2.44-2.36 (m, 1H), 2.25-2.10 (m, 2H), 1.90-1.82 (m, 1H), 1.68-1.61 (m, 1H), 1.56-1.44 (m, 1H), 1.40-1.15 (m, 4H), 1.09-0.98 (m, 2H), 0.89-0.73 (m, 2H). [M+H]⁺=395. The absolute configurations of chiral carbons in D146a and D146b are tentatively assigned as (S) and (R) respectively based on assumption that the binding model of the more potent isomer D146a is the same as that of C101a with IDO1 enzyme, and the relative stereochemistry on cyclohexane is assigned as trans configuration on the cyclohexane.

Example D147: (4-(2-chloro-4-methoxyphenyl)cyclohexyl)(6-cyclopropylimidazo[1,5-a]pyridin-5-yl)methanol

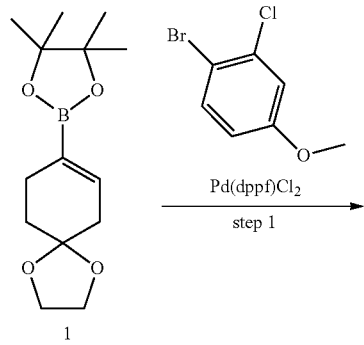

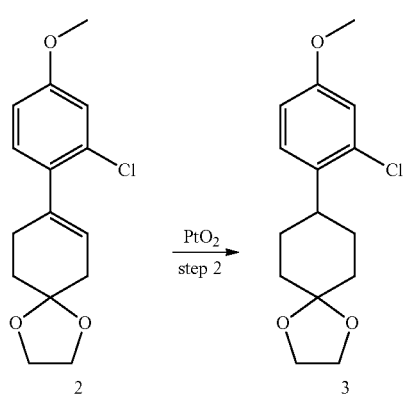

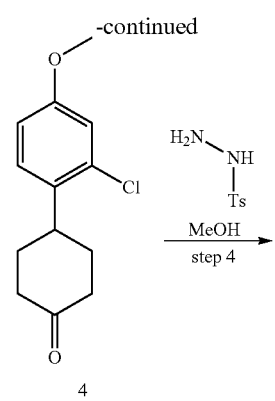

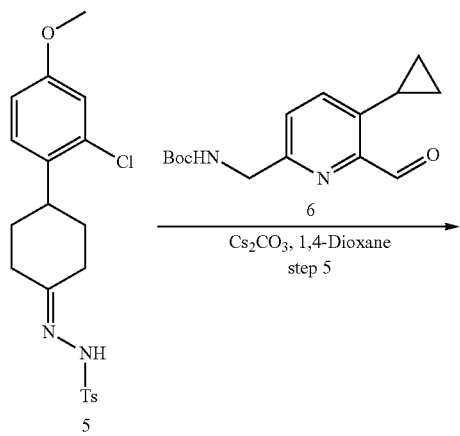

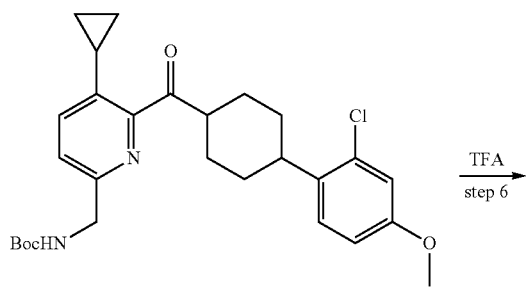

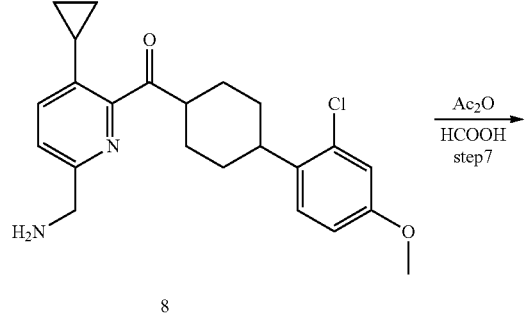

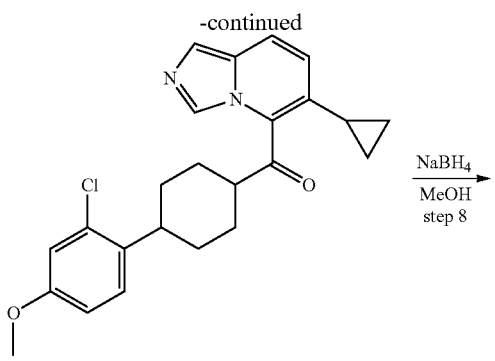

Step 1: 8-(2-chloro-4-methoxyphenyl)-1,4-dioxaspiro[4.5]dec-7-ene

To a solution of 1-bromo-2-chloro-4-methoxybenzene (6.6 g, 30 mmoL) in 1,4-dioxane (150 mL) was added with 4,4,5,5-tetramethyl-2-(1,4-dioxaspiro[4.5]dec-7-en-8-yl)-1,3,2-dioxaborolane (8 g, 30 mmol), Pd(dppf)$_2$Cl$_2$ (2.2 g, 3 mmol) and Cs$_2$CO$_3$ (14.7 g, 45 mmol) and the mixture was heated at 90° C. overnight. After evaporated the solvent under reduced pressure, the residue was added with water (80 mL), extracted with ethyl acetate (80 mL). The organic layer was dried, concentrated and purified by column chromatography (PE:EA=80:1) to give product as a white solid (6.2 g in 74% yield). $^1$H NMR (CDCl$_3$) $\delta_H$ 7.12 (d, J=12.0 Hz, 1H), 6.90 (d, J=1.2 Hz, 1H), 6.75 (dd, J=8.0 Hz, J$_2$=4.0 Hz, 1H), 5.56-5.54 (m, 1H), 4.04-4.01 (m, 4H), 3.79 (s, 3H), 2.55-2.51 (m, 2H), 2.45-2.42 (m, 2H), 1.89 (t, J=6.4 Hz, 2H). [M+H]$^+$=281.1.

Step 2: 8-(2-chloro-4-methoxyphenyl)-1,4-dioxaspiro[4.5]decane

To a solution of 8-(2-chloro-4-methoxyphenyl)-1,4-dioxaspiro[4.5]dec-7-ene (3 g, 11 mmol) in dichloromethane (50 mL) was added with PtO$_2$ (600 mg, 20%) and the mixture was stirred at room temperature under H$_2$ balloon overnight. The solution was filtered and the filtrate was evaporated under reduced pressure to give a crude product, which was used in the next step directly (2.6 g, crude).

Step 3: 4-(2-chloro-4-methoxyphenyl)cyclohexan-1-one

To a solution of 8-(2-chloro-4-methoxyphenyl)-1,4-dioxaspiro[4.5]decane (2.6 g, crude) in dichloromethane (20 mL) was added with trifluoroacetic acid (10 mL) and the mixture was stirred at room temperature overnight. The solvent was evaporated under reduced pressure and water (20 mL) was added, extracted with ethyl acetate (20 mL×2), combined the organic layers and washed with saturated aqueous of NaHCO$_3$ (20 mL), then the organic layer was evaporated in vacuo to give crude product, which was purified by column chromatography (PE:EA=40:1) to get the product as a white solid (760 mg, 30% yield in two steps). $^1$H NMR (CDCl$_3$) $\delta_H$ 7.14 (d, J=12 Hz, 1H), 6.94 (d, J=4.0 Hz, 1H), 6.80 (dd, J$_1$=8.0 Hz, J$_2$=4.0 Hz, 1H), 3.79 (s, 3H), 3.49-3.41 (m, 1H), 2.60-2.47 (m, 4H), 2.24-2.19 (m, 2H), 1.89-1.79 (m, 2H). [M+H]$^+$=239.1.

Step 4: N'-(4-(2-chloro-4-methoxyphenyl)cyclohexylidene)-4-methyl benzene sulfonohydrazide To a solution of 4-(2-chloro-4-methoxyphenyl)cyclohexan-1-one (750 mg, 3.2 mmol) in methanol (10 mL) and chloromethane (3 mL) was added with 4-methylbenzene sulfono hydrazide (586 mg, 3.2 mmol) and the mixture was stirred at room temperature overnight. After concentrated under reduced pressure, the residue was redissolved in PE/EA solvent (v/v=10:1, 20 mL), and then filtered to give product as a white solid (1.2 g in 92% yield).

Step 5: tert-butyl ((6-(4-(2-chloro-4-methoxyphenyl)cyclohexane-1-carbonyl)-5-cyclo propylpyridine-2-yl)methyl)carbamate To a solution of tert-butyl ((5-cyclopropyl-6-formylpyridin-2-yl)methyl) carbamate (860 mg, 3.1 mmol) in 1,4-dioxane (40 mL) was added with N'-(4-(2-chloro-4-methoxyphenyl)cyclohexylidene)-4-methyl benzene sulfonohydrazide (1.2 g, 3.1 mmol) and Cs$_2$CO$_3$ (1.5 g, 4.7 mmol) at room temperature, and the mixture was heated at 90° C. overnight. The solvent was evaporated in vacuo and water (20 mL) was added, extracted with ethyl acetate (20 mL×2) and combined the organic layers, the solvent was evaporated under reduced pressure to give the crude product, which was used in the next step directly (1.5 g, crude).

Step 6: (6-(aminomethyl)-3-cyclopropylpyridin-2-yl)(4-(2-chloro-4-methoxyphenyl)cyclohexyl)methanone To a solution of tert-butyl ((6-(4-(2-chloro-4-methoxyphenyl)cyclohexane-1-carbonyl)-5-cyclo propylpyridin-2-yl)methyl)carbamate (1.5 g, crude) in DCM (30 mL) was added with trifluoroacetic acid (5 mL) and the mixture was stirred at room temperature for 2 hours. The solvent was evaporated under reduced pressure to give the crude product, which was used in the next step directly.

Step 7: (4-(2-chloro-4-methoxyphenyl)cyclohexyl)(6-cyclopropylimidazo[1,5-a]pyridin-5-yl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(2-chloro-4-methoxyphenyl)cyclohexyl)methanone (1.2 g, 3.1 mmol) in HCOOH (5 mL) was added drop wise and the mixture was heated at 70° C. for 2 hours. The solvent was evaporated under reduced pressure and water (20 mL) was added, washed with saturated aqueous of NaHCO$_3$ (20 mL), then extracted with ethyl acetate (20 mL×2) and combined the organic layers, the solvent was evaporated under reduced pressure and the residue was purified by column chromatography (PE:EA=10:1 to 6:1) to give the product as a yellow oil (395 mg, 31% yield in three steps). $^1$H NMR (CDCl$_3$) $\delta_H$ 8.06-8.03 (m, 1H), 7.47-7.43 (m, 2H), 7.11 (d, J=8.0 Hz, 1H), 6.91 (d, J=4.0 Hz, 1H), 6.77 (dd, J$_1$=8.0 Hz, J$_2$=4.0 Hz, 1H), 6.45-6.42 (m, 1H), 3.77 (s, 3H), 3.29 (t, J=12.0 Hz, 1H), 3.02 (t, J=12.0 Hz, 1H), 2.11 (d, J=12.0 Hz, 2H), 2.05-2.01 (m, 2H), 1.94-1.85 (m, 1H), 1.84-1.74 (m, 2H), 1.49-1.39 (m, 2H), 1.05-1.03 (m, 2H), 0.78-0.77 (m, 2H). [M+H]$^+$=409.1.

Step 8: (4-(2-chloro-4-methoxyphenyl)cyclohexyl)(6-cyclopropylimidazo[1,5-a]pyridin-5-yl)methanol

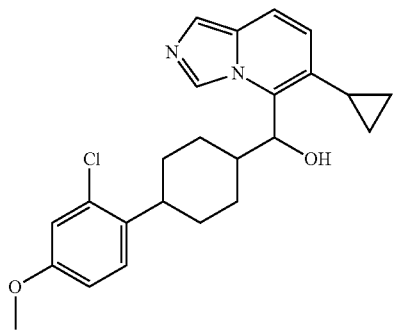 [SMILES: COc1ccc(C2CCC(C(O)c3c(C4CC4)ccc4cncn34)CC2)c(Cl)c1]

To a solution of (4-(2-chloro-4-methoxyphenyl)cyclohexyl)(6-cyclopropy limidazo[1,5-a]pyridin-5-yl)methanone (290 mg, 0.71 mmol) in methanol (10 mL) was added with NaBH$_4$ (135 mg, 3.5 mmol) at room temperature and the mixture was stirred for 1 hour. Then the solvent was evaporated under reduced pressure and water (10 mL) was added, extracted with ethyl acetate (10 mL×2) and combined the organic layer, the solvent was evaporated under reduced pressure to give the residue, which was purified by column chromatography (PE:EA=6:1 to 4:1) to get the product as a white solid (210 mg in 72% yield). $^1$H NMR (DMSO-d$_6$) $\delta_H$ 8.63 (s, 1H), 7.40 (d, J=8.0 Hz, 1H), 7.31 (s, 1H), 7.23 (d, J=12.0 Hz, 1H), 6.95 (d, J=4.0 Hz, 1H), 6.85 (dd, J$_1$=8.0 Hz, J$_2$=4.0 Hz, 1H), 6.47 (d, J=8.0 Hz, 1H), 5.81 (d, J=4.0 Hz, 1H), 5.27 (dd, J$_1$=12.0 Hz, J$_2$=4.0 Hz, 1H), 3.70 (s, 3H), 2.85-2.81 (m, 1H), 2.43 (d, J=12.0 Hz, 1H), 2.25-2.20 (m, 1H), 2.05-1.99 (m, 1H), 1.85 (d, J=12.0 Hz, 1H), 1.65-1.61 (m, 1H), 1.52-1.43 (m, 1H), 1.35-1.17 (m, 4H), 0.97-0.90 (m, 2H), 0.77-0.74 (m, 1H), 0.67-0.65 (m, 1H). [M+H]$^+$=411.1.

Example D147a and D147b: (S)-((1r,4S)-4-(2-chloro-4-methoxyphenyl)cyclohexyl)(6-cyclopropylimidazo[1,5-a]pyridin-5-yl)methanol and (R)-((1r,4R)-4-(2-chloro-4-methoxyphenyl)cyclohexyl)(6-cyclopropylimidazo[1,5-a]pyridin-5-yl)methanol

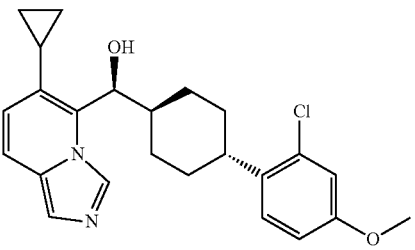

Fast isomer in CHIRALPAK IC HPLC
Eluting reagent: Hex:EtOH = 80:20

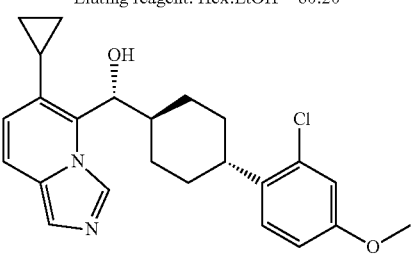

Slow isomer in CHIRALPAK IC HPLC
Eluting reagent: Hex:EtOH = 80:20

Each enantiomer of racemic D147a and D147b was separated using preparative HPLC on a CHIRALPAK IC with Hex:EtOH=80:20 as an eluent. The enantiomeric excesses were determined by using HPLC on a CHIRALPAK IC-3 with Hex (0.1% IPAmine):EtOH=70:30 as an eluent at a flow rate of 1.0 mL/min. The first one enantiomer eluted at the retention time of 1.225 min (D147a), and the other enantiomer eluted at the retention time of 1.948 min (D147b). To a solution of D147a (103 mg) in DCM (5 mL) was added dropwise of 1,4-dioxane solution of hydrochloric acid (0.5 mL, 4.0M) at room temperature. After stirred at r.t for 30 mins, the solvent was evaporated under reduced pressure and the residue was added with water (5 mL), lyophilized to give the desired product of HCl salt as a white solid (90 mg in 80% yield). $^1$H NMR (DMSO-d$_6$) $\delta_H$ 9.62 (s, 1H), 8.06 (s, 1H), 7.70 (d, J=8.0 Hz, 1H), 7.20 (d, J=8.0 Hz, 1H), 6.97 (d, J=2.4 Hz, 1H), 6.86 (dd, J$_1$=8.0 Hz, J$_2$=4.0 Hz, 1H), 6.83 (d, J=8.0 Hz, 1H), 6.20 (br, 1H), 5.34 (d, J=8.0 Hz, 1H), 3.73 (s, 3H), 2.86-2.84 (m, 1H), 2.40 (d, J=12.0 Hz, 1H), 2.25-2.15 (m, 2H), 1.86 (d, J=12.0 Hz, 1H), 1.68-1.64 (m, 1H), 1.48-1.23 (m, 5H), 1.07-1.03 (m, 2H), 0.86-0.76 (m, 2H). [M+H]$^+$=411.1. To a solution of D147b (101 mg) in DCM (5 mL) was added dropwise of 1,4-dioxane solution of hydrochloric acid (0.5 mL, 4.0M) at room temperature. After stirred at r.t for 30 mins, the solvent was evaporated under reduced pressure and the residue was added with water (5 mL), lyophilized to give the desired product of HCl salt as a white solid (92 mg in 83% yield). $^1$H NMR (DMSO-d$_6$) $\delta_H$ 9.61 (s, 1H), 8.05 (s, 1H), 7.70 (d, J=8.0 Hz, 1H), 7.20 (d, J=8.0 Hz, 1H), 6.97 (d, J=2.4 Hz, 1H), 6.86 (dd, J$_1$=8.0 Hz, J$_2$=4.0 Hz, 1H), 6.83 (d, J=12.0 Hz, 1H), 6.19 (br, 1H), 5.33 (d, J=9.6 Hz, 1H), 3.73 (s, 3H), 2.86-2.84 (m, 1H), 2.41 (d, J=12.0 Hz, 1H), 2.25-2.15 (m, 2H), 1.86 (d, J=12.0 Hz, 1H), 1.67-1.65 (m, 1H), 1.48-1.25 (m, 5H), 1.05

(d, J=8.0 Hz, 2H), 0.84-0.78 (m, 2H). [M+H]⁺=411.1. The absolute configurations of chiral carbons in D147a and D147b are tentatively assigned as (S) and (R) respectively based on assumption that the binding model of the more potent isomer D147a is the same as that of C101a with IDO1 enzyme, and the relative stereochemistry on cyclohexane is assigned as trans configuration on the cyclohexane.

Example D148: (4-(3-chloro-4-methoxyphenyl)cyclohexyl)(6-cyclopropylimidazo[1,5-a]pyridin-5-yl)methanol

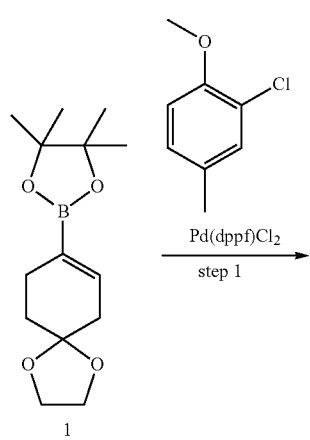

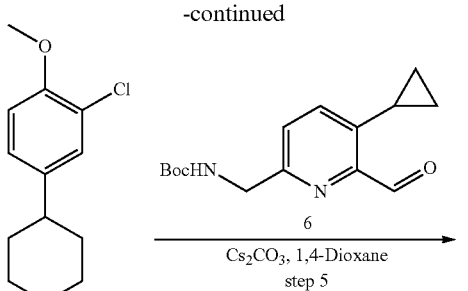

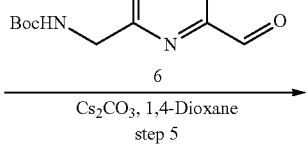

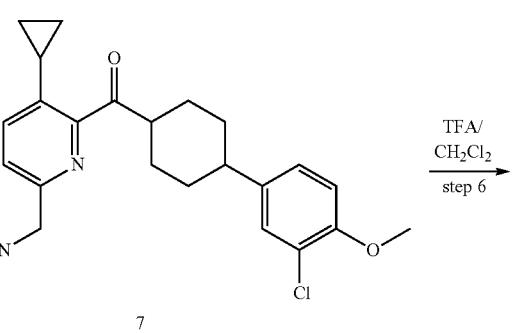

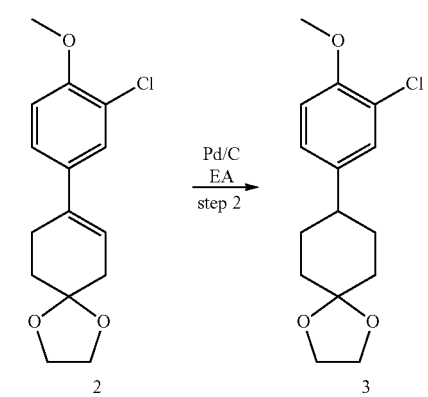

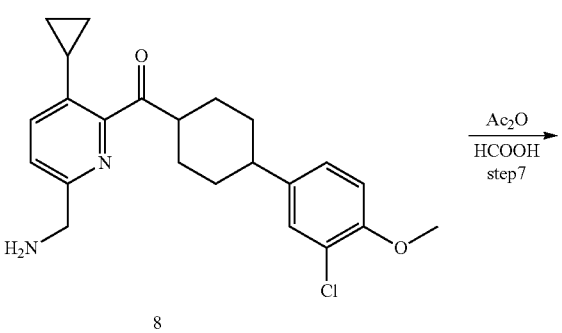

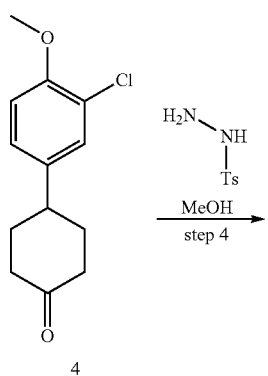

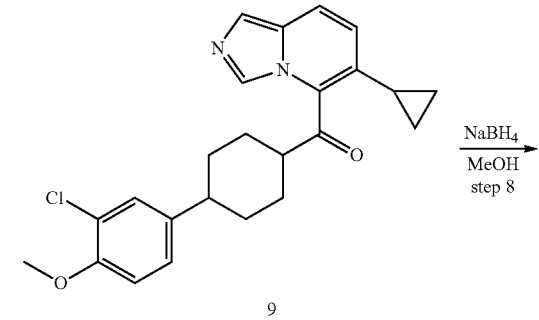

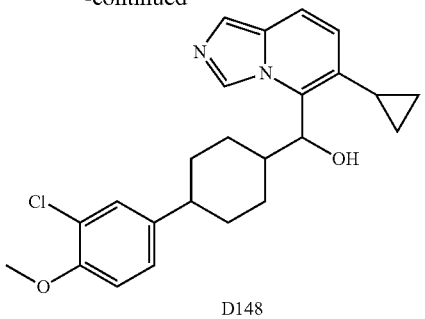

D148

Step 1: 8-(3-chloro-4-methoxyphenyl)-1,4-dioxaspiro[4.5]dec-7-ene

To a solution of 2-chloro-4-iodo-1-methoxybenzene (2.68 g, 10 mmoL) in 1,4-dioxane (100 mL) was added 4,4,5,5-tetramethyl-2-(1,4-dioxaspiro[4.5]dec-7-en-8-yl)-1,3,2-dioxaborolane (2.66 g, 10 mmol), Pd(dppf)Cl$_2$ (0.73 g, 1 mmol) and Cs$_2$CO$_3$ (6.4 g, 20 mmol) and the mixture was heated at 90° C. for 3 hours. Then evaporated the solvent under reduced pressure and the residue was purified by column chromatography (PE:EA=5:1) to give product as a yellow solid (1.7 g in 60.7% yield).

Step 2: 8-(3-chloro-4-methoxyphenyl)-1,4-dioxaspiro[4.5]decane

To a solution of 8-(3-chloro-4-methoxyphenyl)-1,4-dioxaspiro[4.5]dec-7-ene (1.7 g, 6 mmol) in CH$_2$Cl$_2$ (40 mL) was added PtO$_2$ (0.2 g). The mixture was stirred overnight under H$_2$ (1 atm). The reaction mixture was filtered and the filtrate was concentrated to give target compound (1.7 g, 100%) as a white solid.

Step 3: 4-(3-chloro-4-methoxyphenyl)cyclohexan-1-one

To a solution of 8-(3-chloro-4-methoxyphenyl)-1,4-dioxaspiro[4.5]decane (1.7 g, 6 mmol) in THF/H$_2$O (30 m/10 mL) was added TFA (3 mL). After the addition, the reaction mixture was stirred at 70° C. for 3 hours. The reaction mixture was concentrated to give the residue, treated with EtOAc (100 mL), washed with aq.K$_2$CO$_3$, brine, dried over Na$_2$SO$_4$, concentrated and purified by column chromatography (petroleum ether/EtOAc=20:1-5:1) to give target compound (0.6 g, 49.3%) as a white solid.

Step 4: N'-(4-(3-chloro-4-methoxyphenyl)cyclohexylidene)-4-methylbenzenesulfonohydrazide To a solution of 4-(3-chloro-4-methoxyphenyl)cyclohexan-1-one (600 mg, 2.52 mmol) in CH$_2$Cl$_2$/methol (30 mL/10 mL) was added 4-methylbenzenesulfonohydrazide (469 mg, 2.52 mmol) at room temperature and the mixture was stirred for overnight. Evaporate half the solvent under reduced pressure and then filtered to give product as a white solid (922 mg in 90.1% yield). $^1$H NMR (DMSO-d$_6$) δ 10.17 (s, 1H), 7.74-7.72 (d, J=8.0 Hz, 2H), 7.41-7.39 (d, J=8.0 Hz, 2H), 7.26 (s, 1H), 7.16-7.14 (d, J=8.4 Hz, 1H), 7.05-7.03 (d, J=8.4 Hz, 1H), 3.80 (s, 3H), 2.91-2.88 (m, 1H), 2.77-2.71 (m, 1H), 2.39 (s, 3H), 2.24-2.21 (m, 2H), 1.94-1.87 (m, 3H), 1.58-1.37 (m, 2H) ppm.

Step 5: tert-butyl ((6-(4-(3-chloro-4-methoxyphenyl)cyclohexane-1-carbonyl)-5-cyclopropylpyridin-2-yl)methyl)carbamate To a solution of tert-butyl ((5-cyclopropyl-6-formylpyridin-2-yl)methyl)carbamate (626 mg, 2.27 mmol) in 1,4-dioxane (50 mL) was added N'-(4-(3-chloro-4-methoxyphenyl)cyclohexylidene)-4-methylbenzenesulfonohydrazide (922 mg, 2.27 mmol) and Cs$_2$CO$_3$ (1.11 g, 3.4 mmol) at room temperature, and the mixture was heated at 90° C. overnight. The solvent was evaporated in vacuo and water (100 mL) was added, extracted with ethyl acetate (50 mL×3) and combined the organic layer, the solvent was evaporated under reduced pressure to give crude target compound as light yellow oil (crude product in 100% yield). [M+H]$^+$=499

Step 6: (6-(aminomethyl)-3-cyclopropylpyridin-2-yl)(4-(3-chloro-4-methoxyphenyl)cyclohexyl)methanone Trifluoracetic acid To a solution of tert-butyl ((6-(4-(3-chloro-4-methoxyphenyl)cyclohexane-1-carbonyl)-5-cyclopropylpyridin-2-yl)methyl)carbamate (crude, 2.27 mmol) in DCM (40 mL) was added trifluoracetic acid (10 mL) and the mixture was stirred at room temperature overnight. The solvent was evaporated under reduced pressure to give crude product as yellow oil. [M+H]$^+$=399.

Step 7: (4-(3-chloro-4-methoxyphenyl)cyclohexyl)(6-cyclopropylimidazo[1,5-a]pyridin-5-yl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(3-chloro-4-methoxyphenyl)cyclohexyl)methanone Trifluoracetic acid (crude, 2.27 mmol) in HCOOH (5 mL) was added dropwise and the mixture was heated at 70° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=5:1-2:1) to give crude product as a solid (198 mg in 21.3% yield over 3 steps). [M+H]$^+$=409.

Step 8: (4-(3-chloro-4-methoxyphenyl)cyclohexyl)(6-cyclopropylimidazo[1,5-a]pyridin-5-yl)methanol

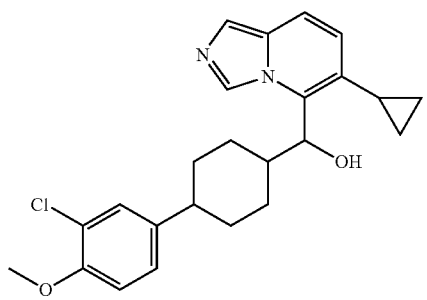 [SMILES: COc1ccc(C2CCC(C(O)c3c(C4CC4)ccc4cncn34)CC2)cc1Cl]

To a solution of (4-(3-chloro-4-methoxyphenyl)cyclohexyl)(6-cyclopropylimidazo[1,5-a]pyridin-5-yl)methanone (198 g, 0.45 mmol) in methol (10 mL) was added NaBH$_4$ (50 mg, 1.2 mmol) at room temperature and the mixture was stirred for 20 min. Then the reaction was quenched with acetone and concentrated and purified by column chromatography (petroleum ether/EtOAc=4:1-100% EtOAc) to give product as a white solid (155 mg in 83.8% yield). $^1$H NMR (DMSO-$d_6$) δ 8.62 (s, 1H), 7.41-7.39 (d, J=9.2 Hz, 1H), 7.31 (s, 1H), 7.24 (d, J=2.0 Hz, 1H), 7.14-7.11 (m, 1H), 7.03-7.00 (d, J=8.4 Hz, 1H), 6.48-6.46 (d, J=9.2 Hz, 1H), 5.80 (d, J=4.0 Hz, 1H), 5.26-5.23 (m, 1H), 3.83-3.79 (s, 3H), 2.41 (m, 1H), 2.20 (m, 1H), 1.99 (m, 1H), 1.84 (m, 1H), 1.62 (m, 1H), 1.55-1.41 (m, 1H), 1.34-1.11 (m, 4H), 1.01-0.91 (m, 2H), 0.84 (m, 1H), 0.81-0.65 (m, 2H) ppm. [M+H]$^+$=411.

Example D148a and D148b: (S)-((1r,4S)-4-(3-chloro-4-methoxyphenyl)cyclohexyl)(6-cyclopropylimidazo[1,5-a]pyridin-5-yl)methanol hydrochloride and (R)-((1 r,4R)-4-(3-chloro-4-methoxyphenyl)cyclohexyl)(6-cyclopropylimidazo[1,5-a]pyridin-5-yl)methanol hydrochloride

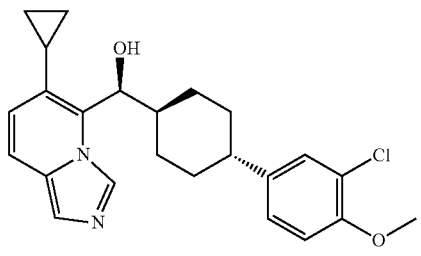

Fast isomer in CHIRALPAK IC HPLC
Eluting reagent: Hex:EtOH = 70:30

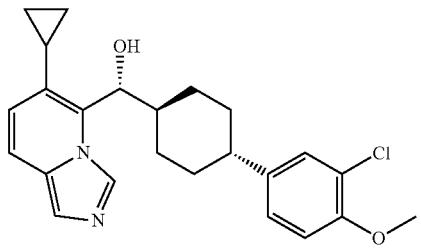

Slow isomer in CHIRALPAL IC HPLC
Eluting reagent: Hex:EtOH = 70:30

Each enantiomer of racemic D148a and D148b was separated using preparative HPLC on a CHIRALPAK IC with Hex:EtOH=70:30 as an eluent. The enantiomeric excesses were determined by using HPLC on a CHIRALPAK ICC-3 with Hex (0.1% IPAmine):EtOH=70:30 as an eluent at a flow rate of 1.0 mL/min. The first one enantiomer eluted at the retention time of 2.905 min, and the other enantiomer eluted at the retention time of 3.858 min. To a solution of D148a (63 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (58 mg in 89% yield). $^1$H NMR (DMSO-$d_6$) δ 9.59 (s, 1H), 8.04 (s, 1H), 7.71-7.68 (d, J=9.6 Hz, 1H), 7.22 (s, 1H), 7.13-7.11 (d, J=8.4 Hz, 1H), 7.04-7.02 (d, J=8.4 Hz, 1H), 6.84-6.81 (d, J=9.6 Hz, 1H), 6.18 (s, 1H), 5.32-5.30 (d, J=9.6 Hz, 1H), 3.80 (s, 3H), 2.39 (m, 2H), 2.16 (s, 2H), 1.90-1.87 (d, J=12.4 Hz, 1H), 1.66 (s, 1H), 1.49-1.40 (m, 1H), 1.38-1.17 (m, 4H), 1.09-0.98 (m, 2H), 0.87-0.75 (m, 2H) ppm. [M+H]$^+$=411. To a solution of D148b (65 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (61 mg in 84% yield). $^1$H NMR (DMSO-$d_6$) δ 9.59 (s, 1H), 8.04 (s, 1H), 7.71-7.68 (d, J=9.6 Hz, 1H), 7.22 (s, 1H), 7.13-7.11 (d, J=8.4 Hz, 1H), 7.04-7.02 (d, J=8.4 Hz, 1H), 6.84-6.81 (d, J=9.6 Hz, 1H), 6.18 (s, 1H), 5.32-5.30 (d, J=9.6 Hz, 1H), 3.80 (s, 3H), 2.39 (m, 2H), 2.16 (s, 2H), 1.90-1.87 (d, J=12.4 Hz, 1H), 1.66 (s, 1H), 1.49-1.40 (m, 1H), 1.38-1.17 (m, 4H), 1.09-0.98 (m, 2H), 0.87-0.75 (m, 2H) ppm. [M+H]$^+$=411. The absolute configurations of chiral carbons in D148a and D148b are tentatively assigned as (S) and (R) respectively based on assumption that the binding model of the more potent isomer D148a is the same as that of C101a with IDO1 enzyme, and the relative stereochemistry on cyclohexane is assigned as trans configuration on the cyclohexane.

Example D149: (6-cyclopropylimidazo[1,5-a]pyridin-5-yl)(4-(2,4,5-trifluorophenyl)cyclohexyl)methanol

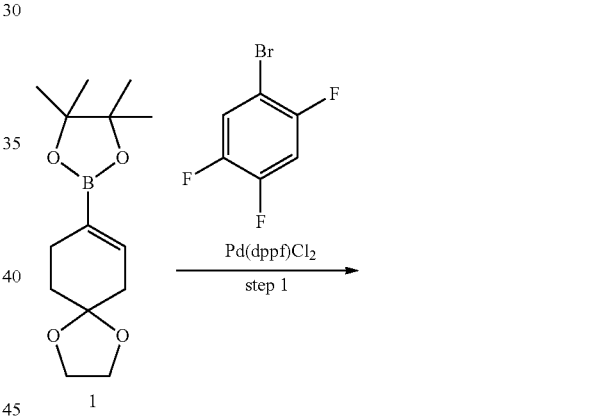

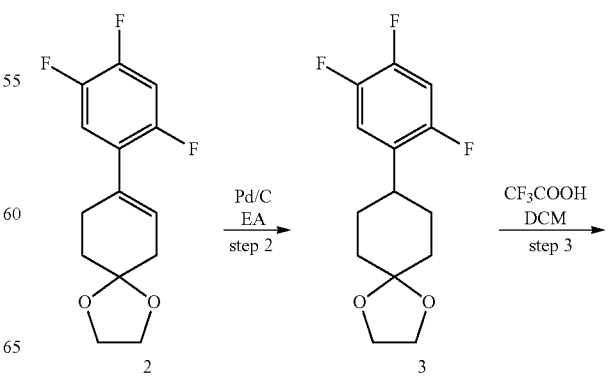

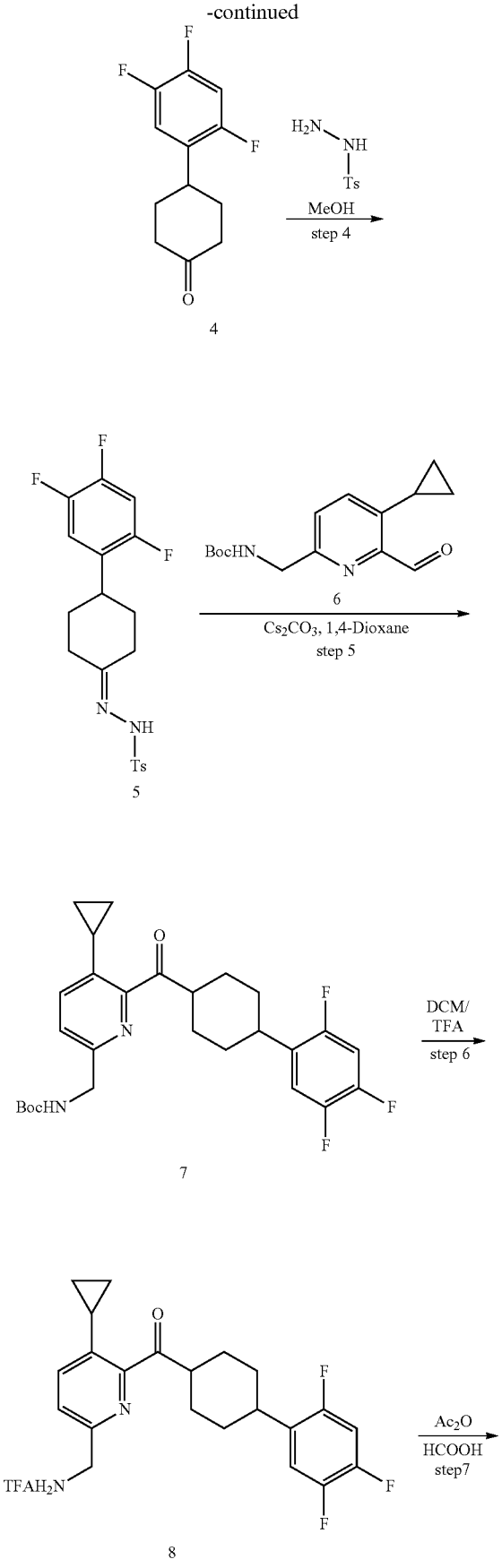

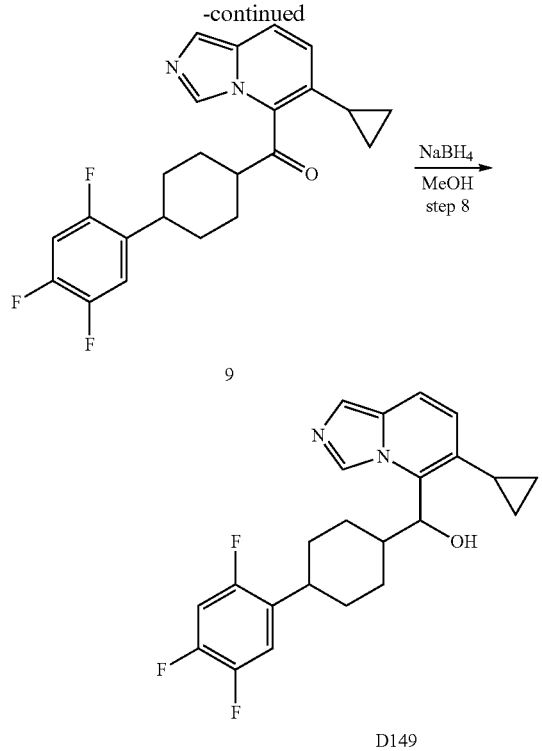

Step 1: 8-(2,4,5-trifluorophenyl)-1,4-dioxaspiro[4.5]dec-7-ene

To a solution of 1-bromo-2,4,5-trifluorobenzene (5 g, 24 mmol) in 1,4-dioxane (150 mL) was added 4,4,5,5-tetramethyl-2-(1,4-dioxaspiro[4.5]dec-7-en-8-yl)-1,3,2-dioxaborolane (7 g, 68 mmol), Pd(dppf)Cl$_2$ (1.0 g, 1.3 mmol) and Cs$_2$CO$_3$ (12.5 g, 26 mmol) and the mixture was heated at 70° C. for 5 hours. Then evaporated the solvent under reduced pressure and the residue was purified by column chromatography (PE:EA=5:1) to give product as an oil (4.5 g in 69% yield).

Step 2: 8-(2,4,5-trifluorophenyl)-1,4-dioxaspiro[4.5]decane

To a solution of 8-(2,4,5-trifluorophenyl)-1,4-dioxaspiro[4.5]dec-7-ene (4.5 g, 16.7 mmol) in methanol (200 mL) was added Pd/C (500 mg, 10%, wet) and the mixture was stirred for 2 hours at room temperature under H$_2$ (1 atm). Then filtered to remove Pd/C and the filtrate was evaporated under reduced pressure to give a crude product, and then purified by column chromatography (PE as eluent) to give product as yellow oil (3.6 g in 69% yield).

Step 3: 4-(2,4,5-trifluorophenyl)cyclohexan-1-one

To a solution of 8-(2,4,5-trifluorophenyl)-1,4-dioxaspiro[4.5]decane (3.6 g, 13.2 mmol) in dichloromethane (50 mL) was added trifluoroacetic acid (25 mL) at room temperature and the mixture was stirred for overnight. The solvent was evaporated under reduced pressure and water (50 mL) was added, extracted with ethyl acetate (50 mL×3), combined the organic layer and washed with saturated aqueous of NaHCO$_3$, then the organic layer was evaporated in vacuo to give crude product and the residue was purified by column chromatography (PE:EA=10:1) to give product as a light yellow oil (2.2 g in 73% yield). [M+H]⁺=228.1

Step 4: N-(4-(2,4,5-trifluorophenyl)cyclohexylidene)-4-methylbenzenesulfonohydrazide To a solution of 4-(2,4,5-trifluorophenyl)cyclohexan-1-one (2.2 g, 9.6 mmol) in DCM/methanol (30 mL/10 mL) was added 4-methylbenzenesulfonohydrazide (3.26 g, 17.5 mmol) at room temperature and the mixture was stirred for overnight. Evaporate half the solvent under reduced pressure and then filtered to give crude product, this residue was recycled with 2-methoxy-2-methylpropane (30 mL) and then got the target compound as a white solid (2.0 g in 53% yield).

Step 5: tert-butyl ((5-cyclopropyl-6-(4-(2,4,5-trifluorophenyl)cyclohexane-1-carbonyl)pyridin-2-yl)methyl)carbamate To a solution of tert-butyl ((5-cyclopropyl-6-formylpyridin-2-yl)methyl)carbamate (600 mg, 2.2 mmol) in 1,4-dioxane (50 mL) was added N-(4-(2,4,5-trifluorophenyl)cyclohexylidene)-4-methylbenzenesulfonohydrazide (871 mg, 2.2 mmol) and Cs₂CO₃ (700 m g, 3.3 mmol) at room temperature, and the mixture was heated at 100° C. for 16 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (400 mg in 37% yield). [M+H]⁺=489.5

Step 6: (5-(aminomethyl)-2-cyclopropylphenyl)(4-(2,4,5-trifluorophenyl)cyclohexyl) methanone Trifluoracetic acid To a solution of tert-butyl ((5-cyclopropyl-6-(4-(2,4,5-trifluorophenyl)cyclohexane-1-carbonyl)pyridin-2-yl)methyl)carbamate (0.4 g, 0.82 mmol) in DCM (40 mL) was added trifluoracetic acid (10 mL) and the mixture was stirred at room temperature for overnight. The solvent was evaporated under reduced pressure to give crude product as solid. [M+H]⁺=389.4.

Step 7: (6-cyclopropylimidazo[1,5-a]pyridin-5-yl)(4-(2,4,5-trifluorophenyl)cyclohexyl)methanone A mixture of Ac₂O (30 mL) and HCOOH (10 mL) was heated at 50° C. for 1 hour and then a solution of (5-(aminomethyl)-2-cyclopropylphenyl)(4-(2,4,5-trifluorophenyl)cyclohexyl) methanone Trifluoracetic acid (crude, 0.82 mmol) in HCOOH (5 mL) was added drop wise and the mixture was heated at 70° C. for 2 hours. The solvent was evaporated under reduced pressure and water (100 mL) was added, washed with saturated aqueous of NaHCO₃, then extracted with ethyl acetate (50 mL×3) and combined the organic layers, the solvent was evaporated under reduced pressure and the residue was purified by column chromatography (PE:EA=4:1) to give crude product as a solid (300 mg in 90% yield).

Step 8: (6-cyclopropylimidazo[1,5-a]pyridin-5-yl)(4-(2,4,5-trifluorophenyl)cyclohexyl)methanol

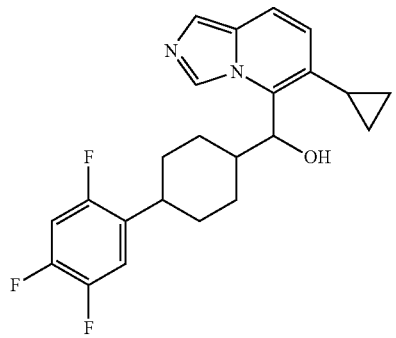 [SMILES: OC(c1c(C2CC2)ccc2cncn12)C1CCC(c2cc(F)c(F)cc2F)CC1]

To a solution of (6-cyclopropylimidazo[1,5-a]pyridin-5-yl)(4-(2,4,5-trifluorophenyl)cyclohexyl)methanone (300 g, 0.75 mmol) in methanol (10 mL) was added NaBH₄ (143 mg, 3.8 mmol) at room temperature and the mixture was stirred for 4 h. Then the solvent was evaporated under reduced pressure and water (100 mL) was added, extracted with ethyl acetate (100 mL×3) and combined the organic layers, the solvent was evaporated under reduced pressure and the residue was purified by column chromatography (PE:EA=3:1) to give product as a white solid (140 mg in 54% yield). ¹H NMR (400 MHz, DMSO-d₆) δ 8.69 (s, 1H), 7.48-7.38 (m, 3H), 6.50 (d, J=9.2 Hz, 1H), 5.85 (d, J=3.6 Hz, 1H), 5.26 (dd, J=9.6, 3.6 Hz, 1H), 2.76 (t, J=11.2 Hz, 1H), 2.42 (d, J=12.8 Hz, 1H), 2.28-2.12 (m, 1H), 2.03 (s, 1H), 1.84 (d, J=12.8 Hz, 1H), 1.66-1.47 (m, 2H), 1.39-1.21 (m, 3H), 1.20-1.10 (m, 1H), 1.05-0.85 (m, 2H), 0.85-0.60 (m, 2H). [M+H]⁺=401.1.

Example D149a and D149b: (S)-(6-cyclopropylimidazo[1,5-a]pyridin-5-yl)((1r,4S)-4-(2,4,5-trifluorophenyl)cyclohexyl)methanol and (R)-(6-cyclopropylimidazo[1,5-a]pyridin-5-yl)((1r,4R)-4-(2,4,5-trifluorophenyl)cyclohexyl)methanol

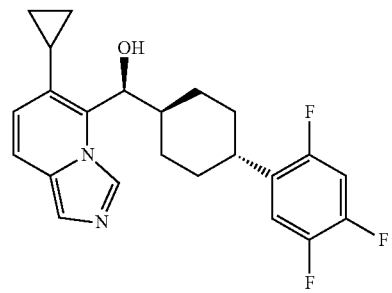

Fast isomer in CHIRALPAK IC HPLC
Eluting reagent: Hex:EtOH = 80:20

401

-continued

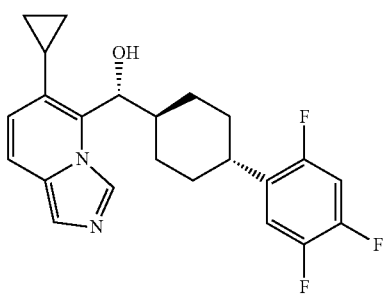

Slow isomer in CHIRALPAL IC HPLC
Eluting reagent: Hex:EtOH = 80:20

Each enantiomer of racemic D149a and D149b was separated using preparative HPLC on a CHIRALPAK Cellulose-SB with Hex:EtOH=80:20 as an eluent. D149a: $^1$H NMR (DMSO-d$_6$) δ 9.63 (s, 1H), 8.07 (s, 1H), 7.71 (d, J=9.7 Hz, 1H), 7.46-7.34 (m, 2H), 6.84 (d, J=9.7 Hz, 1H), 6.22 (s, 1H), 5.32 (d, J=9.7 Hz, 1H), 2.76 (s, 1H), 2.40 (d, J=12.5 Hz, 1H), 2.18 (s, 2H), 1.86 (d, J=11.5 Hz, 1H), 1.64 (s, 1H), 1.60-1.45 (m, 1H), 1.42-1.18 (m, 4H), 1.05 (d, J=8.3 Hz, 2H), 0.85-0.76 (m, 2H). D149b: $^1$H NMR (DMSO-d$_6$) δ 9.64 (s, 1H), 8.08 (s, 1H), 7.71 (d, J=9.6 Hz, 1H), 7.57-7.15 (m, 2H), 6.84 (d, J=9.6 Hz, 1H), 6.25 (s, 1H), 5.33 (d, J=9.7 Hz, 1H), 2.76 (s, 1H), 2.40 (d, J=11.6 Hz, 1H), 2.18 (s, 2H), 1.86 (d, J=12.2 Hz, 1H), 1.63 (s, 1H), 1.53 (dd, J=23.3, 12.4 Hz, 1H), 1.43-1.17 (m, 4H), 1.14-0.98 (m, 2H), 0.91-0.73 (m, 2H). The absolute configurations of chiral carbons in D149a and D149b are tentatively assigned as (S) and (R) respectively based on assumption that the binding model of the more potent isomer D149a is the same as that of C101a with IDO1 enzyme, and the relative stereochemistry on cyclohexane is assigned as trans configuration on the cyclohexane.

Example D150: (6-cyclopropylimidazo[1,5-a]pyridin-5-yl)(4-(6-fluoroquinolin-4-yl)cyclohexyl)methanol

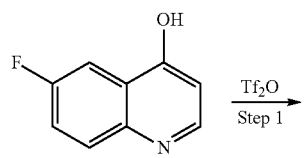

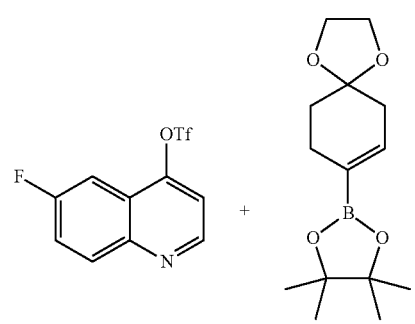

402

-continued

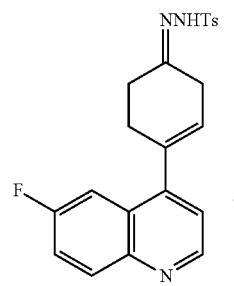

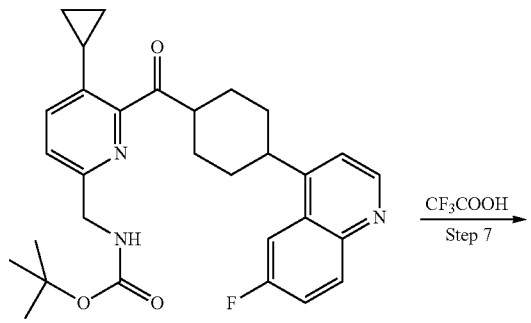

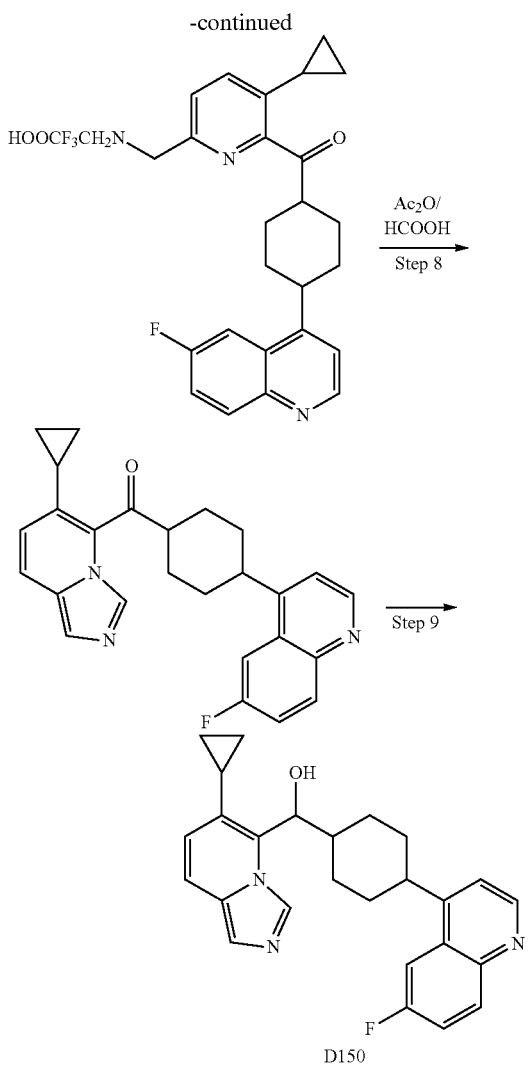

Step 1: 6-fluoroquinolin-4-yl trifluoromethanesulfonate

To a solution of 6-fluoroquinolin-4-ol (10 g, 61.3 mmol) in DCM (60 mL) and Et$_3$N (12.5 g, 122.6 mmol) was slowly dropwised T$_{12}$O (21 g, 73.56 mmol) at 0° C. under N$_2$. The mixture was stirred overnight at r.t. The mixture was quenched by H$_2$O (30 mL) and extracted with DCM (50 mL×3). The organic layer was dried over with Na$_2$SO$_4$, filtered and concentrated to give crude product which was further purified by column chromatography, eluting with EA:PE=1:10 to give the product (8.56 g, 47%). [M+H]$^+$=296.

Step 2: 6-fluoro-4-(1,4-dioxaspiro[4.5]dec-7-en-8-yl)quinolone

To a solution of 6-fluoroquinolin-4-yl trifluoromethanesulfonate (8.56 g, 28.9 mmol) in 1,4-dioxane (60 mL) and H$_2$O (20 mL) was added 4,4,5,5-tetramethyl-2-(1,4-dioxaspiro[4.5]dec-7-en-8-yl)-1,3,2-dioxaborolane (7.7 g, 28.9 mmol), Pd(dppf)C2 (3.1 g, 4.3 mmol) and Cs$_2$CO$_3$ (18.8 g, 57.8 mmol) and the mixture was heated at 80° C. overnight under N$_2$. Then evaporated the solvent under reduced pressure and the residue was purified by column chromatography (PE:EA=1:0-4:1) to give product as a brown solid (8.3 g, 85%). [M+H]$^+$=286.

Step 3: 4-(6-fluoroquinolin-4-yl)cyclohex-3-en-1-one

To a solution of 6-fluoro-4-(1,4-dioxaspiro[4.5]dec-7-en-8-yl)quinolone (8.3 g, 29 mmol) in dichloromethane (20 mL) was added trifluoroacetic acid (20 mL) at room temperature and the mixture was stirred for overnight. The solvent was evaporated under reduced pressure and water (100 mL) was added and adjusted the PH>7 by Na$_2$CO$_3$, extracted with ethyl acetate (50 mL×3), then the organic layer was further purified by column chromatography, on silica, eluting with EA:PE=0:1-1:5 to give the product (1.2 g, 17%) as a brown oil. [M+H]$^+$=242.

Step 4: 4-(6-fluoroquinolin-4-yl)cyclohexan-1-one

To a solution of 4-(6-fluoroquinolin-4-yl)cyclohex-3-en-1-one (1.2 g, 5.0 mmol) in MeOH (15 mL) was added Pd/C (0.24 g, 10%) and the mixture was stirred overnight at room temperature under H$_2$ (0.1 Mpa). Then filtered to remove Pd/C and the filtrate was evaporated under reduced pressure to give the product which was purified by column chromatography, on silica, eluting with EA:PE=1:5-1:1 to give the product (750 mg, 61%) as a yellow solid. [M+H]$^+$=244.

Step 5: N'-(4-(6-fluoroquinolin-4-yl)cyclohexylidene)-4-methylbenzenesulfonohydrazide To a solution of 4-(6-fluoroquinolin-4-yl)cyclohexan-1-one (750 mg, 3.07 mmol) in methol (10 mL) was added 4-methylbenzenesulfonohydrazide (628 mg, 3.38 mmol) at room temperature and the mixture was stirred for overnight. The solid was filtered and dried to give product (1 g, 77%) as a white solid. [M+H]$^+$=412.

Step 6: tert-butyl ((5-cyclopropyl-6-(4-(6-fluoroquinolin-4-yl)cyclohexane-1-carbonyl)pyridin-2-yl)methyl)carbamate To a solution of tert-butyl ((5-cyclopropyl-6-formylpyridin-2-yl)methyl)carbamate (673 mg, 2.43 mmol) in 1,4-dioxane (20 mL) was added N'-(4-(6-fluoroquinolin-4-yl)cyclohexylidene)-4-methylbenzenesulfonohydrazide (1.0 g, 2.43 mmol) and Cs$_2$CO$_3$ (1.6 g, 4.86 mmol) at room temperature, and the mixture was heated at 100° C. overnight under N$_2$. The mixture was purified by column chromatography (PE:EA=5:1) to give product as a brown oil (600 mg in 49% yield). [M+H]$^+$=504.

Step 7: (3-cyclopropyl-6-((methyleneamino)methyl)pyridin-2-yl)(4-(6-fluoroquinolin-4-yl)cyclohexyl)methanone compound with trifluoro(hydroperoxy)methane (1:1)

To a solution of tert-butyl ((5-cyclopropyl-6-(4-(6-fluoroquinolin-4-yl)cyclohexane-1-carbonyl)pyridin-2-yl)methyl)carbamate (600 mg, 1.2 mmol) in DCM (10 mL) was added CF$_3$COOH (4 mL). The mixture was stirred at room temperature for 2 h. The solvent was evaporated under reduced pressure to give crude product as oil (900 mg, crude). [M+H]$^+$=404.

Step 8: (6-cyclopropylimidazo[1,5-a]pyridin-5-yl)
(4-(6-fluoroquinolin-4-yl)cyclohexyl)methanone A mixture of $Ac_2O$ (30 mL) and HCOOH (10 mL) was heated at 50° C. for 1 hour and then a solution of (3-cyclopropyl-6-((methyleneamino)methyl)pyridin-2-yl)(4-(6-fluoroquinolin-4-yl)cyclohexyl)methanone compound with trifluoro(hydroperoxy)methane (1:1) (900 mg, crude) in HCOOH (5 mL) was added drop wise and the mixture was heated at 50° C. for 2 hours. The solvent was evaporated under reduced pressure and water (70 mL) was added, washed with saturated aqueous of $NaHCO_3$, then extracted with ethyl acetate (50 mL×3) and combined the organic layer, the solvent was evaporated to give crude product as a solid (360 mg). $[M+H]^+=414$.

Step 9: (6-cyclopropylimidazo[1,5-a]pyridin-5-yl)
(4-(6-fluoroquinolin-4-yl)cyclohexyl)methanol To a solution of (6-cyclopropylimidazo[1,5-a]pyridin-5-yl)(4-(6-fluoroquinolin-4-yl)cyclohexyl)methanone (360 mg, 0.87 mmol) in methol (30 mL) was added $NaBH_4$ (165 mg, 4.35 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give product which was further purified by prepare TLC to give the product (160 mg). H NMR (DMSO-$d_6$) $\delta_H$ 8.77 (d, J=4.4 Hz, 1H), 8.68 (s, 1H), 7.96-8.09 (m, 2H), 7.63-7.69 (m, 1H), 7.34-7.45 (m, 3H), 6.53 (d, J=9.6 Hz, 1H), 5.88 (d, J=4.0 Hz, 1H), 5.33 (dd, J=4.0, 10.0 Hz, 1H), 3.28-3.30 (m, 1H), 2.46-2.48 (m, 1H), 2.27-2.33 (m, 1H), 1.98-2.05 (m, 2H), 1.76-1.80 (m, 1H), 1.36-1.67 (m, 4H), 1.21-1.23 (m, 1H), 0.98-1.02 (m, 2H), and 0.72-0.79 (m, 2H). $[M+H]^+=416$.

Example D150a and D150b: (S)-(6-cyclopropylimidazo[,5-a]pyridin-5-yl)((1r,4S)-4-(6-fluoroquinolin-4-yl)cyclohexyl)methanol and (R)-(6-cyclopropylimidazo[1,5-a]pyridin-5-yl)((1r,4R)-4-(6-fluoroquinolin-4-yl)cyclohexyl)methanol

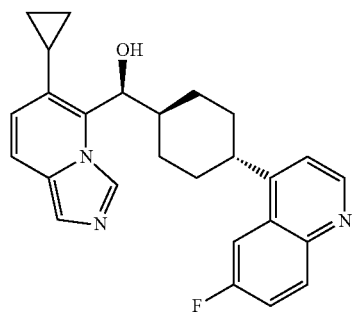

Fast isomer in CHIRALPAK IC HPLC
Eluting reagent: Hex(0.1%DEA):EtOH = 50:50

-continued

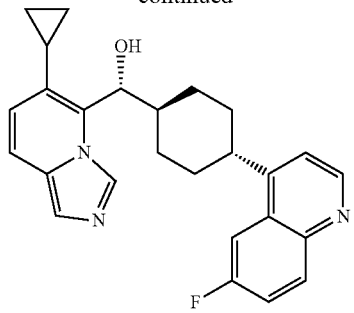

Slow isomer in CHIRALPAK IC HPLC
Eluting reagent: Hex(0.1%DEA):EtOH = 50:50

Each enantiomer of racemic D150a and D150b was separated using preparative HPLC on a CHIRALPAK IC with Hex (0.1% DEA): EtOH=50:50 as an eluent. The enantiomeric excesses were determined by using HPLC on a CHIRALPAK IC with Hex (0.1% IPAmine):EtOH=50:50 as an eluent at a flow rate of 1.0 mL/min. The first one enantiomer eluted at the retention time of 1.976 min (D150a), and the other enantiomer eluted at the retention time of 2.190 min (D150b). To a solution of D150a (46.3 mg) in DCM (2 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give the desired product as white solid (48.14 mg). $^1$H NMR (DMSO-$d_6$) $\delta_H$ 9.71 (s, 1H), 9.02 (d, J=5.2 Hz, 1H), 8.20-8.32 (m, 2H), 8.13 (s, 1H), 7.88-7.93 (m, 1H), 7.75 (d, J=9.6 Hz, 1H), 7.68 (d, J=5.2 Hz, 1H), 6.91 (d, J=9.6 Hz, 1H), 6.34 (brs, 1H), 5.40 (d, J=9.2 Hz, 1H), 3.41-3.47 (m, 1H), 2.15-2.33 (m, 2H), 2.01-2.05 (m, 1H), 1.80-1.84 (m, 1H), 1.42-1.64 (m, 4H), 1.30-1.32 (m, 2H), 1.07-1.12 (m, 2H), and 0.82-0.94 (m, 2H). $[M+H]^+=416$. To a solution of D150b (38.0 mg) in DCM (2 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give the desired product as white solid (31.06 mg). $^1$H NMR (DMSO-$d_6$) $\delta_H$ 9.72 (s, 1H), 9.05 (d, J=4.4 Hz, 1H), 8.24-8.38 (m, 2H), 8.14 (s, 1H), 7.91-7.97 (m, 1H), 7.73-7.77 (m, 2H), 6.91 (d, J=9.2 Hz, 1H), 6.34 (brs, 1H), 5.40 (d, J=9.2 Hz, 1H), 3.48-3.54 (m, 1H), 2.18-2.34 (m, 2H), 2.01-2.05 (m, 1H), 1.82-1.84 (m, 1H), 1.46-1.68 (m, 4H), 1.15-1.27 (m, 2H), 1.03-1.10 (m, 2H), and 0.81-0.93 (m, 2H). $[M+H]^+=416$. The absolute configurations of chiral carbons in D150a and D150b are tentatively assigned as (S) and (R) respectively based on assumption that the binding model of the more potent isomer D150a is the same as that of C101a with IDO1 enzyme, and the relative stereochemistry on cyclohexane is assigned as trans configuration on the cyclohexane.

Example D151: 1-(4-((1 S,4r)-4-((S)-(6-cyclopropylimidazo[1,5-a]pyridin-5-yl)(hydroxy)methyl)cyclohexyl)phenoxy)propan-2-one

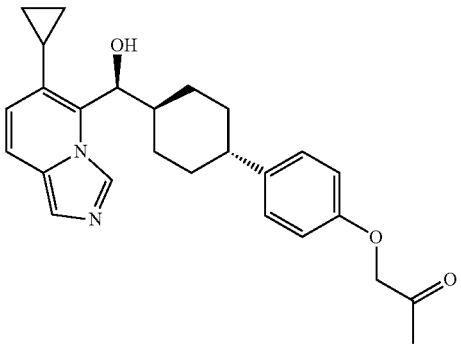 [SMILES: CC(=O)COc1ccc([C@H]2CC[C@H]([C@H](O)c3c(C4CC4)ccc4cncn34)CC2)cc1]

To a solution of 4-(1S,4r)-4-((S)-(6-cyclopropylimidazo[1,5-a]pyridin-5-yl)(hydroxy)methyl)cyclohexyl)phenol (D106a, 0.2 g, 0.55 mmol) in DMF (10 mL) was added 1-bromopropan-2-one (0.1 g, 0.66 mol) and $K_2CO_3$ (114 mg, 0.83 mmol) at room temperature and the mixture was stirred for 4 h. Then the solvent was evaporated under reduced pressure and water (50 mL) was added, extracted with ethyl acetate (50 mL×3) and combined the organic layer, the solvent was evaporated under reduced pressure to give crude product, further purified by Pre-HPLC to give product as a white solid (43 mg in 19% yield). $^1$H NMR (DMSO-d$_6$) $\delta_H$ 8.62 (s, 1H), 7.40 (d, J=9.6 Hz, 1H), 7.31 (s, 1H), 7.09 (d, J=8.8 Hz, 2H), 6.76 (d, J=8.4 Hz, 2H), 6.47 (d, J=9.6 Hz, 1H), 5.79 (d, J=3.6 Hz, 1H), 5.25 (dd, J=9.6 Hz, 1H), 4.73 (s, 2H), 2.40-2.43 (m, 2H), 2.15-2.18 (m, 1H), 2.13 (s, 3H), 2.00-2.03 (m, 1H), 1.84-1.87 (m, 1H), 1.63-1.65 (m, 1H), 1.41-1.50 (m, 1H), 1.15-1.31 (m, 4H), 0.90-0.98 (m, 2H), 0.75-0.78 (m, 1H), 0.64-0.66 (m, 1H). [M+H]$^+$=419.2.

Example D152: 2-(4-((1S,4r)-4-((S)-(6-cyclopropylimidazo[1,5-a]pyridin-5-yl)(hydroxy)methyl)cyclohexyl) henoxy)-1-phenylethan-1-one

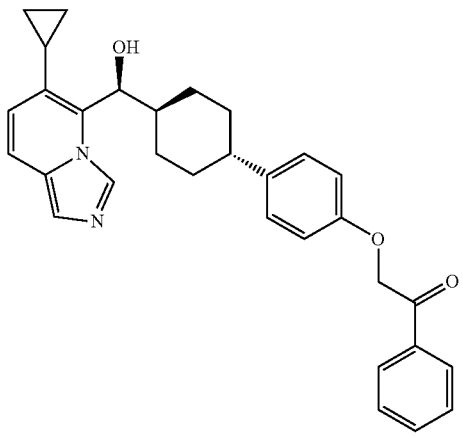 [SMILES: O=C(COc1ccc([C@H]2CC[C@H]([C@H](O)c3c(C4CC4)ccc4cncn34)CC2)cc1)c1ccccc1]

To a solution of 4-(4-((6-cyclopropylimidazo[1,5-a]pyridin-5-yl)(hydroxy)methyl)cyclohexyl)phenol (D106a, 0.1 g, 0.28 mmol) in DMF (10 mL) was added 2-bromo-1-phenylethan-1-one (60 mg, 0.28 mol) and $K_2CO_3$ (80 mg, 0.56 mmol) at room temperature and the mixture was stirred for overnight. Then the solvent was evaporated under reduced pressure and water (50 mL) was added, extracted with ethyl acetate (50 mL×3) and combined the organic layer, the solvent was evaporated under reduced pressure to give crude product, further purified by Pre-HPLC to give product as a white solid (15 mg in 11% yield). $^1$H NMR (DMSO-d$_6$) $\delta_H$ 8.61 (s, 1H), 8.00 (d, J=7.6 Hz, 2H), 7.68 (t, J=7.6 Hz, 1H), 7.56 (t, J=7.6 Hz, 2H), 7.40 (d, J=9.2 Hz, 1H), 7.31 (s, 1H), 7.09 (d, J=8.8 Hz, 2H), 6.84 (d, J=8.4 Hz, 2H), 6.47 (d, J=9.6 Hz, 1H), 5.79 (d, J=3.6 Hz, 1H), 5.50 (s, 2H), 5.25 (dd, J=9.6, 3.6 Hz, 1H), 2.40-2.43 (m, 2H), 2.18-2.20 (m, 1H), 1.99-2.01 (m, 1H), 1.85-1.88 (m, 1H), 1.64 (s, 1H), 1.42-1.51 (m, 1H), 1.15-1.31 (m, 4H), 0.90-0.98 (m, 2H), 0.75-0.78 (m, 1H), 0.64-0.66 (m, 1H). [M+H]$^+$=481.2.

Example D153: 4-((1S,4r)-4-(S)-(6-cyclopropylimidazo[1,5-a]pyridin-5-yl(hydroxy)methyl)cyclohexyl)benzamide

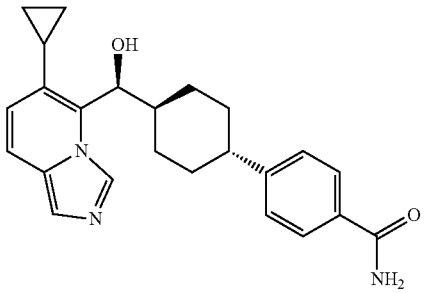 [SMILES: NC(=O)c1ccc([C@H]2CC[C@H]([C@H](O)c3c(C4CC4)ccc4cncn34)CC2)cc1]

To a solution of (S)-4-(4-((6-cyclopropylimidazo[1,5-a]pyridin-5-yl)(hydroxy)methyl)cyclohexyl)benzonitrile (67.3 mg, 0.18 mmol) in DMSO (4 mL) was added $K_2CO_3$ (50 mg, 0.36 mmol) at room temperature and followed by addition of $H_2O_2$ (0.5 mL, 30%) and the mixture was stirred at room temperature for 4 hours. Then water (40 mL) was added with stirring and filtered to give product as a white solid (30 mg in 43% yield). $^1$H NMR (DMSO-d$_6$) 8.62 (s, 1H), 7.85 (s, 1H), 7.75 (d, J=8.0 Hz, 2H), 7.40 (d, J=9.6 Hz, 1H), 7.31 (s, 1H), 7.27 (d, J=8.4 Hz, 2H), 7.24 (s, 1H), 6.48 (d, J=9.6 Hz, 1H), 5.81 (d, J=3.2 Hz, 1H), 5.26 (dd, J=9.6, 3.2 Hz 1H), 2.42-2.45 (m, 1H), 2.21-2.24 (m, 1H), 2.02 (s, 1H), 1.88-1.91 (m, 1H), 1.66-1.69 (m, 1H), 1.49-1.57 (m, 1H), 1.18-1.34 (m, 4H), 0.93-0.99 (m, 2H), 0.76-0.78 (m, 1H), 0.65-0.67 (m, 1H). [M+H]$^+$=390.2.

Example D154: (4-(benzo[b]thiophen-2-yl)cyclohexyl)(6-cyclopropylimidazo[1,5-a]pyridin-5-yl)methanol

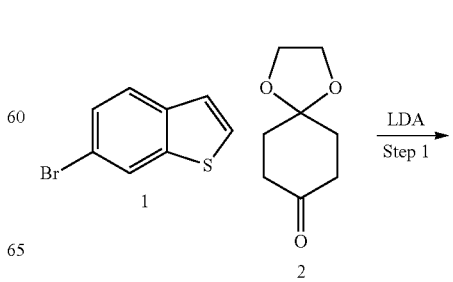

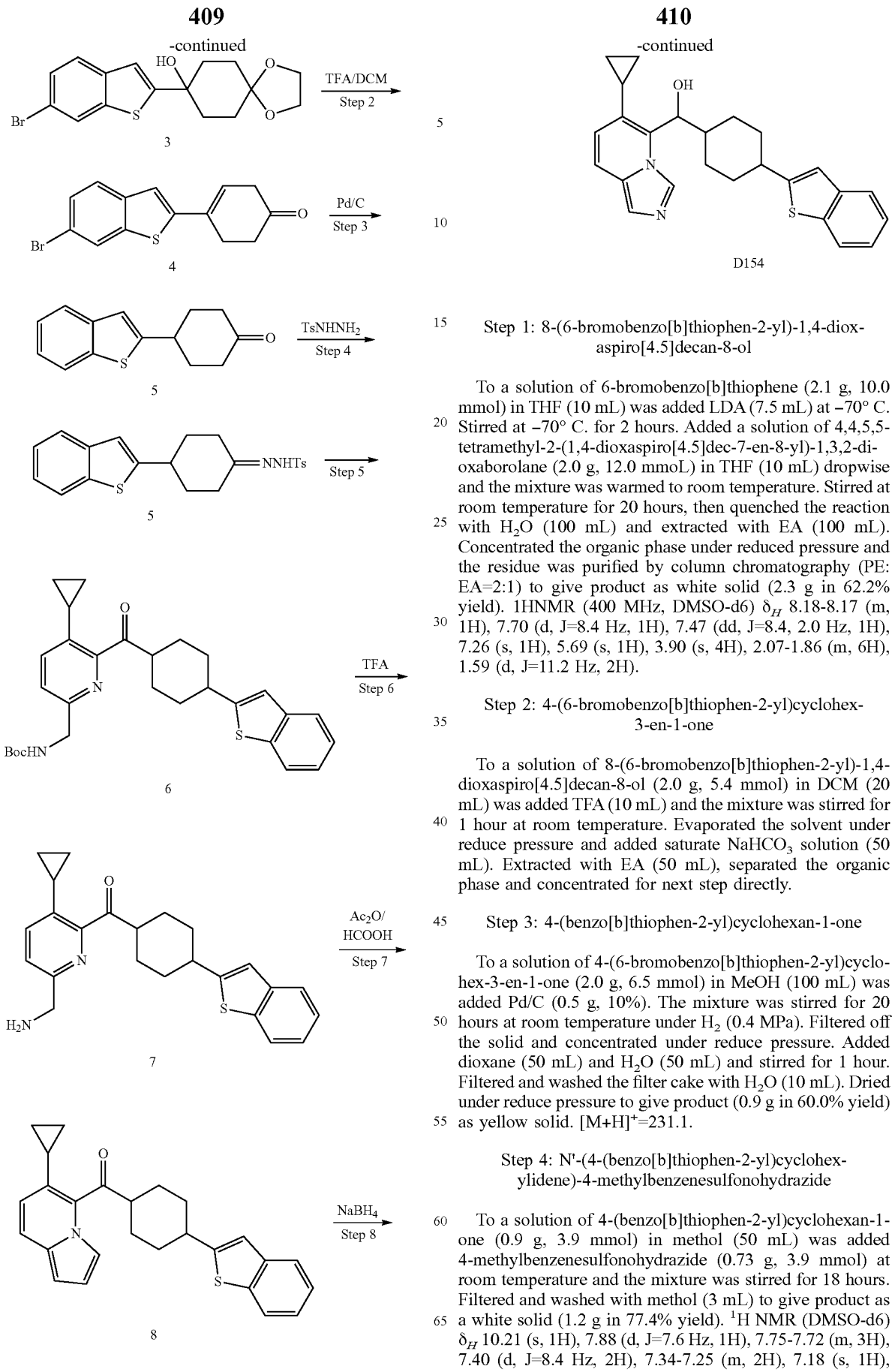

Step 1: 8-(6-bromobenzo[b]thiophen-2-yl)-1,4-dioxaspiro[4.5]decan-8-ol

To a solution of 6-bromobenzo[b]thiophene (2.1 g, 10.0 mmol) in THF (10 mL) was added LDA (7.5 mL) at −70° C. Stirred at −70° C. for 2 hours. Added a solution of 4,4,5,5-tetramethyl-2-(1,4-dioxaspiro[4.5]dec-7-en-8-yl)-1,3,2-dioxaborolane (2.0 g, 12.0 mmoL) in THF (10 mL) dropwise and the mixture was warmed to room temperature. Stirred at room temperature for 20 hours, then quenched the reaction with H$_2$O (100 mL) and extracted with EA (100 mL). Concentrated the organic phase under reduced pressure and the residue was purified by column chromatography (PE:EA=2:1) to give product as white solid (2.3 g in 62.2% yield). 1HNMR (400 MHz, DMSO-d6) $\delta_H$ 8.18-8.17 (m, 1H), 7.70 (d, J=8.4 Hz, 1H), 7.47 (dd, J=8.4, 2.0 Hz, 1H), 7.26 (s, 1H), 5.69 (s, 1H), 3.90 (s, 4H), 2.07-1.86 (m, 6H), 1.59 (d, J=11.2 Hz, 2H).

Step 2: 4-(6-bromobenzo[b]thiophen-2-yl)cyclohex-3-en-1-one

To a solution of 8-(6-bromobenzo[b]thiophen-2-yl)-1,4-dioxaspiro[4.5]decan-8-ol (2.0 g, 5.4 mmol) in DCM (20 mL) was added TFA (10 mL) and the mixture was stirred for 1 hour at room temperature. Evaporated the solvent under reduce pressure and added saturate NaHCO$_3$ solution (50 mL). Extracted with EA (50 mL), separated the organic phase and concentrated for next step directly.

Step 3: 4-(benzo[b]thiophen-2-yl)cyclohexan-1-one

To a solution of 4-(6-bromobenzo[b]thiophen-2-yl)cyclohex-3-en-1-one (2.0 g, 6.5 mmol) in MeOH (100 mL) was added Pd/C (0.5 g, 10%). The mixture was stirred for 20 hours at room temperature under H$_2$ (0.4 MPa). Filtered off the solid and concentrated under reduce pressure. Added dioxane (50 mL) and H$_2$O (50 mL) and stirred for 1 hour. Filtered and washed the filter cake with H$_2$O (10 mL). Dried under reduce pressure to give product (0.9 g in 60.0% yield) as yellow solid. [M+H]$^+$=231.1.

Step 4: N'-(4-(benzo[b]thiophen-2-yl)cyclohexylidene)-4-methylbenzenesulfonohydrazide To a solution of 4-(benzo[b]thiophen-2-yl)cyclohexan-1-one (0.9 g, 3.9 mmol) in methol (50 mL) was added 4-methylbenzenesulfonohydrazide (0.73 g, 3.9 mmol) at room temperature and the mixture was stirred for 18 hours. Filtered and washed with methol (3 mL) to give product as a white solid (1.2 g in 77.4% yield). $^1$H NMR (DMSO-d6) $\delta_H$ 10.21 (s, 1H), 7.88 (d, J=7.6 Hz, 1H), 7.75-7.72 (m, 3H), 7.40 (d, J=8.4 Hz, 2H), 7.34-7.25 (m, 2H), 7.18 (s, 1H), 3.22-3.17 (m, 1H), 2.89 (d, J=14.8 Hz, 1H), 2.39 (s, 3H), 2.32-2.28 (m, 2H), 2.16 (d, J=12.0 Hz, 2H), 2.08-2.00 (m, 1H), and 1.64-1.49 (m, 2H).

Step 5: tert-butyl ((6-(4-(benzo[b]thiophen-2-yl)cyclohexane-1-carbonyl)-5-cyclopropylpyridin-2-yl)methyl)carbamate To a solution of N'-(4-(benzo[b]thiophen-2-yl)cyclohexylidene)-4-methylbenzenesulfonohydrazide (1.2 g, 3.0 mmol) in 1,4-dioxane (50 mL) was added tert-butyl ((5-cyclopropyl-6-formylpyridin-2-yl)methyl)carbamate (0.8 g, 3.0 mmol) and $Cs_2CO_3$ (1.5 g, 4.5 mmol) at room temperature, and the mixture was heated at 85° C. for 18 hours. Water (100 mL) was added, extracted with ethyl acetate (100 mL×2) and combined the organic layer, the solvent was evaporated under reduced pressure and the residue was purified by column chromatography (PE:EA=8:1) to give product (0.7 g in 47.6% yield) as yellow solid. [M+H]=491.2

Step 6: (6-(aminomethyl)-3-cyclopropylpyridin-2-yl)(4-(benzo[b]thiophen-2-yl)cyclohexyl)methanone 2,2,2-trifluoroacetate To a solution of tert-butyl ((6-(4-(benzo[b]thiophen-2-yl)cyclohexane-1-carbonyl)-5-cyclopropylpyridin-2-yl)methyl)carbamate (0.7 g, 1.4 mmol) in DCM (10 mL) was added trifluoracetic acid (10 mL) and the mixture was stirred at room temperature for 2 hours. The solvent was evaporated under reduced pressure to give crude product for next step directly without further purification.

Step 7: (4-(benzo[b]thiophen-2-yl)cyclohexyl)(6-cyclohexyl)(6-cyclopropylimidazo[1,5-a]pyridin-5-yl)methanone A mixture of $Ac_2O$ (32 mL) and HCOOH (8 mL) was heated at 55° C. for 1 hour and then a solution of (6-(aminomethyl)-3-cyclopropylpyridin-2-yl)(4-(benzo[b]thiophen-2-yl)cyclohexyl)methanone 2,2,2-trifluoroacetate (0.7, 1.4 mmol) in HCOOH (5 mL) was added drop wise and the mixture was heated at 55° C. for 18 hours. The solvent was evaporated under reduced pressure and saturated aqueous of $NaHCO_3$ (50 mL) was added, then extracted with ethyl acetate (50 mL) and separated the organic layer, the solvent was evaporated under reduced pressure and the residue was purified pre-TLC (PE:EA=1:1) to give crude product as yellow solid (0.2 g) as yellow solid. $[M+H]^+$=401.1.

Step 8: (4-(benzo[b]thiophen-2-yl)cyclohexyl)(6-cyclopropylimidazo[1,5-a]pyridin-5-yl)methanol To a solution of (4-(benzo[b]thiophen-3-yl)cyclohexyl)(6-cyclopropylimidazo[1,5-a]pyridin-5-yl)methanone (0.2 g, 0.5 mmol) in MeOH (10 mL) and DCM (10 mL) was added $NaBH_4$ (0.2 g, 5.3 mmol) at room temperature in portions. The mixture was stirred at 25° C. for 18 hours. Then quenched the reaction with water (50 mL) and extracted with DCM (50 mL). Concentrated the organic phase and purified by pre-TLC (DCM/MeOH=20:1) (50.0 mg in 25.0% yield). $^1$H NMR (DMSO-d6) $\delta_H$ 8.63 (s, 1H), 7.85 (d, J=8.0 Hz, 1H), 7.70 (d, J=8.0 Hz, 1H), 7.41 (d, J=9.6 Hz, 1H), 7.32-7.23 (m, 3H), 7.13 (s, 1H), 6.48 (d, J=9.6 Hz, 1H), 5.83 (d, J=3.6 Hz, 1H), 5.27 (dd, J=9.6, 3.6 Hz, 1H), 2.86 (b, 1H), 2.50-2.43 (m, 1H), 2.23-2.15 (m, 2H), 2.02-1.94 (m, 2H), 1.59-1.50 (m, 1H), 1.38-1.19 (m, 4H), 0.97-0.95 (m, 2H), 0.76 (b, 1H), and 0.67 (b, Hz, 1H). $[M+H]^+$=403.2.

Example D155: (4-(benzo[b]thiophen-3-yl)cyclohexyl)(6-cyclopropylimidazo[1,5-a]pyridin-5-yl)methanol

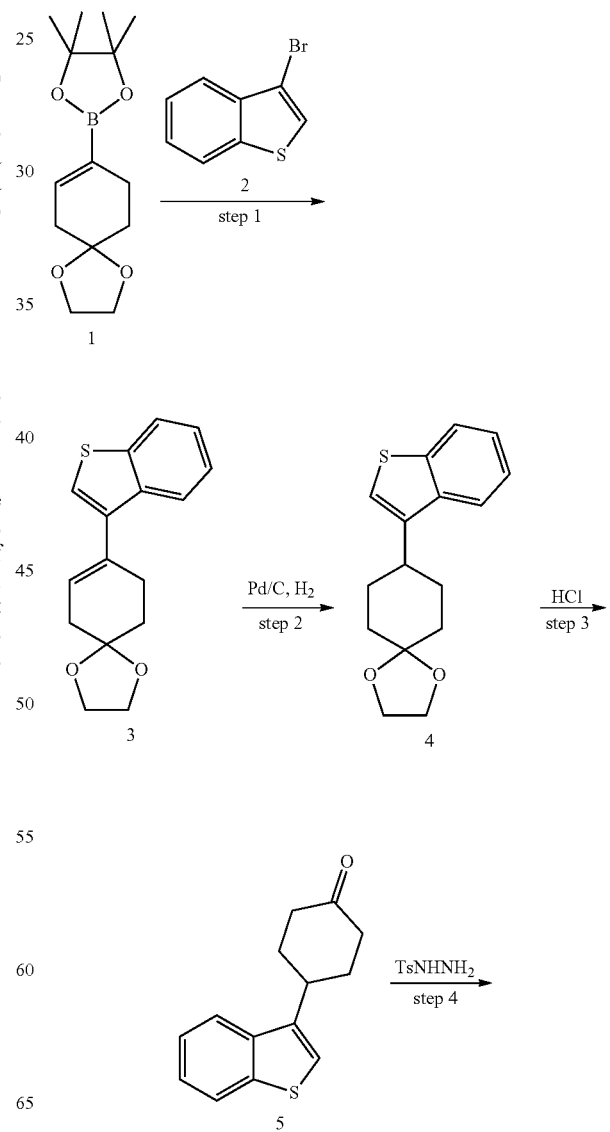

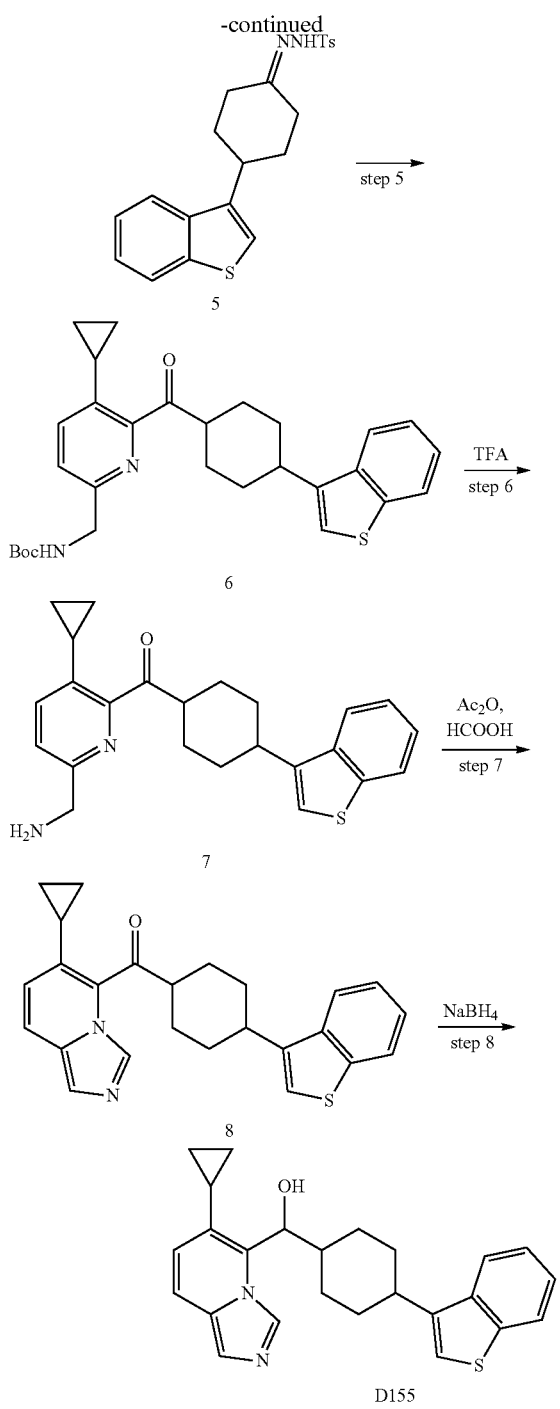

(400 MHz, DMSO-d6) $\delta_H$ 8.04-7.94 (m, 1H), 7.94-7.87 (m, 1H), 7.60 (s, 1H), 7.42-7.34 (m, 2H), 5.94 (t, J=3.6 Hz, 1H), 3.95 (s, 4H), 2.62-2.59 (m, 2H), 2.44 (b, 2H), 1.86 (t, J=6.4 Hz, 2H).

Step 2: 8-(benzo[b]thiophen-3-yl)-1,4-dioxaspiro[4.5]decane

To a solution of 8-(benzo[b]thiophen-3-yl)-1,4-dioxaspiro[4.5]dec-7-ene (4.7 g, 17.5 mmol) in ethyl acetate (100 mL) was added Pd/C (1.0 g, 10%) and the mixture was stirred for 18 hours at room temperature under $H_2$ (0.4 Mpa). Then filtered to remove Pd/C and the filtrate was evaporated under reduced pressure to give a crude product (3.0 g) for next step directly without further purification. $[M+H]^+=275.1$.

Step 3: 4-(benzo[b]thiophen-3-yl)cyclohexan-1-one

To a solution of 8-(benzo[b]thiophen-3-yl)-1,4-dioxaspiro[4.5]decane (4.8 g, 17.5 mmol) in dioxane (50 mL) and $H_2O$ (50 mL) was added HCl (conc. 10 mL). The mixture was stirred for 3 hours at room temperature. Separated the oil phase for next step directly. (2.3 g in 57.1% yield) as yellow oil. $[M+H]^+=231.1$.

Step 4: N'-(4-(benzo[b]thiophen-3-yl)cyclohexylidene)-4-methylbenzenesulfonohydrazide To a solution of 4-(benzo[b]thiophen-3-yl)cyclohexan-1-one (2.3 g, 10.0 mmol) in methol (50 mL) was added 4-methylbenzenesulfonohydrazide (1.86 g, 10.0 mmol) at room temperature and the mixture was stirred for 18 hours. Filtered and washed with methol (6 mL) to give product as a white solid (3.0 g in 75.4% yield).

Step 5: tert-butyl ((6-(4-(benzo[b]thiophen-3-yl)cyclohexane-1-carbonyl)-5-cyclopropylpyridin-2-yl)methyl)carbamate To a solution of N'-(4-(benzo[b]thiophen-3-yl)cyclohexylidene)-4-methylbenzenesulfonohydrazide (1.0 g, 2.5 mmol) in 1,4-dioxane (50 mL) was added tert-butyl ((5-cyclopropyl-6-formylpyridin-2-yl)methyl)carbamate (0.7 g, 2.5 mmol) and $Cs_2CO_3$ (1.2 g, 3.6 mmol) at room temperature, and the mixture was heated at 85° C. for 18 hours. Water (100 mL) was added, extracted with ethyl acetate (100 mL×2) and combined the organic layer, the solvent was evaporated under reduced pressure and the residue was purified by column chromatography (PE:EA=8:1) to give product. (0.6 g in 48.8% yield). $[M+H]^+=491.2$ Step 6: (6-aminomethyl)-3-cyclopropylpyridin-2-yl)(4-(benzo[b]thiophen-3-yl)cyclohexyl)methanone 2,2,2-trifluoroacetate To a solution of tert-butyl ((6-(4-(4-(((benzyloxy)carbonyl)amino)phenyl)cyclohexane-1-carbonyl)-5-cyclopropylpyridin-2-yl)methyl)carbamate (0.6 g, 1.22 mmol) in DCM (10 mL) was added trifluoracetic acid (10 mL) and the mixture was stirred at room temperature for 2 hours. The solvent was evaporated under reduced pressure to give crude product for next step directly without purification.

Step 7: (4-(benzo[b]thiophen-3-yl)cyclohexyl)(6-cyclopropylimidazo[1,5-a]pyridin-5-yl)methanone A mixture of $Ac_2O$ (32 mL) and HCOOH (8 mL) was heated at 55° C. for 1 hour and then a solution of (6-

Step 1: 8-(benzo[b]thiophen-3-yl)-1,4-dioxaspiro[4.5]dec-7-ene

To a solution of 4,4,5,5-tetramethyl-2-(1,4-dioxaspiro[4.5]dec-7-en-8-yl)-1,3,2-dioxaborolane (5.3 g, 20.0 mmoL) in 1,4-dioxane (50 mL) was added 3-bromobenzo[b]thiophene (4.3 g, 20.0 mmol), Pd(dppf)Cl$_2$ (1.5 g, 2.0 mmol) and $Cs_2CO_3$ (9.7 g, 30.0 mmol) and the mixture was heated at 80° C. for 18 hours. Then filter off the solid, the filtrate was evaporated under reduced pressure and the residue was purified by column chromatography (PE:EA=5:1) to give product as yellow solid (4.76 g in 87.3% yield). $^1$HNMR (aminomethyl)-3-cyclopropylpyridin-2-yl)(4-(benzo[b]thiophen-3-yl)cyclohexyl)methanone 2,2,2-trifluoroacetate (crude, 0.9 mmol) in HCOOH (5 mL) was added drop wise and the mixture was heated at 55° C. for 18 hours. The solvent was evaporated under reduced pressure and saturated aqueous of NaHCO$_3$(50 mL) was added, then extracted with ethyl acetate (50 mL) and separated the organic layer, the solvent was evaporated under reduced pressure and the residue was purified pre-TLC (PE:EA=1:1) to give crude product as yellow solid (0.17 g). [M+H]$^+$=401.1.

Step 8: (4-(benzo[b]thiophen-3-yl)cyclohexyl)(6-cyclopropylimidazo[1,5-a]pyridin-5-yl)methanol

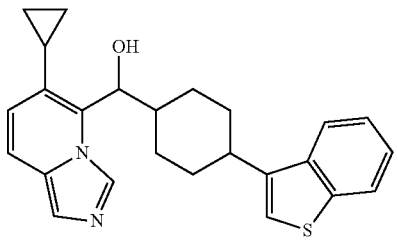 [SMILES: OC(c1c(C2CC2)ccc2cncn12)C1CCC(c2csc3ccccc23)CC1]

To a solution of (4-(benzo[b]thiophen-3-yl)cyclohexyl)(6-cyclopropylimidazo[1,5-a]pyridin-5-yl)methanone (0.17 g, 0.4 mmol) in MeOH (10 mL) and DCM (10 mL) was added NaBH$_4$ (0.2 g, 5.3 mmol) at room temperature in portions. The mixture was stirred at 25° C. for 18 hours. Then quenched the reaction with water (50 mL) and extracted with DCM (50 mL). Concentrated the organic phase and purified by pre-TLC (PE/EA=1:2) (74.0 mg in 46.0% yield). 1H NMR (DMSO-d6) δ$_H$ 8.65 (s, 1H), 7.95 (d, J=7.6 Hz, 1H), 7.84 (d, J=7.6 Hz, 1H), 7.42-7.33 (m, 5H), 6.49 (d, J=9.2 Hz, 1H), 5.84 (d, J=3.9 Hz, 1H), 5.31 (dd, J=9.6, 3.6 Hz, 1H), 2.93 (t, J=9.6 Hz, 1H), 2.50-2.44 (m, 1H), 2.26-2.24 (m, 1H), 2.12-1.99 (m, 2H), 1.89 (b, 1H), 1.61-1.52 (m, 1H), 1.35-1.18 (m, 4H), 0.95-0.85 (m, 2H), and 0.80-0.68 (m, 2H). [M+H]$^+$=403.1.

Example D155a and D155b: (S)-((1 r,4S)-4-(benzo[b]thiophen-3-yl)cyclohexyl)(6-cyclopropylimidazo[1,5-a]pyridin-5-yl)methanol and (R)-((1 r,4R)-4-(benzo[b]thiophen-3-yl)cyclohexyl(6-cyclopropylimidazo[1,5-a]pyridin-5-yl)methanol Fast isomer in CHIRALPAK IC HPLC
Eluting reagent: Hex(0.1%DEA):EtOH = 80:20

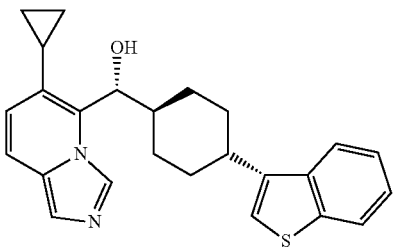

Slow isomer in CHIRALPAL IC HPLC
Eluting reagent: Hex(0.1%DEA):EtOH = 80:20

Each enantiomer of racemic D155a and D155b was separated using preparative HPLC on a CHIRALPAK IC with Hex (0.1% DEA):EtOH=80:20 as an eluent. The enantiomeric excesses were determined by using HPLC on a CHIRALPAK IC with Hex (0.1% IPAmine):EtOH=80:20 as an eluent at a flow rate of 1.0 mL/min. The first one enantiomer eluted at the retention time of 1.698 min (D155a), and the other enantiomer eluted at the retention time of 3.363 min (D155b). To a solution of D155a (20.6 mg) in MeOH (5 mL) was added drop wise of Ethyl acetate solution of hydrochloric acid (2 mL, 4.0M) at room temperature, stirred at room temperature for 10 min, then the solvent was evaporated under reduced pressure to give the desired product as white solid (17.6 mg in 78.4% yield). $^1$H NMR (DMSO-d6) δ$_H$ 9.61 (s, 1H), 8.04 (s, 1H), 7.95 (d, J=8.0 Hz, 1H), 7.84 (d, J=8.0 Hz, 1H), 7.70 (d, J=10.0 Hz, 1H), 7.41-7.31 (m, 3H), 6.85 (d, J=9.2 Hz, 1H), 6.20 (s, 1H), 5.37 (d, J=9.6 Hz, 1H), 2.94 (b, 1H), 2.46-2.43 (m, 1H), 2.20-2.11 (m, 3H), 1.91 (d, J=10.8 Hz, 1H), 1.58-1.49 (m, 1H), 1.46-1.34 (m, 4H), 1.08-1.06 (m, 2H), 0.86-0.80 (m, 2H). [M+H]$^+$=403.2. To a solution of D155b (22.0 mg) in MeOH (5 mL) was added drop wise of ethyl acetate solution of hydrochloric acid (2 mL, 4.0M) at room temperature, stirred at room temperature for 10 min, then the solvent was evaporated under reduced pressure to give the desired product as white solid (13.2 mg in 55.0% yield). $^1$H NMR (DMSO-d6) δ$_H$ 9.65 (s, 1H), 8.07 (s, 1H), 7.95 (d, J=7.6 Hz, 1H), 7.84 (d, J=7.6 Hz, 1H), 7.71 (d, J=9.6 Hz, 1H), 7.41-7.33 (m, 3H), 6.86 (d, J=9.6 Hz, 1H), 6.23 (s, 1H), 5.37 (d, J=9.2 Hz, 1H), 2.94 (b, 1H), 2.50-2.43 (m, 1H), 2.19-2.11 (m, 3H), 1.91 (d, J=10.8 Hz, 1H), 1.58-1.25 (m, 5H), 1.08-1.06 (m, 2H), and 0.87-0.81 (m, 2H). [M+H]$^+$=403.2. The absolute configurations of chiral carbons in D155a and D155b are tentatively assigned as (S) and (R) respectively based on assumption that the binding model of the more potent isomer D155a is the same as that of C101a with IDO1 enzyme, and the relative stereochemistry on cyclohexane is assigned as trans configuration on the cyclohexane.

Example D156: (6-cyclopropylimidazo[1,5-a]pyridin-5-yl)(4-(3-fluorophenyl)cyclohexyl)methanol

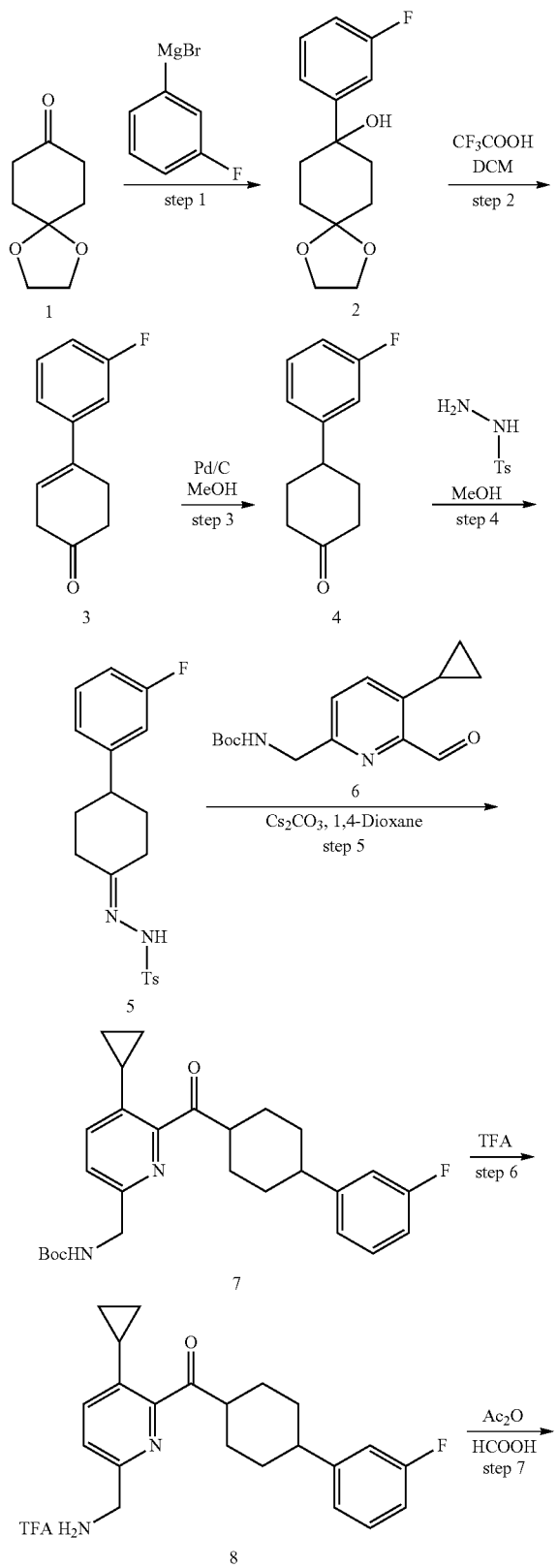

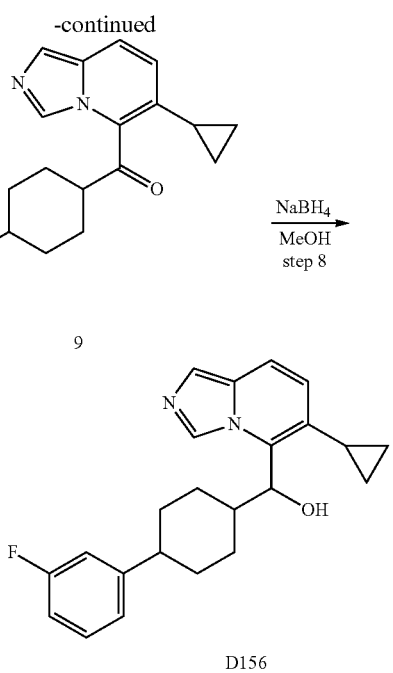

Step 1: 8-(3-fluorophenyl)-1,4-dioxaspiro[4.5]decan-8-ol

To a solution of 1,4-dioxaspiro[4.5]decan-8-one (7.8 g, 50 mmoL) in dry THF (100 mL) was added drop wise of (3-fluorophenyl)magnesium bromide (50 mL, 1.0 M) at −70° C., and the mixture was stirred for 5 hours. Then quenched with saturated aqueous of NH$_4$Cl, extracted with ethyl acetate (50 mL×3), combined the organic layer and the solvent was evaporated under reduced pressure to give crude product as oil which was used for next step without further purification.

Step 2: 3'-fluoro-2,5-dihydro-[1,1'-biphenyl]-4(3H)-one

To a solution of 8-(3-fluorophenyl)-1,4-dioxaspiro[4.5] decan-8-ol (50 mmol) in dichloromethane (50 mL) was added trifluoroacetic acid (50 mL) at room temperature and the mixture was stirred for 6 hours. The solvent was evaporated under reduced pressure and water (100 mL) was added, extracted with ethyl acetate (100 mL×3), combined the organic layer and washed with saturated aqueous of NaHCO$_3$, then the organic layer was evaporated in vacuo to give crude product, further purified by column chromatography (PE:EA=10:1) to give product as a light yellow oil (4.0 g in 42% yield). $^1$H NMR (400 MHz, DMSO-d$_6$) $\delta_H$ 7.37-7.43 (m, 1H), 7.28-7.32 (m, 2H), 7.31-7.13 (m, 1H), 6.25 (t, J=4.0 Hz, 1H), 3.03-3.04 (m, 2H), 2.84 (t, J=6.8 Hz, 2H) and 2.55 (t, J=6.8 Hz, 1H), MS (ESI) m/e [M+1]$^+$=191.1.

Step 3: 4-(3-fluorophenyl)cyclohexan-1-one

To a solution of 3'-fluoro-2,5-dihydro-[1,1'-biphenyl]-4 (3H)-one (4.0 g, 21 mmol) in methol (100 mL) was added Pd/C (0.4 g, 10%) and the mixture was stirred for 6 hours at room temperature under H$_2$ (0.1 Mpa). Then filtered to remove Pd/C and the filtrate was evaporated under reduced pressure to give a crude product. ¹H NMR (400 MHz, DMSO-d₆) δ_H 7.32-7.38 (m, 1H), 7.15 (d, J=8.0 Hz, 2H), 7.00-7.05 (m, 1H), 3.06-3.14 (m, 1H), 2.53-2.62 (m, 2H), 2.25-2.29 (m, 2H), 2.04-2.10 (m, 2H) and 1.84-1.94 (m, 2H), MS (ESI) m/e [M+1]⁺=193.1.

Step 4: N'-(4-(3-fluorophenyl)cyclohexylidene)-4-methylbenzenesulfonohydrazide

To a solution of 4-(3-fluorophenyl)cyclohexan-1-one (21 mmol) in methol (100 mL) was added 4-methylbenzenesulfonohydrazide (3.9 g, 21 mmol) at room temperature and the mixture was stirred for overnight. Evaporate half the solvent under reduced pressure and then filtered to give product as a white solid (5.0 g in 66% yield). ¹H NMR (400 MHz, DMSO-d₆) δ_H 10.19 (s, 1H), 7.74 (d, J=8.0 Hz, 2H), 7.40 (d, J=8.0 Hz, 2H), 7.29-7.34 (m, 1H), 7.31 (s, 1H), 7.05 (d, J=4.8 Hz, 1H), 6.98-7.02 (m, 1H), 2.79-2.93 (m, 2H), 2.39 (s, 3H), 2.20-2.27 (m, 2H), 1.90-1.97 (m, 3H) and 1.43-1.60 (m, 2H). MS (ESI) m/e [M+1]⁺=361.1.

Step 5: tert-butyl ((5-cyclopropyl-6-(4-(3-fluorophenyl)cyclohexane-1-carbonyl)pyridin-2-yl)methyl)carbamate To a solution of tert-butyl ((5-cyclopropyl-6-formylpyridin-2-yl)methyl)carbamate (0.8 g, 2.9 mmol) in 1,4-dioxane (0.1 L) was added N'-(4-(3-fluorophenyl)cyclohexylidene)-4-methylbenzenesulfonohydrazide (1.3 g, 3.5 mmol) and Cs₂CO₃ (1.4 g, 4.4 mmol) at room temperature, and the mixture was heated at 100° C. for 6 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (0.8 g in 61% yield). MS (ESI) m/e [M+1]⁺=453.2.

Step 6: (6-(aminomethyl)-3-cyclopropylpyridin-2-yl)(4-(3-fluorophenyl)cyclohexyl)methanone To a solution of tert-butyl ((5-cyclopropyl-6-(4-(3-fluorophenyl)cyclohexane-1-carbonyl)pyridin-2-yl)methyl)carbamate (0.8 g, 1.77 mmol) in DCM (20 mL) was added trifluoracetic acid (20 mL) and the mixture was stirred at room temperature for overnight. The solvent was evaporated under reduced pressure to give crude product as solid. MS (ESI) m/e [M+1]⁺=353.2.

Step 7: (6-cyclopropylimidazo[1,5-a]pyridin-5-yl)(4-(3-fluorophenyl)cyclohexyl)methanone A mixture of Ac₂O (30 mL) and HCOOH (10 mL) was heated at 50° C. for 1 hour and then a solution of (6-(aminomethyl)-3-cyclopropylpyridin-2-yl)(4-(3-fluorophenyl)cyclohexyl)methanone (crude, 1.77 mmol) in HCOOH (5 mL) was added drop wise and the mixture was heated at 50° C. for 2 hours. The solvent was evaporated under reduced pressure and water (100 mL) was added, washed with saturated aqueous of NaHCO₃, then extracted with ethyl acetate (50 mL×3) and combined the organic layer, the solvent was evaporated under reduced pressure and the residue was purified by column chromatography (PE:EA=5:1) to give product as light yellow oil. (0.3 g in 47% yield). MS (ESI) m/e [M+1]⁺=363.1.

Step 8: (6-cyclopropylimidazo[1,5-a]pyridin-5-yl)(4-(3-fluorophenyl)cyclohexyl)methanol

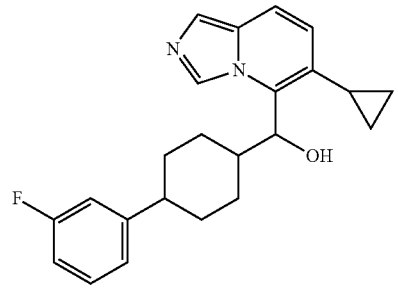 [SMILES: OC(c1c(C2CC2)ccc2cncn12)C1CCC(c2cccc(F)c2)CC1]

To a solution of (6-cyclopropylimidazo[1,5-a]pyridin-5-yl)(4-(3-fluorophenyl)cyclohexyl)methanone (0.3 g, 0.83 mmol) in methol (20 mL) was added NaBH₄ (157 mg, 4.15 mmol) at room temperature and the mixture was stirred for 0.5 h. Then the solvent was evaporated under reduced pressure and water (50 mL) was added, extracted with ethyl acetate (20 mL×3) and combined the organic layer, the solvent was evaporated under reduced pressure to give crude product, further purified by column chromatography (PE:EA=4:1) to give product as a white solid (190 mg in 63% yield). ¹H NMR (400 MHz, DMSO-d₆) δ_H 8.62 (s, 1H), 7.40 (d, J=9.2 Hz, 1H), 7.32 (s, 1H), 7.27 (t, J=7.6 Hz, 1H), 7.02-7.05 (m, 2H), 6.96 (t, J=8.4 Hz, 1H), 6.47 (d, J=9.6 Hz, 1H), 5.81 (d, J=3.6 Hz, 1H), 5.25 (dd, J=3.6 Hz, J=9.6 Hz, 1H), 2.41-2.44 (m, 1H), 2.18-2.23 (m, 1H), 1.99-2.01 (m, 1H), 1.87-1.91 (m, 1H), 1.66-1.69 (m, 1H), 1.46-1.56 (m, 1H), 1.17-1.29 (m, 4H), 0.93-0.96 (m, 2H), 0.76-0.79 (m, 1H) and 0.64-0.67 (m, 1H). MS (ESI) m/e [M+1]⁺=365.2.

Example D156a and D156b: (S)-(6-cyclopropylimidazo[1,5-a]pyridin-5-yl)(4-(3-fluorophenyl)cyclohexyl)methanol and (R)-(6-cyclopropylimidazo[1,5-a]pyridin-5-yl)(4-(3-fluorophenyl)cyclohexyl)methanol

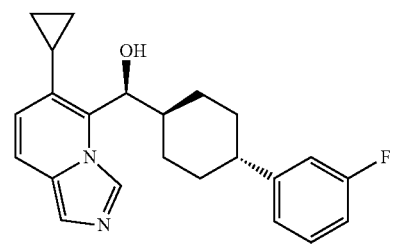

Fast isomer in CHIRALPAK IC HPLC
Eluting reagent: Hex:EtOH = 85:15

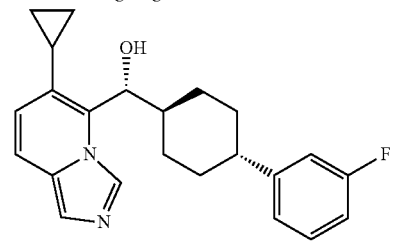

Slow isomer in CHIRALPAK IC HPLC
Eluting reagent: Hex(:EtOH = 85:15

Each enantiomer of racemic D156a and D156b was separated using preparative HPLC on a CHIRALPAK IC with Hex:EtOH=85:15 as an eluent. The enantiomeric excesses were determined by using HPLC on a CHIRALPAK IC-3 with Hex (0.1% IPAmine):EtOH=85:15 as an eluent at a flow rate of 1.0 mL/min. The first one enantiomer eluted at the retention time of 1.884 min, and the other enantiomer eluted at the retention time of 4.604 min. To a solution of D156a (51 mg) in THF (10 mL) was added drop wise of Ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (45 mg in 70% yield). $^1$H NMR (400 MHz, DMSO-$d_6$) $\delta_H$ 9.63 (s, 1H), 8.07 (s, 1H), 7.71 (d, J=9.6 Hz, 1H), 7.27-7.33 (m, 1H), 6.96-7.05 (m, 3H), 6.84 (d, J=9.6 Hz, 1H), 6.21 (s, 1H), 5.32 (d, J=9.6 Hz, 1H), 2.39-2.42 (m, 1H), 2.17 (s, 2H), 1.90-1.93 (m, 1H), 1.70 (s, 1H), 1.44-1.53 (m, 1H), 1.23-1.37 (m, 4H), 1.02-1.07 (m, 2H), 0.85-0.88 (m, 1H) and 0.76-0.79 (m, 1H). MS (ESI) m/e [M+1]$^+$=365.2. To a solution of D156b (54 mg) in THF (10 mL) was added drop wise of ethyl acetate solution of hydrochloric acid (0.5 mL, 4.0M) at room temperature, followed by addition of methol until the precipitate was dissolved, then the solvent was evaporated under reduced pressure and the residue was washed by PE to give the desired product as white solid (36 mg in 61% yield). $^1$H NMR (400 MHz, DMSO-$d_6$) $\delta_H$ 9.64 (s, 1H), 8.08 (s, 1H), 7.71 (d, J=9.6 Hz, 1H), 7.27-7.33 (m, 1H). 6.96-7.05 (m, 3H), 6.85 (d, J=9.6 Hz, 1H), 6.23 (s, 1H), 5.32 (d, J=9.6 Hz, 1H), 2.39-2.42 (m, 1H), 2.17 (s, 2H), 1.90-1.93 (m, 1H), 1.69 (s, 1H), 1.44-1.53 (m, 1H), 1.23-1.34 (m, 4H), 1.04-1.06 (m, 2H), 0.85-0.88 (m, 1H) and 0.76-0.79 (m, 1H). MS (ESI) m/e [M+1]$^+$=365.2. The absolute configurations of chiral carbons in D156a and D156b are tentatively assigned as (S) and (R) respectively based on assumption that the binding model of the more potent isomer D156a is the same as that of C101a with IDO1 enzyme, and the relative stereochemistry on cyclohexane is assigned as trans configuration on the cyclohexane.

Example D157 was synthesized using the same procedure as discriped in Example D156

Example D157: (6-cyclopropylimidazo[1,5-a]pyridin-5-yl)(4-(quinolin-6-yl)cyclohexyl)methanol

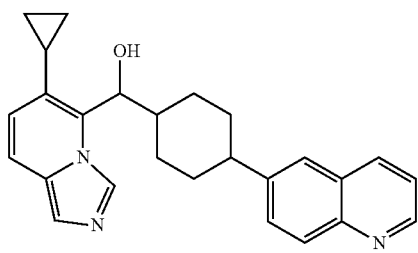 [SMILES: OC(c1c(C2CC2)ccc2cncn12)C1CCC(c2ccc3ncccc3c2)CC1]

$^1$H NMR (DMSO-$d_6$) $\delta_H$ 8.80-8.82 (m, 1H), 8.65 (s, 1H), 8.25 (d, J=8.0 Hz, 1H), 7.90 (d, J=8.8 Hz, 1H), 7.76 (s, 1H), 7.65-7.68 (m, 1H), 7.42-7.49 (m, 2H), 7.33 (s, 1H), 6.48 (d, J=9.2 Hz, 1H), 5.83 (d, J=4.0 Hz, 1H), 5.29 (dd, J=4.0, 10.0 Hz, 1H), 2.65-2.73 (m, 1H), 2.46-2.48 (m, 1H), 2.25-2.29 (m, 1H), 2.02-2.03 (m, 1H), 1.77-1.81 (m, 1H), 1.61-1.65 (m, 1H), 1.19-1.41 (m, 5H), 0.97-0.99 (m, 2H), and 0.77-0.86 (m, 2H). [M+H]$^+$=398.

Example D157a and D157b: (S)-(6-cyclopropylimidazo[1,5-a]pyridin-5-yl)((1r,4S)-4-(quinolin-6-yl)cyclohexyl)methanol and (R)-(6-cyclopropylimidazo[1,5-a]pyridin-5-yl)((1r,4R)-4-(quinolin-6-yl)cyclohexyl)methanol

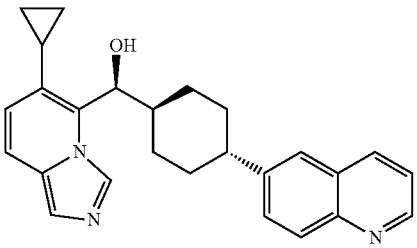

Fast isomer in CHIRALPAK IC HPLC
Eluting reagent: Hex:EtOH = 50:50

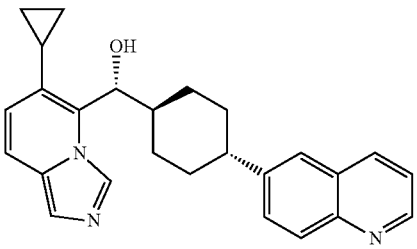

Slow isomer in CHIRALPAK IC HPLC
Eluting reagent: Hex:EtOH = 50:50

Each enantiomer of racemic D157a and D157b was separated using preparative HPLC on a CHIRALPAK IC with Hex:EtOH=50:50 as an eluent. The enantiomeric excesses were determined by using HPLC on a CHIRALPAK IC with Hex (0.1% DEAmine):EtOH=50:50 as an eluent at a flow rate of 1.0 mL/min. The first one enantiomer eluted at the retention time of 2.136 min, and the other enantiomer eluted at the retention time of 4.855 min. To a solution of D157a (20.3 mg) in DCM (2 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give desired product as white solid (17.98 mg). $^1$H NMR (DMSO-$d_6$) $\delta_H$ 9.71 (s, 1H), 9.10-9.11 (m, 1H), 8.82-8.82 (m, 1H), 8.18-8.21 (m, 1H), 8.12 (s, 1H), 8.02-8.06 (m, 1H), 7.86-7.95 (m, 2H), 7.73 (d, J=9.6 Hz, 1H), 6.87 (d, J=9.6 Hz, 1H), 6.27 (brs, 1H), 5.37 (d, J=9.6 Hz, 1H), 2.76-2.84 (m, 1H), 2.45-2.46 (m, 1H), 2.21-2.26 (m, 2H), 2.03-2.07 (m, 1H), 1.85-1.91 (m, 1H), 1.57-1.69 (m, 1H), 1.28-1.46 (m, 4H), 1.05-1.20 (m, 2H), and 0.76-0.91 (m, 2H). [M+H]$^+$=398. To a solution of D157b (20.5 mg) in DCM (2 mL) was added drop wise of Ethyl acetate solution of hydrochloric acid (1.0 mL, 4.0M) at room temperature, followed by addition of methol until the precipitate was dissolved, then the solvent was evaporated under reduced pressure and the residue was washed by PE to give desired product as white solid (15.87 mg). H NMR (DMSO-$d_6$) $\delta_H$ 9.71 (s, 1H), 9.10-9.11 (m, 1H), 8.80-8.82 (m, 1H), 8.15-8.19 (m, 1H), 8.13 (s, 1H), 8.01-8.05 (m, 1H), 7.83-7.94 (m, 2H), 7.73 (d, J=9.6 Hz, 1H), 6.87 (d, J=9.6 Hz, 1H), 6.32 (brs, 1H), 5.37 (d, J=9.6 Hz, 1H), 2.75-2.79 (m, 1H), 2.42-2.47 (m, 1H), 2.16-2.26 (m, 2H), 2.01-2.04 (m, 1H), 1.82-1.86 (m, 1H), 1.58-1.62 (m, 1H), 1.34-1.46 (m, 4H), 1.05-1.10 (m, 2H), and 0.78-0.91 (m, 2H). The absolute configurations of chiral carbons in D157a and D157b are tentatively assigned as (S) and (R) respectively based on assumption that the binding model of the more potent isomer D157a is the same as that of C101a with IDO1 enzyme, and the relative stereochemistry on cyclohexane is assigned as trans configuration on the cyclohexane.

Example D158: 1-(4-(4-(6-cyclopropylimidazo[1,5-a]pyridin-5-yl hydroxy)methyl)cyclohexyl)phenyl) ethan-1-one

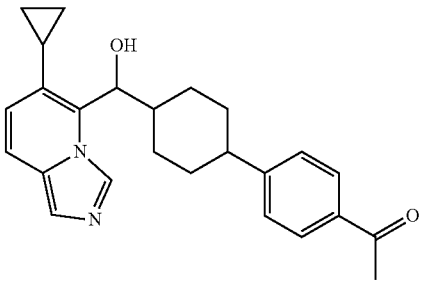 [SMILES: CC(=O)c1ccc(C2CCC(C(O)c3c(C4CC4)ccc4cncn34)CC2)cc1]

To a solution of 4-(4-((6-cyclopropylimidazo[1,5-a]pyridin-5-yl)(hydroxy)methyl)cyclohexyl)benzonitrile (100 mg, 0.26 mmol) in THF (10 mL) was added CuI (20 mg, 0.1 mmol) at room temperature and followed by addition of CH₃MgBr (0.6 mL, 3.0 M) and the mixture was stirred at room temperature for 24 hours. Then saturated aqueous of NH₄Cl was added and extracted with ethyl acetate (10 mL×3), combined the organic layer and washed with saturated aqueous of NaHCO₃, then the organic layer was evaporated under reduced pressure to give crude product, which was further purified by column chromatography (PE: EA=4:1) to give product as a white solid. (28 g in 28% yield). ¹H NMR (400 MHz, DMSO-d₆) $\delta_H$ 8.63 (s, 1H), 7.85 (d, J=8.4 Hz, 2H), 7.41 (d, J=9.6 Hz, 1H), 7.36 (d, J=8.0 Hz, 1H), 7.32 (s, 1H), 6.48 (d, J=9.2 Hz, 1H), 5.82 (d, J=3.6 Hz, 1H), 5.26 (dd, J=3.6 Hz, J=10.0 Hz, 1H), 2.63 (s, 3H), 2.42-2.44 (m, 1H), 2.22-2.25 (m, 1H), 2.01 (s, 1H), 1.88-1.91 (m, 1H), 1.62-1.66 (m, 1H), 1.53-1.56 (m, 1H), 1.43-1.48 (m, 1H), 1.28-1.38 (m, 4H), 0.82-0.89 (m, 2H), 0.75-0.79 (m, 1H) and 0.64-0.68 (m, 1H), MS (ESI) m/e [M+1]⁺=389.2;

Example D159: N-(4-((1S,4r)-4-((S)-(6-cyclopropylimidazo[1,5-a]pyridin-5-yl)hydroxy)methylcyclohexyl)phenyl)acetamide

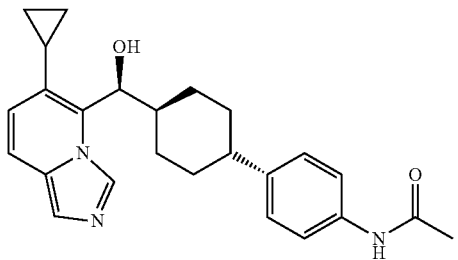

To a solution of (S)-((1r,4S)-4-(4-aminophenyl)cyclohexyl)(6-cyclopropylimidazo[1,5-a]pyridin-5-yl)methanol (12 mg, 0.03 mmoL) in pyridine (2 mL) was added Ac₂O (0.1 mL) and the mixture was heated at 25-35° C. for 12 hours. Then the reaction mixture was concentrated and purified by pre-HPLC to give product (6 mg, in 44.8% yield) as white solid. ¹H NMR (MeOD) $\delta_H$ 9.70 (s, 1H), 7.95 (s, 1H), 7.66 (d, J=9.6 Hz, 1H), 7.38 (d, J=8.4 Hz, 2H), 7.11 (d, J=8.4 Hz, 2H), 6.94 (d, J=9.6 Hz, 1H), 5.45 (d, J=9.6 Hz, 1H), 2.51-2.48 (m, 2H), 2.20-2.07 (m, 2H), 2.07 (s, 3H), 1.98 (d, J=12.8 Hz, 1H), 1.78-1.76 (m, 1H), 1.58-1.47 (m, 1H), 1.42-1.27 (m, 4H), 1.14-1.08 (m, 2H), 0.91-0.79 (m, 2H). [M+H]⁺=404.2.

Example D160: 1-(4-((1S,4r)-4-((S)-(6-cyclopropylimidazo[1,5-a]pyridin-5-yl)(hydroxy)methyl)cyclohexyl)phenyl)urea

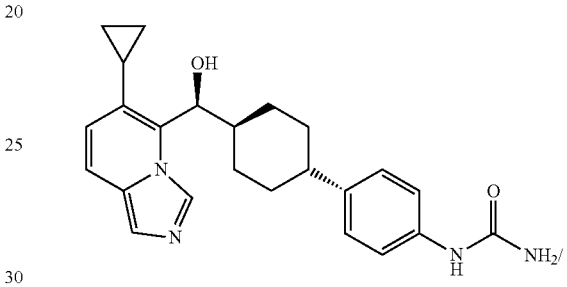

To a solution of (S)-((1 r,4S)-4-(4-aminophenyl)cyclohexyl)(6-cyclopropylimidazo[1,5-a]pyridin-5-yl)methanol (40.0 mg, 0.1 mmol) in H₂O (2 mL) and acetic acid (2 mL) was added a solution of sodium cyanate (20 mg) in H₂O (1 mL). Then the reaction mixture was stirred at 25-35° C. for 2 hours. Adjusted pH to 7-8 with saturate NaHCO₃ solution. Extracted with EA (20 mL×2) and combined the organic phase. Concentrated and purified by pre-TLC with DCM/MeOH (10:1) to give product (27.3 mg) as white solid. ¹HNMR (400 MHz, DMSO-d6) $\delta_H$8.61 (s, 1H), 8.39 (b, 1H), 7.40 (d, J=9.2 Hz, 1H), 7.31 (s, 1H), 7.24 (d, J=8.0 Hz, 2H), 7.03 (d, J=8.0 Hz, 2H), 6.47 (d, J=9.6 Hz, 1H), 5.84-5.73 (m, 3H), 5.26-5.23 (m, 1H), 2.42-2.33 (m, 2H), 2.18 (b, 1H), 1.99 (b, 1H), 1.91-1.84 (m, 1H), 1.63 (b, 1H), 1.49-1.40 (m, 1H), 1.30-1.14 (m, 4H), 0.96-0.92 (m, 2H), 0.76 (b, 1H), 0.65 (b, 1H). [M+H]⁺=405.2

Example D161: (6-cyclopropylimidazo[1,5-a]pyridin-5-yl)(4-(quinolin-7-yl)cyclohexyl)methanol

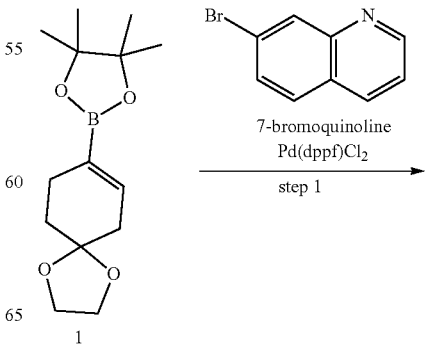

7-bromoquinoline
Pd(dppf)Cl₂
step 1

1

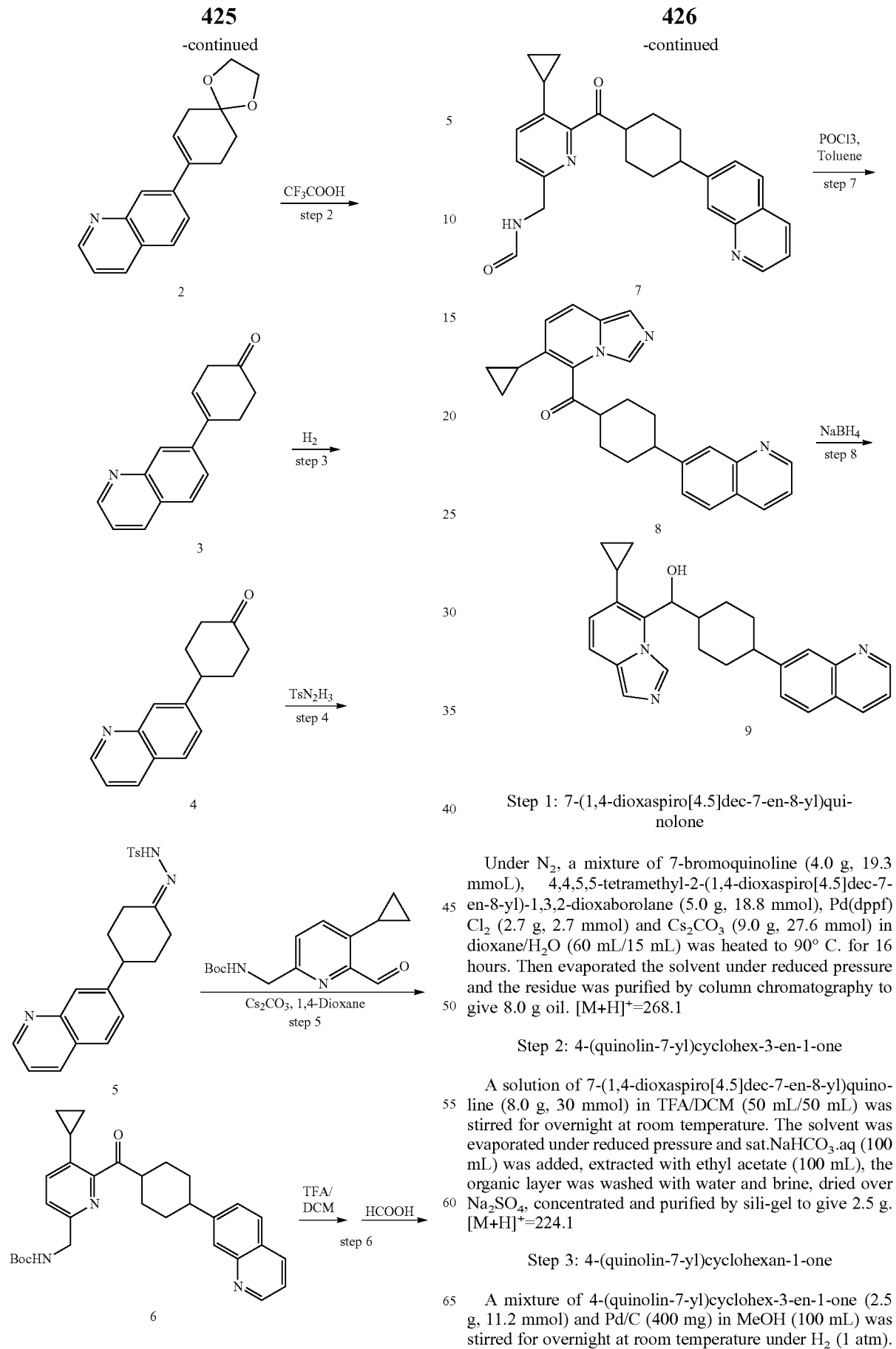

Step 1: 7-(1,4-dioxaspiro[4.5]dec-7-en-8-yl)qui-nolone

Under N₂, a mixture of 7-bromoquinoline (4.0 g, 19.3 mmoL), 4,4,5,5-tetramethyl-2-(1,4-dioxaspiro[4.5]dec-7-en-8-yl)-1,3,2-dioxaborolane (5.0 g, 18.8 mmol), Pd(dppf)Cl₂ (2.7 g, 2.7 mmol) and Cs₂CO₃ (9.0 g, 27.6 mmol) in dioxane/H₂O (60 mL/15 mL) was heated to 90° C. for 16 hours. Then evaporated the solvent under reduced pressure and the residue was purified by column chromatography to give 8.0 g oil. [M+H]⁺=268.1

Step 2: 4-(quinolin-7-yl)cyclohex-3-en-1-one

A solution of 7-(1,4-dioxaspiro[4.5]dec-7-en-8-yl)quino-line (8.0 g, 30 mmol) in TFA/DCM (50 mL/50 mL) was stirred for overnight at room temperature. The solvent was evaporated under reduced pressure and sat.NaHCO₃.aq (100 mL) was added, extracted with ethyl acetate (100 mL), the organic layer was washed with water and brine, dried over Na₂SO₄, concentrated and purified by sili-gel to give 2.5 g. [M+H]⁺=224.1

Step 3: 4-(quinolin-7-yl)cyclohexan-1-one

A mixture of 4-(quinolin-7-yl)cyclohex-3-en-1-one (2.5 g, 11.2 mmol) and Pd/C (400 mg) in MeOH (100 mL) was stirred for overnight at room temperature under H₂ (1 atm).

Then filtered to remove Pd/C and the filtrate was evaporated and then purified by column chromatography to give 1.2 g. [M+H]⁺=226.1

Step 4: 4-methyl-N'-(4-(quinolin-7-yl)cyclohex-ylidene)benzenesulfonohydrazide

A solution of 4-(quinolin-7-yl)cyclohexan-1-one (1.2 g, 5.3 mmol) and 4-methylbenzenesulfonohydrazide (1.0 g, 5.3 mmol) in MeOH (30 mL) was stirred for 2 hours at room temperature. The reaction mixture was filtered to give 0.8 g. [M+H]⁺=394.1

Step 5: tert-butyl ((5-cyclopropyl-6-(4-(quinolin-7-yl)cyclohexane-1-carbonyl)pyridin-2-yl)methyl)carbamate A mixture of tert-butyl ((5-cyclopropyl-6-formylpyridin-2-yl)methyl)carbamate (0.5 g, 1.8 mmol), 4-methyl-N'-(4-(quinolin-7-yl)cyclohexylidene)benzenesulfonohydrazide (0.8 g, 2.0 mmol) and Cs$_2$CO$_3$ (1.0 g, 3.06 mmol) in 1,4-dioxane (30 mL) was heated at 90° C. for overnight. After cooled down, EA (30 mL) was added, filtered, and the filtrate was evaporated under reduced pressure and the residue was purified by column chromatography to give 600 mg. [M+H]⁺=486.2

Step 6: N-((5-cyclopropyl-6-(4-(quinolin-7-yl)cyclohexane-1-carbonyl)pyridin-2-yl)methyl)formamide A mixture of tert-butyl ((5-cyclopropyl-6-(4-(quinolin-7-yl)cyclohexane-1-carbonyl)pyridin-2-yl)methyl)carbamate (800 mg, 1.65 mmol) in TFA/DCM (20 mL/20 mL) was stirred for 2 hours at room temperature, concentrated to give crude product. A solution of crude product in HCOOH (15 mL) was stirred for overnight at 80° C. The reaction mixture was concentrated, sat.NaHCO$_3$.aq was added, extracted with EA, the EA layer was washed with brine, dried over Na$_2$SO$_4$, concentrated and purified by sili-gel to give 400 mg. [M+H]⁺=414.2

Step 7: (6-cyclopropylimidazo[1,5-a]pyridin-5-yl)(4-(quinolin-7-yl)cyclohexyl)methanone A mixture of N-((5-cyclopropyl-6-(4-(quinolin-7-yl)cyclohexane-1-carbonyl)pyridin-2-yl)methyl)formamide (300 mg, 0.73 mmol) and POCl$_3$ (1.0 mL) in toluene (30 mL) was heated to 90° C. for 1 hour, after cooled down, the reaction mixture was concentrated, sat.NaHCO$_3$.aq was added, extracted with EA, the EA layer was washed with brine, dried over Na$_2$SO$_4$, concentrated and purified by sili-gel to give 200 mg. [M+H]⁺=396.2

Step 8: (6-cyclopropylimidazo[1,5-a]pyridin-5-yl)(4-(quinolin-7-yl)cyclohexyl)methanol

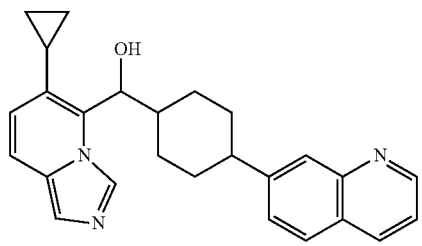 [SMILES: OC(c1c(C2CC2)ccc2cncn12)C1CCC(c2ccc3cccnc3c2)CC1]

A solution of (6-cyclopropylimidazo[1,5-a]pyridin-5-yl)(4-(quinolin-7-yl)cyclohexyl)methanone (200 mg, 0.51 mmol) and NaBH$_4$ (70 mg, 1.84 mmol) in MeOH (20 mL) was stirred for 1 hour at room temperature. Then the solvent was evaporated under reduced pressure and water (50 mL) was added, extracted with ethyl acetate (50 mL), the EA layer was washed with brine, dried over Na$_2$SO$_4$, concentrated and purified by sili-gel and prep-TLC to give 50 mg. $^1$H NMR (DMSO-d$_6$)$^{6H}$ 8.84 (d, J=3.2 Hz, 1H), 8.71 (s, 1H), 8.28-8.30 (d, J=8.0 Hz, 1H), 7.86-7.88 (d, J=8.0 Hz, 1H), 7.79 (s, 1H), 7.36-7.53 (m, 3H), 6.49-6.52 (d, J=9.6 Hz, 1H), 5.85-5.86 (d, J=3.6 Hz, 1H), 5.25-5.33 (m, 1H), 2.64-2.77 (m, 1H), 2.21-2.35 (m, 1H), 1.94-2.08 (m, 2H), 1.59-1.85 (m, 2H), 1.23-1.45 (m, 5H), 0.91-1.05 (m, 2H) and 0.64-0.82 (m, 2H). [M+H]⁺=398.2

Example D161a and D161b

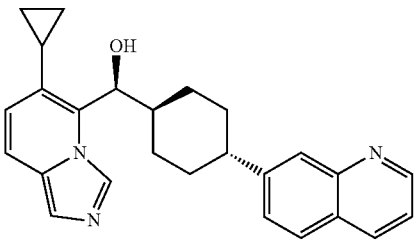

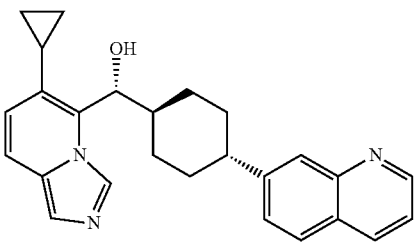

Example 62: 6-cyclopropylimidazo[1,5-a]pyridin-5-yl)(4-(furan-3-yl)cyclohexyl)methanol

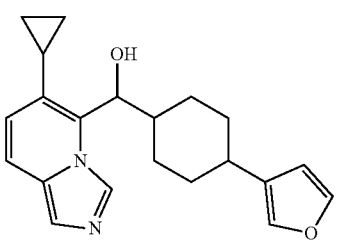 [SMILES: OC(c1c(C2CC2)ccc2cncn12)C1CCC(c2ccoc2)CC1]

Example D163: (6-cyclopropylimidazo[1,5-a]pyridin-5-yl)(4-(8-fluoroquinolin-5-yl)cyclohexyl)methanol

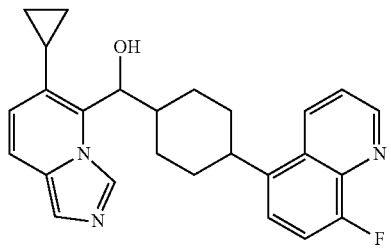 [SMILES: OC(c1c(C2CC2)ccc2cncn12)C1CCC(c2ccc(F)c3ncccc23)CC1]

¹H NMR (400 MHz, MeOD) δ 9.33 (s, 1H), 8.93-8.82 (m, 2H), 8.29 (d, J=7.6 Hz, 1H), 8.09 (s, 1H), 7.77-7.72 (m, 1H), 7.52-7.49 (m, 2H), 6.70 (d, J=7.6 Hz, 1H), 5.30 (d, J=8.0 Hz, 1H), 3.35-3.29 (m, 1H), 2.39-2.36 (m, 1H), 2.25 (b, 1H), 2.08-2.06 (m, 2H), 1.95-1.92 (m, 1H), 1.67-1.49 (m, 5H), 1.60-1.14 (m, 2H), 0.92-0.85 (m, 2H). [M+H]⁺=416.2

Example D163a and D163b: (S)-(6-cyclopropylimidazo[1,5-a]pyridin-5-yl)((1r,4S)-4-(8-fluoroquinolin-5-yl)cyclohexyl)methanol and (R)-(6-cyclopropylimidazo[1,5-a]pyridin-5-yl)(1r,4R)-4-(8-fluoroquinolin-5-yl)cyclohexyl)methanol

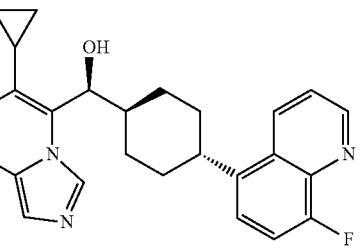

Fast isomer on chiral IC

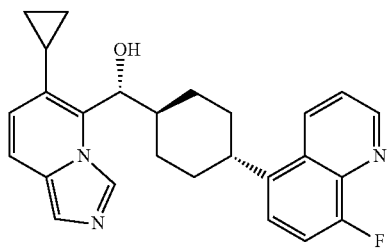

Slow isomer on chiral IC

Example D164: (6-cyclopropylimidazo[1,5-a]pyridin-5-yl)(4-(8-fluoroquinolin-4-yl)cyclohexyl)methanol

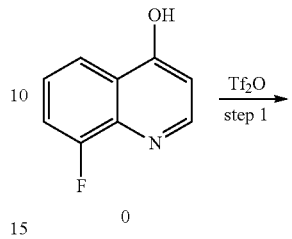

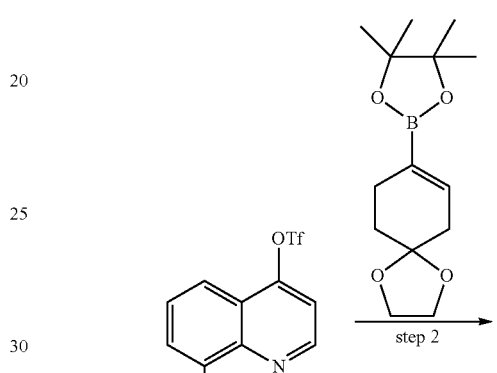

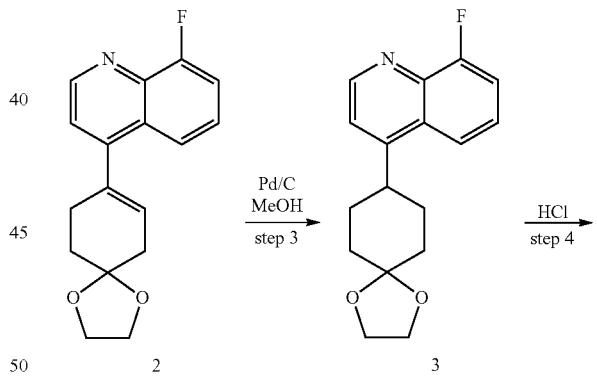

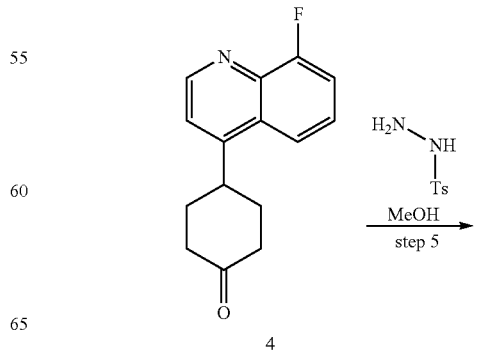

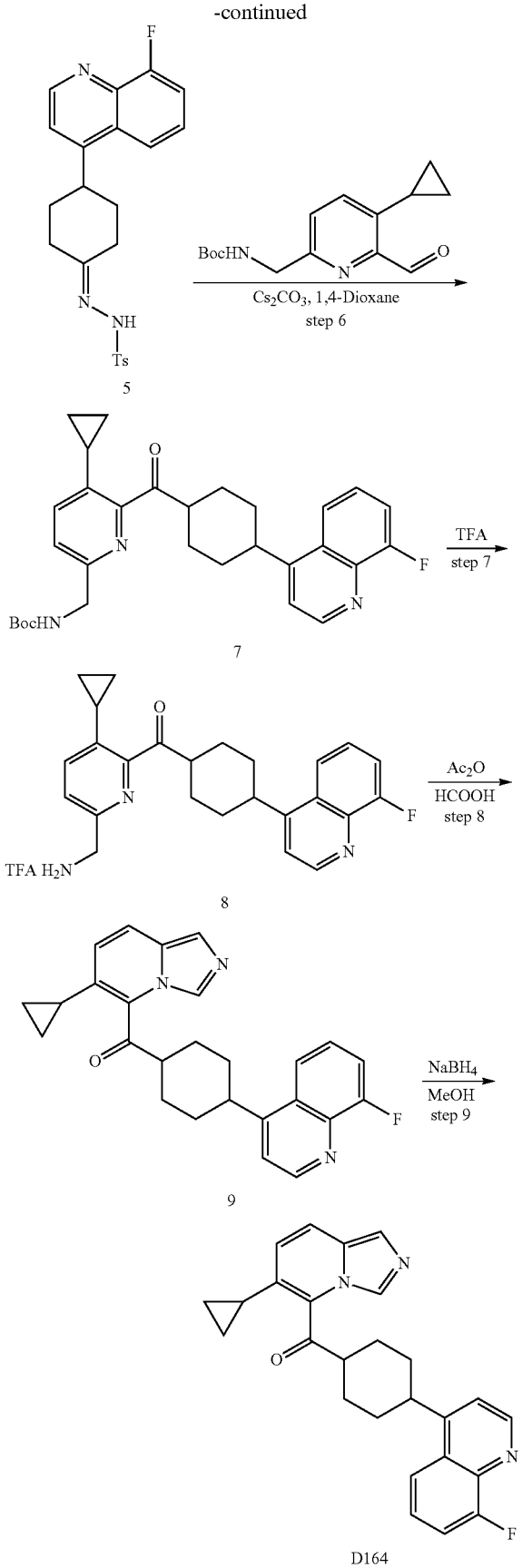

Step 1: 8-fluoroquinolin-4-yl trifluoromethanesulfonate

To a solution of 8-fluoroquinolin-4-ol (20 g, 123 mmoL) in DCM (200 mL) was added DIPEA (24 g, 185 mmol) at room temperature, followed by addition of trifluoromethanesulfonic anhydride (52 g, 185 mmol) drop wise at 0° C. and the mixture was stirred for 1 hour. Saturated aqueous of NaHCO$_3$ was added and extracted with DCM (100 mL×3), combined the organic layer and the organic layer was evaporated under reduced pressure to give crude product, which was further purified by column chromatography (PE:EA=10:1) to give product as an oil (24 g in 66% yield). $^1$H NMR (400 MHz, DMSO-d6) $\delta_H$ 9.15 (d, J=4.8 Hz, 1H), 7.93 (dd, J=1.2 Hz, J=4.8 Hz, 1H), 7.82-7.88 (m, 3H), MS (ESI) n/e [M+1]$^+$=295.9.

Step 2: 8-fluoro-4-(1,4-dioxaspiro[4.5]dec-7-en-8-yl)quinoline

To a solution of 8-fluoroquinolin-4-yl trifluoromethanesulfonate (24 g, 82 mmoL) in 1,4-dioxane (200 mL) was added 4,4,5,5-tetramethyl-2-(1,4-dioxaspiro[4.5]dec-7-en-8-yl)-1,3,2-dioxaborolane (22 g, 82 mmol), Pd(dppf)Cl$_2$ (6.0 g, 8.2 mmol) and Cs$_2$CO$_3$ (40 g, 124 mmol) and the mixture was heated at 70° C. for 5 hours. Then the solvent was evaporated under reduced pressure and the residue was purified by column chromatography (PE:EA=10:1) to give product as light yellow solid. (15 g in 64% yield). $^1$H NMR (400 MHz, DMSO-d$_6$) $\delta_H$ 8.89 (d, J=4.4 Hz, 1H), 7.83-7.85 (m, 1H), 7.58-7.62 (m, 2H), 7.42 (d, J=4.4 Hz, 1H), 5.74 (d, J=0.8 Hz, 1H), 3.99 (s, 4H), 2.54-2.56 (m, 2H), 2.45-2.46 (m, 2H) and 1.92 (t, J=6.4 Hz, 2H), MS (ESI) m/e [M+1]$^+$=286.1.

Step 3: 8-fluoro-4-(1,4-dioxaspiro[4.5]decan-8-yl)quinoline

To a solution of 8-fluoro-4-(1,4-dioxaspiro[4.5]dec-7-en-8-yl)quinoline (10 g, 35 mmol) in ethyl acetate (150 mL) and MeOH (150 mL) was added Pd/C (1.0 g, 10%) and the mixture was stirred for 18 hours at room temperature under H$_2$ (0.1 Mpa). Then filtered to remove Pd/C and the filtrate was evaporated under reduced pressure to give a crude product, further purified by column chromatography (PE:EA=10:1 to 4:1) to give product as light yellow solid. (7.0 g in 70% yield). $^1$H NMR (400 MHz, DMSO-d$_6$) $\delta_H$ 8.87 (d, J=4.4 Hz, 1H), 8.10 (d, J=7.6 Hz, 1H), 7.56-7.65 (m, 2H), 7.51 (d, J=4.4 Hz, 1H), 3.92 (s, 4H), 3.46-3.51 (m, 1H) and 1.76-1.90 (m, 8H), MS (ESI) m/e [M+1]$^+$=288.1.

Step 4: 4-(6-(trifluoromethyl)pyridin-3-yl)cyclohexan-1-one

To a solution of 4-(6-(trifluoromethyl)pyridin-3-yl)cyclohex-3-en-1-one (7.0 g, 24 mmol) in 1,4-Dioxane (40 mL) was added HCl (40 mL, 6 N) at room temperature and the mixture was stirred for overnight. The solvent was evaporated under reduced pressure and saturated aqueous of NaHCO$_3$ (100 mL) was added, extracted with ethyl acetate (50 mL×3), combined the organic layer and the solvent was evaporated under reduced pressure, further purified by column chromatography (PE:EA=4:1) to give product as light yellow solid. (3.13 g in 54% yield). $^1$H NMR (400 MHz, DMSO-d$_6$) $\delta_H$ 8.90 (d, J=4.8 Hz, 1H), 8.22 (d, J=8.4 Hz, 1H), 7.60-7.70 (m, 2H), 7.57 (d, J=4.4 Hz, 1H), 3.99 (t, J=12.0 Hz, 1H), 2.75-2.84 (m, 2H), 2.33-2.37 (m, 2H), 2.16-2.20 (m, 2H) and 1.97-2.07 (m, 2H), MS (ESI) m/e [M+1]$^+$=244.1.

Step 5: N'-(4-(8-fluoroquinolin-4-yl)cyclohex-ylidene)-4-methylbenzenesulfonohydrazide To a solution of 4-(8-fluoroquinolin-4-yl)cyclohexan-1-one (3.13 g, 13 mmol) in methol (100 mL) was added 4-methylbenzenesulfonohydrazide (2.4 g, 13 mmol) at room temperature and the mixture was stirred for overnight. Evaporate half the solvent under reduced pressure and then filtered to give product as a white solid (4.8 g in 90% yield). $^1$H NMR (400 MHz, DMSO-d$_6$) $\delta_H$ 10.25 (s, 1H), 8.86 (d, J=4.4 Hz, 1H), 8.13 (d, J=8.0 Hz, 1H), 7.76 (d, J=8.0 Hz, 2H), 7.57-7.66 (m, 2H), 7.49 (d, J=4.4 Hz, 1H), 7.42 (d, J=8.0 Hz, 2H), 3.72 (t, J=12.0 Hz, 1H), 2.98 (d, J=14.8 Hz, 1H), 2.43-2.46 (m, 1H), 2.40 (s, 3H), 2.32-2.36 (m, 1H), 2.12-2.20 (m, 1H), 2.02-2.05 (m, 2H) and 1.56-1.74 (m, 2H). MS (ESI) m/e [M+1]$^+$=412.1.

Step 6: tert-butyl ((5-cyclopropyl-6-(4-(8-fluoroquinolin-4-yl)cyclohexane-1-carbonyl)pyridin-2-yl)methyl)carbamate To a solution of tert-butyl ((5-cyclopropyl-6-formylpyridin-2-yl)methyl)carbamate (0.5 g, 1.8 mmol) in 1,4-dioxane (0.1 L) was added N'-(4-(8-fluoroquinolin-4-yl)cyclohexylidene)-4-methylbenzenesulfonohydrazide (0.9 g, 2.2 mmol) and Cs$_2$CO$_3$ (0.9 g, 2.7 mmol) at room temperature, and the mixture was heated at 100° C. for 6 hours. The solvent was evaporated in vacuo and water (100 mL) was added, extracted with ethyl acetate (50 mL×3) and combined the organic layer, the solvent was evaporated under reduced pressure and the residue was purified by column chromatography (PE:EA=10:1) to give product as a light yellow oil (0.5 g in 55% yield). MS (ESI) m/e [M+1]$^+$=504.2.

Step 7: (6-(aminomethyl)-3-cyclopropylpyridin-2-yl)(4-(8-fluoroquinolin-4-yl)cyclohexyl)methanone To a solution of tert-butyl ((5-cyclopropyl-6-(4-(8-fluoroquinolin-4-yl)cyclohexane-1-carbonyl)pyridin-2-yl)methyl)carbamate (0.5 g, 1.0 mmol) in DCM (10 mL) was added trifluoracetic acid (10 mL) and the mixture was stirred at room temperature for overnight. The solvent was evaporated under reduced pressure to give crude product as solid. MS (ESI) m/e [M+1]$^+$=404.2.

Step 8: (6-cyclopropylimidazo[1,5-a]pyridin-5-yl)(4-(8-fluoroquinolin-4-yl)cyclohexyl)methanone A mixture of Ac$_2$O (30 mL) and HCOOH (10 mL) was heated at 50° C. for 1 hour and then a solution of (6-(aminomethyl)-3-cyclopropylpyridin-2-yl)(4-(8-fluoroquinolin-4-yl)cyclohexyl)methanone (crude, 1.0 mmol) in HCOOH (5 mL) was added drop wise and the mixture was heated at 50° C. for 2 hours. The solvent was evaporated under reduced pressure and water (100 mL) was added, washed with saturated aqueous of NaHCO$_3$, then extracted with ethyl acetate (50 mL×3) and combined the organic layer, the solvent was evaporated under reduced pressure and the residue was purified by column chromatography (PE:EA=4:1) to give crude product as a light yellow solid. MS (ESI) m/e [M+1]$^+$=414.1.

Step 9: (6-cyclopropylimidazo[1,5-a]pyridin-5-yl)(4-(8-fluoroquinolin-4-yl)cyclohexyl)methanol

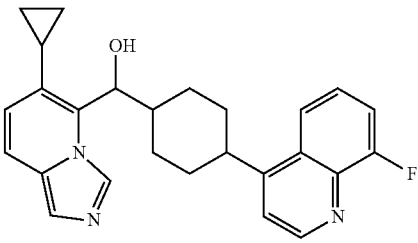 [SMILES: OC(c1c(C2CC2)ccc2cncn12)C1CCC(c2ccnc3c(F)cccc23)CC1]

To a solution of (6-cyclopropylimidazo[1,5-a]pyridin-5-yl)(4-(8-fluoroquinolin-4-yl)cyclohexyl)methanone (1.0 mmol) in methol (10 mL) was added NaBH$_4$ (200 mg, 5.0 mmol) at room temperature and the mixture was stirred for 0.5 h. Then the solvent was evaporated under reduced pressure and water (50 mL) was added, extracted with ethyl acetate (50 mL×3) and combined the organic layer, the solvent was evaporated under reduced pressure to give product as a white solid (300 mg in 72% yield). $^1$H NMR (400 MHz, DMSO-d$_6$) $\delta_H$ 8.84 (d, J=4.4 Hz, 1H), 8.66 (s, 1H), 8.05 (d, J=7.6 Hz, 1H), 7.54-7.59 (m, 2H), 7.48 (d, J=4.8 Hz, 1H), 7.42 (d, J=9.2 Hz, 1H), 7.33 (s, 1H), 6.51 (d, J=8.4 Hz, 1H), 5.87 (d, J=3.6 Hz, 1H), 5.33 (dd, J=3.6 Hz, J=9.6 Hz, 1H), 2.29-2.31 (m, 1H), 1.99-2.03 (m, 1H), 1.78-1.81 (m, 1H), 1.62-1.71 (m, 1H), 1.36-1.55 (m, 4H), 1.16-1.23 (m, 2H), 0.77-0.80 (m, 1H) and 0.69-0.72 (m, 1H). MS (ESI) m/e [M+1]$^+$=416.2.

Example D164a and D164b: (S)-(6-cyclopropylimidazo[1,5-a]pyridin-5-yl)((1r,4S)-4-(8-fluoroquinolin-4-yl)cyclohexyl)methanol and (R)-(6-cyclopropylimidazo[1,5-a]pyridin-5-yl)((1 r,4R)-1-(8-fluoroquinolin-4-yl)cyclohexyl)methanol

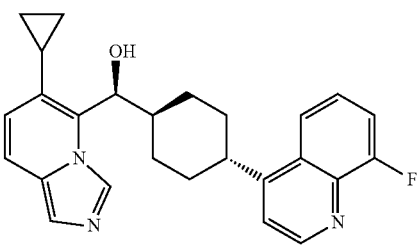

Fast isomer on chiral IC

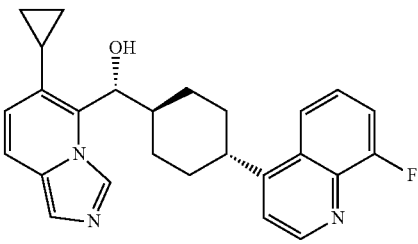

Slow isomer on chiral IC

Example D165: 1-(4-((1S,4r)-4-((S)-(6-cyclopropylimidazo[1,5-a]pyridin-5-yl)(hydroxy)methyl)cyclohexyl)phenyl) sulfuric diamide

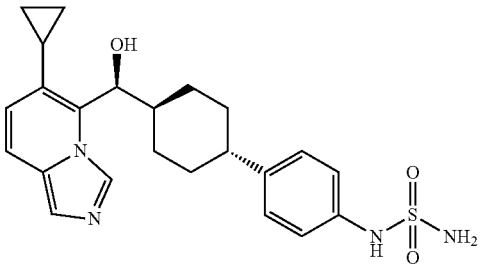 [SMILES: NS(=O)(=O)Nc1ccc([C@H]2CC[C@H]([C@H](O)c3c(C4CC4)ccc4cncn34)CC2)cc1]

To a solution of (S)-((1r,4S)-4-(4-aminophenyl)cyclohexyl)(6-cyclopropylimidazo[1,5-a]pyridin-5-yl)methanol (40.0 mg, 0.1 mmol) in DCM (5 mL) was added DIEA (0.1 mL) and sulfamoyl chloride (20 mg). Then the reaction mixture was stirred at 25-35° C. for 0.5 hour. Quenched the reaction with MeOH (10 mL) and concentrated to dryness under reduce pressure. Added $H_2O$ (20 mL), extracted with EA (10 mL*2) and combined the organic phase. Concentrated the organic phase and purified by pre-TLC with DCM/MeOH (10:1) to give product as white solid. $^1$HNMR (400 MHz, DMSO-d6) $\delta_H$ 9.26 (s, 1H), 8.63 (s, 1H), 7.40 (d, J=9.6 Hz, 1H), 7.32 (s, 1H), 7.10-7.00 (m, 4H), 6.96 (s, 2H), 6.47 (d, J=9.6 Hz, 1H), 5.80 (d, J=3.6 Hz, 1H), 5.25 (dd, J=9.6, 3.6 Hz, 1H), 2.43-2.40 (m, 2H), 2.18 (b, 1H), 2.01 (b, 1H), 1.88-1.84 (m, 1H), 1.63 (b, 1H), 1.51-1.42 (m, 1H), 1.28-1.15 (m, 4H), 0.98-0.92 (m, 2H), 0.78-0.75 (m, 1H), 0.66-0.64 (m, 1H). [M+H]$^+$=441.1

Examples D166 to D181 were synthesized using the similar procedure as example D115

Example D166: (4-(4-fluorophenyl)cyclohexyl)(6-isopropylimidazo[1,5-a]pyridin-5-yl)methanol

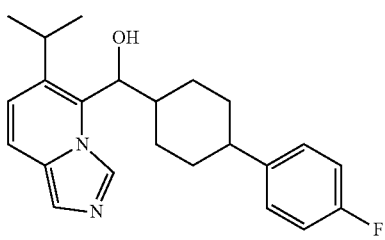 [SMILES: CC(C)c1ccc2cncn2c1C(O)C1CCC(c2ccc(F)cc2)CC1]

$^1$H NMR (DMSO-d$_6$) $\delta_H$ 8.62 (s, 1H), 7.46 (d, J=9.6 Hz, 1H), 7.21-7.30 (m, 3H), 7.03-7.08 (m, 2H), 6.82 (d, J=9.2 Hz, 1H), 5.79 (d, J=4.0 Hz, 1H), 5.00 (dd, J=3.2, 9.2 Hz, 1H), 3.22-3.26 (m, 1H), 2.38-2.42 (m, 1H), 2.16-2.21 (m, 1H), 1.85-1.89 (m, 1H), 1.64-1.68 (m, 1H), and 1.12-1.53 (m, 12H). [M+H]$^+$=367.

Example D166a and D166b: (S)-((1r,4S)-4-(4-fluorophenyl)cyclohexyl)(6-isopropylimidazo[1,5-a]pyridin-5-yl)methanol and (R)-((1r,4R)-4-(4-fluorophenyl)cyclohexyl)(6-isopropylimidazo[1,5-a]pyridin-5-yl)methanol

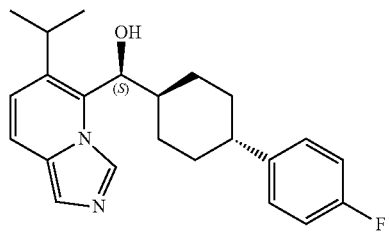

Fast isomer in CHIRALPAK IC
Eluting reagent: Hex:IPA = 70:30

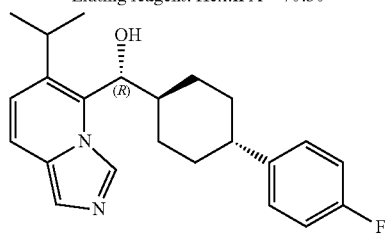

Slow isomer in CHIRALPAK IC
Eluting reagent: Hex:IPA = 70:30

Each enantiomer of racemic D166a and D166b was separated using preparative HPLC on a CHIRALPAK IC with Hex:IPA=70:30 as an eluent. The enantiomeric excesses were determined by using HPLC on a CHIRALPAK IC-3 with Hex (0.1% DEA):IPA=70:30 as an eluent at a flow rate of 1.0 mL/min. The first one enantiomer eluted at the retention time of 1.724 min, and the other enantiomer eluted at the retention time of 4.189 min. To a solution of D166a (140.2 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (103.33 mg). $^1$H NMR (DMSO-d$_6$) $\delta_H$ 9.53 (s, 1H), 7.98 (s, 1H), 7.74 (d, J=9.6 Hz, 1H), 7.20-7.26 (m, 3H), 7.04-7.10 (m, 2H), 6.10 (brs, 1H), 5.08 (d, J=10.0 Hz, 1H), 3.32-3.37 (m, 1H), 2.37-2.40 (m, 1H), 1.87-1.91 (m, 1H), 1.67-1.70 (m, 1H), 1.44-1.49 (m, 1H), and 1.17-1.34 (m, 12H). [M+H]$^+$=367. To a solution of D166b (135.6 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (125.77 mg). $^1$H NMR (DMSO-d$_6$) $\delta_H$ 9.62 (s, 1H), 8.06 (s, 1H), 7.77 (d, J=9.6 Hz, 1H), 7.20-7.30 (m, 3H), 7.05-7.10 (m, 2H), 6.19 (brs, 1H), 5.10 (d, J=10.0 Hz, 1H), 3.32-3.37 (m, 1H), 2.37-2.41 (m, 1H), 2.13-2.16 (m, 1H), 1.87-1.91 (m, 1H), 1.67-1.71 (m, 1H), and 1.17-1.52 (m, 12H). [M+H]$^+$=367. The absolute configurations of chiral carbons in D166a and D166b are tentatively assigned as (S) and (R) respectively based on assumption that the binding model of the more potent isomer D166a is the same as that of C101a with IDO1 enzyme, and the relative stereochemistry on cyclohexane is assigned as trans configuration on the cyclohexane.

Example D167: (4-(3-fluorophenyl)cyclohexyl)(6-isopropylimidazo[1,5-a]pyridin-5-yl)methanol

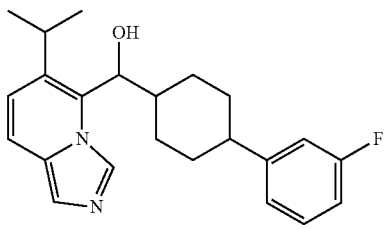 [SMILES: CC(C)c1ccc2cncn2c1C(O)C1CCC(c2cccc(F)c2)CC1]

¹H NMR (DMSO-d₆) $\delta_H$ 8.62 (s, 1H), 7.47 (d, J=9.6 Hz, 1H), 7.25-7.31 (m, 2H), 6.93-7.06 (m, 3H), 6.82 (d, J=9.6 Hz, 1H), 5.79 (d, J=4.0 Hz, 1H), 5.00 (dd, J=3.6, 9.6 Hz, 1H), 3.24-3.27 (m, 1H), 2.38-2.42 (m, 1H), 2.18-2.22 (m, 1H), 1.87-1.91 (m, 1H), 1.66-1.69 (m, 1H), 1.48-1.52 (m, 1H), and 1.12-1.32 (m, 11H). [M+H]⁺=367.

Example D167a and D167b: (S)-((1r,4S)-4-(3-fluorophenyl)cyclohexyl)(6-isopropylimidazo[1,5-a]pyridin-5-yl)methanol and (R)-((1 r,4R)-4-(3-fluorophenyl)cyclohexyl)(6-isopropylimidazo[1,5-a]pyridin-5-yl)methanol

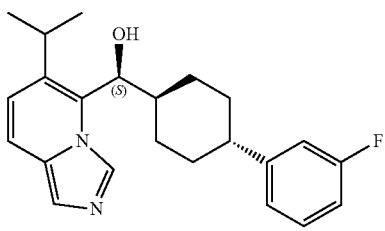

Fast isomer in CHIRAL ART Cellulose-SB
Eluting reagent: Hex:EtOH = 60:40

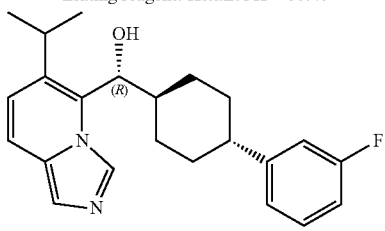

Slow isomer in CHIRAL ART Cellulose-SB
Eluting reagent: Hex:EtOH = 60:40

Each enantiomer of racemic D167a and D167b was separated using preparative HPLC on a CHIRAL ART Cellulose-SB with Hex:EtOH=60:40 as an eluent. The enantiomeric excesses were determined by using HPLC on a chiral-IA. 1 cm with Hex (0.1% DEAmine):EtOH=50:50 as an eluent at a flow rate of 1.0 mL/min. The first one enantiomer eluted at the retention time of 2.198 min, and the other enantiomer eluted at the retention time of 2.938 min. To a solution of D167a (113.7 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (115.44 mg). ¹H NMR (DMSO-d₆) $\delta_H$ 9.56 (s, 1H), 8.01 (s, 1H), 7.76 (d, J=9.6 Hz, 1H), 7.25-7.31 (m, 2H), 7.00-7.04 (m, 3H), 6.15 (brs, 1H), 5.09 (d, J=9.2 Hz, 1H), 3.32-3.34 (m, 1H), 2.36-2.41 (m, 1H), 2.14-2.17 (m, 1H), 1.88-1.93 (m, 1H), 1.68-1.73 (m, 1H), and 1.17-1.51 (m, 12H). [M+H]⁺=367. To a solution of D167b (108.2 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (101.05 mg). ¹H NMR (DMSO-d₆) $\delta_H$ 9.58 (s, 1H), 8.03 (s, 1H), 7.77 (d, J=9.6 Hz, 1H), 7.26-7.33 (m, 2H), 6.95-7.06 (m, 3H), 6.18 (brs, 1H), 5.10 (d, J=9.2 Hz, 1H), 3.33-3.42 (m, 1H), 2.37-2.41 (m, 1H), 2.14-2.16 (m, 1H), 1.89-1.93 (m, 1H), 1.68-1.72 (m, 1H), and 1.17-1.51 (m, 12H). [M+H]⁺=367. The absolute configurations of chiral carbons in D167a and D167b are tentatively assigned as (S) and (R) respectively based on assumption that the binding model of the more potent isomer D167a is the same as that of C101a with IDO1 enzyme, and the relative stereochemistry on cyclohexane is assigned as trans configuration on the cyclohexane.

Example D168: (4-(3-chlorophenyl)cyclohexyl)(6-isopropylimidazo[1,5-a]pyridin-5-yl)methanol

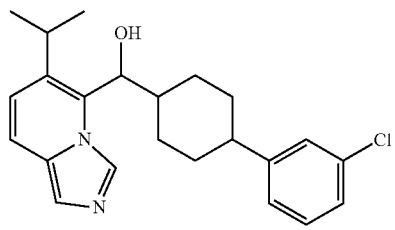 [SMILES: CC(C)c1ccc2cncn2c1C(O)C1CCC(c2cccc(Cl)c2)CC1]

¹H NMR (DMSO-d₆) $\delta_H$ 8.61 (s, 1H), 7.47 (d, J=9.6 Hz, 1H), 7.25-7.31 (m, 3H), 7.16-7.22 (m, 2H), 6.82 (d, J=9.6 Hz, 1H), 5.79 (d, J=4.0 Hz, 1H), 5.00 (dd, J=4.0, 8.8 Hz, 1H), 3.24-3.26 (m, 1H), 2.38-2.42 (m, 1H), 2.20-2.24 (m, 1H), 1.85-1.90 (m, 1H), 1.65-1.68 (m, 1H), 1.46-1.56 (m, 1H), and 1.12-1.35 (m, 11H). [M+H]⁺=383.

Example D168a and D168b: (S)-((1r,4S)-4-(3-chlorophenyl)cyclohexyl)(6-isopropylimidazo[1,5-a]pyridin-5-yl)methanol and (R)-((1r,4R)-4-(3-chlorophenyl)cyclohexyl)(6-isopropylimidazo[1,5-a]pyridin-5-yl)methanol

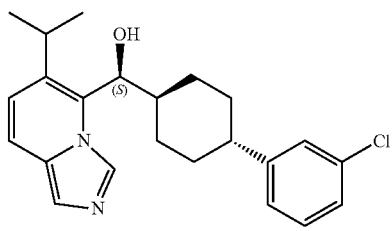

Fast isomer in CHIRALPAK IC HPLC
Eluting reagent: Hex:EtOH = 80:20
(2 mM NH₃—MeOH)

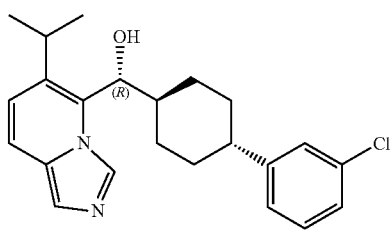

Slow isomer in CHIRALPAK IC HPLC
Eluting reagent: Hex:EtOH = 80:20
(2 mM NH₃—MeOH)

Each enantiomer of racemic D168a and D168b was separated using preparative HPLC on a CHIRALPAK IC with Hex:EtOH=Hex:EtOH=80:20 (2 mMNH3-MeOH) as an eluent. The enantiomeric excesses were determined by using HPLC on a CHIRAL Cellulose-SB with Hex (0.1% DEAmine):EtOH=70:30 as an eluent at a flow rate of 1.0 mL/min. The first one enantiomer eluted at the retention time of 2.502 min, $^1$H NMR (DMSO-d$_6$) $\delta_H$ 9.62 (s, 1H), 8.06 (s, 1H), 7.77 (d, J=10.0 Hz, 1H), 7.15-7.32 (m, 5H), 6.17 (brs, 1H), 5.10 (d, J=9.6 Hz, 1H), 3.32-3.33 (m, 1H), 2.37-2.40 (m, 1H), 2.14-2.15 (m, 1H), 1.88-1.92 (m, 1H), 1.68-1.72 (m, 1H), 1.47-1.51 (m, 1H), and 1.11-1.31 (m, 11H). [M+H]⁺=383. and the other enantiomer eluted at the retention time of 4.081 min, $^1$H NMR (DMSO-d$_6$) $\delta_H$ 9.63 (s, 1H), 8.07 (s, 1H), 7.77 (d, J=10.0 Hz, 1H), 7.15-7.32 (m, 5H), 6.20 (brs, 1H), 5.10 (d, J=9.6 Hz, 1H), 3.32-3.33 (m, 1H), 2.37-2.40 (m, 1H), 2.13-2.16 (m, 1H), 1.88-1.92 (m, 1H), 1.68-1.72 (m, 1H), 1.44-1.51 (m, 1H), and 1.18-1.35 (m, 11H). [M+H]⁺=383. The absolute configurations of chiral carbons in D168a and D168b are tentatively assigned as (S) and (R) respectively based on assumption that the binding model of the more potent isomer D166a is the same as that of C101a with IDO1 enzyme, and the relative stereochemistry on cyclohexane is assigned as trans configuration on the cyclohexane.

Example D169: (6-isopropylimidazo[1,5-a]pyridin-5-yl)(4-(3-methoxyphenyl)cyclohexyl)methanol

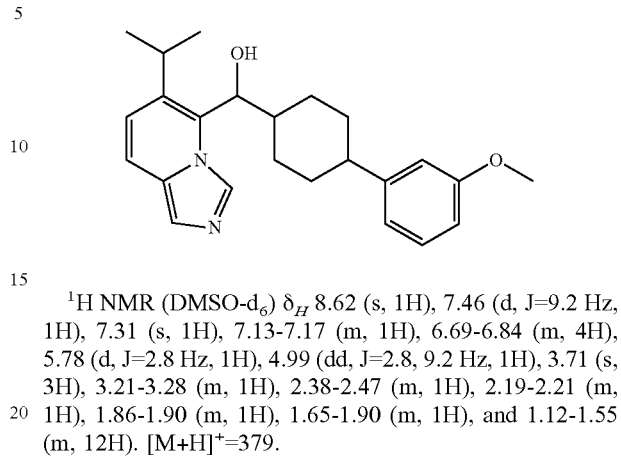

$^1$H NMR (DMSO-d$_6$) $\delta_H$ 8.62 (s, 1H), 7.46 (d, J=9.2 Hz, 1H), 7.31 (s, 1H), 7.13-7.17 (m, 1H), 6.69-6.84 (m, 4H), 5.78 (d, J=2.8 Hz, 1H), 4.99 (dd, J=2.8, 9.2 Hz, 1H), 3.71 (s, 3H), 3.21-3.28 (m, 1H), 2.38-2.47 (m, 1H), 2.19-2.21 (m, 1H), 1.86-1.90 (m, 1H), 1.65-1.90 (m, 1H), and 1.12-1.55 (m, 12H). [M+H]⁺=379.

Example D169a and D169b: (S)-(6-isopropylimidazo[1,5-a]pyridin-5-yl)((1r,4S)-4-(3-methoxyphenyl)cyclohexyl)methanol and (R)-(6-isopropylimidazo[1,5-a]pyridin-5-yl)((1 r,4R)-4-(3-methoxyphenyl)cyclohexyl)methanol

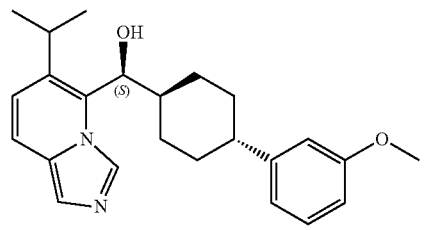

Fast isomer in CHIRALPAK SB
Eluting reagent: Hex:EtOH = 80:20

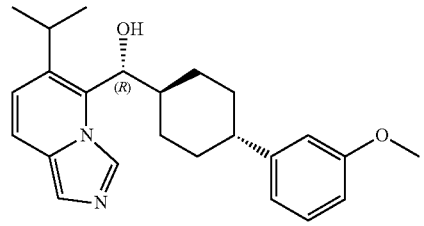

Slow isomer in CHIRALPAK SB
Eluting reagent: Hex:EtOH = 80:20

Each enantiomer of racemic D169a and D169b was separated using preparative HPLC on a CHIRALPAK SB with Hex:EtOH=80:20 as an eluent. The enantiomeric excesses were determined by using HPLC on a chiral-IA. 1 cm with Hex (0.1% DEA):EtOH=80:20 as an eluent at a flow rate of 1.0 mL/min. The first one enantiomer eluted at the retention time of 3.257 min, and the other enantiomer eluted at the retention time of 5.317 min. To a solution of D169a (101.5 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (81.57 mg). $^1$H NMR (DMSO-d$_6$) δ$_H$ 9.59 (s, 1H), 8.03 (s, 1H), 7.76 (d, J=9.6 Hz, 1H), 7.27 (d, J=10.0 Hz, 1H), 7.14-7.19 (m, 1H), 6.70-6.77 (m, 3H), 6.14 (brs, 1H), 5.08 (d, J=9.6 Hz, 1H), 3.75 (s, 3H), 3.35-3.37 (m, 1H), 2.40-2.43 (m, 1H), 2.13-2.14 (m, 1H), 1.88-1.91 (m, 1H), 1.67-1.71 (m, 1H), and 1.17-1.50 (m, 12H). [M+H]$^+$=379. To a solution of D169b (106.3 mg) in DCM (4 mL) was added drop wise of Ethyl acetate solution of hydrochloric acid (3.0 mL, 4.0M) at room temperature, followed by addition of methol until the precipitate was dissolved, then the solvent was evaporated under reduced pressure and the residue was washed by PE to give desired product as white solid (93.95 mg). $^1$H NMR (DMSO-d$_6$) δ$_H$ 9.57 (s, 1H), 8.02 (s, 1H), 7.75 (d, J=9.6 Hz, 1H), 7.26 (d, J=9.2 Hz, 1H), 7.14-7.19 (m, 1H), 6.70-6.77 (m, 3H), 6.14 (brs, 1H), 5.08 (d, J=9.2 Hz, 1H), 3.71 (s, 3H), 3.21-3.28 (m, 1H), 2.37-2.46 (m, 1H), 2.14-2.17 (m, 1H), 1.88-1.91 (m, 1H), 1.67-1.71 (m, 1H), and 1.17-1.51 (m, 12H). [M+H]$^+$=379. The absolute configurations of chiral carbons in D169a and D169b are tentatively assigned as (S) and (R) respectively based on assumption that the binding model of the more potent isomer D169a is the same as that of C101a with IDO1 enzyme, and the relative stereochemistry on cyclohexane is assigned as trans configuration on the cyclohexane.

Example D170: (6-cycloropylimidazo[1,5-a]pyridin-5-yl)(1-phenylpiperidin-4-yl)methanol

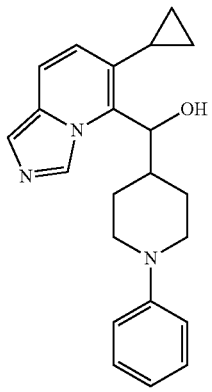 [SMILES: OC(c1c(C2CC2)ccc2cncn12)C1CCN(c2ccccc2)CC1]

$^1$HNMR (400 MHz, DMSO-d6) δ$_H$ 8.64 (s, 1H), 7.42 (d, J=9.6 Hz, 1H), 7.32 (s, 1H), 7.17 (t, J=7.8 Hz, 2H), 6.9 (d, J=8.0 Hz, 2H), 6.73 (t, J=7.2 Hz, 1H), 6.48 (d, J=9.6 Hz, 1H), 5.87 (d, J=3.2 Hz, 1H), 5.29 (dd, J=9.6 Hz, J=4 Hz 1H), 3.78 (d, J=12 Hz, 1H), 3.57 (d, J=12.4 Hz, 1H), 2.69-2.63 (m, 1H), 2.43-2.40 (m, 1H), 2.31-2.24 (m, 2H), 2.05-2.00 (m, 1H), 1.54-1.35 (m, 2H), 1.1-1.08 (m, 1H), 0.93-0.89 (m, 2H), 0.80-0.71 (m, 1H), 0.66-0.63 (m, 1H).

Example D170a and D170b: (S)-(6-cyclopropylimidazo[1,5-a]pyridin-5-yl)(1-phenylpiperidin-4-yl)methanol and (R)-(6-cyclopropylimidazo[1,5-a]pyridin-5-yl)(1-phenylpiperidin-4-yl)methanol

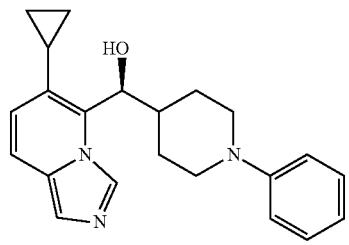

Fast isomer in CHIRALPAK IC-3
Eluting reagent: Hex:EtOH = 70:30

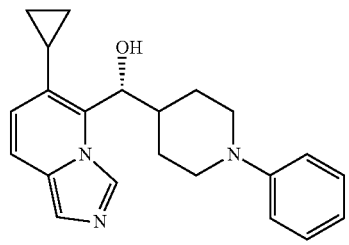

Slow isomer in CHIRALPAK IC-3
Eluting reagent: Hex:EtOH = 70:30

Each enantiomer of racemic D170a and D170b was separated using preparative HPLC on a CHIRAL PAK IC-3 with Hex:EtOH=70:30 as an eluent. The enantiomeric excesses were determined by using HPLC on a CHIRAL PAK IC-3 with Hex:EtOH=70:30 as an eluent at a flow rate of 20 mL/min. The first one enantiomer eluted at the retention time of 2.792 min, which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give desired product (70 mg) as white solid, 1H NMR (DMSO-d6) δ 9.66 (s, 1H), 8.15 (s, 1H), 7.78-7.75 (m, 3H), 7.52-7.49 (m, 2H), 7.45-7.30 (m, 1H), 6.89 (d, J=9.6 Hz, 1H), 6.70-6.40 (m, 1H), 5.40 (d, J=10 Hz, 1H), 3.70-3.67 (m, 1H), 3.47-3.43 (m, 2H), 2.57-2.54 (m, 1H), 2.45-2.42 (m, 1H), 2.20-2.10 (m, 2H), 1.38-1.35 (m, 1H), 1.10-1.04 (m, 3H), 0.95-0.92 (m, 1H), 0.80-0.77 (m, 1H). and the other enantiomer eluted at the retention time of 5.577 min, $^1$H NMR (DMSO-d6) δ 9.66 (s, 1H), 8.14 (s, 1H), 7.7-7.60 (m, 3H), 7.52-7.46 (m, 2H), 7.40-7.25 (m, 1H), 6.89 (d, J=9.6 Hz, 1H), 6.70-6.40 (m, 1H), 5.40 (d, J=9.6 Hz, 1H), 3.71-3.68 (m, 1H), 3.45-3.41 (m, 2H), 2.44-2.40 (m, 1H), 2.15-2.06 (m, 2H), 1.37-1.25 (m, 2H), 1.10-1.04 (m, 3H), 0.92-0.89 (m, 1H), 0.80-0.77 (m, 1H). The absolute configurations of chiral carbons in D170a and D170b are tentatively assigned as (S) and (R) respectively based on assumption that the binding model of the more potent isomer D170a is the same as that of C101a with IDO1.

Example D171: (6-cyclopropylimidazo[1,5-a]pyridin-5-yl)(1-(4-fluorophenyl)piperidin-4-yl)methanol

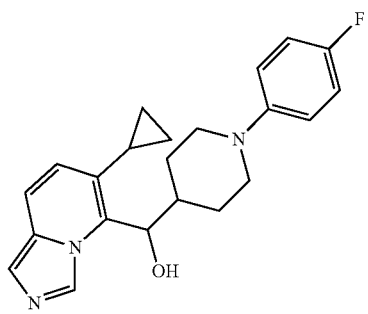 [SMILES: OC(c1c(C2CC2)ccc2cncn12)C1CCN(c2ccc(F)cc2)CC1]

¹HNMR (400 MHz, DMSO-d6) δ$_H$ 8.63 (s, 1H), 7.41 (d, J=9.2 Hz, 1H), 7.32 (s, 1H), 7.02-7.00 (m, 2H), 6.92-6.89 (m, 2H), 6.49 (d, J=9.6 Hz, 1H), 5.87 (d, J=4 Hz, 1H), 5.29 (dd, J=9.6 Hz, J=3.6 Hz 1H), 3.67 (d, J=12 Hz, 1H), 3.46 (d, J=12 Hz, 1H), 2.65-2.59 (m, 1H), 2.41-2.36 (m, 1H), 2.31-2.20 (m, 2H), 2.05-2.00 (m, 1H), 1.55-1.35 (m, 2H), 1.1-1.04 (m, 1H), 0.97-0.84 (m, 2H), 0.78-0.75 (m, 1H), 0.66-0.62 (m, 1H).

Example D171a and D171b: (S)-(6-cyclopropylimidazo[1,5-a]pyridin-5-yl)(1-(4-fluorophenyl)piperidin-4-yl)methanol and (R)-(6-cyclopropylimidazo[1,5-a]pyridin-5-yl)(1-(4-fluorophenyl)piperidin-4-yl)methanol

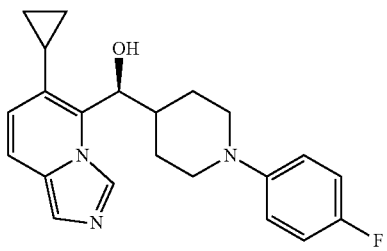

Fast isomer in CHIRALPAK IC
Eluting reagent: Hex:EtOH = 80:20

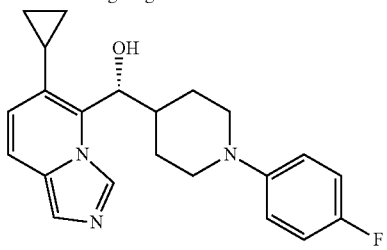

Slow isomer in CHIRALPAK IC
Eluting reagent: Hex:EtOH = 80:20

Each enantiomer of racemic D171a and D171b was separated using preparative HPLC on a CHIRALPAK IC with Hex:EtOH=80:20 as an eluent. The enantiomeric excesses were determined by using HPLC on CHIRALPAK IC with Hex:EtOH=80:20 as an eluent at a flow rate of 20 ml/min. The first one enantiomer eluted at the retention time of 1.779 min, ¹H NMR (DMSO-d6) δ9.66 (s, 1H), 8.15 (s, 1H), 7.96-7.72 (m, 3H), 7.30-7.28 (m, 2H), 6.89 (d, J=9.6 Hz, 1H), 6.55 (s, 1H), 5.40 (d, J=10.0 Hz, 1H), 3.67-3.64 (m, 1H), 3.50-3.36 (m, 2H), 2.60-2.52 (m, 1H), 2.45-2.41 (m, 1H), 2.20-2.08 (m, 2H), 1.37-1.23 (m, 2H), 1.08-1.06 (m, 2H), 0.98-0.90 (m, 1H), 0.79-0.78 (m, 1H). And the other enantiomer eluted at the retention time of 2.987 min. 1H NMR (DMSO-d6) δ9.66 (s, 1H), 8.15 (s, 1H), 7.77-7.70 (m, 3H), 7.40-7.24 (m, 2H), 6.90-6.88 (m, 1H), 6.68-6.40 (m, 1H), 5.40 (d, J=9.6 Hz, 1H), 3.68-3.66 (m, 1H), 3.45-3.43 (m, 2H), 2.60-2.52 (m, 1H), 2.43-2.40 (m, 1H), 2.20-1.98 (m, 3H), 1.35-1.24 (m, 2H), 1.08-1.06 (m, 2H), 0.98-0.90 (m, 1H), 0.80-0.76 (m, 1H). The absolute configurations of chiral carbons in D171a and D171b are tentatively assigned as (S) and (R) respectively based on assumption that the binding model of the more potent isomer D171a is the same as that of C101a Example D172: (6-cyclopropylimidazo[1,5-a]pyridin-5-yl)(1-(3-fluorophenyl)piperidin-4-yl)methanol

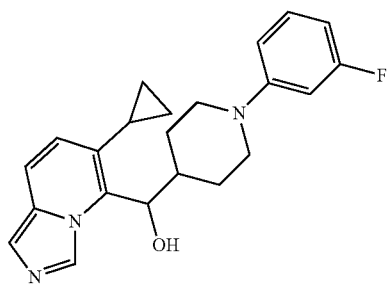 [SMILES: OC(c1c(C2CC2)ccc2cncn12)C1CCN(c2cccc(F)c2)CC1]

¹H NMR (DMSO-d6) δ 8.64 (s, 1H), 7.42 (d, J=9.2 Hz, 1H), 7.32 (s, 1H), 7.16 (q, J=7.8 Hz, 1H), 6.72-6.66 (m, 2H), 6.50-6.46 (m, 2H), 5.88 (d, J=4 Hz, 1H), 5.28 (dd, J=9.2 Hz, J=3.6 Hz 1H), 3.84 (d, J=12.8 Hz, 1H), 3.63 (d, J=12.8 Hz, 1H), 2.74-2.68 (m, 1H), 2.46-2.44 (m, 1H), 2.32-2.26 (m, 2H), 2.05-1.99 (m, 1H), 1.51-1.32 (m, 2H), 1.09-1.06 (m, 1H), 0.92-0.88 (m, 2H), 0.78-0.75 (m, 1H), 0.66-0.63 (m, 1H).

Example D172a and D172b: (S)-(7-cyclopropylimidazo[1,5-a]pyridin-8-yl)(1-(3-fluorophenyl)piperidin-4-yl)methanol and (R)-(7-cyclopropylimidazo[1,5-a]pyridin-8-yl)(1-(3-fluorophenyl)piperidin-4-yl)methanol

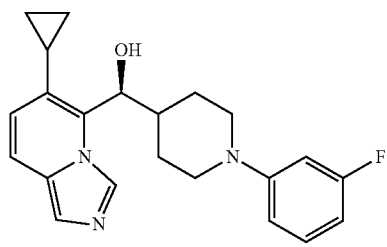

Fast isomer in CHIRALPAK IC
Eluting reagent: Hex:EtOH = 70:30

-continued

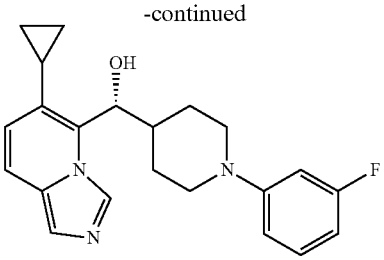

Slow isomer in CHIRALPAK IC
Eluting reagent: Hex:EtOH = 70:30

Each enantiomer of racemic D172a and D172b was separated using preparative HPLC on a CHIRALPAK IC with Hex:EtOH=70:30 as an eluent. The enantiomeric excesses were determined by using HPLC on CHIRALPAK IC with Hex:EtOH=70:30 as an eluent at a flow rate of 20 ml/min. The first one enantiomer eluted at the retention time of 1.251 min, H NMR (DMSO-d6) δ 8.64 (s, 1H), 7.42 (d, J=9.2 Hz, 1H), 7.32 (s, 1H), 7.17 (q, J=7.8 Hz, 1H), 6.72-6.66 (m, 2H), 6.50-6.46 (m, 2H), 5.88 (d, J=3.6 Hz, 1H), 5.27 (dd, J=9.2, J=3.6 Hz, 1H), 3.84 (d, J=12.0 Hz, 1H), 3.63 (d, J=12.4 Hz, 1H), 2.71 (t, J=11.4 Hz, 1H), 2.48-2.45 (m, 1H), 2.32-2.26 (m, 2H), 2.21-1.95 (m, 1H), 1.50-1.31 (m, 2H), 1.09-1.06 (m, 1H), 0.93-0.89 (m, 2H), 0.78-0.74 (m, 1H), 0.66-0.62 (m, 1H). And the other enantiomer eluted at the retention time of 2.373 min. 1H NMR (DMSO-d6) δ 8.64 (s, 1H), 7.42 (d, J=9.6 Hz, 1H), 7.32 (s, 1H), 7.16 (q, J=7.8 Hz, 1H), 6.72-6.66 (m, 2H), 6.50-6.46 (m, 2H), 5.88 (d, J=3.6 Hz, 1H), 5.27 (dd, J=9.6, J=4.0 Hz, 1H), 3.84 (d, J=12.8 Hz, 1H), 3.63 (d, J=12.4 Hz, 1H), 2.71 (t, J=11.6 Hz, 1H), 2.47-2.44 (m, 1H), 2.32-2.26 (m, 2H), 2.06-1.96 (m, 1H), 1.50-1.31 (m, 2H), 1.08-1.06 (m, 1H), 0.94-0.90 (m, 2H), 0.78-0.74 (m, 1H), 0.63-0.63 (m, 1H). The absolute configurations of chiral carbons in D172a and D172b are tentatively assigned as (S) and (R) respectively based on assumption that the binding model of the more potent isomer D172a is the same as that of C101a.

Example D173(1-(3-chlorophenyl)piperidin-4-yl)(6-cyclopropylimidazo[15-a]pyridin-5-yl)methanol

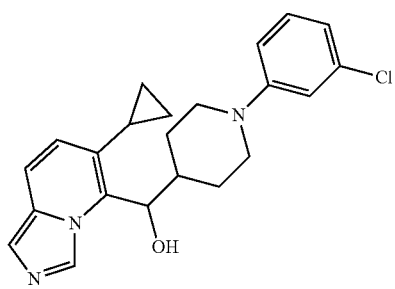 [SMILES: OC(c1c(C2CC2)ccc2cncn12)C1CCN(c2cccc(Cl)c2)CC1]

$^1$H NMR (DMSO-d6) δ 8.63 (s, 1H), 7.42 (d, J=9.2 Hz, 1H), 7.31 (s, 1H), 7.18-7.14 (m, 1H), 6.89-6.84 (m, 2H), 6.72 (dd, J=7.6 Hz, J=1.2 Hz 1H), 6.47 (d, J=9.2 Hz, 1H), 5.88 (d, J=4 Hz, 1H), 5.27 (dd, J=9.6 Hz, J=4 Hz 1H), 3.83 (d, J=12.4 Hz, 1H), 3.62 (d, J=12.4 Hz, 1H), 2.74-2.68 (m, 1H), 2.47-2.45 (m, 1H), 2.32-2.26 (m, 2H), 2.01-1.99 (m, 1H), 1.50-1.31 (m, 2H), 1.09-1.06 (m, 1H), 0.93-0.88 (m, 2H), 0.78-0.75 (m, 1H), 0.66-0.62 (m, 1H).

Example D173a and D173b: (S)-(1-(3-chlorophenyl)piperidin-4-yl)(6-cyclopropylimidazo[1,5-a]pyridin-5-yl)methanol and (R)-(1-(3-chlorophenyl)piperidin-4-yl)(6-cyclopropylimidazo[1,5-a]pyridin-5-yl)methanol

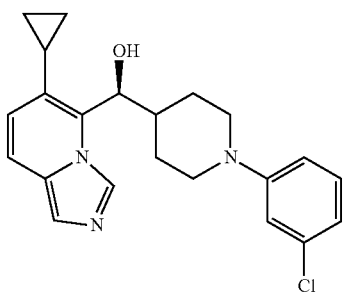

Fast isomer in CHIRALPAK IC-3
Eluting reagent: Hex:EtOH = 80:20

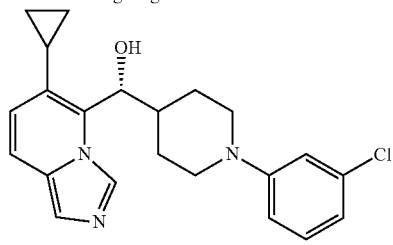

Slow isomer in CHIRALPAK IC-3
Eluting reagent: Hex:EtOH = 80:20

Each enantiomer of racemic D173a and D173b was separated using preparative HPLC on a CHIRAL PAK IC-3 with Hex:EtOH=80:20 as an eluent. The enantiomeric excesses were determined by using HPLC on a CHIRAL PAK IC-3 with Hex:EtOH=80:20 as an eluent at a flow rate of 20 mL/min. The first one enantiomer eluted at the retention time of 2.969 min, which was dissolved in THF (10 mL), and added Ethyl acetate solution of hydrochloric acid (0.5 mL, 4.0M) at room temperature, followed by addition of methol until the precipitate was dissolved, then the solvent was evaporated under reduced pressure and the residue was washed by PE to give desired product (156.77 mg) as white solid, $^1$H NMR (DMSO-d6) δ 9.71 (s, 1H), 8.15 (s, 1H), 7.76 (d, J=10 Hz, 1H), 7.40-7.25 (m, 3H), 6.88 (dd, J=10 Hz, J=2 Hz, 1H), 5.37 (d, J=9.6 Hz, 1H), 3.85-3.75 (m, 1H), 3.65-3.52 (m, 1H), 2.43-2.25 (m, 2H), 2.24-2.10 (m, 1H), 1.90-1.50 (m, 2H), 1.33-1.20 (m, 1H), 1.06-1.04 (m, 2H), 0.89-0.88 (m, 1H), 0.79-0.78 (m, 1H). And the other enantiomer eluted at the retention time of 6.273 min. $^1$H NMR (DMSO-d6) δ 9.71 (s, 1H), 8.15 (s, 1H), 7.75 (d, J=9.6 Hz, 1H), 7.38-7.23 (m, 3H), 6.87 (dd, J=10 Hz, J=1.6 Hz, 1H), 5.36 (d, J=9.6 Hz, 1H), 3.85-3.75 (m, 1H), 3.65-3.54 (m, 1H), 2.45-2.25 (m, 2H), 2.24-2.12 (m, 1H), 1.90-1.50 (m, 2H), 1.30-1.16 (m, 1H), 1.05-1.03 (m, 2H), 0.89-0.88 (m, 1H), 0.79-0.76 (m, 1H). Then the solvent was evaporated under reduced pressure and the residue was washed by PE to give desired product (141.2 mg) as white solid, The absolute configurations of chiral carbons in D173a and D173b are tentatively assigned as (S) and (R) respectively based on assumption that the binding model of the more potent isomer D173a is the same as that of C101a with IDO1.

Example D174: (1-(4-chlorophenyl)piperidin-4-yl)(6-cyclopropylimidazo[1,5-a]pyridin-5-yl)methanol

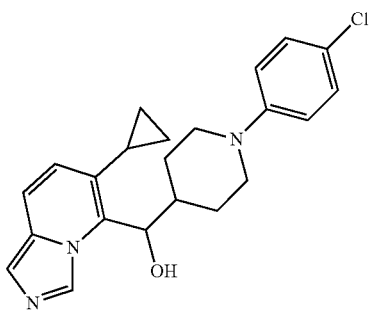 [SMILES: OC(c1c(C2CC2)ccc2cncn12)C1CCN(c2ccc(Cl)cc2)CC1]

¹H NMR (DMSO-d6) δ 8.63 (s, 1H), 7.42 (d, J=9.2 Hz, 1H), 7.32 (s, 1H), 7.18 (d, J=8.8 Hz, 2H), 6.90 (d, J=9.2 Hz, 2H), 6.47 (d, J=9.2 Hz, 1H), 5.88 (d, J=4 Hz, 1H), 5.28 (dd, J=9.2 Hz, J=3.6 Hz 1H), 3.78 (d, J=12.4 Hz, 1H), 3.57 (d, J=12.4 Hz, 1H), 2.70-2.65 (m, 1H), 2.47-2.41 (m, 1H), 2.30-2.27 (m, 2H), 2.02-1.99 (m, 1H), 1.52-1.33 (m, 2H), 1.09-1.06 (m, 1H), 0.98-0.88 (m, 2H), 0.78-0.74 (m, 1H), 0.66-0.63 (m, 1H).

Example D174a and D174b: (S)-(1-(4-chlorophenyl)piperidin-4-yl)(6-cyclopropylimidazo[1,5-a]pyridin-5-yl)methanol and (R)-(1-(4-chlorophenyl)piperidin-4-yl)(6-cyclopropylimidazo[1,5-a]pyridin-5-ylmethanol

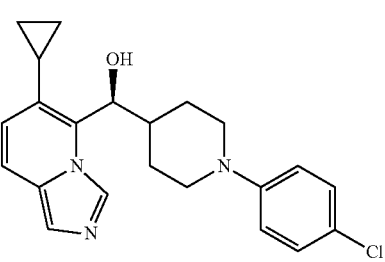

Fast isomer in CHIRALPAK IC
Eluting reagent: Hex:EtOH = 85:15

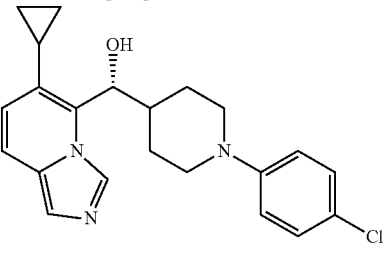

Slow isomer in CHIRALPAK IC
Eluting reagent: Hex:EtOH = 85:15

Each enantiomer of racemic D174a and D174b was separated using preparative HPLC on a CHIRALPAK IC with Hex:EtOH=85:15 as an eluent. The enantiomeric excesses were determined by using HPLC on CHIRALPAK IC with Hex:EtOH=85:15 as an eluent at a flow rate of 20 ml/min. The first one enantiomer eluted at the retention time of 2.434 min, ¹H NMR (DMSO-d6) δ8.63 (s, 1H), 7.42 (d, J=9.2 Hz, 1H), 7.32 (s, 1H), 7.18 (d, J=8.4 Hz, 2H), 6.90 (d, J=8.4 Hz, 2H), 6.47 (d, J=9.6 Hz, 1H), 5.88 (d, J=3.2 Hz, 1H), 5.27 (d, J=6.0 Hz, 1H), 3.78 (d, J=12.8 Hz, 1H), 3.57 (d, J=12.4 Hz, 1H), 2.68 (t, J=12.0 Hz, 1H), 2.42 (d, J=11.6 Hz, 1H), 2.30-2.27 (m, 2H), 2.06-1.96 (m, 1H), 1.52-1.33 (m, 2H), 1.09-1.06 (m, 1H), 0.94-0.92 (m, 2H), 0.80-0.72 (m, 1H), 0.68-0.60 (m, 1H). And the other enantiomer eluted at the retention time of 4.175 min. 1H NMR (DMSO-d6) δ 8.64 (s, 1H), 7.42 (d, J=9.2 Hz, 1H), 7.32 (s, 1H), 7.18 (d, J=8.8 Hz, 2H), 6.90 (d, J=9.2 Hz, 2H), 6.47 (d, J=9.6 Hz, 1H), 5.88 (d, J=4.0 Hz, 1H), 5.27 (dd, J=9.2, J=3.6 Hz, 1H), 3.78 (d, J=12.4 Hz, 1H), 3.57 (d, J=12.0 Hz, 1H), 2.67 (t, J=11.4 Hz, 1H), 2.47-2.41 (m, 1H), 2.29-2.27 (m, 2H), 2.06-1.96 (m, 1H), 1.52-1.33 (m, 2H), 1.09-1.06 (m, 1H), 0.96-0.90 (m, 2H), 0.78-0.74 (m, 1H), 0.66-0.62 (m, 1H). The absolute configurations of chiral carbons in D174a and D174b are tentatively assigned as (S) and (R) respectively based on assumption that the binding model of the more potent isomer D174a is the same as that of C101a.

Example D175: (6-cyclopropylimidazo[1,5-a]pyridin-5-yl)(1-(8-fluoroquinolin-5-yl)piperidin-4-yl)methanol

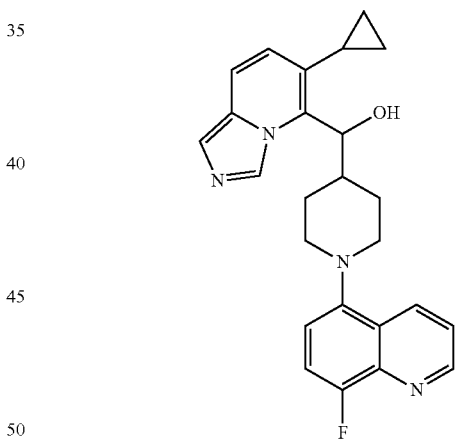

¹H NMR (DMSO-d6) δ H 8.91-8.94 (m, 1H), 8.67 (s, 1H), 8.49-8.52 (d, J=8.8 Hz, 1H), 7.61-7.64 (m, 1H), 7.41-7.48 (m, 2H), 7.33 (s, 1H), 7.08-7.11 (m, 1H), 6.50-6.53 (d, J=9.6 Hz, 1H), 5.92-5.94 (d, J=4.0 Hz, 1H), 5.39-5.44 (dd. J₁=9.6 Hz, J₂=3.6 Hz, 1H), 3.10-3.14 (d, J=10.8 Hz, 1H), 2.76-2.82 (t, J=11.2 Hz, 1H), 2.51-2.57 (m, 1H), 2.28-2.42 (m, 2H), 2.10 (bs, 1H), 1.60-1.82 (m, 2H), 1.14-1.18 (m, 1H), 0.94-1.05 (m, 2H), 0.67-0.82 (m, 2H)

Example D175a and D175b: (S)-(6-cyclopropylimidazo[1,5-a]pyridin-5-yl)(1-(8-fluoroquinolin-5-yl)piperidin-4-yl)methanol and (R)-(6-cyclopropylimidazo[1,5-a]pyridin-5-yl)(1-(8-fluoroquinolin-5-yl)piperidin-4-yl)methanol

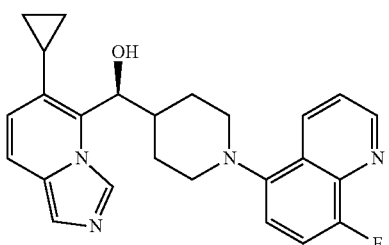

Fast isomer in CHIRAL ART Cellulose-SB
Eluting reagent: MeOH(0.1% DEA) = 10% ~ 50%

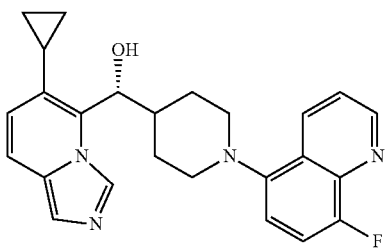

Slow in CHIRAL ART Cellulose-SB
Eluting reagent: MeOH(0.1% DEA) = 10% ~ 50%

Each enantiomer of racemic D175a and D175b was separated using preparative HPLC on a CHIRAL ART Cellulose-BS with $CO_2$:MeOH=55:45 as an eluent. The first one enantiomer eluted at the retention time of 2.423 min, 1H NMR (DMSO-d6) δ H 8.91-8.94 (m, 1H), 8.67 (s, 1H), 8.49-8.52 (d, J=8.8 Hz, 1H), 7.61-7.64 (m, 1H), 7.41-7.48 (m, 2H), 7.33 (s, 1H), 7.08-7.11 (m, 1H), 6.50-6.53 (d, J=9.6 Hz, 1H), 5.92-5.94 (d, J=4.0 Hz, 1H), 5.39-5.44 (dd, $J_1$=9.6 Hz, $J_2$=3.6 Hz, 1H), 3.10-3.14 (d, J=10.8 Hz, 1H), 2.76-2.82 (t, J=11.2 Hz, 1H), 2.51-2.57 (m, 1H), 2.28-2.42 (m, 2H), 2.10 (bs, 1H), 1.60-1.82 (m, 2H), 1.14-1.18 (m, 1H), 0.94-1.05 (m, 2H), 0.67-0.82 (m, 2H); and the other enantiomer eluted at the retention time of 2.994 min, 1H NMR (DMSO-d6) δ H 8.91-8.94 (m, 1H), 8.67 (s, 1H), 8.49-8.52 (d, J=8.8 Hz, 1H), 7.61-7.64 (m, 1H), 7.41-7.48 (m, 2H), 7.33 (s, 1H), 7.08-7.11 (m, 1H), 6.50-6.53 (d, J=9.6 Hz, 1H), 5.92-5.94 (d, J=4.0 Hz, 1H), 5.39-5.44 (dd, $J_1$=9.6 Hz, $J_2$=3.6 Hz, 1H), 3.10-3.14 (d, J=10.8 Hz, 1H), 2.76-2.82 (t, J=11.2 Hz, 1H), 2.51-2.57 (m, 1H), 2.28-2.42 (m, 2H), 2.10 (bs, 1H), 1.60-1.82 (m, 2H), 1.14-1.18 (m, 1H), 0.94-1.05 (m, 2H), 0.67-0.82 (m, 2H). The absolute configurations of chiral carbons in D175a and D175b are tentatively assigned as (S) and (R) respectively based on assumption that the binding model of the more potent isomer D175a is the same as that of C101a with IDO1.

Example D176: (6-cyclopropylimidazo[1,5-a]pyridin-5-yl)(1-(4-(1-methyl-1H-pyrazol-4-yl)phenyl)piperidin-4-yl)methanol

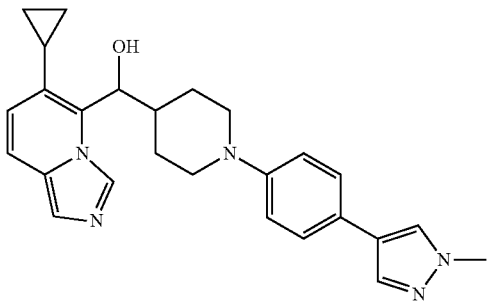 [SMILES: Cn1cc(-c2ccc(N3CCC(C(O)c4c(C5CC5)ccc5cncn45)CC3)cc2)cn1]

$^1$H NMR (DMSO-d$_6$) δ$_H$ 8.64 (s, 1H), 7.95 (s, 1H), 7.70 (s, 1H), 7.42 (d, J=9.6 Hz, 1H), 7.36 (d, J=8.8 Hz, 2H), 7.32 (s, 1H), 6.89 (d, J=8.8 Hz, 2H), 6.48 (d, J=9.6 Hz, 1H), 5.87 (d, J=3.6 Hz, 1H), 5.29 (dd, J=3.6, 9.6 Hz, 1H), 3.82 (s, 3H), 3.78 (d, J=12.8 Hz, 1H), 3.57 (d, J=12.8 Hz, 1H), 2.63-2.69 (m, 1H), 2.39-2.43 (m, 1H), 2.28-2.32 (m, 2H), 2.02-2.04 (m, 1H), 1.37-1.53 (m, 2H), 1.06-1.10 (m, 1H), 0.91-0.97 (m, 2H) and 0.63-0.79 (m, 2H). [M+H]$^+$=428.

Example D177: 2-(4-(4-(4-((6-cyclopropylimidazo[1,5-a]pyridin-5-yl(hydroxy)methyl)piperidin-1-yl)phenyl)-1H-pyrazol-1-yl)ethan-1-ol

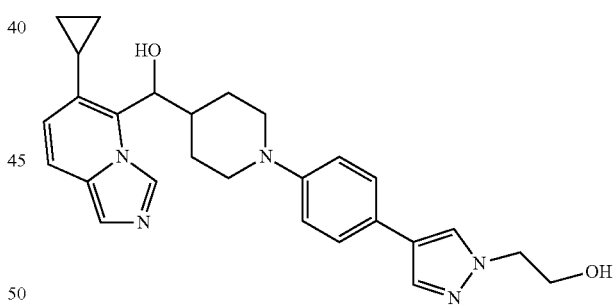

$^1$H NMR (DMSO-d$_6$) δ 8.64 (s, 1H), 7.97 (s, 1H), 7.73 (s, 1H), 7.42 (d, J=9.6 Hz, 1H), 7.37 (d, J=8.8 Hz, 2H), 7.32 (s, 1H), 6.88 (d, J=8.4 Hz, 2H), 6.48 (d, J=9.6 Hz, 1H), 5.87 (d, J=3.6 Hz, 1H), 5.29 (dd, J=3.6, 9.6 Hz, 1H), 4.90 (t, J=5.6 Hz, 1H), 4.12 (t, J=5.6 Hz, 2H), 3.71-3.80 (m, 3H), 3.57 (d, J=12.4 Hz, 1H), 2.63-2.70 (m, 1H), 2.39-2.46 (m, 1H), 2.28-2.32 (m, 2H), 2.02-2.04 (m, 1H), 1.37-1.52 (m, 2H), 1.06-1.10 (m, 1H), 0.88-0.97 (m, 2H), and 0.63-0.79 (m, 2H). [M+H]$^+$=458.

Example D178: (1-(8-chloroquinolin-5-yl)piperidin-4-yl)(6-cyclopropylimidazo[1,5-a]pyridin-5-yl)methanol

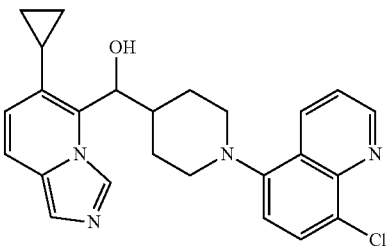 [SMILES: OC(c1c(C2CC2)ccc2cncn12)C1CCN(c2ccc(Cl)c3ncccc23)CC1]

¹H NMR (DMSO-d₆) δ$_H$ 8.98 (d, J=5.6 Hz, 1H), 8.67 (s, 1H), 8.52 (d, J=9.6 Hz, 1H), 7.81 (d, J=8.0 Hz, 1H), 7.36 (q, J=4.0 Hz, 1H), 7.43 (d, J=9.6 Hz, 1H), 7.33 (s, 1H), 7.10 (d, J=8.0 Hz, 1H), 6.51 (d, J=5.6 Hz, 1H), 5.92 (d, J=4.0 Hz, 1H), 5.42 (dd, J=3.6, 9.6 Hz, 1H), 3.38 (d, J=12.0 Hz, 1H), 3.17 (d, J=12.0 Hz, 1H), 2.81 (t, J=10.8 Hz, 1H), 2.53-2.60 (m, 2H), 2.32-2.40 (m, 2H), 2.09-2.12 (m, 1H), 1.64-1.79 (m, 2H), 0.96-1.03 (m, 2H), and 0.69-0.82 (m, 2H). [M+H]⁺=433.

Example D178a and D178b: (S)-(1-(8-chloroquinolin-5-yl)piperidin-4-yl)(6-cyclopropylimidazo[1,5-a]pyridin-5-yl)methanol and (R)-(1-(8-chloroquinolin-5-yl)piperidin-4-yl)(6-cyclopropylimidazo[1,5-a]pyridin-5-yl)methanol

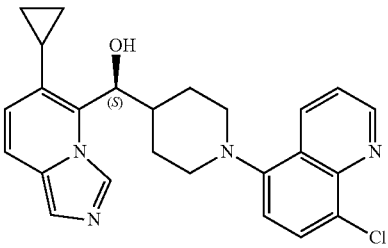

Fast isomer in CHIRALART Cellulose-SB
Eluting reagent: Hex:EtOH = 50:50

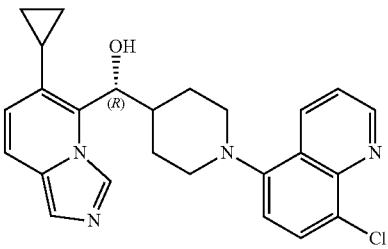

Slow isomer in CHIRALART Cellulose-SB
Eluting reagent: Hex:EtOH = 50:50

Each enantiomer of racemic D178a and D178b was separated using preparative HPLC on a CHIRAL ART Cellulose-SB with Hex:EtOH=50:50 as an eluent. The enantiomeric excesses were determined by using HPLC on a Cellulose-SB with Hex (0.1% DEA):EtOH=50:50 as an eluent at a flow rate of 1.0 mL/min. The first one enantiomer eluted at the retention time of 2.560 min, ¹H NMR (DMSO-d₆) δ$_H$ 8.99 (s, 1H), 8.67 (s, 1H), 8.52 (d, J=8.4 Hz, 1H), 7.82 (d, J=8.4 Hz, 1H), 7.62-7.65 (m, 1H), 7.43 (d, J=10.0 Hz, 1H), 7.34 (s, 1H), 7.11 (d, J=8.4 Hz, 1H), 6.52 (d, J=10.0 Hz, 1H), 5.94 (s, 1H), 5.40-5.44 (m, 1H), 3.36-3.40 (m, 1H), 3.16-3.19 (m, 1H), 2.78-2.84 (m, 1H), 2.56-2.60 (m, 1H), 2.33-2.41 (m, 2H), 2.08-2.11 (m, 1H), 1.65-1.79 (m, 2H), 1.15-1.19 (m, 1H), 0.99-1.01 (m, 2H), and 0.72-0.79 (m, 2H). [M+H]⁺=433, and the other enantiomer eluted at the retention time of 3.316 min, ¹H NMR (DMSO-d₆) δ$_H$ 8.98 (s, 1H), 8.67 (s, 1H), 8.51 (d, J=8.4 Hz, 1H), 7.81 (d, J=7.6 Hz, 1H), 7.61-7.64 (m, 1H), 7.42 (d, J=9.6 Hz, 1H), 7.33 (s, 1H), 7.09 (d, J=8.4 Hz, 1H), 6.52 (d, J=9.6 Hz, 1H), 5.93 (s, 1H), 5.40-5.43 (m, 1H), 3.35-3.39 (m, 1H), 3.15-3.18 (m, 1H), 2.76-2.83 (m, 1H), 2.55-2.59 (m, 1H), 2.33-2.40 (m, 2H), 2.07-2.10 (m, 1H), 1.65-1.81 (m, 2H), 1.14-1.19 (m, 1H), 0.99-1.00 (m, 2H), and 0.71-0.78 (m, 2H). [M+H]⁺=433.

Example D179: (1-(4-chloroquinolin-6-yl)piperidin-4-yl)(6-cyclopropylimidazo[1,5-a]pyridin-5-yl)methanol

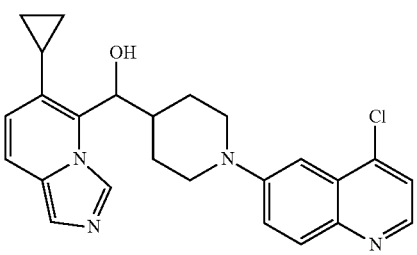 [SMILES: OC(c1c(C2CC2)ccc2cncn12)C1CCN(c2ccc3nccc(Cl)c3c2)CC1]

¹H NMR (DMSO-d₆) δ$_H$ 8.63 (s, 1H), 8.49 (d, J=5.6 Hz, 1H), 7.85 (d, J=9.2 Hz, 1H), 7.66 (q, J=9.6 Hz, 1H), 7.56 (d, J=5.6 Hz, 1H), 7.39 (d, J=9.6 Hz, 1H), 7.30 (s, 1H), 7.17 (s, 1H), 6.45 (d, J=9.2 Hz, 1H), 5.87 (d, J=2.8 Hz, 1H), 5.27 (dd, J=4.0, 9.2 Hz, 1H), 4.02 (d, J=12.4 Hz, 1H), 3.83 (d, J=12.4 Hz, 1H), 2.83-2.90 (m, 1H), 2.60-2.67 (m, 1H), 2.31-2.37 (m, 2H), 1.98-2.00 (m, 1H), 1.40-1.54 (m, 2H), 1.10-1.20 (m, 1H), 0.88-0.93 (m, 2H), and 0.61-0.74 (m, 2H). [M+H]⁺=433.

Example D180: (6-cyclopropylimidazo[1,5-a]pyridin-5-yl)(1-(quinazolin-5-yl)piperidin-4-yl)methanol

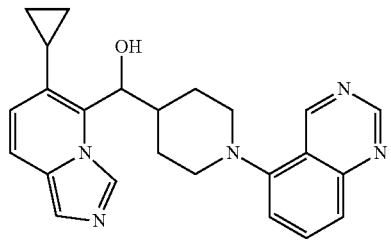

¹H NMR (DMSO-d₆) δ$_H$ 9.57 (s, 1H), 9.23 (s, 1H), 8.67 (s, 1H), 7.85-7.89 (t, J=8.0 Hz, 1H), 7.57-7.59 (d, J=8.4 Hz, 1H), 7.41-7.44 (d, J=9.6 Hz, 1H), 7.33 (s, 1H), 7.18-7.21 (d, J=7.6 Hz, 1H), 6.50-6.52 (d, J=9.2 Hz, 1H), 5.93-5.94 (d, J=3.6 Hz, 1H), 5.40-5.44 (dd, J=3.6 Hz, J₂=9.6 Hz, 1H), 4.34-4.38 (t, J=4.8 Hz, 2H), 2.86-2.96 (t, J=11.6 Hz, 1H), 2.61-2.67 (t, J=11.6 Hz, 1H), 2.30-2.43 (m, 2H), 2.12 (s, 1H), 1.68-1.85 (m, 2H), 1.12-1.20 (m, 1H), 0.94-1.07 (m, 2H), 0.68-0.82 (m, 2H).
Example D181: (6-cyclopropylimidazo[1,5-a]pyridin-5-yl)(1-(quinazolin-6-yl)piperidin-4-yl)methanol
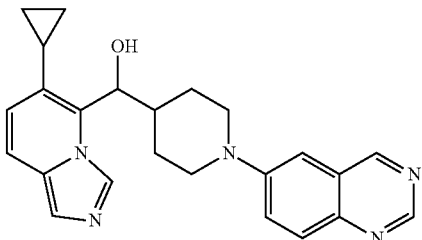
$^1$H NMR (DMSO-d$_6$) δ$_H$ 9.32 (s, 1H), 9.00 (s, 1H), 8.68 (s, 1H), 7.78-7.88 (m, 2H), 7.42-7.45 (d, J=9.2 Hz, 1H), 7.35 (s, 1H), 7.27 (s, 1H), 6.47-6.50 (d, J=9.6 Hz, 1H), 5.90-5.91 (d, J=3.6 Hz, 1H), 5.28-5.32 (dd, J$_1$=2.8 Hz, J$_2$=9.6 Hz, 1H), 4.02-4.05 (d, J=12.8 Hz, 1H), 3.83-3.86 (d, J=12.8 Hz, 1H), 2.84-2.92 (t, J=12.4 Hz, 1H), 2.61-2.68 t, J=12.4 Hz, 1H), 2.30-2.44 (m, 2H), 2.02 (s, 1H), 1.38-1.60 (m, 2H), 1.11-1.18 (m, 1H), 0.88-0.97 (m, 2H), 0.61-0.80 (m, 2H).
Example E: Synthesis of 5-substituted imidazo[1,5-a]pyridines
Example E101: (7-chloroimidazo[1,5-a]pyridin-5-yl)(4-(4-chlorophenyl)cyclohexyl)methanol
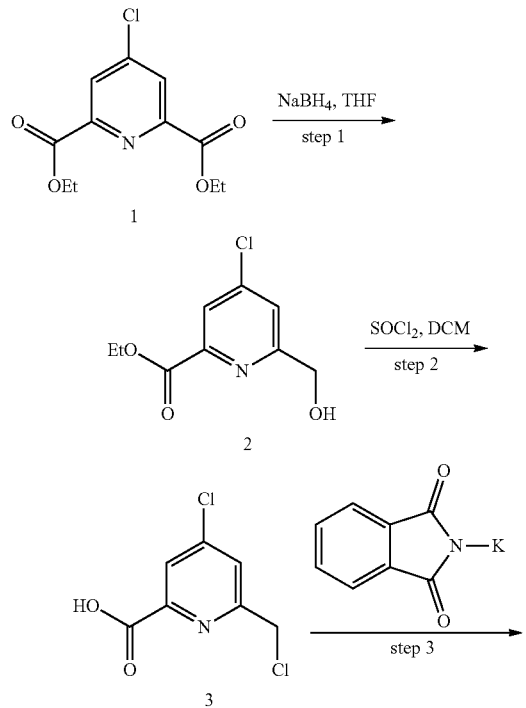
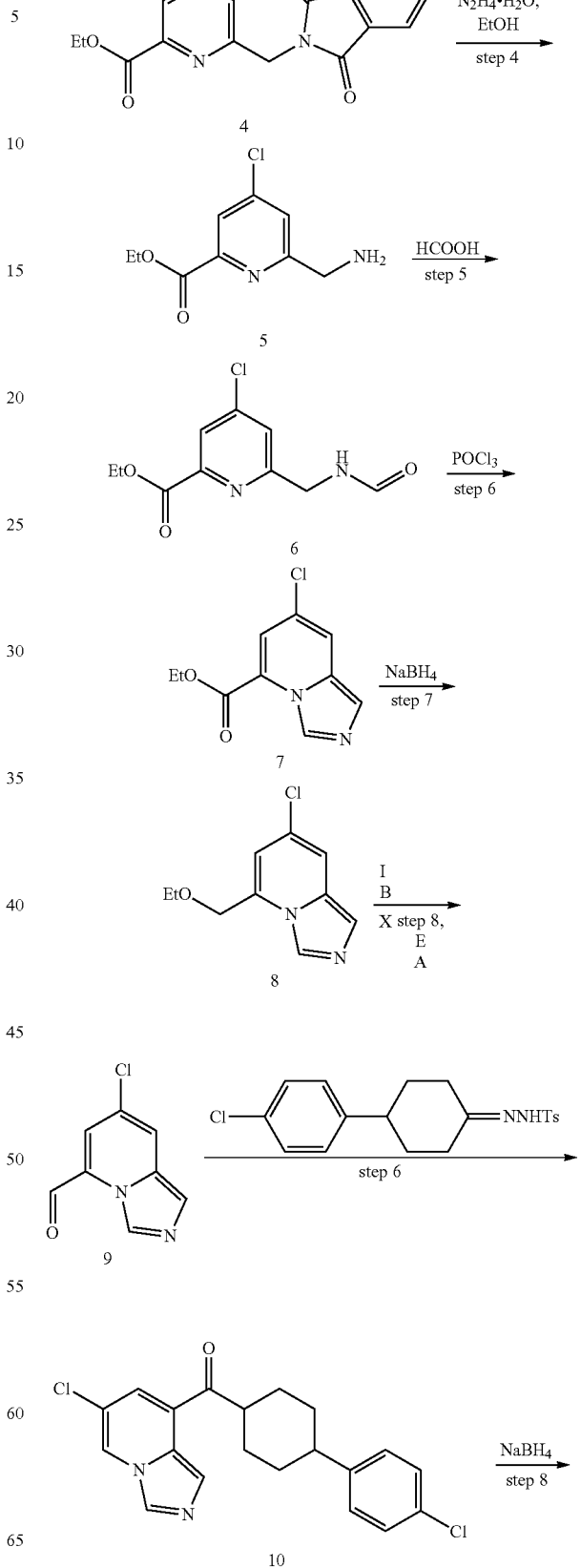

-continued

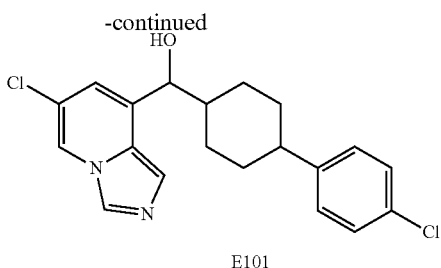

E101

Step 1: Ethyl 4-chloro-6-(hydroxymethyl)picolinate

At 40° C., to a mixture of diethyl 4-chloropyridine-2,6-dicarboxylate (100 g, 388 mmol) in EtOH (600 mL) was added NaBH$_4$ (9 g, 240 mmol) slowly, the reaction mixture was stirred for 2 hours at room temperature, concentrated, EA (1 L) was added, washed with water (1 L), the water phase was extracted with EA (500 mL×2), the combined organic layer was dried over Na$_2$SO$_4$, filtered by a short sili-gel, concentrated to give 70 g oil.

Step 2: Ethyl 4-chloro-6-(chloromethyl)picolinate

Under water cooling, to a solution of ethyl 4-chloro-6-(hydroxymethyl)picolinate (70 g, 324 mmol) in DCM (800 mL) was added dropwise SOCl$_2$ (30 mL, 413 mmol). The mixture was stirred 1 hour at room temperature, concentrated, EA (500 mL) was added, washed with sat.NaHCO$_3$.aq (500 mL). The EA layer was washed with water and brine, dried over Na$_2$SO$_4$, concentrated to give the desired product.

Step 3: Ethyl 4-chloro-6-(chloromethyl)picolinate

A mixture of ethyl 4-chloro-6-(hydroxymethyl)picolinate (67 g, 286 mmol) and potassium 1,3-dioxoisoindolin-2-ide (75 g, 405 mmol) in DMF (700 mL) was stirred 1.5 days at room temperature. The reaction mixture was poured into ice (3 kg), the solid was collected, washed with water and Et$_2$O, dried in vacuo to give 72 g. $^1$H NMR (DMSO-d$_6$) δ$_H$ 7.86-7.96 (m, 6H), 4.98 (s, 2H), 4.24 (q, J=7.2 Hz, 2H), and 1.18 (t, J=7.2 Hz, 3H)

Step 4: Ethyl 6-(aminomethyl)-4-chloropicolinate

A mixture of ethyl 4-chloro-6-((1,3-dioxoisoindolin-2-yl) methyl)picolinate (87 g, 252 mmol) and N$_2$H$_4$.H$_2$O (13 mL, 252 mmol) in EtOH (1.5 L) was heated to reflux for 1 hour, after cooled down, the mixture was filtered, the filtrate was concentrated to give 81 g crude.

Step 5: Ethyl 4-chloro-6-(formamidomethyl)picolinate

A solution of ethyl 6-(aminomethyl)-4-chloropicolinate (80 g crude) in HCOOH/Ac$_2$O (300 mL/100 mL) was heated to 60° C. for 2 hours, after cooled down, the mixture was concentrated, sat.NaHCO$_3$.aq was added, extracted with EA, the organic layer was dried over Na$_2$SO$_4$, concentrated and purified by sili-gel to give 25 g pure. 1H NMR (DMSO-d$_6$) δ$_H$ 8.69 (s, 1H), 8.19 (s, 1H), 7.97 (m, 1H), 7.66 (m, 1H), 4.46 (d, J=6.4 Hz, 2H), 4.35 (q, J=7.2 Hz, 2H), and 1.34 (t, J=7.2 Hz, 3H)

Step 6: Ethyl 7-chloroimidazo[1,5-a]pyridine-5-carboxylate

A solution of ethyl 4-chloro-6-(formamidomethyl)picolinate (23 g, 94.8 mmol) and POCl$_3$ (25 mL) in toluene (200 mL) was heated to 100° C. for 2 hours, after cooled down, the mixture was concentrated, sat.NaHCO$_3$.aq was added, extracted with EA, the organic layer was dried over Na$_2$SO$_4$, concentrated and purified by sili-gel to give 12 g pure. $^1$H NMR (DMSO-d$_6$) δ$_H$ 9.09 (s, 1H), 8.16 (d, J=2.0 Hz, 1H), 7.62 (s, 1H), 7.51 (d, J=2.0 Hz, 1H), 4.35 (q, J=7.2 Hz, 2H), and 1.33 (t, J=7.2 Hz, 3H)

Step 7: (7-chloroimidazo[1,5-a]pyridin-5-yl)methanol

A mixture of ethyl 7-chloroimidazo[1,5-a]pyridine-5-carboxylate (7.0 g, 31.2 mmol) and NaBH$_4$ (2.0 g, 52.6 mmol) in EtOH (400 mL) was heated to 80° C. for 2 hours, after cooled down, the mixture was concentrated, H$_2$O (200 mL) was added, the mixture was concentrated, the solid was collected by filtrated and washed with water, dried in air to give 5.2 g crude.

Step 8: 7-chloroimidazo[1,5-a]pyridine-5-carbaldehyde

A mixture of (7-chloroimidazo[1,5-a]pyridin-5-yl)methanol (5.2 g, 28.5 mmol) and IBX (12 g, 42.9 mmol) in EA (250 mL) was heated to reflux for overnight, after cooled down, the mixture was filtered, and the filtrate was concentrated and purified by sili-gel to give 1.6 g. $^1$H NMR (DMSO-d$_6$) δ$_H$ 9.93 (s, 1H), 9.29 (s, 1H), 8.29 (d, J=7.2 Hz, 1H), 7.89 (d, J=7.2 Hz, 1H), and 7.71 (s, 1H).

Step 9: (7-chloroimidazo[1,5-a]pyridin-5-yl)(4-(4-chlorophenyl)cyclohexyl)methanone Under N$_2$, a mixture of 7-chloroimidazo[1,5-a]pyridine-5-carbaldehyde (180 mg, 1.0 mmol), N'-(4-(4-chlorophenyl)cyclohexylidene)-4-methylbenzenesulfonohydrazide (400 mg, 1.06 mmol) and Cs$_2$CO$_3$ (500 mg, 1.53 mmol) in dioxane (20 mL) was heated to 100° C. for overnight, after cooled down, EA(20 mL) was added, the mixture was filtered, the filtrate was concentrated and purified by sili-gel to give 200 mg.

Step 10: (7-chloroimidazo[1,5-a]pyridin-5-yl)(4-(4-chlorophenyl)cyclohexyl)methanol A mixture of (7-chloroimidazo[1,5-a]pyridin-5-yl)(4-(4chlorophenyl)cyclohexyl)methanone (200 mg, 0.54 mmol) and NaBH$_4$ (50 mg, 1.32 mmol) in MeOH (20 mL) was stirred for 30 min at room temperature, the reaction mixture was concentrated, EA (20 mL) was added, washed with brine (20 mL×2), dried over Na$_2$SO$_4$, concentrated and purified by perp-TLC to give 60 mg yellow solid. $^1$H NMR (DMSO-d$_6$) δ$_H$ 8.58 (s, 1H), 7.69 (s, 1H), 7.29-7.31 (d, J=8.4 Hz, 2H), 7.21-7.24 (d, J=8.4 Hz, 2H), 6.67 (s, 1H), 5.91-5.93 (d, J=4.4 Hz, 1H), 4.72-4.76 (t, J=4.8 Hz, 1H), 1.87-2.00 (m, 2H), 1.70-1.82 (m, 2H), and 1.27-1.49 (m, 6H).

Example E101a and E101b: (S)-(7-chloroimidazo[1,5-a]pyridin-5-yl)((1r,4S)-4-(4-chlorophenyl)cyclohexyl)methanol and (R)-(7-chloroimidazo[1,5-a]pyridin-5-yl)((1r,4R)-4-(4-chlorophenyl)cyclohexyl)methanol

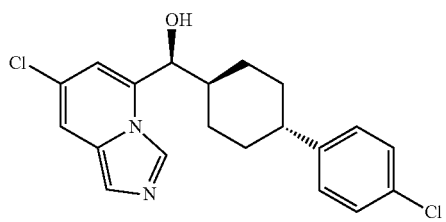

Fast isomer in CHIRALART Cellulose-SB
Eluting reagent: Hex:EtOH = 90:10

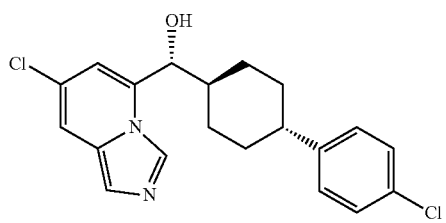

Slow isomer in CHIRALART Cellulose-SB
Eluting reagent: Hex:EtOH = 90:10

Each enantiomer of racemic E101a and E101b was separated using preparative HPLC on a CHIRALART Cellulose-SB with Hex:EtOH=90:10 as an eluent. The first one enantiomer eluted at the retention time of 6.547 min, which was dissolved in THF (5 ml), and HCl in EA(4N, 0.5 mL) was added and stirred at r.t for 1 h, the solvent was evaporated to give product (E101a) as white solid, $^1$H NMR (DMSO-$d_6$) $\delta_H$ 9.34 (s, 1H), 7.91 (s, 1H), 7.87 (s, 1H), 7.31 (d, J=8.4 Hz, 2H), 7.22 (d, J=8.4 Hz, 2H), 6.99 (s, 1H), 4.78 (d, J=6.4 Hz, 1H), 1.89-2.03 (m, 2H), 1.71-1.88 (m, 2H), and 1.28-1.55 (m, 6H), MS (ESI) m/e [M+1]$^+$375; and the other enantiomer eluted at the retention time of 7.744 min, which was dissolved in THF (5 ml), and HCl in EA(4N, 0.5 mL) was added and the solvent was evaporated to give product (E101b) as white solid, $^1$H NMR (DMSO-$d_6$) $\delta_H$ 9.16 (s, 1H), 7.86 (s, 1H), 7.77 (s, 1H), 7.31 (d, J=8.4 Hz, 2H), 7.22 (d, J=8.4 Hz, 2H), 6.92 (s, 1H), 4.77 (d, J=6.4 Hz, 1H), 1.89-2.03 (m, 2H), 1.71-1.88 (m, 2H), and 1.27-1.53 (m, 6H), MS (ESI) m/e [M+1]$^+$=375. The absolute configurations of chiral carbons in E101a and E101b are tentatively assigned as (S) and (R) respectively based on assumption that the binding model of the more potent isomer E101a is the same as that of C101a with IDO1 enzyme, and the relative stereochemistry on cyclohexane is assigned as trans configuration on the cyclohexane.

Example E102: (4-(4-chlorophenyl)cyclohexyl)(7-cyclopropylimidazo[1,5-a]pyridin-5-yl)methanol

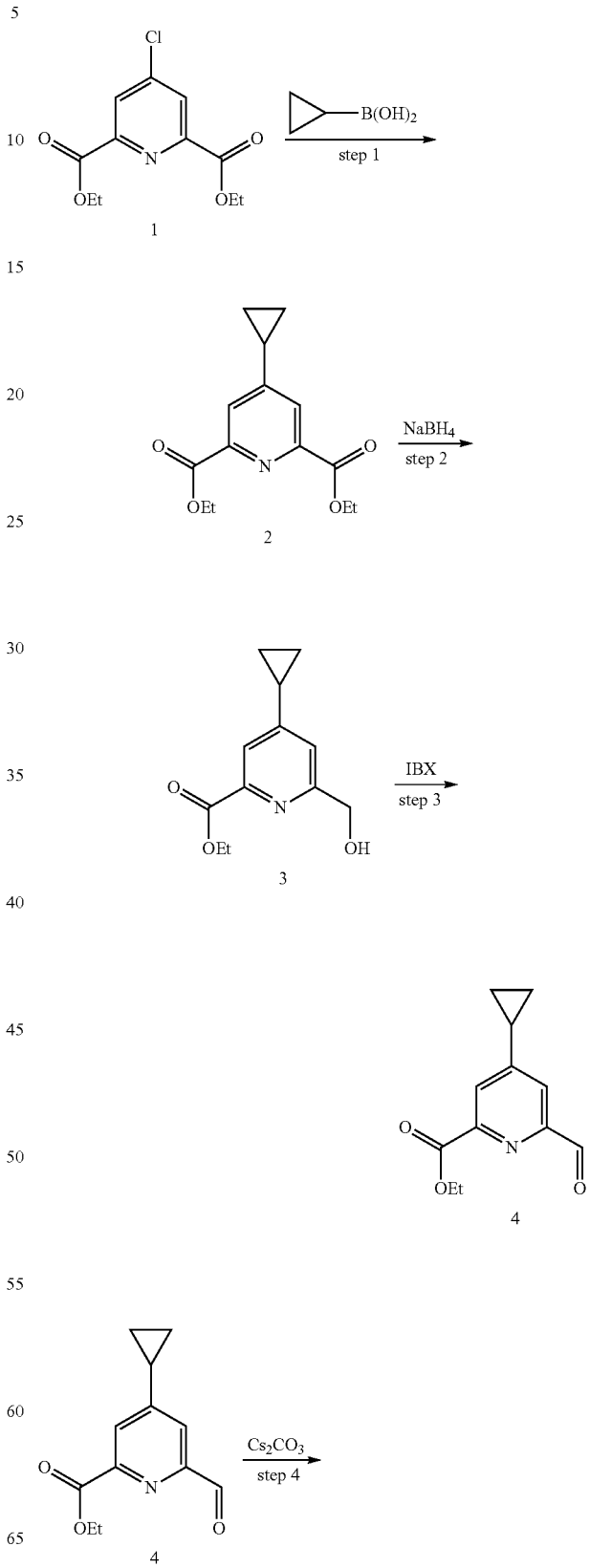

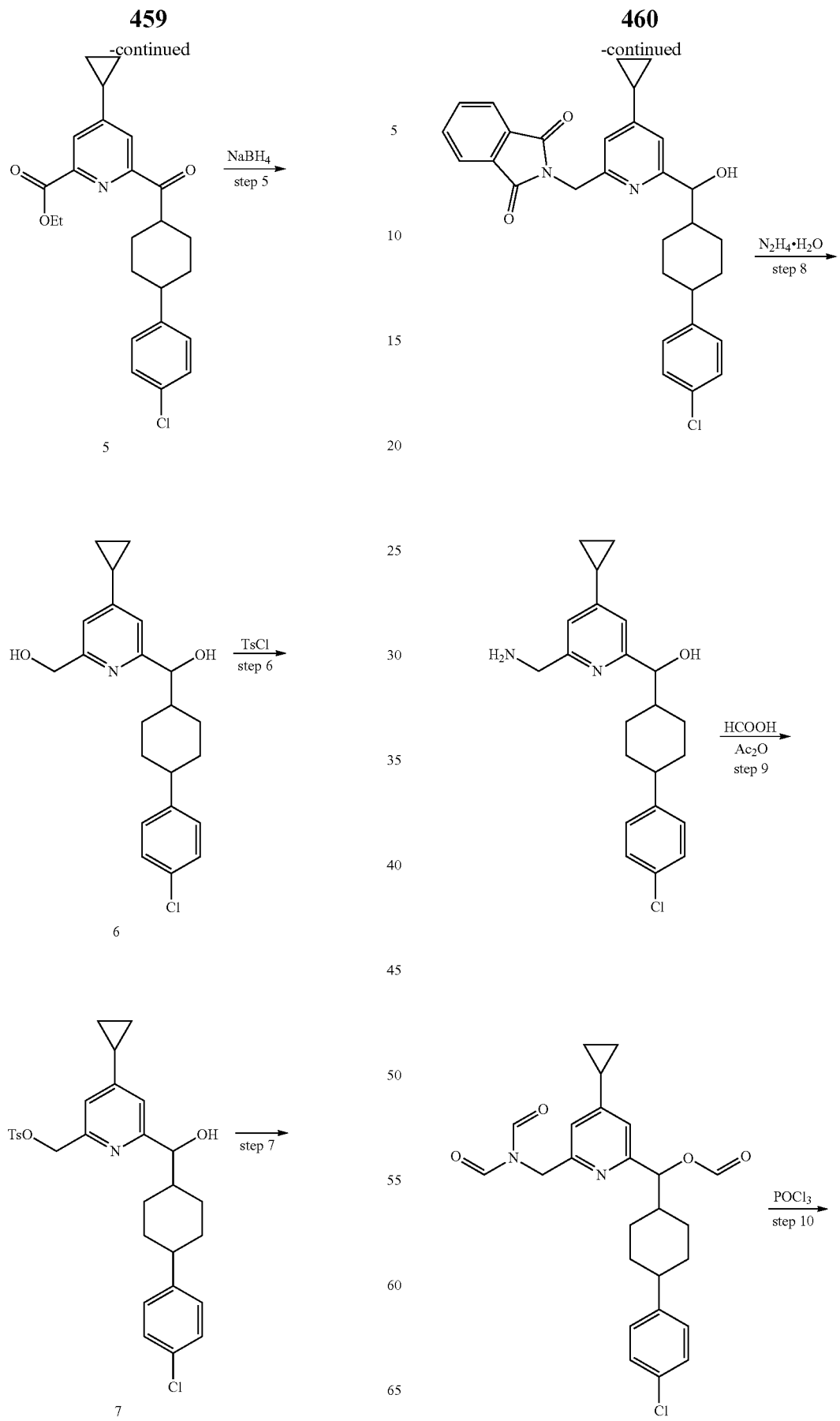

-continued

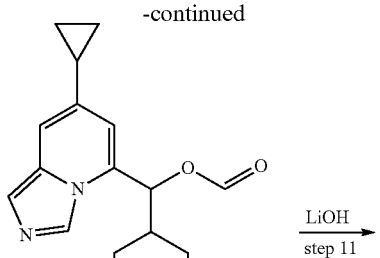

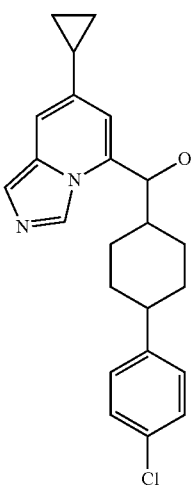

E102

Step 1: Diethyl 4-cyclopropylpyridine-2,6-dicarboxylate

Under $N_2$, a mixture of diethyl 4-chloropyridine-2,6-dicarboxylate (32 g, 124 mmol), cyclopropylboronic acid (22 g, 256 mmol) Pd(dppf)Cl$_2$ (10 g, 13.6 mmol) and K$_2$CO$_3$ (35 g, 253 mmol) in Toluene (600 mL) was heated to 100° C. for 3 hours, after cooled down, the reaction mixture was filtered, the filtrate was concentrated and purified by sili-gel to give 17 g. $^1$H NMR (DMSO-d6) $\delta_H$ 7.90 (s, 2H), 4.35 (q, J=7.2 Hz, 4H), 2.17-2.24 (m, 1H), 1.34 (t, J=7.2 Hz, 6H), 1.13-1.19 (m, 2H), and 0.90-0.94 (m, 2H)

Step 2: Ethyl 4-cyclopropyl-6-(hydroxymethyl)picolinate

At 50° C., to a solution of diethyl 4-cyclopropylpyridine-2,6-dicarboxylate (17 g, 64.6 mmol) in EtOH (400 mL) was added NaBH$_4$ (1.5 g, 39.5 mmol). The reaction mixture was stirred for 1 hour at 50° C., quenched with 30 mL water. The mixture was concentrated, EA (500 mL) was added, washed with water and brine, dried over Na$_2$SO$_4$, concentrated to give 9.0 g crude.

Step 3: Ethyl 4-cyclopropyl-6-formylpicolinate

A mixture of ethyl 4-cyclopropyl-6-(hydroxymethyl)picolinate (9.0 g, 40.7 mmol) and IBX (17 g, 60.7 mmol) in EA (300 mL) was heated to reflux for overnight. After cooled down, the reaction mixture was filtered, concentrated and purified by sili-gel to give 6.2 g. $^1$H NMR (DMSO-d$_6$) $\delta_H$ 9.98 (s, 1H), 8.00 (d, J=1.6 Hz, 1H), 7.79 (d, J=1.6 Hz, 1H), 4.38 (q, J=7.2 Hz, 2H), 2.20-2.27 (m, 1H), 1.35 (t, J=7.2 Hz, 3H), 1.15-1.20 (m, 2H), and 0.93-0.97 (m, 2H)

Step 4: Ethyl 6-(4-(4-chlorophenyl)cyclohexane-1-carbonyl)-4-cyclopropylpicolinate Under $N_2$, a mixture of ethyl 4-cyclopropyl-6-formylpicolinate (3.5 g, 16 mmol), N'-(4-(4-chlorophenyl)cyclohexylidene)-4-methylbenzenesulfonohydrazide (7.5 g, 20 mmol) and Cs$_2$CO$_3$ (8.5 g, 26 mmol) in dioxane (100 mL) was heated to 100° C. for overnight, after cooled down, water (100 mL) was added, extracted with EA (100 mL×2), the combined organic layer was dried over Na$_2$SO$_4$, concentrated and purified by sili-gel to give product 1.8 g. MS (ESI) m/e [M+1]$^+$=412

Step 5: (4-(4-Chlorophenyl)cyclohexyl)(4-cyclopropyl-6-(hydroxymethyl)pyridin-2-yl)methanol A mixture of ethyl 6-(4-(4-chlorophenyl)cyclohexane-1-carbonyl)-4-cyclopropylpicolinate (1.8 g, 4.4 mmol) and NaBH$_4$ (0.6 g, 15.8 mmol) in EtOH (30 mL) was heated to 60° C. for 2 hours, the mixture was concentrated, HCl.aq (2M, 80 mL) was added, stirred for 30 min at room temperature, the pH value was adjust to 8 with Na$_2$CO$_3$ solid, extracted with EA (100 mL), the EA layer was concentrated and purified by sili-gel to give 1.1 g. MS (ESI) m/e [M+1]-372

Step 6: (6-((4-(4-chlorophenyl)cyclohexyl)(hydroxy)methyl)-4-cyclopropylpyridin-2-yl)methyl 4-methylbenzenesulfonate A mixture of (4-(4-Chlorophenyl)cyclohexyl)(4-cyclopropyl-6-(hydroxymethyl)pyridin-2-yl)methanol (1.0 g, 2.7 mmol), TsCl (0.7 g, 3.67 mmol), TEA (600 mg, 5.9 mmol) and DMAP (30 mg, 0.25 mmol) in DCM (50 mL) was stirred for 4 hours at room temperature, the mixture was concentrated, EA was added, the organic layer was washed with brine, dried over Na$_2$SO$_4$, concentrated to give crude product (1.6 g).

Step 7: 2-((6-((4-(4-Chlorophenyl)cyclohexyl)(hydroxy)methyl)-4-cyclopropylpyridin-2-yl)methyl)isoindoline-1,3-dione A mixture of (6-((4-(4-chlorophenyl)cyclohexyl)(hydroxy)methyl)-4-cyclopropylpyridin-2-yl)methyl 4-methylbenzenesulfonate (1.6 g, 3.0 mmol) and potassium 1,3-dioxoisoindolin-2-ide (0.8 g, 4.3 mmol) in DMF (30 mL) was stirred for overnight at room temperature, EA (200 mL) was added, the mixture was washed with water and brine, dried over Na$_2$SO$_4$, concentrated and purified by sili-gel to give 1.0 g. MS (ESI) m/e [M+1]$^+$501

Step 8: (6-(aminomethyl)-4-cyclopropylpyridin-2-yl)(4-(4-chlorophenyl)cyclohexyl)methanol A mixture of 2-((6-((4-(4-Chlorophenyl)cyclohexyl)(hydroxy)methyl)-4-cyclopropylpyridin-2-yl)methyl)isoindoline-1,3-dione (1.0 g, 2.0 mmol) and N$_2$H$_4$.H$_2$O (0.2 g, 4.0 mmol) in EtOH (30 mL) was heated to 90° C. for 2 hours, after cooled down, the mixture was filtered, and the filtrate was concentrated to give 0.6 g crude product. MS (ESI) m/e [M+1]$^+$371

Step 9: (4-(4-chlorophenyl)cyclohexyl)(4-cyclopropyl-6-((N-formylformamide)methyl)pyridin-2-yl) methyl formate A solution of (6-(aminomethyl)-4-cyclopropylpyridin-2-yl)(4-(4-chlorophenyl)cyclohexyl)methanol (0.6 g crude) in HCOOH/Ac$_2$O (10 mL/30 mL) was heated to 60° C. for overnight, after cooled down, the mixture was concentrated, sat.NaHCO$_3$.aq was added, extracted with EA, the organic layer was washed with water and brine, dried over Na$_2$SO$_4$, concentrated and purified by sili-gel to give product (0.3 g). MS (ESI) m/e [M+1]$^+$455

Step 10: (4-(4-chlorophenyl)cyclohexyl)(7-cyclopropylimidazo[1,5-a]pyridin-5-yl)methyl formate A solution of (4-(4-chlorophenyl)cyclohexyl)(4-cyclopropyl-6-((N-formylformamide)methyl)p-yridin-2-yl)methyl formate (300 mg, 0.66 mmol) and POCl$_3$ (1.5 mL) in toluene (15 mL) was heated to 90° C. for overnight, after cooled down, the mixture was concentrated, sat.NaHCO$_3$.aq was added, extracted with EA, the organic layer was washed with water and brine, dried over Na$_2$SO$_4$, concentrated and purified by prep-TLC to give product (45 mg). MS (ESI) m/e [M+1]$^+$409

Step 11: (4-(4-chlorophenyl)cyclohexyl)(7-cyclopropylimidazo[1,5-a]pyridin-5-yl)methanol

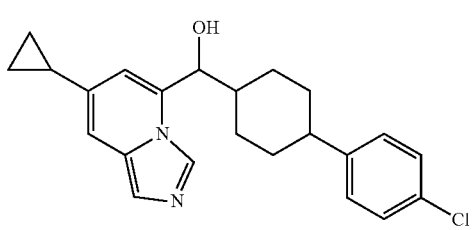 [SMILES: OC(c1cc(C2CC2)cc2cncn12)C1CCC(c2ccc(Cl)cc2)CC1]

A mixture of (4-(4-chlorophenyl)cyclohexyl)(7-cyclopropylimidazo[1,5-a]pyridin-5-yl)methyl formate (45 mg, 0.11 mmol) and LiOH—H$_2$O (20 mg, 0.47 mmol) in MeOH (25 mL) was stirred for 2 hours at room temperature, the reaction mixture was concentrated, EA was added, the organic layer was washed with water and brine, dried over Na$_2$SO$_4$, concentrated and purified by prep-HPLC to give 5 mg. $^1$H NMR (DMSO-d$_6$) δ$_H$ 9.27 (s, 1H), 7.77 (s, 1H), 7.41 (s, 1H), 7.30 (d, J=8.4 Hz, 2H), 7.22 (d, J=8.4 Hz, 2H), 6.72 (s, 1H), 5.98 (s, 1H), 5.34 (t, J=4.8 Hz, 1H), 4.71 (d, J=6.8 Hz, 1H), 1.91-2.07 (m, 4H), 1.69-1.87 (m, 2H), 1.29-1.49 (m, 4H), 0.98-1.06 (m, 2H), and 0.73-0.81 (m, 2H), MS (ESI) m/e [M+1]$^+$381.

Example E103: (7-chloroimidazo[1,5-a]pyridin-5-yl)(4-(naphthalen-1-yl)cyclohexyl)methanol

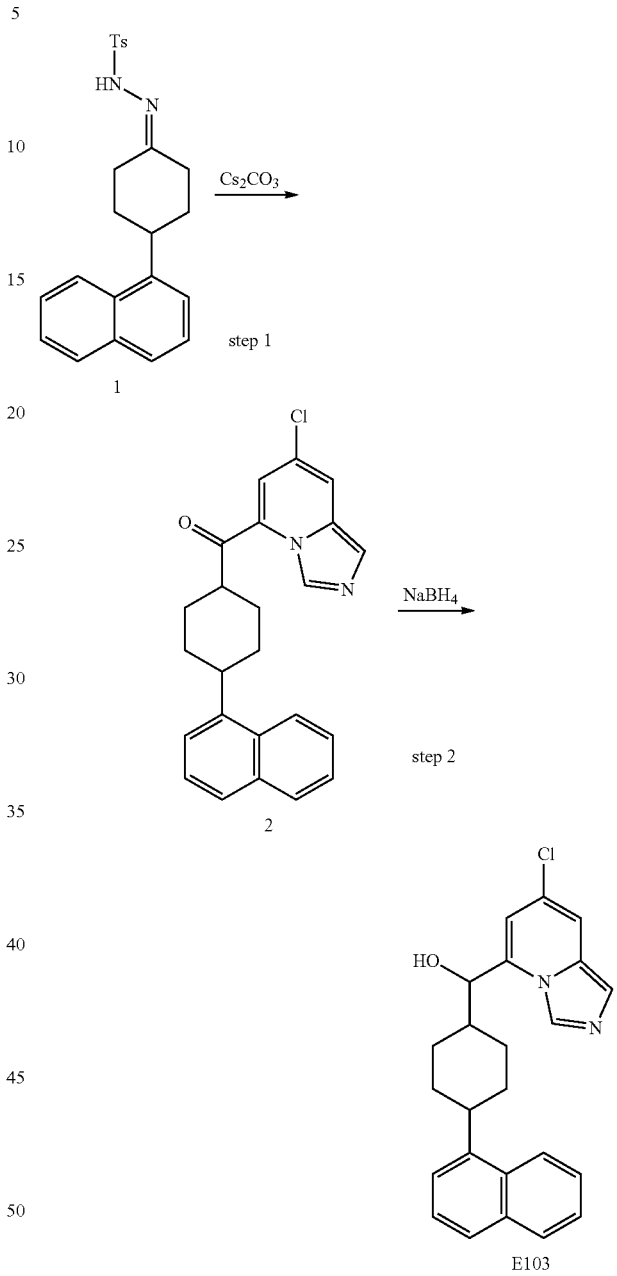

Step 1: (7-chloroimidazo[1,5-a]pyridin-5-yl)(4-(naphthalen-1-yl)cyclohexyl)methanone Under N$_2$, a mixture of 7-chloroimidazo[1,5-a]pyridine-5-carbaldehyde (400 mg, 2.2 mmol), 4-methyl-N'-(4-(naphthalen-1-yl)cyclohexylidene)benzenesulfonohydrazide (1.0 g, 2.55 mmol) and Cs$_2$CO$_3$ (2.0 g, 6.1 mmol) in dioxane (30 mL) was heated to 100° C. for overnight, after cooled down, EA(30 mL) was added, the mixture was filtered, the filtrate was concentrated and purified by sili-gel to give product (300 mg).

Step 2: (7-chloroimidazo[1,5-a]pyridin-5-yl)(4-(naphthalen-1-yl)cyclohexyl)methanol A mixture of (7-chloroimidazo[1,5-a]pyridin-5-yl)(4-(naphthalen-1-yl)cyclohexyl)methanone (300 mg, 0.77 mmol) and NaBH$_4$ (200 mg, 5.3 mmol) in MeOH (30 mL) was stirred for 30 min at room temperature, the reaction mixture was concentrated, EA (20 mL) was added, washed with brine (20 mL×2), dried over Na$_2$SO$_4$, concentrated and purified by sili-gel to give 120 mg yellow solid. $^1$H NMR (DMSO-d$_6$) $\delta_H$ 8.61 (s, 1H), 8.13 (d, J=8.4 Hz, 1H), 7.90 (d, J=7.6 Hz, 1H), 7.74 (d, J=8.0 Hz, 1H), 7.69 (s, 1H), 7.36-7.56 (m, 5H), 7.71 (d, J=1.6 Hz, 1H), 5.97 (d, J=4.4 Hz, 1H), 4.80 (t, J=5.2 Hz, 1H), 1.84-2.09 (m, 5H), and 1.44-1.63 (m, 5H)

Example E103a and E103b: (S)-(7-chloroimidazo[1,5-a]pyridin-5-yl)((1 r,4S)-4-(naphthalen-1-yl)cyclohexyl)methanol and (R)-(7-chloroimidazo[1,5-a]pyridin-5-yl)((1 r,4R)-4-(naphthalen-1-yl)cyclohexyl)methanol

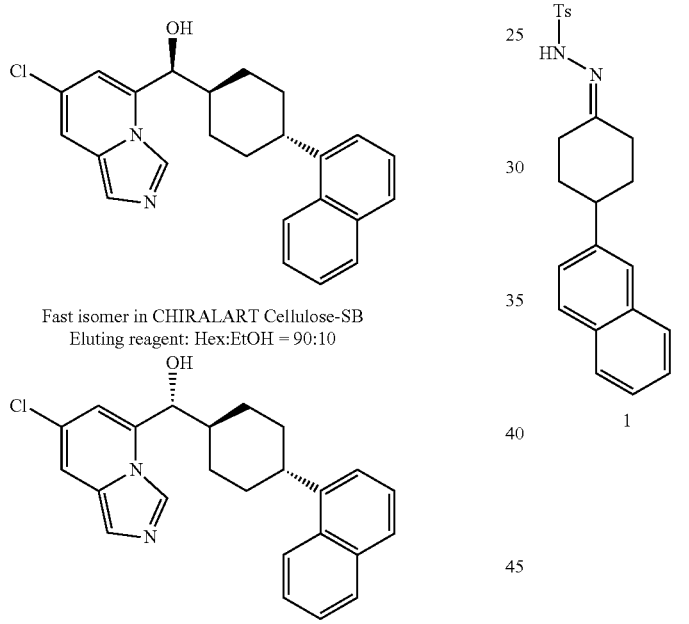

Fast isomer in CHIRALART Cellulose-SB
Eluting reagent: Hex:EtOH = 90:10

Slow isomer in CHIRALART Cellulose-SB
Eluting reagent: Hex:EtOH = 90:10

Each enantiomer of racemic E103a and E103b was separated using preparative HPLC on a CHIRALART Cellulose-SB with Hex:EtOH=90:10 as an eluent. The first one enantiomer eluted at the retention time of 8.698 min, which was dissolved in THF (5 ml), and HCl in EA(4N, 0.5 mL) was added and stirred at r.t for 1 h, the solvent was evaporated to give product as white solid, $^1$H NMR (DMSO-d$_6$) $\delta_H$ 9.39 (s, 1H), 8.13 (d, J=8.4 Hz, 1H), 7.89-7.93 (m, 3H), 7.74 (d, J=8.4 Hz, 1H), 7.35-7.55 (m, 5H), 7.03 (s, 1H), 4.85 (d, J=6.4 Hz, 1H), 1.87-2.11 (m, 5H), and 1.44-1.65 (m, 5H), MS (ESI) m/e [M+1]$^+$391; and the other enantiomer eluted at the retention time of 9.421 min, which was dissolved in THF (5 ml), and HCl in EA(4N, 0.5 mL) was added and the solvent was evaporated to give product as white solid, $^1$H NMR (DMSO-d$_6$) $\delta_H$ 9.43 (s, 1H), 8.13 (d, J=8.4 Hz, 1H), 7.90-7.94 (m, 3H), 7.74 (d, J=8.4 Hz, 1H), 7.35-7.55 (m, 5H), 7.05 (s, 1H), 4.85 (d, J=6.8 Hz, 1H), 1.86-2.13 (m, 5H), and 1.50-1.62 (m, 5H), MS (ESI) m/e [M+1]$^+$391. The absolute configurations of chiral carbons in E103a and E103b are tentatively assigned as (S) and (R) respectively based on assumption that the binding model of the more potent isomer E103a is the same as that of C101a with IDO1 enzyme, and the relative stereochemistry on cyclohexane is assigned as trans configuration on the cyclohexane.

Example E104: (7-chloroimidazo[1,5-a]pyridin-5-yl)(4-(naphthalen-2-yl)cyclohexyl)methanol

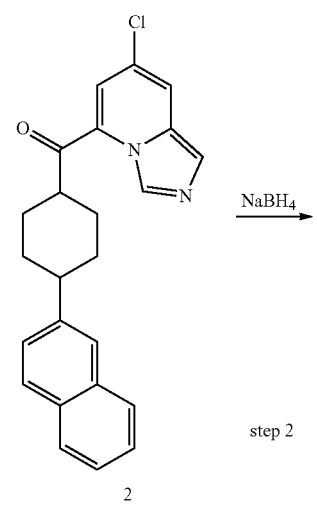

467
-continued

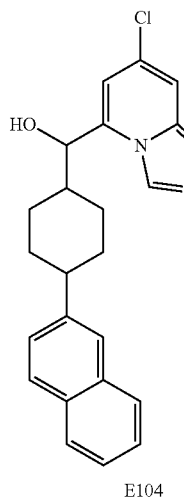

E104

Step 1: (7-chloroimidazo[1,5-a]pyridin-5-yl)(4-(naphthalen-2-yl)cyclohexyl)methanone Under $N_2$, a mixture of 7-chloroimidazo[1,5-a]pyridine-5-carbaldehyde (400 mg, 2.2 mmol), 4-methyl-N'-(4-(naphthalen-2-yl)cyclohexylidene)benzenesulfonohydrazide (1.0 g, 2.55 mmol) and $Cs_2CO_3$ (2.0 g, 6.1 mmol) in dioxane (30 mL) was heated to 100° C. for overnight, after cooled down, EA(30 mL) was added, the mixture was filtered, the filtrate was concentrated and purified by sili-gel to give 280 mg.

Step 2: (7-chloroimidazo[1,5-a]pyridin-5-yl)(4-(naphthalen-2-yl)cyclohexyl)methanol A mixture of (7-chloroimidazo[1,5-a]pyridin-5-yl)(4-(naphthalen-2-yl)cyclohexyl)methanone (280 mg, 0.72 mmol) and $NaBH_4$ (200 mg, 5.3 mmol) in MeOH (30 mL) was stirred for 30 min at room temperature, the reaction mixture was concentrated, EA (20 mL) was added, washed with brine (20 mL×2), dried over $Na_2SO_4$, concentrated and purified by sili-gel to give 110 mg yellow solid. $^1$H NMR (DMSO-$d_6$) $\delta_H$ 8.60 (s, 1H), 7.79-7.85 (m, 3H), 7.68-7.69 (d, J=4.0 Hz, 2H), 7.40-7.46 (m, 4H), 6.70 (d, J=1.6 Hz, 1H), 5.94-5.95 (d, J=4.4 Hz, 1H), 4.76-4.79 (t, J=5.2 Hz, 1H), 2.55-2.68 (m, 1H), 1.81-2.09 (m, 4H), and 1.31-1.56 (m, 5H)

Example E104a and E104b: (S)-(7-chloroimidazo [1,5-a]pyridin-5-yl)((1r,4S)-4-(naphthalen-2-yl)cyclohexyl)methanol and (R)-(7-chloroimidazo[1,5-a]pyridin-5-yl)((1 r,4R)-4-(naphthalen-2-yl)cyclohexyl)methanol

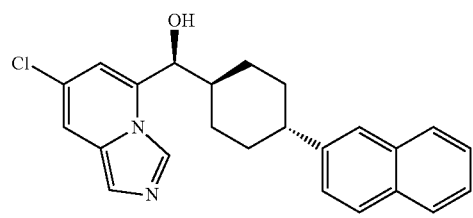

Fast isomer in CHIRALART Cellulose-SB
Eluting reagent: Hex:EtOH = 90:10

468
-continued

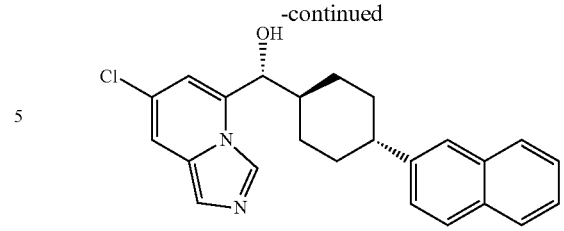

Slow isomer in CHIRALART Cellulose-SB
Eluting reagent: Hex:EtOH = 90:10

Each enantiomer of racemic E104a and E104b was separated using preparative HPLC on a CHIRALART Cellulose-SB with Hex:EtOH=90:10 as an eluent. The first one enantiomer eluted at the retention time of 7.385 min, which was dissolved in THF (5 ml), and HCl in EA(4N, 0.5 mL) was added and stirred at r.t for 1 h, the solvent was evaporated to give product as white solid, $^1$H NMR (DMSO-$d_6$) $\delta_H$ 9.35 (s, 1H), 7.80-7.92 (m, 5H), 7.68 (s, 1H), 7.39-7.48 (m, 3H), 7.02 (s, 1H), 4.82 (d, J=6.4 Hz, 1H), 2.56-2.67 (m, 1H), 1.82-2.31 (m, 4H), and 1.31-1.60 (m, 5H), MS (ESI) m/e [M+1]$^+$391; and the other enantiomer eluted at the retention time of 9.238 min, which was dissolved in THF (5 ml), and HCl in EA(4N, 0.5 mL) was added and the solvent was evaporated to give product as white solid, $^1$H NMR (DMSO-$d_6$) $\delta_H$ 9.19 (s, 1H), 7.78-7.87 (m, 5H), 7.68 (s, 1H), 7.39-7.48 (m, 3H), 6.95 (s, 1H), 4.51 (d, J=6.4 Hz, 1H), 2.56-2.67 (m, 1H), 1.83-2.03 (m, 4H), and 1.31-1.56 (m, 5H), MS (ESI) m/e [M+1]-391. The absolute configurations of chiral carbons in E104a and E104b are tentatively assigned as (S) and (R) respectively based on assumption that the binding model of the more potent isomer E104a is the same as that of C101a with IDO1 enzyme, and the relative stereochemistry on cyclohexane is assigned as trans configuration on the cyclohexane.

Example F: Biological Assays

IDO1 Enzymatic Assay

Recombinant IDO1 was overexpressed and purified from E. coli cells with an N-terminal His tag. IDO1 enzymatic assay was carried out using a methodology similar to described in the literature (J. Biol. Chem. (1980), 255, 1339-1345.). The reaction mixture contains 50 nM IDO1, 1.3 mM D-tryptophan, 5 mM L-ascorbic acid, 6.25 M methylene Blue, 0.4 mg/mL catalase and compound (or DMSO) in a buffer containing 50 mM potassium phosphate pH 7.5 and 0.1% BSA. After incubation at 24'C for 1.5 hours, absorbance of the reaction mixture was continuously read at 321 nm to monitor the formation of N'-formylkynurenine by a FULOstar OMEGA plate reader (BMG LABTECH) for 1 hour. The enzymatic activity was determined by measuring the slope of the linear absorbance increase as a function of time. The $IC_{50}$s are calculated based on remaining enzyme activity in the presence of increasing concentrations of compounds.

TDO Enzymatic Assay

Recombinant TDO was overexpressed and purified from E. coli cells with a C-terminal His tag. TDO enzymatic assay was performed using the same methodology as IDO1 enzymatic assay except that 100 nM TDO and 0.5 mM L-tryptophan (Km concentration) were used in the TDO assay.

HeLa Cell-Based IDO1 Kyn (Kynurenine) Production Assay:

The inhibitory activity of IDO1 inhibitors is determined by using a colorimetric reaction to measure Kyn generated from L-Trp (L-Tryptophon) oxidation by cellular IDO1 in HeLa cells after induction of IDO1 expression by IFN-γ.

Hela cells were obtained from the American Type Culture Collection and recovered in 10% FBS-containing phenol red-free DMEM medium. Cells were plated onto a 96-well plate (100 μl/well) at 8000 cells per well and kept at 37° C. in a humidified incubator supplied with 5% $CO_2$ 4 hours later, Human recombinant IFN-γ (8901SC, CST) was added to cells (final concentration 100 ng/mL) to stimulate endogenous IDO11. Compounds at different concentrations diluted in dimethylsulfoxide (DMSO) were added simultaneously with IFN-γ and 0.4 mM L-Trp. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 30 minutes and then centrifugation at 2500 rpm for 10 minutes to remove sediments. 80 μl supernatants were carefully removed to a new clean plate and added with an equal volume of 2% 4-(Dimethylamino) benzaldehyde (D2004, sigma) dissolved in glacial acetic acid. The absorbance at 480 nm wavelength derived from Kyn was measured using a PHERAstar FS plate reader (BMG LABTECH). The $IC_{50}$ for each compound was derived from fitting the dose-response data to the four-parameter logistic model by using XLfit software (IDBS).

SK-OV-3 cell-based IDO1 Kyn (kynurenine) production assay:

The inhibitory activity of IDO1 inhibitors is determined by using a colorimetric reaction to measure Kyn generated from L-Trp (L-Tryptophon) oxidation by cellular IDO1 in SK-OV-3 cells.

SK-OV-3 cells were obtained from the American Type Culture Collection and recovered in 10% FBS-containing phenol red-free RIPM 1640 medium. Cells were plated onto a 96-well plate (100 μl/well) at 8000 cells per well and kept at 37° C. in a humidified incubator supplied with 5% $CO_2$. 4 hours later, Compounds at different concentrations diluted in dimethylsulfoxide (DMSO) were added to plate. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 30 minutes and then centrifugation at 2500 rpm for 10 minutes to remove sediments. 80 μl supernatants were carefully removed to a new clean plate and added with an equal volume of 2% 4-(Dimethylamino) benzaldehyde (D2004, sigma) dissolved in glacial acetic acid. The absorbance at 480 nm wavelength derived from Kyn was measured using a PHERAstar FSplate reader (BMG LABTECH). The $IC_{50}$ for each compound was derived from fitting the dose-response data to the four-parameter logistic model by using XLfit software (IDBS).

293-TDO2 Cell-Based TDO2 Kyn (Kynurenine) Production Assay:

The inhibitory activity of TDO2 inhibitors is determined by using a colorimetric reaction to measure Kyn generated from L-Trp (L-Tryptophon) oxidation by cellular TDO2 in HEK293-TDO2 cells stably transfected with a plasmid expression of Tryptophan 2,3-dioxygenase (for short, 293-TDO2).

HEK293 cells were obtained from the American Type Culture Collection and 293-TDO2 were recovered in 10% FBS-containing phenol red-free DMEM medium. Cells were plated onto a 96-well plate (100 μl/well) at 10000 cells per well and kept at 37° C. in a humidified incubator supplied with 5% $CO_2$. 4 hours later, Compounds at different concentrations diluted in dimethylsulfoxide (DMSO) were added to plate. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 30 minutes and then centrifugation at 2500 rpm for 10 minutes to remove sediments. 80 μl supernatants were carefully removed to a new clean plate and added with an equal volume of 2% 4-(Dimethylamino) benzaldehyde (D2004, sigma) dissolved in glacial acetic acid. The absorbance at 480 nm wavelength derived from Kyn was measured using a PHERAstar FS plate reader (BMG LABTECH). The $IC_{50}$ for each compound was derived from fitting the dose-response data to the four-parameter logistic model by using XLfit software (IDBS).

Protein Purification and Co-Crystallization (C101a)

IDO1 protein was expressed and purified following a protocol similar to described in the literature (Biochimica et. Al. Biophysica Acta 1814 (2011) 1947-1954). IDO1 protein was concentrated to 40 mg/ml in a buffer containing 10 mM MES pH6.5, 25 mM NaCl, and 0.5 mM TCEP. Protein solution was incubated with C101a by a molar ratio 1:5 for 1 h at 20° C., and then mixed with a reservoir solution containing 0.1M CHES pH9.5, 0.2M NaCl, 10% PEG8000. Co-crystals of IDO1 with C101a were obtained by vapor diffusion from sitting drops at 20° C.

X-Ray Data Collection and Structure Determination (C101a)

Nylon loops were used to harvest the IDO1 crystals and then immersed the crystals in mother liquor supplemented with 20% ethylene glycol for 1 min. Data were collected on RIGAKU in-house X-ray generator from Institute of Biophysics Chinese Academy of Sciences. Diffraction images were processed with the program MOSFLM. The preliminary structure of the IDO1 was solved by molecular replacement using the program MOLREP. The IDO1 crystal structure (PDB code 2D0T) was used as the search model. REFMAC5 was used to perform rigid body, TLS, restrained refinement against X-ray data, followed by manually adjustment in COOT program and further refinement in REFMAC5 program.

Data Collection and Refinement Statistics (C101a).

| Data collection | | | |
|---|---|---|---|
| Beam line | RIGAKU in-house X-ray generator from Institute of Biophysics | | |
| Space group | P212121 | | |
| Cell dimensions (Å) | a = 85.742 | b = 96.234 | c = 130.690 |
| Angles (°) | α = 90.000 | β = 90.000 | γ = 90.000 |
| Resolution (Å) | 48.12-3.10 | | |
| Total number of reflections | 133577 | | |
| Number of unique reflections | 20192 | | |
| Completeness (%) | 99.7 (98.9) | | |
| Average redundancy | 6.6 (6.3) | | |
| $R^a$ merge | 0.197 (0.534) | | |
| I/sigma (I) | 8.0 (3.5) | | |
| Wilson B factor (Å) | 30.4 | | |

-continued

| Data collection | |
|---|---|
| Refinement | |
| Resolution (Å) | 48.12-3.10 (3.27-3.10) |
| Number of reflections | 19120 |
| rmsd bond lengths (Å) | 0.011 |
| rmsd bond angles (°) | 1.534 |
| $R_{work}{}^b$ (%) | 20.8 |
| $R_{free}{}^c$ (%) | 27.5 |
| Average B-factors of protein | 30 |
| Ramachandran plot (%) | |
| Allowed | 93.31 |
| Generously allowed | 5.16 |
| Disallowed | 1.76 |

$^a R_{merge} = \Sigma\Sigma|I(h)_i - \langle I(h)\rangle|/\Sigma\Sigma|I(h)_i|$, where $\langle I(h)\rangle$ is the mean intensity of equivalent
$^b R = \Sigma|Fo - Fc|/\Sigma|Fo|$, where Fo and Fc are the observed and calculated structure factor amplitudes, respectively.
$^c R_{free} = \Sigma|Fo - Fc|/\Sigma|Fo|$, calculated using a test data set, 5% of total data randomly selected from the observed reflections.

TABLE 1

Enzymatic activity data IC$_{50}$s (IDO1 and TDO) and cellular activity data EC$_{50}$s (Hela Cell-Based IDO1 and 293-TDO2) of 8-substituted imidazo[1,5-a]pyridines

| Ex. No. | Enzyme IC$_{50}$ (nM) | | Cell-Based EC$_{50}$ (nM) | |
|---|---|---|---|---|
| | IDO1 | TDO | Hela IDO1 | 293-TDO2 |
| C101 | 41 | — | 200 | >10000 |
| C101a | 17 | 4200 | 110 | >10000 |
| C101b | 9400 | — | >10000 | >10000 |
| C102 | 100 | — | 261 | >10000 |
| C102a | 36 | 16000 | 471 | >10000 |
| C102b | >10000 | — | >10000 | >10000 |
| C103 | 62 | — | 95 | >10000 |
| C103a | 21 | 10000 | 167 | >10000 |
| C103b | 1200 | — | 2976 | >10000 |
| C104 | 36 | — | 82 | >10000 |
| C104a | 18 | 2500 | 50 | >10000 |
| C104b | 5200 | — | >10000 | >10000 |
| C105 | 210 | — | 2007 | >10000 |
| C105a | 48 | 9100 | 1142 | >10000 |
| C105b | 2000 | — | >10000 | >10000 |
| C106 | 50 | — | 429 | >10000 |
| C106a | 20 | 5200 | 141 | >10000 |
| C106b | 2300 | — | >10000 | >10000 |
| C107 | 65 | — | 157 | >10000 |
| C107a | 31 | 6500 | 109 | >10000 |
| C107b | 5100 | — | >10000 | >10000 |
| C108 | 59 | — | 320 | >10000 |
| C108a | 28 | 5100 | 112 | >10000 |
| C108b | 7300 | — | >10000 | >10000 |
| C109 | 87 | — | 100 | >10000 |
| C109a | 43 | 8500 | 49 | >10000 |
| C109b | >10000 | — | >10000 | >10000 |
| C110 | — | — | — | — |
| C110a | 35 | 21000 | 283 | >10000 |
| C110b | >10000 | — | >10000 | >10000 |
| C111 | 82 | — | 200 | >10000 |
| C111a | 28 | 8000 | 131 | >10000 |
| C111b | >10000 | — | >10000 | >10000 |
| C112 | 92 | — | 285 | >10000 |
| C112a | 40 | 5100 | 183 | >10000 |
| C112b | >10000 | — | >10000 | >10000 |
| C113 | 55 | — | 149 | >10000 |
| C113a | 28 | 5700 | 89 | >10000 |
| C113b | 8200 | — | >10000 | >10000 |
| C114 | 51 | — | 195 | >10000 |
| C114a | 27 | 8300 | 180 | >10000 |
| C114b | 4700 | — | >10000 | >10000 |
| C115 | — | — | — | — |
| C115a | 67 | 11000 | 2401 | >10000 |
| C115b | >10000 | — | 9451 | >10000 |
| C116 | 160 | — | 1100 | >10000 |
| C116a | 77 | 6300 | 500 | >10000 |
| C116b | 5400 | — | >10000 | >10000 |
| C117 | 35 | — | 184 | >10000 |
| C117a | 15 | 3400 | 131 | >10000 |
| C117b | 1100 | — | >10000 | >10000 |
| C118 | 120 | — | 259 | >10000 |
| C118a | 63 | 6200 | 147 | >10000 |
| C118b | 3000 | — | >10000 | >10000 |
| C119 | 39 | — | 148 | >10000 |
| C120 | 96 | — | 2176 | >10000 |
| C120a | 39 | 7400 | 1102 | >10000 |
| C120b | 4800 | — | >10000 | >10000 |
| C121 | 94 | — | 125 | >10000 |
| C121a | 39 | 3600 | 59 | >10000 |
| C121b | 1500 | — | >10000 | >10000 |
| C122 | 74 | — | 382 | >10000 |
| C123 | 15 | — | 372 | >10000 |
| C124 | 56 | — | 236 | >10000 |
| C125 | 41 | 6100 | 915 | >10000 |
| C126 | 29 | — | 30 | >10000 |
| C126a | 16 | — | 20 | >10000 |
| C126b | 1900 | — | 6047 | >10000 |
| C128 | 39 | — | 51 | >10000 |
| C129 | 33 | — | 51 | >10000 |
| C130 | 36 | — | 93 | >10000 |
| C130a | 17 | — | 44 | >10000 |
| C130b | 2500 | — | 6224 | >10000 |
| C131 | 110 | — | — | >10000 |
| C132 | 120 | — | 384 | >10000 |
| C132a | 64 | — | 188 | >10000 |
| C132b | 2500 | — | >10000 | >10000 |
| C133 | 88 | — | 256 | >10000 |
| C136 | 74 | — | 29 | >10000 |
| C136a | 21 | — | 47 | >10000 |
| C136b | 5400 | — | >10000 | >10000 |
| C137 | 79 | — | 177 | >10000 |
| C137a | 26 | — | 74 | >10000 |
| C137b | 4100 | — | >10000 | >10000 |
| C138 | 67 | — | 149 | >10000 |
| C139 | 890 | — | >10000 | >10000 |
| C140 | 140 | — | 304 | >10000 |
| C141 | 76 | — | 105 | >10000 |
| C142 | 32 | — | 267 | >10000 |
| C143 | 130 | — | 1103 | >10000 |
| C144 | 40 | — | 748 | >10000 |
| C144a | 19 | — | 476 | >10000 |
| C144b | >10000 | — | >10000 | >10000 |
| C145 | 90 | — | >10000 | >10000 |
| C146 | 47 | — | 2234 | >10000 |
| C147 | 2300 | — | >10000 | >10000 |
| C148 | 74 | — | 1295 | >10000 |
| C149 | 40 | — | 42 | >10000 |
| C149a | 25 | 1500 | 19 | >10000 |
| C149b | 2400 | — | 2915 | >10000 |
| C150 | 160 | — | 1506 | >10000 |
| C151 | 35 | — | 373 | >10000 |
| C152 | 29 | 3300 | 520 | >10000 |
| C153 | 47 | 6700 | 1051 | >10000 |
| C154 | 36 | — | 49 | >10000 |
| C154a | 16 | — | 18 | >10000 |
| C154b | 2900 | — | 6447 | >10000 |
| C155 | 61 | — | 149 | >10000 |
| C155a | 7500 | — | >10000 | >10000 |
| C155b | 26 | — | 40 | >10000 |

TABLE 2

Enzymatic activity data IC$_{50}$s (IDO1 and TDO) and cellular activity data EC$_{50}$ (Hela Cell-Based IDO1 and 293-TDO2) of 5-substituted imidazo[1,5-a]pyridines

| Ex. No. | Enzyme IC$_{50}$ (nM) IDO1 | TDO | Cell-Based EC$_{50}$ (nM) Hela IDO1 | 293-TDO2 |
|---|---|---|---|---|
| D101 | 27 | — | 100 | >10000 |
| D101a | 14 | 9200 | 35 | >10000 |
| D101b | 1300 | — | 6142 | >10000 |
| D102 | 23 | — | 74 | >10000 |
| D102a | 14 | 5300 | 29 | >10000 |
| D102b | >10 | — | 6772 | >10000 |
| D103 | 38 | — | 163 | >10000 |
| D103a | 1900 | — | >10000 | >10000 |
| D103b | 7800 | — | 6882 | >10000 |
| D103c | 22 | 8100 | 131 | >10000 |
| D103d | 67 | — | >10000 | >10000 |
| D104 | 33 | — | 44 | >10000 |
| D104a | 18 | 7500 | 23 | >10000 |
| D104b | 9900 | — | 6826 | >10000 |
| D105 | 76 | — | 869 | >10000 |
| D105a | 44 | 11000 | 631 | >10000 |
| D105b | >10000 | — | 3896 | >10000 |
| D106 | 30 | — | 68 | >10000 |
| D106a | 11 | 4000 | 21 | >10000 |
| D106b | 1100 | — | 2581 | >10000 |
| D107 | 30 | — | 1477 | >10000 |
| D107a | 36 | — | 1258 | >10000 |
| D107b | 2300 | — | >10000 | >10000 |
| D108 | 30 | — | 72 | >10000 |
| D109 | 39 | — | 206 | >10000 |
| D110 | 40 | — | 373 | >10000 |
| D110a | 16 | 6400 | 186 | >10000 |
| D110b | >10000 | — | >10000 | >10000 |
| D111 | 25 | — | 470 | >10000 |
| D111a | 17 | — | 351 | >10000 |
| D111b | 1200 | — | >10000 | >10000 |
| D112 | 43 | — | 50 | >10000 |
| D112a | 15 | — | 26 | >10000 |
| D112b | 1700 | — | >10000 | >10000 |
| D113 | 43 | — | 95 | >10000 |
| D114 | 32 | — | 155 | >10000 |
| D114a | 17 | 1700 | 572 | >10000 |
| D114b | 2600 | — | 3966 | >10000 |
| D114c | 17 | 5600 | 67 | >10000 |
| D114d | 1400 | — | 5106 | >10000 |
| D115 | 57 | — | 157 | >10000 |
| D115a | 34 | 10000 | 83 | >10000 |
| D115b | 4300 | — | 5684 | >10000 |
| D116 | 44 | — | 107 | >10000 |
| D116a | 15 | 9400 | 43 | >10000 |
| D116b | 5900 | — | 6147 | >10000 |
| D117 | 48 | — | 275 | >10000 |
| D117a | 30 | — | 492 | >10000 |
| D117b | >10000 | — | 99 | >10000 |
| D118 | 44 | — | 546 | >10000 |
| D118a | 25 | 7700 | 306 | >10000 |
| D118b | >10000 | — | 8408 | >10000 |
| D119 | 64 | — | 668 | >10000 |
| D119a | 34 | 5100 | 344 | >10000 |
| D119b | 2200 | — | 3530 | >10000 |
| D120 | 100 | — | 700 | >10000 |
| D120a | 80 | 6700 | 370 | >10000 |
| D120b | 3700 | — | 4314 | >10000 |
| D121 | 73 | — | 606 | >10000 |
| D122 | 28 | — | 228 | >10000 |
| D122a | 18 | — | 103 | >10000 |
| D122b | 5200 | — | >10000 | >10000 |
| D123 | 54 | — | 462 | >10000 |
| D123a | 19 | 13000 | 278 | >10000 |
| D123b | >10000 | — | 9495 | >10000 |
| D124 | 22 | — | 188 | >10000 |
| D124a | 19 | — | 138 | >10000 |
| D124b | 970 | — | 5232 | >10000 |
| D125 | 24 | — | 843 | >10000 |
| D125a | 14 | — | 460 | >10000 |
| D125b | 1600 | — | 9775 | >10000 |
| D126 | 40 | — | 64 | >10000 |
| D126a | 18 | — | 31 | >10000 |
| D126b | >10000 | — | 6522 | >10000 |
| D127 | 40 | — | 170 | >10000 |
| D127a | 16 | — | 83 | >10000 |
| D127b | 2700 | — | 4618 | >10000 |
| D128 | 41 | — | 260 | >10000 |
| D128a | 19 | — | 127 | >10000 |
| D128b | >10000 | — | 8570 | >10000 |
| D129 | 53 | — | 148 | >10000 |
| D129a | 21 | — | 56 | >10000 |
| D129b | 7668 | — | 5125 | >10000 |
| D130 | 50 | — | 279 | >10000 |
| D130a | 30 | — | 203 | >10000 |
| D130b | >10000 | — | 9366 | >10000 |
| D131 | 47 | — | 578 | >10000 |
| D131a | 32 | — | 275 | >10000 |
| D132b | >10000 | — | 6489 | >10000 |
| D132 | 55 | — | 378 | >10000 |
| D132a | 21 | — | 113 | >10000 |
| D132b | 7500 | — | >10000 | >10000 |
| D133 | 44 | — | 496 | >10000 |
| D133a | 21 | 6700 | 220 | >10000 |
| D133b | >10000 | — | 8895 | >10000 |
| D134 | 61 | — | 364 | >10000 |
| D134a | 15 | 6100 | 135 | >10000 |
| D134b | 2700 | — | 5669 | >10000 |
| D135 | 32 | — | 32 | >10000 |
| D135a | 25 | 11000 | 32 | >10000 |
| D135b | 5200 | — | 6746 | >10000 |
| D136 | 51 | — | 358 | >10000 |
| D136a | 21 | 16000 | 254 | >10000 |
| D136b | >10000 | — | 7195 | >10000 |
| D137 | 62 | — | 98 | >10000 |
| D137a | 19 | 7400 | 36 | >10000 |
| D137b | 1700 | — | 2095 | >10000 |
| D138 | 62 | — | 583 | >10000 |
| D139 | 75 | — | 977 | >10000 |
| D139a | 33 | — | 443 | >10000 |
| D139b | >10000 | — | 4470 | >10000 |
| D140 | 24 | — | 42 | >10000 |
| D140a | 20 | 11000 | 38 | >10000 |
| D140b | 1800 | — | 1750 | >10000 |
| D141 | 23 | — | 21 | >10000 |
| D141a | 15 | 6100 | 12 | >10000 |
| D141b | 3800 | — | 7584 | >10000 |
| D142 | 32 | — | 40 | >10000 |
| D143 | 33 | — | 62 | >10000 |
| D144 | 42 | — | 96 | >10000 |
| D144a | 23 | — | 52 | >10000 |
| D144b | 8000 | — | 6407 | >10000 |
| D145 | 54 | — | 462 | >10000 |
| D145a | 19 | 13000 | 277 | >10000 |
| D145b | >10000 | — | 9495 | >10000 |
| D146 | 28 | — | 210 | >10000 |
| D146a | 19 | — | 122 | >10000 |
| D146b | 2900 | — | 4567 | >10000 |
| D147 | 43 | — | 443 | >10000 |
| D147a | 20 | — | 198 | >10000 |
| D147b | >10000 | — | 4505 | >10000 |
| D148 | 40 | — | 188 | >10000 |
| D148a | 17 | — | 80 | >10000 |
| D148b | >10000 | — | 7010 | >10000 |
| D149 | 26 | — | 492 | >10000 |
| D150 | 36 | — | 37 | >10000 |
| D150a | 16 | — | 18 | >10000 |
| D150b | 1400 | — | 1095 | >10000 |
| D151 | 15 | — | 33 | >10000 |
| D152 | 37 | — | 118 | >10000 |
| D153 | 11 | — | 145 | >10000 |
| D154 | 68 | — | 648 | >10000 |
| D155 | 70 | — | 87 | >10000 |
| D155a | 28 | — | 27 | >10000 |

TABLE 2-continued

Enzymatic activity data IC$_{50}$s (IDO1 and TDO) and cellular activity data EC$_{50}$ (Hela Cell-Based IDO1 and 293-TDO2) of 5-substituted imidazo[1,5-a]pyridines

| Ex. No. | Enzyme IC$_{50}$ (nM) | | Cell-Based EC$_{50}$ (nM) | |
|---|---|---|---|---|
| | IDO1 | TDO | Hela IDO1 | 293-TDO2 |
| D155b | 9000 | — | 5635 | >10000 |
| D156 | 57 | — | 75 | >10000 |
| D156a | 20 | 12000 | 31 | >10000 |
| D156b | >10000 | — | 6991 | >10000 |
| D157 | 31 | — | 75 | >10000 |
| D157a | 15 | — | 52 | >10000 |
| D157b | >10000 | — | >10000 | >10000 |
| D158 | 58 | — | 836 | >10000 |
| D159 | 12 | — | 80 | >10000 |
| D160 | 15 | — | 128 | >10000 |
| D161 | 34 | — | 263 | >10000 |
| D163 | 40 | | 48 | >10000 |
| D164 | 33 | | 51 | >10000 |
| D165 | 28 | | 344 | >10000 |
| D166 | 41 | | 29 | >10000 |
| D166a | 26 | | 14 | >10000 |
| D166b | >10000 | | 5212 | >10000 |
| D167 | 69 | | 40 | >10000 |
| D167a | 18 | | 15 | >10000 |
| D167b | 9800 | | 2790 | >10000 |
| D168 | 38 | | 42 | >10000 |
| D168a | 17 | | 25 | >10000 |
| D168b | >10000 | | 6470 | >10000 |
| D169 | 28 | | 22 | >10000 |
| D169a | 15 | | 14 | >10000 |
| D169b | 7500 | | 5952 | >10000 |
| D170 | 21 | | 43 | >10000 |
| D170a | 10 | | 22 | >10000 |
| D170b | 8823 | | 7938 | >10000 |
| D171 | 22 | | 36 | >10000 |
| D171a | 15 | | 30 | >10000 |
| D171b | 8263 | | 5739 | >10000 |
| D172 | 28 | | 58 | >10000 |
| D172a | 14 | | 23 | >10000 |
| D172b | 2700 | | 5402 | >10000 |
| D173 | 30 | | 65 | >10000 |
| D173a | 18 | | 33 | >10000 |
| D173b | 2700 | | 7387 | >10000 |
| D174 | 38 | | 167 | >10000 |
| D174a | 15 | | 80 | >10000 |
| D174b | >10000 | | 5498 | >10000 |
| D175 | 22 | | 21 | >10000 |
| D175a | 12 | | 7.7 | >10000 |
| D175b | 740 | | 407 | >10000 |
| D176 | 25 | | 109 | >10000 |
| D177 | 25 | | 107 | >10000 |
| D178 | 24 | | 40 | >10000 |
| D178a | 10 | | 9.7 | >10000 |
| D178b | 2300 | | 1470 | >10000 |
| D179 | 26 | | 187 | >10000 |
| D180 | 30 | | 40 | >10000 |
| D181 | 31 | | 1020 | >10000 |

TABLE 3

Enzymatic activity data IC$_{50}$s (IDO1 and TDO) and cellular activity data EC$_{50}$s (Hela Cell-Based IDO1 and 293-TDO2) of 5-substituted imidazo[1,5-a]pyridines

| Ex. No. | Enzyme IC$_{50}$ (nM) | | Cell-Based EC$_{50}$ (nM) | |
|---|---|---|---|---|
| | IDO1 | TDO | Hela IDO1 | 293-TDO2 |
| E101 | 62 | — | 6312 | >10000 |
| E101a | 27 | 1700 | 2530 | >10000 |
| E101b | 2800 | — | >10000 | >10000 |
| E102 | 270 | — | 4843 | >10000 |
| E103 | 43 | — | 2321 | >10000 |
| E103a | 17 | 1400 | 777 | >10000 |
| E103b | 1400 | — | >10000 | >10000 |
| E104 | 80 | — | 5444 | >10000 |
| E104a | 29 | — | 3701 | >10000 |
| E104b | 3500 | 1400 | >10000 | >10000 |

Examples C101 to C156, Examples D101 to D181 and Examples E101 to E104 exhibited activity of inhibiting both IDO1 and TDO with IC$_{50}$ values ranging from 0.1 nM to 10 µM as well as activity of inhibiting Hela Cell-Based IDO1 with EC$_{50}$ values ranging less than 10000 nM.

It is to be understood that, if any prior art publication is referred to herein; such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

The invention claimed is:

1. A compound of Formula (IA) or (IB):

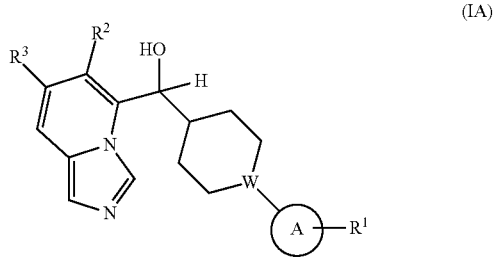

(IA)

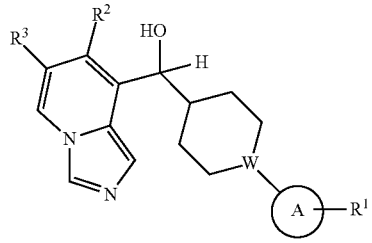

(IB)

or a stereoisomer thereof, or a pharmaceutically acceptable salt thereof,
wherein:
W is CH or N;
Ring A is a $C_{3-8}$ cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;
$R^1$, at each occurrence, is independently selected from hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^6$;
$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^4$, or —$SR^4$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^6$, provided that $R^2$ and $R^3$ are not both hydrogen;
$R^4$ is independently selected from hydrogen, $C_{1-8}$ alkyl, $C_{2-8}$ alkenyl, $C_{2-8}$ alkynyl, $C_{1-8}$ haloalkyl, C3-8 cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, and heteroaryl are each independently optionally substituted with 1 or 2 substituent $R^6$;
$R^5$ is independently selected from hydrogen, $C_{1-8}$ alkyl, $C_{2-8}$ alkenyl, $C_{2-8}$ alkynyl, $C_{1-8}$ haloalkyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{1-8}$ haloalkyl, C3-8 cycloalkyl, heterocyclyl, aryl, and heteroaryl are each independently optionally substituted with 1 or 2 substituent $R^6$;
$R^6$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-$NR^aR^b$, —CN, —$R^a$, —$NR^aR^b$, —$COR^a$, —$CO_2R^a$, —$CONR^aR^b$, —$C(=NR^a)NR^bR^c$, nitro, —$NR^aCOR^b$, —$NR^aCONR^aR^b$, —$NR^aCO_2R^b$, —$SO_2R^a$, —$SO_2$aryl, —$NR^aSO_2NR^bR^c$, $NR^aSO_2R^b$, or —$NR^aSO_2$aryl, wherein said $C_{1-4}$ alkyl, $C_{1-4}$ haloalkyl, $C_{3-6}$ cycloalkyl, aryl, heteroaryl, and heterocyclyl group are each independently optionally substituted by one, two or three substituents selected from halo, hydroxyl, $C_{1-4}$ alkyl or $C_{1-4}$ haloalkyl, wherein $R^a$, $R^b$, and $R^c$ are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, or heteroaryl;
with the proviso that the compound is not (7-cyclopropylimidazo[1,5-a]pyridin-8-yl)(4-phenylcyclohexyl) methanol.

2. The compound of claim 1, wherein:
W is CH or N;
Ring A is a C3-8 cycloalkyl ring or a monocyclic or bicyclic aromatic hydrocarbon ring or a monocyclic or bicyclic aromatic heterocyclic ring, said monocyclic or bicyclic aromatic hydrocarbon ring or monocyclic or bicyclic aromatic heterocyclic ring each having 5- to 10-ring members; Ring A is substituted with at least one substituent $R^1$;
$R^1$, at each occurrence, is independently hydrogen, halogen, cyano, $OR^4$, $NR^4R^5$, $COR^4$, $SO_2R^4$, $C(=O)OR^4$, $C(=O)NR^4R^5$, $N(R^4)C(=O)R^5$, $N(R^4)C(=O)OR^5$, $N(R^4)C(O)NR^4R^5$, $N(R^4)S(O)_2NR^4R^5$, $C_{1-8}$ alkyl, $C_{1-8}$ haloalkyl, or aryl;
$R^2$ and $R^3$ are each independently selected from hydrogen, halogen, $C_{1-8}$ alkyl, or $C_{3-8}$ cycloalkyl, provided that $R^2$ and $R^3$ are not both hydrogen;
$R^4$ is independently selected from hydrogen, $C_{1-8}$ alkyl, $C_{1-8}$ haloalkyl, $C_{3-8}$ cycloalkyl, heterocyclyl, or aryl, wherein said $C_{1-8}$ alkyl is optionally substituted with halogen, OH, —$OC_{1-4}$alkyl, —$C(O)C_{1-4}$alkyl or —C(O)phenyl, and said aryl optionally substituted by halogen;
$R^5$ is independently selected from hydrogen or $C_{1-8}$ alkyl, wherein said $C_{1-8}$ alkyl is optionally substituted with phenyl;
with the proviso that the compound is not (7-cyclopropylimidazo[1,5-a]pyridin-8-yl)(4-phenylcyclohexyl) methanol.

3. The compound of claim 1, wherein $R^2$ is halogen, $C_{1-4}$alkyl, $C_{1-4}$haloalkyl, or $C_{3-6}$cycloalkyl, and $R^3$ is hydrogen.

4. The compound of claim 1, wherein:
a) $R^2$ is hydrogen, and $R^3$ is halogen, $C_{1-4}$alkyl, $C_{1-4}$haloalkyl, or C3-6cycloalkyl, or
b) $R^2$ is hydrogen, and $R^3$ is chloro, fluoro, isopropyl, or cyclopropyl.

5. The compound of claim 1, wherein ring A is a $C_{3-8}$ cycloalkyl ring and W is N.

6. The compound of claim 1, wherein ring A is phenyl or naphthalenyl ring.

7. The compound of claim 1, wherein ring A is a monocyclic or bicyclic aromatic heterocyclic ring having 5- to 10-ring members comprising 1, 2, 3, or 4 heteroatoms selected from O, S, and N.

8. The compound of claim 7, wherein ring A is a monocyclic aromatic heterocyclic ring having 5- to 6-ring members comprising 1 or 2 heteroatoms selected from O, S, and N.

9. The compound of claim 8, wherein ring A is pyridinyl, furanyl, pyrazinyl, pyrimidinyl, pyridazinyl, pyrrolyl, thienyl, triazinyl, or pyrazolyl.

10. The compound of claim 9, wherein ring A is furan-3-yl or thien-3-yl.

11. The compound of claim 7, wherein ring A is a bicyclic aromatic heterocyclic ring having 8- to 10-ring members comprising 1 or 2 or 3 heteroatoms selected from O, S, and N.

12. The compound of claim 11, wherein ring A is cinnolinyl, benzothienyl, benzofuryl, benzoimidazolyl, indolyl, isoindolyl, indolinyl, phthalazinyl, quinolinyl, isoquinolinyl, pyrrolopyridinyl, pyrazolopyridinyl, benzodioxolyl, benzoxazolyl, pteridinyl, purinyl, benzofurazanyl, benzothiophenyl, benzothiazolyl, benzoxazolyl, quinazolinyl, quinoxalinyl, naphthyridinyl, furopyridinyl, benzothiazolyl, or indazolyl.

13. The compound according of claim 12, wherein ring A is benzothiophenyl or quinolinyl or benzodioxolyl.

14. The compound of claim 13, wherein ring A is benzo[b]thiophen-2-yl, benzo[b]thiophen-3-yl, benzo[b]thiophen- 5-yl, benzo[b]thiophen-6-yl, quinolin-4-yl, quinolin-5-yl, quinolin-6-yl, quinolin-7-yl, quinolin-8-yl or benzo[d][1,3]dioxol-5-yl.

15. The compound of claim 1, wherein ring A is a phenyl group, which is optionally substituted by one or two or three substituents $R^1$, which is F, Cl, Br, $C_{1-6}$alkyl, $C_{1-6}$haloalkyl, —$OR^4$, wherein $R^4$ is hydrogen; $C_{1-6}$alkyl optionally substituted by halogen, $C_{1-6}$alkyl-O—, $C(O)C_{1-6}$alkyl or $C(O)$phenyl; heterocyclyl; aryl or $C_{3-6}$cycloalkyl.

16. The compound claim 15, wherein ring A is a phenyl group, which is optionally substituted by one or two or three substituents $R^1$, which is F, Cl, Br, —OH, $C_{1-4}$alkyl, $C_{1-4}$haloalkyl, $C_{1-4}$alkyl-O—, $C_{1-4}$alkyl-O—C1-4alkyl-O—, —$OC_{1-4}$haloalkyl, phenoxy, —$OC_{3-6}$cycloalkyl or —O—(4- to 6-membered heterocyclyl comprising one oxygen heteroatom).

17. The compound of claim 15, wherein ring A is a phenyl group which is substituted by one substituent $R^1$, which is F, Cl, Br, OH or methoxy.

18. The compound of claim 15, wherein in the formula (IA) or (IB), $R^2$ is isopropyl or cyclopropyl, $R^3$ is hydrogen, ring A is a phenyl group which is substituted by one or two substituents $R^1$, which is F, Cl, Br, OH or methoxy.

19. The compound of claim 15, wherein in the formula (IA), $R^2$ is cyclopropyl, $R^3$ is hydrogen, ring A is a phenyl group which is substituted by one substituent $R^1$, which is F, Cl, Br, OH or methoxy.

20. The compound of claim 15, wherein ring A is a phenyl group, which is optionally substituted by one or two or three substituents selected from F, Cl, Br, —OH, methyl, $CF_3$, —$OCF_3$, methoxy or methoxyethoxy.

21. The compound of claim 1, wherein ring A is an unsubstituted quinolinyl group.

22. The compound of claim 1, wherein ring A is a quinolinyl group substituted by fluoro or chloro.

23. The compound according to claim 1, wherein ring A is quinolin-4-yl, quinolin-5-yl, quinolin-6-yl or quinolin-7-yl.

24. The compound of claim 1, wherein the chiral α-carbon atom attached to the imidazo[1,5-a]pyridine structure is in an S-configuration.

25. The compound of claim 1, wherein ring A is attached to the 4-cyclohexyl structure in a trans-configuration.

26. The compound of claim 1, wherein the compounds of Formula (IA) and (IB) have the following configurations, respectively

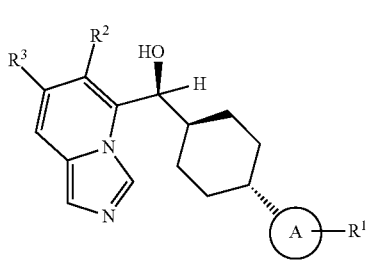

(IA)

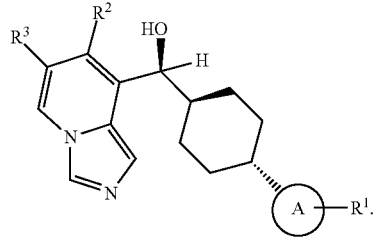

(IB)

27. A compound selected from the compound in Table A or a stereoisomer thereof, or a pharmaceutically acceptable salt thereof.

28. A compound selected from the compound in Table B or a pharmaceutically acceptable salt thereof.

29. A pharmaceutical composition comprising at least one pharmaceutically acceptable excipient and a therapeutically effective amount of a compound of claim 1, or a stereoisomer thereof, or a pharmaceutically acceptable salt thereof.

30. A method for treating hyperproliferative disorders responsive to inhibition of IDO and/or TDO comprising administering to a subject in recognized need thereof a compound of claim 1 or a stereoisomer thereof, or a pharmaceutically acceptable salt thereof in an amount effective to inhibit said IDO and/or TDO; wherein the hyperproliferative disorder is cancer.

31. The method claim 30, wherein the hyperproliferative disorder is selected from melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of biliary tract, non-small cell lung cancer, endometrium cancer, blood cancer, large intestinal colon carcinoma, histiocytic lymphoma, or lung adenocarcinoma.

32. A method for treating HIV infection/AIDS comprising administering to a subject in recognized need thereof therapeutically effective amount of a compound of claim 1, or a stereoisomer thereof, or a pharmaceutically acceptable salt thereof.

33. A method for enhancing the effectiveness of an anti-retroviral therapy comprising administering to a subject in recognized need thereof therapeutically effective amount of a compound of claim 1, or a stereoisomer thereof, or a pharmaceutically acceptable salt thereof.

* * * * *

UNITED STATES PATENT AND TRADEMARK OFFICE
CERTIFICATE OF CORRECTION

PATENT NO. : 10,882,856 B2
APPLICATION NO. : 16/335811
DATED : January 5, 2021
INVENTOR(S) : Hexiang Wang et al.

Page 1 of 1

It is certified that error appears in the above-identified patent and that said Letters Patent is hereby corrected as shown below:

On the Title Page

Please insert after Item (65):
--(30) Foreign Application Priority Data
Sep. 24, 2016 (CN) PCT/CN2016/100001--.

In the Claims

In Claim 1, Column 477, Line 48, please replace:
"-$R^a$," with -- -$OR^a$,--.

In Claim 13, Column 478, Line 64, please replace:
"compound according of" with --compound of--.

In Claim 16, Column 479, Line 9, please replace:
"compound claim" with --compound of claim--.

In Claim 23, Column 479, Line 34, please replace:
"compound according of" with --compound of--.

In Claim 31, Column 480, Line 32, please replace:
"method claim" with --method of claim--.

Signed and Sealed this
First Day of June, 2021

Drew Hirshfeld
*Performing the Functions and Duties of the
Under Secretary of Commerce for Intellectual Property and
Director of the United States Patent and Trademark Office*